United States Patent
Zhang et al.

(10) Patent No.: US 11,725,000 B2
(45) Date of Patent: *Aug. 15, 2023

(54) APOPTOSIS INHIBITORS

(71) Applicant: National Institute of Biological Sciences, Beijing, Beijing (CN)

(72) Inventors: Zhiyuan Zhang, Beijing (CN); Xiaodong Wang, Beijing (CN); Shaoqiang Huang, Beijing (CN); Xian Jiang, Beijing (CN); Li Li, Beijing (CN); Zhaolan Zhang, Beijing (CN); Jianguang Han, Beijing (CN)

(73) Assignee: National Institute of Biological Sciences, Beijing, Beijing (CN)

( * ) Notice: Subject to any disclaimer, the term of this patent is extended or adjusted under 35 U.S.C. 154(b) by 60 days.

This patent is subject to a terminal disclaimer.

(21) Appl. No.: 17/333,033

(22) Filed: May 28, 2021

(65) Prior Publication Data

US 2021/0309647 A1  Oct. 7, 2021

Related U.S. Application Data

(63) Continuation of application No. 16/248,755, filed on Jan. 15, 2019, now Pat. No. 11,034,680, which is a continuation of application No. PCT/CN2017/093096, filed on Jul. 17, 2017.

(51) Int. Cl.
| | | |
|---|---|---|
| *C07D 409/04* | (2006.01) | |
| *A61P 25/16* | (2006.01) | |
| *C07D 401/14* | (2006.01) | |
| *C07D 405/14* | (2006.01) | |
| *C07D 413/14* | (2006.01) | |
| *C07D 401/04* | (2006.01) | |
| *C07D 401/10* | (2006.01) | |
| *C07D 403/04* | (2006.01) | |
| *C07D 239/38* | (2006.01) | |
| *C07D 239/47* | (2006.01) | |
| *C07D 409/14* | (2006.01) | |
| *C07D 417/14* | (2006.01) | |
| *C07D 495/04* | (2006.01) | |
| *A61K 31/506* | (2006.01) | |
| *A61P 37/00* | (2006.01) | |
| *A61K 31/505* | (2006.01) | |
| *A61P 25/00* | (2006.01) | |
| *A61P 9/10* | (2006.01) | |
| *A61P 25/28* | (2006.01) | |
| *C07D 471/04* | (2006.01) | |

(52) U.S. Cl.
CPC .......... *C07D 409/04* (2013.01); *A61K 31/505* (2013.01); *A61K 31/506* (2013.01); *A61P 9/10* (2018.01); *A61P 25/00* (2018.01); *A61P 25/16* (2018.01); *A61P 25/28* (2018.01); *A61P 37/00* (2018.01); *C07D 239/38* (2013.01); *C07D 239/47* (2013.01); *C07D 401/04* (2013.01); *C07D 401/10* (2013.01); *C07D 401/14* (2013.01); *C07D 403/04* (2013.01); *C07D 405/14* (2013.01); *C07D 409/14* (2013.01); *C07D 413/14* (2013.01); *C07D 417/14* (2013.01); *C07D 471/04* (2013.01); *C07D 495/04* (2013.01)

(58) Field of Classification Search
CPC ............................ C07D 401/04; A61K 31/505
See application file for complete search history.

(56) References Cited

U.S. PATENT DOCUMENTS

2019/0152960 A1* 5/2019 Zhang .................. C07D 239/47

FOREIGN PATENT DOCUMENTS

WO  2015058160  4/2015

OTHER PUBLICATIONS

ISR-WO of PCT/CN2017/093096.
Zhai et al., High-Throughput Fluorescence Polarization Assay for Chemical Library Screening against Anti-Apoptotic Bcl-2 Family Member Bfl-1, J Biomolecular Screening, Oct. 4, 2011, No. 3 vol. 17, 350-360.
Supp European Search Report for 17830436.6.

* cited by examiner

*Primary Examiner* — Marcos L Sznaidman
(74) *Attorney, Agent, or Firm* — Richard Aron Osman

(57) ABSTRACT

The invention provides compounds that are inhibitors or covalent modifiers of succinate dehydrogenase subunit B (SDHB) and/or inhibitors of apoptosis, and pharmaceutically acceptable salts, hydrates and stereoisomers thereof. The compounds are employed in pharmaceutical compositions, and methods of making and use, including treating a person in need thereof with an effective amount of the compound or composition.

14 Claims, No Drawings

APOPTOSIS INHIBITORS

INTRODUCTION

Physiological apoptosis plays an essential role in maintaining homeostasis in multicellular organisms, and aberrant apoptosis is known to be a major feature of many diseases. Excessive apoptosis is closely related to ischemia-associated injury, immunodeficient diseases, and neurodegenerative diseases including Alzheimer's syndrome, Parkinson's syndrome, Huntington's syndrome, and amyotrophic lateral sclerosis (ALS). Apoptosis is regulated by two main pathways: the death receptor pathway and the mitochondrial apoptosis pathway. Upon recognition of stimulus that initiate mitochondrial apoptosis, the decision of whether or not to initiate apoptosis is determined via the complicated regulation of pro- and anti-apoptotic Bcl-2 protein family members. BH-3 only proteins (tBid, Bim, etc) trigger the conformational activation of Bax and/or Bak, which in turn translocate to the mitochondrial outer membrane and lead to changes in the permeability of the mitochondrial outer membrane. These changes enable the release of proapoptotic proteins such as cytochrome c and Smac to cytoplasm and these pro-apoptotic factors results in the activation of caspases, and ultimately cell death.

The great majority of research into apoptosis inhibitors has been focused on targeting caspases or proteins of the pro-apoptotic Bcl-2 family. Blocking caspase activity can stop the final execution step of apoptosis, but, by this stage, cells have already suffered considerable damage. Indeed, the degree of stress endured by these cells would typically induce other types of cell death such as necrosis. Thus, it is clear that the identification of drug targets that function upstream in apoptosis signaling would represent an attractive alternative to targeting caspases. Several small molecule and peptide inhibitors have been developed that target the upstream pro-apoptotic Bcl-2 family members Bax and Bid, and some of these have shown protective effects in a global brain ischemia model. However, all of these apoptosis inhibitors have only moderate potency, with $EC_{50}$ values above the micromolar level. Additionally, blocking a single pro-apoptotic Bcl-2 protein may have only limited effects because other pro-apoptotic Bcl-2 family proteins have complementary function.

Here, a new class of apoptosis inhibitors (TC09) that block cytochrome c release was developed through a phenotype-based high-throughput screen and a detailed structure-activity relationship study. We optimized the cellular activity of TC09 series to the low nanomolar level, and used cellular reversibility assays to demonstrate the covalent binding mode for the interaction of TC09 with the target protein. Our data indicate that TC09 apoptosis inhibitors function as stabilizers of the mitochondrial electron transport chain by targeting succinate dehydrogenase subunit B, and showed neuron protection effects in animal models.

Pyrimidinyl compounds are disclosed in WO2008/157003, US2009/163545, U.S. Pat. No. 3,149,109, US2005/80111, Eng, et al.; Drug Metabolism and Disposition; vol. 41; nb. 8; (2013); p. 1470-1479.

SUMMARY OF THE INVENTION

The invention provides sulfonyl and sulfinyl pyrimidinyl compounds for use in a person in need thereof, or in the manufacture of a medicament, to modify succinate dehydrogenase subunit B (SDHB), inhibit apoptosis, insulate or protect cells, like dopaminergic neurons, from damage from apoptotic insults or treat Parkinson's disease. In an aspect the compound is of formula I:

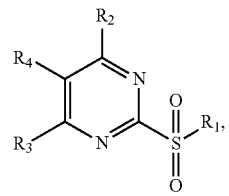

wherein:
R1 is an optionally substituted, optionally hetero-, optionally cyclic C1-C18 hydrocarbyl;
R2 is an optionally substituted heteroatom, or an optionally substituted, optionally hetero-, optionally cyclic C1-C18 hydrocarbyl;
R3 is an optionally substituted, optionally hetero-, cyclic C3-C18 hydrocarbyl; and
R4 is H or an optionally substituted heteroatom, or an optionally substituted, optionally hetero-, optionally cyclic C1-C18 hydrocarbyl;
or a corresponding sulfinyl, or a stereoisomer, hydrate, salt or acetate thereof, wherein the corresponding sulfinyl is:

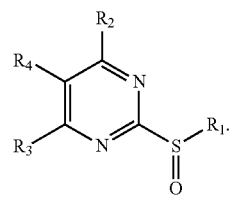

The invention includes embodiments of the compound, including the sulfonyl, corresponding sulfinyl, or a stereoisomer, hydrate, salt or acetate thereof, such as wherein R1 is an optionally substituted, optionally hetero-, optionally cyclic C1-C18 alkyl, or an optionally substituted, optionally hetero-, optionally cyclic C2-C18 alkenyl or alkynyl, or an optionally substituted, optionally hetero-, optionally cyclic C2-C18 aryl;
R1 is an optionally substituted, optionally hetero-, C1-C18 alky;
R1 is an optionally substituted C1-C4 alky; or
R1 is Me or Et;
R2 is an optionally substituted, optionally hetero-, optionally cyclic C1-C18 alkyl, or an optionally substituted, optionally hetero-, optionally cyclic C2-C18 alkenyl or alkynyl, or an optionally substituted, optionally hetero-, optionally cyclic C2-C18 aryl;
R2 is an optionally substituted C1-C4 alkyl, alkenyl or alkynyl;
R2 is an optionally substituted, optionally hetero-, cyclic C5-C6 alkyl, alkenyl or alkynyl;
R2 is an amine, halide or azido;
R2 is F, CH2F, CHF2, or CF3; or
R2 is CF3;
R3 is an optionally substituted, heterocyclic C3-C18 hydrocarbyl;
R3 is an optionally substituted, optionally hetero-, C5-C18 or C5-C6 aryl;
R3 is an optionally substituted, heterocyclic, C5-C18 or C5-C6 aryl;

R3 is an optionally substituted, N-heterocyclic, C3-C18 hydrocarbyl;
R3 is an optionally substituted, N-heterocyclic, C5-C18 or C5-C6 aryl;
R3 is an optionally substituted pyridinyl, pyrrolyl or pyrazolyl;
R3 is an optionally substituted phenyl or thiophene; or
R3 is an optionally substituted 5-pyridin-2 (1H)-one;
R4 is H or an optionally substituted, optionally hetero-, optionally cyclic C1-C18 alkyl, or an optionally substituted, optionally hetero-, optionally cyclic C2-C18 alkenyl or alkynyl, or an optionally substituted, optionally hetero-, optionally cyclic C2-C18 aryl;
R4 is an optionally substituted C1-C4 alkyl, alkenyl or alkynyl;
R4 is an optionally substituted, optionally hetero-, cyclic C5-C6 alkyl, alkenyl or alkynyl;
R4 is H, amine, halide or azido; or
R4 is H;
and/or R3 is an optionally substituted 5-pyridin-2 (1H)-one, of formula II:

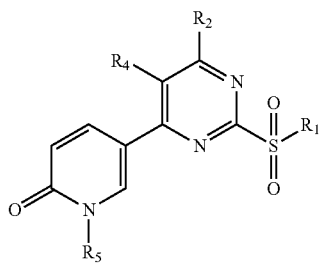

II wherein:
R5 is an optionally substituted, optionally hetero-, optionally cyclic C3-C18 hydrocarbyl;
R5 is optionally substituted benzyl; or
R5 is 3,4-dimethoxybenzyl.

In another aspect the invention provides sulfonyl pyrimidinyl compound of formula I:

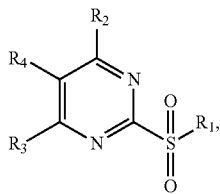

I wherein:
R1 is an optionally substituted, optionally hetero-, optionally cyclic C1-C18 hydrocarbyl;
R2 is an optionally substituted heteroatom, or an optionally substituted, optionally hetero-, optionally cyclic C1-C18 hydrocarbyl;
R3 is an optionally substituted, N-heterocyclic C3-C18 hydrocarbyl; and
R4 is H or an optionally substituted heteroatom, or an optionally substituted, optionally hetero-, optionally cyclic C1-C18 hydrocarbyl;
or a corresponding sulfinyl, or a stereoisomer, hydrate, salt or acetate thereof.

The invention includes embodiments of the compound, including the sulfonyl, corresponding sulfinyl, or a stereoisomer, hydrate, salt or acetate thereof, such as wherein
R1 is an optionally substituted, optionally hetero-, optionally cyclic C1-C18 alkyl, or an optionally substituted, optionally hetero-, optionally cyclic C2-C18 alkenyl or alkynyl, or an optionally substituted, optionally hetero-, optionally cyclic C2-C18 aryl;
R1 is an optionally substituted, optionally hetero-, C1-C18 alky;
R1 is an optionally substituted C1-C4 alky; or
R1 is Me or Et;
R2 is an optionally substituted, optionally hetero-, optionally cyclic C1-C18 alkyl, or an optionally substituted, optionally hetero-, optionally cyclic C2-C18 alkenyl or alkynyl, or an optionally substituted, optionally hetero-, optionally cyclic C2-C18 aryl;
R2 is an optionally substituted C1-C4 alkyl, alkenyl or alkynyl;
R2 is an optionally substituted, optionally hetero-, cyclic C5-C6 alkyl, alkenyl or alkynyl;
R2 is an amine, halide or azido;
R2 is F, CH2F, CHF2, or CF3; or
R2 is CF3;
R3 is an optionally substituted, heterocyclic C3-C18 hydrocarbyl;
R3 is an optionally substituted, optionally hetero-, C5-C18 or C5-C6 aryl;
R3 is an optionally substituted, heterocyclic, C5-C18 or C5-C6 aryl;
R3 is an optionally substituted, N-heterocyclic, C3-C18 hydrocarbyl;
R3 is an optionally substituted, N-heterocyclic, C5-C18 or C5-C6 aryl;
R3 is an optionally substituted pyridinyl, pyrrolyl or pyrazolyl;
R3 is an optionally substituted phenyl or thiophene; or
R3 is an optionally substituted 5-pyridin-2 (1H)-one;
R4 is H or an optionally substituted, optionally hetero-, optionally cyclic C1-C18 alkyl, or an optionally substituted, optionally hetero-, optionally cyclic C2-C18 alkenyl or alkynyl, or an optionally substituted, optionally hetero-, optionally cyclic C2-C18 aryl;
R4 is an optionally substituted C1-C4 alkyl, alkenyl or alkynyl;
R4 is an optionally substituted, optionally hetero-, cyclic C5-C6 alkyl, alkenyl or alkynyl;
R4 is H, amine, halide or azido; or
R4 is H;
R3 is an optionally substituted 5-pyridin-2 (1H)-one, of formula II:

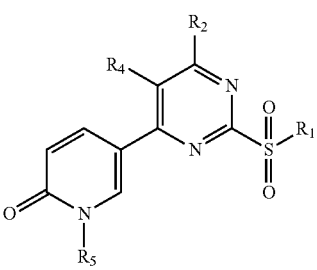

II wherein:

R5 is an optionally substituted, optionally hetero-, optionally cyclic C3-C18 hydrocarbyl;

R5 is optionally substituted benzyl; or

R5 is 3,4-dimethoxybenzyl;

and/or the compound is a disclosed compound (e.g. see Tables, herein), or is 1-(3,4-dimethoxybenzyl)-5-(2-(methylsulfonyl)-6-(trifluoromethyl)pyrimidin-4-yl)pyridin-2 (1H):

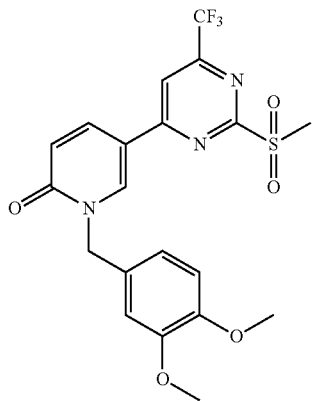 [SMILES: COc1ccc(Cn2cc(-c3cc(C(F)(F)F)nc(S(C)(=O)=O)n3)ccc2=O)cc1OC]

or a stereoisomer, hydrate, salt or acetate thereof.

In embodiments, the hydrocarbyl is an optionally substituted, optionally cyclic, C1-C10 alkyl, C2-C9 alkenyl, C2-C9 alkynyl, or C5-C14 aryl hydrocarbon, comprising 1-5 heteroatoms that are N, S, O or P, including 1-5 nitrogen atoms, which heteroatoms may be substituted. In embodiments, the hydrocarbyl is a C3-C18 cyclic hydrocarbyl, such as a heterocyclic C3-C18 hydrocarbyl, such as: a 3 membered ring that is an optionally substituted (e.g. aziridine, oxirane, oxaziridine); a 4 membered ring that is an optionally substituted (e.g. azetidine, oxetane, oxazetidine); a 5 membered ring that is an optionally substituted (e.g. pyrrole, 1,2-diazole (pyrazole), 1,3 diazole (imidazole), thiazole, isothiazole, oxazole, isoxazole, furan, dioxole, thiophene, triazole, furazan, tetrazole); a 6 membered ring that is an optionally substituted (e.g. pyridine, pyran, thiopyran, diazine, triazine, oxazine, thiazine, dioxine, oxathiine, dithiine, pentazine); a 7 membered ring that is optionally substituted (e.g. azapine, oxepine, thiepine, diazepine, thiazepine); a 8 membered ring that is optionally substituted (e.g. azocine, oxocine, thiocine); a 9 membered ring that is an optionally substituted (e.g. indole, benzothiazole, benzooxazole, benzofuran, benzodioxole, benzothiophene, benzodithiole); or a 10 membered ring that is an optionally substituted (e.g. quinoline, quinoxaline, quinazoline, chromene, benzodioxine, thiochromene, benzodithiine).

In embodiments, the compound is an inhibitor or covalent modifier of succinate dehydrogenase subunit B (SDHB) and/or inhibitor of apoptosis.

In embodiments, the compound is of formula I wherein R1, R2, R3 and R4 are defined as follows:

| Compound | $R_1$ | $R_2$ | $R_3$ | $R_4$ |
|---|---|---|---|---|
| Hit | ![acylamino-methylphenol group] | *—CF$_3$ | ![2-thienyl] | H |
| 1 | *—CH$_3$ | | | H |
| 2 | *—CH$_2$CH$_3$ | | | H |
| 3 | *—(CH$_2$)$_2$COOEt | | | H |
| 4 | ![biphenylmethyl] | | | H |
| 5 | ![quinoline N-oxide methyl] | | | H |
| 6 | *—Me | | —CH$_3$ | H |
| 7 | | | —N$_3$ | H |
| 8 | | | ![2-thienyl] | H |
| 9 | | | ![pyrrolidinone-N] | H |
| 10 | | *—CF$_3$ | phenyl | H |
| 11 | | | 2-methyl-phenyl | H |
| 12 | | | 3-methyl-phenyl | H |
| 13 | | | 4-methyl-phenyl | H |
| 14 | | | 2-methylbenzoate | H |

-continued

| Compound | $R_1$ | $R_2$ | $R_3$ | $R_4$ |
|---|---|---|---|---|
| 15 | | | 3-methylbenzoate | H |
| 16 | | | 4-methylbenzoate | H |
| 17 | | | 5-pyridin-2(1H)-one, | H. | inclusive of a corresponding sulfinyl, or a stereoisomer, hydrate, salt or acetate thereof.

In embodiments, the compound is of formula II wherein Ra is Me, R2 is CF3, R4 is H, and R5 is defined as follows: compound R5

| compound | $R_5$ |
|---|---|
| 17 | —H |
| 18 | -benzyl |
| 19 | 2-chlorobenzyl |
| 20 | 3-chlorobenzyl |
| 21 | 4-chlorobenzyl |
| 22 | 3-hydroxybenzyl |
| 23 | 3-methoxybenzyl |
| 24 | 3-ethoxybenzyl |
| 25 | 3-propoxybenzyl |
| 26 | 4-methoxybenzyl |
| 27 | 3,4-dimethoxybenzyl |
| 28 | 2-propynyl |
| 29 | 4-methoxy-3-(2-propynyl loxy)benzyl |
| 30 | (CH2CH2O)3CH2CH2NH-biotin (structure) |
| 31 | (CH2CH2O)3CH2CH2NH-biotin (structure) |
| 32 | 3-methoxy-4-(2-propynyl loxy)benzyl |
| 33 | 3-ethynylbenzene |
| 34 | 4-ethynylbenzene |
| 35 | (CH2CH2)2CH2CH2fluorescein, (structure) | again, inclusive of a corresponding sulfinyl, or a stereoisomer, hydrate, salt or acetate thereof.

In embodiments the invention provides a pharmaceutical composition comprising a disclosed compound or composition in unit dosage form, and/or coformulated or copackaged or coadministered with a different anti-Parkinson's drug The invention also provides methods of using a disclosed compound or composition comprising administering it to a person determined to be in need thereof, and optionally, detecting a resultant therapeutic effect, and may also optionally include the antecedent step of determining that the person, particularly diagnosing and applicable disease or condition (herein), or use thereof in the manufacture of a medicament.

The invention encompasses all combination of the particular embodiments recited herein, as if each combination had been laboriously recited.

DESCRIPTION OF PARTICULAR EMBODIMENTS OF THE INVENTION

The following descriptions of particular embodiments and examples are provided by way of illustration and not by way of limitation. Those skilled in the art will readily recognize a variety of noncritical parameters that could be changed or modified to yield essentially similar results.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

A hydrocarbyl group is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which comprises 1-15 carbon atoms and optionally includes one or more heteroatoms in its carbon skeleton.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, C(O)R (e.g. carbonyl), halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH$_2$—CH$_2$—CH$_2$—CH$_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from/zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO₂R', —CONR'R", —OC(O)NR'R", —NR"C(O)R', —NR'—C(O)NR"R'", —NR'—SO₂NR', —NR"CO₂R', —NH—C(NH₂)=NH, —NR'C(NH₂)=NH, —NH—C(NH₂)=NR', —S(O)R', —SO₂R', —SO₂NR'R", —NR"SO₂R, —CN and —NO₂, in a number ranging from/zero to three, with those groups having zero, one or two substituents being particularly preferred. R', R" and R'" each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from/zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF₃ and —CH₂CF₃).

Preferred substituents for the alkyl and heteroalkyl radicals are selected from: —OR', =O, —NR'R", —SR', halogen, —SiR'R"R'", —OC(O)R', —C(O)R', —CO₂R', —CONR'R", —OC(O)NR'R", —NR"C(O)R', —NR"CO₂R', —NR'—SO₂NR"R'", —S(O)R', —SO₂R', —SO₂NR'R", —NR"SO₂R, —CN and —NO₂, where R' and R" are as defined above. Further preferred substituents are selected from: —OR', =O, —NR'R", halogen, —OC(O)R', —CO₂R', —CONR'R", —OC(O)NR'R", —NR"C(O)R', —NR"CO₂R', —NR'—SO₂NR"R'", —SO₂R', —SO₂NR'R", —NR"SO₂R, —CN and —NO₂.

Similarly, substituents for the aryl and heteroaryl groups are varied and selected from: halogen, —OR', —OC(O)R', —NR'R", —SR', —R', —CN, —NO₂, —CO₂R', —CONR'R", —C(O)R', —OC(O)NR'R", —NR"C(O)R', —NR"CO2R', —NR'—C(O)NR"R'", —NR'—SO₂NR"R'", —NH—C(NH2)=NH, —NR'C(NH₂)=NH, —NH—C(NH₂)=NR', —S(O)R', —SO₂R', —SO₂NR'R", —NR"SO₂R, —N₃, —CH(Ph)₂, perfluoro(C1-C4)alkoxy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from/zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO₂, —CO₂R', —CONR'R", —C(O)R', —OC(O)NR'R", —NR"C(O)R', —S(O)R', —SO₂R', —SO₂NR'R", —NR"SO₂R, —N₃, —CH(Ph)₂, perfluoro(C1-C4)alkoxy and perfluoro(C1-C4)alkyl, where R' and R" are as defined above. Further preferred substituents are selected from: halogen, —OR', —OC(O)R', —NR"R", —R', —CN, —NO₂, —CO₂R', —CONR'R", —NR"C(O)R', —SO₂R', —SO₂NR'R", —NR"SO₂R, perfluoro(C1-C4) alkoxy and perfluoro(C1-C4)alkyl.

The substituent —CO₂H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH₂)q-U—, wherein T and U are independently —NH—, —O—, —CH₂— or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH₂—, —O—, —NH—, —S—, —S(O)—, —S(O)₂—, —S(O)₂NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)s-X—(CH₂)t-, where s and t are independently integers of from 0 to 3, and X is —O—, —NR'—, —S—, —S(O)—, —S(O)₂—, or —S(O)₂NR'—. The substituent R' in —NR'— and —S(O)₂NR'— is selected from hydrogen or unsubstituted (C1-C6)alkyl.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, optionally heteroatom C1-C6 alkyl, substituted or unsubstituted, optionally heteroatom C2-C6 alkenyl, substituted or unsubstituted, optionally heteroatom C2-C6 alkynyl, or substituted or unsubstituted, optionally heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, C(O)R (e.g. carbonyl), carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Some of the subject compounds possess asymmetric carbon atoms (optical centers) or double bonds; the racemates, diastereomers, geometric isomers and specifically designated or depicted chirality is preferred and in many cases critical for optimal activity; however all such isomers are all intended to be encompassed within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the compounds may be advantageously used in conjunction with other therapeutic agents as described herein or otherwise known in the art, particularly other anti-diabetes or anti-obesity agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

Highly Potent Apoptosis Inhibitors that Target the Mitochondrial Respiratory Chain Here, we report the development of a series of unique and highly potent apoptosis inhibitors (TC09 series). They have low-nanomolar $EC_{50}$ values, and target events in the apoptosis signaling pathway that occur between the regulation of Bcl-2 family proteins and mitochondrial cytochrome c release. Target identification based on affinity based protein profiling (ABPP) revealed that the molecular target of TC09 apoptosis inhibitor compounds is succinate dehydrogenase subunit B (SDHB) of mitochondrial respiratory complex II.

A chemical library containing 200,000 small molecules was screened for compounds that block apoptosis using a cell line with inducible overexpression of Bim (U2OS_Bim). [7] Several active hits were identified, and these had an EC50 between 2 to 20 µM in increasing cell survival rates following apoptosis as induced by Bim overexpression. Mitochondrial release of cytochrome c was checked by immunofluorescence assays to detect if these hits functioned upstream of apoptosis-associated mitochondrial changes that occur after the induced Bimprotein overxexpression One hit with an $EC_{50}$ of 4.0 µM could prevent cytochrome c release: this compound was selected for further optimization (TC09-hit, Table 1).

We undertook a structure activity relationship based optimization with the aim of improving the activity of the screening hit. We initially optimized fragment $R_1$ (Table 1). In each case, replacement of $R_1$ with aliphatic groups of varying sizes increased the apoptosis inhibition activity by 3-5 fold (compound 1-3). Aromatic substitutes were also tested, and activity remained at similar levels as the hit. (compound 4,5) This indicated that fragment $R_1$ could tolerate a relatively large change in structure. Since compound 1 had the strongest apoptosis inhibition activity, we replaced the original structure of $R_1$ with a methyl group for further SAR study. We next substituted the —$CF_3$ group at the $R_2$ position with different groups-, all such variations led to the total loss of activity. (compounds 6-9) This may relate to either a constrained binding environment or the necessity of the strong electron withdrawing property of the original —$CF_3$ group.

TABLE 1

SAR study of compounds TC09 1-17

| Compound | $R_1$ | $R_2$ | $R_3$ | $EC_{50}$ (nM) |
|---|---|---|---|---|
| Hit | (butanamide-methylphenol group) | *—$CF_3$ | (thiophene) | 4010 |
| 1 | *—$CH_3$ | | | 749 |
| 2 | *—$CH_2CH_3$ | | | 1428 |

TABLE 1-continued

SAR study of compounds TC09 1-17

| Compound | R₁ | R₂ | R₃ | EC₅₀ (nM) |
|---|---|---|---|---|
| 3 | *—(CH$_2$)$_2$COOEt | | | 1135 |
|  | *-CH$_2$-biphenyl | | | 4207 |
| 4 |  | | | |
| 5 | *-CH$_2$-(quinoline N-oxide) | | | 1172 |
| 6 | | —CH$_3$ | | >20000 |
| 7 | | —N$_3$ | | >20000 |
| 8 | | *-(2-thienyl) | | >20000 |
| 9 | | *-(2-oxopyrrolidin-1-yl) | | >20000 |
| 10 | *—Me | *—CF$_3$ | phenyl | 2201 |
| 11 | | | 2-methyl-phenyl | 6642 |
| 12 | | | 3-methyl-phenyl | 3487 |
| 13 | | | 4-methyl-phenyl | 6355 |
| 14 | | | 2-methylbenzoate | 7033 |
| 15 | | | 3-methylbenzoate | 3516 |
| 16 | | | 4-methylbenzoate | >20000 |
| 17 | | | 5-pyridin-2(1H)-one | >20000 |

We then conducted SAR optimization of fragment R$_3$ (Table 1). Although the replacement of the original thiophene group with phenyl rings (10) resulted in decreased activity, it did offer more options for testing the influence of substitutes on different positions of the ring. Compounds with methyl substitution at the 2-, 3-, and 4-positions of the phenyl ring showed different trends in their activity (compounds 11-13). Methyl substitution at both the 2- and 4-positions (11, 13) led to a 3 fold decreases in activity compared with compound 10, while methyl substitution at the 3-position (compound 12) had a similar EC$_{50}$ to compound 10. Additionally, activity of compounds with —COOCH$_3$ substitution at 2, 3, 4-position shared similar pattern that only 3-substitution kept the activity (compounds 14-16). These results hinted that the area near 3-position of phenyl ring had a bigger tolerance than other positions. We then synthesized compound 17, by replacing the original thiophene group with a pyridone ring. It served as an intermediate for further SAR exploration at 3-position, and the activity was completely lost. However, the addition of a benzyl group to the N atom in the pyridone (compound 18) restored the activity to an EC$_{50}$ of 1157 nM. (Table 2) This interesting finding indicates that extending the skeleton of the compound by adding the benzyl ring may form new interaction(s) with the target.

TABLE 2

SAR study of compounds TC09 13-35

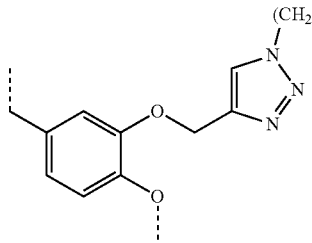

| compound | R₄ | EC$_{50}$ (nM) |
|---|---|---|
| 17 | —H | >20000 |
| 18 | -benzyl | 1157 |
| 19 | 2-chlorobenzyl | 1143 |
| 20 | 3-chlorobenzyl | 257 |
| 21 | 4-chlorobenzyl | 66 |
| 22 | 3-hydroxybenzyl | 1415 |
| 23 | 3-methoxybenzyl | 57 |
| 24 | 3-ethoxybenzyl | 110 |
| 25 | 3-propoxybenzyl | 69 |
| 26 | 4-methoxybenzyl | 94 |
| 27 | 3,4-dimethoxybenzyl | 13 |
| 28 | 2-propynyl | 499 |
| 29 | 4-methoxy-3-(2-propynyl loxy)benzyl | 104 |
| 30 | 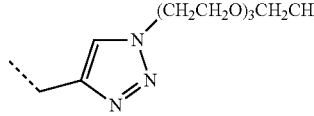 (CH₂CH₂O)₃CH₂CH₂NH-biotin | 4877 |
| 31 | (CH₂CH₂O)₃CH₂CH₂NH-biotin | >20000 |
| 32 | 3-methoxy-4-(2-propynyl loxy)benzyl | 64 |
| 33 | 3-ethynylbenzene | 4477 |
| 34 | 4-ethynylbenzene | 817 |
| 35 | 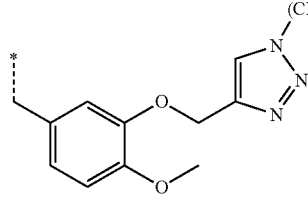 (CH₂CH₂)₂CH₂CH₂fluorescein | 995 |

Encouraged by these results, exploration of SAR on the benzyl ring was then performed in more details. Chloro-substitution at different positions of the benzyl ring (compounds 19-21) was examined. As shown in Table 2, the 2-chloro compound 19 had only a mild increase in activity compared with compound 18, but 3- and 4-chloro compounds 20 and 21 were both found to be more potent in inhibiting apoptosis. Compound 20 had an EC$_{50}$ of 257 nM, about 4 fold more potent than compound 18. Compound 21 was 17 fold more potent than compound 18. We next focused on substitution on the 3- and 4-positions of the benzyl ring. 3-position —OH, —OMe, —OEt, and —OPr substituted compounds were all synthesized and tested (compounds 22-25). The compound with 3-OH substitution had the same activity as compound 18, and was less potent than the 3-chloro compound 20. Addition of a methyl group at the oxygen atom (compound 23) raised the activity by about 20 fold; its EC$_{50}$ was only 57 nM. —OEt and —OPr substituted compounds 24 and 25 also displayed similar enhancements as compound 23 in activity. The influence of 4-OMe substitution (compound 26) was then examined, and the same as 3-OMe substitution, it also promoted the activity by ~12 folds compared with compound 18. Enlightened by compounds 23 and 26, we next combined 3- and 4-position —OMe substitutions in compound 27 (1-(3,4-dimethoxybenzyl)-5-(2-(methylsulfonyl)-6-(trifluoromethyl)pyrimidin-4-yl)pyridin-2 (1H), which showed a yet further increased inhibition activity, with an $EC_{50}$ as low as 11 nM, more than 300 fold higher than with the initial hit compound.

In addition to testing the apoptosis inhibition activity of TC09 compounds on Bim-induced apoptosis, we also evaluated if they could block apoptosis as induced by the overexpression of tBid, another pro-apoptotic protein of the Bcl-2 family. Comparable inhibition potency properties were observed in both apoptosis induction models, and the best compound 27 reached an $EC_{50}$ of 66 nM. To the best of our knowledge, TC09 compounds are the first to fully inhibit apoptosis at the low-nanomolar level in a cellular assay.

It has been reported that sulfone can serve as a good leaving group in $SN_2$ substitution reactions when linked to electron withdrawing groups. [8] Active compounds in our SAR study all contained a —$CF_3$ substituted pyrimidine ring linked to the sulfone group. Replacement of $CF_3$ at the $R_2$ position with groups with less powerful electron-withdrawing properties totally abolished the apoptosis inhibition activity. The fact that the observed variation in apoptosis inhibition activity correlated with changes in the electrophilicity of the fragment linked to the sulfone group suggested that TC09 compounds may function via covalent binding through an $SN_2$ substitution reaction with nucleophilic residues. To test the reactivity of representative TC09 compounds, we performed model reactions using different nucleophilic reagent (cysteine, lysine, and glutathione) with compounds 1, 6, and 27. LC-MS analysis of reaction indicated that nucleophilic substitution products of compound 1 and 27 were observed in the reactions with cysteine and glutathione, but not in the lysine reactions. No products of compound 6 were observed in any of the nucleophilic reagent reactions. To further explore the binding mode of the active compounds in a cellular context, we next performed a cellular wash/no wash assay for determining the reversibility of compound-target interactions. Following compound incubation, one subset of cells was washed several times to eliminate the free test compounds, and the other subset was not washed. Apoptosis was induced and the viability of cells was then measured and $EC_{50}$ under wash conditions was compared with no wash conditions.[9] Most of the compounds had a similar $EC_{50}$ values under these two conditions (Table 3), indicating an irreversible binding mode between these compounds and the target. Results from both the model reactions and the cellular assays indicated that TC09 apoptosis inhibitors function through covalent binding with the target, and possibly through —SH residue attack.

TABLE 3

Comparision of $EC_{50}$ values between the wash and no wash assay

| compound | $EC_{50}$ (no wash, nM) | $EC_{50}$ (wash assay, nM) | compound | $EC_{50}$ (no wash, nM) | $EC_{50}$ (wash assay, nM) |
| --- | --- | --- | --- | --- | --- |
| 1 | 749 | 661 | 25 | 69 | 66 |
| 3 | 1135 | 1268 | 26 | 94 | 168 |
| 10 | 2201 | 5058 | 9 | 13 | 7 |
| 17 | 1157 | 1069 | 28 | 499 | 499 |
| 19 | 1143 | 997 | 29 | 104 | 55 |
| 20 | 257 | 305 | hit | 4010 | 3895 |
| 21 | 66 | 45 | zVAD | 69217 | nd. |
| 23 | 57 | 62 | | | |

Given that TC09 apoptosis inhibitors function upstream of mitochondrial cytochrome c release to inhibit apoptosis and maintain cell survival, we next examined if they could block the dysfunction of mitochondria that occurs following the induction of apoptosis. We first measured changes in the mitochondrial membrane potential using TMRM, a fluorescent dye under different conditions. Dox induction of Bim overexpression is known to result in the loss of mitochondrial membrane potential and thus diminish TMRM enrichment during apoptosis. Compounds at concentration that are completely block apoptosis can maintain the mitochondria membrane potential and TMRM enrichment, an outcome that cannot be achieved with zVAD, a caspase inhibitor. The mitochondria protection effect of TC09 compounds was also supported by the measurement of ROS levels after apoptosis induction. ROS level is upregulated due to the interruption of the electron transport chain and the changes of membrane permeability that occur during apoptosis, and the overproduced ROS again act as a stimulative factor and cause further damage[13]. TC09 compounds treatment maintained the normal ROS level even upon apoptosis induction, and showed a dose-dependent effect.

In order to identify the target protein of tTC09 apoptosis inhibitors, we synthesized two sets of probes for target identification based on the SAR study. The first set of probes was designed for direct activity based protein profiling (ABPP) with biotin tag linked at different site. The addition of these biotin tags resulted in varying degrees of activity loss, possibly owing to steric hindrance of the bulky fragment or a change of cellular permeability (Table 2). Compounds 30 and 31 were selected as positive and negative probes for pulldown assays and identified succinate dehydrogenase subunit B (SDHB), a component of the respiratory complex II located on the mitochondrial inner membrane, as the covalent binding target. TC09 apoptosis inhibitors could stabilize the mitochondrial respiratory chain after Bim/tBid overexpression and help maintain the normal function of mitochondria. A second set of probes with a terminal alkyne group designed for click-reaction-assisted ABPP were also prepared. Most of these compounds (28, 29, 32-34) retained relatively potent activity, with $EC_{50}$ values below 1 μM. Click-reaction-assisted ABPP was performed using compound 29 as a positive probe and compound 27 as a competitor; these probes also identified SDHB as the cellular target. To further verify that SDHB was indeed the molecular target, we also synthesized a derivative of compound 29 with an FITC tag for fluorescence imaging (compound 35, $EC_{50}$=995 nM). The green fluorescence of compound 35 merged well with the specific red fluorescent staining of mitochondria, indicating that most of compound 35 was localized in mitochondria.

TC09 Compounds Save Cells from Apoptotic Insults

Despite intensive efforts, researchers have as yet failed to identify a small molecule that can confer long-term survivability to cells when the mitochondrial apoptosis pathway is activated. The pan-caspase inhibitor z-VAD-FMK is able to keep cells alive (as measured by cellular ATP levels) during a short time frame (usually less than 24 hours), but is not able to save cells from death when the upstream insults to mitochondria persist.

We therefore tested the long-term impact of TC09 compounds on cells experiencing constant apoptotic insult. Control U2OS_Bim cells completely died off within 24 hours after the addition of DOX, and although the presence of z-VAD-FMK clearly delayed death, most of the cells had died by the third day. Remarkably, in the presence of tested TC09 compounds, the cells continued to proliferate, similar to cells grown under normal conditions.

The long-term cell survivability conferred by TC09 compounds was again demonstrated when the cells were cultured for 1 week and the resulting cell colonies were visualized with crystal violet dye. The U2OS_Bim cells were all killed when DOX was added, even in the presence of z-VAD-FMK. In contrast, when a TC09 compound was present, the cell colonies grown in the media containing DOX were indistinguishable from the ones grown without DOX, demonstrating that TC09 compounds, unlike the caspase inhibitors that only delay cell death, are able to keep the cells alive and proliferating even after their mitochondrial apoptotic pathway has been activated.

TC09 Compounds are Effective in Protecting Neuronal Death in an Animal Model of Parkinson's Disease The remarkable cell-protection effect of TC09 compounds that we observed with our in vitro experiments prompted us to test if the compounds show similar effects in in vivo experiments. For this purpose, we chose a 6-OHDA-induced Parkinson's disease model in rat. The injection of the dopamine derivative 6-OHDA into the medial forebrain bundle region of the rat brain caused specific depletion of dopaminergic neurons in the substantial nigra region. The co-injection of increasing amounts of an exemplary TC09 compound (compound 27) showed dose-dependent protection of these neurons, while an inactive derivative, even at the highest injected concentration, did not show any protective effect. Treatment with the TC09 compound alone did not increase the area of the substantial nigra region, indicating that the effect of the TC09 compound occurred via cell protection, not from increased cell proliferation. The protective effect of the TC09 compound did not result from a chemical reaction that neutralized 6-OHDA, as similar amounts of 6-OHDA were detected in rat brain tissue regardless of the presence or absence of Compound A. The dopaminergic neurons protected by the TC09 compound appeared to be functional, as the Parkinson-like behavior of 6-OHDA-injected rats was corrected by the TC09 compound. We concluded that TC09 compounds can confer dose-dependent protection of the dopaminergic neurons and correct the neurological phenotype associated with the disease It is known that excessive apoptosis plays an important role in neurological disorders, and we established that TC09 compounds can confer a protective effect in a mouse model of Parkinson's disease. Here, we tested the potential therapeutic bioactivity of TC09 compounds in an ischemia model in rat. Following cerebral ischemia, it is known that BH3-only proteins are upregulated and activate the intrinsic apoptosis pathway and that caspase inhibitors can attenuate the volume of dead tissue in focal ischemia. For in vivo evaluation, a transient focal cerebral ischemia was induced by middle cerebral artery occlusion (MCAO) in rats. Injection of TC09 compound showed a dose-dependent protection effect; treatment reduced brain infarct volume after induction of focal cerebral ischemia, thereby demonstrating the application of TC09 compounds for neuron protection.

In conclusion, we have developed a unique series of irreversible apoptosis inhibitors based on an initial hit from high-throughput screening and SAR optimization, and improved the cellular activity to an $EC_{50}$ at the low-nanomolar level. These compounds bond covalently with the SDHB subunit of mitochondrial respiratory complex II and confer mitochondrial protection effects by stabilizing mitochondrial respiratory chain, maintaining the mitochondrial membrane potential, and inhibiting ROS generation. The compounds also show remarkable protection effect in transient focal cerebral ischemia, further demonstrating their application as novel therapies for excessive apoptosis related diseases.

Experimental Protocol:

High-Throughput Screening

A chemical library containing 200000 compounds was screened according to the following procedure: U2OS_Bim cells (a cell line in which the BH3-only protein Bim can be inducibly expressed by the addition of Doxycycline to the growth medium)[2] were plated in 384-well plates with 30 μl medium at a density of 500 cells per well. 16 hrs after plating, test compounds were transferred from stock plates to the assay plates with the cultured cells. Positive control (20 μM zVAD) and negative control (DMSO) were added to every plate. 1 hr after compound treatment, 0.1 ug/mL Doxycyclin (DOX) was added to induce the expression of the Bim protein. After 24 hrs, cell viability was determined by measuring the ATP levels using a Cell Titer-Glo kit (Promega, G7570) according to the manufacturer's instructions. Luminescence was recorded with a PerkinElmer EnSpire Multimode Plate Reader. Compounds that could rescue cell viability to a level above 50% were selected; these compounds were then screened a second time for assurance.

Immunostaining of Cytochrome c

U2OS_Bim cells were plated in Lab-Tek eight-chambered slides (Thermo Scientific). 24 hrs later, cells were treated with experimental compounds for one hour. Cell were washed by PBS for 10 min and fixed with 2% PFA for 30 min at room temperature. Following three additional washes in PBS, cells were incubated in PBS containing 0.1% Triton X-100 for 10 min. Cytochrome c antibody (diluted in 5% BSA in PBST) was incubated with the cells at 4° C. overnight. Cells were then washed three times with PBST and incubated with secondary antibody at room temperature for 1 h. Following three additional washes in PBS, the slides were covered and sealed and then examined with a Zeiss LSM 510 confocal microscope.

Apoptosis Inhibition Assay

U2OS_Bim or U2OS_tBid cells were plated at a density of 3000 cells per well in 96-well plates. 24 hrs later, cells were treated with experimental compounds, zVAD (positive control) and DMSO (Negative control) for one hour. The cells were then treated with 0.1 μg/mL DOX to trigger apoptosis. 24 hours after the addition of DOX, cell viability was determined by measuring the ATP levels using a Cell Titer-Glo kit. Cell survival rate was calculated.

Irreversibility Binding Assay

U2OS_Bim cells were plated at a density of 3000 cells per well in 96-well plates. 24 hrs later, duplicate sets of cells were treated with experimental compounds for 3 hrs. One subset of these cells were treated with 0.1 μg/mL DOX to trigger apoptosis. The remaining subset of cells was washed free of the experimental compound using warmed medium, 3 times, before being treated with 0.1 μg/mL DOX. 24 hours after DOX addition, cell viability was determined by measuring the ATP levels using a CellTiter-Glo kit. Cell survival rate was calculated. zVAD (20 μM) was used as a positive control.

TMRM Staining

U2OS_Bim cells were plated at a density of 3000 cells per well in 96-well optical plates. 24 hrs later, cells were treated with experimental compounds for one hour. The cells were then treated with 0.1 μg/mL DOX to trigger apoptosis. 4 hrs later, 50 nM TMRM was added to each well and incubated for 30 min. Cells were washed 3 times with warmed PBS buffer and examined with a Zeiss LSM 510 confocal microscope.

ROS Measurement

U2OS_Bim cells were plated at a density of 3000 cells per well in 96-well optical plate. 24 hrs later, cells were treated with experimental compounds for 2 hrs. The cells were then treated with 0.1 µg/mL DOX to trigger apoptosis. 4 hrs later, cells were washed 3 times with PBS and then incubated in PBS with 2 µM DCFH-DA for 30 min at 37° C. Cells were then washed twice with PBS and fluorescence was detected with a PerkinElmer EnSpire Multimode Plate Reader ($\lambda_{ex}$=485 nm and $\lambda_{em}$=525 nm). As a positive control, following the DCFH-DA incubation and PBS washing, 50 µM of $H_2O_2$ was added to untreated cells and followed by fluorescence analysis. Immediately after fluorescence detection, cell viability was determined by measuring the ATP levels using a CellTiter-Glo kit. Mean ROS levels were recorded as ROS fluorescence/cell viability, and the ratio of ROS increase was calculated. Data are represented as means±standard deviation of duplicates.

Click-Assisted, Activity-Based Protein Profiling

U2OS_Bim cells were treated with competitor compound 27 for 1 hr in arrange of concentration from 20 µM to 200 µM. Compound 27 was then washed off with PBS (3 washes), and of 20 µM compound 29 was added and incubated for 3 hrs. Cells were then lysed and the lysate was adjusted to a concentration of 1 mg/mL protein. Click reactions were performed with compound biotin-$N_3$ (N-(2-(2-(2-(2-azidoethoxy)ethoxy)ethoxy)ethyl)-5-((3aS,4S,6aR)-2-oxohexahydro-1H-thieno[3,4-d]imidazol-4-yl)pentanamide) (500 µM), TBTA (500 µM), $CuSO_4$ (1 mM), and sodium L-ascorbate (1 mM) for 1 hr at 37° C. Lysates were then precipitated using 5 volumes of methanol, washed 3 times with methanol, and then redissolved with 1 mL PBS buffer containing 0.2% SDS. 200 uL of streptavidin agrose was added to each sample. Samples were incubated for 2 hr at room temperature, centrifuged at 3000 rpm for 3 min, and then washed 3 times with PBS buffer. 30 ul 1× loading buffer was used for elution. Sample elutates were then used in Western blot detecting biotin and SDHB.

Cellular Fluorescence Staining

U2OS_Bim cells were plated on the optical plates. 24 hrs later, cells were treated with compound for 3 hrs and then incubated with Mitotracker Red CMXRos (50 nM) for 5 min. Cells were washed with PBS for 10 min and fixed with 2% PFA for 30 min at room temperature. Following another three additional washes in PBS, cells were examined with a Nikon A1-R confocal microscope using 488 nm and 561 nm lasers.

Transient Focal Cerebral Ischemia

Transient focal cerebral ischemia was induced by middle cerebral artery occlusion (MCAO) in rats as described previously, with slight modifications (Uluc, Miranpuri et al. 2011). Briefly, male Sprague Dawley rats (weight 280-320 g) were anesthetized with 2% isoflurane. The left common, external, and internal carotid arteries (CCA, ECA, and ICA) were exposed. A 4-0 monofilament nylon suture with a silicon-coated tip was introduced through an incision of the ECA into the ICA to occlude the origin of the MCA for 1 h. Compound was injected into the left striatum after the suture insertion, at the following coordinates in reference to the bregma: AP, 0.4; ML, 3.0; DV, −5.0 mm (from the dura). Solution was injected at a rate of 1 µL/minute using a Hamilton syringe. The syringe was left in place for 5 min before being slowly retracted. Animals were sacrificed 24 h after the MCAO. Brains were removed and sliced into sections of 2 mm thickness. Infarct size was examined via staining with 1.5% 2, 3, 5-triphenyltetrazolium chloride.

Representative, Exemplary Compounds

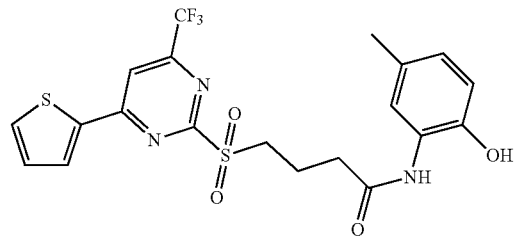 [SMILES: Cc1ccc(O)c(NC(=O)CCCS(=O)(=O)c2nc(-c3cccs3)cc(C(F)(F)F)n2)c1]

Hit.

TABLE 4a

SAR optimization:

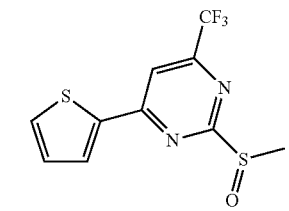 [SMILES: CS(=O)c1nc(-c2cccs2)cc(C(F)(F)F)n1]

1

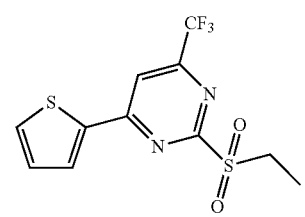 [SMILES: CCS(=O)(=O)c1nc(-c2cccs2)cc(C(F)(F)F)n1]

2

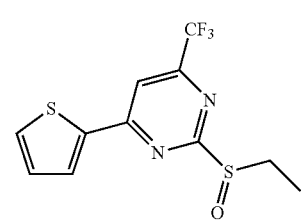 [SMILES: CCS(=O)c1nc(-c2cccs2)cc(C(F)(F)F)n1]

3

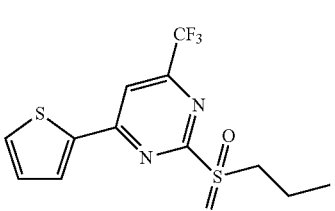

4

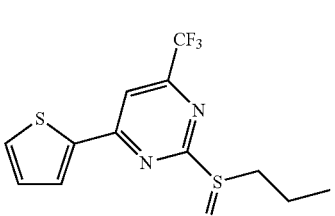

5

TABLE 4a-continued
SAR optimization:
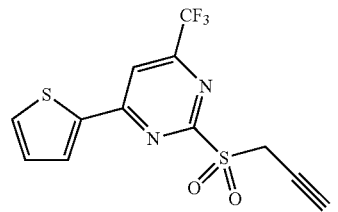 [SMILES: C#CCS(=O)(=O)c1nc(-c2cccs2)cc(C(F)(F)F)n1] 6
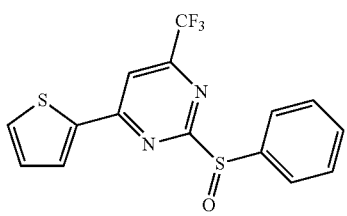 [SMILES: O=S(c1ccccc1)c1nc(-c2cccs2)cc(C(F)(F)F)n1] 7
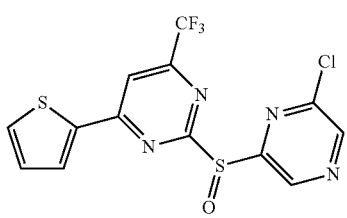 [SMILES: O=S(c1cncc(Cl)n1)c1nc(-c2cccs2)cc(C(F)(F)F)n1] 8
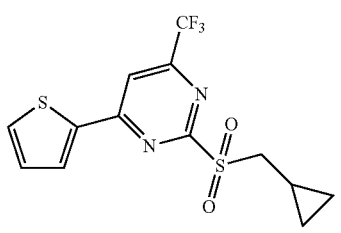 [SMILES: O=S(=O)(CC1CC1)c1nc(-c2cccs2)cc(C(F)(F)F)n1] 9
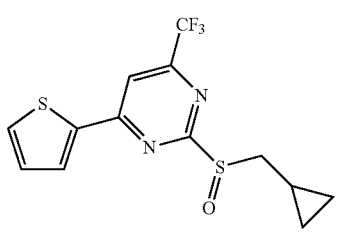 [SMILES: O=S(CC1CC1)c1nc(-c2cccs2)cc(C(F)(F)F)n1] 10
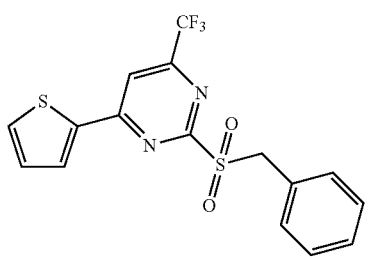 [SMILES: O=S(=O)(Cc1ccccc1)c1nc(-c2cccs2)cc(C(F)(F)F)n1] 11
TABLE 4a-continued
SAR optimization:
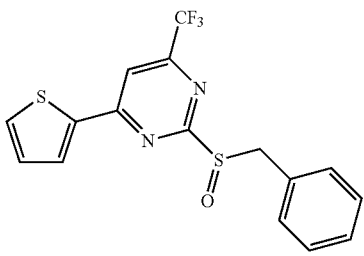 [SMILES: O=S(Cc1ccccc1)c1nc(-c2cccs2)cc(C(F)(F)F)n1] 12
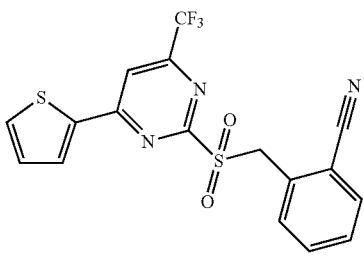 [SMILES: N#Cc1ccccc1CS(=O)(=O)c1nc(-c2cccs2)cc(C(F)(F)F)n1] 13
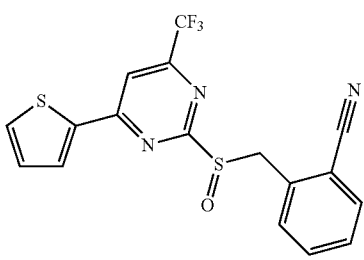 [SMILES: N#Cc1ccccc1CS(=O)c1nc(-c2cccs2)cc(C(F)(F)F)n1] 14
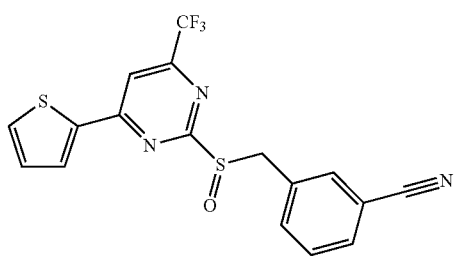 [SMILES: N#Cc1cccc(CS(=O)c2nc(-c3cccs3)cc(C(F)(F)F)n2)c1] 15
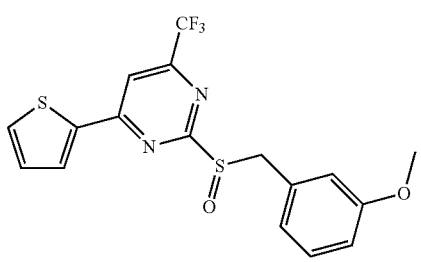 [SMILES: COc1cccc(CS(=O)c2nc(-c3cccs3)cc(C(F)(F)F)n2)c1] 16
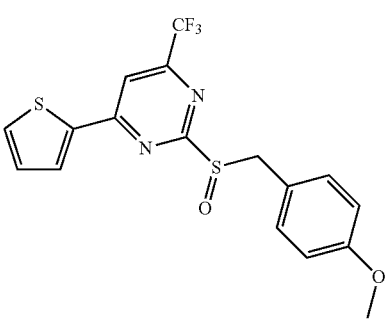 [SMILES: COc1ccc(CS(=O)c2nc(-c3cccs3)cc(C(F)(F)F)n2)cc1] 17

TABLE 4a-continued
SAR optimization:
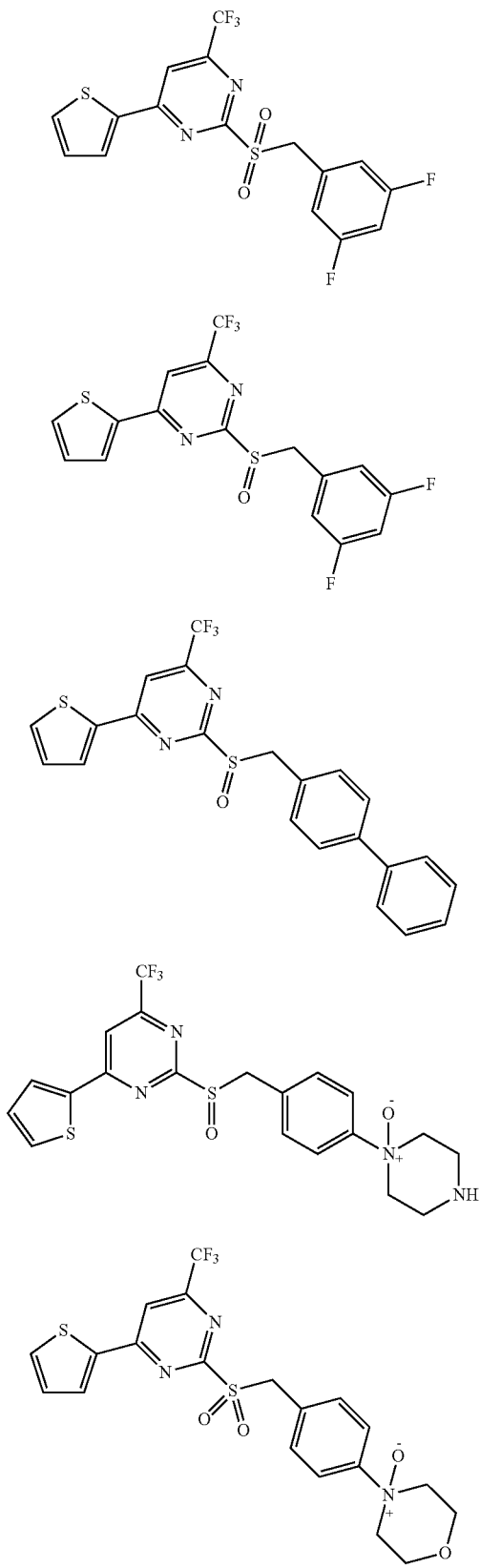
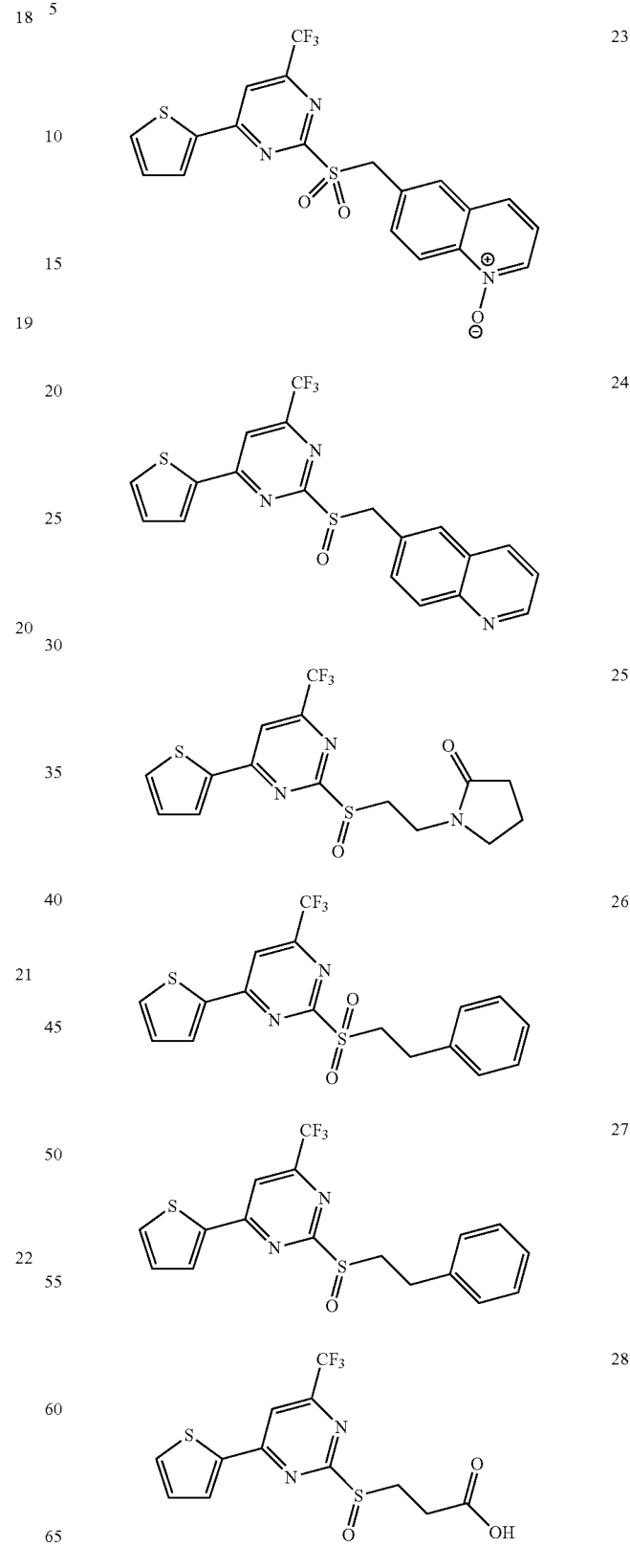

TABLE 4a-continued

SAR optimization:

29. 4-(thiophen-2-yl)-6-(trifluoromethyl)pyrimidin-2-yl sulfonyl propanoate ethyl ester 30. 4-(thiophen-2-yl)-6-(trifluoromethyl)pyrimidin-2-yl sulfinyl propanoate ethyl ester 31. methyl 4-((4-(thiophen-2-yl)-6-(trifluoromethyl)pyrimidin-2-yl)sulfonyl)butanoate 32. methyl 4-((4-(thiophen-2-yl)-6-(trifluoromethyl)pyrimidin-2-yl)sulfinyl)butanoate 33. 4-chloro-6-(thiophen-2-yl)-2-(methylsulfinyl)pyrimidine 34. 4-methyl-6-(thiophen-2-yl)-2-(methylsulfonyl)pyrimidine 35. 4-ethynyl-6-(thiophen-2-yl)-2-(methylsulfonyl)pyrimidine 36. 2-(methylsulfonyl)-4-(1H-pyrazol-1-yl)-6-(thiophen-2-yl)pyrimidine 37. 2-(methylsulfonyl)-4,6-di(thiophen-2-yl)pyrimidine 38. 1-(2-(methylsulfonyl)-6-(thiophen-2-yl)pyrimidin-4-yl)pyrrolidin-2-one 39. 1-(2-(methylsulfonyl)-6-(thiophen-2-yl)pyrimidin-4-yl)pyridin-2(1H)-one 40. 4-morpholino-2-(methylsulfonyl)-6-(thiophen-2-yl)pyrimidine 41. 4-azido-2-(methylsulfonyl)-6-(thiophen-2-yl)pyrimidine TABLE 4a-continued
SAR optimization:
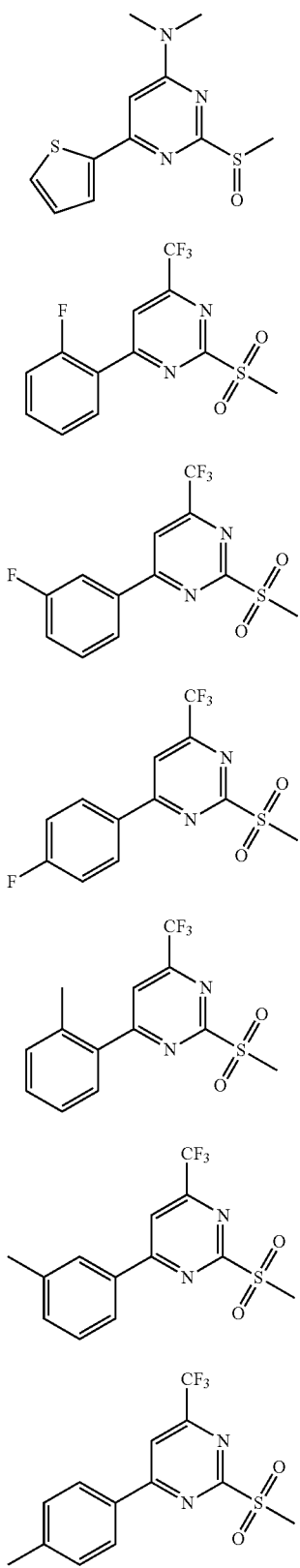
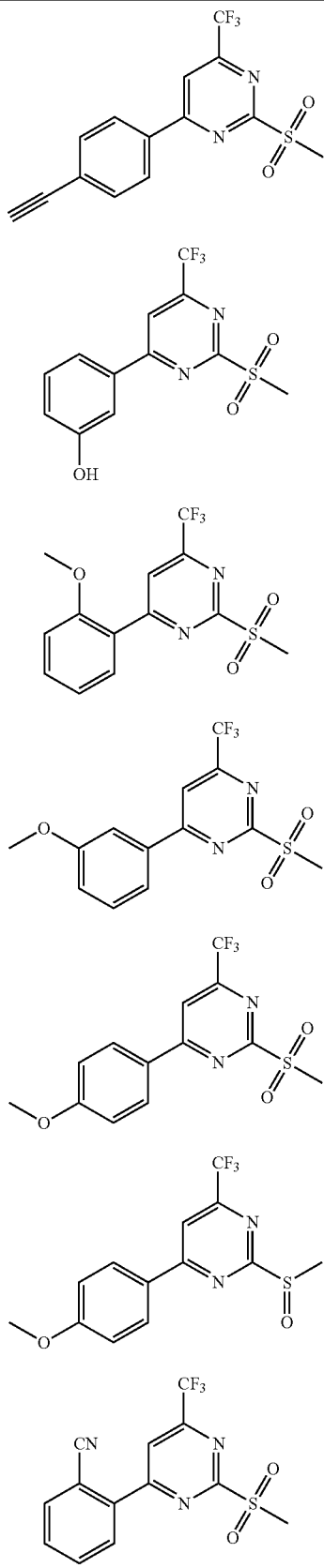

TABLE 4a-continued
SAR optimization:
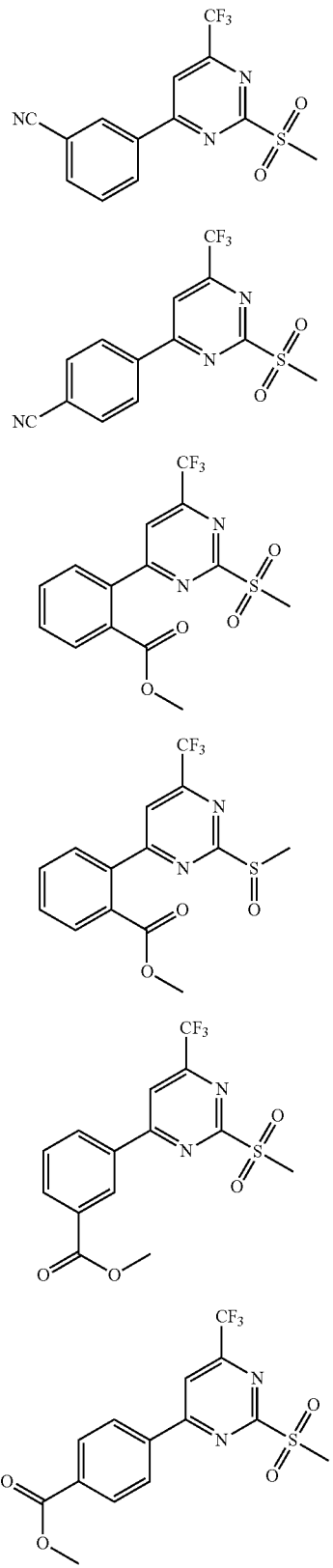
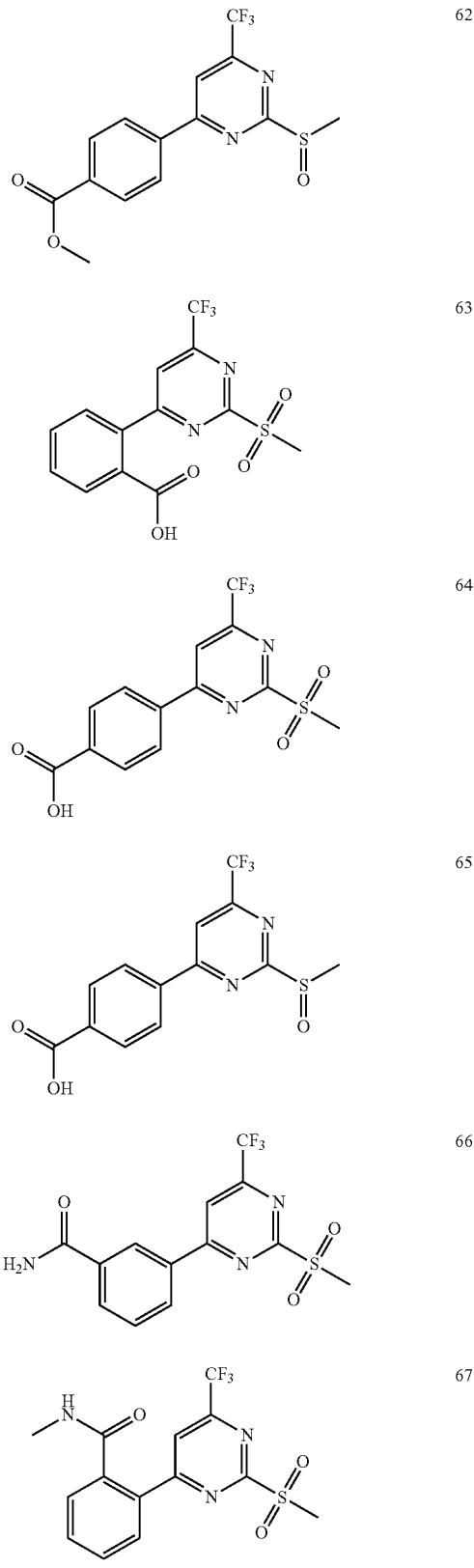

TABLE 4a-continued
SAR optimization:
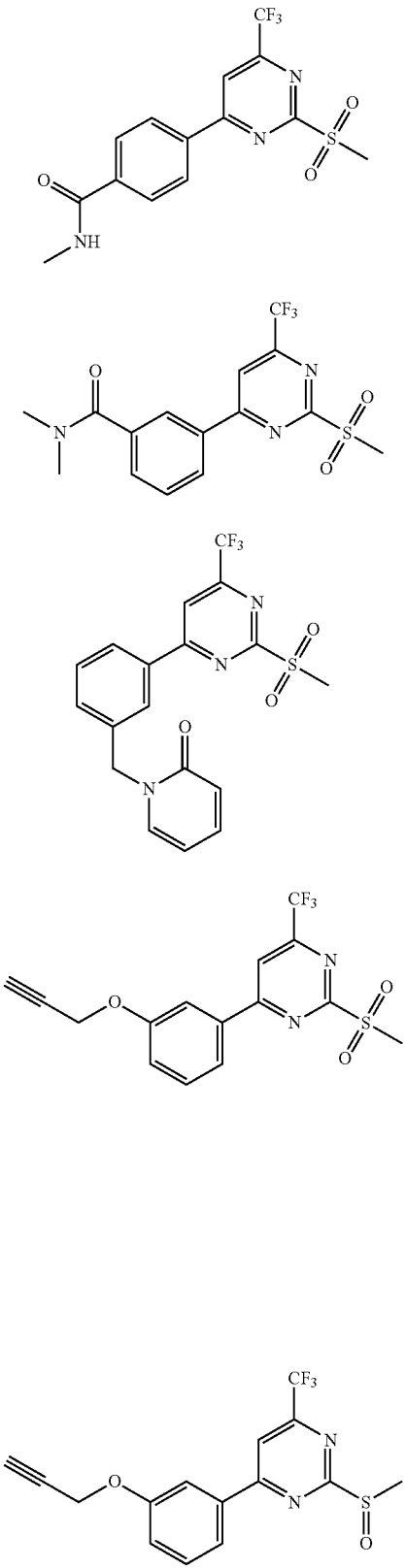
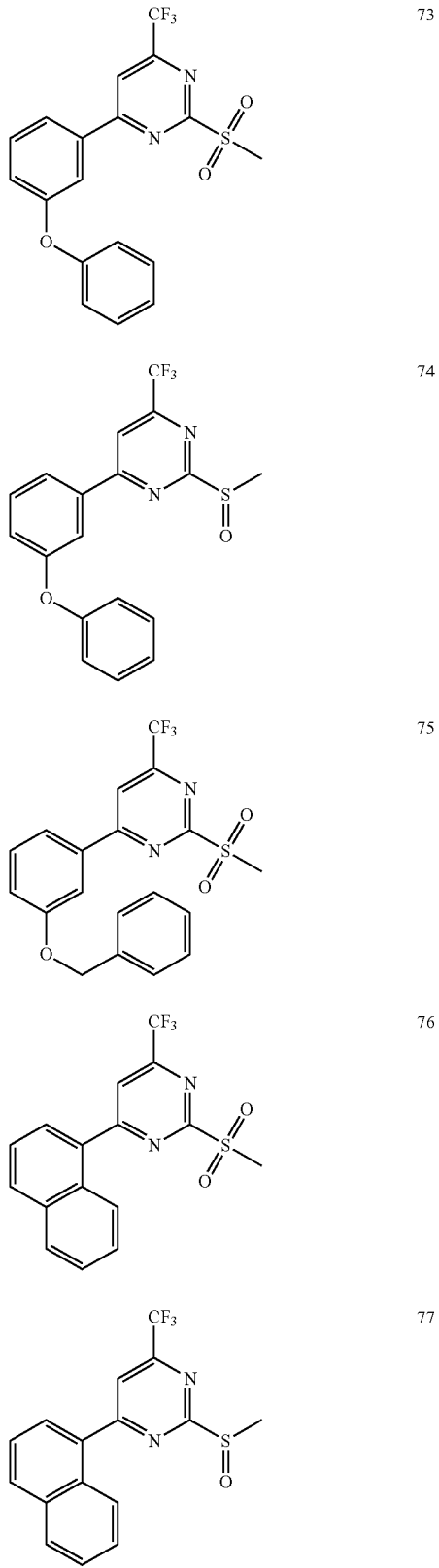

TABLE 4a-continued

SAR optimization:

| # | Structure |
|---|---|
| 78 | 4-(2-methoxypyridin-3-yl)-6-(trifluoromethyl)-2-(methylsulfonyl)pyrimidine |
| 79 | 4-(2-methoxypyridin-3-yl)-6-(trifluoromethyl)-2-(methylsulfinyl)pyrimidine |
| 80 | 3-[2-(methylsulfonyl)-6-(trifluoromethyl)pyrimidin-4-yl]pyridin-2(1H)-one |
| 81 | 3-[2-(methylsulfinyl)-6-(trifluoromethyl)pyrimidin-4-yl]pyridin-2(1H)-one |
| 82 | 4-morpholino-2-(methylsulfinyl)-6-(trifluoromethyl)pyrimidine |
| 83 | 4-(1H-pyrazol-1-yl)-2-(methylsulfonyl)-6-(trifluoromethyl)pyrimidine |
| 84 | 4-(1H-pyrrol-2-yl)-2-(methylsulfonyl)-6-(trifluoromethyl)pyrimidine |
| 85 | 4-[1-(3,4-dimethoxybenzyl)-1H-pyrrol-2-yl]-2-(methylsulfonyl)-6-(trifluoromethyl)pyrimidine |
| 86 | 4-[1-(3,4-dimethoxybenzyl)-1H-pyrrol-2-yl]-2-(methylsulfinyl)-6-(trifluoromethyl)pyrimidine |
| 87 | 4-(1H-pyrrol-3-yl)-2-(methylsulfonyl)-6-(trifluoromethyl)pyrimidine |
| 88 | 4-(1H-pyrrol-3-yl)-2-(methylsulfinyl)-6-(trifluoromethyl)pyrimidine |

TABLE 4a-continued

SAR optimization:

TABLE 4a-continued

SAR optimization:

| # | Structure |
|---|---|
| 97 | 4-(CF3)-6-(1-(3-cyanobenzyl)-1H-pyrrol-3-yl)-2-(methylsulfonyl)pyrimidine |
| 98 | 4-(CF3)-6-(1-(3-cyanobenzyl)-1H-pyrrol-3-yl)-2-(methylsulfinyl)pyrimidine |
| 99 | 5-(6-(CF3)-2-(methylsulfonyl)pyrimidin-4-yl)pyridin-2(1H)-one |
| 100 | 5-(6-(CF3)-2-(methylsulfonyl)pyrimidin-4-yl)-1-(prop-2-yn-1-yl)pyridin-2(1H)-one |
| 101 | 5-(6-(CF3)-2-(methylsulfinyl)pyrimidin-4-yl)-1-(prop-2-yn-1-yl)pyridin-2(1H)-one |
| 102 | 1-(2-azidoethyl)-5-(6-(CF3)-2-(methylsulfonyl)pyrimidin-4-yl)pyridin-2(1H)-one |
| 103 | 1-benzyl-5-(6-(CF3)-2-(methylsulfonyl)pyrimidin-4-yl)pyridin-2(1H)-one |
| 104 | 1-(2-chlorobenzyl)-5-(6-(CF3)-2-(methylsulfonyl)pyrimidin-4-yl)pyridin-2(1H)-one |
| 105 | 1-(3-chlorobenzyl)-5-(6-(CF3)-2-(methylsulfonyl)pyrimidin-4-yl)pyridin-2(1H)-one |

TABLE 4a-continued
SAR optimization:
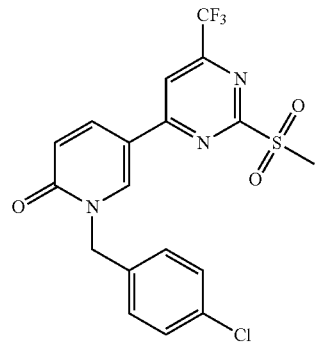 [SMILES: CS(=O)(=O)c1nc(-c2ccc(=O)n(Cc3ccc(Cl)cc3)c2)cc(C(F)(F)F)n1]
106
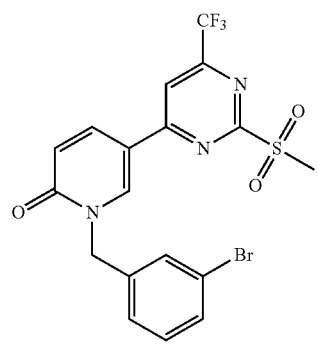 [SMILES: CS(=O)(=O)c1nc(-c2ccc(=O)n(Cc3cccc(Br)c3)c2)cc(C(F)(F)F)n1]
107
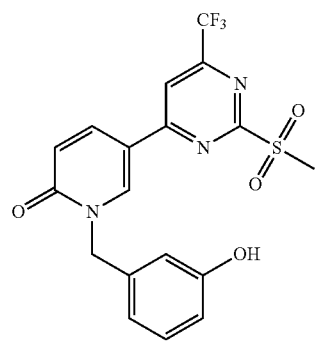 [SMILES: CS(=O)(=O)c1nc(-c2ccc(=O)n(Cc3cccc(O)c3)c2)cc(C(F)(F)F)n1]
108
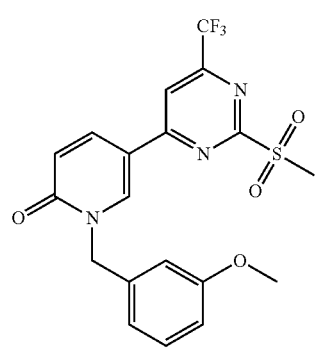 [SMILES: COc1cccc(Cn2cc(-c3cc(C(F)(F)F)nc(S(C)(=O)=O)n3)ccc2=O)c1]
109
TABLE 4a-continued
SAR optimization:
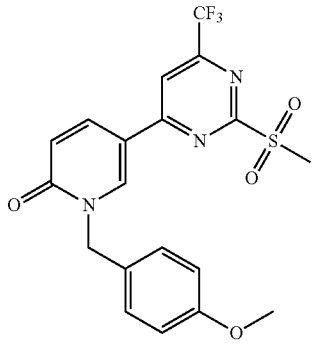 [SMILES: COc1ccc(Cn2cc(-c3cc(C(F)(F)F)nc(S(C)(=O)=O)n3)ccc2=O)cc1]
110
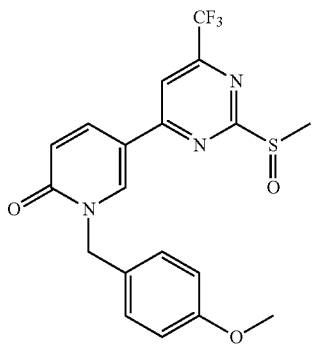 [SMILES: COc1ccc(Cn2cc(-c3cc(C(F)(F)F)nc(S(C)=O)n3)ccc2=O)cc1]
111
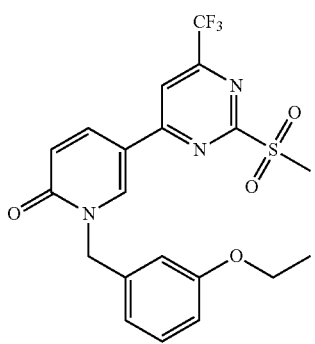 [SMILES: CCOc1cccc(Cn2cc(-c3cc(C(F)(F)F)nc(S(C)(=O)=O)n3)ccc2=O)c1]
112
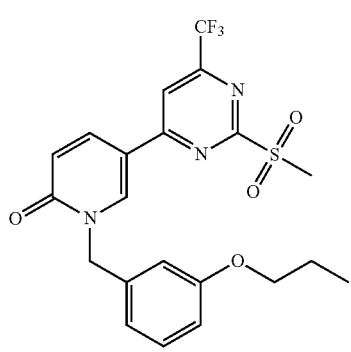 [SMILES: CCCOc1cccc(Cn2cc(-c3cc(C(F)(F)F)nc(S(C)(=O)=O)n3)ccc2=O)c1]
113

TABLE 4a-continued
SAR optimization:
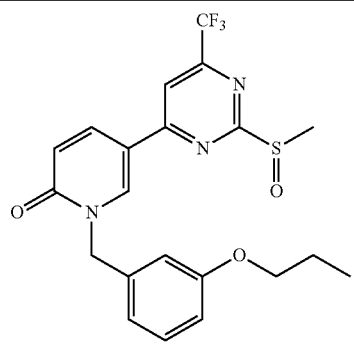 114
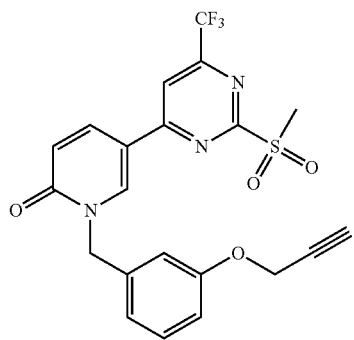 [SMILES: C#CCOc1cccc(Cn2cc(-c3cc(C(F)(F)F)nc(S(C)(=O)=O)n3)ccc2=O)c1] 115
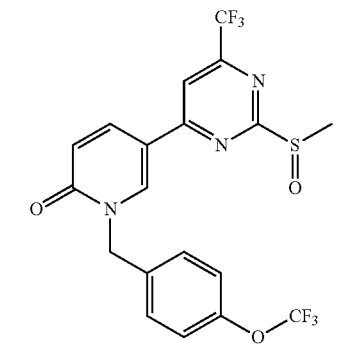 [SMILES: CS(=O)c1nc(-c2ccc(=O)n(Cc3ccc(OC(F)(F)F)cc3)c2)cc(C(F)(F)F)n1] 116
 117
TABLE 4a-continued
SAR optimization:
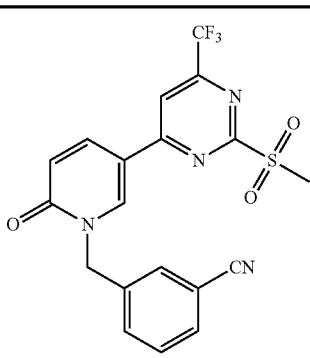 118
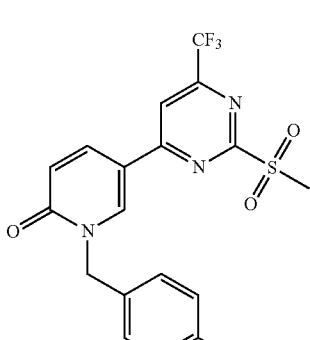 119
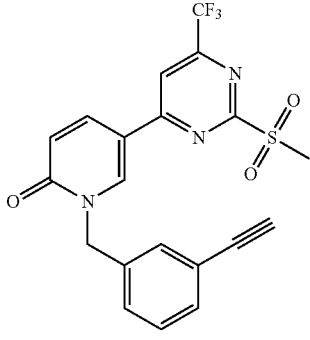 [SMILES: C#Cc1cccc(Cn2cc(-c3cc(C(F)(F)F)nc(S(C)(=O)=O)n3)ccc2=O)c1] 120
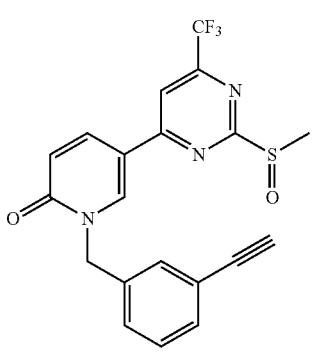 [SMILES: C#Cc1cccc(Cn2cc(-c3cc(C(F)(F)F)nc(S(C)=O)n3)ccc2=O)c1] 121

TABLE 4a-continued
SAR optimization:
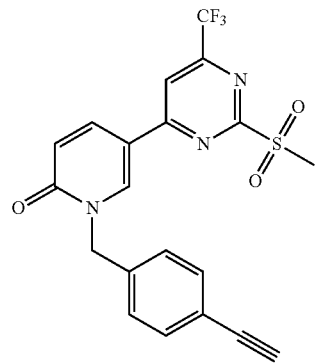 [SMILES: C#Cc1ccc(Cn2cc(-c3cc(C(F)(F)F)nc(S(C)(=O)=O)n3)ccc2=O)cc1] 122
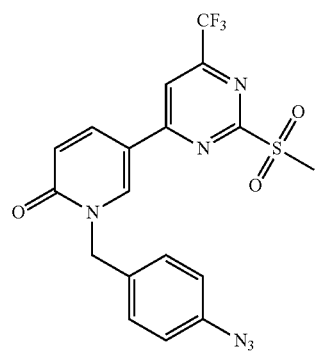 [SMILES: CS(=O)(=O)c1nc(-c2ccc(=O)n(Cc3ccc(N=[N+]=[N-])cc3)c2)cc(C(F)(F)F)n1] 123
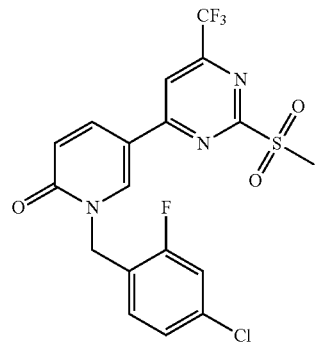 [SMILES: CS(=O)(=O)c1nc(-c2ccc(=O)n(Cc3ccc(Cl)cc3F)c2)cc(C(F)(F)F)n1] 124
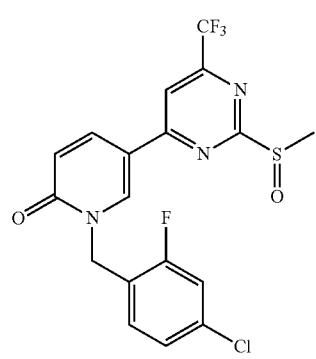 [SMILES: CS(=O)c1nc(-c2ccc(=O)n(Cc3ccc(Cl)cc3F)c2)cc(C(F)(F)F)n1] 125
TABLE 4a-continued
SAR optimization:
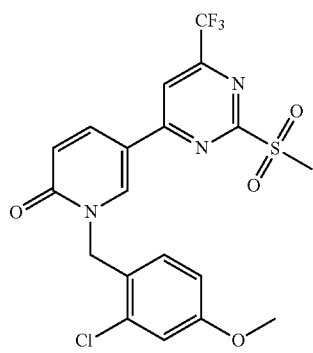 [SMILES: COc1ccc(Cn2cc(-c3cc(C(F)(F)F)nc(S(C)(=O)=O)n3)ccc2=O)c(Cl)c1] 126
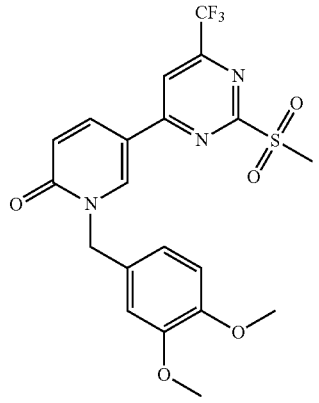 [SMILES: COc1ccc(Cn2cc(-c3cc(C(F)(F)F)nc(S(C)(=O)=O)n3)ccc2=O)cc1OC] 127
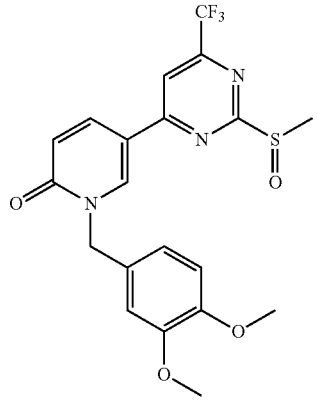 [SMILES: COc1ccc(Cn2cc(-c3cc(C(F)(F)F)nc(S(C)=O)n3)ccc2=O)cc1OC] 128
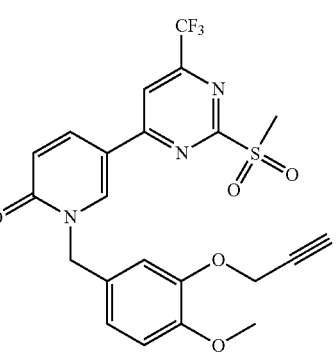 129

TABLE 4a-continued
SAR optimization:
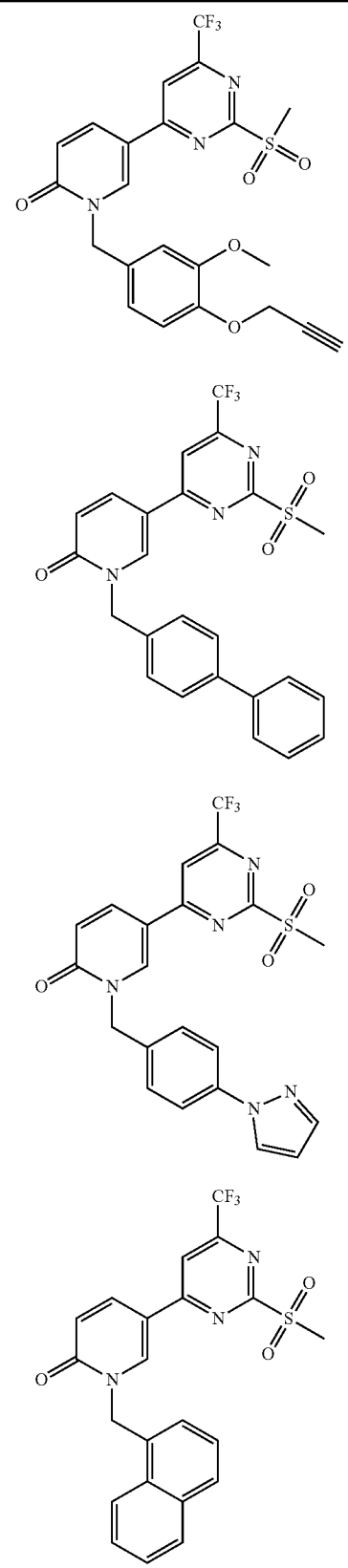
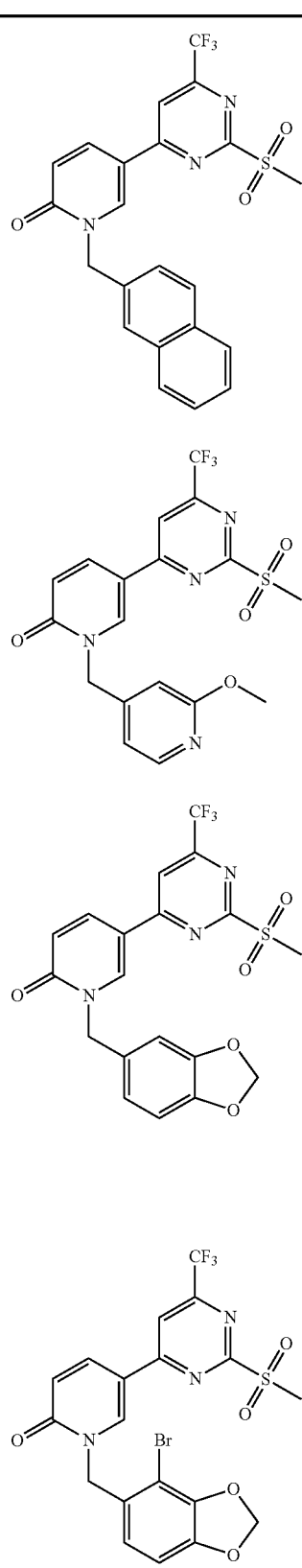

TABLE 4a-continued
SAR optimization:
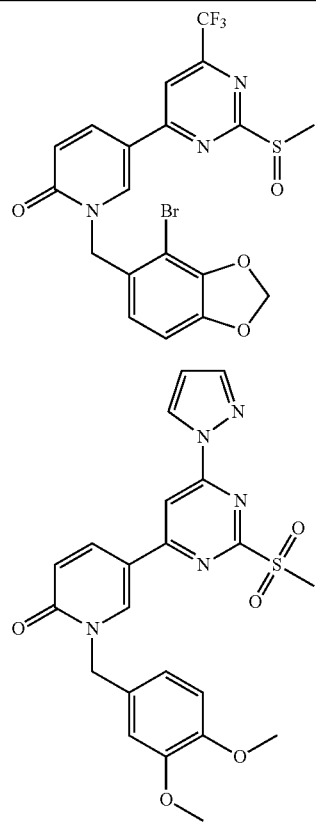
138
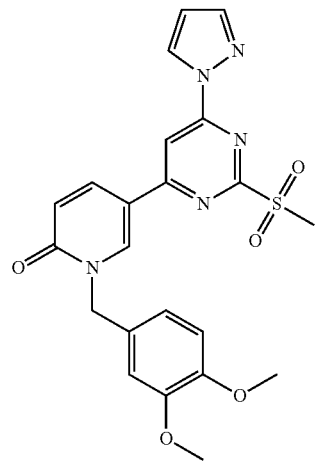 [SMILES: COc1ccc(Cn2cc(-c3cc(-n4cccn4)nc(S(C)(=O)=O)n3)ccc2=O)cc1OC]
139
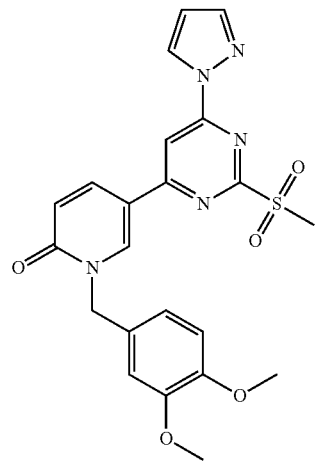 [SMILES: COc1ccc(Cn2cc(-c3cc(-n4cccn4)nc(S(C)(=O)=O)n3)ccc2=O)cc1OC]
140
TABLE 4a-continued
SAR optimization:
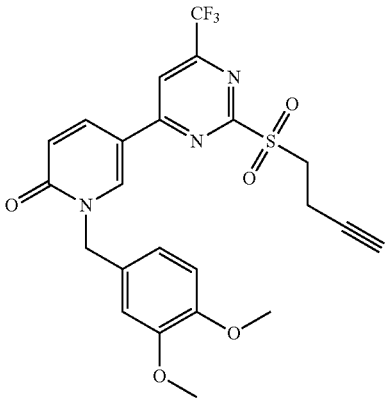 [SMILES: C#CCCS(=O)(=O)c1nc(-c2ccc(=O)n(Cc3ccc(OC)c(OC)c3)c2)cc(C(F)(F)F)n1]
141
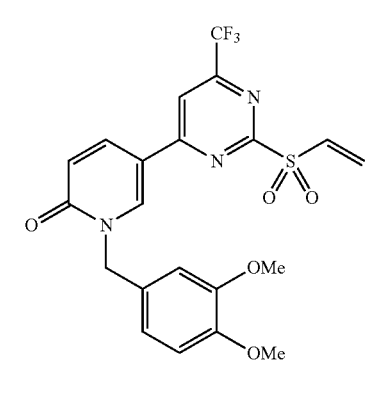 [SMILES: C=CS(=O)(=O)c1nc(-c2ccc(=O)n(Cc3ccc(OC)c(OC)c3)c2)cc(C(F)(F)F)n1]
142
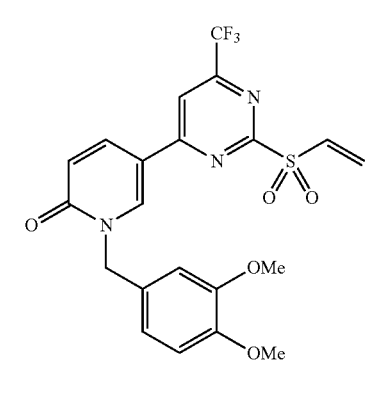 [SMILES: C=CS(=O)(=O)c1nc(-c2ccc(=O)n(Cc3ccc(OC)c(OC)c3)c2)cc(C(F)(F)F)n1]
143
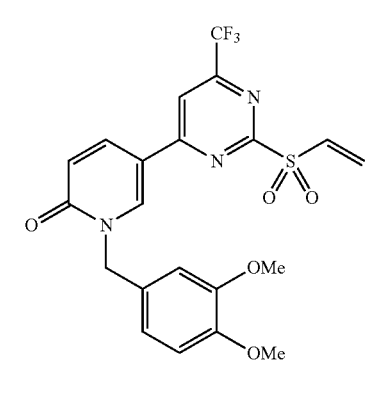 [SMILES: C=CS(=O)(=O)c1nc(-c2ccc(=O)n(Cc3ccc(OC)c(OC)c3)c2)cc(C(F)(F)F)n1]
144

TABLE 4a-continued
SAR optimization:
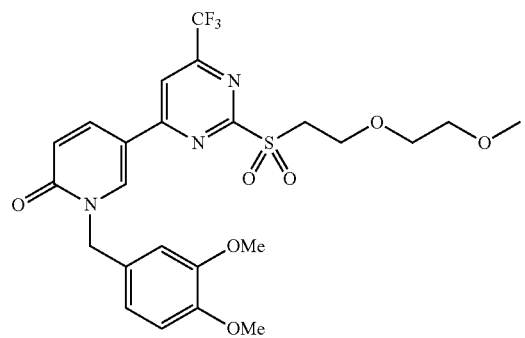 [SMILES: COCCOCCS(=O)(=O)c1nc(-c2ccc(=O)n(Cc3ccc(OC)c(OC)c3)c2)cc(C(F)(F)F)n1] 145
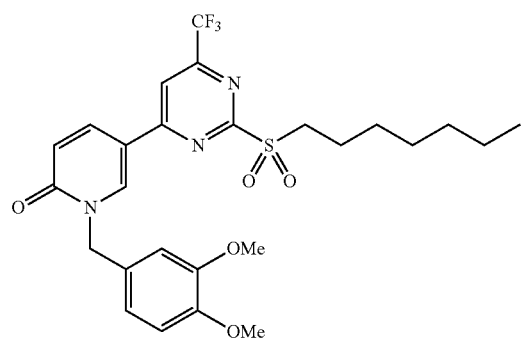 [SMILES: CCCCCCCS(=O)(=O)c1nc(-c2ccc(=O)n(Cc3ccc(OC)c(OC)c3)c2)cc(C(F)(F)F)n1] 146
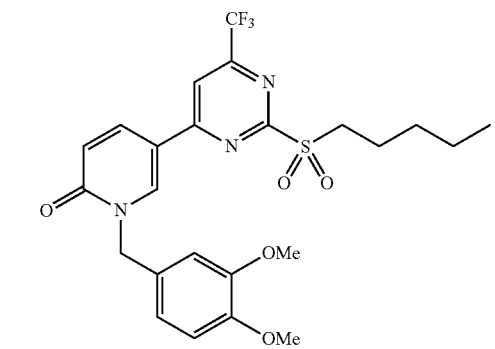 [SMILES: CCCCCS(=O)(=O)c1nc(-c2ccc(=O)n(Cc3ccc(OC)c(OC)c3)c2)cc(C(F)(F)F)n1] 147
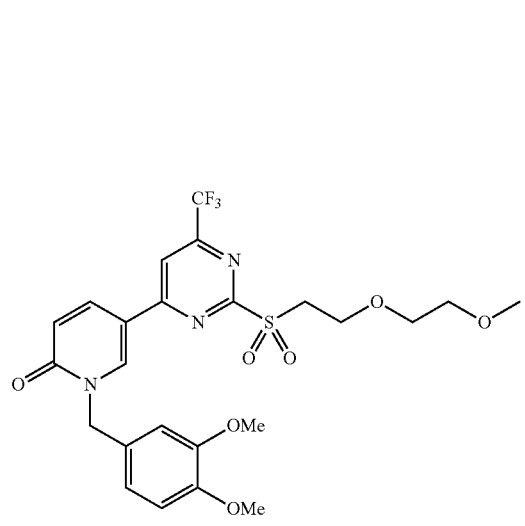 [SMILES: COCCOCCS(=O)(=O)c1nc(-c2ccc(=O)n(Cc3ccc(OC)c(OC)c3)c2)cc(C(F)(F)F)n1] 148
TABLE 4a-continued
SAR optimization:
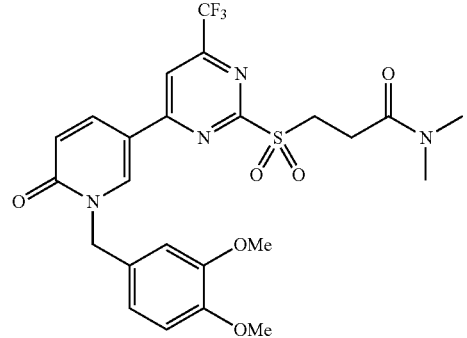 [SMILES: COc1ccc(Cn2cc(-c3cc(C(F)(F)F)nc(S(=O)(=O)CCC(=O)N(C)C)n3)ccc2=O)cc1OC] 149
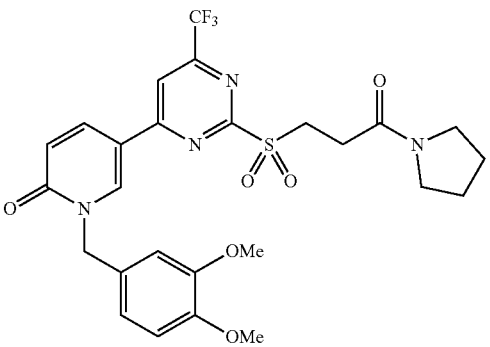 [SMILES: COc1ccc(Cn2cc(-c3cc(C(F)(F)F)nc(S(=O)(=O)CCC(=O)N4CCCC4)n3)ccc2=O)cc1OC] 150
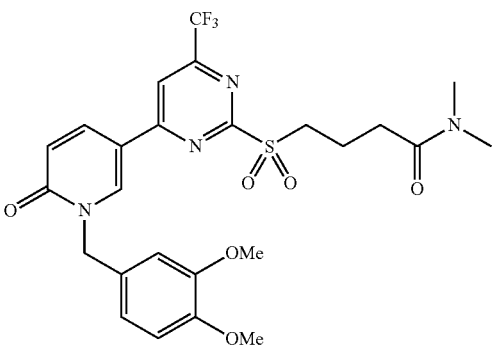 [SMILES: COc1ccc(Cn2cc(-c3cc(C(F)(F)F)nc(S(=O)(=O)CCCC(=O)N(C)C)n3)ccc2=O)cc1OC] 151
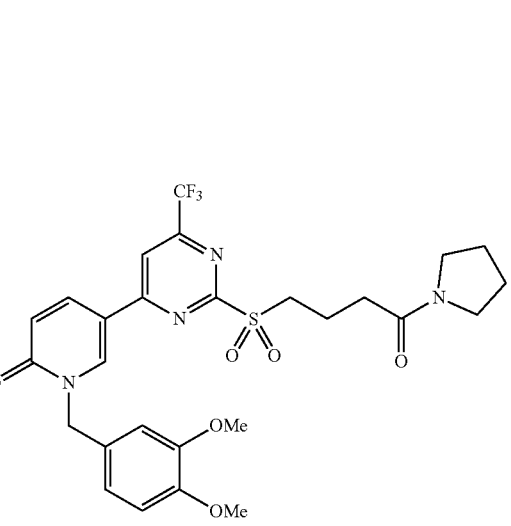 152

TABLE 4a-continued
SAR optimization:
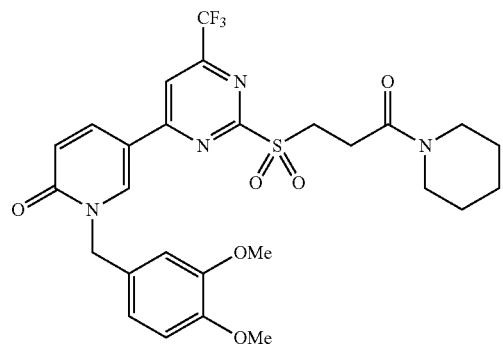 [SMILES: COc1ccc(Cn2cc(-c3cc(C(F)(F)F)nc(S(=O)(=O)CCC(=O)N4CCCCC4)n3)ccc2=O)cc1OC] 153
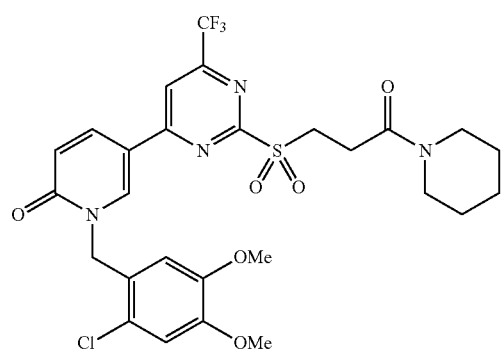 [SMILES: COc1cc(Cl)c(Cn2cc(-c3cc(C(F)(F)F)nc(S(=O)(=O)CCC(=O)N4CCCCC4)n3)ccc2=O)cc1OC] 154
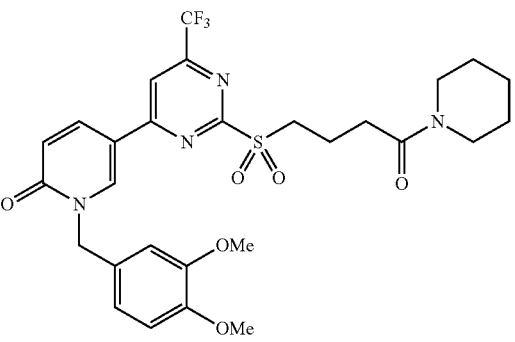 [SMILES: COc1ccc(Cn2cc(-c3cc(C(F)(F)F)nc(S(=O)(=O)CCCC(=O)N4CCCCC4)n3)ccc2=O)cc1OC] 155
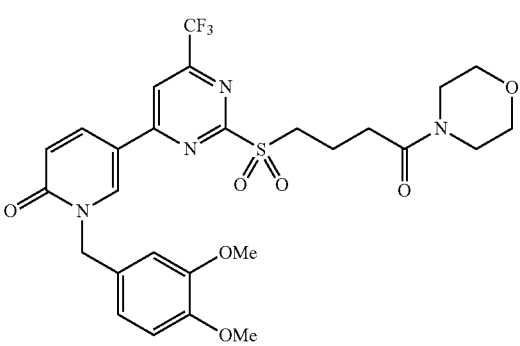 [SMILES: COc1ccc(Cn2cc(-c3cc(C(F)(F)F)nc(S(=O)(=O)CCCC(=O)N4CCOCC4)n3)ccc2=O)cc1OC] 156
TABLE 4a-continued
SAR optimization:
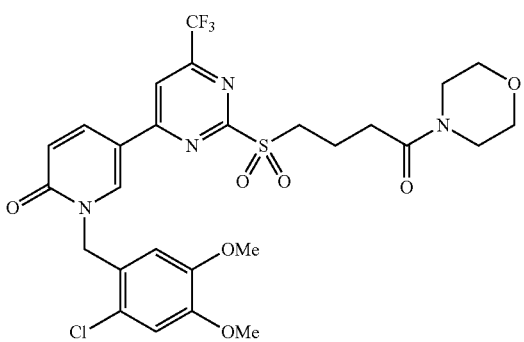 [SMILES: COc1cc(Cl)c(Cn2cc(-c3cc(C(F)(F)F)nc(S(=O)(=O)CCCC(=O)N4CCOCC4)n3)ccc2=O)cc1OC] 157
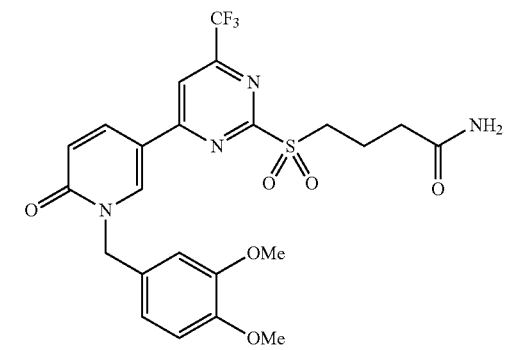 [SMILES: COc1ccc(Cn2cc(-c3cc(C(F)(F)F)nc(S(=O)(=O)CCCC(N)=O)n3)ccc2=O)cc1OC] 158
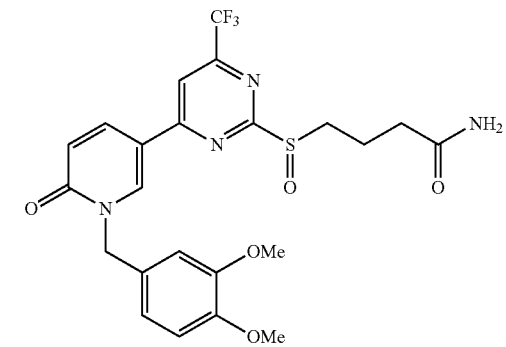 [SMILES: COc1ccc(Cn2cc(-c3cc(C(F)(F)F)nc(S(=O)CCCC(N)=O)n3)ccc2=O)cc1OC] 159
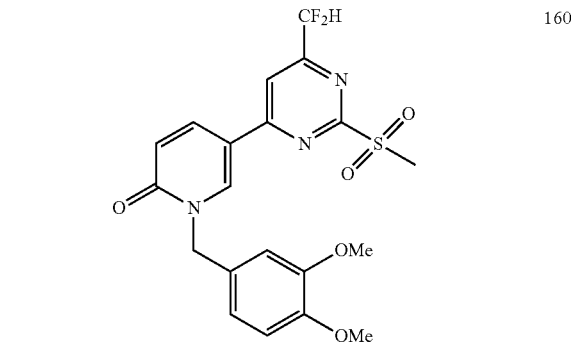 160

TABLE 4a-continued
SAR optimization:
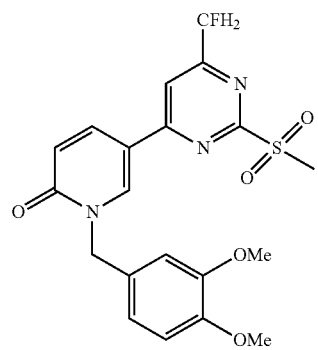 161
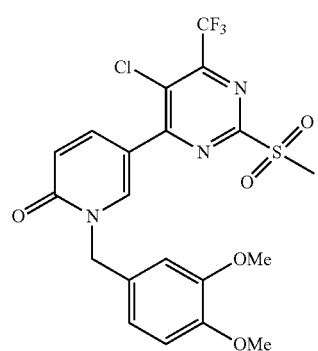 [SMILES: COc1ccc(Cn2cc(-c3nc(S(C)(=O)=O)nc(C(F)(F)F)c3Cl)ccc2=O)cc1OC] 162
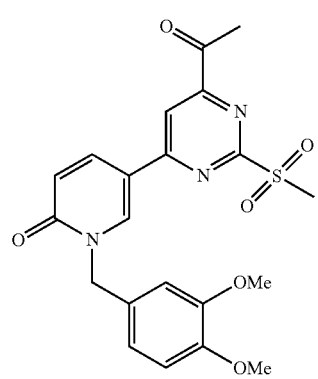 [SMILES: COc1ccc(Cn2cc(-c3cc(C(C)=O)nc(S(C)(=O)=O)n3)ccc2=O)cc1OC] 163
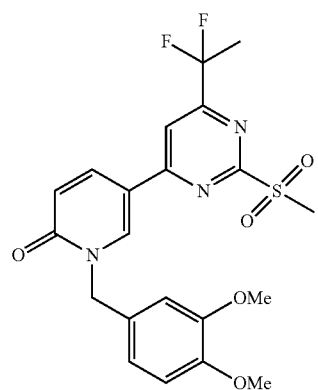 [SMILES: COc1ccc(Cn2cc(-c3cc(C(C)(F)F)nc(S(C)(=O)=O)n3)ccc2=O)cc1OC] 164
TABLE 4a-continued
SAR optimization:
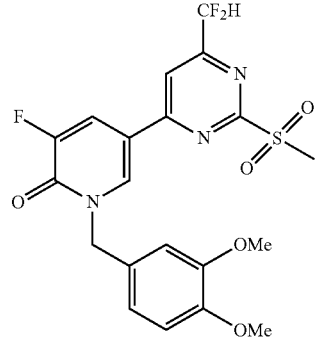 [SMILES: COc1ccc(Cn2cc(-c3cc(C(F)F)nc(S(C)(=O)=O)n3)cc(F)c2=O)cc1OC] 165
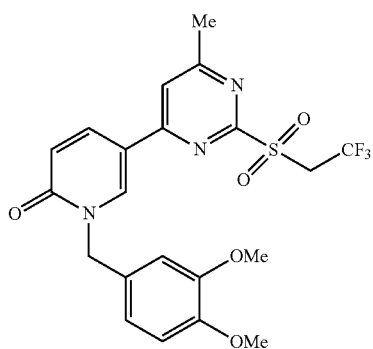 [SMILES: COc1ccc(Cn2cc(-c3cc(C)nc(S(=O)(=O)CC(F)(F)F)n3)ccc2=O)cc1OC] 166
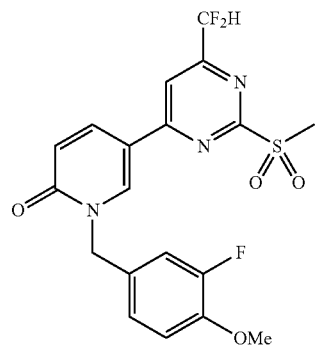 [SMILES: COc1ccc(Cn2cc(-c3cc(C(F)F)nc(S(C)(=O)=O)n3)ccc2=O)cc1F] 167
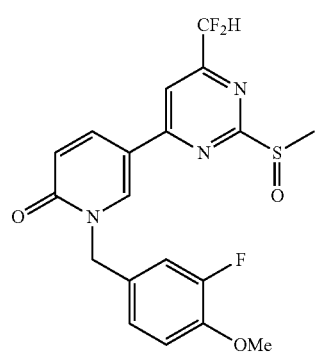 [SMILES: COc1ccc(Cn2cc(-c3cc(C(F)F)nc(S(C)=O)n3)ccc2=O)cc1F] 168

TABLE 4a-continued
SAR optimization:
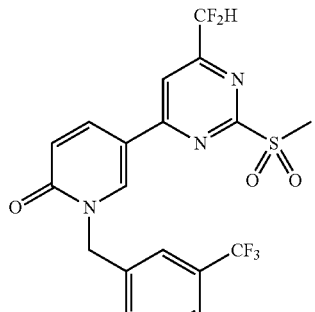 169
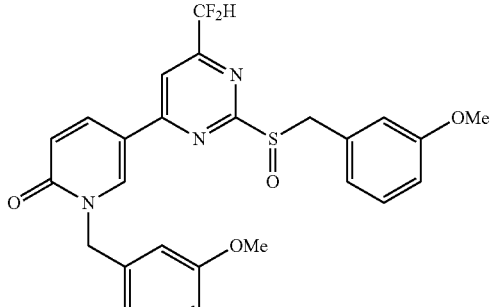 173
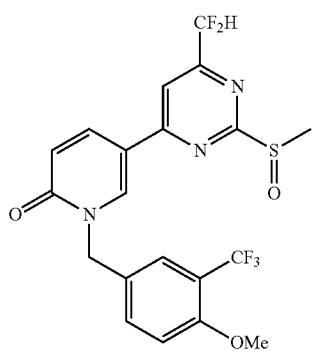 [SMILES: COc1ccc(Cn2cc(-c3cc(C(F)F)nc(S(C)=O)n3)ccc2=O)cc1C(F)(F)F] 170
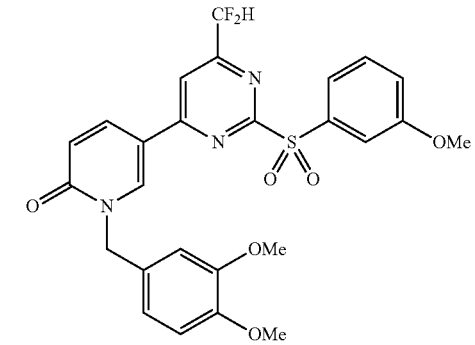 174
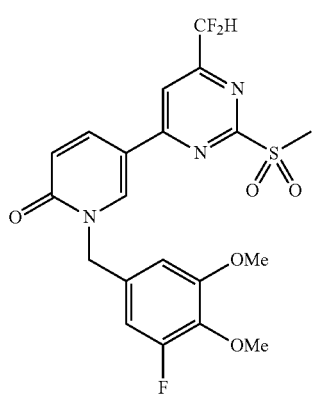 [SMILES: COc1cc(Cn2cc(-c3cc(C(F)F)nc(S(C)(=O)=O)n3)ccc2=O)cc(F)c1OC] 171
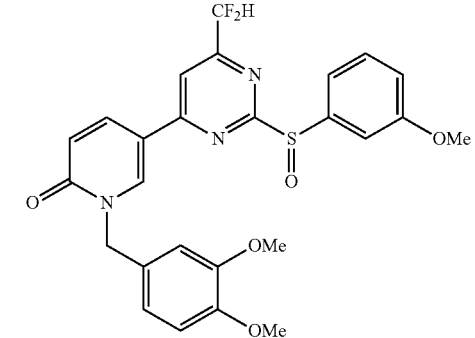 175
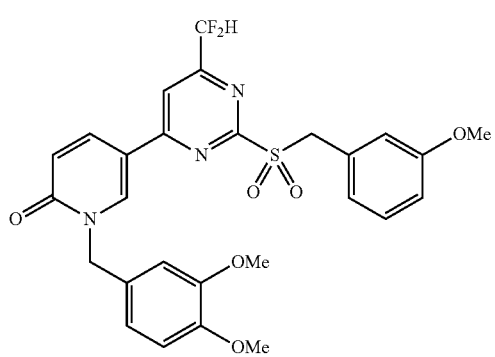 [SMILES: COc1cccc(CS(=O)(=O)c2nc(-c3ccc(=O)n(Cc4ccc(OC)c(OC)c4)c3)cc(C(F)F)n2)c1] 172
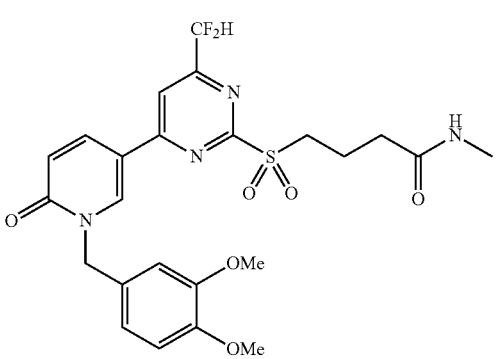 [SMILES: CNC(=O)CCCS(=O)(=O)c1nc(-c2ccc(=O)n(Cc3ccc(OC)c(OC)c3)c2)cc(C(F)F)n1] 176

TABLE 4a-continued
SAR optimization:
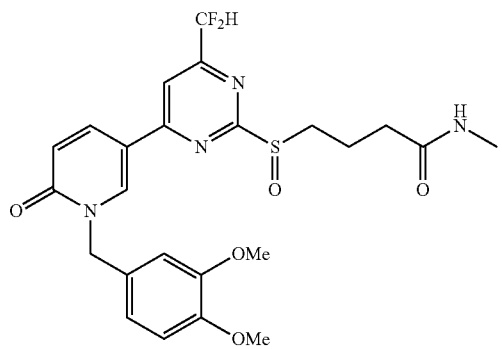 [SMILES: CNC(=O)CCCS(=O)c1nc(-c2ccc(=O)n(Cc3ccc(OC)c(OC)c3)c2)cc(C(F)F)n1] 177
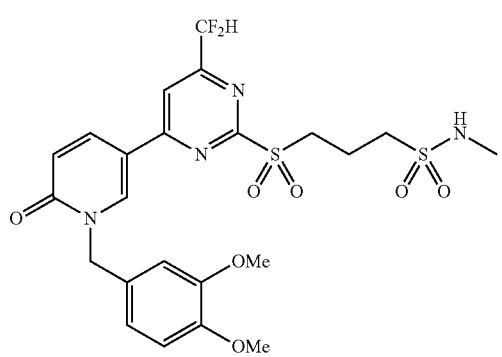 [SMILES: CNS(=O)(=O)CCCS(=O)(=O)c1nc(-c2ccc(=O)n(Cc3ccc(OC)c(OC)c3)c2)cc(C(F)F)n1] 178
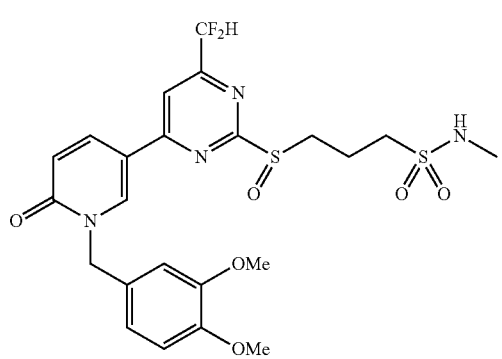 [SMILES: CNS(=O)(=O)CCCS(=O)c1nc(-c2ccc(=O)n(Cc3ccc(OC)c(OC)c3)c2)cc(C(F)F)n1] 179
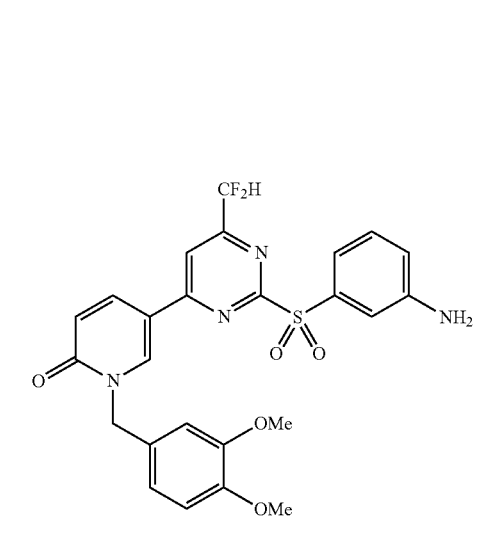 [SMILES: COc1ccc(Cn2cc(-c3cc(C(F)F)nc(S(=O)(=O)c4cccc(N)c4)n3)ccc2=O)cc1OC] 180
TABLE 4a-continued
SAR optimization:
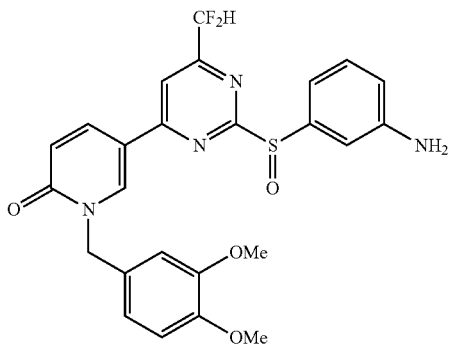 [SMILES: COc1ccc(Cn2cc(-c3cc(C(F)F)nc(S(=O)c4cccc(N)c4)n3)ccc2=O)cc1OC] 181
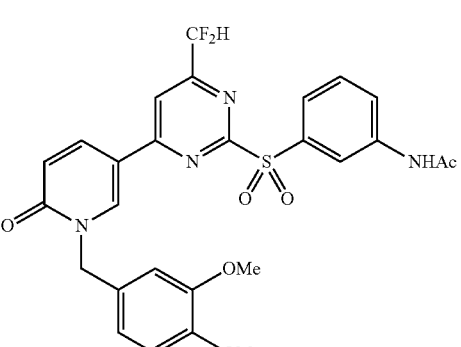 182
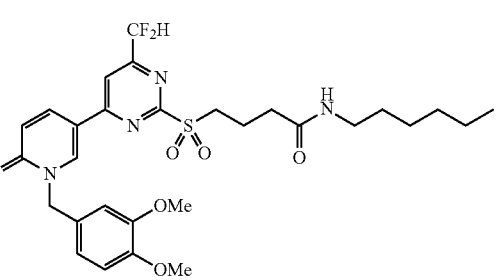 183
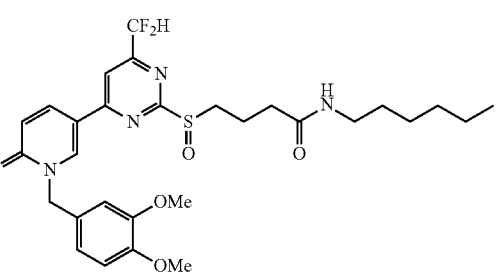 184
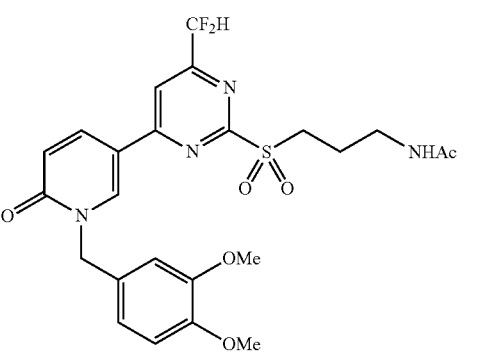 [SMILES: COc1ccc(Cn2cc(-c3cc(C(F)F)nc(S(=O)(=O)CCCNC(C)=O)n3)ccc2=O)cc1OC] 185

TABLE 4a-continued
SAR optimization:
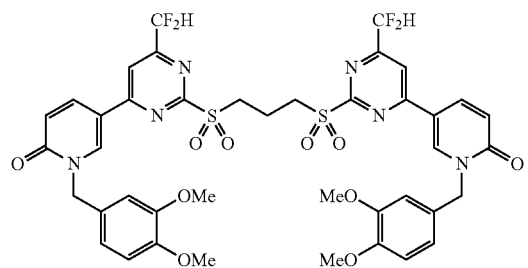 [SMILES: COc1ccc(Cn2cc(-c3cc(C(F)F)nc(S(=O)(=O)CCCS(=O)(=O)c4nc(-c5ccc(=O)n(Cc6ccc(OC)c(OC)c6)c5)cc(C(F)F)n4)n3)ccc2=O)cc1OC] 186
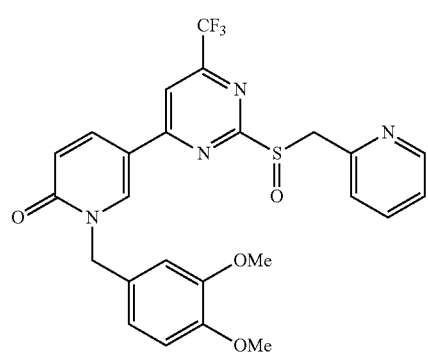 [SMILES: COc1ccc(Cn2cc(-c3cc(C(F)(F)F)nc(S(=O)Cc4ccccn4)n3)ccc2=O)cc1OC] 187
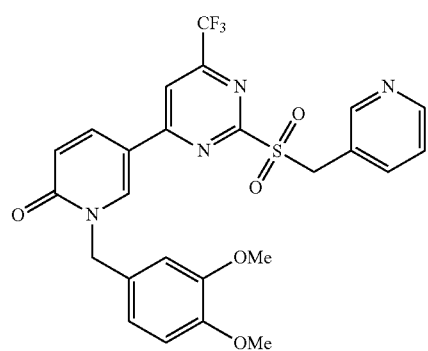 [SMILES: COc1ccc(Cn2cc(-c3cc(C(F)(F)F)nc(S(=O)(=O)Cc4cccnc4)n3)ccc2=O)cc1OC] 188
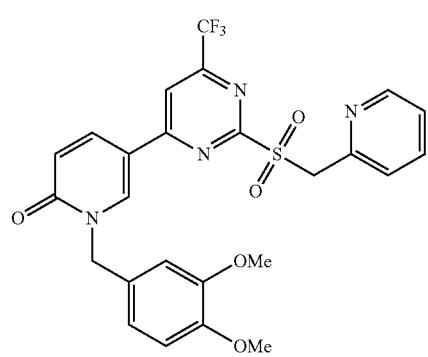 [SMILES: COc1ccc(Cn2cc(-c3cc(C(F)(F)F)nc(S(=O)(=O)Cc4ccccn4)n3)ccc2=O)cc1OC] 189
TABLE 4a-continued
SAR optimization:
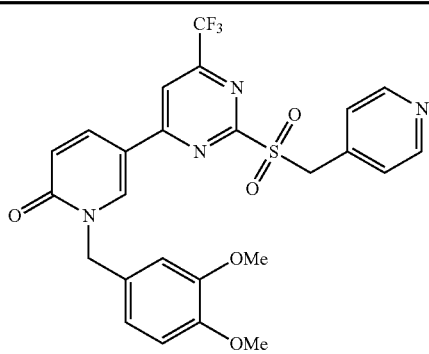 190
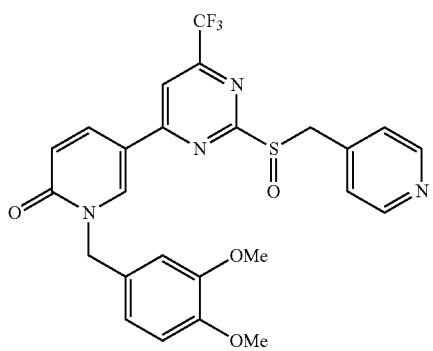 [SMILES: COc1ccc(Cn2cc(-c3cc(C(F)(F)F)nc(S(=O)Cc4ccncc4)n3)ccc2=O)cc1OC] 191
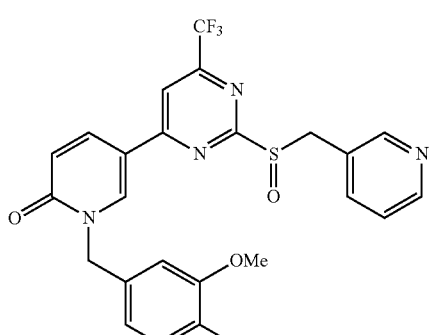 192
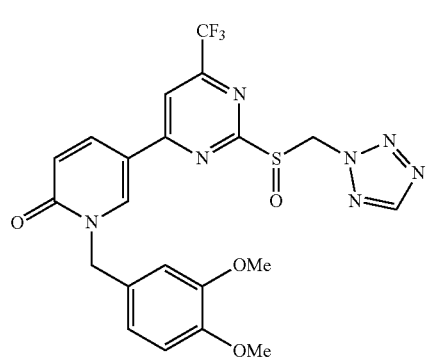 [SMILES: COc1ccc(Cn2cc(-c3cc(C(F)(F)F)nc(S(=O)Cn4ncnn4)n3)ccc2=O)cc1OC] 193

TABLE 4a-continued
SAR optimization:
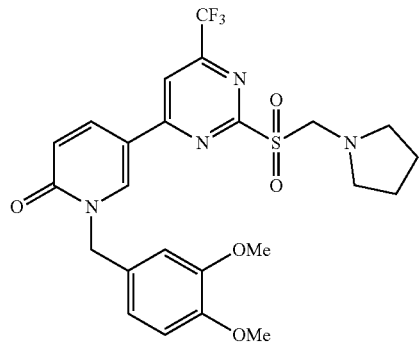 [SMILES: COc1ccc(Cn2cc(-c3cc(C(F)(F)F)nc(S(=O)(=O)CN4CCCC4)n3)ccc2=O)cc1OC] 194
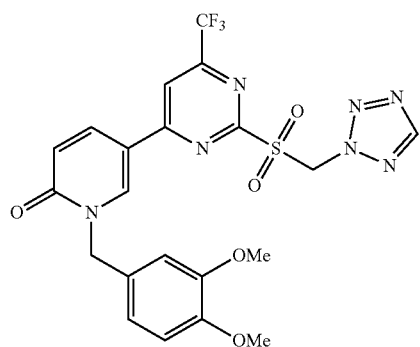 [SMILES: COc1ccc(Cn2cc(-c3cc(C(F)(F)F)nc(S(=O)(=O)Cn4ncnn4)n3)ccc2=O)cc1OC] 195
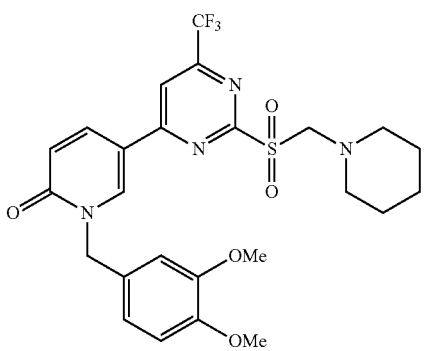 [SMILES: COc1ccc(Cn2cc(-c3cc(C(F)(F)F)nc(S(=O)(=O)CN4CCCCC4)n3)ccc2=O)cc1OC] 196
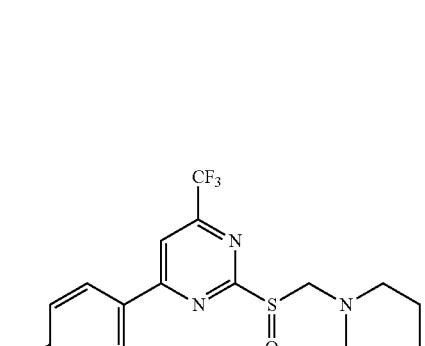 197
TABLE 4a-continued
SAR optimization:
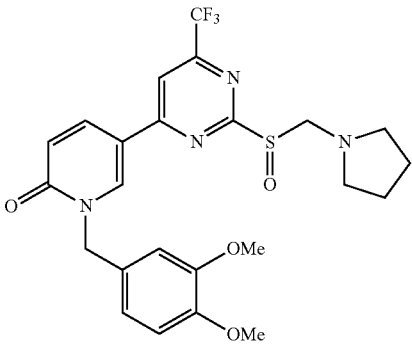 [SMILES: COc1ccc(Cn2cc(-c3cc(C(F)(F)F)nc(S(=O)CN4CCCC4)n3)ccc2=O)cc1OC] 198
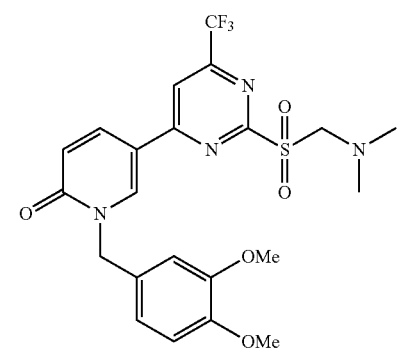 [SMILES: COc1ccc(Cn2cc(-c3cc(C(F)(F)F)nc(S(=O)(=O)CN(C)C)n3)ccc2=O)cc1OC] 199
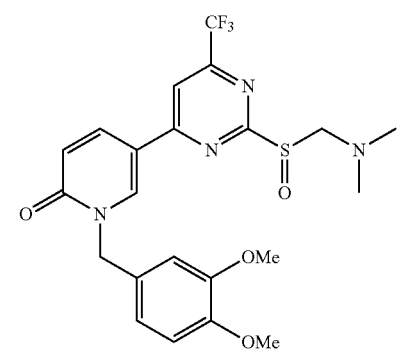 [SMILES: COc1ccc(Cn2cc(-c3cc(C(F)(F)F)nc(S(=O)CN(C)C)n3)ccc2=O)cc1OC] 200
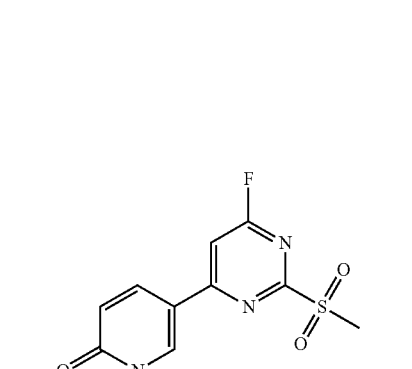 201

TABLE 4a-continued

SAR optimization:

| | |
|---|---|
| 202 | 206 |
| 203 | 207 |
| 204 | 208 |
| 205 | 209 |

TABLE 4a-continued
SAR optimization:
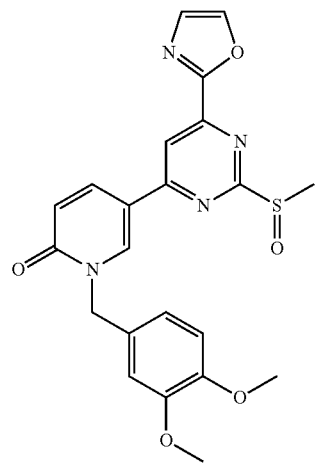 [SMILES: COc1ccc(Cn2cc(-c3cc(-c4ncco4)nc(S(C)=O)n3)ccc2=O)cc1OC]
210
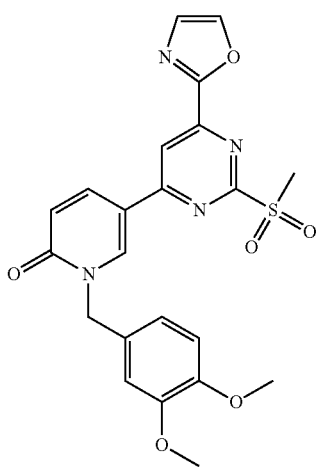 [SMILES: COc1ccc(Cn2cc(-c3cc(-c4ncco4)nc(S(C)(=O)=O)n3)ccc2=O)cc1OC]
211
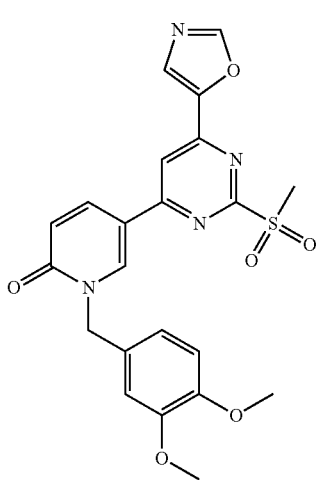 [SMILES: COc1ccc(Cn2cc(-c3cc(-c4cnco4)nc(S(C)(=O)=O)n3)ccc2=O)cc1OC]
212
TABLE 4a-continued
SAR optimization:
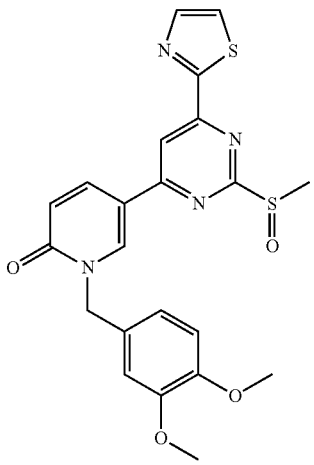 [SMILES: COc1ccc(Cn2cc(-c3cc(-c4nccs4)nc(S(C)=O)n3)ccc2=O)cc1OC]
213
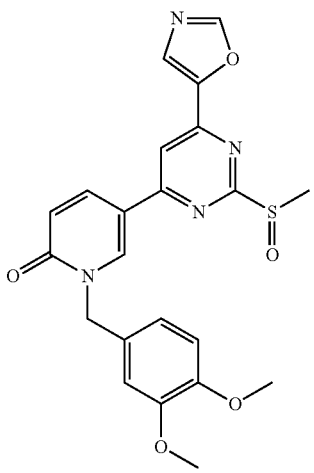
214
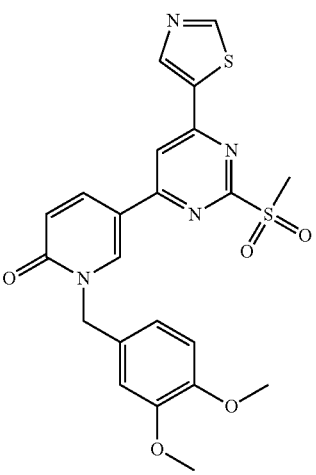
215

TABLE 4a-continued
SAR optimization:
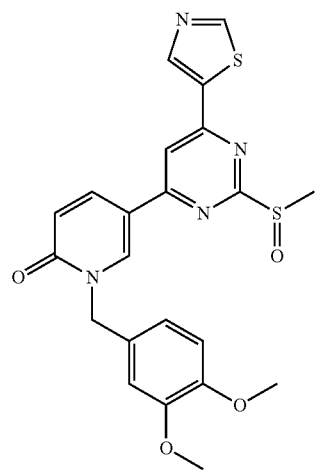 [SMILES: COc1ccc(Cn2cc(-c3cc(-c4cnco4)nc(S(C)=O)n3)ccc2=O)cc1OC] 216
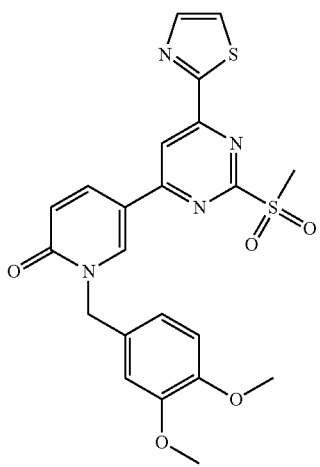 217
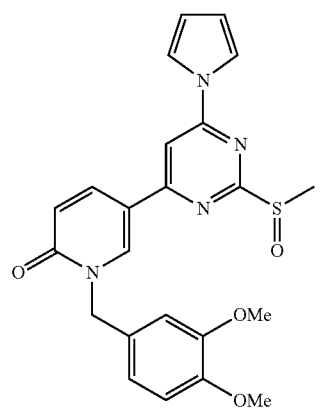 [SMILES: COc1ccc(Cn2cc(-c3cc(-n4cccc4)nc(S(C)=O)n3)ccc2=O)cc1OC] 218
TABLE 4a-continued
SAR optimization:
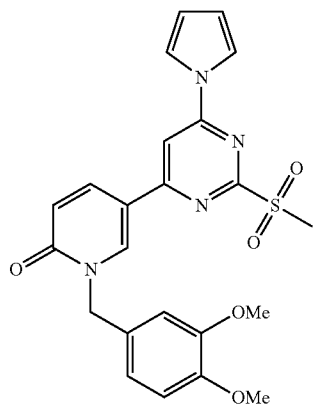 [SMILES: COc1ccc(Cn2cc(-c3cc(-n4cccc4)nc(S(C)(=O)=O)n3)ccc2=O)cc1OC] 219
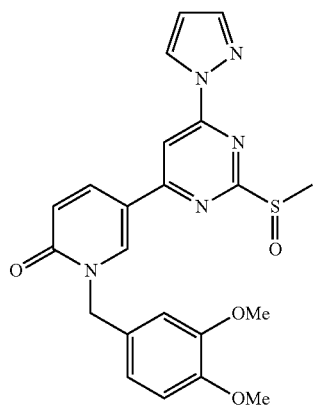 [SMILES: COc1ccc(Cn2cc(-c3cc(-n4cccn4)nc(S(C)=O)n3)ccc2=O)cc1OC] 220
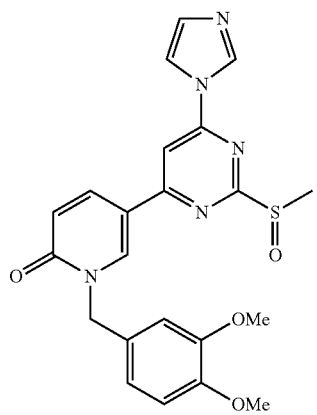 [SMILES: COc1ccc(Cn2cc(-c3cc(-n4ccnc4)nc(S(C)=O)n3)ccc2=O)cc1OC] 221

TABLE 4a-continued
SAR optimization:
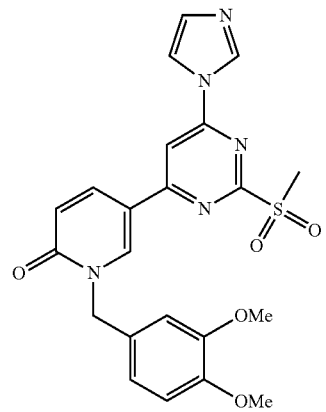 [SMILES: COc1ccc(Cn2cc(-c3cc(-n4ccnc4)nc(S(C)(=O)=O)n3)ccc2=O)cc1OC]
222
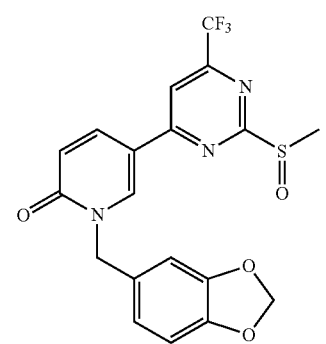 [SMILES: CS(=O)c1nc(-c2ccc(=O)n(Cc3ccc4c(c3)OCO4)c2)cc(C(F)(F)F)n1]
223
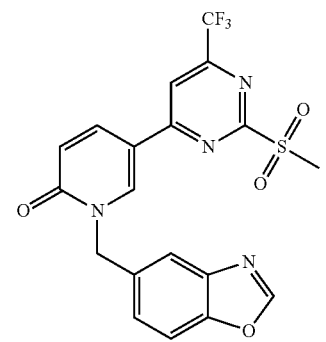 [SMILES: CS(=O)(=O)c1nc(-c2ccc(=O)n(Cc3ccc4ocnc4c3)c2)cc(C(F)(F)F)n1]
224
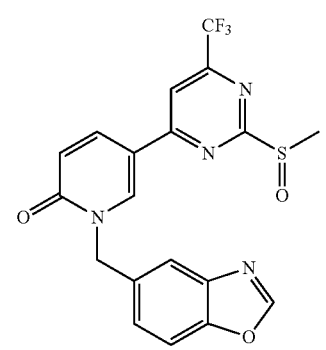 [SMILES: CS(=O)c1nc(-c2ccc(=O)n(Cc3ccc4ocnc4c3)c2)cc(C(F)(F)F)n1]
225
TABLE 4a-continued
SAR optimization:
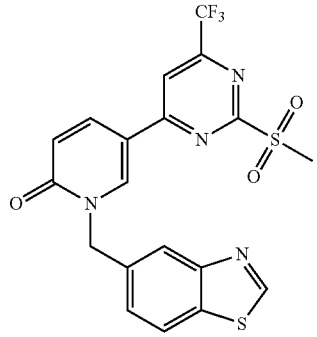 [SMILES: CS(=O)(=O)c1nc(-c2ccc(=O)n(Cc3ccc4scnc4c3)c2)cc(C(F)(F)F)n1]
226
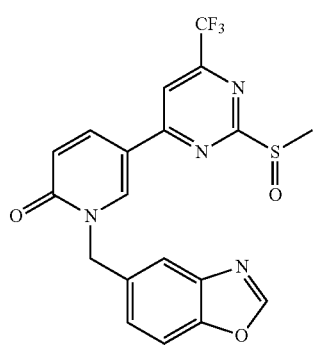 [SMILES: CS(=O)c1nc(-c2ccc(=O)n(Cc3ccc4ocnc4c3)c2)cc(C(F)(F)F)n1]
227
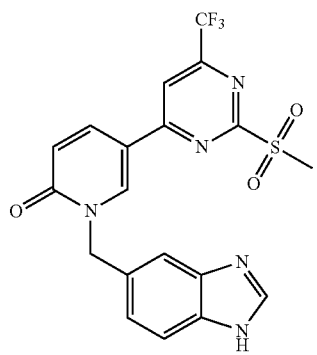 [SMILES: CS(=O)(=O)c1nc(-c2ccc(=O)n(Cc3ccc4[nH]cnc4c3)c2)cc(C(F)(F)F)n1]
228
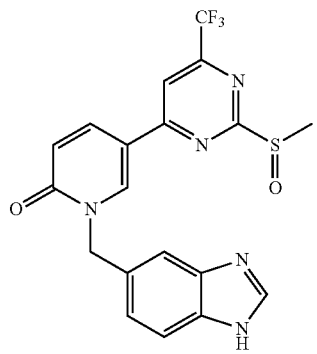 [SMILES: CS(=O)c1nc(-c2ccc(=O)n(Cc3ccc4[nH]cnc4c3)c2)cc(C(F)(F)F)n1]
229

TABLE 4a-continued
SAR optimization:
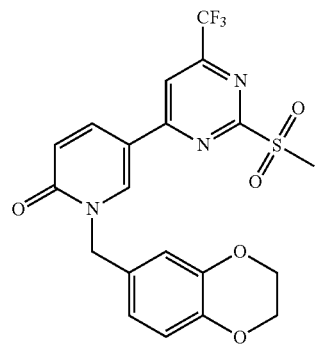 [SMILES: CS(=O)(=O)c1nc(-c2ccc(=O)n(Cc3ccc4c(c3)OCCO4)c2)cc(C(F)(F)F)n1] 230
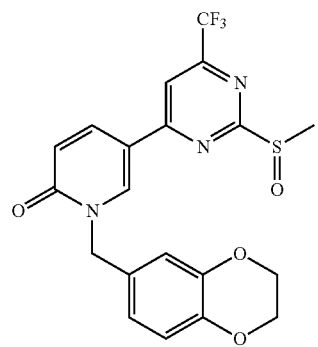 [SMILES: CS(=O)c1nc(-c2ccc(=O)n(Cc3ccc4c(c3)OCCO4)c2)cc(C(F)(F)F)n1] 231
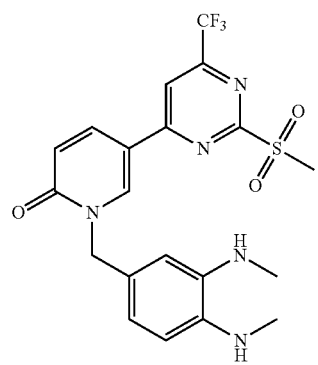 [SMILES: CNc1ccc(Cn2cc(-c3cc(C(F)(F)F)nc(S(C)(=O)=O)n3)ccc2=O)cc1NC] 232
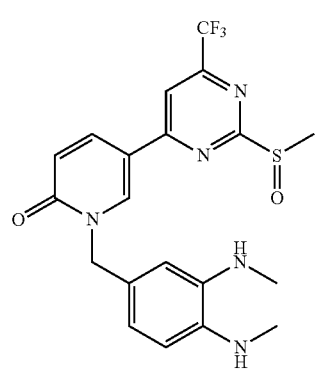 [SMILES: CNc1ccc(Cn2cc(-c3cc(C(F)(F)F)nc(S(C)=O)n3)ccc2=O)cc1NC] 233
TABLE 4a-continued
SAR optimization:
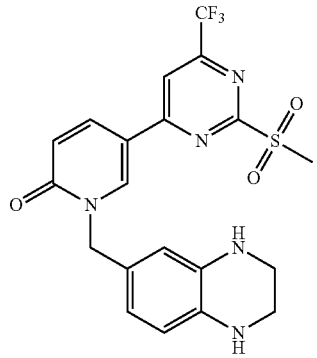 [SMILES: CS(=O)(=O)c1nc(-c2ccc(=O)n(Cc3ccc4c(c3)NCCN4)c2)cc(C(F)(F)F)n1] 234
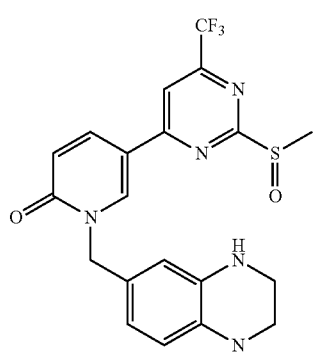 235
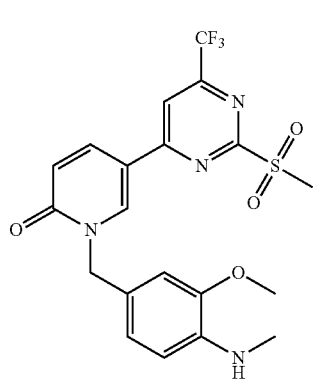 [SMILES: CNc1ccc(Cn2cc(-c3cc(C(F)(F)F)nc(S(C)(=O)=O)n3)ccc2=O)cc1OC] 236
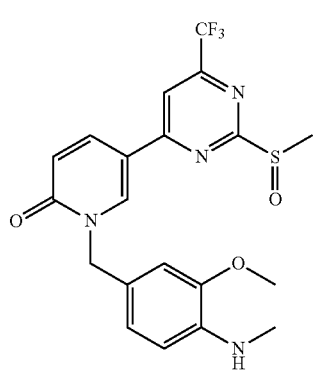 [SMILES: CNc1ccc(Cn2cc(-c3cc(C(F)(F)F)nc(S(C)=O)n3)ccc2=O)cc1OC] 237

TABLE 4a-continued

SAR optimization:

| | |
|---|---|
| 238 | 242 |
| 239 | 243 |
| 240 | 244 |
| 241 | 245 |

TABLE 4a-continued
SAR optimization:
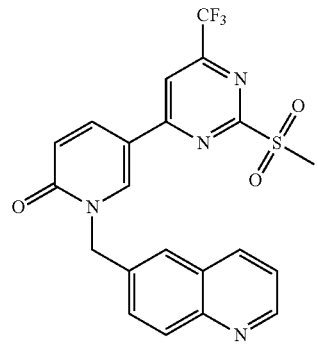 [SMILES: CS(=O)(=O)c1nc(-c2ccc(=O)n(Cc3ccc4ncccc4c3)c2)cc(C(F)(F)F)n1] 246
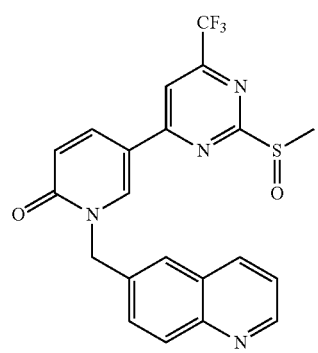 [SMILES: CS(=O)c1nc(-c2ccc(=O)n(Cc3ccc4ncccc4c3)c2)cc(C(F)(F)F)n1] 247
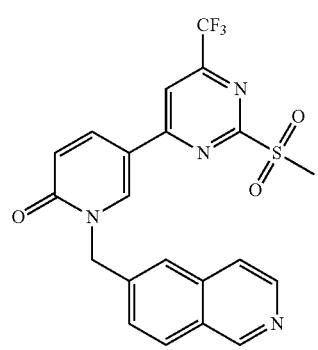 [SMILES: CS(=O)(=O)c1nc(-c2ccc(=O)n(Cc3ccc4cnccc4c3)c2)cc(C(F)(F)F)n1] 248
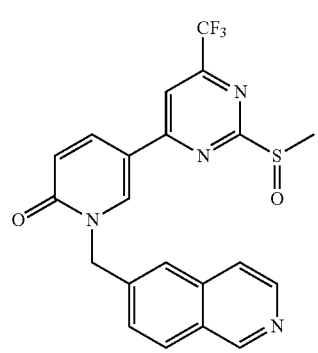 [SMILES: CS(=O)c1nc(-c2ccc(=O)n(Cc3ccc4cnccc4c3)c2)cc(C(F)(F)F)n1] 249
TABLE 4a-continued
SAR optimization:
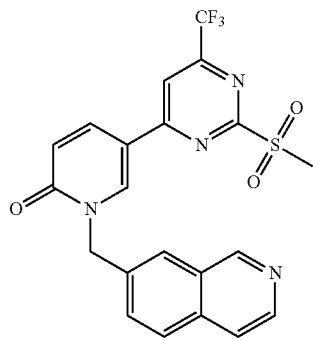 [SMILES: CS(=O)(=O)c1nc(-c2ccc(=O)n(Cc3ccc4ccncc4c3)c2)cc(C(F)(F)F)n1] 250
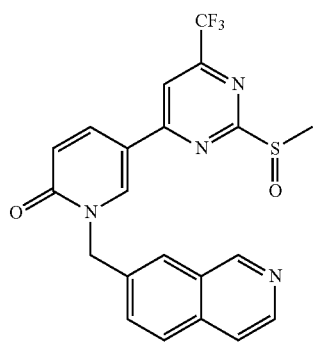 [SMILES: CS(=O)c1nc(-c2ccc(=O)n(Cc3ccc4ccncc4c3)c2)cc(C(F)(F)F)n1] 251
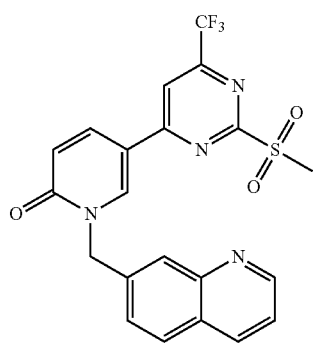 [SMILES: CS(=O)(=O)c1nc(-c2ccc(=O)n(Cc3ccc4cccnc4c3)c2)cc(C(F)(F)F)n1] 252
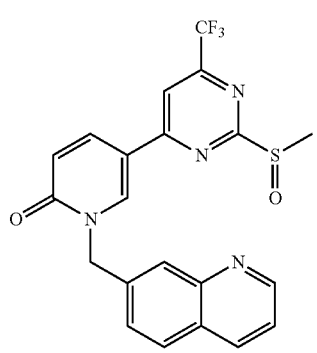 [SMILES: CS(=O)c1nc(-c2ccc(=O)n(Cc3ccc4cccnc4c3)c2)cc(C(F)(F)F)n1] 253

TABLE 4a-continued
SAR optimization:
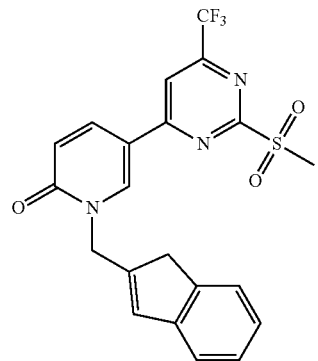 [SMILES: CS(=O)(=O)c1nc(-c2ccc(=O)n(CC3=Cc4ccccc4C3)c2)cc(C(F)(F)F)n1] 254
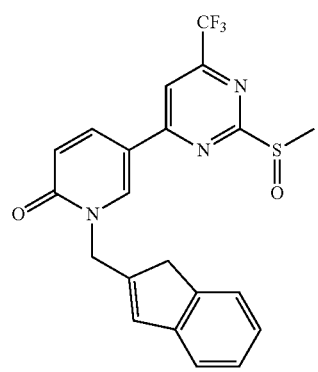 [SMILES: CS(=O)c1nc(-c2ccc(=O)n(CC3=Cc4ccccc4C3)c2)cc(C(F)(F)F)n1] 255
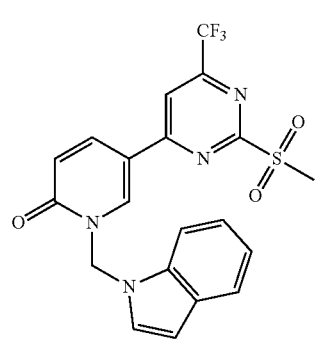 [SMILES: CS(=O)(=O)c1nc(-c2ccc(=O)n(Cn3ccc4ccccc43)c2)cc(C(F)(F)F)n1] 256
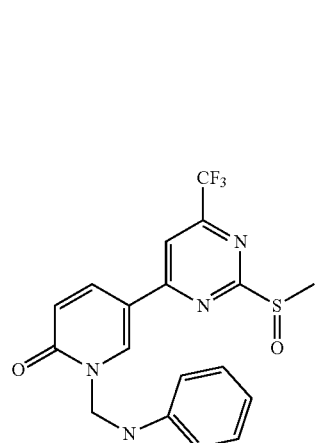 257
TABLE 4a-continued
SAR optimization:
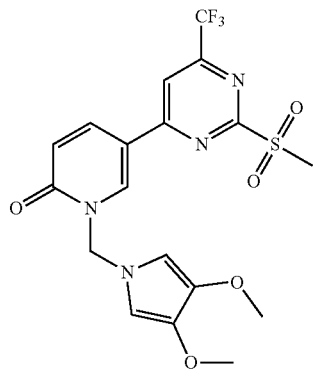 [SMILES: COc1cn(Cn2cc(-c3cc(C(F)(F)F)nc(S(C)(=O)=O)n3)ccc2=O)cc1OC] 258
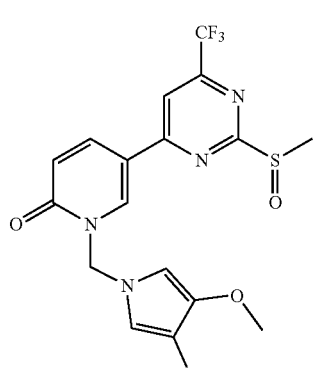 259
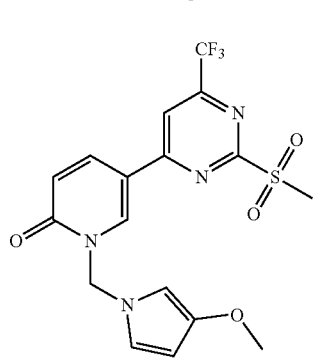 [SMILES: COc1ccn(Cn2cc(-c3cc(C(F)(F)F)nc(S(C)(=O)=O)n3)ccc2=O)c1] 260
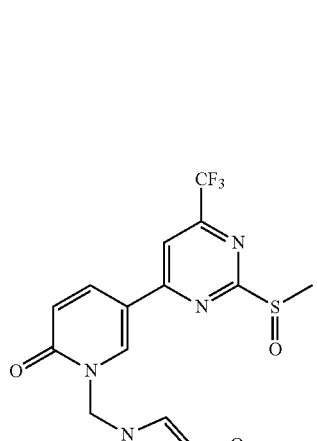 261

TABLE 4a-continued
SAR optimization:
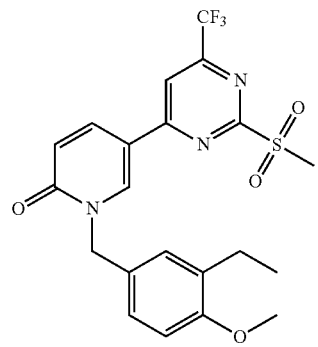 [SMILES: CCc1cc(Cn2cc(-c3cc(C(F)(F)F)nc(S(C)(=O)=O)n3)ccc2=O)ccc1OC] 262
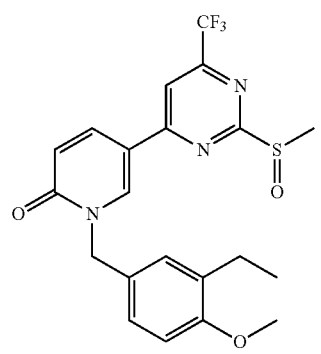 [SMILES: CCc1cc(Cn2cc(-c3cc(C(F)(F)F)nc(S(C)=O)n3)ccc2=O)ccc1OC] 263
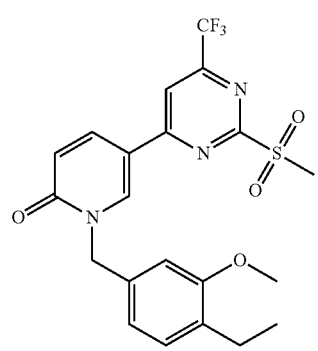 [SMILES: CCc1ccc(Cn2cc(-c3cc(C(F)(F)F)nc(S(C)(=O)=O)n3)ccc2=O)cc1OC] 264
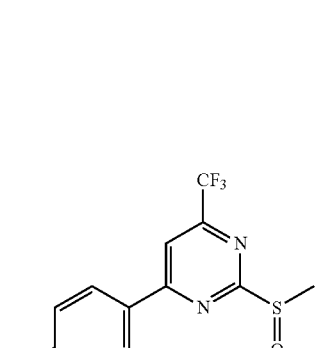 265
TABLE 4a-continued
SAR optimization:
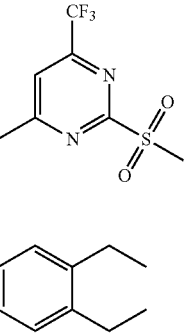 266
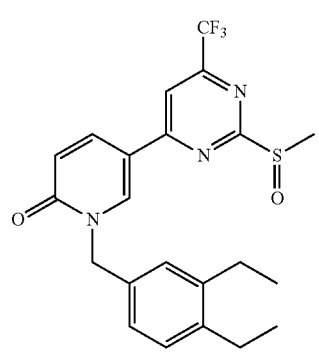 [SMILES: CCc1ccc(Cn2cc(-c3cc(C(F)(F)F)nc(S(C)=O)n3)ccc2=O)cc1CC] 267
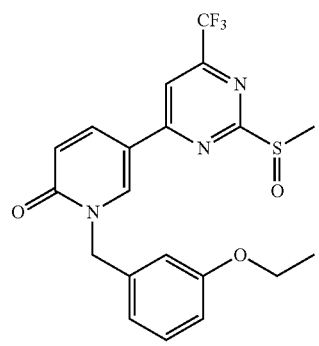 [SMILES: CCOc1cccc(Cn2cc(-c3cc(C(F)(F)F)nc(S(C)=O)n3)ccc2=O)c1] 268
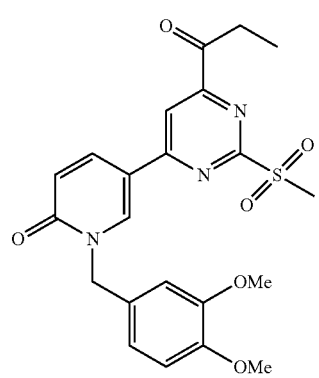 [SMILES: CCC(=O)c1cc(-c2ccc(=O)n(Cc3ccc(OC)c(OC)c3)c2)nc(S(C)(=O)=O)n1] 269

TABLE 4a-continued
SAR optimization:
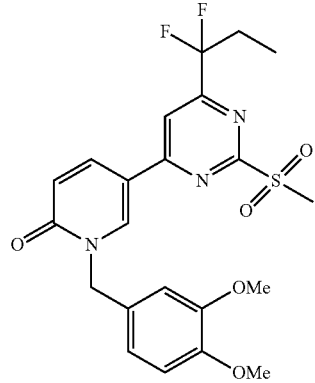 [SMILES: CCC(F)(F)c1cc(-c2ccc(=O)n(Cc3ccc(OC)c(OC)c3)c2)nc(S(C)(=O)=O)n1] 270
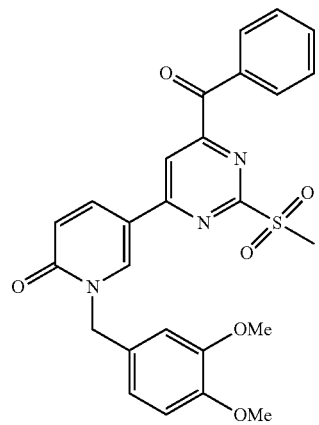 [SMILES: COc1ccc(Cn2cc(-c3cc(C(=O)c4ccccc4)nc(S(C)(=O)=O)n3)ccc2=O)cc1OC] 271
TABLE 4b
SAR optimization:
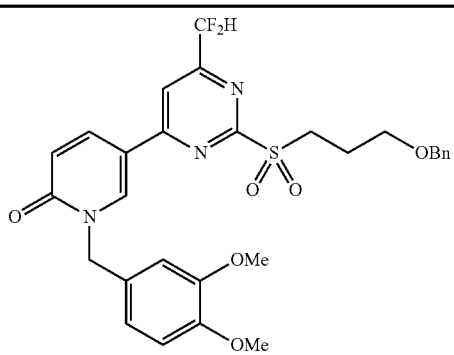 9272
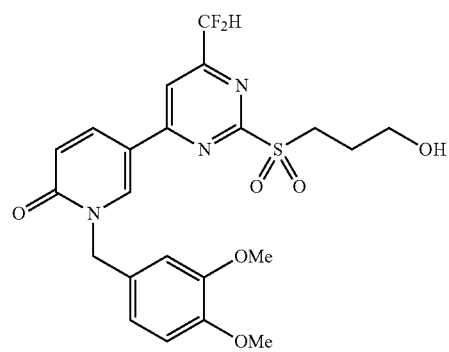 [SMILES: COc1ccc(Cn2cc(-c3cc(C(F)F)nc(S(=O)(=O)CCCO)n3)ccc2=O)cc1OC] 9273
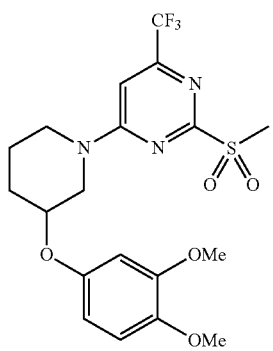 [SMILES: COc1ccc(OC2CCCN(c3cc(C(F)(F)F)nc(S(C)(=O)=O)n3)C2)cc1OC] 274

TABLE 4b-continued
SAR optimization:
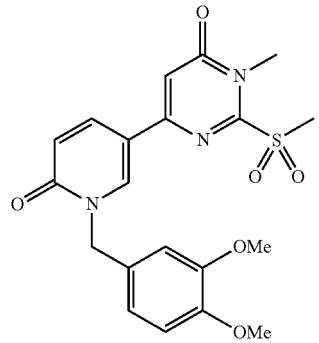
275
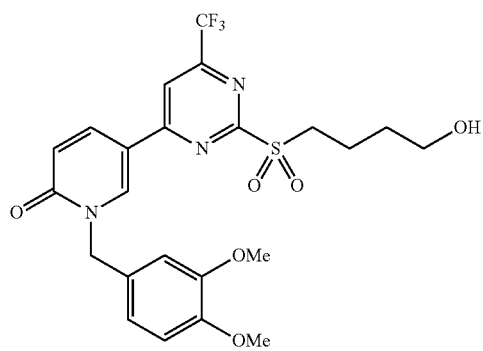 [SMILES: COc1ccc(Cn2cc(-c3cc(C(F)(F)F)nc(S(=O)(=O)CCCCO)n3)ccc2=O)cc1OC]
276
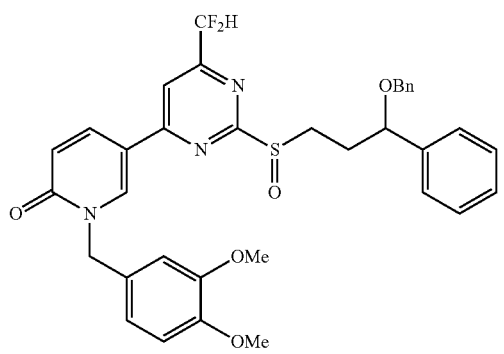 [SMILES: COc1ccc(Cn2cc(-c3cc(C(F)F)nc(S(=O)CCC(OCc4ccccc4)c4ccccc4)n3)ccc2=O)cc1OC]
277
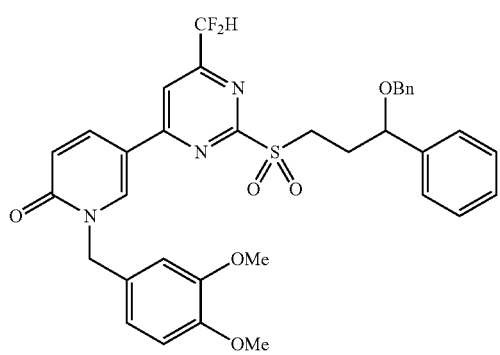
278

TABLE 4b-continued
SAR optimization:
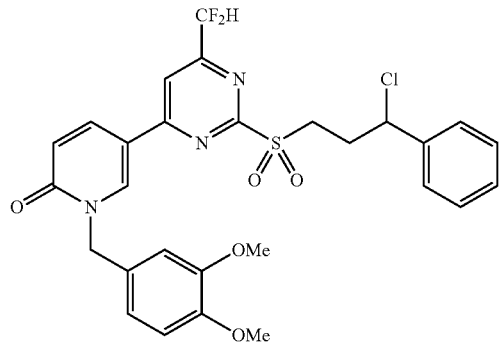 [SMILES: COc1ccc(Cn2cc(-c3cc(C(F)F)nc(S(=O)(=O)CCC(Cl)c4ccccc4)n3)ccc2=O)cc1OC]
279
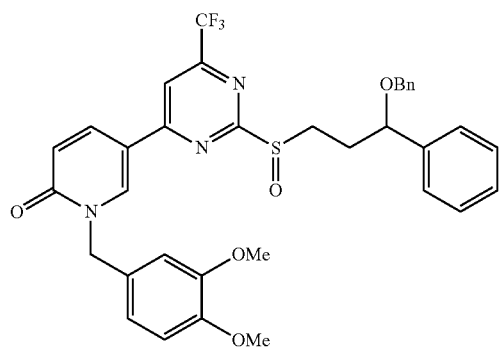
280
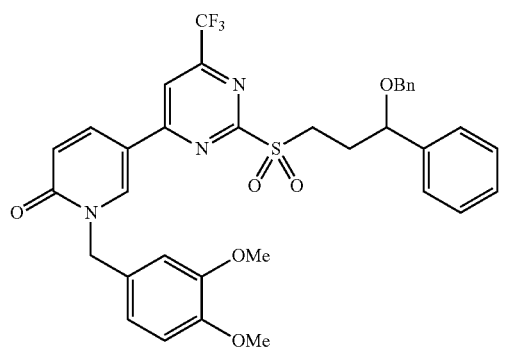 [SMILES: COc1ccc(Cn2cc(-c3cc(C(F)(F)F)nc(S(=O)(=O)CCC(OCc4ccccc4)c4ccccc4)n3)ccc2=O)cc1OC]
281
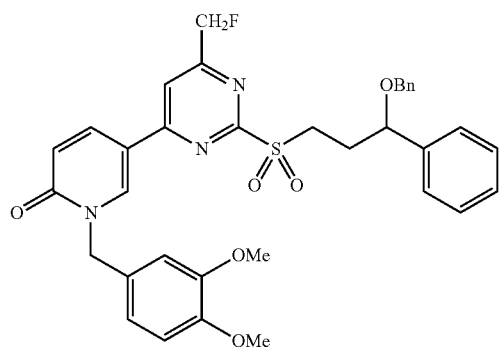
282

TABLE 4b-continued
SAR optimization:
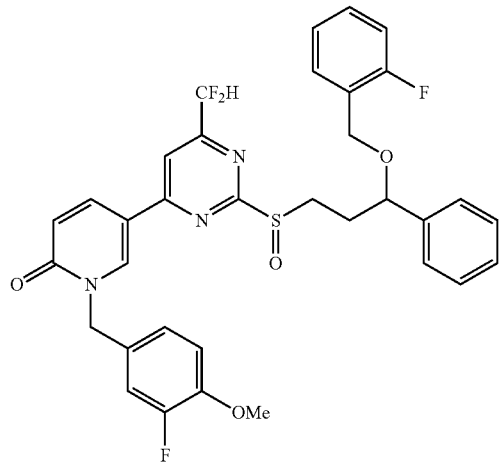 [SMILES: COc1ccc(Cn2cc(-c3cc(C(F)F)nc(S(=O)CCC(OCc4ccccc4F)c4ccccc4)n3)ccc2=O)cc1F]
283
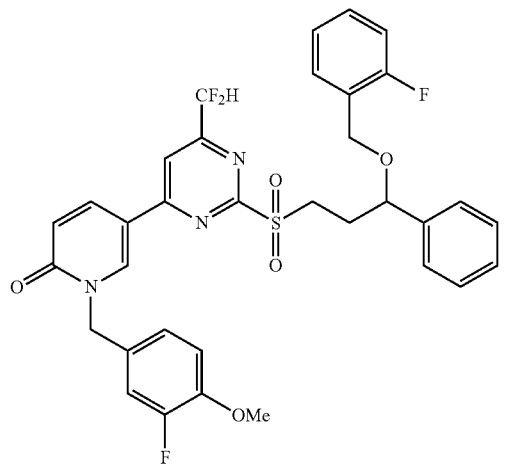 [SMILES: COc1ccc(Cn2cc(-c3cc(C(F)F)nc(S(=O)(=O)CCC(OCc4ccccc4F)c4ccccc4)n3)ccc2=O)cc1F]
284
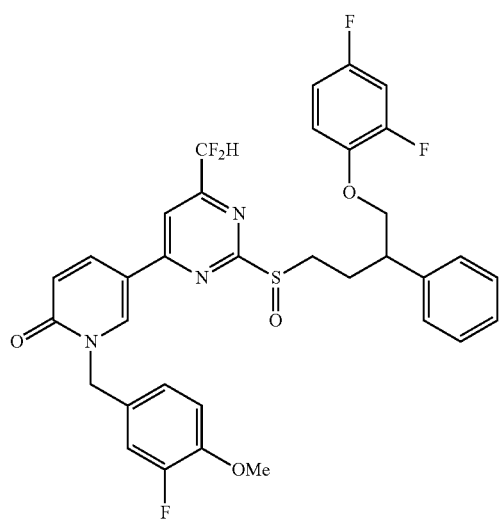 [SMILES: COc1ccc(Cn2cc(-c3cc(C(F)F)nc(S(=O)CCC(COc4ccc(F)cc4F)c4ccccc4)n3)ccc2=O)cc1F]
285

TABLE 4b-continued
SAR optimization:
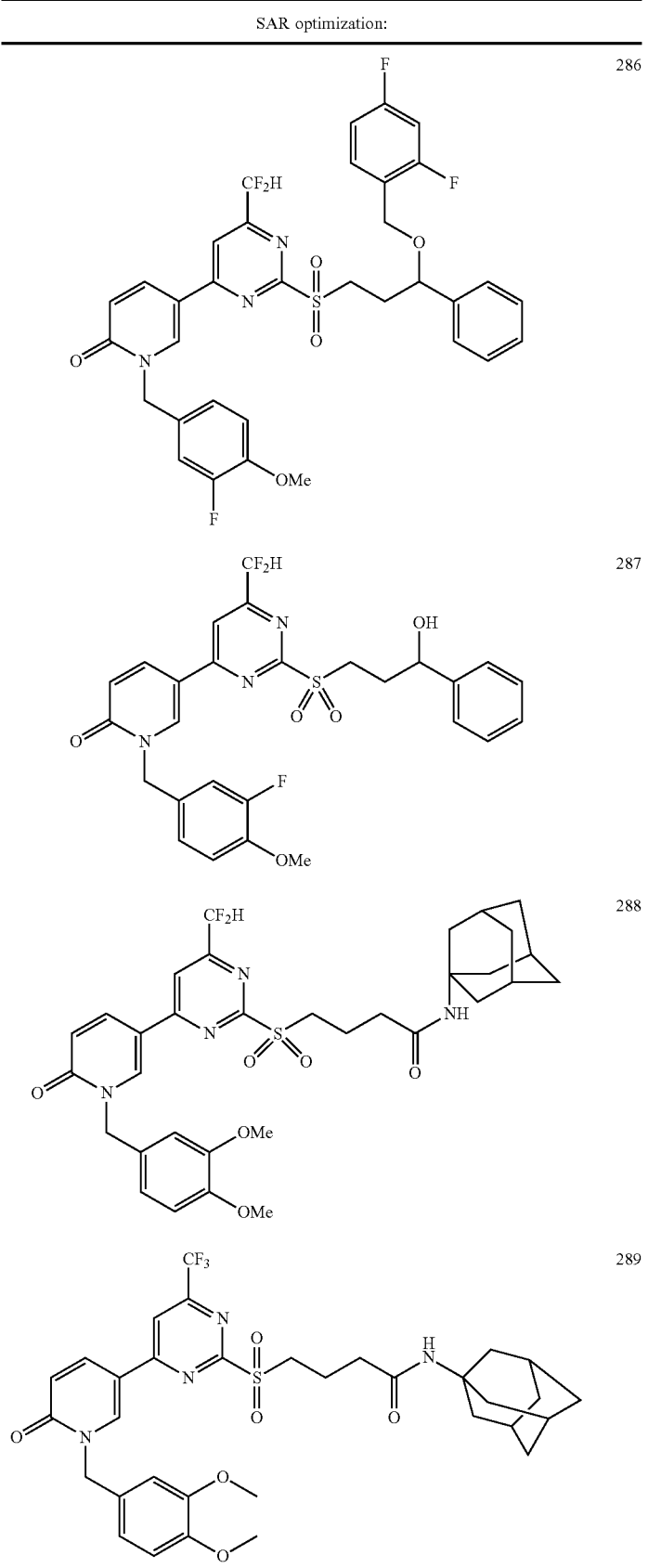

TABLE 4b-continued
SAR optimization:
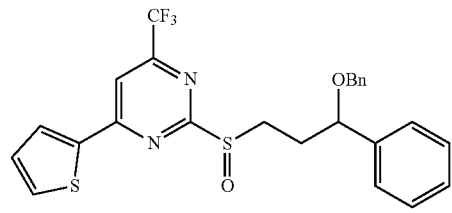 [SMILES: O=S(CCC(OCc1ccccc1)c1ccccc1)c1nc(-c2cccs2)cc(C(F)(F)F)n1] 290
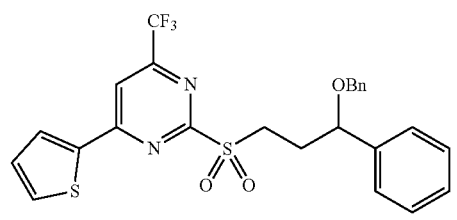 [SMILES: O=S(=O)(CCC(OCc1ccccc1)c1ccccc1)c1nc(-c2cccs2)cc(C(F)(F)F)n1] 291
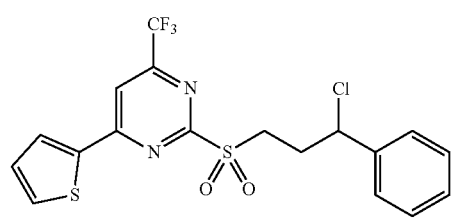 [SMILES: O=S(=O)(CCC(Cl)c1ccccc1)c1nc(-c2cccs2)cc(C(F)(F)F)n1] 292
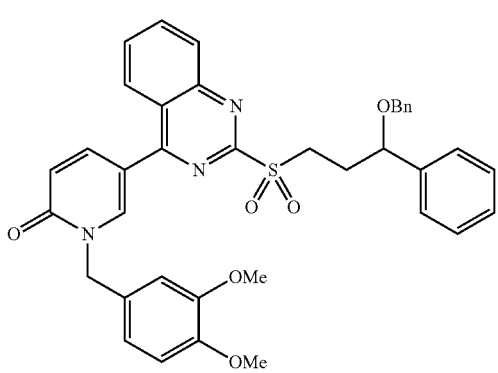 [SMILES: COc1ccc(Cn2cc(-c3nc(S(=O)(=O)CCC(OCc4ccccc4)c4ccccc4)nc4ccccc34)ccc2=O)cc1OC] 293
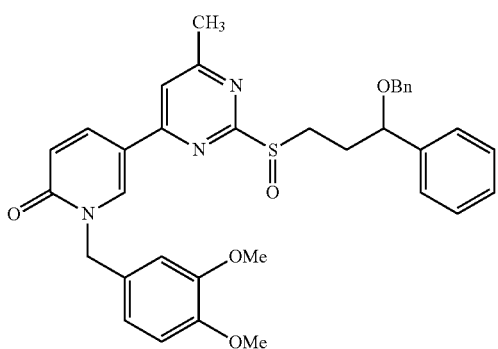 [SMILES: COc1ccc(Cn2cc(-c3cc(C)nc(S(=O)CCC(OCc4ccccc4)c4ccccc4)n3)ccc2=O)cc1OC]

TABLE 4b-continued
SAR optimization:
295
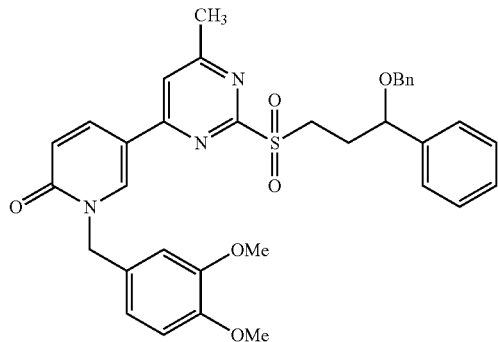 [SMILES: COc1ccc(Cn2cc(-c3cc(C)nc(S(=O)(=O)CCC(OCc4ccccc4)c4ccccc4)n3)ccc2=O)cc1OC]
296
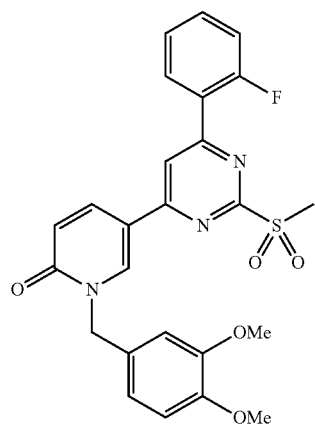 [SMILES: COc1ccc(Cn2cc(-c3cc(-c4ccccc4F)nc(S(C)(=O)=O)n3)ccc2=O)cc1OC]
297
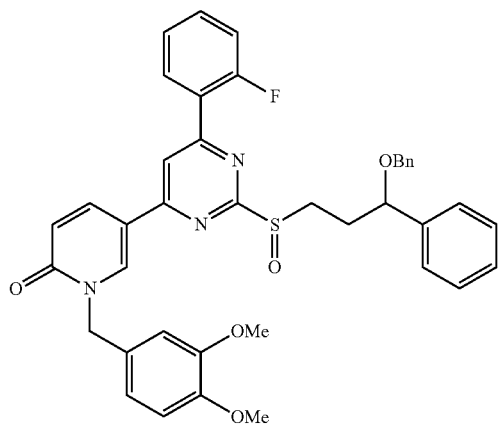 [SMILES: COc1ccc(Cn2cc(-c3cc(-c4ccccc4F)nc(S(=O)CCC(OCc4ccccc4)c4ccccc4)n3)ccc2=O)cc1OC]

TABLE 4b-continued
SAR optimization:
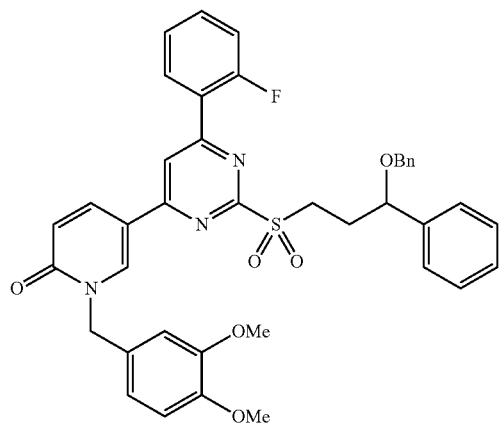 [SMILES: COc1ccc(Cn2cc(-c3cc(-c4ccccc4F)nc(S(=O)(=O)CCC(OCc4ccccc4)c4ccccc4)n3)ccc2=O)cc1OC]
298
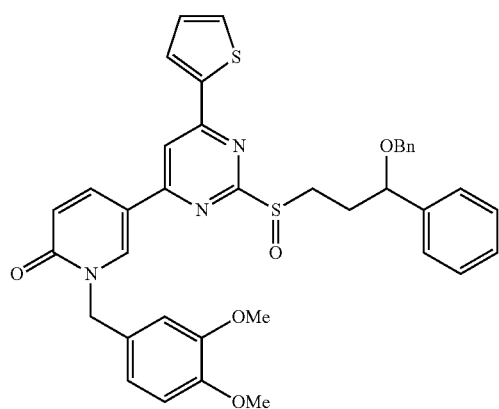 [SMILES: COc1ccc(Cn2cc(-c3cc(-c4cccs4)nc(S(=O)CCC(OCc4ccccc4)c4ccccc4)n3)ccc2=O)cc1OC]
299
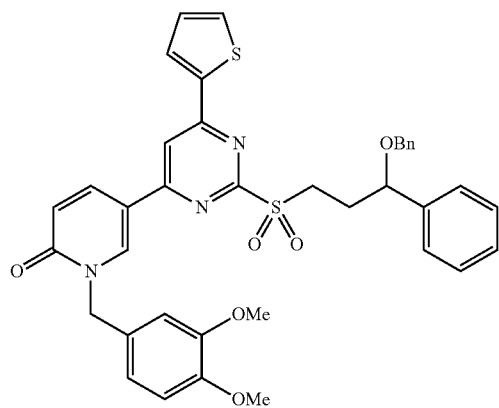 [SMILES: COc1ccc(Cn2cc(-c3cc(-c4cccs4)nc(S(=O)(=O)CCC(OCc4ccccc4)c4ccccc4)n3)ccc2=O)cc1OC]
300

TABLE 4b-continued
SAR optimization:
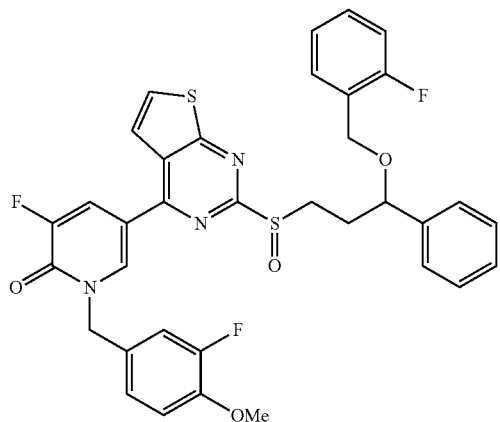 [SMILES: COc1ccc(Cn2cc(-c3nc(S(=O)CCC(OCc4ccccc4F)c4ccccc4)nc4sccc34)cc(F)c2=O)cc1F]
301
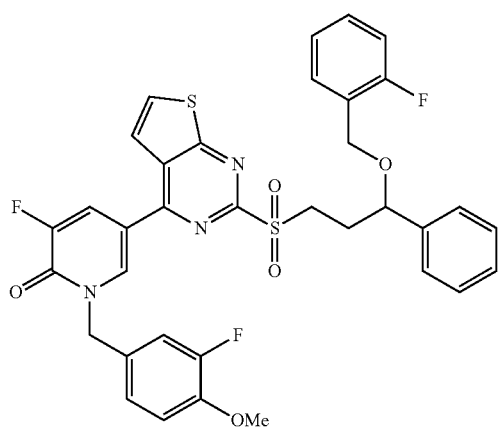 [SMILES: COc1ccc(Cn2cc(-c3nc(S(=O)(=O)CCC(OCc4ccccc4F)c4ccccc4)nc4sccc34)cc(F)c2=O)cc1F]
302
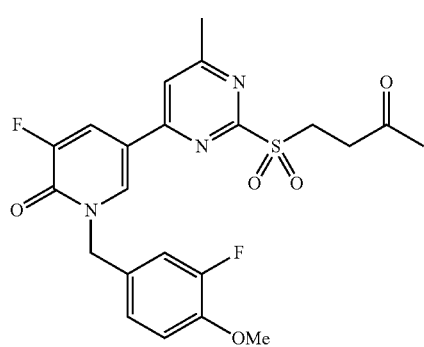 [SMILES: COc1ccc(Cn2cc(-c3cc(C)nc(S(=O)(=O)CCC(C)=O)n3)cc(F)c2=O)cc1F]
303
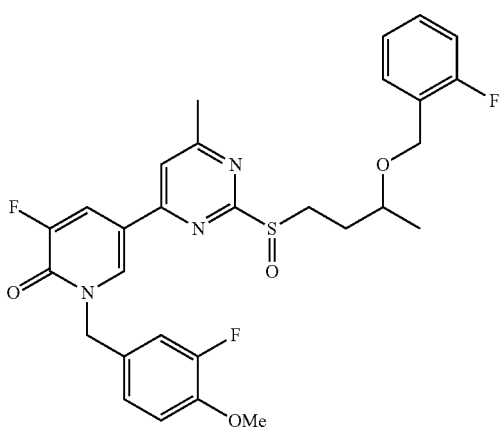 [SMILES: COc1ccc(Cn2cc(-c3cc(C)nc(S(=O)CCC(C)OCc4ccccc4F)n3)cc(F)c2=O)cc1F]
304

TABLE 4b-continued
SAR optimization:
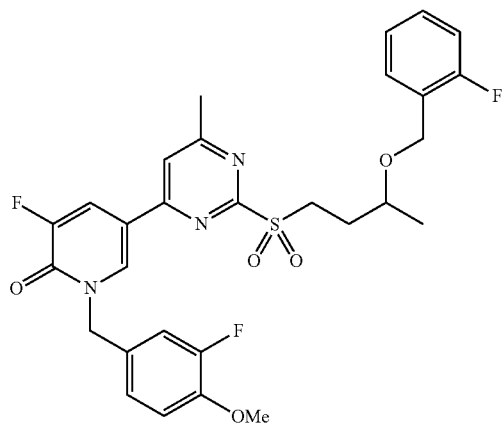 [SMILES: COc1ccc(Cn2cc(-c3cc(C)nc(S(=O)(=O)CCC(C)OCc4ccccc4F)n3)cc(F)c2=O)cc1F]
305
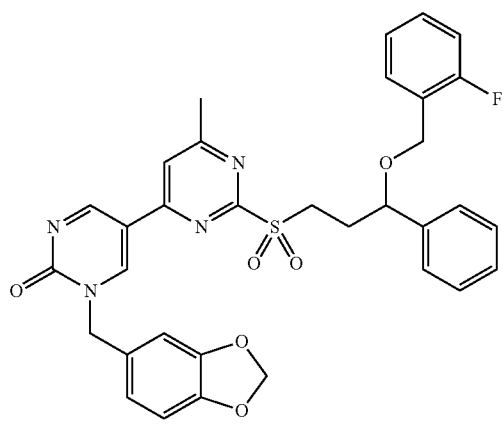 [SMILES: Cc1cc(-c2cnc(=O)n(Cc3ccc4c(c3)OCO4)c2)nc(S(=O)(=O)CCC(OCc2ccccc2F)c2ccccc2)n1]
306
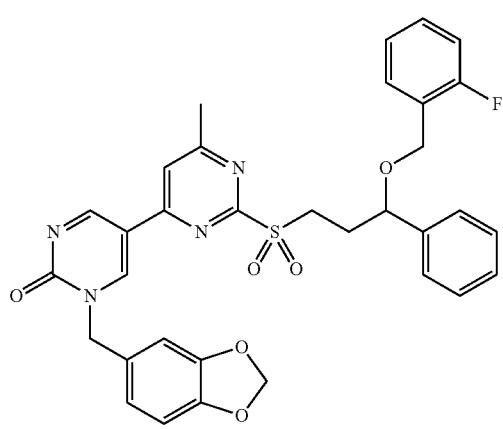 [SMILES: Cc1cc(-c2cnc(=O)n(Cc3ccc4c(c3)OCO4)c2)nc(S(=O)(=O)CCC(OCc2ccccc2F)c2ccccc2)n1]
307

TABLE 4b-continued
SAR optimization:
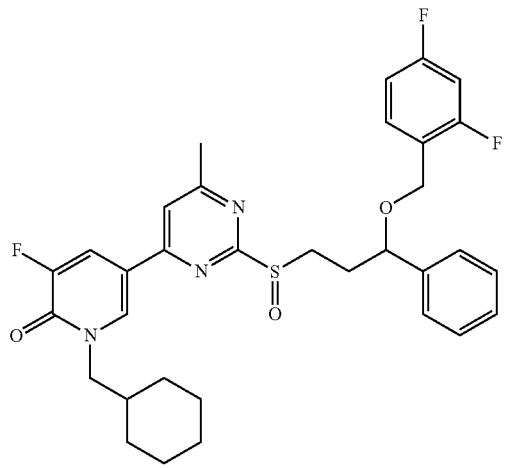 [SMILES: Cc1cc(-c2cc(F)c(=O)n(CC3CCCCC3)c2)nc(S(=O)CCC(OCc2ccc(F)cc2F)c2ccccc2)n1]
308
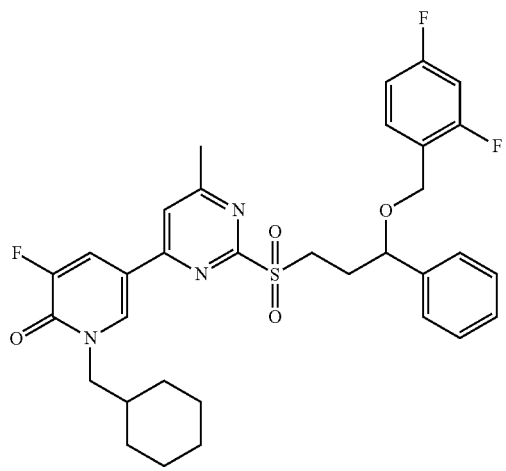 [SMILES: Cc1cc(-c2cc(F)c(=O)n(CC3CCCCC3)c2)nc(S(=O)(=O)CCC(OCc2ccc(F)cc2F)c2ccccc2)n1]
309
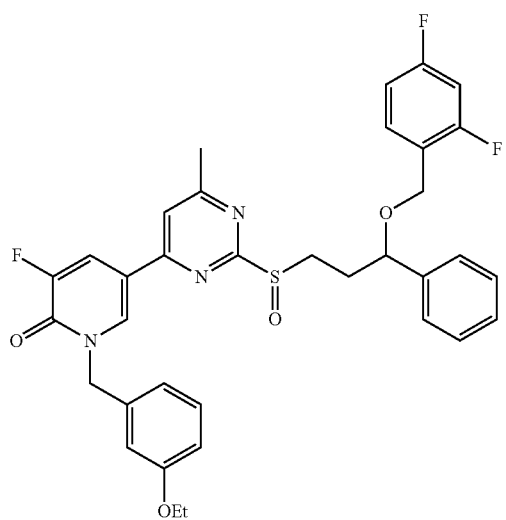 [SMILES: CCOc1cccc(Cn2cc(-c3cc(C)nc(S(=O)CCC(OCc4ccc(F)cc4F)c4ccccc4)n3)cc(F)c2=O)c1]
310

TABLE 4b-continued
SAR optimization:
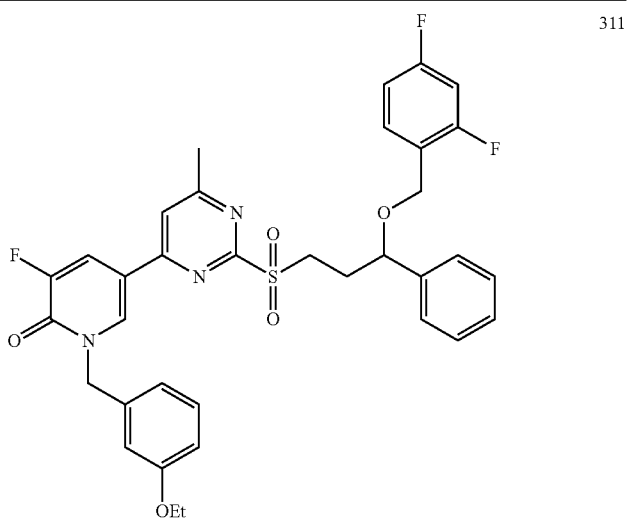
311
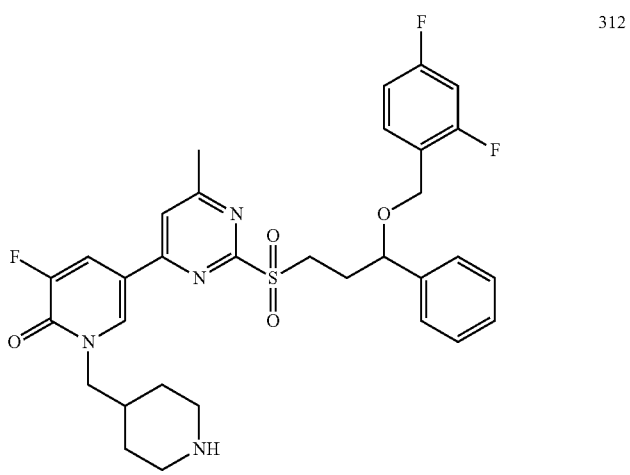
312
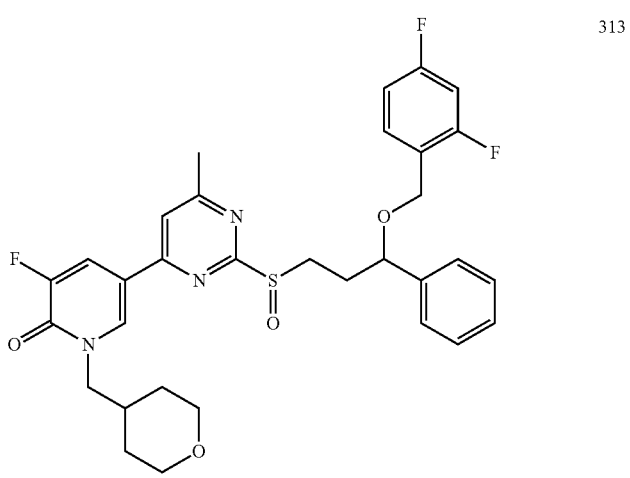
313

TABLE 4b-continued
SAR optimization:
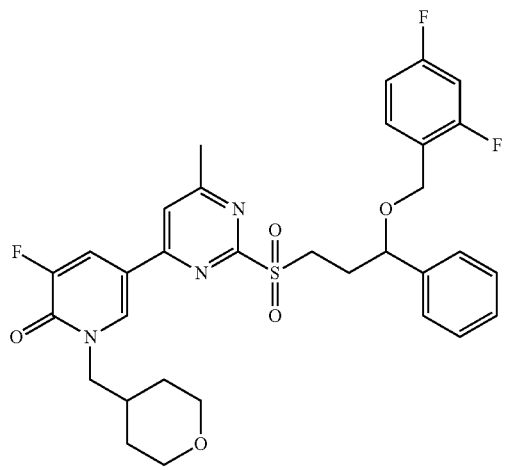 [SMILES: Cc1cc(-c2cc(F)c(=O)n(CC3CCOCC3)c2)nc(S(=O)(=O)CCC(OCc2ccc(F)cc2F)c2ccccc2)n1]
314
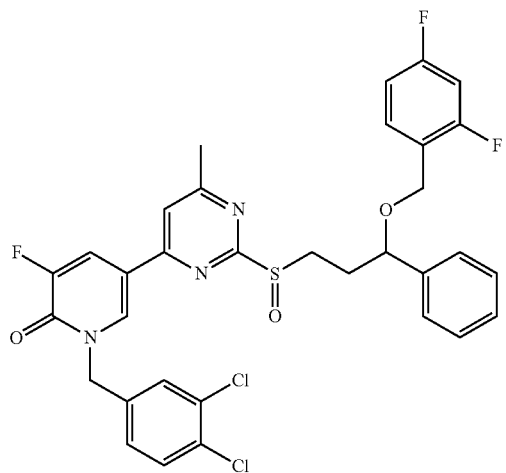 [SMILES: Cc1cc(-c2cc(F)c(=O)n(Cc3ccc(Cl)c(Cl)c3)c2)nc(S(=O)CCC(OCc2ccc(F)cc2F)c2ccccc2)n1]
315
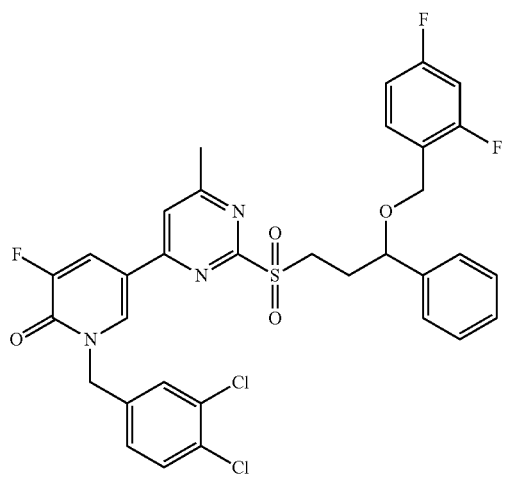 [SMILES: Cc1cc(-c2cc(F)c(=O)n(Cc3ccc(Cl)c(Cl)c3)c2)nc(S(=O)(=O)CCC(OCc2ccc(F)cc2F)c2ccccc2)n1]
316

TABLE 4b-continued
SAR optimization:
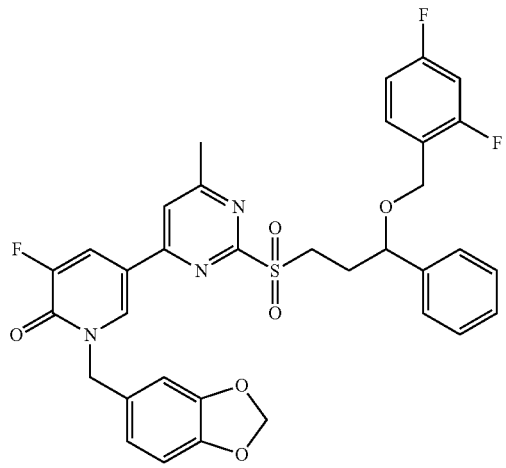 [SMILES: Cc1cc(-c2cc(F)c(=O)n(Cc3ccc4c(c3)OCO4)c2)nc(S(=O)(=O)CCC(OCc2ccc(F)cc2F)c2ccccc2)n1]
317
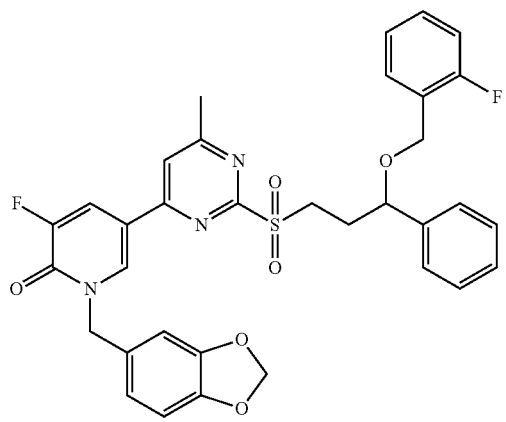 [SMILES: Cc1cc(-c2cc(F)c(=O)n(Cc3ccc4c(c3)OCO4)c2)nc(S(=O)(=O)CCC(OCc2ccccc2F)c2ccccc2)n1]
318
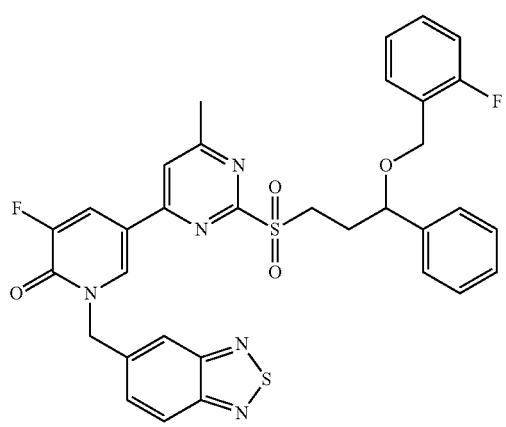 [SMILES: Cc1cc(-c2cc(F)c(=O)n(Cc3ccc4nsnc4c3)c2)nc(S(=O)(=O)CCC(OCc2ccccc2F)c2ccccc2)n1]
319

TABLE 4b-continued
SAR optimization:
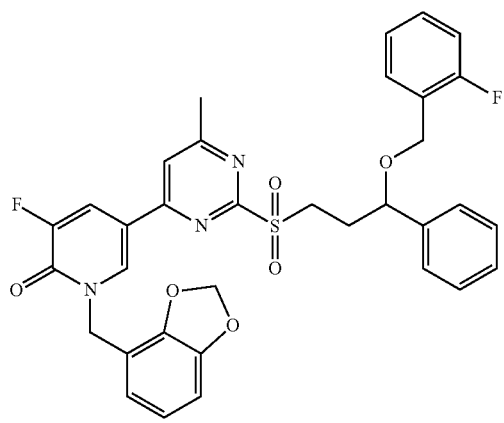 [SMILES: Cc1cc(-c2cc(F)c(=O)n(Cc3cccc4c3OCO4)c2)nc(S(=O)(=O)CCC(OCc2ccccc2F)c2ccccc2)n1]
320
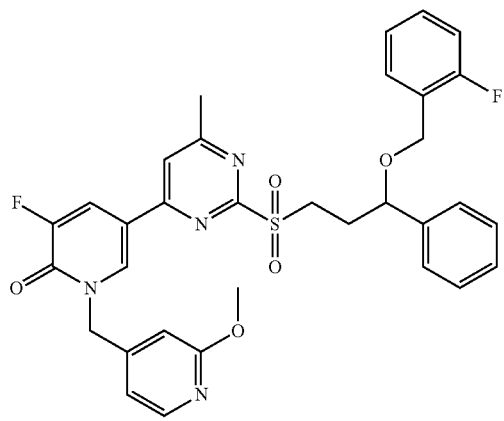 [SMILES: COc1cc(Cn2cc(-c3cc(C)nc(S(=O)(=O)CCC(OCc4ccccc4F)c4ccccc4)n3)cc(F)c2=O)ccn1]
321
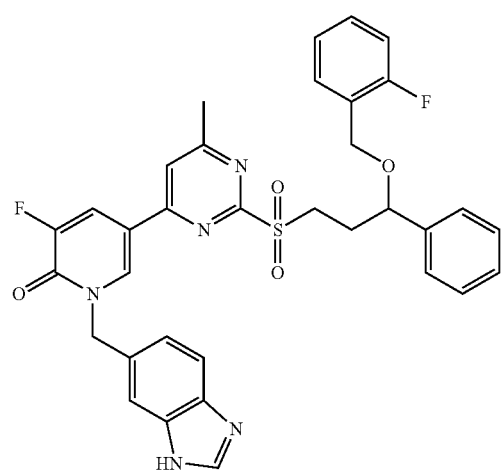 [SMILES: Cc1cc(-c2cc(F)c(=O)n(Cc3ccc4nc[nH]c4c3)c2)nc(S(=O)(=O)CCC(OCc2ccccc2F)c2ccccc2)n1]
322

TABLE 4b-continued
SAR optimization:
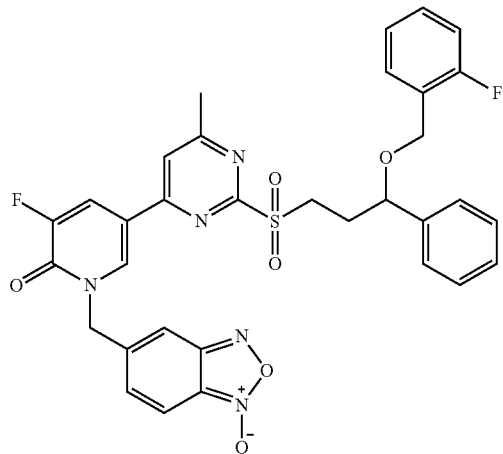 [SMILES: Cc1cc(-c2cc(F)c(=O)n(Cc3ccc4c(c3)no[n+]4[O-])c2)nc(S(=O)(=O)CCC(OCc2ccccc2F)c2ccccc2)n1]
323
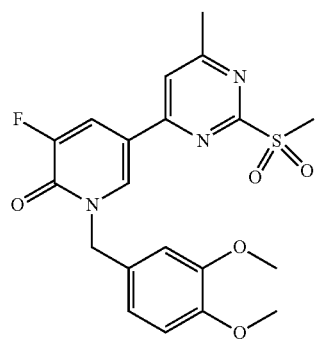 [SMILES: COc1ccc(Cn2cc(-c3cc(C)nc(S(C)(=O)=O)n3)cc(F)c2=O)cc1OC]
324
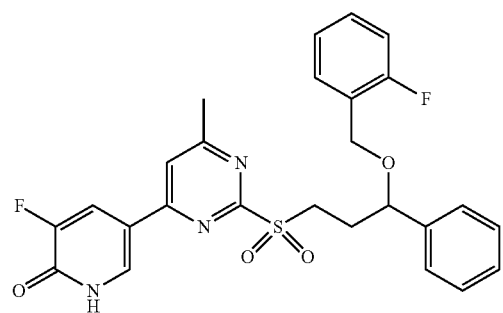 [SMILES: Cc1cc(-c2c[nH]c(=O)c(F)c2)nc(S(=O)(=O)CCC(OCc2ccccc2F)c2ccccc2)n1]
325
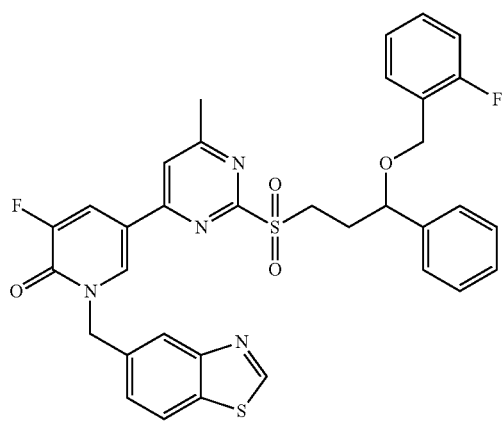 [SMILES: Cc1cc(-c2cc(F)c(=O)n(Cc3ccc4scnc4c3)c2)nc(S(=O)(=O)CCC(OCc2ccccc2F)c2ccccc2)n1]
326

TABLE 4b-continued
SAR optimization:
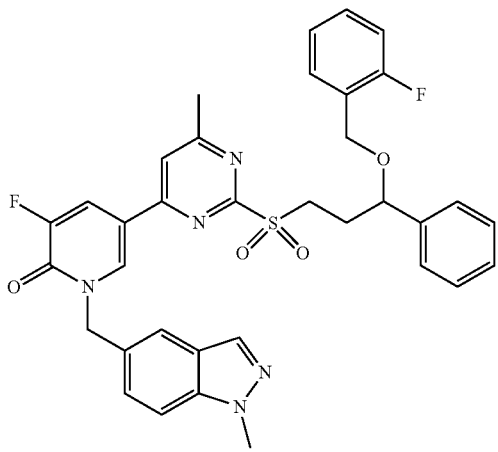 [SMILES: Cc1cc(-c2cc(F)c(=O)n(Cc3ccc4c(cnn4C)c3)c2)nc(S(=O)(=O)CCC(OCc2ccccc2F)c2ccccc2)n1]
327
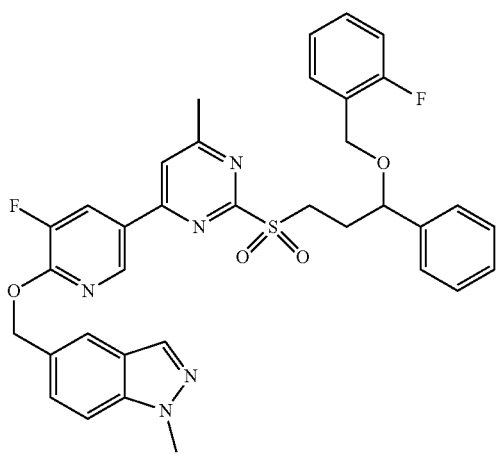 [SMILES: Cc1cc(-c2cnc(OCc3ccc4c(cnn4C)c3)c(F)c2)nc(S(=O)(=O)CCC(OCc2ccccc2F)c2ccccc2)n1]
328
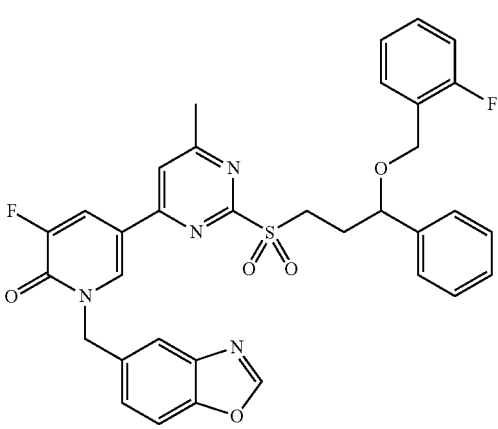 [SMILES: Cc1cc(-c2cc(F)c(=O)n(Cc3ccc4ocnc4c3)c2)nc(S(=O)(=O)CCC(OCc2ccccc2F)c2ccccc2)n1]
329

TABLE 4b-continued
SAR optimization:
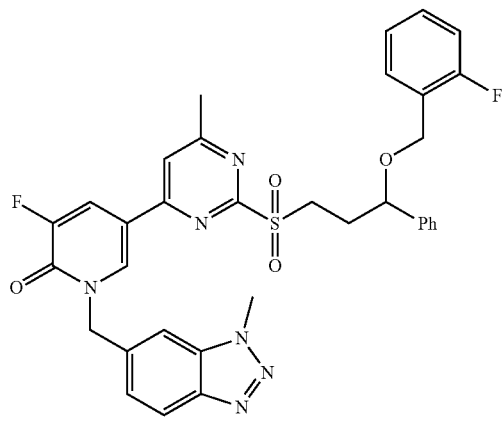 [SMILES: Cc1cc(-c2cc(F)c(=O)n(Cc3ccc4nnn(C)c4c3)c2)nc(S(=O)(=O)CCC(OCc2ccccc2F)c2ccccc2)n1]
330
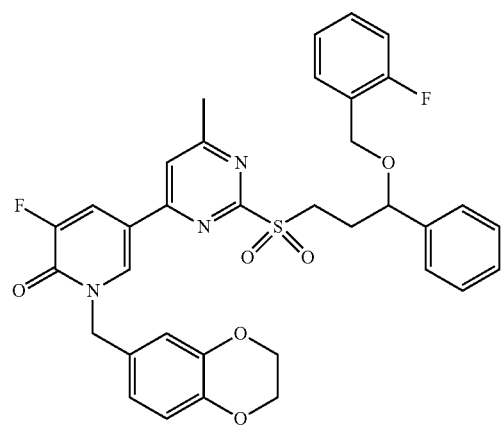 [SMILES: Cc1cc(-c2cc(F)c(=O)n(Cc3ccc4c(c3)OCCO4)c2)nc(S(=O)(=O)CCC(OCc2ccccc2F)c2ccccc2)n1]
331
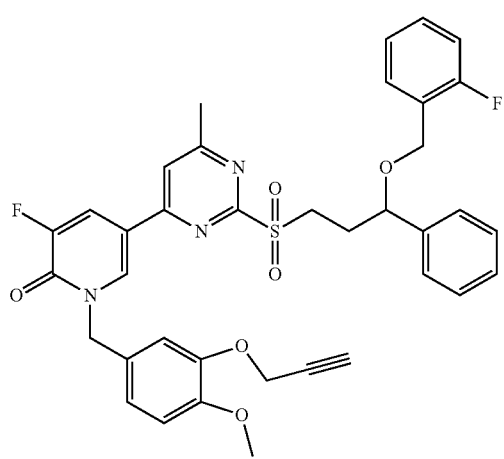 [SMILES: C#CCOc1cc(Cn2cc(-c3cc(C)nc(S(=O)(=O)CCC(OCc4ccccc4F)c4ccccc4)n3)cc(F)c2=O)ccc1OC]
332

TABLE 4b-continued
SAR optimization:
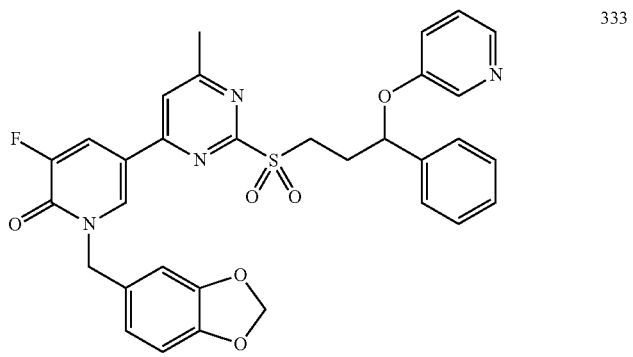
333
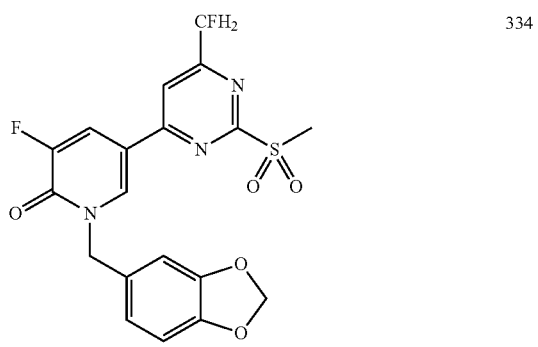
334
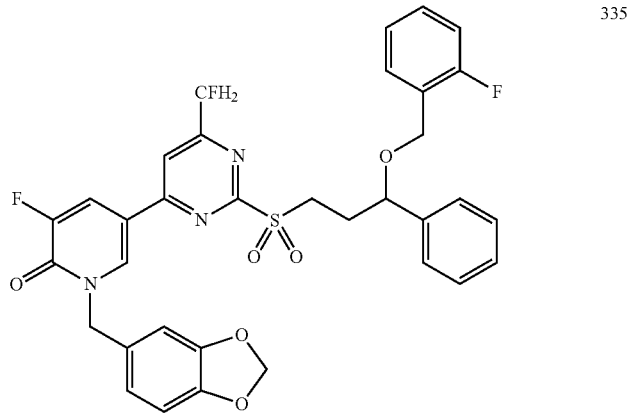
335
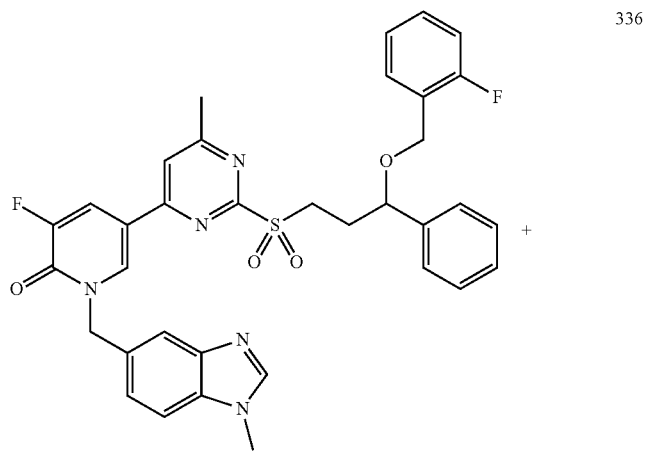
336

TABLE 4b-continued
SAR optimization:
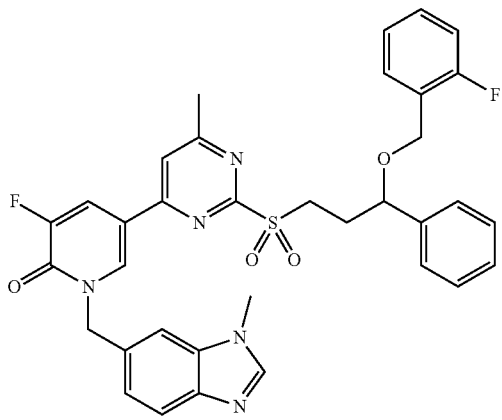 [SMILES: Cc1cc(-c2cc(F)c(=O)n(Cc3ccc4ncn(C)c4c3)c2)nc(S(=O)(=O)CCC(OCc2ccccc2F)c2ccccc2)n1]
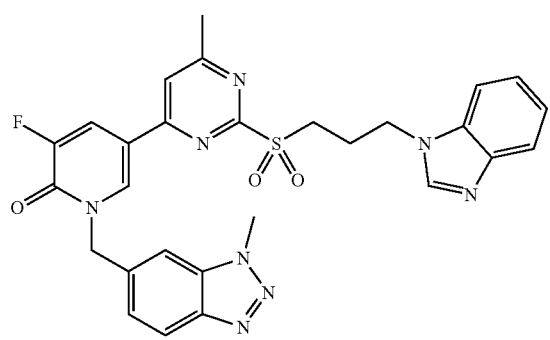 [SMILES: Cc1cc(-c2cc(F)c(=O)n(Cc3ccc4nnn(C)c4c3)c2)nc(S(=O)(=O)CCCn2cnc3ccccc32)n1]
337
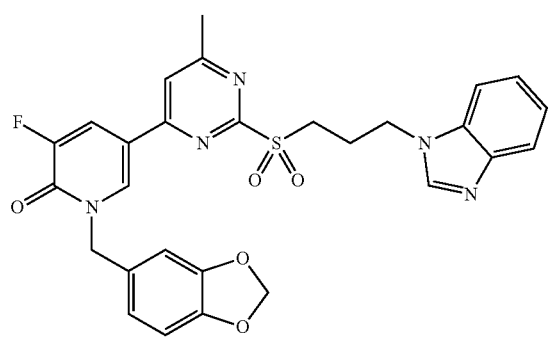 [SMILES: Cc1cc(-c2cc(F)c(=O)n(Cc3ccc4c(c3)OCO4)c2)nc(S(=O)(=O)CCCn2cnc3ccccc32)n1]
338
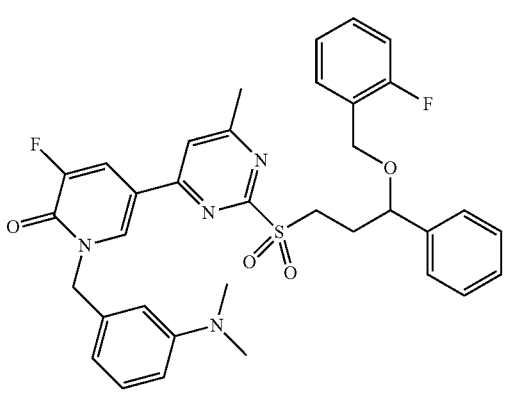 [SMILES: Cc1cc(-c2cc(F)c(=O)n(Cc3cccc(N(C)C)c3)c2)nc(S(=O)(=O)CCC(OCc2ccccc2F)c2ccccc2)n1]
339

TABLE 4b-continued
SAR optimization:
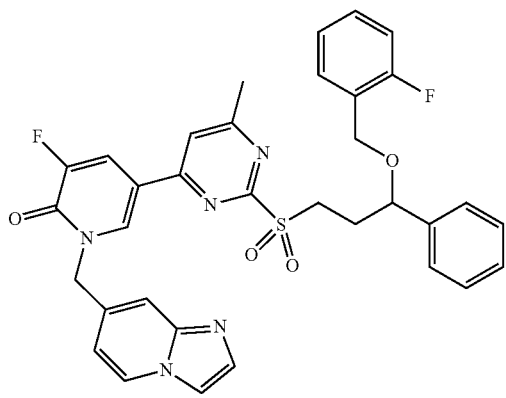 [SMILES: Cc1cc(-c2cc(F)c(=O)n(Cc3ccn4ccnc4c3)c2)nc(S(=O)(=O)CCC(OCc2ccccc2F)c2ccccc2)n1]
340
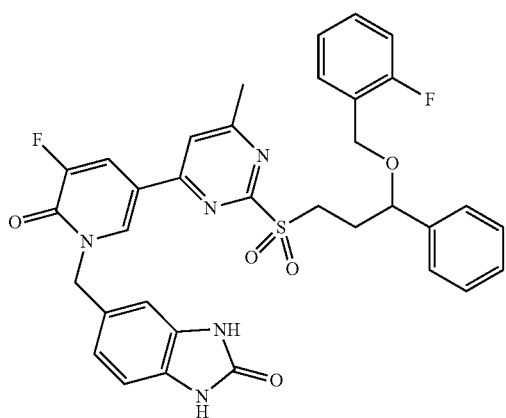 [SMILES: Cc1cc(-c2cc(F)c(=O)n(Cc3ccc4[nH]c(=O)[nH]c4c3)c2)nc(S(=O)(=O)CCC(OCc2ccccc2F)c2ccccc2)n1]
341
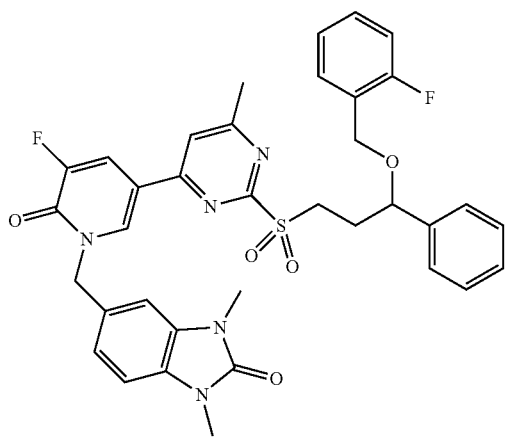 [SMILES: Cc1cc(-c2cc(F)c(=O)n(Cc3ccc4c(c3)n(C)c(=O)n4C)c2)nc(S(=O)(=O)CCC(OCc2ccccc2F)c2ccccc2)n1]
342

TABLE 4b-continued
SAR optimization:
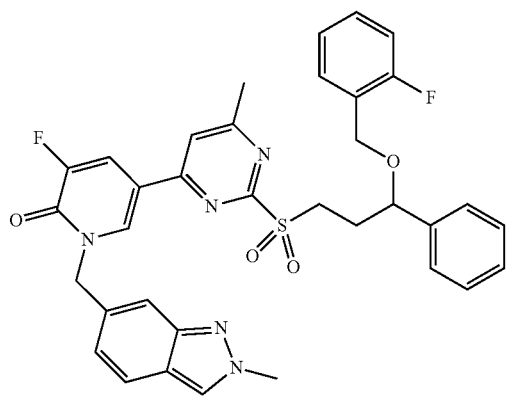 [SMILES: Cc1cc(-c2cc(F)c(=O)n(Cc3ccc4cn(C)nc4c3)c2)nc(S(=O)(=O)CCC(OCc2ccccc2F)c2ccccc2)n1]
343
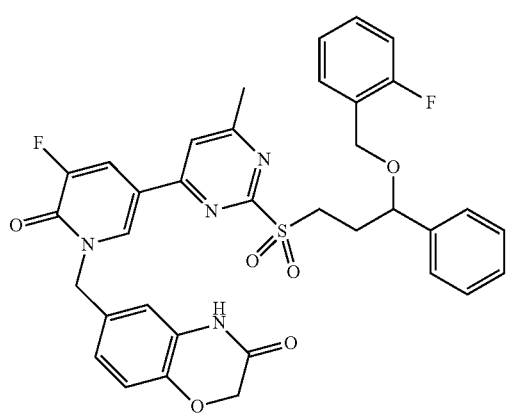 [SMILES: Cc1cc(-c2cc(F)c(=O)n(Cc3ccc4c(c3)NC(=O)CO4)c2)nc(S(=O)(=O)CCC(OCc2ccccc2F)c2ccccc2)n1]
344
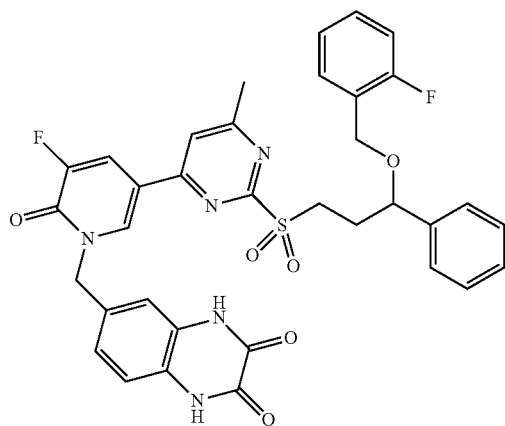 [SMILES: Cc1cc(-c2cc(F)c(=O)n(Cc3ccc4[nH]c(=O)c(=O)[nH]c4c3)c2)nc(S(=O)(=O)CCC(OCc2ccccc2F)c2ccccc2)n1]
345

TABLE 4b-continued
SAR optimization:
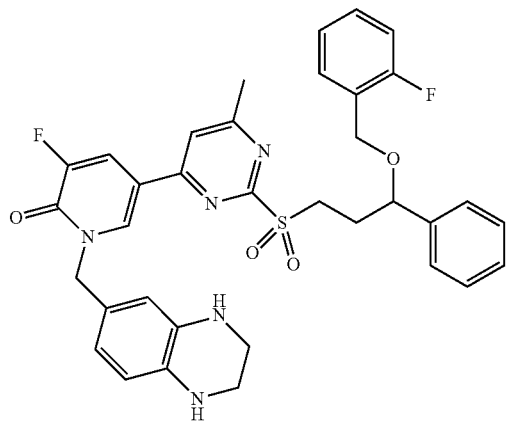 [SMILES: Cc1cc(-c2cc(F)c(=O)n(Cc3ccc4c(c3)NCCN4)c2)nc(S(=O)(=O)CCC(OCc2ccccc2F)c2ccccc2)n1]
346
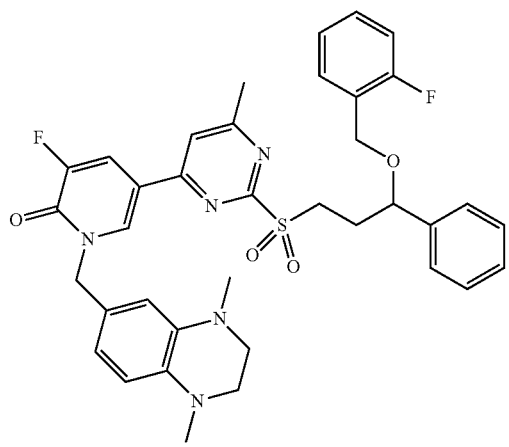 [SMILES: Cc1cc(-c2cc(F)c(=O)n(Cc3ccc4c(c3)N(C)CCN4C)c2)nc(S(=O)(=O)CCC(OCc2ccccc2F)c2ccccc2)n1]
347
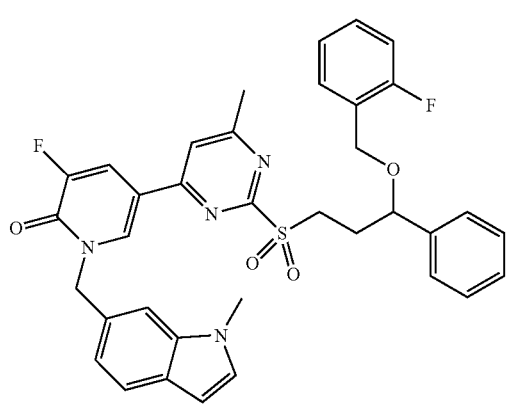 [SMILES: Cc1cc(-c2cc(F)c(=O)n(Cc3ccc4ccn(C)c4c3)c2)nc(S(=O)(=O)CCC(OCc2ccccc2F)c2ccccc2)n1]
348

TABLE 4b-continued
SAR optimization:
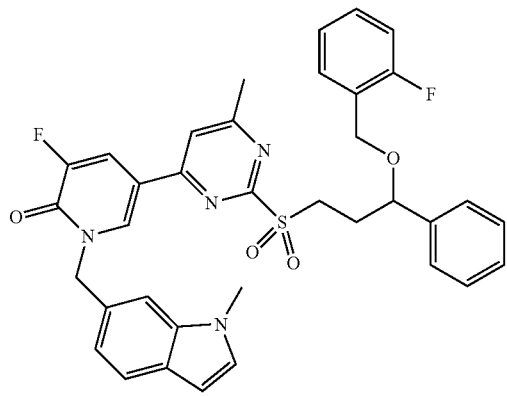 [SMILES: Cc1cc(-c2cc(F)c(=O)n(Cc3ccc4ccn(C)c4c3)c2)nc(S(=O)(=O)CCC(OCc2ccccc2F)c2ccccc2)n1]
349
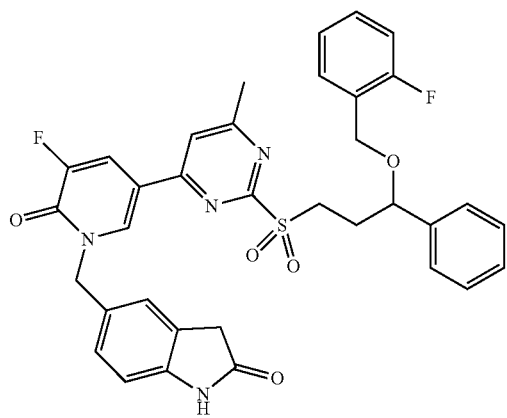 [SMILES: Cc1cc(-c2cc(F)c(=O)n(Cc3ccc4c(c3)CC(=O)N4)c2)nc(S(=O)(=O)CCC(OCc2ccccc2F)c2ccccc2)n1]
350
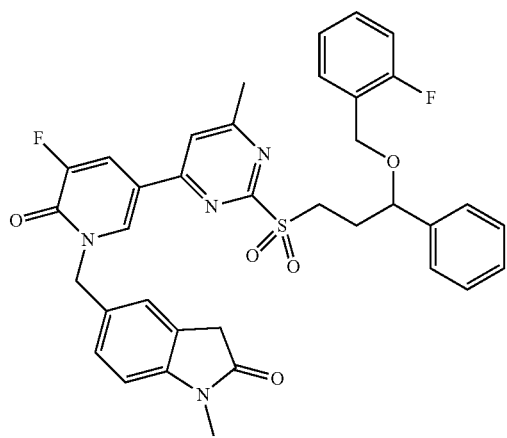 [SMILES: Cc1cc(-c2cc(F)c(=O)n(Cc3ccc4c(c3)CC(=O)N4C)c2)nc(S(=O)(=O)CCC(OCc2ccccc2F)c2ccccc2)n1]
351

TABLE 4b-continued
SAR optimization:
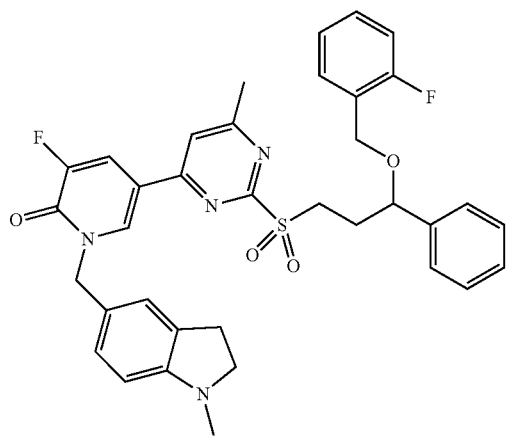 [SMILES: Cc1cc(-c2cc(F)c(=O)n(Cc3ccc4c(c3)CCN4C)c2)nc(S(=O)(=O)CCC(OCc2ccccc2F)c2ccccc2)n1]
352
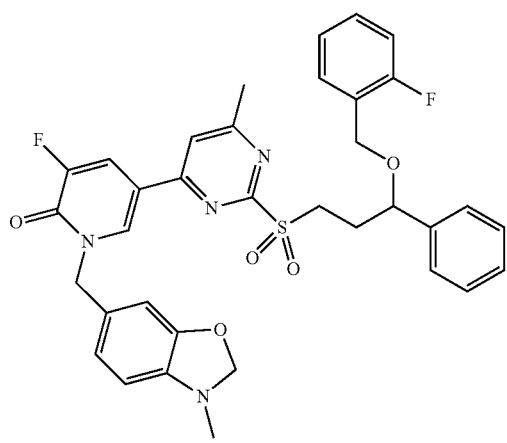 [SMILES: Cc1cc(-c2cc(F)c(=O)n(Cc3ccc4c(c3)OCN4C)c2)nc(S(=O)(=O)CCC(OCc2ccccc2F)c2ccccc2)n1]
353
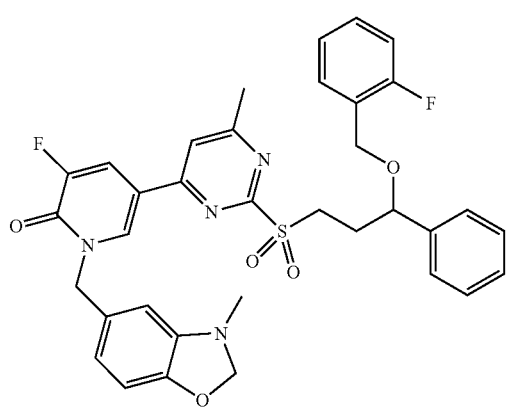 [SMILES: Cc1cc(-c2cc(F)c(=O)n(Cc3ccc4c(c3)N(C)CO4)c2)nc(S(=O)(=O)CCC(OCc2ccccc2F)c2ccccc2)n1]
354

TABLE 4b-continued
SAR optimization:
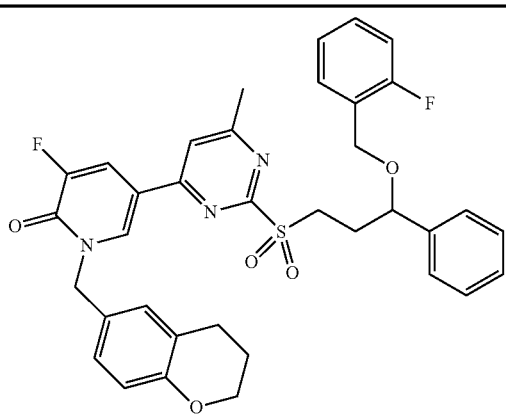
355
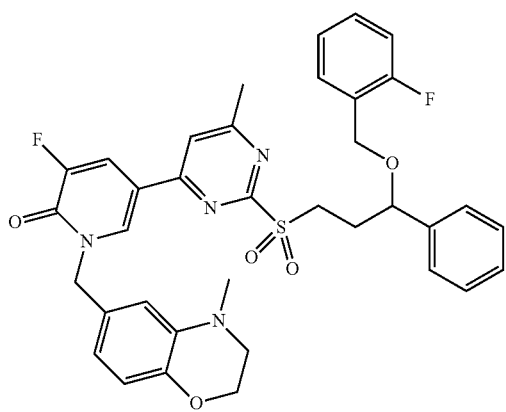 [SMILES: Cc1cc(-c2cc(F)c(=O)n(Cc3ccc4c(c3)N(C)CCO4)c2)nc(S(=O)(=O)CCC(OCc2ccccc2F)c2ccccc2)n1]
356
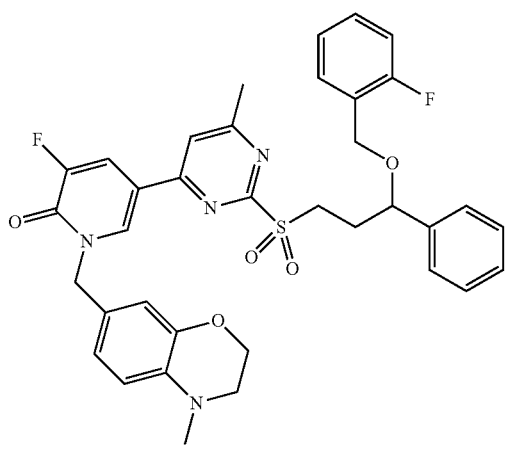 [SMILES: Cc1cc(-c2cc(F)c(=O)n(Cc3ccc4c(c3)OCCN4C)c2)nc(S(=O)(=O)CCC(OCc2ccccc2F)c2ccccc2)n1]
357

TABLE 4b-continued
SAR optimization:
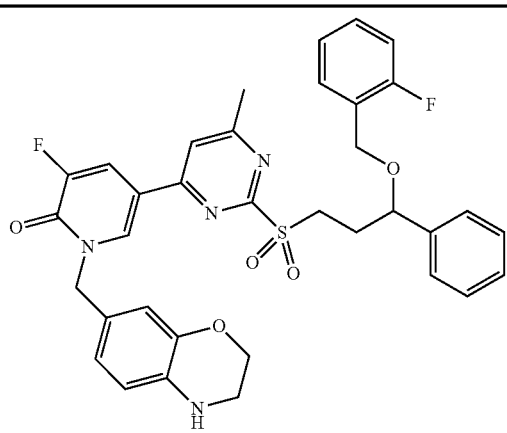
358
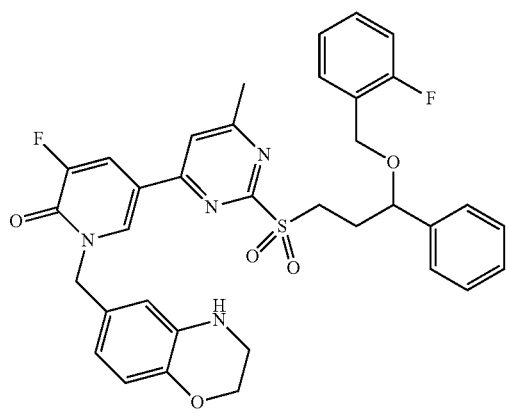
359
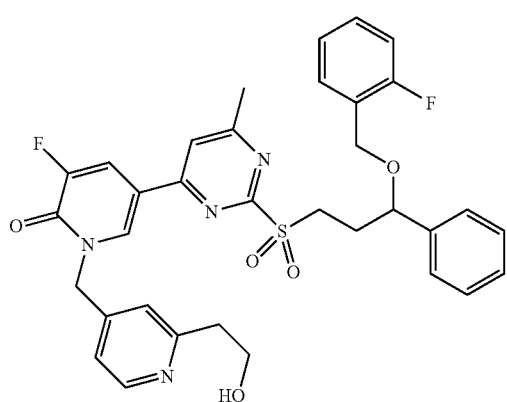 [SMILES: Cc1cc(-c2cc(F)c(=O)n(Cc3ccnc(CCO)c3)c2)nc(S(=O)(=O)CCC(OCc2ccccc2F)c2ccccc2)n1]
360

TABLE 4b-continued
SAR optimization:
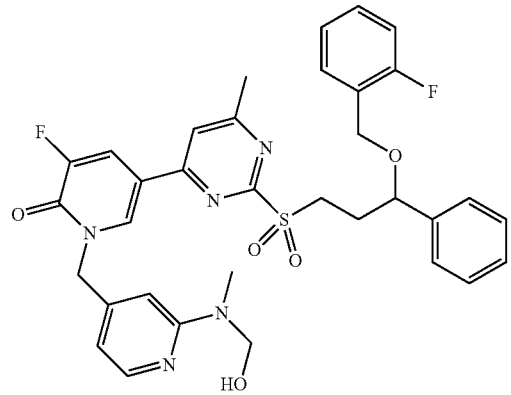 [SMILES: Cc1cc(-c2cc(F)c(=O)n(Cc3ccnc(N(C)CO)c3)c2)nc(S(=O)(=O)CCC(OCc2ccccc2F)c2ccccc2)n1]
361
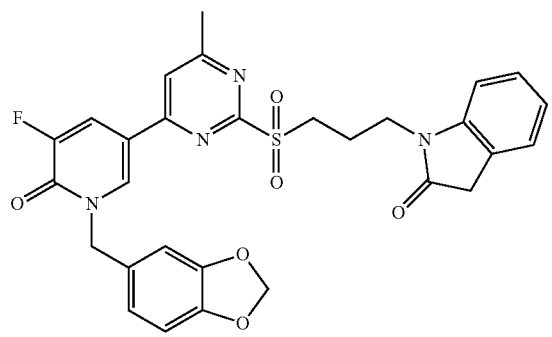
362
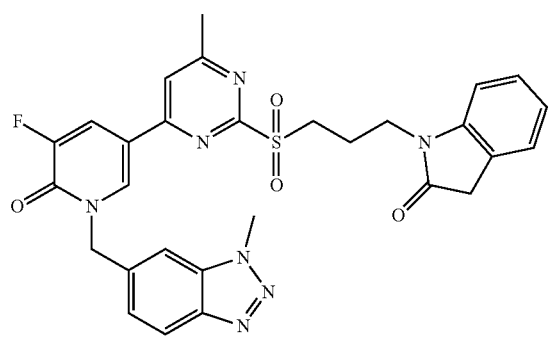 [SMILES: Cc1cc(-c2cc(F)c(=O)n(Cc3ccc4nnn(C)c4c3)c2)nc(S(=O)(=O)CCCN2C(=O)Cc3ccccc32)n1]
363
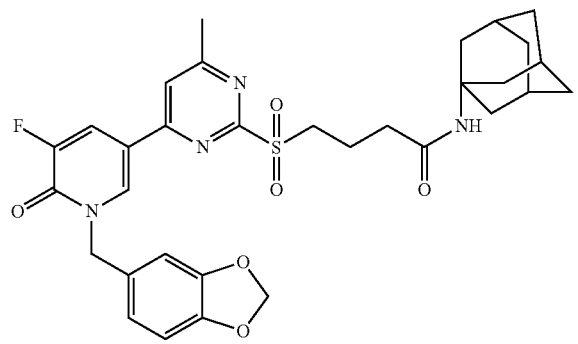 [SMILES: Cc1cc(-c2cc(F)c(=O)n(Cc3ccc4c(c3)OCO4)c2)nc(S(=O)(=O)CCCC(=O)NC23CC4CC(CC(C4)C2)C3)n1]
364

TABLE 4b-continued
SAR optimization:
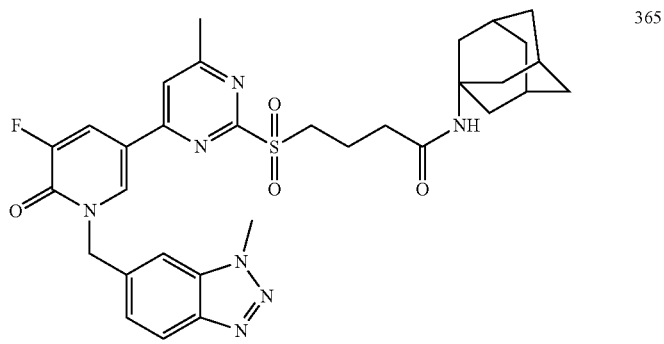
365
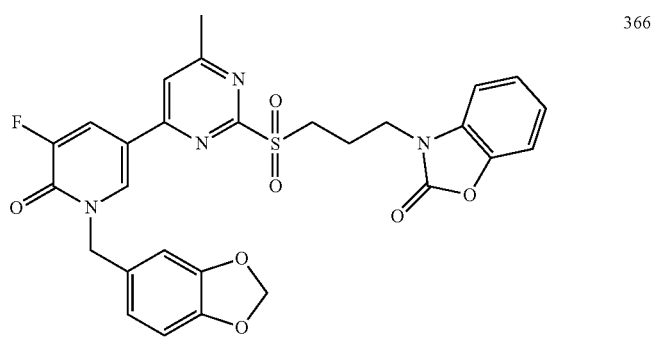
366
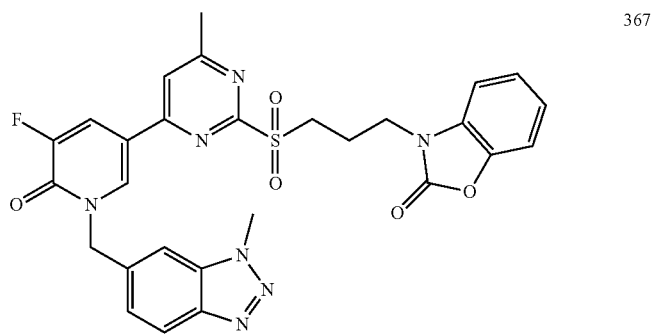
367
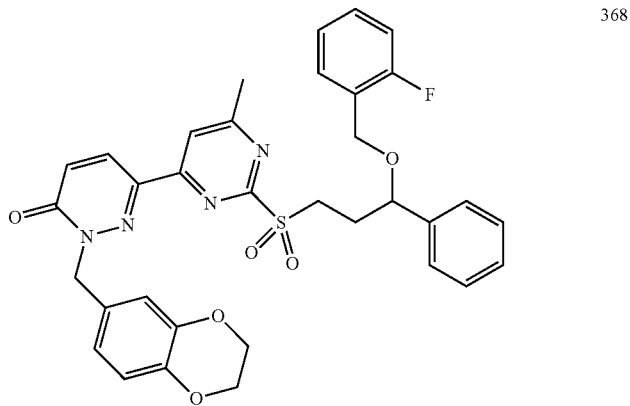
368

TABLE 4b-continued
SAR optimization:
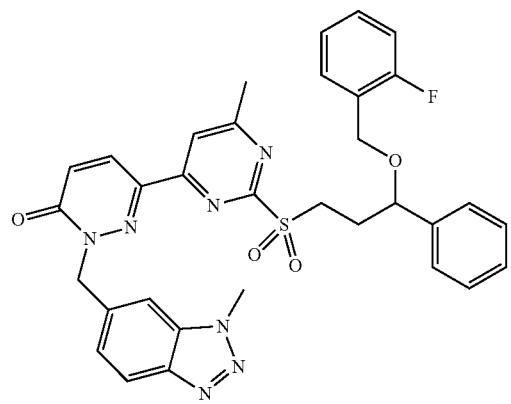 [SMILES: Cc1cc(-c2ccc(=O)n(Cc3ccc4nnn(C)c4c3)n2)nc(S(=O)(=O)CCC(OCc2ccccc2F)c2ccccc2)n1]
369
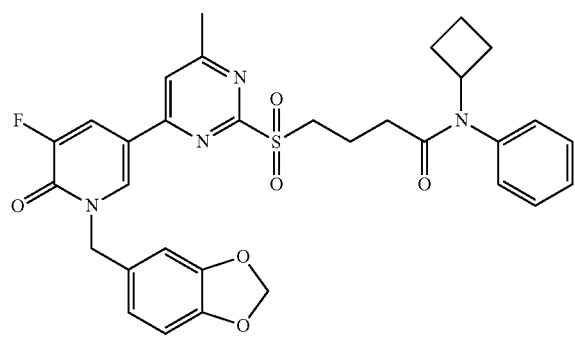 [SMILES: Cc1cc(-c2cc(F)c(=O)n(Cc3ccc4c(c3)OCO4)c2)nc(S(=O)(=O)CCCC(=O)N(c2ccccc2)C2CCC2)n1]
370
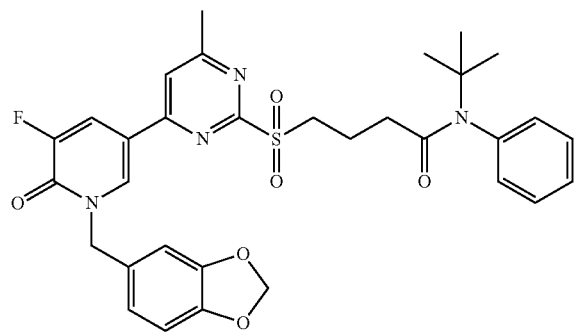 [SMILES: Cc1cc(-c2cc(F)c(=O)n(Cc3ccc4c(c3)OCO4)c2)nc(S(=O)(=O)CCCC(=O)N(c2ccccc2)C(C)(C)C)n1]
371
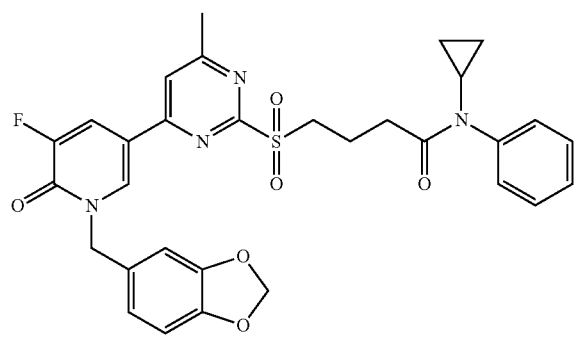 [SMILES: Cc1cc(-c2cc(F)c(=O)n(Cc3ccc4c(c3)OCO4)c2)nc(S(=O)(=O)CCCC(=O)N(c2ccccc2)C2CC2)n1]
372

TABLE 4b-continued
SAR optimization:
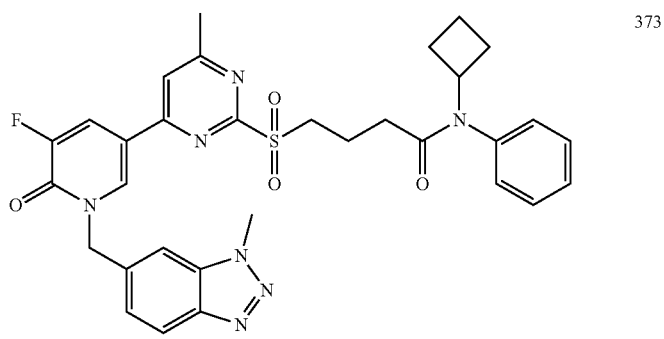
373
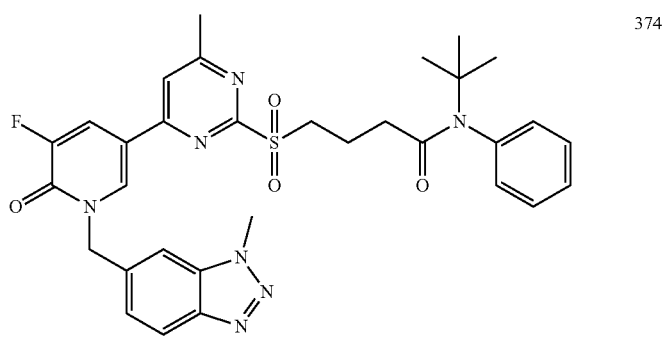
374
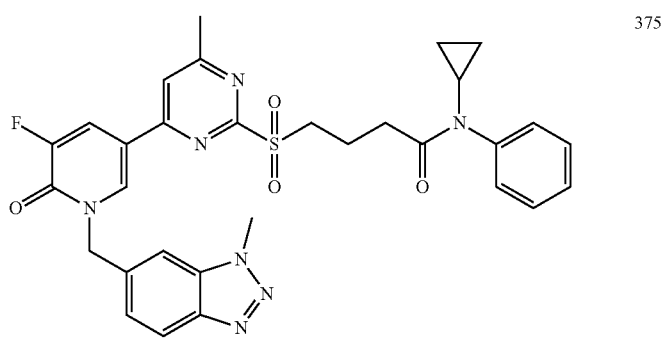
375
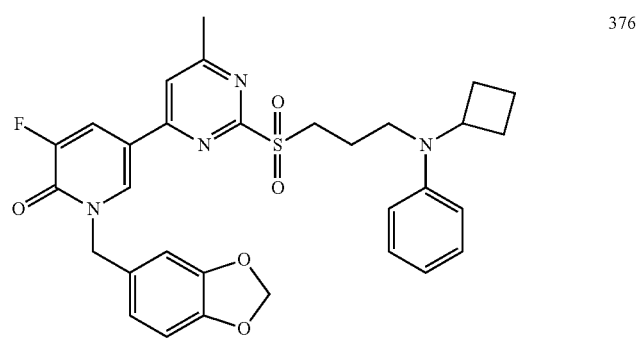
376

TABLE 4b-continued
SAR optimization:
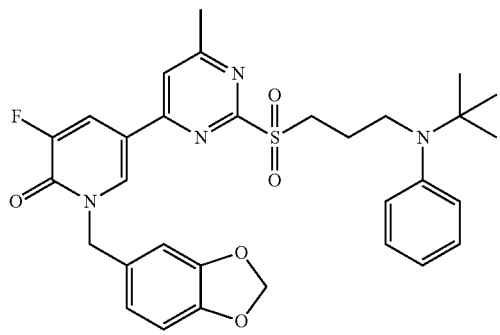 [SMILES: Cc1cc(-c2cc(F)c(=O)n(Cc3ccc4c(c3)OCO4)c2)nc(S(=O)(=O)CCCN(c2ccccc2)C(C)(C)C)n1]
377
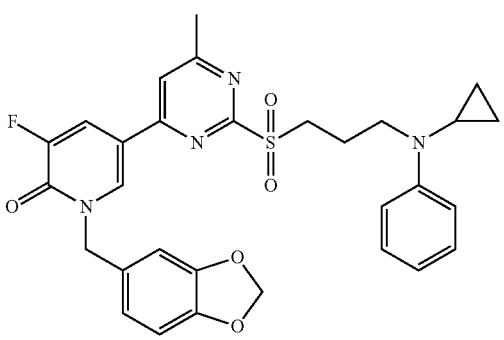 [SMILES: Cc1cc(-c2cc(F)c(=O)n(Cc3ccc4c(c3)OCO4)c2)nc(S(=O)(=O)CCCN(c2ccccc2)C2CC2)n1]
378
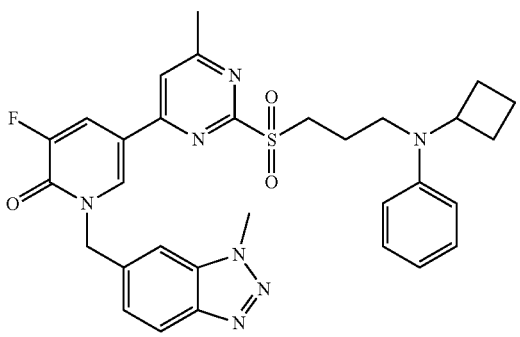 [SMILES: Cc1cc(-c2cc(F)c(=O)n(Cc3ccc4nnn(C)c4c3)c2)nc(S(=O)(=O)CCCN(c2ccccc2)C2CCC2)n1]
379
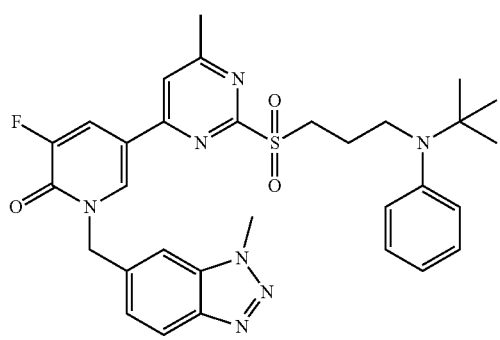 [SMILES: Cc1cc(-c2cc(F)c(=O)n(Cc3ccc4nnn(C)c4c3)c2)nc(S(=O)(=O)CCCN(c2ccccc2)C(C)(C)C)n1]
380

TABLE 4b-continued
SAR optimization:
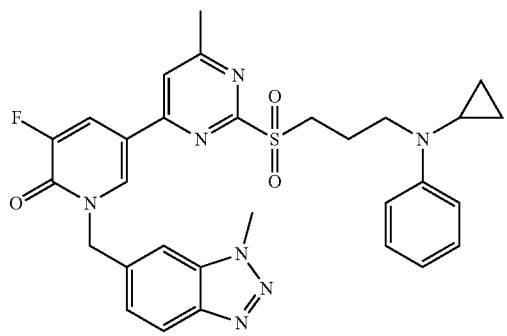
381
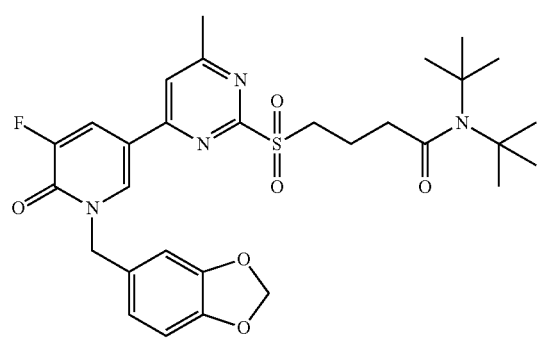 [SMILES: Cc1cc(-c2cc(F)c(=O)n(Cc3ccc4c(c3)OCO4)c2)nc(S(=O)(=O)CCCC(=O)N(C(C)(C)C)C(C)(C)C)n1]
382
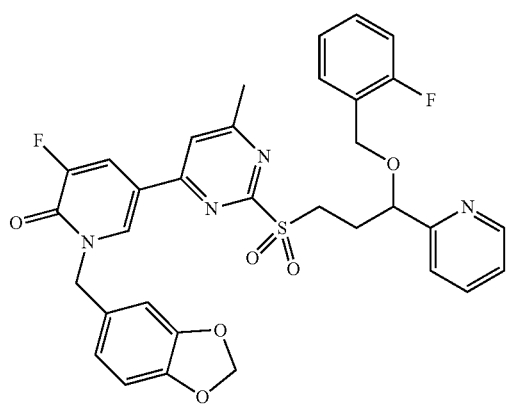 [SMILES: Cc1cc(-c2cc(F)c(=O)n(Cc3ccc4c(c3)OCO4)c2)nc(S(=O)(=O)CCC(OCc2ccccc2F)c2ccccn2)n1]
383
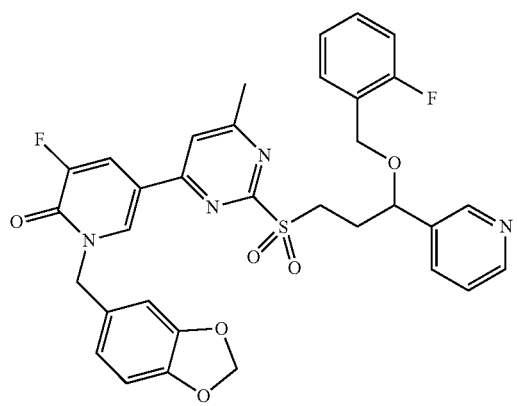 [SMILES: Cc1cc(-c2cc(F)c(=O)n(Cc3ccc4c(c3)OCO4)c2)nc(S(=O)(=O)CCC(OCc2ccccc2F)c2cccnc2)n1]
384

153
154
TABLE 4b-continued
SAR optimization:
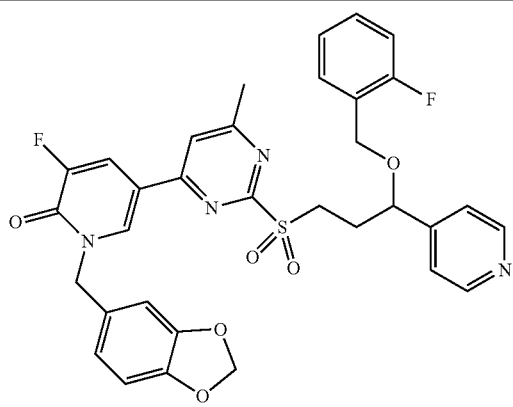
385
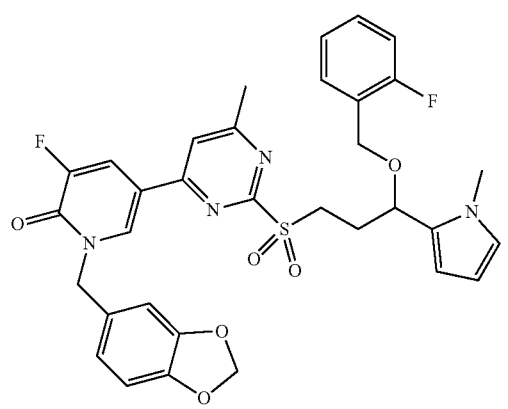 [SMILES: Cc1cc(-c2cc(F)c(=O)n(Cc3ccc4c(c3)OCO4)c2)nc(S(=O)(=O)CCC(OCc2ccccc2F)c2cccn2C)n1]
386
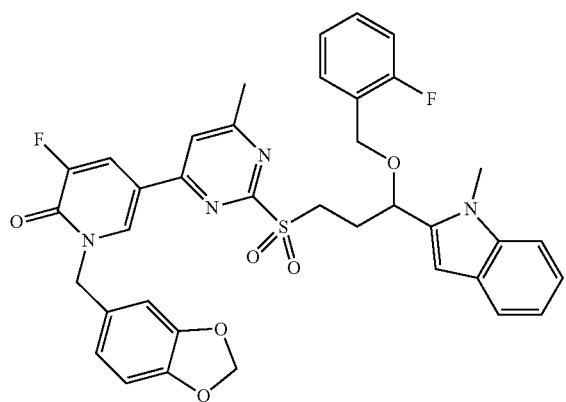 [SMILES: Cc1cc(-c2cc(F)c(=O)n(Cc3ccc4c(c3)OCO4)c2)nc(S(=O)(=O)CCC(OCc2ccccc2F)c2cc3ccccc3n2C)n1]
387
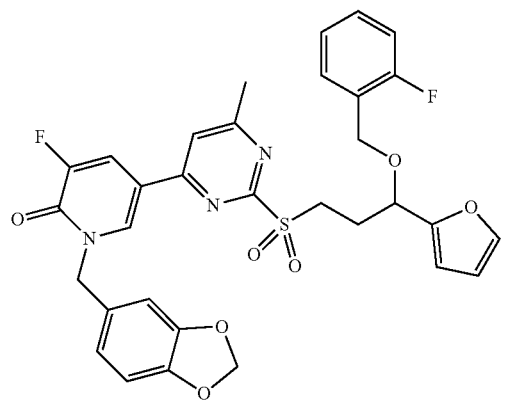
388

TABLE 4b-continued
SAR optimization:
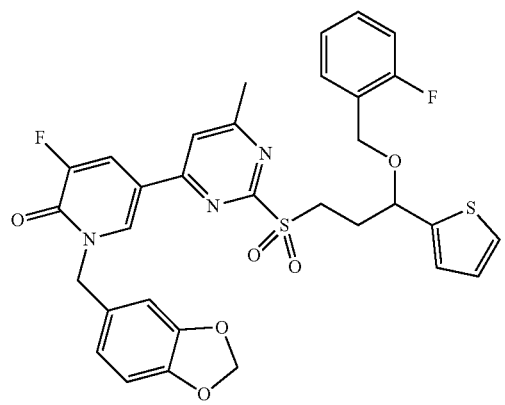 [SMILES: Cc1cc(-c2cc(F)c(=O)n(Cc3ccc4c(c3)OCO4)c2)nc(S(=O)(=O)CCC(OCc2ccccc2F)c2cccs2)n1]
389
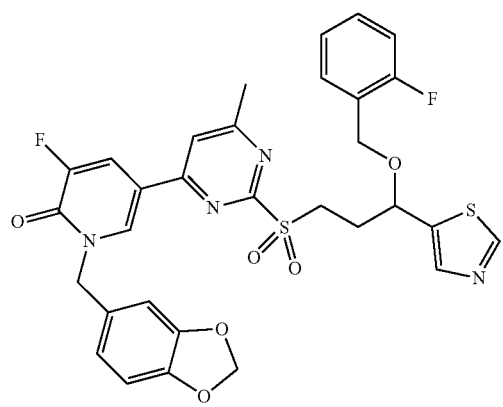 [SMILES: Cc1cc(-c2cc(F)c(=O)n(Cc3ccc4c(c3)OCO4)c2)nc(S(=O)(=O)CCC(OCc2ccccc2F)c2cncs2)n1]
390
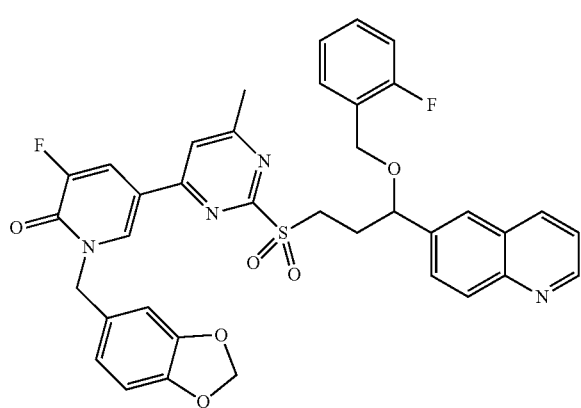 [SMILES: Cc1cc(-c2cc(F)c(=O)n(Cc3ccc4c(c3)OCO4)c2)nc(S(=O)(=O)CCC(OCc2ccccc2F)c2ccc3ncccc3c2)n1]
391

TABLE 4b-continued
SAR optimization:
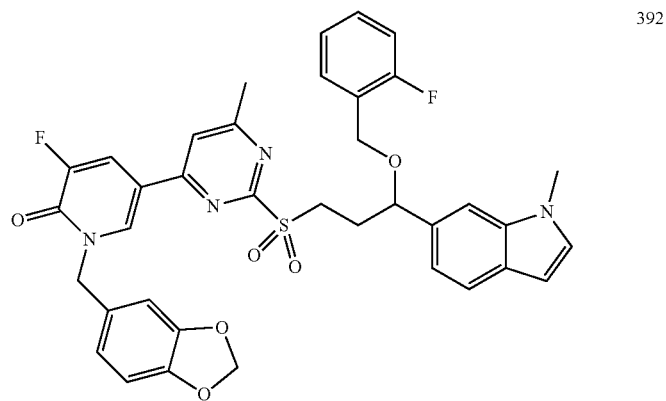
392
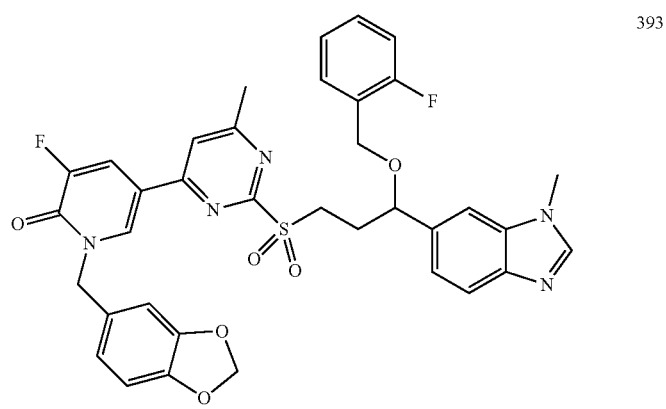
393
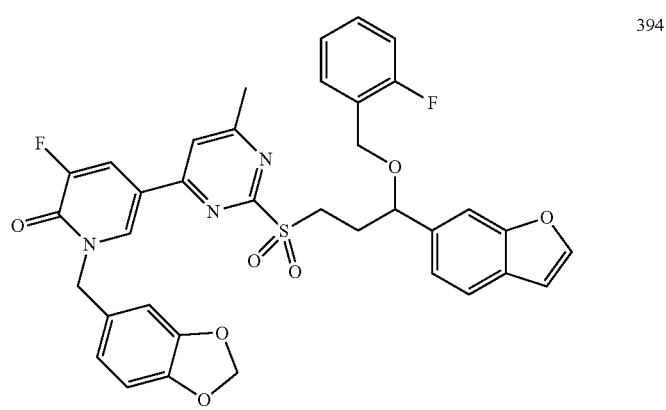
394
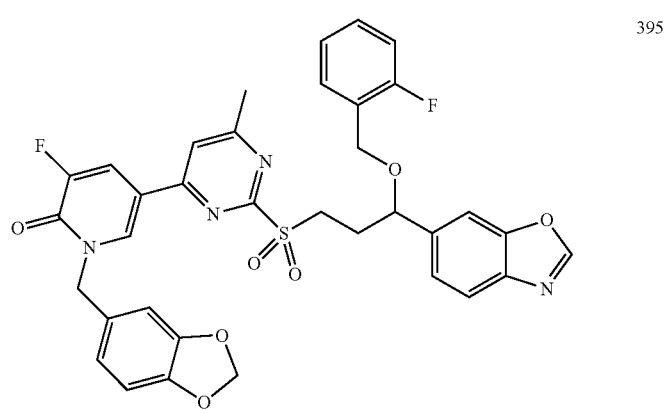
395

TABLE 4b-continued
SAR optimization:
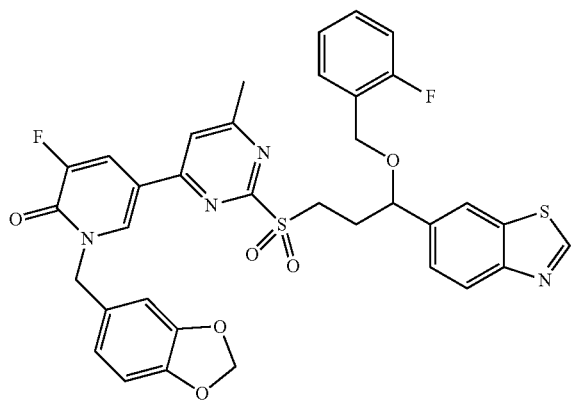 [SMILES: Cc1cc(-c2cc(F)c(=O)n(Cc3ccc4c(c3)OCO4)c2)nc(S(=O)(=O)CCC(OCc2ccccc2F)c2ccc3ncsc3c2)n1]
396
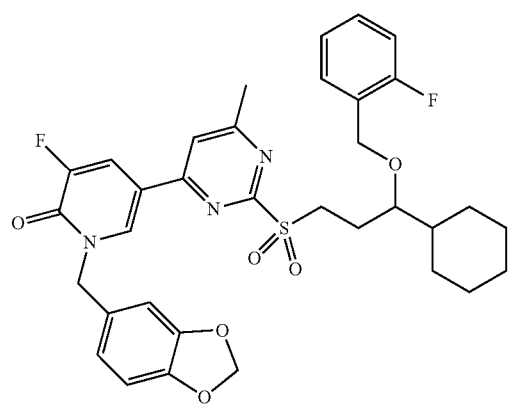 [SMILES: Cc1cc(-c2cc(F)c(=O)n(Cc3ccc4c(c3)OCO4)c2)nc(S(=O)(=O)CCC(OCc2ccccc2F)C2CCCCC2)n1]
397
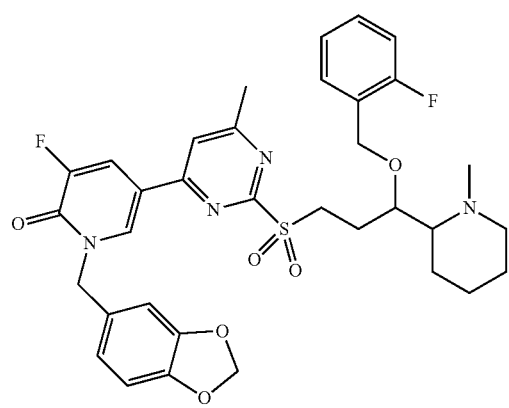 [SMILES: Cc1cc(-c2cc(F)c(=O)n(Cc3ccc4c(c3)OCO4)c2)nc(S(=O)(=O)CCC(OCc2ccccc2F)C2CCCCN2C)n1]
398

161
TABLE 4b-continued
SAR optimization:
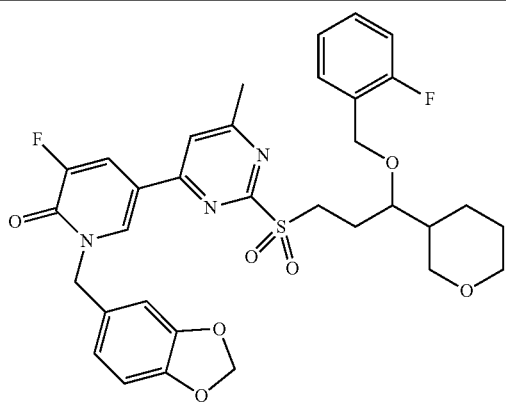
399
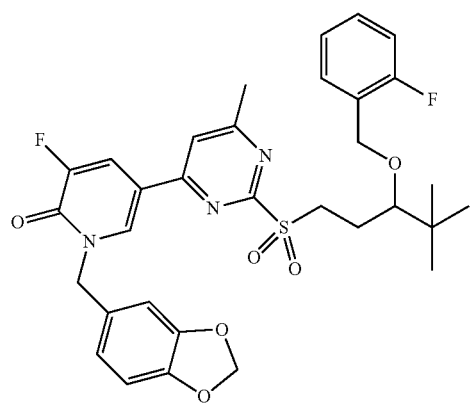 [SMILES: Cc1cc(-c2cc(F)c(=O)n(Cc3ccc4c(c3)OCO4)c2)nc(S(=O)(=O)CCC(OCc2ccccc2F)C(C)(C)C)n1]
400
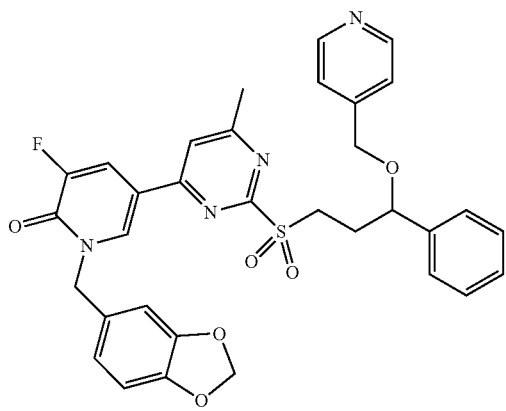 [SMILES: Cc1cc(-c2cc(F)c(=O)n(Cc3ccc4c(c3)OCO4)c2)nc(S(=O)(=O)CCC(OCc2ccncc2)c2ccccc2)n1]
401
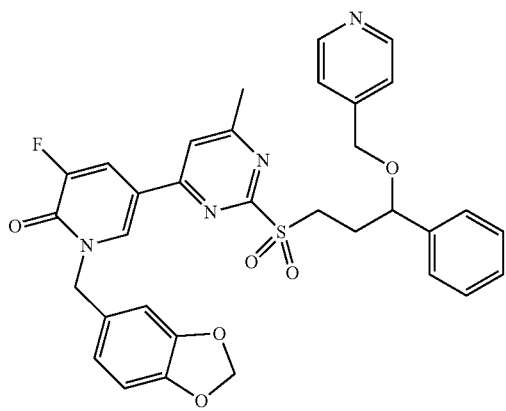 [SMILES: Cc1cc(-c2cc(F)c(=O)n(Cc3ccc4c(c3)OCO4)c2)nc(S(=O)(=O)CCC(OCc2ccncc2)c2ccccc2)n1]
402

TABLE 4b-continued
SAR optimization:
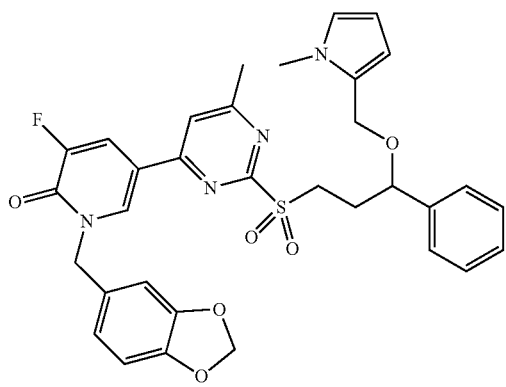 [SMILES: Cc1cc(-c2cc(F)c(=O)n(Cc3ccc4c(c3)OCO4)c2)nc(S(=O)(=O)CCC(OCc2cccn2C)c2ccccc2)n1]
403
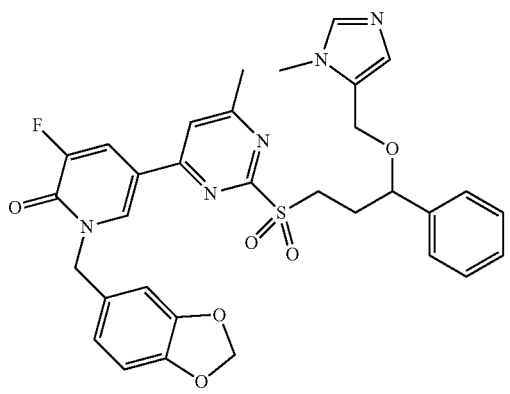 [SMILES: Cc1cc(-c2cc(F)c(=O)n(Cc3ccc4c(c3)OCO4)c2)nc(S(=O)(=O)CCC(OCc2cncn2C)c2ccccc2)n1]
404
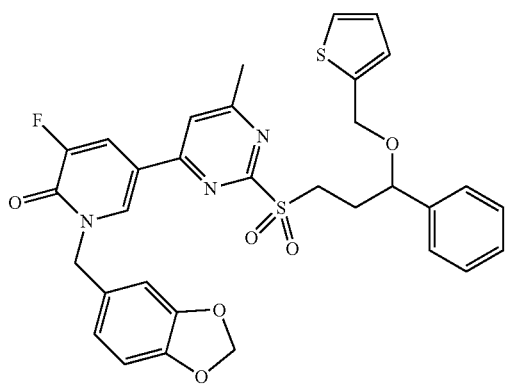 [SMILES: Cc1cc(-c2cc(F)c(=O)n(Cc3ccc4c(c3)OCO4)c2)nc(S(=O)(=O)CCC(OCc2cccs2)c2ccccc2)n1]
405
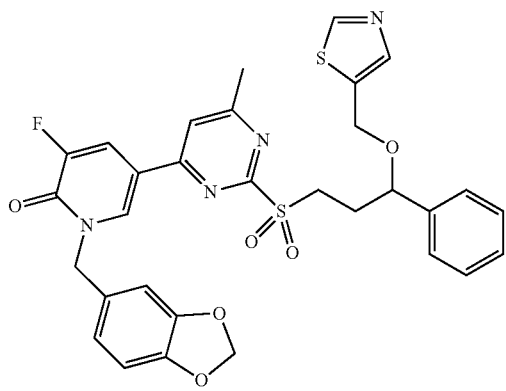 [SMILES: Cc1cc(-c2cc(F)c(=O)n(Cc3ccc4c(c3)OCO4)c2)nc(S(=O)(=O)CCC(OCc2cncs2)c2ccccc2)n1]
406

TABLE 4b-continued
SAR optimization:
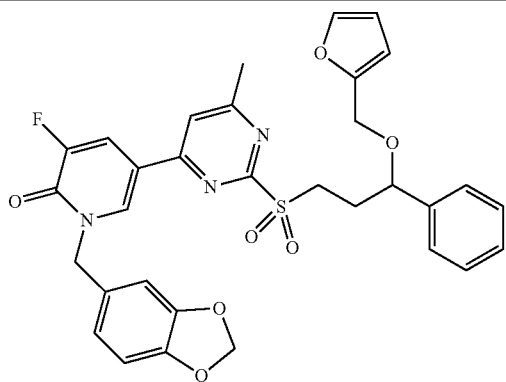
407
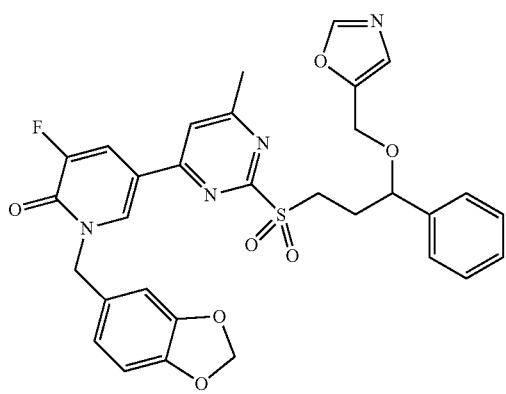 [SMILES: Cc1cc(-c2cc(F)c(=O)n(Cc3ccc4c(c3)OCO4)c2)nc(S(=O)(=O)CCC(OCc2cnco2)c2ccccc2)n1]
408
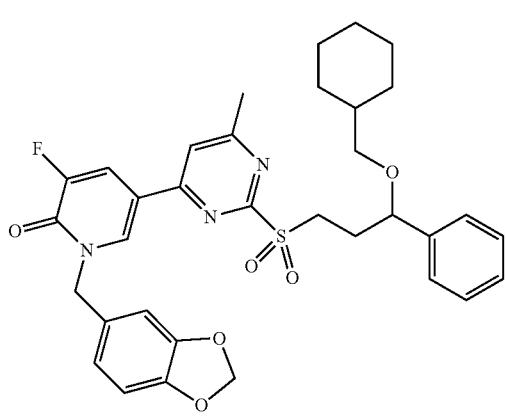 [SMILES: Cc1cc(-c2cc(F)c(=O)n(Cc3ccc4c(c3)OCO4)c2)nc(S(=O)(=O)CCC(OCC2CCCCC2)c2ccccc2)n1]
409
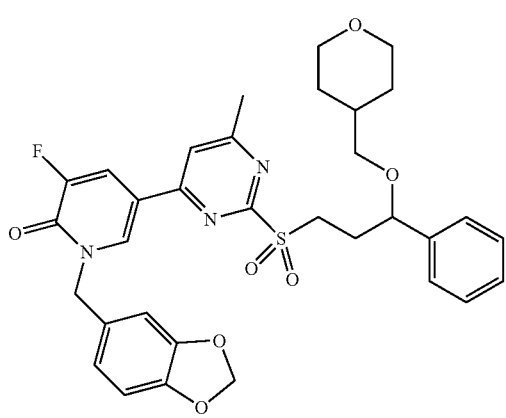 [SMILES: Cc1cc(-c2cc(F)c(=O)n(Cc3ccc4c(c3)OCO4)c2)nc(S(=O)(=O)CCC(OCC2CCOCC2)c2ccccc2)n1]
410

TABLE 4b-continued
SAR optimization:
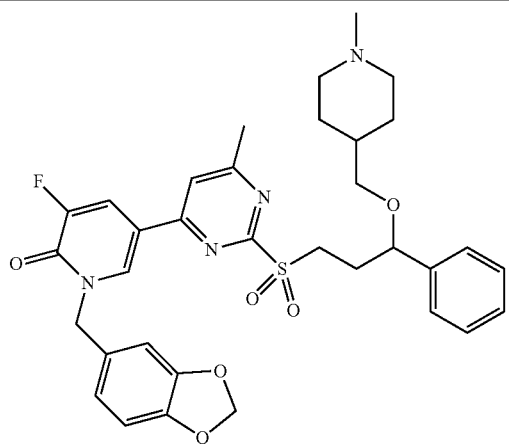
411
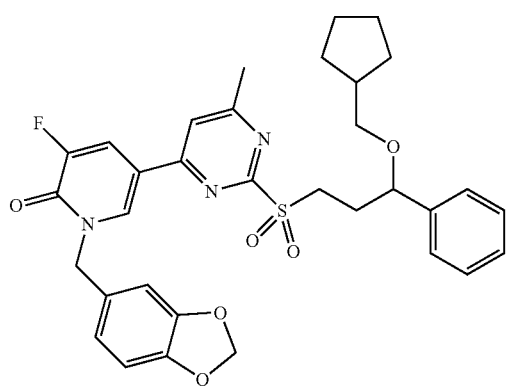 [SMILES: Cc1cc(-c2cc(F)c(=O)n(Cc3ccc4c(c3)OCO4)c2)nc(S(=O)(=O)CCC(OCC2CCCC2)c2ccccc2)n1]
412
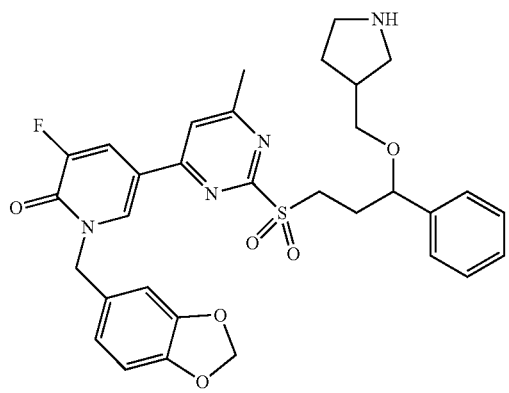 [SMILES: Cc1cc(-c2cc(F)c(=O)n(Cc3ccc4c(c3)OCO4)c2)nc(S(=O)(=O)CCC(OCC2CCNC2)c2ccccc2)n1]
413
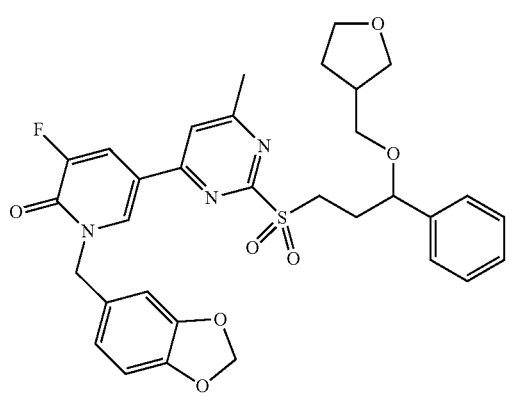 [SMILES: Cc1cc(-c2cc(F)c(=O)n(Cc3ccc4c(c3)OCO4)c2)nc(S(=O)(=O)CCC(OCC2CCOC2)c2ccccc2)n1]
414

TABLE 4b-continued
SAR optimization:
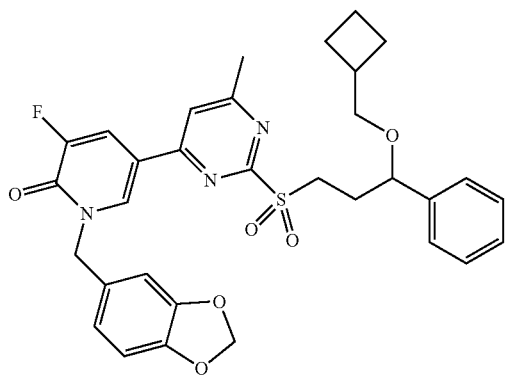 [SMILES: Cc1cc(-c2cc(F)c(=O)n(Cc3ccc4c(c3)OCO4)c2)nc(S(=O)(=O)CCC(OCC2CCC2)c2ccccc2)n1]
415
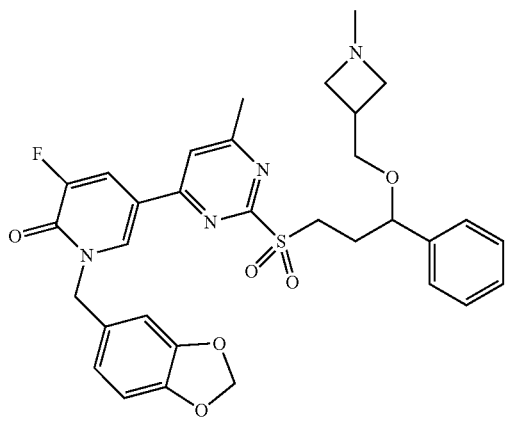 [SMILES: Cc1cc(-c2cc(F)c(=O)n(Cc3ccc4c(c3)OCO4)c2)nc(S(=O)(=O)CCC(OCC2CN(C)C2)c2ccccc2)n1]
416
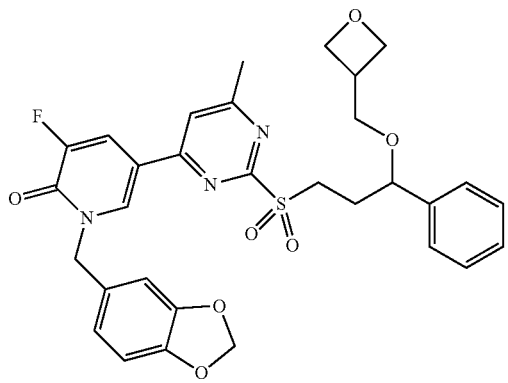 [SMILES: Cc1cc(-c2cc(F)c(=O)n(Cc3ccc4c(c3)OCO4)c2)nc(S(=O)(=O)CCC(OCC2COC2)c2ccccc2)n1]
417
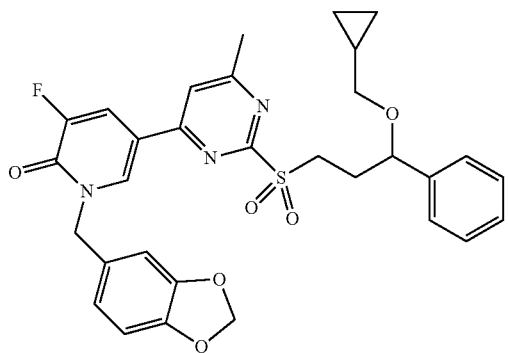 [SMILES: Cc1cc(-c2cc(F)c(=O)n(Cc3ccc4c(c3)OCO4)c2)nc(S(=O)(=O)CCC(OCC2CC2)c2ccccc2)n1]
418

TABLE 4b-continued
SAR optimization:
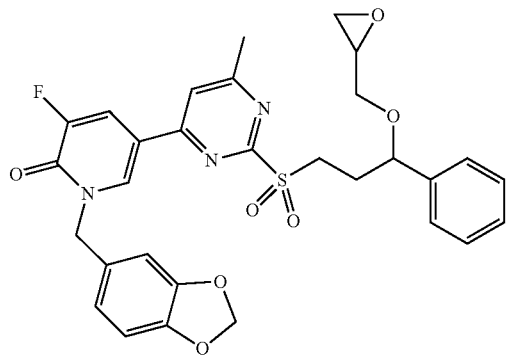 [SMILES: Cc1cc(-c2cc(F)c(=O)n(Cc3ccc4c(c3)OCO4)c2)nc(S(=O)(=O)CCC(OCC2CO2)c2ccccc2)n1]
419
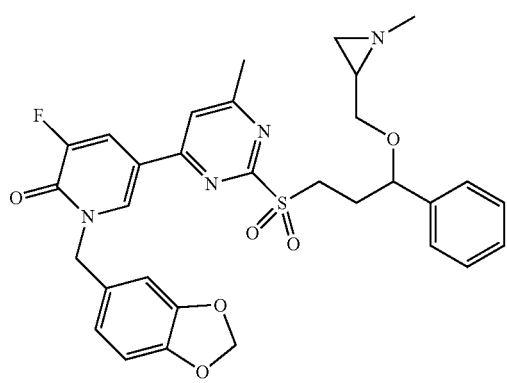 [SMILES: Cc1cc(-c2cc(F)c(=O)n(Cc3ccc4c(c3)OCO4)c2)nc(S(=O)(=O)CCC(OCC2CN2C)c2ccccc2)n1]
420
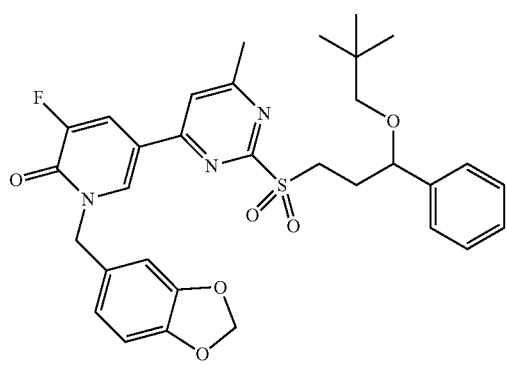 [SMILES: Cc1cc(-c2cc(F)c(=O)n(Cc3ccc4c(c3)OCO4)c2)nc(S(=O)(=O)CCC(OCC(C)(C)C)c2ccccc2)n1]
421

Compound Preparation 2-(methylsulfinyl)-4-(thiophen-2-yl)-6-(trifluoromethyl)pyrimidine (1)

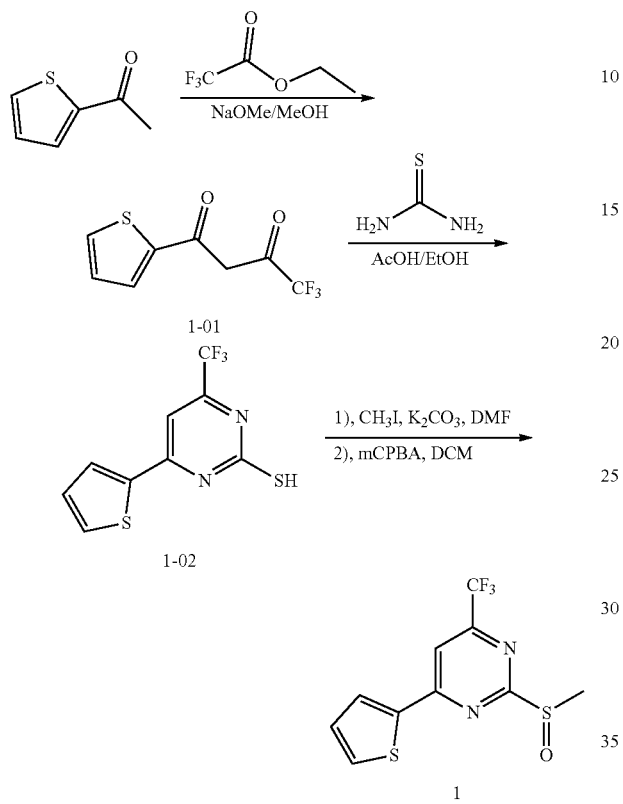

Step 1. Preparation of 4,4,4-trifluoro-1-(thiophen-2-yl)butane-1,3-dione (1-01)

1-(thiophen-2-yl)ethanone (20 g, 16 mmol) was added to a solution of NaOMe (10.3 g, 19 mmol) in MeOH at 0° C. dropwise, and the mixture was stirred at room temperature for 1 hr. Then the mixture was cooled to 0° C., and ethyl 2,2,2-trifluoroacetate (27 g, 19 mmol) was added in portions, and the whole reaction mixture was stirred and refluxed at 80° C. overnight. After the organic solvent was evaporated in vacuo, the risidue was dissolved in H$_2$O (200 mL), acified by HCl (120 mL, 1N), and extracted by EtOAc (200 mL) 3 times. The organic layer was combined, washed with brine, dried over Na$_2$SO$_4$, concentrated and further purified by silica gel column chromatography (PE/EA=20/1), to give 11 g of 4,4,4-trifluoro-1-(thiophen-2-yl)butane-1,3-dione (1-01) as a light red solid (32%).

Step 2. Preparation of 4-(thiophen-2-yl)-6-(trifluoromethyl)pyrimidine-2-thiol (1-02)

AcOH (0.8 mL) was added to a solution of 4,4,4-trifluoro-1-(thiophen-2-yl)butane-1,3-dione (1 g, 4.5 mmol) and thiourea (1.7 g, 22.5 mmol) in MeOH (4 mL) in a 25 mL microwave tube under N$_2$ atmosphere. The reaction mixture was microwaved at 95° C. for 2 hrs. The reaction mixture was filtered. Solvents were removed in vacuo from the filtrate, then the residue was extracted 3 times with EtOAc and H$_2$O. The organic layer was combined, washed by brine, dried over Na$_2$SO$_4$, then the solvent was evaporated in vacuo. The solid residue was further purified by silica gel column chromatograpy (PE/EA=1/1) to give 0.6 g of 4-(thiophen-2-yl)-6-(trifluoromethyl) pyrimidine-2-thiol as an orange solid (1-02) (50%). $^1$H NMR (CDCl$_3$) δ 7.86 (dd, J=1.2, 4.0 Hz, 1H), 7.63 (dd, J=1.2, 5.2 Hz, 1H), 7.51 (s, 1H), 7.20 (dd, J=4.0, 5.2 Hz, 1H).

Step 3. Preparation of 2-(methylsulfinyl)-4-(thiophen-2-yl)-6-(trifluoromethyl)pyrimidine (1)

1.1 eq of K$_2$CO$_3$ (35 mg, 0.25 mmol) was added to a solution of 1-02 (60 mg, 023 mmol) and CH$_3$I (36 mg, 0.25 mmol) in DMF (1 mL), and the reaction mixture was stirred at room temperature for 2 hrs. The reaction mixture was then extracted by EtOAc/H$_2$O (15 mL/15 mL) 3 times. The organic layer was combined, washed with brine, dried over Na$_2$SO$_4$, concentrated and further purified by silica gel column chromatography (PE/EA=1/1) to give 2-(methylthio)-4-(thiophen-2-yl)-6-(trifluoromethyl)pyrimidine as a white solid.

mCPBA (85 mg, 0.49 mmol) was added to a solution of 2-(methylthio)-4-(thiophen-2-yl)-6-(trifluoromethyl) pyrimidine (54 mg, 0.196 mmol) in DCM, and the reaction mixture was stirred at room temperature for 2 hrs. The reaction mixture was extracted by satured NaHCO$_3$/DCM (10 mL/10 mL) 3 times. The organic layer was combined, washed by brine, dried over Na$_2$SO$_4$ and further purified silica gel column chromatography (PE/EA=1/1) to give 1 in a yield of 18% (10 mg, 0.04 mmol) as a white solid. Compound 1 $^1$H NMR (400 MHz, CDCl$_3$): δ 8.02 (dd, J=1.2, 4.0 Hz, 1H0, 7.84 (s, 1H), 7.12 (dd, J=1.2, 5.2 Hz, 1H), 7.25 (dd, J=4.0, 5.2 Hz, 1H), 3.05 (s, 1H).

2-(ethylsulfonyl)-4-(thiophen-2-yl)-6-(trifluoromethyl)pyrimidine (2)

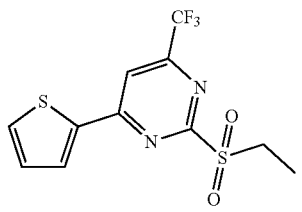 [SMILES: CCS(=O)(=O)c1nc(-c2cccs2)cc(C(F)(F)F)n1]

The titled compound 2 was prepared in a yield of 15% (12 mg, 0.04 mmol) as a light yellow solid from 1-02 (60 mg, 023 mmol) and iodoethane (27 mg, 0.25 mmol) according to the procedure for 1. $^1$H NMR (400 MHz, DMSO-d$_6$): δ 8.78 (s, 1H), 8.52 (dd, J=1.2, 4.0 Hz, 1H), 8.11 (dd, J=1.2, 4.8 Hz, 1H), 7.38 (dd, J=4.0, 4.8 Hz, 1H), 3.67 (q, J=7.2 Hz, 2H), 1.34 (t, J=7.2 Hz, 3H).

2-(ethylsulfinyl)-4-(thiophen-2-yl)-6-(trifluoromethyl)pyrimidine (3)

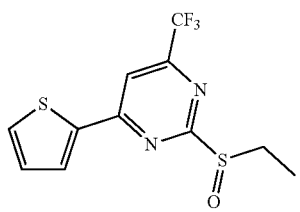 [SMILES: CCS(=O)c1nc(-c2cccs2)cc(C(F)(F)F)n1]

The titled compound 3 was prepared in a yield of 24% (18 mg, 0.06 mmol) as a light yellow solid from 1-02 (60 mg, 023 mmol) and iodoethane (27 mg, 0.25 mmol) according to the procedure for TC009014. ¹H NMR (400 MHz, CDCl₃): δ 8.02 (dd, J=1.2, 3.6 Hz, 1H), 7.82 (s, 1H), 7.71 (dd, J=1.2, 4.8 Hz, 1H), 7.25 (dd, J=3.6, 4.8 Hz, 1H, 3.26-3.35 (m, 1H), 3.14-3.24 (m, 1H), 1.34 (t, J=7.2 Hz, 3H). LC-MS (ESI) m/z: calcd for [C11H10F3N2OS2+], 307.0, found 307.3.

2-(propylsulfonyl)-4-(thiophen-2-yl)-6-(trifluoromethyl)pyrimidine (4)

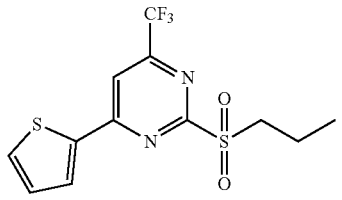 [SMILES: CCCS(=O)(=O)c1nc(-c2cccs2)cc(C(F)(F)F)n1]

The titled compound 4 was prepared in a yield of 25% (19 mg, 0.06 mmol) as a light yellow solid from 1-02 (60 mg, 0.23 mmol) and 1-iodopropane (30 mg, 0.25 mmol) according to the procedure for 1. ¹H NMR (400 MHz, DMSO-dd): δ 8.78 (s, 1H), 8.52 (d, J=3.6 Hz, 1H), 8.11 (d, J=4.8 Hz, 1H), 7.36-7.39 (m, 1H), 3.62-3.67 (m, 2H), 1.77-1.87 (m, 2H), 1.04 (t, J=7.2 Hz, 3H). LC-MS (ESI) m/z: calcd for [C₁₂H₁₂F₃N₂O₂S₂⁺], 337.0, found 337.2.

2-(propylsulfinyl)-4-(thiophen-2-yl)-6-(trifluoromethyl)pyrimidine (5)

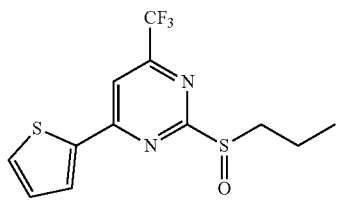 [SMILES: CCCS(=O)c1nc(-c2cccs2)cc(C(F)(F)F)n1]

The titled compound 5 was prepared in a yield of 19% (14 mg, 0.04 mmol) as a light yellow solid from 1-02 (60 mg, 0.23 mmol) and 1-iodopropane (30 mg, 0.25 mmol) according to the procedure for 1. LC-MS (ESI) m/z: calcd for [C₁₂H₁₂F₃N₂OS₂⁺], 321.0, found 321.4.

2-(prop-2-yn-1-ylsulfonyl)-4-(thiophen-2-yl)-6-(trifluoromethyl) pyrimidine (6)

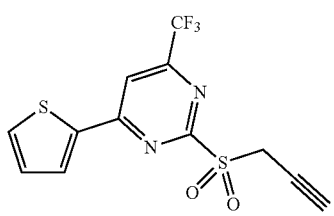 [SMILES: C#CCS(=O)(=O)c1nc(-c2cccs2)cc(C(F)(F)F)n1]

The titled compound 6 was prepared in a yield of 48% (120 mg, 0.36 mmol) as a white solid from 1-02 (200 mg, 0.76 mmol) and 3-bromoprop-1-yne (100 mg, 0.95 mmol) according to the procedure for 1. ¹H NMR (400 Hz, CDCl3) δ 8.05 (dd, J=1.2, 4.0 Hz, 1H), 7.95 (s, 1H), 7.77 (dd, J=1.2, 5.2 Hz, 1H), 7.27 (dd, J=4.0, 5.2 Hz, 1H), 4.52 (d, J=2.8 Hz, 2H), 3.92 (t, J=2.8 Hz, 1H). LC-MS (ESI) m/z: calcd for [C₁₂H₈F₃N₂O₂S₂⁺], 333.0, found 333.2.

2-(phenylsulfinyl)-4-(thiophen-2-yl)-6-(trifluoromethyl)pyrimidine (7)

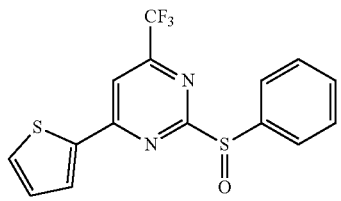 [SMILES: O=S(c1ccccc1)c1nc(-c2cccs2)cc(C(F)(F)F)n1]

The titled compound 7 was prepared in a yield of 12%(10 mg, 0.03 mmol) as a light yellow solid from 1-02 (60 mg, 0.23 mmol) and 1-iodobenzene (51 mg, 0.25 mmol) according to the procedure for TC009014. ¹H NMR (400 MHz, DMSO-d₆): δ 8.69 (s, 1H), 8.438 (dd, J=1.2, 4.0 Hz, 1H), 8.06-8.09 (m, 2H), 8.05 (dd, J=1.2, 4.0 Hz, 1H), 7.83-7.86 (m, 1H), 7.73-7.76 (m, 2H), 7.33 (dd, J=4.0, 4.8 Hz, 1H).

2-chloro-6-(4-(thiophen-2-yl)-6-(trifluoromethyl)pyrimidin-2-ylsulfinyl)pyrazine (8)

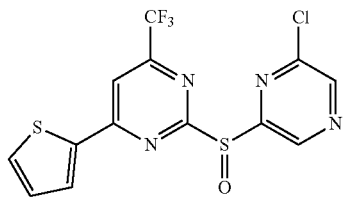 [SMILES: O=S(c1cncc(Cl)n1)c1nc(-c2cccs2)cc(C(F)(F)F)n1]

The titled compound 8 was prepared in a yield of 8%(7 mg, 0.02 mmol) as a light yellow solid from 1-02 (60 mg, 0.23 mmol) and 1-iodobenzene 2,6-dichloropyrazine (37 mg, 0.25 mmol) according to the procedure for 1. ¹H NMR (400 MHz, DMSO-d₆): δ 9.11 (s, 1H), 8.93 (s, 1H), 8.332-8.35 (m, 1H), 8.30 (s, 1H), 7.96 (dd, J=1.2, 4.8 Hz, 1H), 7.29 (dd, J=4.8 Hz, 1H).

2-((cyclopropylmethyl)sulfonyl)-4-(thiophen-2-yl)-6-(trifluoromethyl)pyrimidine (9)

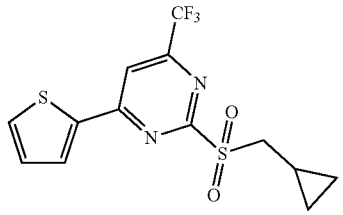 [SMILES: O=S(=O)(CC1CC1)c1nc(-c2cccs2)cc(C(F)(F)F)n1]

The titled compound 9 was prepared in a yield of 12%(7 mg, 0.02 mmol) as a white solid from 1-02 (50 mg, 0.19 mmol) and (bromomethyl)cyclopropane (46 mg, 0.21 mmol) according to the procedure for 1. ¹H NMR (400 Hz, CDCl₃) δ8.03 (d, J=3.6 Hz, 1H), 7.93 (s, 1H), 7.74 (d, J=4.8 Hz, 1H), 7.25 (m. 1H), 3.56 (d, J=7.2 Hz, 2H), 0.83-0.89 (m, 1H), 0.65-0.71 (m, 2H), 0.40-0.45 (m, 2H).

2-((cyclopropylmethyl)sulfinyl)-4-(thiophen-2-yl)-6-(trifluoromethyl)pyrimidine (10)

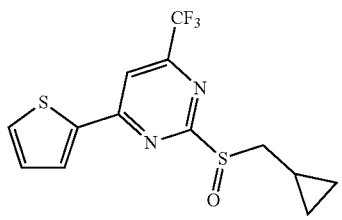 [SMILES: O=S(CC1CC1)c1nc(-c2cccs2)cc(C(F)(F)F)n1]

The titled compound 10 was prepared in a yield of 8%(4.3 mg, 0.013 mmol) as a white solid from 1-02 (50 mg, 0.19 mmol) and (bromomethyl)cyclopropane (46 mg, 0.21 mmol) according to the procedure for 1. ¹H NMR (400 Hz, CDCl₃) δ8.01 (d, J=3.6 Hz, 1H), 7.82 (s, 1H), 7.71 (d, J=4.8 Hz, 1H), 7.24 (m, 1H), 3.08-3.18 (m, 2H), 0.86-0.89 (m, 1H), 0.68-0.74 (m, 1H), 0.61-0.66 (m, 1H). 0.35-0.42 (m, 1H), 0.23-0.28 (m, 1H).

2-(benzylsulfonyl)-4-(thiophen-2-yl)-6-(trifluoromethyl)pyrimidine (11)

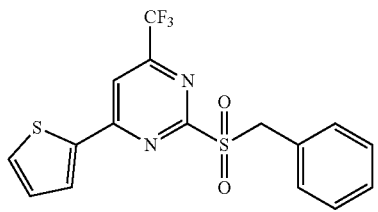 [SMILES: O=S(=O)(Cc1ccccc1)c1nc(-c2cccs2)cc(C(F)(F)F)n1]

The titled compound 11 was prepared in a yield of 25% (19 mg, 0.06 mmol) as a light yellow solid from 1-02 (60 mg, 0.23 mmol) and 1-(bromomethyl)benzene (43 mg, 0.25 mmol) according to the procedure for 1. ¹H NMR (400 MHz, DMSO-d₆): δ 8.78 (s, 1H), 8.53 (dd, J=1.2, 4.0 Hz, 1H), 8.13 (dd, J=1.2, 4.8 Hz, 1H), 7.32-7.42 (m, 6H), 5.05 (s, 2H).

2-(benzylsulfinyl)-4-(thiophen-2-yl)-6-(trifluoromethyl)pyrimidine (12)

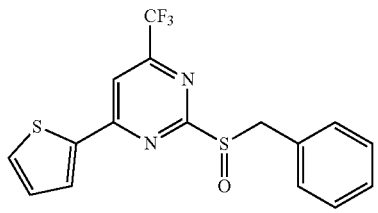 [SMILES: O=S(Cc1ccccc1)c1nc(-c2cccs2)cc(C(F)(F)F)n1]

The titled compound 12 was prepared in a yield of 11%(9 mg, 0.03 mmol) as a light yellow solid from 1-02 (60 mg, 0.23 mmol) and 1-(bromomethyl)benzene (43 mg, 0.25 mmol) according to the procedure for 1. ¹H NMR (400 MHz, CDCl₃) δ 7.97 (dd, J=0.8, 4.0 Hz, 1H), 7.77 (s, 1H), 7.71 (dd, J=0.8, 4.8 Hz, 1H), 7.25-7.28 (m, 3H), 7.24 (dd, J=4.0, 4.8 Hz, 1H), 7.18-7.21 (m, 2H), 4.47 (d, J=13.2 Hz, 1H), 4.34 (d, J=13.2 Hz, 1H).

2-(((4-(thiophen-2-yl)-6-(trifluoromethyl) pyrimidin-2-yl) sulfonyl) methyl) benzonitrile (13)

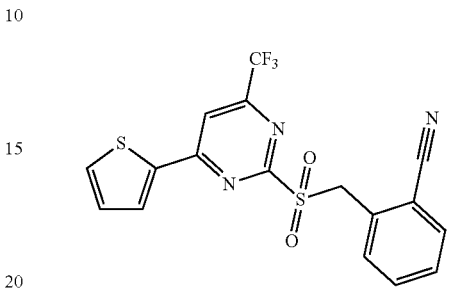

The titled compound 13 was prepared in a yield of 10%(8 mg, 0.02 mmol) as a white solid from 1-02 (50 mg, 0.19 mmol) and 2-(bromomethyl)benzonitrile (29 mg, 0.21 mmol) according to the the procedure for 1. ¹H NMR (400 Hz, CDCl₃) δ 8.05 (dd, J=0.8, 4.0 Hz, 1H), 7.94 (s, 1H), 7.75-7.79 (m, 2H), 7.72 (dd, J=0.8, 7.6 Hz, 1H), 7.62-7.67 (m, 1H), 7.48-7.53 (m, 1H), 7.25-7.27 (m, 1H), 5.10 (s, 2H).

2-(((4-(thiophen-2-yl)-6-(trifluoromethyl)pyrimidin-2-yl)sulfinyl)methyl) benzonitrile (14)

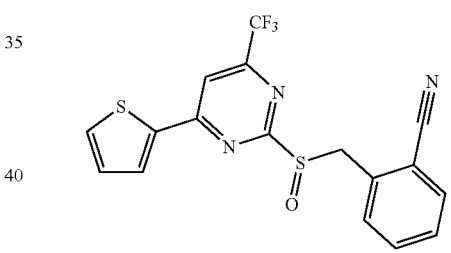

The titled compound 14 was prepared in a yield of 8%(6 mg, 0.02 mmol) as a white solid from 1-02 (50 mg, 0.19 mmol) and 2-(bromomethyl)benzonitrile (29 mg, 0.21 mmol) according to the the procedure for 1. ¹H NMR (400 Hz, CDCl₃) δ 7.99 (dd, J=0.8, 4.0 Hz, 1H), 7.84 (s, 1H), 7.71 (dd, J=0.8, 4.8 Hz, 1H), 7.54-7.63 (m, 3H), 7.41-7.46 (m, 1H), 7.24 (dd, J=4.0, 4.8 Hz, 1H), 4.73 (d, J=13.2 Hz, 1H), 4.53 (d, J=13.2 Hz, 1H).

3-(((4-(thiophen-2-yl)-6-(trifluoromethyl)pyrimidin-2-yl)sulfinyl)methyl) benzonitrile (15)

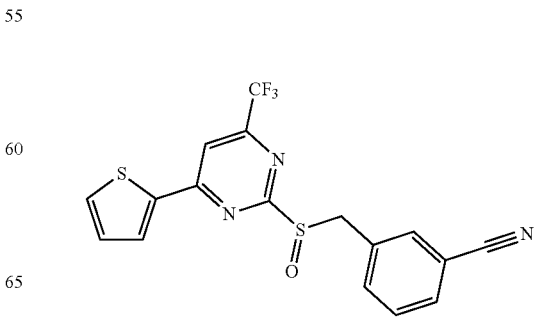

The titled compound 15 was prepared in a yield of 20% (17 mg, 0.03 mmol) as a white solid from 1-02 (60 mg, 0.23 mmol) and 3-(bromomethyl)benzonitrile (49 mg, 0.26 mmol) according to the the procedure for 1. $^1$H NMR (400 Hz, CDCl$_3$) δ 7.99 (d, J=4.0, 1H), 7.81 (s. 1H), 7.74 (d, J=4.8, 1H), 7.57 (d, J=7.6, 1H), 7.51 (d, J=7.6, 1H), 7.44 (s, 1H), 7.41 (t, J=7.6, 1H), 7.24 (dd, J=4.0, 4.8 Hz, 1H), 4.48 (d, J=13.2 Hz, 1H), 4.38 (d, J=13.2 Hz, 1H).

2-((3-methoxybenzyl)sulfinyl)-4-(thiophen-2-yl)-6-(trifluoromethyl)pyrimidine (16)

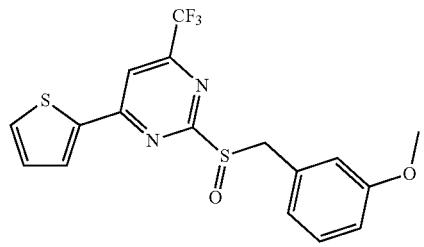 [SMILES: COc1cccc(CS(=O)c2nc(-c3cccs3)cc(C(F)(F)F)n2)c1]

The titled compound 16 was prepared in a yield of 51% (47 mg, 0.12 mmol) as a white solid from 1-02 (60 mg, 0.23 mmol) and 1-(chloromethyl)-3-methoxybenzene (40 mg, 0.26 mmol) according to the the procedure for 1. $^1$H NMR (400 Hz, CDCl$_3$) δ 7.98 (d, J=3.2 Hz, 1H), 7.78 (s, 1H), 7.71 (d, J=4.8 Hz, 1H), 7.24 (dd, J=4.0, 4.8 Hz, 1H), 7.18 (t, J=8.0 Hz, 1H), 6.82-6.78 (3, 3H), 4.44 (d, J=12.8 Hz, 2H), 4.32 (d, J=12.8 Hz, 2H), 3.74 (s, 3H).

2-((4-methoxybenzyl)sulfinyl)-4-(thiophen-2-yl)-6-(trifluoromethyl)pyrimidine (17)

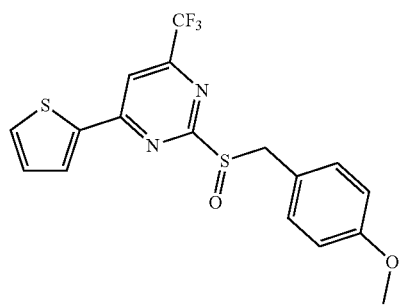 [SMILES: COc1ccc(CS(=O)c2nc(-c3cccs3)cc(C(F)(F)F)n2)cc1]

The titled compound 17 was prepared in a yield of 45% (43 mg, 0.11 mmol) as a white solid from 1-02 (60 mg, 0.23 mmol) and 1-(chloromethyl)-4-methoxybenzene (40 mg, 0.26 mmol) according to the the procedure for 1. $^1$H NMR (400 Hz, CDCl$_3$) δ 7.98 (d, J=3.6 Hz, 1H), 7.77 (s, 1H), 7.71 (d, J=5.2 Hz, 1H), 7.24 (t, J=4.4 Hz, 1H), 7.11 (d, J=8.8 Hz, 2H), 6.79 (d, J=8.8 Hz, 2H), 4.42 (d, J=13.2 Hz, 1H), 4.30 (d, J=13.2 Hz, 1H), 3.74 (s, 3H).

2-((3,5-difluorobenzyl)sulfonyl)-4-(thiophen-2-yl)-6-(trifluoromethyl)pyrimidine (18)

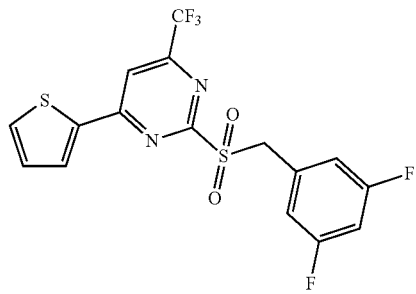 [SMILES: O=S(=O)(Cc1cc(F)cc(F)c1)c1nc(-c2cccs2)cc(C(F)(F)F)n1]

The titled compound 18 was prepared in a yield of 12% (9 mg, 0.02 mmol) as a white solid from 1-02 (50 mg, 0.19 mmol) and 1-(bromomethyl)-3,5-difluorobenzene (29 mg, 0.21 mmol) according to the procedure for 1. $^1$H NMR (400 Hz, CDCl$_3$) δ 8.03 (dd, J=0.8, 4.0 Hz, 1H), 7.92 (s, 1H), 7.77 (dd, J=0.8, 4.8 Hz, 1H), 7.27 (dd, J=4.0, 4.8 Hz, 1H), 7.04-7.07 (m, 2H), 6.76-6.82 (m, 1H), 4.86 (s, 2H).

2-((3,5-difluorobenzyl)sulfinyl)-4-(thiophen-2-yl)-6-(trifluoromethyl)pyrimidine (19)

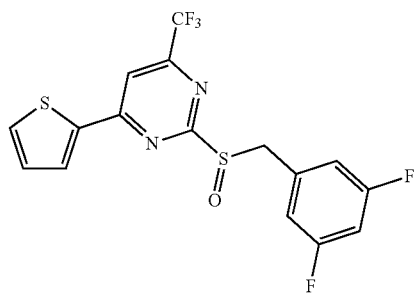 [SMILES: O=S(Cc1cc(F)cc(F)c1)c1nc(-c2cccs2)cc(C(F)(F)F)n1]

The titled compound 19 was prepared in a yield of 10% (8 mg, 0.02 mmol) as a white solid from 1-02 (50 mg, 0.19 mmol) and 1-(bromomethyl)-3,5-difluorobenzene (29 mg, 0.21 mmol) according to the procedure for 1. $^1$H NMR (400 Hz, CDCl3) δ 8.00 (dd, J=0.8, 4.0 Hz, 1H), 7.81 (s, 1H), 7.73 (dd, J=0.8, 4.8 Hz, 1H), 7.25 (dd, J=4.0, 4.8 Hz, 1H), 6.71-6.80 (m, 3H), 4.43 (d, J=13.2 Hz, 1H), 4.29 (d, J=13.2 Hz, 1H).

2-(([1,1'-biphenyl]-4-ylmethyl)sulfinyl)-4-(thiophen-2-yl)-6-(trifluoromethyl) pyrimidine (20)

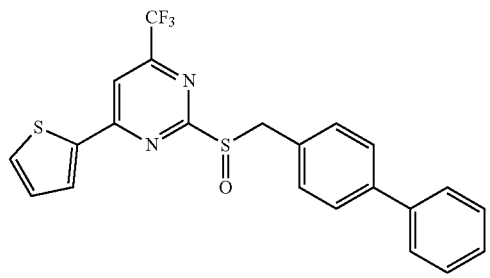 [SMILES: O=S(Cc1ccc(-c2ccccc2)cc1)c1nc(-c2cccs2)cc(C(F)(F)F)n1]

The titled compound 20 was prepared in a yield of 12%(12 mg, 0.03 mmol) as a light yellow solid from 1-02 (60 mg, 0.23 mmol) and 4-(chloromethyl)-1,1'-biphenyl (51 mg, 0.25 mmol) according to the procedure for 1. ¹H NMR (400 MHz, DMSO-$d_6$): δ 8.79 (s, 1H), 8.54 (dd, J=1.2, 4.0 Hz, 1H), 8.13 (dd, J=1.2, 5.2 Hz, 1H), 7.64-7.68 (m, 4H), 7.48-7.52 (m, 2H), 7.43-7.48 (m, 2H), 7.36-7.40 (m, 2H)

4-(4-(((4-(thiophen-2-yl)-6-(trifluoromethyl)pyrimidin-2-yl)sulfinyl)methyl)phenyl)morpholine 4-oxide (21)

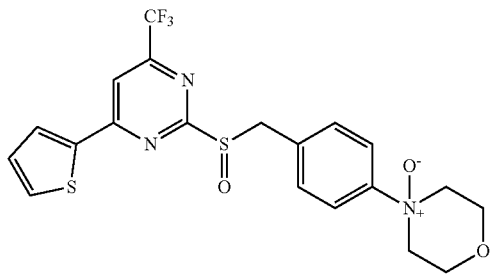 [SMILES: O=S(Cc1ccc([N+]2([O-])CCOCC2)cc1)c1nc(-c2cccs2)cc(C(F)(F)F)n1]

To a solution of 1-02 (75 mg, 0.28 mmol) and (4-morpholinophenyl)methanol (50 mg, 0.26 mmol) in dry THF (1.7 mL) was added PPh₃ (88 mg, 0.31 mmol) and DIAD (70 mg, 0.34 mmol) in portions under N₂ atmosphere at 0° C. The reaction mixture was stirred at 0° C. for 8 hrs. The reaction mixture was raised to room temperature, then solvents were removed in vacuo. The residue was extracted by DCM/H₂O 3 times. The organic layer was washed by brine, dried over Na₂SO₄ and further purified by silica gel column chromatography (PE/EA=1/1) to give 2-((4-(piperazin-1-yl)benzyl)thio)-4-(thiophen-2-yl)-6-(trifluoromethyl)pyrimidine as a white solid (90%).

The titled compound 21 was prepared in a yield of 87%(94 mg, 0.20 mmol) as a white solid from 2-((4-(piperazin-1-yl)benzyl)thio)-4-(thiophen-2-yl)-6-(trifluoromethyl)pyrimidine (100 mg, 0.23 mmol) and mCPBA (50 mg, 0.29 mmol) according to the general procedure for 1. ¹H NMR (400 Hz, CDCl3) δ 7.96 (dd, J=0.8, 4.0 Hz, 1H), 7.88-7.92 (m, 2H), 7.76 (s, 1H), 7.71 (dd, J=0.8, 4.8 Hz, 1H), 7.29-7.33 (m, 2H), 7.24 (dd, J=4.0, 4.8 Hz, 1H), 4.61-4.70 (m, 2H), 4.49 (d, J=13.2 Hz, 1H), 4.38 (d, J=13.2 Hz, 1H), 3.77-3.92 (m, 4H), 2.91-3.08 (m, 2H). LC-MS (ESI) m/z: calcd for [C₂₀H₁₉F₃N₃O₃S₂⁺], 470.1, found 470.2.

4-(4-(((4-(thiophen-2-yl)-6-(trifluoromethyl)pyrimidin-2-yl)sulfonyl)methyl)phenyl)morpholine 4-oxide (22)

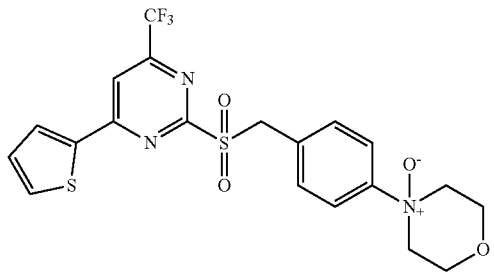 [SMILES: O=S(=O)(Cc1ccc([N+]2([O-])CCOCC2)cc1)c1nc(-c2cccs2)cc(C(F)(F)F)n1]

The titled compound 22 was prepared in a yield of 81%(150 mg, 0.31 mmol) as a white solid from 1-02 (113 mg, 0.42 mmol) and (4-morpholinophenyl)methanol (75 mg, 0.39 mmol) according to the general procedure for 1. ¹H NMR (400 Hz, CDCl3) δ 8.02 (dd, J=0.8, 4.0 Hz, 1H), 8.01~7.98 (m, 2H), 7.91 (s, 1H), 7.77 (dd, J=0.8, 5.2 Hz, 1H), 7.66~7.63 (m, 2H), 7.24 (dd, J=4.0, 5.2 Hz, 1H), 4.94 (s, 2H), 4.72~4.66 (m, 2H), 3.92~3.85 (m, 4H), 3.14~3.09 (m, 2H). LC-MS (ESI) m/z: calcd for [C₂₀H₁₉F₃N₃O₄S₂⁺], 486.1, found 486.2.

6-(((4-(thiophen-2-yl)-6-(trifluoromethyl)pyrimidin-2-yl)sulfonyl)methyl) quinoline 1-oxide (23)

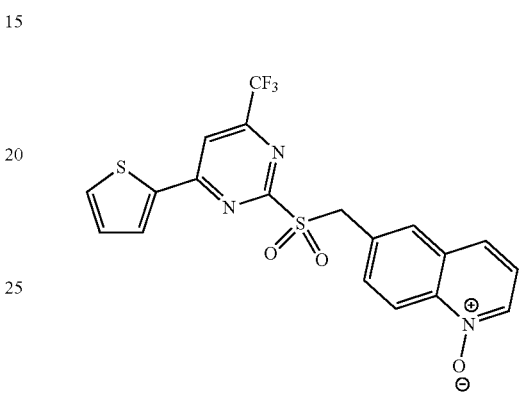

The titled compound 23 was prepared in a yield of 23%(62 mg, 0.14 mmol) as a white solid from 1-02 (158 mg, 0.61 mmol) and 6-(bromomethyl)quinoline (150 mg, 0.67 mmol) according to the procedure for 1. ¹H NMR (400 Hz, DMSO) δ 8.78 (s, 1H), 8.59 (d, J=6 Hz, 1H), 8.53-8.49 (m, 2H), 8.16 (s, 1H), 8.12 (d, J=5.2 Hz, 1H), 7.90 (d, J=8.4 Hz, 1H), 7.85 (dd, J=2, 8.4 Hz, 1H), 7.48 (dd, J=6, 8.4 Hz, 1H), 7.38 (t, J=4.4 Hz, 1H), 5.31 (s, 2H). LC-MS (ESI) m/z: calcd for [C₁₉H₁₃F₃N₃O₃S₂⁺], 452.0, found 452.2.

6-(((4-(thiophen-2-yl)-6-(trifluoromethyl)pyrimidin-2-yl)sulfinyl)methyl) quinoline (24)

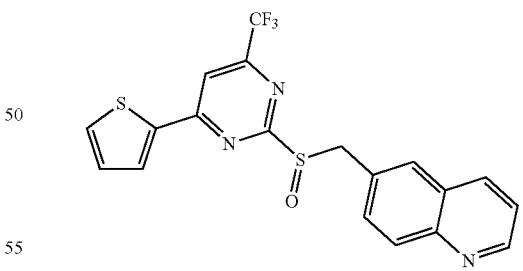

The titled compound 24 was prepared in a yield of 10% (11 mg, 0.03 mmol) as a white solid from 1-02 (70 mg, 0.27 mmol) and 6-(bromomethyl)quinoline (65 mg, 0.29 mmol) according to the procedure for 1. ¹H NMR (400 MHz, DMSO-$d_6$): δ 8.86-8.88 (m, 1H), 8.56 (s, 1H), 8.44-8.50 (m, 1H), 8.25-8.28 (m, 1H), 8.03 (dd, J=4.0, 4.8 Hzm 1H), 7.89 (d, J=13.2 Hz, 1H), 7.76 (s, 1H), 7.46-7.52 (m, 2H), 7.34 (dd, J=3.6, 4.8 Hz, 1H), 4.73 (d, J=13.2 Hzm 1H), 4.60 (d, J=13.2 Hz, 1H). LC-MS (ESI) m/z: calcd for [C₁₉H₁₃F₃N₃OS₂⁺], 420.0, found 420.1.

1-(2-((4-(thiophen-2-yl)-6-(trifluoromethyl)pyrimidin-2-yl)sulfinyl)ethyl) pyrrolidin-2-one (25)

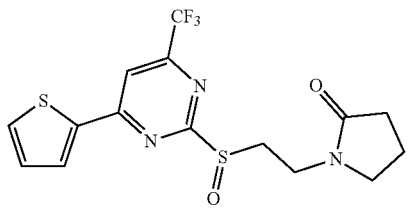 [SMILES: O=C1CCCN1CCS(=O)c1nc(-c2cccs2)cc(C(F)(F)F)n1]

The titled compound 25 was prepared in a yield of 11% (10 mg, 0.02 mmol) as a light yellow solid from 1-02 (60 mg, 0.23 mmol) and 1-(2-chloroethyl)pyrrolidin-2-one (37 mg, 0.25 mmol) according to the the procedure for 1. $^1$H NMR (400 MHz, DMSO-d$_6$): δ 8.80 (s, 1H), 8.54 (dd, J=1.2, 4.0 Hz, 1H), 8.12 (dd, J=1.2, 5.2 Hz, 1H), 7.38 (dd, J=4.0, 5.2 Hz, 1H), 3.91 (t, J=6.8 Hz, 2H), 3.71 (t, J=4.8 Hz, 2H), 3.38 (t, J=6.8 Hz, 2H), 2.08 (t, J=8.0 Hz, 2H), 1.77-1.86 (m, 2H).

2-(phenethylsulfonyl)-4-(thiophen-2-yl)-6-(trifluoromethyl)pyrimidine (26)

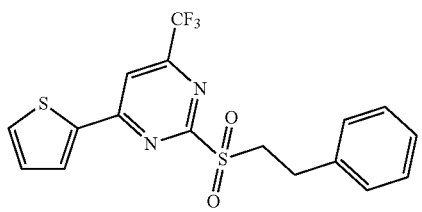 [SMILES: O=S(=O)(CCc1ccccc1)c1nc(-c2cccs2)cc(C(F)(F)F)n1]

The titled compound 26 was prepared in a yield of 8% (6 mg, 0.015 mmol) as a white solid from 1-02 (50 mg, 0.19 mmol) and (2-bromoethyl)benzene (39 mg, 0.21 mmol) according to the procedure for 1. $^1$H NMR (400 Hz, CDCl$_3$) δ 7.98 (dd, J=0.8, 4.0 Hz, 1H), 7.84 (s, 1H), 7.74 (dd, J=0.8, 4.8 Hz, 1H), 7.24 (dd, J=4.0, 4.8 Hz, 1H), 7.12-7.21 (m, 5H), 3.87-3.92 (m, 2H), 3.21-3.27 (m, 2H).

2-(phenethylsulfinyl)-4-(thiophen-2-yl)-6-(trifluoromethyl)pyrimidine (27)

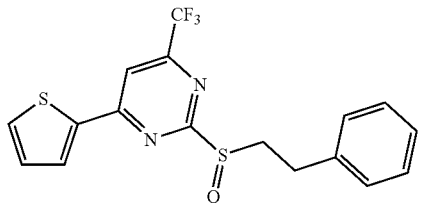 [SMILES: O=S(CCc1ccccc1)c1nc(-c2cccs2)cc(C(F)(F)F)n1]

The titled compound 27 was prepared in a yield of 10% (7 mg, 0.02 mmol) as a white solid from 1-02 (50 mg, 0.19 mmol) and (2-bromoethyl)benzene (39 mg, 0.21 mmol) according to the procedure for 1. $^1$H NMR (400 Hz, CDCl$_3$) δ 7.96 (dd, J=0.8, 4.0 Hz, 1H), 7.71 (s, 1H), 7.69 (dd, J=0.8, 4.8 Hz, 1H), 7.11-7.25 (m, 6H), 3.49-3.54 (m, 2H), 3.18-3.27 (m, 1H), 3.02-3.10 (m, 1H).

3-((4-(thiophen-2-yl)-6-(trifluoromethyl)pyrimidin-2-yl)sulfinyl)propanoic acid (28)

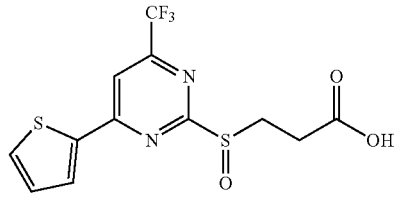 [SMILES: O=C(O)CCS(=O)c1nc(-c2cccs2)cc(C(F)(F)F)n1]

The titled compound 28 was prepared in a yield of 18% as a white solid from 1-02 (25 mg, 0.09 mmol) and 3-chloropropanoic acid (11 mg, 0.10 mmol) according to the procedure for 1. $^1$H NMR (400 Hz, CDCl3) δ 12.40 (br, 1H), 8.57 (s, 1H), 8.44 (d, J=3.2 Hz, 1H), 8.02 (d, J=4.4 Hz, 1H), 7.32 (dd, 0.1=3.2, 4.4 Hz, 1H), 3.53-3.46 (m, 1H), 3.28-3.21 (m, 1H), 2.76-2.61 (m, 2H).

Ethyl 3-((4-(thiophen-2-yl)-6-(trifluoromethyl)pyrimidin-2-yl)sulfonyl)propanoate (29)

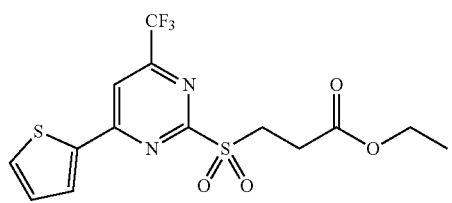 [SMILES: CCOC(=O)CCS(=O)(=O)c1nc(-c2cccs2)cc(C(F)(F)F)n1]

The titled compound 29 was prepared in a yield of 36% as a white solid from 1-02 and ethyl 3-chloropropanoate according to the procedure for 1. $^1$H NMR (400 Hz, CDCl$_3$) δ8.03 (dd. J=1.2, 4.0 Hz, 1H), 7.94 (s, 1H), 7.75 (dd, J=1.2, 4.8 Hz, 1H), 7.26 (dd, J=4.0, 4.8 Hz, 1H), 4.17 (q, J=7.2 Hz, 2H), 3.95 (t, J=7.6 Hz, 2H), 3.01 (t, J=7.6 Hz, 2H), 1.27 (t, J=7.2 Hz, 3H).

ethyl 3-((4-(thiophen-2-yl)-6-(trifluoromethyl)pyrimidin-2-yl)sulfinyl) propanoate (30)

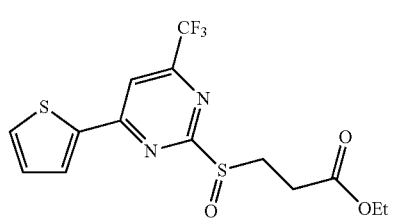 [SMILES: CCOC(=O)CCS(=O)c1nc(-c2cccs2)cc(C(F)(F)F)n1]

The titled compound 30 was prepared in a yield of 26% (90 mg, 0.24 mmol) as a white solid from 1-02 (100 mg, 0.38 mmol) and ethyl 3-chloropropanoate (57 mg, 0.42 mmol) according to the procedure for 1. $^1$H NMR (400 Hz, CDCl$_3$) δ 8.01 (dd, J=0.8, 3.6 Hz, 1H), 7.83 (s, 1H), 7.72 (dd, J=0.8, 4.8 Hz, 1H), 7.25 (dd, J=3.6, 4.8 Hz, 1H), 4.09 (m, 2H), 3.59 (m, 1H), 3.42 (m, 1H), 3.00 (m, 1H), 2.77 (m, 1H), 1.22 (t, J=7.2 Hz, 3H).

methyl 4-((4-(thiophen-2-yl)-6-(trifluoromethyl)pyrimidin-2-yl)sulfonyl) butanoate (31)

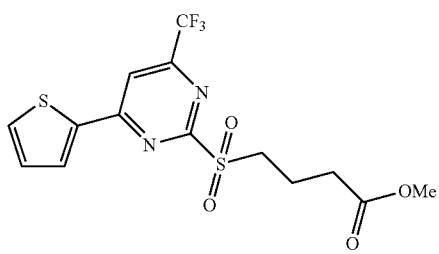 [SMILES: COC(=O)CCCS(=O)(=O)c1nc(-c2cccs2)cc(C(F)(F)F)n1]

The titled compound 31 (30 mg, 0.08 mmol) was prepared in a yield of 20% as a white solid from 1-02 (76 mg, 0.28 mmol) and methyl 4-chlorobutanoate (39 mg, 0.32 mmol) according to the procedure for 1. $^1$H NMR (400 Hz, CDCl$_3$) δ 8.04 (dd, J=0.8, 4.0 Hz, 1H), 7.94 (s, 1H), 7.76 (dd, J=0.8, 5.2 Hz, 1H), 7.26 (dd, J=4.0, 5.2 Hz, 1H), 3.70-3.74 (m, 2H), 3.69 (s, 3H), 2.60 (t, J=7.2 Hz, 2H), 2.24-2.33 (m, 2H).

methyl 4-((4-(thiophen-2-yl)-6-(trifluoromethyl)pyrimidin-2-yl)sulfinyl) butanoate (32)

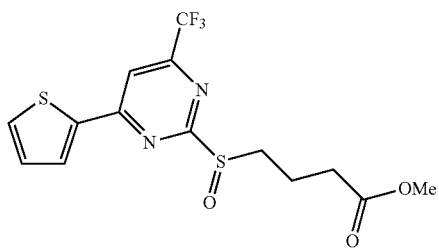 [SMILES: COC(=O)CCCS(=O)c1nc(-c2cccs2)cc(C(F)(F)F)n1]

The titled compound 32 (60 mg, 0.158 mmol) was prepared in a yield of 38% as a white solid from 1-02 (76 mg, 0.28 mmol) and methyl 4-chlorobutanoate (39 mg, 0.32 mmol) according to the procedure for 1. $^1$H NMR (400 Hz, CDCl$_3$) δ 8.00 (dd, J=0.8, 4.0 Hz, 1H), 7.83 (s, 1H), 7.68 (dd, J=0.8, 5.2 Hz, 1H), 7.21 (dd, J=4.0, 5.2 Hz, 1H), 3.60 (s, 3H), 3.15-3.32 (m, 2H), 2.48-2.51 (m, 2H), 2.21-2.31 (m, 1H), 1.98-2.08 (m, 1H).

4-chloro-2-(methylsulfonyl)-6-(thiophen-2-yl)pyrimidine (33)

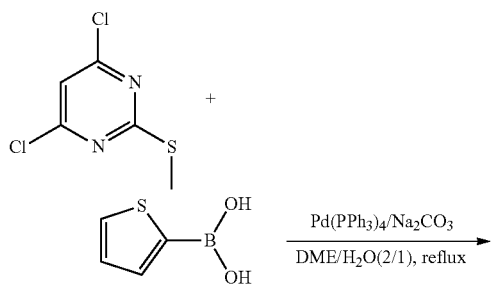

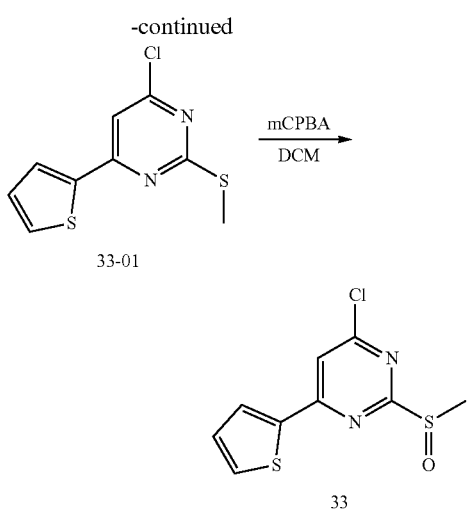

Step 1. Preparation of 4-chloro-2-(methylthio)-6-(thiophen-2-yl)pyrimidine (33-01)

To a solution of 4,6-dichloro-2-(methylthio)pyrimidine (400 mg, 2.06 mmol) and thiophen-2-ylboronic acid (300 mg, 2.26 mmol) in DME/H$_2$O (4 mL/2 mL) was added Pd(PPh$_3$)$_4$ (69 mg, 0.06 mmol) and Na$_2$CO$_3$ (546 mg, 4.12 mmol) in portions under N$_2$ atmosphere. The reaction mixture was heated and refluxed for 2 hrs. The reaction mixture was cooled to room temperature, and filtered over celite. Solvent was evaporated in vacuo, and the residue was extracted by EtOAc/H$_2$O (30 ml/30 mL) 3 times. The organic layer was combined, washed by brine, dried over Na$_2$SO$_4$, and further purified by silica gel column chromatography (PE/EA=20/1) to give 112 mg of 4-chloro-2-(methylthio)-6-(thiophen-2-yl)pyrimidine (33-01) as a white solid (27%). $^1$H NMR (400 Hz, CDCl$_3$) δ 7.76 (dd, J=0.8, 4.0 Hz, 1H), 7.56 (dd, J=0.8, 4.8 Hz, 1H), 7.72 (s, 1H), 7.16 (dd, J=4.0, 4.8 Hz, 1H), 2.62 (s, 3H).

Step 2. Preparation of 33 mCPBA (15 mg, 0.09 mmol) was added to a solution of 33-01 (30 mg, 0.09 mmol) in DCM and the reaction mixture was stirred at room temperature for 2 hrs. The reaction mixture was extracted by DCM and satured NaHCO$_3$ solution 3 times. The organic layer was combined, washed with brine, dried over Na$_2$SO$_4$ and further purified by silica gel column chromatography (PE/EA=1/1) to give 25 mg of 4-chloro-2-(methylsulfinyl)-6-(thiophen-2-yl) pyrimidine as a white solid (78%). $^1$H NMR (400 Hz, CDCl3) δ 7.90 (dd, J=0.8, 3.6 Hz, 1H), 7.64 (dd, J=1.2, 4.8 Hz, 1H), 7.57 (s, 1H), 7.19 (dd, J=3.6, 4.8 Hz, 1H), 3.00 (s, 3H). LC-MS (ESI) m/z: calcd for [C$_9$H$_8$ClN$_2$OS$^+$], 259.0, found 259.1.

187

4-methyl-2-(methylsulfonyl)-6-(thiophen-2-yl)pyrimidine (34)

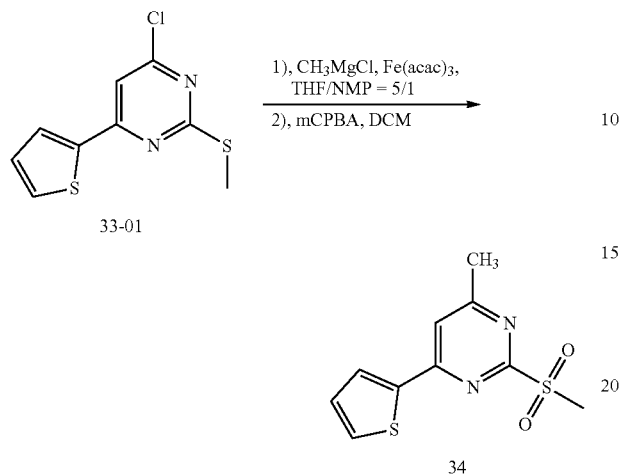

To a solution of 4-chloro-2-(methylthio)-6-(thiophen-2-yl)pyrimidine (33-01)(70 mg, 0.29 mmol) in THF/NMP (2 mL/0.4 mL) was added Fe(acac)₃ (6 mg, 0.01 mmol) followed by CH₃MgCl (30 mg, 0.35 mmol) dropwise at −20° C. under N₂ atmosphere. The reaction mixture was stirred at −20° C. to room temperature overnight. The reaction mixture was filtered, and solvents were removed from the filtrate in vacuo. The residue was extracted by EtOAc/H₂O 3 times. The organic layer was washed with brine, dried over Na₂SO₄ and further purified by silica gel column chromatography (PE/EA=10/1) to give 12 mg of 4-methyl-2-(methylthio)-6-(thiophen-2-yl) pyrimidine as a light yellow oil (20%).

mCPBA (24 mg, 0.14 mmol) was added to a solution of 4-methyl-2-(methylthio)-6-(thiophen-2-yl) pyrimidine (12 mg, 0.05 mmol) in DCM and the reaction mixture was stirred at room temperature for 2 hrs. The reaction mixture was extracted by DCM and satured NaHCO₃ solution 3 times. The organic layer was combined, washed with brine, dried over Na₂SO₄ and further purified by silica gel column chromatography (PE/EA=1/1) to give 2 mg of 4-methyl-2-(methylsulfonyl)-6-(thiophen-2-yl) pyrimidine as a white solid (14%). LC-MS (ESI) m/z: calcd for [C₁₀H₁₁N₂O₂S₂⁺], 255.0, found 255.1.

4-ethynyl-2-(methylsulfonyl)-6-(thiophen-2-yl)pyrimidine (35)

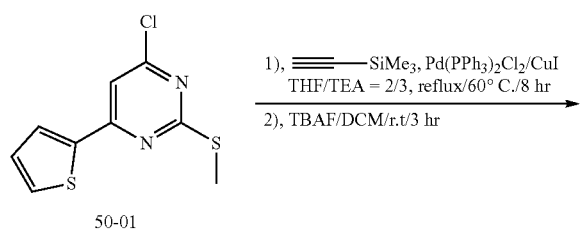

188

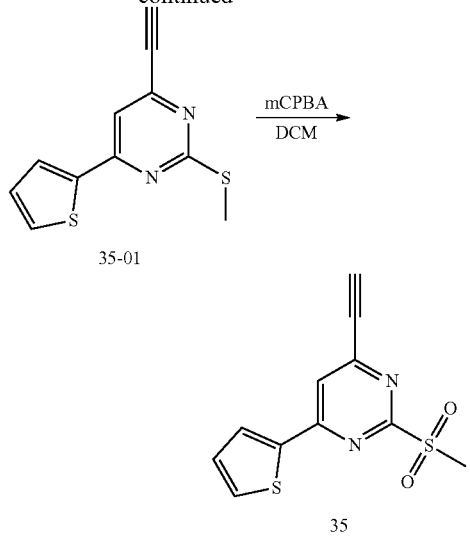

Step 1. Preparation of 4-ethynyl-2-(methylthio)-6-(thiophen-2-yl) (35-01)

Pd(PPh₃)₂Cl₂ (1.2 mg, 0.002 mmol) and CuI (1 mg, 0.005 mmol) was added to as solution of 4-chloro-2-(methylthio)-6-(thiophen-2-yl)pyrimidine (33-01)(40 mg, 0.16 mmol) in THF/TEA (1 mL/1.5 mL) under N₂ atmosphere, followed by the addition of ethynyltrimethylsilane(18 mg, 0.18 mmol) dropwise. The reaction mixture was refluxed at 60° C. for 8 hrs. The reaction mixture was cooled to room temperature and filtered over celite. Solvents was evaporated in vacuo, and the residue was dissolved in dry DCM at room temperature, followed by the addition of TBAF (47 mg, 0.18 mmol). The reaction mixture was stirred at room temperature for 3 hrs. Then the reaction mixture was extracted by DCM/H₂O 3 times. The organic layer was combined, washed with brine, dried over Na₂SO₄ and further purified by silica gel column chromatography (PE/EA=10/1) to give 12 mg of 4-ethynyl-2-(methylthio)-6-(thiophen-2-yl) pyrimidine as a white solid (31%).

Step 2. Preparation of 35 mCPBA (35 mg, 0.20 mmol) was added to a solution of 35-01 (12 mg, 0.05 mmol) in DCM and the reaction mixture was stirred at room temperature for 2 hrs. The reaction mixture was extracted by DCM and satured NaHCO₃ solution 3 times. The organic layer was combined, washed with brine, dried over Na₂SO₄ and further purified by silica gel column chromatography (PE/EA=1/1) to give 5 mg of 4-ethynyl-2-(methylsulfonyl)-6-(thiophen-2-yl) pyrimidine as a white solid (37%). ¹H NMR (400 Hz, CDCl3) δ 7.92 (dd, J=0.8, 4.0 Hz, 1H), 7.75 (s, 1H), 7.67 (dd, J=1.2, 4.8 Hz, 1H), 7.21 (dd, J=4.0, 4.8 Hz, 1H), 3.53 (s, 1H), 3.40 (s, 3H). LC-MS (ESI) m/z: calcd for [C₁₁H₉N₂O₂S₂⁺], 265.0, found 265.2.

2-(methylsulfonyl)-4-(1H-pyrazol-1-yl)-6-(thiophen-2-yl)pyrimidine (36)

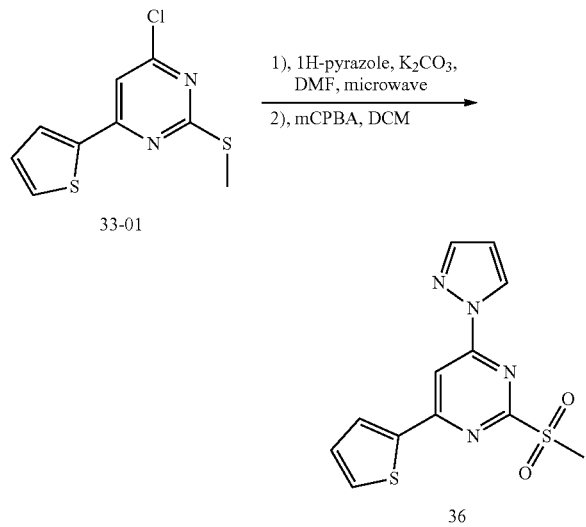

K₂CO₃ (34 mg, 0.25 mmol) was added to a solution of 4-chloro-2-(methylthio)-6-(thiophen-2-yl)pyrimidine (51-01)(30 mg, 0.13 mmol) and 1H-pyrazole (12 mg, 0.18 mmol) in DMF. The reaction mixture was microwaved at 100° C. for 2 hrs. The reaction mixture was cooled to room temperature, and extracted by EtOAc/H₂O 3 times. The organic layer was combined, washed with brine, dried over Na₂SO₄ and further purified by silica gel column chromatography (PE/EA=10/1) to give 16 mg of 2-(methylthio)-4-(1H-pyrazol-1-yl)-6-(thiophen-2-yl)pyrimidine as a white solid (47%).

mCPBA (30 mg, 0.17 mmol) was added to a solution of 2-(methylthio)-4-(1H-pyrazol-1-yl)-6-(thiophen-2-yl)pyrimidine (16 mg, 0.06 mmol) in DCM and the reaction mixture was stirred at room temperature for 2 hrs. The reaction mixture was extracted by DCM and satured NaHCO₃ solution 3 times. The organic layer was combined, washed with brine, dried over Na₂SO₄ and further purified by silica gel column chromatography (PE/EA=1/1) to give 5 mg of 2-(methylsulfonyl)-4-(1H-pyrazol-1-yl)-6-(thiophen-2-yl) pyrimidine as a white solid (28%). $^1$H NMR (400 Hz, CDCl3) δ 8.67 (d, J=0.8 Hz, 1H), 8.24 (s, 1H), 7.98 (dd, J=0.8, 4.0 Hz, 1H), 7.85 (d, J=1.6 Hz, 1H), 7.64 (dd, J=0.8, 5.2 Hz, 1H), 7.21 (dd, J=4.0, 5.2 Hz, 1H), 6.56 (dd, J=1.6, 2.8 Hz, 1H), 3.45 (s, 3H). LC-MS (ESI) m/z: calcd for [$C_{12}H_{11}N_4O_2S_2^+$], 307.0, found 307.2.

2-(methylsulfonyl)-4,6-di(thiophen-2-yl)pyrimidine (37)

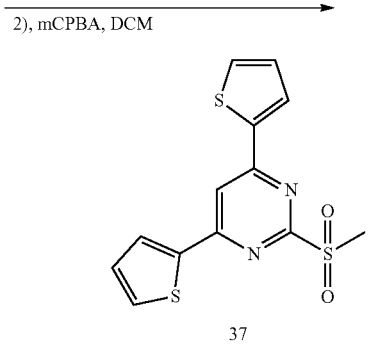

To a solution of 4,6-dichloro-2-(methylthio)pyrimidine (300 mg, 1.54 mmol) and thiophen-2-ylboronic acid (800 mg, 6.19 mmol) in DME/H₂O (4 mL/2 mL) was added Pd(PPh₃)₄ (56 mg, 0.05 mmol) followed by Na₂CO₃ (655 mg, 6.19 mmol) under N₂ atmosphere. The reaction mixture was microwaved at 150° C. for 2 hrs. The reaction mixture was cooled to room temperature, and filtered over celite. Solvent was evaporated in vacuo, and the residue was extracted by EtOAc and H₂O 3 times. The organic layer was combined, washed by brine, dried over Na₂SO₄, and further purified by silica gel column chromatography (PE/EA=100/1) to give 110 mg of 2-(methylthio)-4,6-di(thiophen-2-yl) pyrimidine as a white solid (30%).

mCPBA (32 mg, 0.19 mmol) was added to a solution of 2-(methylthio)-4,6-di(thiophen-2-yl)pyrimidine (27 mg, 0.09 mmol) in DCM and the reaction mixture was stirred at room temperature for 2 hrs. The reaction mixture was extracted by DCM and satured NaHCO₃ solution 3 times. The organic layer was combined, washed with brine, dried over Na₂SO₄ and further purified by silica gel column chromatography (PE/EA=1/1) to give 6 mg of 2-(methylsulfonyl)-4,6-di(thiophen-2-yl)pyrimidine as a white solid (20/%). $^1$H NMR (400 Hz, DMSO) δ8.67 (s, 1H), 8.37 (d, J=3.6 Hz, 2H), 7.99 (d, J=4.8 Hz, 2H), 7.35 (dd, J=3.6, 4.8 Hz, 2H), 3.46 (s, 3H). LC-MS (ESI) m/z: calcd for [$C_{13}H_{11}N_2O_2S_3^+$], 323.0, found 323.4.

1-(2-(methylsulfonyl)-6-(thiophen-2-yl)pyrimidin-4-yl)pyrrolidin-2-one (38)

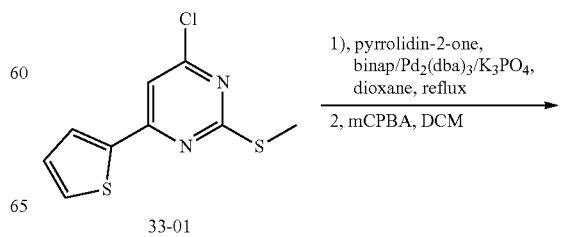

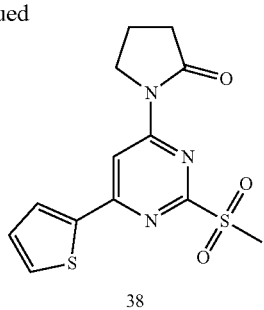

38

To a solution of 4-chloro-2-(methylthio)-6-(thiophen-2-yl)pyrimidine (33-01)(30 mg, 0.12 mmol) and pyrrolidin-2-one (21 mg, 0.24 mmol) in dry dioxane was added binap (8 mg, 0.01 mmol), Pd$_2$(dba)$_3$ (6 mg, 0.006 mmol) and K$_3$PO$_4$ (65 mg, 0.30 mmol) under N$_2$ atmosphere. The reaction was refluxed at 160° C. for 8 hrs. The reaction mixture was cooled to room temperature, filtered over celite. Solvents were removed from the filtrate in vacuo, then the residue was extracted by EtOAc/H$_2$O 3 times. The organic layer was combined, washed with brine, dried over Na$_2$SO$_4$ and further purified by silica gel column chromatography (PE/EA=4/1) to give 12 mg of 1-(2-(methylthio)-6-(thiophen-2-yl)pyrimidin-4-yl)pyrrolidin-2-one as a yellow oil (33%).

mCPBA (20 mg, 0.12 mmol) was added to a solution of 1-(2-(methylthio)-6-(thiophen-2-yl)pyrimidin-4-yl)pyrrolidin-2-one (12 mg, 0.04 mmol) in DCM and the reaction mixture was stirred at room temperature for 2 hrs. The reaction mixture was extracted by DCM and satured NaHCO$_3$ solution 3 times. The organic layer was combined, washed with brine, dried over Na$_2$SO$_4$ and further purified by silica gel column chromatography (PE/EA=1/1) to give 2 mg of 1-(2-(methylsulfonyl)-6-(thiophen-2-yl) pyrimidin-4-yl) pyrrolidin-2-one as a white solid (15%). $^1$H NMR (400 Hz, CDCl3) δ 8.33 (s, 1H), 7.91 (d, J=4.0 Hz, 1H), 7.58 (d, J=4.8 Hz, 1H), 7.17-7.20 (m, 1H), 4.20 (t, J=7.2 Hz, 2H), 3.40 (s, 3H), 2.73 (t, J=8.0 Hz, 2H), 2.16-2.24 (m, 2H).

1-(2-(methylsulfonyl)-6-(thiophen-2-yl)pyrimidin-4-yl)pyridine-2 (1H)-one (39)

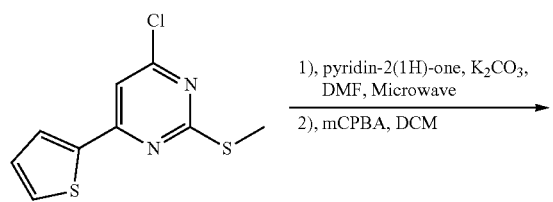

The titled compound was prepared in a yield of 55% (19 mg, 0.07 mmol) as a white solid from 4-chloro-2-(methylthio)-6-(thiophen-2-yl)pyrimidine (33-01) (30 mg, 0.12 mmol) and pyridin-2 (1H)-one (20 mg, 0.15 mmol) according to the procedure for 36. $^1$H NMR (400 Hz, DMSO) δ8.72 (s, 1H), 8.25 (dd, J=1.2, 4.0 Hz, 1H), 8.09 (dd, J=1.2, 7.2 Hz, 1H), 8.04 (dd, J=1.2, 4.8 Hz, 1H), 7.62 (ddd, J=2.0, 7.6, 9.4 Hz, 1H), 7.34 (dd, J=4.0, 4.8 Hz, 1H), 6.62 (d, J=9.2 Hz, 1H), 6.51 (td, J=7.2, 1.2 Hz, 1H), 3.50 (s, 3H). LC-MS (ESI) m/z: calcd for [C$_{14}$H$_{12}$N$_3$O$_3$S$_2$$^+$], 334.0, found 334.2.

4-(2-(methylsulfonyl)-6-(thiophen-2-yl)pyrimidin-4-yl)morpholine (40)

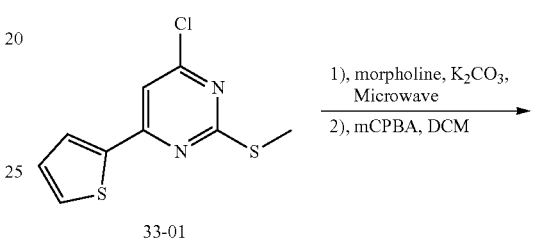

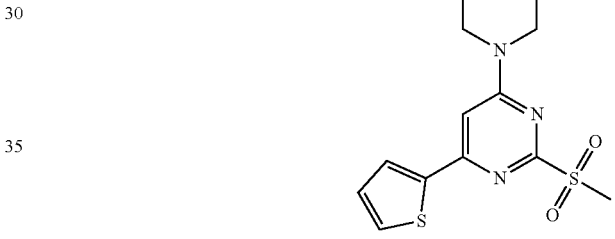

40

The titled compound 40 was prepared in a yield of 13%(5 mg, 0.02 mmol) as a white solid from 4-chloro-2-(methylthio)-6-(thiophen-2-yl)pyrimidine (33-01) (30 mg, 0.12 mmol) and morpholine (15 mg, 0.17 mmol) according to the procedure for 53. $^1$H NMR (400 Hz, CDCl3) δ 7.76 (dd, J=1.2, 4.0 Hz, 1H), 7.51 (dd, J=1.2, 5.2 Hz, 1H), 7.14 (dd, J=4.0, 5.2 Hz, 1H), 6.78 (s, 1H), 3.83-3.73 (m, 8H), 3.35 (s, 3H).

4-azido-2-(methylsulfonyl)-6-(thiophen-2-yl)pyrimidine (41)

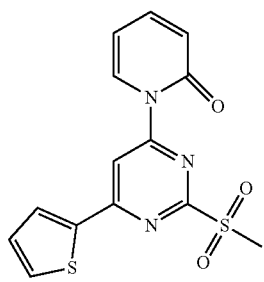

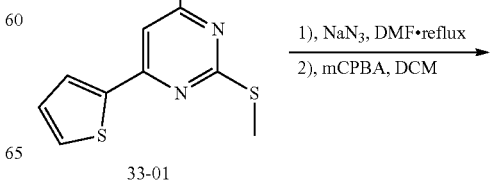

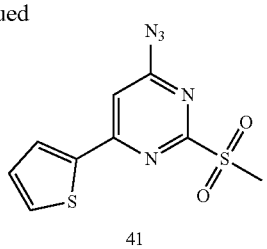

41

NaN₃ (20 mg, 0.31 mmol) was added to a solution of 4-chloro-2-(methylthio)-6-(thiophen-2-yl)pyrimidine (33-01)(50 mg, 0.21 mmol) in DMF in portions, and the reaction mixture was refluxed at 90° C. for 8 hrs. The reaction mixture was extracted by EtOAc/H₂O 3 times. The organic layer was combined, washed with brine, dried over Na₂SO₄ and further purified by silica gel column chromatography (PE/EA=20/1) to give 21 mg of 4-azido-2-(methylthio)-6-(thiophen-2-yl)pyrimidine as a white solid (41%).

mCPBA (36 mg, 0.21 mmol) was added to a solution of 4-azido-2-(methylthio)-6-(thiophen-2-yl) pyrimidine (21 mg, 0.08 mmol) in DCM and the reaction mixture was stirred at room temperature for 2 hrs. The reaction mixture was extracted by DCM and satured NaHCO₃ solution 3 times. The organic layer was combined, washed with brine, dried over Na₂SO₄ and further purified by silica gel column chromatography (PE/EA=1/1) to give 2 mg of 4-azido-2-(methylsulfonyl)-6-(thiophen-2-yl) pyrimidine as a white solid (10%). ¹H NMR (400 Hz, CDCl₃) δ 7.94 (dd, J=1.2, 4.0 Hz, 1H), 7.90 (s, 1H), 7.68 (dd, J=1.2, 4.8 Hz, 1H), 7.23 (dd, J=4.0, 4.8 Hz, 1H), 3.27 (s, 3H). LC-MS (ESI) m/z: calcd for [C₉H₈N₅O₂S₂⁺], 282.0, found 282.2.

N,N-dimethyl-2-(methylsulfinyl)-6-(thiophen-2-yl) pyrimidin-4-amine (42)

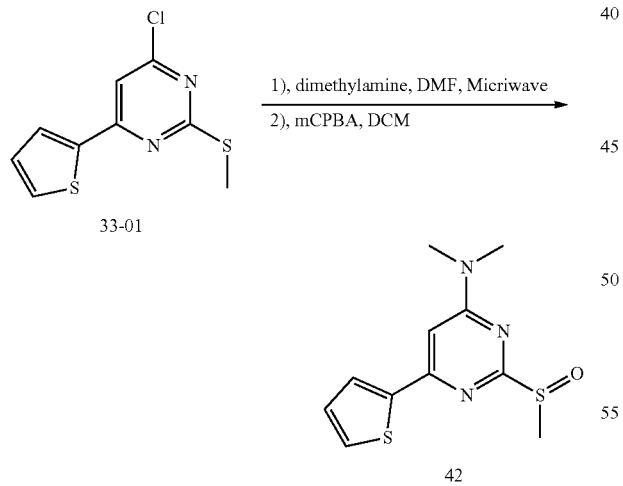

To a solution of 4-chloro-2-(methylthio)-6-(thiophen-2-yl)pyrimidine (33-01) (50 mg, 0.21 mmol) in DMF (2 mL) was added dimethylamine (48 mg, 1.04 mmol) dropwise. The reaction mixture was microwaved at 150° C. for 30 min. the reaction mixture was cooled to room temperature, then extracted by EtOAc and H₂O 3 times. The organic layer was combined, washed with brine, dried over Na₂SO₄, and then further purified by silica gel column chromatography (PE/EA=10/1) to give 64 mg of N,N-dimethyl-2-(methylthio)-6-(thiophen-2-yl) pyrimidin-4-amine as a light yellow oil (100%).

mCPBA (46 mg, 0.27 mmol) was added to a solution of N,N-dimethyl-2-(methylthio)-6-(thiophen-2-yl) pyrimidin-4-amine (60 mg, 0.27 mmol) in DCM and the reaction mixture was stirred at room temperature for 2 hrs. The reaction mixture was extracted by DCM and satured NaHCO₃ solution 3 times. The organic layer was combined, washed with brine, dried over Na₂SO₄ and further purified by silica gel column chromatography (PE/EA=1/1) to give 25 mg of N,N-dimethyl-2-(methylsulfinyl)-6-(thiophen-2-yl) pyrimidin-4-amine as a white solid (40%). ¹H NMR (400 Hz, CDCl3) δ 7.76 (dd, J=1.2, 4.0 Hz, 1H), 7.46 (dd, 1.2, 5.2 Hz, 1H), 7.12 (dd, J=4.0, 5.2 Hz, 1H), 6.62 (s, 1H), 3.23 (s, 6H), 2.94 (s, 3H). LC-MS (ESI) m/z: calcd for [C₁₁H₁₄N₃OS₂⁺], 278.0, found 268.1.

4-(2-fluorophenyl)-2-(methylsulfonyl)-6-(trifluoromethyl)pyrimidine (43)

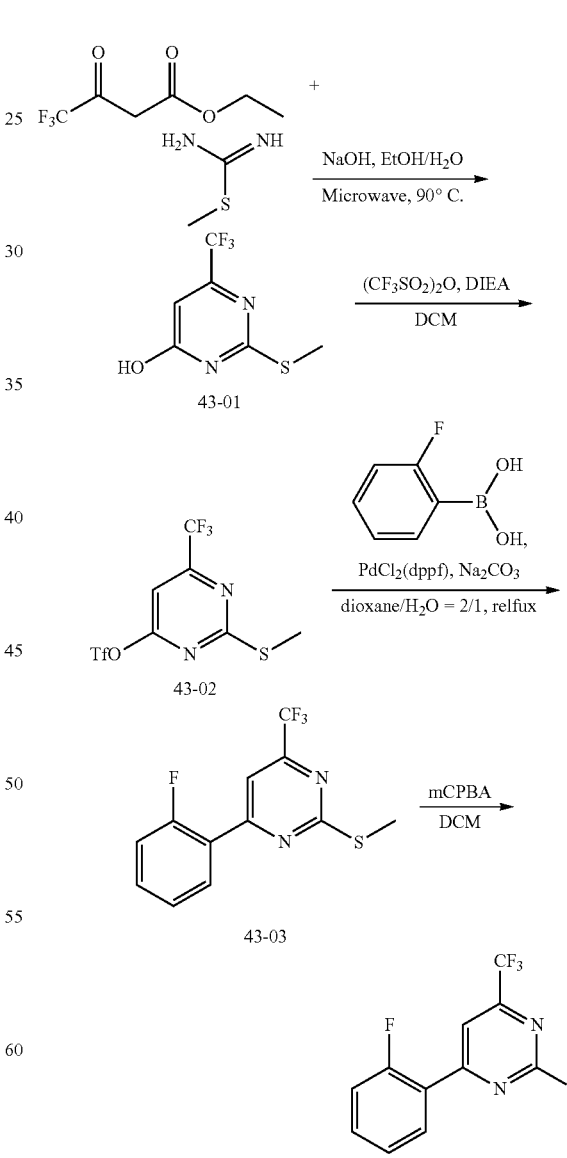

Step 1. Preparation of 2-(methylthio)-6-(trifluoromethyl)pyrimidin-4-ol (43-01)

To a solution of ethyl 4,4,4-trifluoro-3-oxobutanoate (2 g, 10.9 mmol) and methyl carbamimidothioate (4 g, 21.3 mmol) in EtOH (10 mL) was added 10N NaOH solution (2 mL) dropwise under $N_2$ atmosphere. The reaction mixture was microwaved at 90° C. for 2 hrs. The reaction mixture was cooled to room temperature, then solvents were evaporated in vacuo. The residue was dissolved in $H_2O$ and acidified to PH=2.0 with 1N HCl, then extracted by DCM 3 times. The organic layer was combined, washed with brine, dried over $Na_2SO_4$ and further purified by recrystallization with DCM/PE to give 1.8 g of 2-(methylthio)-6-(trifluoromethyl)pyrimidin-4-ol as a white solid (43-01)(8.5 mmol, 78%). $^1$H NMR (400 MHz, DMSO): δ 6.59 (s, 1H), 2.51 (s, 3H).

Step 2. Preparation of 2-(methylthio)-6-(trifluoromethyl)pyrimidin-4-yl trifluoromethanesulfonate (43-02)

To a solution of 2-mercapto-6-(trifluoromethyl)pyrimidin-4-ol (100 mg, 0.48 mmol) and DIEA (184 mg, 1.4 mmol) in DCM (2 ml) was added drop wise trifluoromethane sulfonic anhydride and (201 mg, 0.71 mmol) at 0° C. and stirred at RT over night. The mixture was extracted with $H_2O$/DCM (50 mL/50 ml) 3 times, washed with brine (50 ml×3) and dried with $Na_2SO_4$, and then concentrated in vacuo and purified by chromatography (PE/EA=10/1) to give 90 mg the desired product as a light yellow oil, 2-(methylthio)-6-(trifluoromethyl)pyrimidin-4-yl trifluoromethanesulfonate (0.26 mmol, y=55%)

Step 3. Preparation of 4-(2-fluorophenyl)-2-(methylthio)-6-(trifluoromethyl)pyrimidine (43-03)

To a solution of 2-(methylthio)-6-(trifluoromethyl)pyrimidin-4-yl trifluoromethanesulfonate (50 mg, 0.146 mmol) and 2-fluorophenylboronic acid (18 mg, 0.146 mmol) in dioxane (2 mL) was added $PdCl_2$(dppf) (10 mg, 0.01 mmol) followed by $Na_2CO_3$ (2N, 1 mL) under $N_2$ atmosphere. The reaction mixture was refluxed at 90° C. for 5 hrs. The reaction mixture was cooled to room temperature and filtered over celite. Solvents were removed from the filtrate in vacuo, and the residue was extracted by DCM/$H_2O$ (20 mL/20 mL) 3 times. The organic layer was combined, washed with brine, dried over $Na_2SO_4$ and further purified by silica gel column chromatography (PE/EA)=30/1 to give 30 mg of 4-(2-fluorophenyl)-2-(methylthio)-6-(trifluoromethyl)pyrimidine as a light yellow solid (0.11 mmol, 76%).

Step 4. Preparation of 4-(2-fluorophenyl)-2-(methylsulfonyl)-6-(trifluoromethyl)pyrimidine (43)

mCPBA (48 mg, 0.28 mmol) was added to a solution of 4-(2-fluorophenyl)-2-(methylthio)-6-(trifluoromethyl)pyrimidine (30 mg, 0.11 mmol) in DCM and the reaction mixture was stirred at room temperature for 2 hrs. The reaction mixture was extracted by DCM and satured $NaHCO_3$ solution 3 times. The organic layer was combined, washed with brine, dried over $Na_2SO_4$ and further purified by silica gel column chromatography (PE/EA=1/1) to give 12 mg of 42-(methylsulfonyl)-4-phenyl-6-(trifluoromethyl) pyrimidine as a light yellow solid (0.04 mmol, 35.8%). $^1$H NMR (400 MHz, CDCl$_3$): δ 8.36-8.43 (m, 1H), 8.3 (s, 1H), 7.60-7.66 (m, 1H), 7.37-7.42 (m, 1H), 7.25-7.31 (m, 1H), 3.48 (s, 3H). LC-MS (ESI) m/z: calcd for [$C_{12}H_9F_4N_2O_2S^+$], 321.0, found 321.4.

4-(3-fluorophenyl)-2-(methylsulfonyl)-6-(trifluoromethyl)pyrimidine (44)

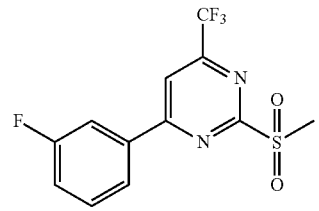 [SMILES: CS(=O)(=O)c1nc(-c2cccc(F)c2)cc(C(F)(F)F)n1]

The titled compound 44 (7 mg, 0.02 mmol) was prepared in a yield of 15% as a light yellow solid from 43-02 (50 mg, 0.146 mmol) and 3-fluorophenylboronic acid (20 mg, 0.146 mmol) according to the procedure for 60. $^1$H NMR (400 MHz, CDCl$_3$): 8.18 (s, 1H), 8.01-8.04 (m, 1H), 7.96-8.00 (m, 1H), 7.55-7.61 (m, 1H), 7.33-7.39 (m, 1H), 3.48 (s, 3H). LC-MS (ESI) m/z: calcd for [$C_{12}H_9F_4N_2O_2S^+$], 321.0, found 321.4.

4-(4-fluorophenyl)-2-(methylsulfonyl)-6-(trifluoromethyl)pyrimidine (45)

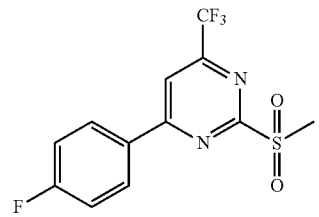 [SMILES: CS(=O)(=O)c1nc(-c2ccc(F)cc2)cc(C(F)(F)F)n1]

The titled compound 45 (7 mg, 0.02 mmol) was prepared in a yield of 15% as a light yellow solid from 43-02 (50 mg, 0.146 mmol) and 3-fluorophenylboronic acid (20 mg, 0.146 mmol) according to the procedure for 60. LC-MS (ESI) m/z: calcd for [$C_{12}H_9F_4N_2O_2S^+$], 321.0, found 321.4.

2-(methylsulfonyl)-4-(o-tolyl)-6-(trifluoromethyl) pyrimidine (46)

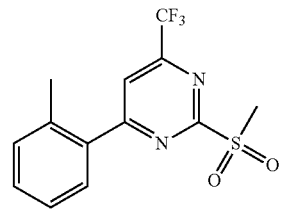 [SMILES: Cc1ccccc1-c1cc(C(F)(F)F)nc(S(C)(=O)=O)n1]

The titled compound 46 (2 mg, 0.006 mmol) was prepared in a yield of 4% as a light yellow solid from 43-02 (50 mg, 0.146 mmol) and o-tolylboronic acid (20 mg, 0.146 mmol) according to the procedure for 43. $^1$H NMR (400 MHz, CDCl3-d$_6$): δ 7.86 (s, 1H), 7.58-7.61 (m, 1H), 7.46-7.61 (m, 1H), 7.37-7.41 (m, 2HH), 3.46 (s, 3H), 2.56 (s, 3H). LC-MS (ESI) m/z: calcd for [$C_{13}H_{12}F_3N_2O_2S^+$], 317.0, found 317.4.

2-(methylsulfonyl)-4-(m-tolyl)-6-(trifluoromethyl)pyrimidine (47)

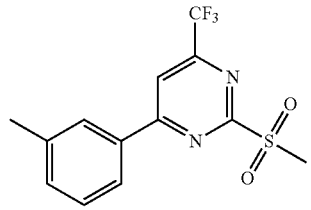

The titled compound 47 (2 mg, 0.006 mmol) was prepared in a yield of 4% as a light yellow solid from 43-02 (50 mg, 0.146 mmol) and m-tolylboronic acid (20 mg, 0.146 mmol) according to the procedure for 43. $^1$H NMR (400 MHz, CDCl3-$d_6$): δ 8.18 (s, 1H), 8.06 (s, 1H), 8.00-8.03 (m, 1H), 7.46-7.68 (m, 2H), 3.48 (s, 3H), 2.49 (s, 3H). LC-MS (ESI) m/z: calcd for [$C_{13}H_{12}F_3N_2O_2S^+$], 317.0, found 317.4.

2-(methylsulfonyl)-4-(p-tolyl)-6-(trifluoromethyl)pyrimidine (48)

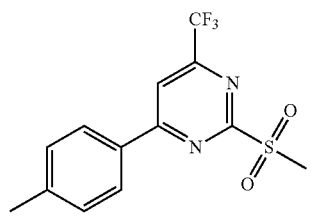

The titled compound 48 (2 mg, 0.006 mmol) was prepared in a yield of 4% as a light yellow solid from 43-02 (50 mg, 0.146 mmol) and p-tolylboronic acid (20 mg, 0.146 mmol) according to the procedure for 43. $^1$H NMR (400 MHz, CDCl3-$d_6$): δ 8.15 (d, J=8.4 Hz, 1H), 8.14 (s, 1H), 7.38 (d, J=8.4 Hz, 2H), 3.47 (s, 3H), 2.48 (s, 3H). LC-MS (ESI) m/z: calcd for [$C_{13}H_{12}F_3N_2O_2S^+$], 317.0, found 317.4.

4-(4-ethynylphenyl)-2-(methylsulfonyl)-6-(trifluoromethyl)pyrimidine (49)

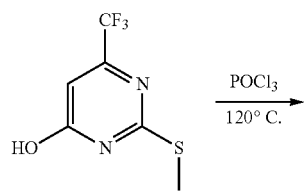

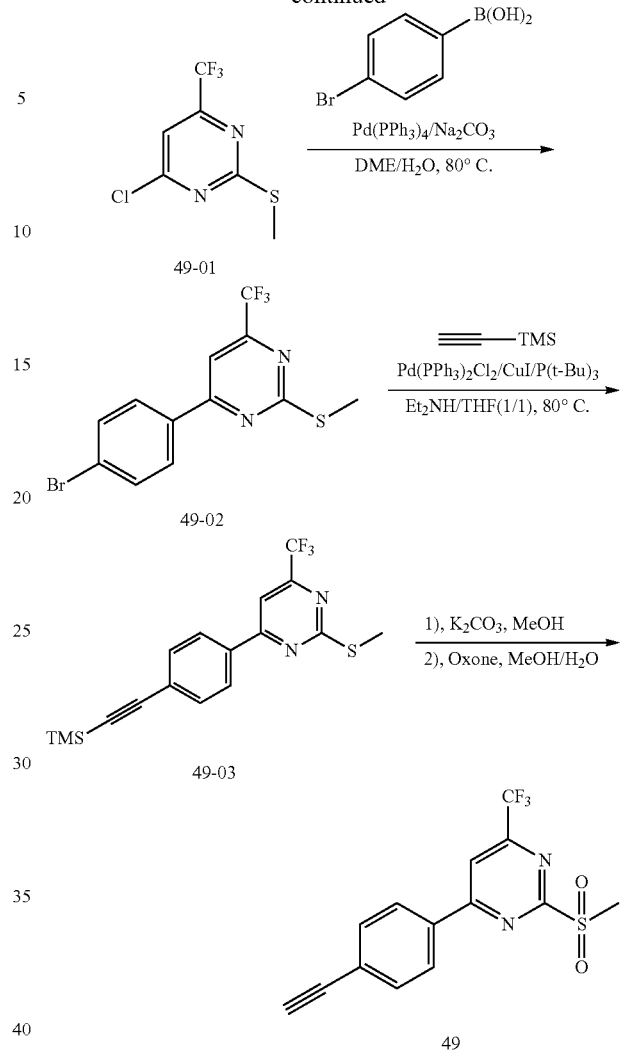

Step 1. Preparation of 4-chloro-2-(methylthio)-6-(trifluoromethyl)pyrimidine (49-01)

A solution of 2-(methylthio)-6-(trifluoromethyl)pyrimidin-4-ol (43-01)(1.4 g, 6.67 mmol) in POCl$_3$ (15 mL) was refluxed at 120° C. for 3 hrs. The reaction mixture was cooled to room temperature, and POCl$_3$ was removed in vacuo. The residue was extracted by DCM and icy H$_2$O 3 times. The organic layer was combined, washed with brine, dried over Na$_2$SO$_4$ and concentrated to give 1.38 g of 4-chloro-2-(methylthio)-6-(trifluoromethyl)pyrimidine as a light yellow oid (90%). LC-MS (ESI) m/z: calcd for [$C_6H_5ClF_3N_2S^+$], 229.0, found 229.0.

Step 2. Preparation of 4-(4-bromophenyl)-2-(methylthio)-6-(trifluoromethyl)pyrimidine (49-02)

To a solution of 49-01 (200 mg, 0.87 mmol) and (4-bromophenyl)boronic acid (195 mg, 0.97 mmol) in DME/H$_2$O (5 mL/1 mL) was added Pd(PPh$_3$)$_4$ (51 mg, 0.04 mmol) followed by Na$_2$CO$_3$ (186 mg, 1.75 mmol) under N$_2$ atmosphere. The reaction mixture was refluxed at 80° C. for 5 hrs. The reaction mixture was cooled to room temperature and filtered over celite. Solvents were removed in vacuo, and the residue was extracted by DCM and H₂O 3 times. The organic layer was combined, washed with brine, dried over Na₂SO₄ and further purified by silica gel column chromatography (PE/EA)=50/1 to give 176 mg of 4-(4-bromophenyl)-2-(methylthio)-6-(trifluoromethyl) pyrimidine (57%). ¹H NMR (400 Hz, CDCl3) δ 8.00-8.03 (m, 2H), 7.66-7.68 (m, 2H), 7.62 (s, 1H), 2.69 (s, 3H).

Step 3. Preparation of 2-(methylthio)-4-(trifluoromethyl)-6-(4-((trimethylsilyl)ethynyl) phenyl)pyrimidine (49-03)

To a solution of 49-02 (176 mg, 0.50 mmol) in dry TEA was added Pd(PPh₃)₂Cl₂ (18 mg, 0.03 mmol), CuI (5 mg, 0.03 mmol) and P(t-Bu)₃ (5 mg, 0.03 mmol) under N₂ atmosphere. The reaction mixture was stirred for 5 mins, followed by addition of ethynyltrimethylsilane(110 mg, 0.03 mmol) dropwise. The reaction mixture was then refluxed at 80° C. for 4 hrs. The reaction mixture was cooled to room temperature, filtered over celite. Solvents were removed from the filtrate in vacuo, then the residue was extracted by EtOAc/H₂O 3 times. The organic layer was combined, washed with brine, dried over Na₂SO₄ and further purified by silica gel column chromatography (PE/EA=4/1) to give 120 mg of 2-(methylthio)-4-(trifluoromethyl)-6 (4-((trimethylsilyl) ethynyl) phenyl) pyrimidine as a white solid (65%). ¹H NMR (400 Hz, CDCl3) δ 8.07-8.11 (m, 2H), 7.64 (s, 1H), 7.59-7.62 (m, 2H), 2.67 (s, 3H), 0.28 (s, 9H).

Step 4. Preparation of 4-(4-ethynylphenyl)-2-(methylsulfonyl)-6-(trifluoromethyl)pyrimidine K₂CO₃ (140 mg, 1.0 mmol) was added to a solution of 49-03 (120 mg, 0.33 mmol) in MeOH dropwise. The reaction mixture was stirred at room temperature for 3 hrs. Solvents were removed in vacuo, and the residue was extracted by EtOAc/H₂O 3 times. The organic layer was combined, washed with brine, dried over Na₂SO₄ and purified by silica gel column chromatography (PE/EA=10/1) to give 35 mg of 4-(4-ethynylphenyl)-2-(methylthio)-6-(trifluoromethyl)pyrimidine as a colorless oil (36%).

An aqueous solution of Oxone (226 mg, 0.36 mmol) was added dropwise to a solution of 4-(4-ethynylphenyl)-2-(methylthio)-6-(trifluoromethyl)pyrimidine (15 mg, 0.05 mmol) in MeOH (2 mL). The reaction mixture was stirred at room temperature for 8 hrs. Solvents were evaporated from the reaction mixture, then the residue was extracted by EtOAc/H₂O 3 times. The organic layer was combined, washed with brine, dried over Na₂SO₄ and further purified by silica gel column chromatography (PE/EA=10/1) to give 10 mg of 4-(4-ethynylphenyl)-2-(methylsulfonyl)-6-(trifluoromethyl)pyrimidine as a light yellow solid (61%). ¹H NMR (400 Hz, CDCl3) δ 8.23 (d, J=8.4 Hz, 2H), 8.19 (s, 1H), 7.69 (d, J=8.4 Hz, 2H), 3.48 (s, 1H), 3.33 (s, 1H).

3-(2-(methylsulfonyl)-6-(trifluoromethyl)pyrimidin-4-yl)phenol (50)

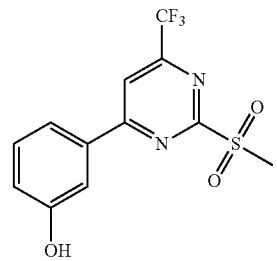 [SMILES: CS(=O)(=O)c1nc(-c2cccc(O)c2)cc(C(F)(F)F)n1]

The titled compound 50 (3 mg, 0.006 mmol) was prepared in a yield of 8% as a white solid from 43-02 (21 mg, 0.058 mmol) and (3-hydroxyphenyl)boronic acid (16 mg, 0.058) according to the procedure for 43. ¹H NMR (400 MHz, CDCl₃): δ 8.16 (s, 1H), 7.79 (t, J=2.0 Hz, 1H), 7.74 (d, J=8.0 Hz, 1H), 7.45 (t, J=8.0 Hz, 1H), 7.13 (dd, J=2.0, 8.0 Hz, 1H), 3.48 (s, 3H). Mass (m/z): 319.4 [M+H]⁺.

4-(2-methoxyphenyl)-2-(methylsulfonyl)-6-(trifluoromethyl)pyrimidine (51)

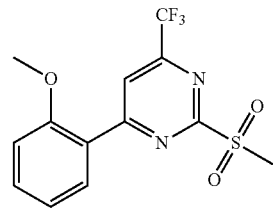 [SMILES: COc1ccccc1-c1cc(C(F)(F)F)nc(S(C)(=O)=O)n1]

The titled compound 51 (20 mg, 0.06 mmol) was prepared in a yield of 42% as a light yellow solid from 43-02 (50 mg, 0.146 mmol) and 2-methoxyphenylboronic acid (22 mg, 0.146 mmol) according to the procedure for 43. LC-MS (ESI) m/z: calcd for [C₁₃H₁₂F₃N₂O₃S₂⁺], 333.0, found 333.4.

4-(2-methoxyphenyl)-3-methylsulfonyl)-6-(trifluoromethyl)pyrimidine (52)

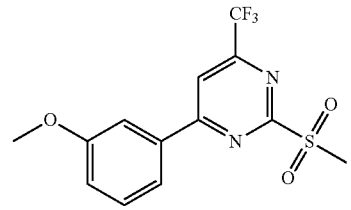

The titled compound (8 mg, 0.02 mmol) was prepared in a yield of 17% as a light yellow solid from 43-02 (50 mg, 0.146 mmol) and 3-methoxyphenylboronic acid (22 mg, 0.146 mmol) according to the procedure for 43. LC-MS (ESI) m/z: calcd for [C₁₃H₁₂F₃N₂O₃S₂⁺], 333.0, found 333.4.

4-(4-methoxyphenyl)-2-(methylsulfonyl)-6-(trifluoromethyl)pyrimidine (53) and 4-(4-methoxyphenyl)-2-(methylsulfinyl)-6-(trifluoromethyl)pyrimidine (54)

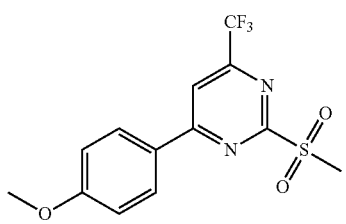

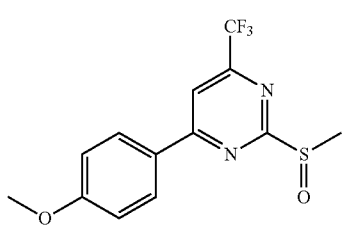

The titled compound 53 (11 mg, 0.03 mmol) was prepared in a yield of 23% as a light yellow solid from 43-02 (50 mg, 0.146 mmol) and 4-methoxyphenylboronic acid (22 mg, 0.146 mmol) according to the procedure for 43. LC-MS (ESI) m/z: calcd for $[C_{13}H_{12}F_3N_2O_3S_2^+]$, 333.0, found 333.4.

The titled compound 54 (11 mg, 0.03 mmol) was prepared in a yield of 23% as a light yellow solid from 43-02 (50 mg, 0.146 mmol) and 4-methoxyphenylboronic acid (22 mg, 0.146 mmol) according to the procedure for 43. LC-MS (ESI) m/z: calcd for $[C_{13}H_{12}F_3N_2O_2S_2^+]$, 317.0, found 317.4.

2-(2-(methylsulfonyl)-6-(trifluoromethyl)pyrimidin-4-yl)benzonitrile (55)

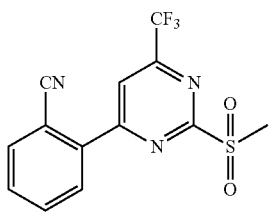 [SMILES: CS(=O)(=O)c1nc(-c2ccccc2C#N)cc(C(F)(F)F)n1]

The titled compound 55 (14 mg, 0.04 mmol) was prepared in a yield of 29% as a light yellow solid from 43-02 (50 mg, 0.146 mmol) and 2-cyanophenylboronic acid (21.4 mg, 0.146 mmol) according to the procedure for 43. LC-MS (ESI) m/z: calcd for $[C_{13}H_9F_3N_3O_2S_2^+]$, 328.0, found 328.4.

3-(2-(methylsulfonyl)-6-(trifluoromethyl)pyrimidin-4-yl)benzonitrile (56)

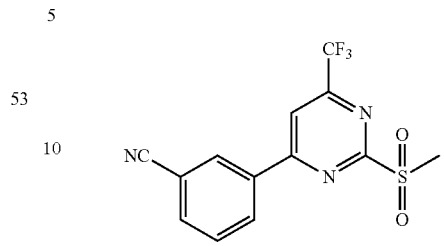

The titled compound 56 (18 mg, 0.06 mmol) was prepared in a yield of 38% as a light yellow solid from 43-02 (50 mg, 0.146 mmol) and 3-cyanophenylboronic acid (21.4 mg, 0.146 mmol) according to the procedure for 43. $^1$H NMR (400 MHz, CDCl3-d$_6$): δ 8.23 (s, 1H), 7.92-7.96 (m, 1H), 7.78-7.81 (m, 1H), 7.60-7.62 (m, 2H), 3.50 (s, 3H). LC-MS (ESI) m/z: calcd for $[C_{13}H_9F_3N_3O_2S_2^+]$, 328.0, found 328.4.

4-2-(methylsulfonyl)-6-(trifluoromethyl)pyrimidin-4-yl)benzonitrile (57)

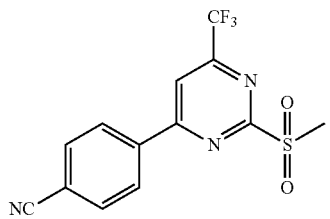 [SMILES: CS(=O)(=O)c1nc(-c2ccc(C#N)cc2)cc(C(F)(F)F)n1]

The titled compound (18 mg, 0.06 mmol) was prepared in a yield of 40% as a light yellow solid from 43-02 (50 mg, 0.146 mmol) and 4-cyanophenylboronic acid (21.4 mg, 0.146 mmol) according to the procedure for 43. $^1$H NMR (400 MHz, CDCl3-d$_6$): δ 8.36-8.39 (m, 2H), 8.24 (s, 1H), 7.89-7.92 (m, 2H), 3.49 (s, 3H).

methyl 2-(2-(methylsulfonyl)-6-(trifluoromethyl)pyrimidin-4-yl)benzoate (58) and methyl 2-(2-(methylsulfinyl)-6-(trifluoromethyl)pyrimidin-4-yl)benzoate (59)

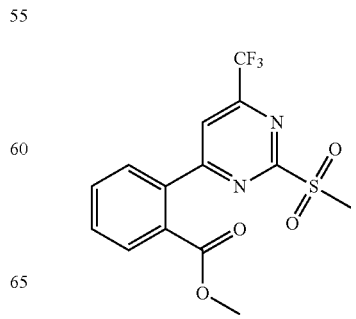

59

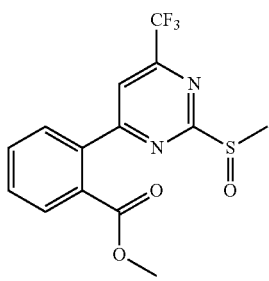

The titled compound 58 (13 mg, 0.04 mmol) was prepared in a yield of 25% as a light yellow solid from 43-02 (50 mg, 0.146 mmol) and 2-(methoxycarbonyl)phenylboronic acid (26 mg, 0.146 mmol) according to the procedure for 43. $^1$H NMR (400 MHz, CDCl3-d$_6$): δ 7.96-8.00 (m, 1H), 7.97 (s, 1H), 7.63-7.73 (m, 3H), 3.81 (s, 3H), 3.42 (s, 3H). LC-MS (ESI) m/z: calcd for [$C_{14}H_{12}F_3N_2O_4S^+$], 361.0, found 361.4.

The titled compound 59 (3 mg, 0.01 mmol) was prepared in a yield of 7% as a light yellow solid from 43-02 (50 mg, 0.146 mmol) and 2-(methoxycarbonyl)phenylboronic acid (26 mg, 0.146 mmol) according to the procedure for 43. $^1$H NMR (400 MHz, CDCl3-d$_6$): δ 7.96-7.99 (m, 1H), 7.82 (s, 1H), 7.61-7.69 (m, 3H), 3.81 (s, 3H), 3.02 (s, 3H). LC-MS (ESI) m/z: calcd for [$C_{14}H_{12}F_3N_2O_3S^+$], 345.0, found 345.4.

methyl 3-(2-(methylsulfonyl)-6-(trifluoromethyl)pyrimidin-4-yl)benzoate (60)

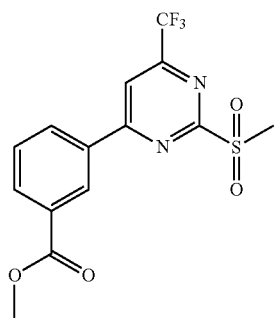 [SMILES: COC(=O)c1cccc(-c2cc(C(F)(F)F)nc(S(C)(=O)=O)n2)c1]

The titled compound 60 (14 mg, 0.04 mmol) was prepared in a yield of 26% as a light yellow solid from 43-02 (50 mg, 0.146 mmol) and 3-methoxycarbonyl)phenylboronic acid (26 mg, 0.146 mmol) according to the procedure for 43. $^1$H NMR (400 MHz, CDCl3-d$_6$): δ 8.17 (s, 1H), 7.76-7.79 (m, 2H), 7.50 (t, J=8.4 Hz, 1H), 7.18 (dd, J=3.4, 8.4 Hz, 1H), 3.93 (s, 3H), 3.48 (s, 3H). LC-MS (ESI) m/z: calcd for [$C_{14}H_{12}F_3N_2O_4S^+$], 361.0, found 361.4.

methyl 4-(2-(methylsulfonyl)-6-(trifluoromethyl)pyrimidin-4-yl)benzoate (61) and methyl 4-(2-(methylsulfinyl)-6-(trifluoromethyl)pyrimidin-4-yl)benzoate (62)

61

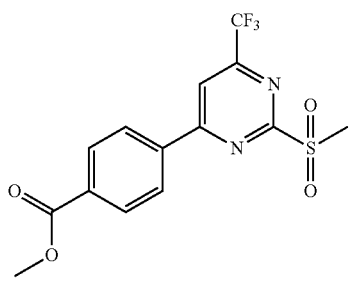

62

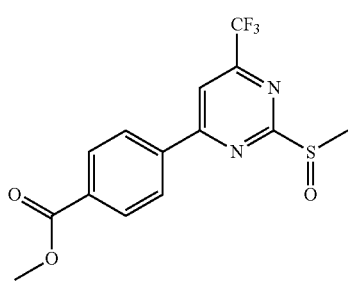

The titled compound 61 (7 mg, 0.02 mmol) was prepared in a yield of 13% as a light yellow solid from 43-02 (50 mg, 0.146 mmol) and 4-methoxycarbonyl)phenylboronic acid (26 mg, 0.146 mmol) according to the procedure for 43. $^1$H NMR (400 MHz, CDCl3-d$_6$): δ 8.31-8.34 (m, 2H), 8.23-8.26 (m, 2H), 8.25 (s, 1H), 3.99 (s, 3H), 3.49 (s, 3H).

The titled compound 62 (7 mg, 0.02 mmol) was prepared in a yield of 17% as a light yellow solid from 43-02 (50 mg, 0.146 mmol) and 4-methoxycarbonyl)phenylboronic acid (26 mg, 0.146 mmol) according to the procedure for 43. LC-MS (ESI) m/z: calcd for [$C_{14}H_{12}F_3N_2O_3S^+$], 345.0, found 345.4.

2-(2-(methylsulfonyl)-6-(trifluoromethyl)pyrimidin-4-yl)benzoic acid (63)

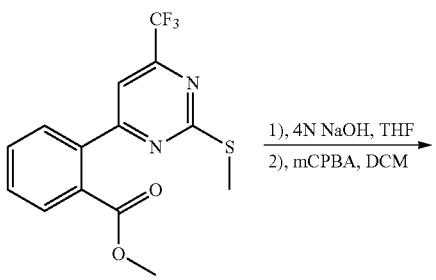

-continued

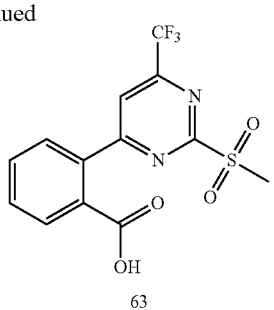

63 methyl 2-(2-(methylthio)-6-(trifluoromethyl)pyrimidin-4-yl)benzoate (100 mg, 0.305 mmol) in THF (8 mL) was added 4N NaOH (aq, 1 mL) dropwise. The reaction mixture was then stirred at room temperature for 4 hrs. Solvents were evaporated in vacuo, and the residue was extracted by EtOAC and H$_2$O 3 times. The organic layer was combined, washed with brine, dried over Na$_2$SO$_4$, concentrated and further purified by silica gel column chromatography to give 95 mg of 2-(2-(methylthio)-6-(trifluoromethyl)pyrimidin-4-yl)benzoic acid as a white solid.

mCPBA (10 mg, 0.04 mmol) was added to a solution of 2-(2-(methylthio)-6-(trifluoromethyl)pyrimidin-4-yl)benzoic acid (10 mg, 0.03 mmol) in DCM and the reaction mixture was stirred at room temperature for 2 hrs. The reaction mixture was extracted by DCM and satured NaHCO$_3$ solution 3 times. The organic layer was combined, washed with brine, dried over Na$_2$SO$_4$ and further purified by silica gel column chromatography (PE/EA=1/1) to give 3 mg of 2-(2-(methylsulfonyl)-6-(trifluoromethyl)pyrimidin-4-yl)benzoic acid as a light yellow solid (0.006 mmol, 27%). $^1$H NMR (400 MHz, CDCl3-d$_6$): δ 8.10 (d, J=8.0 Hz, 1H), 8.00 (s, 1H), 7.69-7.75 (m, 2H), 7.40 (d, J=8.0 Hz, 1H), 3.42 (s, 3H). LC-M S (ESI) m % z: calcd for [C$_{13}$H$_{10}$F$_3$N$_2$O$_4$S$^+$], 347.0, found 347.4.

4-(2-(methylsulfonyl)-6-(trifluoromethyl)pyrimidin-4-yl)benzoic acid (64) and 4-(2-(methylsulfinyl)-6-(trifluoromethyl)pyrimidin-4-yl)benzoic acid (65)

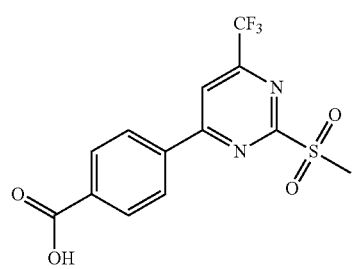

64

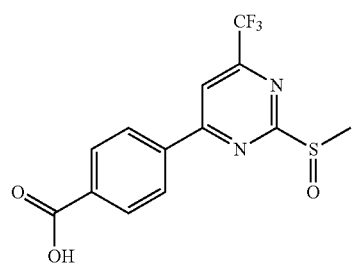

65

The titled compound 64 (5 mg, 0.01 mmol) was prepared in a yield of 32% as a light yellow solid from 4-(2-(methylthio)-6-(trifluoromethyl)pyrimidin-4-yl)benzoic acid (10 mg, 0.03 mmol) and according to the procedure for 63. LC-MS (ESI) m/z: calcd for [C$_{13}$H$_{10}$F$_3$N$_2$O$_4$S$^+$], 347.0, found 347.4.

The titled compound 65 (3 mg, 0.006 mmol) was prepared in a yield of 20% as a light yellow solid from 4-(2-(methylthio)-6-(trifluoromethyl)pyrimidin-4-yl)benzoic acid (10 mg, 0.03 mmol) and according to the procedure for 63. $^1$H NMR (400 MHz, CDCl3-d$_6$): δ 8.29-8.33 (m, 2H), 8.19-8.23 (m, 2H), 8.11 (s, 1H), 3.13 (s, 3H).

3-(2-(methylsulfonyl)-6-(trifluoromethyl)pyrimidin-4-yl)benzamide (66)

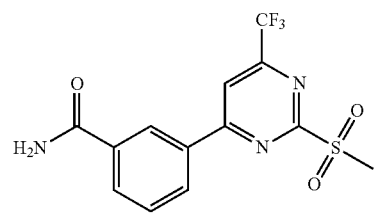 [SMILES: CS(=O)(=O)c1nc(-c2cccc(C(N)=O)c2)cc(C(F)(F)F)n1]

The titled compound (7 mg, 0.02 mmol) was prepared in a yield of 14% as a light yellow solid from 43-02 (50 mg, 0.146 mmol) and (3-((tert-butoxycarbonyl)carbamoyl)phenyl)boronic acid (40 mg, 0.146 mmol) according to the procedure for 43. $^1$H NMR (400 MHz, CDCl3-d$_6$): δ 8.95 (s, 1H), 8.85 (s, 1H), 8.60 (d, J=8.0 Hz, 1H), 8.23 (s, 1H), 8.18 (d, J=8.0 Hz, 1H), 7.75 (t, J=8.0 Hz, 1H0, 7.64 (s, 1H0, 3.58 (s, 3H).

N-methyl-2-(2-(methylsulfonyl)-6-(trifluoromethyl)pyrimidin-4-yl)benzamide (67)

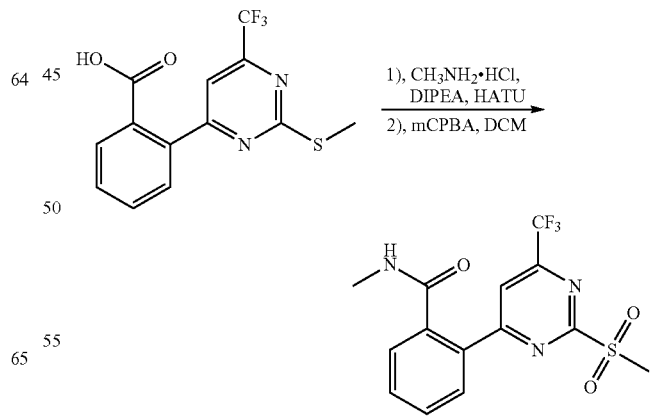

To a solution of 2-(2-(methylthio)-6-(trifluoromethyl)pyrimidin-4-yl)benzoic acid (10 mg, 0.03 mmol) in DMF (1 mL) was added CH$_3$NH$_2$·HCl (1 eq), DIPEA (2.5 eq), HATU (1.2 eq) and the reaction mixture was stirred at room temperature overnight. Solvents were evaporated in vacuo, and the residue was extracted by EtOAC and H$_2$O 3 times. The organic layer was combined, washed with brine, dried over Na$_2$SO$_4$, concentrated and further purified by silica gel column chromatography to give 10 mg of N-methyl-2-(2-(methylthio)-6-(trifluoromethyl)pyrimidin-4-yl)benzamide (89%) as a white solid.

mCPBA (10 mg, 0.04 mmol) was added to a solution of N-methyl-2-(2-(methylthio)-6-(trifluoromethyl)pyrimidin-4-yl)benzamide (10 mg, 0.03 mmol) in DCM and the reaction mixture was stirred at room temperature for 2 hrs. The reaction mixture was extracted by DCM and satured NaHCO$_3$ solution 3 times. The organic layer was combined, washed with brine, dried over Na$_2$SO$_4$ and further purified by silica gel column chromatography (PE/EA=1/1) to give 8 mg of 2-(2-(methylsulfonyl)-6-(trifluoromethyl)pyrimidin-4-yl)benzoic acid as a light yellow solid (0.02 mmol, 70%). LC-MS (ESI) m/z: calcd for [C$_{14}$H$_{13}$F$_3$N$_3$O$_3$S$^+$], 360.1, found 360.4.

Synthesis of N-methyl-4-(2-(methylsulfonyl)-6-(trifluoromethyl)pyrimidin-4-yl)benzamide (68)

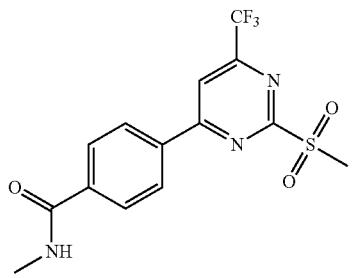 [SMILES: CNC(=O)c1ccc(-c2cc(C(F)(F)F)nc(S(C)(=O)=O)n2)cc1]

The titled compound 68 (7 mg, 0.02 mmol) was prepared in a yield of 62% as a light yellow solid from 4-(2-(methylthio)-6-(trifluoromethyl)pyrimidin-4-yl)benzoic acid (10 mg, 0.03 mmol) and CH$_3$NH$_2$·HCl according to the procedure for 67. $^1$H NMR (400 MHz, CDCl3-d$_6$): δ 8.29 (d, J=8.8 Hz, 2H), 8.23 (s, 1H), 7.96 (d, J=8.8 Hz, 2H), 3.48 (s, 3H), 3.06 (d, J=4.8 Hz, 3H). LC-MS (ESI) m/z: calcd for [C$_{14}$H$_{13}$F$_3$N$_3$O$_3$S$^+$], 360.1, found 360.4.

N,N-dimethyl-3-(2-(methylsulfonyl)-6-(trifluoromethyl)pyrimidin-4-yl)benzamide (69)

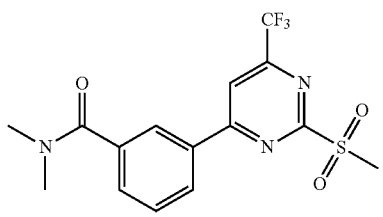

The titled compound 69 (2 mg, 0.004 mmol) was prepared in a yield of 8% as a light yellow solid from 3-(2-(methylthio)-6-(trifluoromethyl)pyrimidin-4-yl)benzoic acid (20 mg, 0.06 mmol) and dimethylamine according to the procedure for 67. $^1$H NMR (400 MHz, DMSO): δ 8.97 (s, 1H), 8.49-8.53 (m, 1H), 8.46 (s, 1H), 7.70-7.72 (m, 2H), 3.56 (s, 3H), 3.04 (s, 3H), 2.94 (s, 3H). LC-MS (ESI) m/z: calcd for [C$_{15}$H$_{15}$F$_3$N$_3$O$_3$S$^+$], 374.0, found 374.5.

1-(3-(2-(methylsulfonyl)-6-(trifluoromethyl)pyrimidin-4-yl)benzyl) pyridin-2 (1H)-one (70)

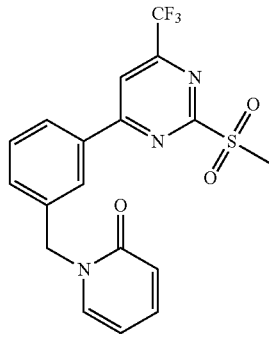 [SMILES: CS(=O)(=O)c1nc(-c2cccc(Cn3ccccc3=O)c2)cc(C(F)(F)F)n1]

The titled compound 70 (12 mg, 0.03 mmol) was prepared in a yield of 21% as a light yellow solid from 43-02 (50 mg, 0.146 mmol) and 1-(3-(4,4,5,5-tetramethyl-1,3,2-dioxaborolan-2-yl)benzyl)pyridin-2 (1H)-one (45 mg, 0.146 mmol) according to the procedure for 43. $^1$H NMR (400 Hz, DMSO) δ 8.86 (s, 1H), 8.41 (s, 1H), 8.37 (d, J=8.0 Hz, 1H), 7.89 (s, J=2.0, 6.8 Hz, 1H), 7.59-7.64 (m, 1H), 7.56 (d, J=8.0 Hz, 1H), 7.42-7.48 (m, 1H), 6.44 (d, J=9.2 Hz, 1H), 6.26-6.30 (m, 1H), 5.24 (s, 2H), 3.54 (s, 3H). LC-MS (ESI) m/z: calcd for [C$_{18}$H$_{15}$F$_3$N$_3$O$_3$S$^+$], 410.1, found 410.5.

2-(methylsulfonyl)-4-(3-(prop-2-yn-1-yloxy)phenyl)-6-(trifluoromethyl) pyrimidine (71) and
2-(methylsulfinyl)-4-(3-(prop-2-yn-1-yloxy)phenyl)-6-(trifluoromethyl) pyrimidine (72)

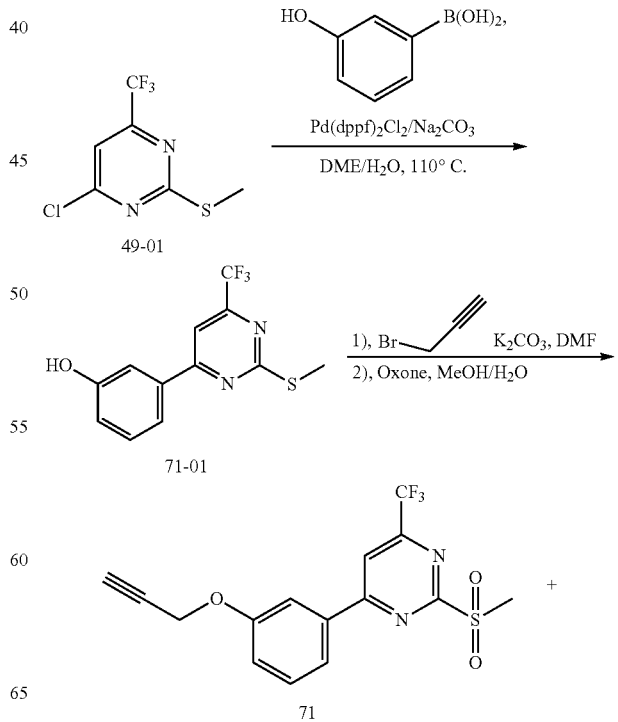

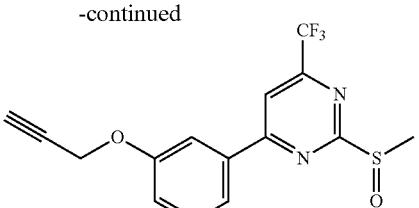

72

Step 1. Preparation of 3-(2-(methylthio)-6-(trifluoromethyl)pyrimidin-4-yl)phenol (71-01)

To a solution of 4-chloro-2-(methylthio)-6-(trifluoromethyl)pyrimidine (200 mg, 0.87 mmol) and (3-hydroxyphenyl)boronic acid (150 mg, 1.05 mmol) in DME/H$_2$O (5 mL/1 mL) was added Pd(dppf)$_2$Cl$_2$ (32 mg, 0.04 mmol) followed by Na$_2$CO$_3$ (280 mg, 2.62 mmol) under N$_2$ atmosphere. The reaction mixture was refluxed at 110° C. for 5 hrs. The reaction mixture was cooled to room temperature and filtered over celite. Solvents were removed in vacuo, and the residue was extracted by DCM and H$_2$O 3 times. The organic layer was combined, washed with brine, dried over Na$_2$SO$_4$ and further purified by silica gel column chromatography (PE/EA=30/1) to give 104 mg of 3-(2-(methylthio)-6-(trifluoromethyl)pyrimidin-4-yl)phenol (71-01) as a white solid (41%).

Step 2. Preparation of 2-(methylsulfonyl)-4-(3-(prop-2-yn-1-yloxy)phenyl)-6-(trifluoromethyl)pyrimidine (89) and 2-(methylsulfinyl)-4-(3-(prop-2-yn-1-yloxy)phenyl)-6-(trifluoromethyl) pyrimidine (90)

K$_2$CO$_3$ (76 mg, 0.54 mmol) was added to a solution of 71-01 (104 mg, 0.36 mmol) and 3-bromoprop-1-yne (52 mg, 0.44 mmol) in DMF (2 mL). The reaction mixture was stirred at room temperature for 3 hrs. The reaction mixture was extracted by EtOAc and H$_2$O 3 times. The organic layer was combined, washed with brine, dried over Na$_2$SO$_4$, concentrated and further purified by silica gel column chromatography (PE/EA=4/1), to give 105 mg of 2-(methylthio)-4-(3-(prop-2-yn-1-yloxy)phenyl)-6-(trifluoromethyl)pyrimidine as a white solid (90%). An aqueous solution of Oxone (1 g, 1.51 mmol) was added dropwise to a solution of 2-(methylthio)-4-(3-(prop-2-yn-1-yloxy)phenyl)-6-(trifluoromethyl)pyrimidine (70 mg, 0.22 mmol) in MeOH. The reaction mixture was stirred at room temperature for 8 hrs. Solvents were evaporated from the reaction mixture, then the residue was extracted by EtOAc/H$_2$O 3 times. The organic layer was combined, washed with brine, dried over Na$_2$SO$_4$ and further purified by silica gel column chromatography (PE/EA=6/1) to give 22 mg of 2-(methylsulfonyl)-4-(3-(prop-2-yn-1-yloxy)phenyl)-6-(trifluoromethyl)pyrimidine (71) as a colorless oil and 6 mg of 2-(methylsulfinyl)-4-(3-(prop-2-yn-1-yloxy)phenyl)-6-(trifluoromethyl) pyrimidine as a colorless oil (72). $^1$H NMR for 71 (400 Hz, CDCl3) δ 8.04 (s, 1H), 7.86-7.83 (m, 1H), 7.51 (t, J=8.0 Hz, 1H), 7.24 (dd, J=2.0, 8.0 Hz, 1H), 4.81 (d, J=2.4 Hz, 2H), 3.07 (s, 3H), 2.57 (t, J=2.4 Hz, 1H). LC-MS (ESI) m/z: calcd for [C$_{15}$H$_{12}$F$_3$N$_2$O$_2$S$^+$], 341.1, found 341.0.

$^1$H NMR for 72 (400 Hz, CDCl$_3$) δ 8.16 (s, 1H), 7.85-7.80 (m, 2H), 7.51 (t, J=8.0 Hz, 1H), 7.25 (dd, J=2.0, 8.0 Hz, 1H), 4.80 (d, J=2.4 Hz, 2H), 3.47 (s, 3H), 2.57 (t, J=2.4 Hz, 1H). LC-MS (ESI) m/z: calcd for [C$_{15}$H$_{12}$F$_3$N$_2$O$_3$S$^+$], 357.1, found 357.0.

2-(methylsulfonyl)-4-(3-phenoxyphenyl)-6-(trifluoromethyl)pyrimidine (73) and 2-(methylsulfinyl)-4-(3-phenoxyphenyl)-6-(trifluoromethyl)pyrimidine (74)

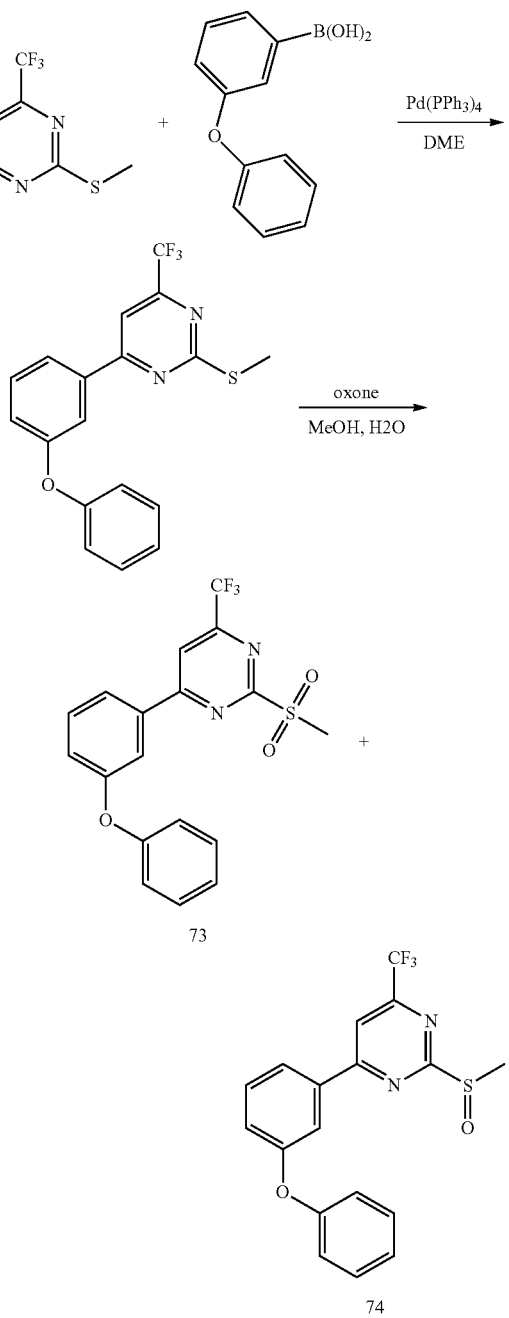

Step 1. Preparation of 2-(methylthio)-4-(3-phenoxyphenyl)-6-(trifluoromethyl)pyrimidine A solution of 4-chloro-2-(methylthio)-6-(trifluoromethyl) pyrimidine (30 mg, 0.13 mmol), (3-phenoxyphenyl)boronic acid (41 mg, 0.14 mmol), Pd(PPh₃)₄ (8 mg, 0.007 mmol) and 1 M Na₂CO₃ aqueous solution (0.39 mL, 0.39 mmol) in DME (2 mL) under nitrogen was heated 100° C. for 5 h. The mixture was cooled to RT and extracted with DCM (30 mL). The organic layer was separated, dried over Na₂SO₄, filtered and concentrated. The crude product was purified by Pre-TLC (EtOAc/PE=1:30) to obtain the product as a white solid (10 mg, 21%). Mass (m/z): 363.4 [M+H]⁺.

Step 2. Preparation of 2-(methylsulfonyl)-4-(3-phenoxyphenyl)-6-(trifluoromethyl)pyrimidine (73) and 2-(methylsulfinyl)-4-(3-phenoxyphenyl)-6-(trifluoromethyl)pyrimidine (74)

To a solution of 2-(methylthio)-4-(3-phenoxyphenyl)-6-(trifluoromethyl)pyrimidine (10 mg, 0.03 mmol) in MeOH (2 mL) was added oxone (51 mg, 0.09 mmol) in H₂O (2 mL). Then the mixture was stirred at RT for 3 h. The solvent was removed and extracted with DCM (20 mL). The organic layer was separated, dried over Na₂SO₄, filtered and concentrated. The crude product was purified by Pre-TLC (EtOAc/PE=1:2) to obtain 73 as a white solid (3 mg) and 74 as a white solid (4 mg). For 73, ¹H NMR: (400 Mz, CDCl3): δ 8.13 (s, 1H), 7.95 (dd, J=0.8, 7.6 Hz, 1H), 7.87 (s, 1H), 7.54 (t, J=8.0 Hz, 1H), 7.39 (t, J=8.0 Hz, 2H), 7.18 (dt, J=0.8, 7.6 Hz, 2H), 7.06 (d, J=8.0 Hz, 2H), 3.44 (s, 3H). Mass (m/z): 395.3 [M+H]⁺. For 74, ¹H NMR: (400 Mz, CDCl3): δ 8.01 (s, 1H), 7.97 (dd, J=0.8, 7.6 Hz, 1H), 7.88 (s, 1H), 7.52 (t, J=8.0 Hz, 1H), 7.38 (t, J=8.0 Hz, 2H), 7.18 (dt, J=0.8, 7.6 Hz, 2H), 7.06 (d, J=8.0 Hz, 2H), 3.05 (s, 3H). Mass (m/z): 379.4 [M+H]⁺.

4-(3-(benzyloxy)phenyl)-2-(methylsulfonyl)-6-(trifluoromethyl)pyrimidine (75)

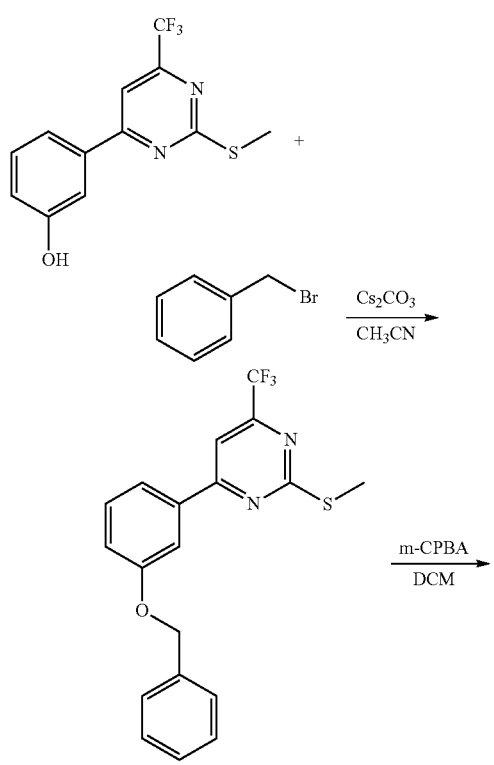

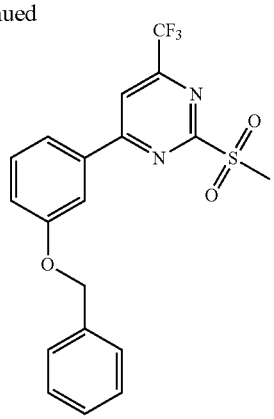

Step 1. Preparation of 4-(3-(Benzyloxy)phenyl)-2-(methylthio)-6-(trifluoromethyl)pyrimidine Cs₂CO₃ (68 mg, 0.20 mmol) was added to a solution of 3-(2-(methylthio)-6-(trifluoromethyl)pyrimidin-4-yl)phenol (30 mg, 0.10 mmol) in anhydrous CH₃CN (5 mL) at 0° C. After stirring for 30 min, benzyl bromide (27 mg, 0.15 mmol) was added dropwise and stirred at RT for 3 h. After evaporation the organic solvents, the residue was purified by column chromatography (200-300 mesh silica gel, eluted with EtOAc/PE=1:25) to give the product as a white solid (10 mg, 26%). Mass (m/z): 377.4 [M+H]⁺.

Step 2. Preparation of 4-(3-(benzyloxy)phenyl)-2-(methylsulfonyl)-6-(trifluoromethyl)pyrimidine (93)

To a solution of 4-(3-(Benzyloxy)phenyl)-2-(methylthio)-6-(trifluoromethyl)pyrimidine (10 mg, 0.03 mmol) in DCM (2 mL) was added m-CPBA (14 mg, 0.09 mmol) at RT. Then the mixture was stirred at RT for 3 h. The solvent was removed and extracted with DCM (20 mL). The organic layer was separated, dried over Na₂SO₄, filtered and concentrated. The crude product was purified by Pre-TLC (EtOAc/PE=1:2) to obtain 75 as a white solid (3 mg, 24%): ¹H NMR (400 MHz, CDCl₃) of: δ 8.15 (s, 1H), 7.86 (s, 1H), 7.79 (d, J=8.0 Hz, 1H), 7.51-7.34 (m, 7H), 5.18 (s, 2H), 3.46 (s, 3H). Mass (m/z): 409.4 [M+H]⁺.

2-(methylsulfonyl)-4-(naphthalen-1-yl)-6-(trifluoromethyl)pyrimidine (76) and 2-(methylsulfinyl)-4-(naphthalen-1-yl)-6-(trifluoromethyl)pyrimidine (77)

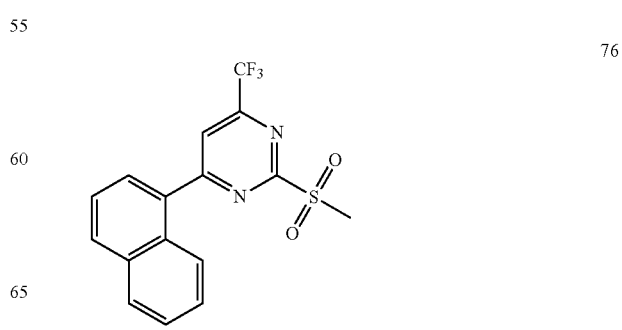

77

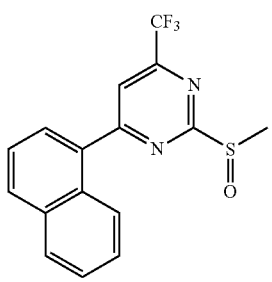

The titled compound 76 (2 mg, 0.003 mmol) was prepared in a yield of 2% as a light yellow solid from 43-02 (50 mg, 0.146 mmol) and naphthalen-1-ylboronic acid (25 mg, 0.146 mmol) according to the procedure for 43. $^1$H NMR (400 MHz, CDCl3-d$_6$): δ 8.21-8.24 (m, 1H), 8.17 (s, 1H), 8.08 (d, J=8.4 Hz, 1H), 7.95-8.00 (m, 1H), 7.83 (dd, J=1.2, 7.2 Hz, 1H), 7.58-7.66 (m, 3H), 3.48 (s, 3H). LC-MS (ESI) m/z: calcd for [$C_{16}H_{12}F_3N_2O_2S^+$], 353.1, found 337.4.

The titled compound 77 (8 mg, 0.012 mmol) was prepared in a yield of 7% as a light yellow solid from 43-02 (50 mg, 0.146 mmol) and naphthalen-1-ylboronic acid (25 mg, 0.146 mmol) according to the procedure for 43. LC-MS (ESI) m/z: calcd for [$C_{16}H_{12}F_3N_2OS^+$], 337.0, found 337.4.

4-(2-Methoxypyridin-3-yl)-2-(methylsulfinyl)-6-(trifluoromethyl)pyrimidine (78)

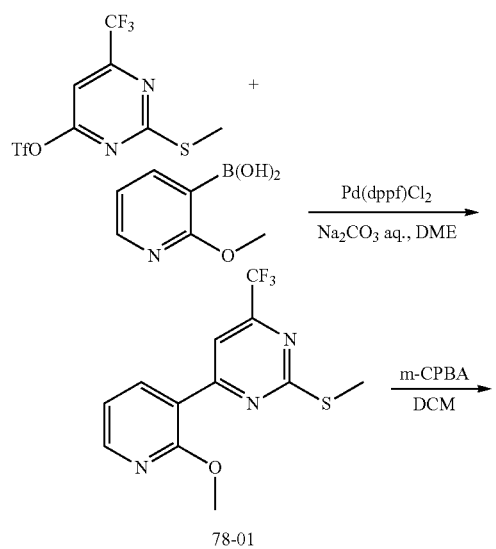

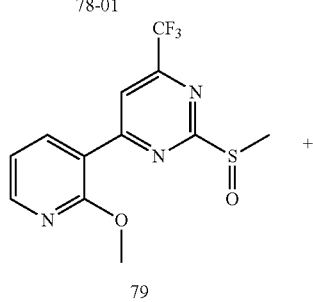

79

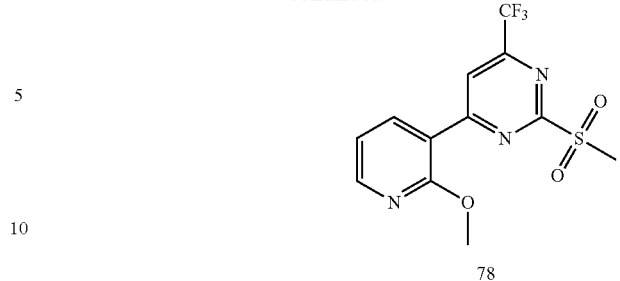

78

Step 1. Preparation of 4-(2-Methoxypyridin-3-yl)-2-(methylthio)-6-(trifluoromethyl)pyrimidine (78-01)

To a solution of 2-(methylthio)-6-(trifluoromethyl)pyrimidin-4-yl trifluoromethanesulfonate (112 mg, 0.33 mmol), (2-methoxypyridin-3-yl)boronic acid (50 mg, 0.33 mmol), Pd(dppf)Cl$_2$ (12 mg, 0.02 mmol) and 2 M Na$_2$CO$_3$ aqueous solution (0.49 mL, 0.99 mmol) in DME (10 mL) under nitrogen was heated 100° C. for 4 h. The mixture was cooled to RT and extracted with DCM (3×20 mL). The organic layer was separated, dried over Na$_2$SO$_4$, filtered and concentrated. The crude product was purified by column chromatography (200-300 mesh silica gel, eluted with EtOAc/PE=1:40) to obtain the product as a white solid (10 mg, 10%): $^1$H NMR (400 MHz, CDCl$_3$): δ 8.57 (dd, J=2.0, 7.6 Hz, 1H), 8.32 (dd, J=2.0, 4.8 Hz, 1H), 8.11 (s, 1H), 7.08 (dd, J=4.8, 7.6 Hz, 1H), 4.10 (s, 3H), 2.65 (s, 3H). Mass (m/z): 302.3 [M+H]$^+$.

Step 2. Preparation of 4-(2-Methoxypyridin-3-yl)-2-(methylsulfinyl)-6-(trifluoromethyl)pyrimidine (79) and 4-(2-methoxypyridin-3-yl)-2-(methylsulfonyl)-6-(trifluoromethyl)pyrimidine (78)

To a solution of 4-(2-methoxypyridin-3-yl)-2-(methylthio)-6-(trifluoromethyl)pyrimidine (10 mg, 0.03 mmol) in DCM (2 mL) was added m-CPBA (16 mg, 0.09 mmol) at RT. Then the mixture was stirred at RT for 3 h. The solvent was removed and extracted with DCM (20 mL). The organic layer was separated, dried over Na$_2$SO$_4$, filtered and concentrated. The crude product was purified by Pre-TLC (EtOAc/PE=1:2) to obtain 79 as a white solid (3 mg) and 78 as a white solid (4 mg). For 79, $^1$H NMR (400 MHz, CDCl$_3$) of: θ 8.81 (dd, J=2.0, 7.6 Hz, 1H), 8.60 (s, 1H), 8.39 (dd, J=2.0, 4.8 Hz, 1H), 7.13 (d, J=4.8, 7.6 Hz, 1H), 4.15 (s, 3H), 3.05 (s, 3H). Mass (m/z): 318.4 [M+H]$^+$. For 78, $^1$H NMR (400 MHz, CDCl$_3$) of: δ 8.78 (dd, J=2.0, 7.6 Hz, 1H), 8.73 (s, 1H), 8.41 (dd, J=2.0, 4.8 Hz, 1H), 7.15 (dd, J=4.8, 7.6 Hz, 1H), 4.16 (s, 3H), 3.46 (s, 3H). Mass (m/z): 334.3 [M+H]$^+$.

3-(2-(methylsulfinyl)-6-(trifluoromethyl)pyrimidin-4-yl)pyridin-2 (1H)-one (81) and 3-(2-(methylsulfonyl)-6-(trifluoromethyl)pyrimidin-4-yl)pyridin-2 (1H)-one (80)

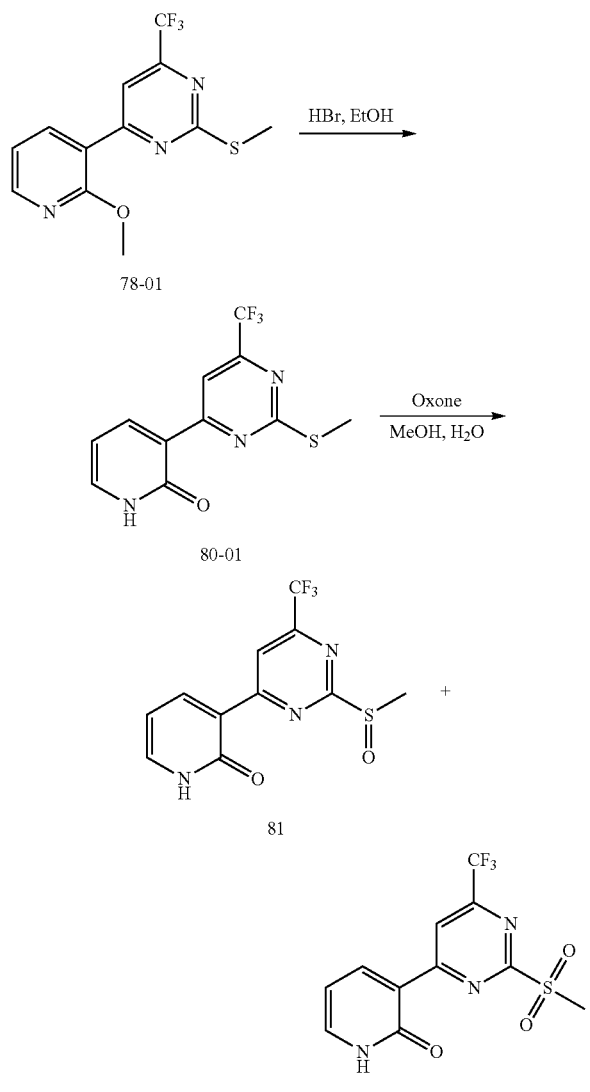

Step 1. Preparation of 3-(2-(methylthio)-6-(trifluoromethyl)pyrimidin-4-yl) pyridine-2 (1H)-one (80-01)

A solution of 4-(2-methoxypyridin-3-yl)-2-(methylthio)-6-(trifluoromethyl)pyrimidine (50 mg, 0.17 mmol) in 10/3 (v:v) of HBr/EtOH (2.5 mL) was heated to 100° C. for 2 h. Then the solvents were removed and adjusted pH to 7 with saturated aqueous NaHCO$_3$ solution. Then the solid was precipitate out and filtered to give product as a white solid (42 mg, 94%). $^1$H NMR (400 MHz, DMSO-d$_6$): δ 12.46 (br, 1H), 8.85 (s, 1H), 8.78 (dd, J=2.4, 7.2 Hz, 1H), 7.79 (dd, J=2.4, 6.4 Hz, 1H), 6.52 (dd, J=6.4, 7.2 Hz, 1H), 2.63 (s, 3H). Mass (m/z): 288.03 [M+H]$^+$.

Step 2. 3-(2-(methylsulfinyl)-6-(trifluoromethyl)pyrimidin-4-yl)pyridin-2 (1H)-one (81) and 3-(2-(methylsulfonyl)-6-(trifluoromethyl)pyrimidin-4-yl)pyridin-2 (1H)-one (80)

To a solution of 3-(2-(methylthio)-6-(trifluoromethyl)pyrimidin-4-yl)pyridin-2 (1H)-one (10 mg, 0.03 mmol) in MeOH (1 mL) was added oxone (64 mg, 0.09 mmol) in H$_2$O (1 mL). Then the mixture was stirred at RT for 3 h. The solvent was removed and extracted with DCM (20 mL). The organic layer was separated, dried over Na$_2$SO$_4$, filtered and concentrated. The crude product was purified by Pre-TLC (EtOAc/PE=3:2) to obtain 81 as a white solid (3 mg) and 80 as a white solid (3 mg). For 81, $^1$H NMR: (400 Mz, CD$_3$OD): δ 9.29 (s, 1H), 9.08 (dd, J=1.6, 7.2 Hz, 1H), 7.78 (dd, J=1.6, 6.4 Hz, 1H), 6.64 (dd, J=6.4, 7.2 Hz, 1H), 3.06 (s, 3H). Mass (m/z): 304.2 [M+H]$^+$. For 80, $^1$H NMR: (400 Mz, CD$_3$OD): δ 9.42 (s, 1H), 9.03 (dd, J=1.6, 7.2 Hz, 1H), 7.81 (dd, J=1.6, 6.4 Hz, 1H), 6.66 (dd, J=6.4, 7.2 Hz, 1H), 3.48 (s, 3H). Mass (m/z): 320.3 [M+H]$^+$.

4-(2-(methylsulfinyl)-6-(trifluoromethyl)pyrimidin-4-yl)morpholine (82)

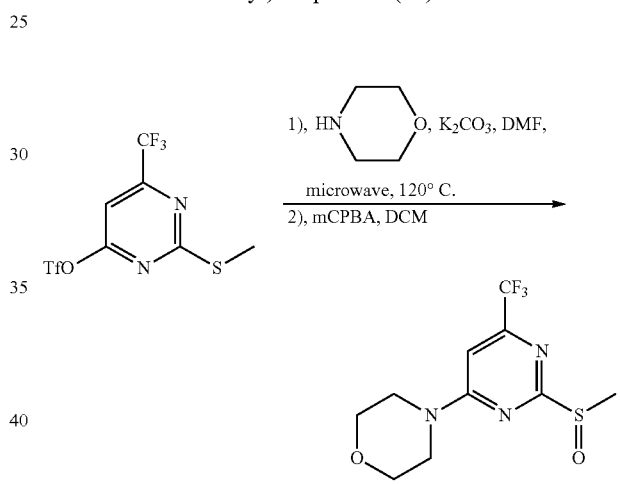

The titled compound 82 was prepared in a yield of 55% (5 mg, 0.02 mmol) as a white solid from 43-02 (50 mg, 0.146 mmol) and morpholine (13 mg, 0.15 mmol) according to the procedure for 36. $^1$H NMR (400 MHz, CDCl3-d$_6$): δ 6.78 (s, 1H), 3.80-3.83 (m, 4H), 2.93 (s, 3H).

2-(methylsulfonyl)-4-(1H-pyrazol-1-yl)-6-(trifluoromethyl)pyrimidine (83)

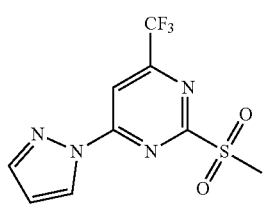

The titled compound (10 mg, 0.02 mmol) was prepared in a yield of 10% as a light yellow solid from 43-02 (50 mg, 0.146 mmol) and 1H-pyrazole (10 mg, 0.146 mmol) according to the procedure for 36. $^1$H NMR (400 MHz, CDCl3-d$_6$):

δ 8.70 (dd, J=0.8, 2.0 Hz, 1H), 8.43 (s, 1H), 7.91 (m, 1H), 6.63 (dd, J=1.6, 2.4 Hz, 1H), 3.45 (s, 3H).

2-(methylsulfonyl)-4-(1H-pyrrol-2-yl)-6-(trifluoromethyl)pyrimidine (84)

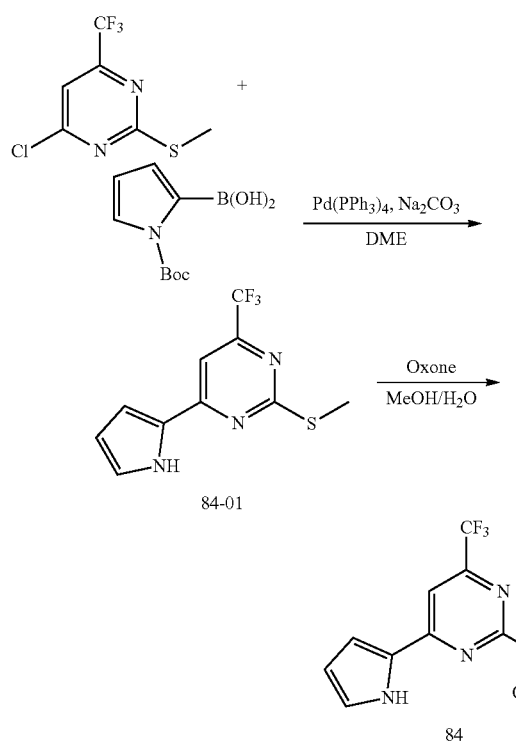

Step 1. Preparation of 2-(methylthio)-4-(1H-pyrrol-2-yl)-6-(trifluoromethyl)pyrimidine (84-01)

To a solution of 4-chloro-2-(methylthio)-6-(trifluoromethyl)pyrimidine (94.9 mg, 0.42 mmol), 1-(tert-butoxycarbonyl)-1H-pyrrol-2-ylboronic acid (87 mg, 0.42 mmol), Pd(pph$_3$)$_4$ (24.1 mg, 0.02 mmol) and Na$_2$CO$_3$ (1 ml) in DME (3 ml) under nitrogen was heated 105° C. for 3 h. The mixture was cooled to RT and extracted with DCM (3*20 mL). The organic layer was separated, dried over Na$_2$SO$_4$, filtered and concentrated. The crude product was purified by Prep.TLC to obtain the product (60 mg) as a white solid. Mass (m/z): 260.04 [M+H]$^+$.

Step 2. Preparation of 2-(methylsulfonyl)-4-(1H-pyrrol-2-yl)-6-(trifluoromethyl)-pyrimidine To a solution of 2-(methylthio)-4-(1H-pyrrol-2-yl)-6-(trifluoromethyl)pyrimidine (10 mg, 0.038 mmol) in MeOH (2 ml) was added oxone (108 mg, 0.17 mmol) in H$_2$O (2 ml). Then the mixture was stirred at RT for 5 h. The solvent was removed and extracted with DCM (3*15 ml). The organic layer was separated, dried over Na$_2$SO$_4$, filtered and concentrated. The crude product was purified by Prep.TLC to obtain the product (5.1 mg, 45.1%) as a white solid. $^1$H-NMR (400 MHz, CDCl$_3$): δ 10.17 (s, 1H), 7.74 (s, 1H), 7.17-7.16 (m, 2H), 6.44-6.42 (m, 1H), 3.40 (s, 3H). Mass (m/z): 292.03 [M+H]$^+$.

4-(1-(3,4-dimethoxybenzyl)-1H-pyrrol-2-yl)-2-(methylsulfonyl)-6-(trifluoromethyl)pyrimidine (85) and 4-(1-(3,4-dimethoxybenzyl)-1H-pyrrol-2-yl)-2-(methylsulfinyl)-6-(trifluoromethyl)pyrimidine (86)

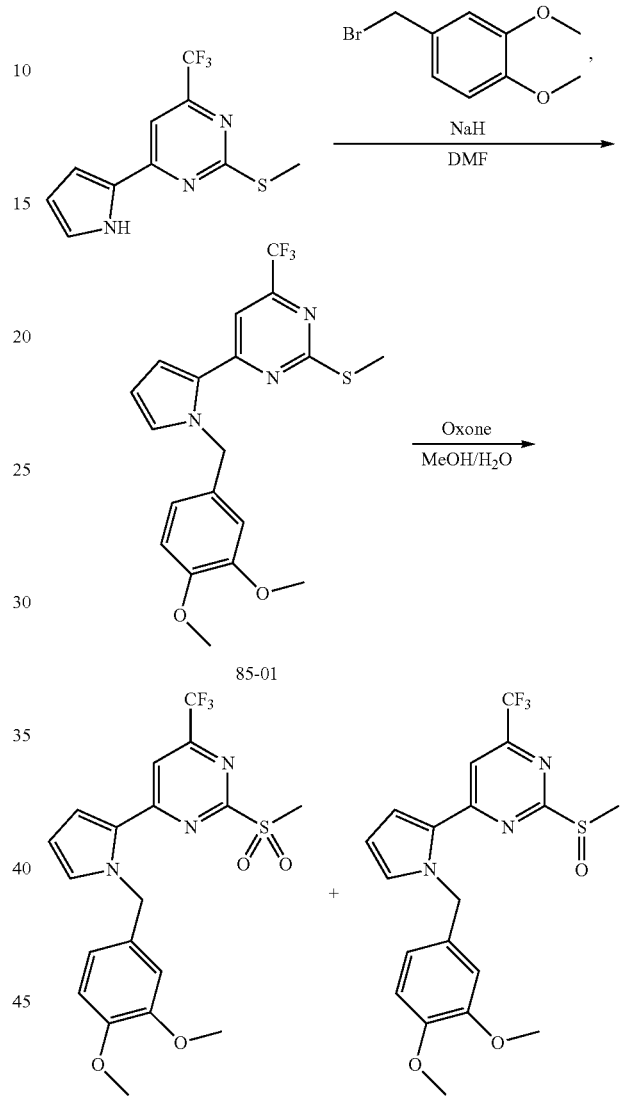

Step 1. Preparation of 4-(1-(3,4-dimethoxybenzyl)-1H-pyrrol-2-yl)-2-(methylthio)-6-(tri-fluoromethyl)pyrimidine (85-01)

To a solution of 2-(methylthio)-4-(1H-pyrrol-2-yl)-6-(trifluoromethyl)pyrimidine (40.0 mg, 0.15 mmol) and NaH (14.0 mg, 0.28 mmol) in anhydrous DMF (3 ml) was stirred at 0° C. for 15 min. Then to the mixture was added 4-(bromomethyl)-1,2-dimethoxybenzene (42.6 mg, 0.18 mmol) and stirred at RT for 4 h. Then the reaction mixture was poured into water and extracted with EA (3*15 mL) and the organic layer was separated, dried over Na$_2$SO$_4$, filtered and concentrated. The crude product was purified by Prep.TLC to obtain the product (43.0 mg) as a white solid. Mass (m/z): 410.11[M+H]$^+$.

Step 2. Preparation of 4-(1-(3,4-dimethoxybenzyl)-1H-pyrrol-2-yl)-2-(methylsulfonyl)-6-(trifluoromethyl)pyrimidine (85) and 4-(1-(3,4-dimethoxybenzyl)-1H-pyrrol-2-yl)-2-(methylsulfinyl)-6-(trifluoromethyl)pyrimidine (86)

To a solution of 4-(1-(3,4-dimethoxybenzyl)-1H-pyrrol-2-yl)-2-(methylthio)-6-(trifluoromethyl)pyrimidine (40 mg, 0.097 mmol) in MeOH (3 ml) was added oxone (293.4 mg, 0.47 mmol) in H₂O (3 ml). Then the mixture was stirred at RT for 4 h. The solvent was removed and extracted with DCM (3*15 ml). The organic layer was separated, dried over Na₂SO₄, filtered and concentrated. The crude product was purified by Prep.TLC to obtain the 85 (15 mg, 23.25%) as a white solid. And 86 5.0 mg (12.07%) as a white solid 85 $^1$H-NMR (400 Mz, CDCl₃): δ 7.76 (s, 1H), 7.18-7.15 (m, 2H), 6.82 (d, J=2.0 Hz, 1H), 6.73 (d, J=8.0 Hz, 1H), 6.57 (dd, J=2.0 Hz, $^2$J=8 Hz, 1H), 6.39-6.37 (m, 1H), 5.79 (s, 2H), 3.83 (s, 3H), 3.80 (s, 3H), 3.45 (s, 3H). Mass (m/z): 442.10[M+H]⁺.

86 $^1$H-NMR (400 Mz, CDCl₃): δ 7.72 (s, 1H), 7.08-7.07 (m, 2H), 6.85 (d, J=2.4 Hz, 1H), 6.76 (d, J=7.2 Hz, 1H), 6.63 (dd, $^1$J=2.4 Hz, $^2$J=7.2 Hz, 1H), 6.63-6.61 (m, 1H), 5.74 (s, 2H), 3.85 (s, 3H), 3.82 (s, 3H), 3.28 (s, 3H). Mass (m/z): 426.10[M+H]⁺.

2-(methylsulfonyl)-4-(1H-pyrrol-3-yl)-6-(trifluoromethyl)pyrimidine (87) and 2-(methylsulfinyl)-4-(1H-pyrrol-3-yl)-6-(trifluoromethyl)pyrimidine (88)

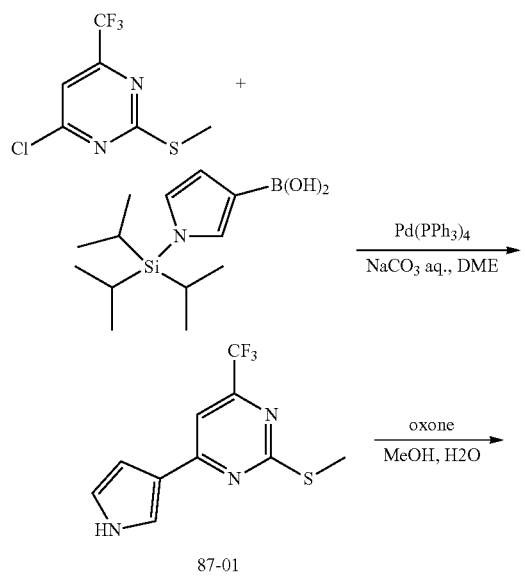

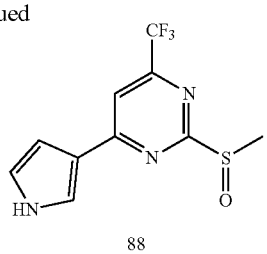

Step 1. Preparation of 2-(methylthio)-4-(1H-pyrrol-3-yl)-6-(trifluoromethyl)pyrimidine (87-01)

To a solution of 4-chloro-2-(methylthio)-6-(trifluoromethyl)pyrimidine (228 mg, 1 mmol), (1-(triisopropylsilyl)-1H-pyrrol-3-yl)boronic acid (267 mg, 1 mmol), Pd(PPh₃)₄ (58 mg, 0.05 mmol) and 1 M Na₂CO₃ aqueous solution (3 mL, 3 mmol) in DME (10 mL) under nitrogen was heated 100° C. for 5 h. The mixture was cooled to RT and extracted with DCM (3×30 mL). The organic layer was separated, dried over Na₂SO₄, filtered and concentrated. The crude product was purified by column chromatography (200~300 mesh silica gel, eluted with EtOAc/PE=1:50-1:10) to obtain the product as a white solid (190 mg, 73%). Mass (m/z): 260.2 [M+H]⁺.

Step 2. 2-(methylsulfonyl)-4-(1H-pyrrol-3-yl)-6-(trifluoromethyl)pyrimidine (87) and 2-(methylsulfinyl)-4-(1H-pyrrol-3-yl)-6-(trifluoromethyl)pyrimidine (88)

To a solution of 2-(methylthio)-4-(1H-pyrrol-3-yl)-6-(trifluoromethyl)pyrimidine (50 mg, 0.2 mmol) in MeOH (3 mL) was added oxone (356 mg, 0.6 mmol) in H₂O (3 mL). Then the mixture was stirred at RT for 3 h. The solvent was removed and extracted with DCM (50 mL). The organic layer was separated, dried over Na₂SO₄, filtered and concentrated. The crude product was purified by Pre-TLC (EtOAc/PE=1:2) to obtain 87 as a white solid (12 mg, 13%) and 88 as a white solid (15 mg, 17%). For 87, $^1$H NMR: (400 Mz, CDCl3): δ 8.80-8.75 (m, 1H), 7.86-7.82 (m, 1H), 7.75 (s, 1H), 6.94-6.91 (m, 1H), 6.86-6.82 (m, 1H), 3.42 (s, 3H). Mass (m/z): 292.2 [M+H]⁺. For 88, $^1$H NMR: (400 Mz, CDCl3): δ 9.39-9.36 (m, 1H), 7.86-7.84 (m, 1H), 7.64 (s, 1H), 6.92-6.90 (m, 1H), 6.81-6.78 (m, 1H), 3.02 (s, 3H). Mass (m/z): 276.3 [M+H]⁺.

4-(1-(3-methoxybenzyl)-1H-pyrrol-3-yl)-2-(methylsulfonyl)-6-(trifluoromethyl)pyrimidine (89) and 4-(1-(3-methoxybenzyl)-1H-pyrrol-3-yl)-2-(methylsulfinyl)-6-(trifluoromethyl)pyrimidine (90)

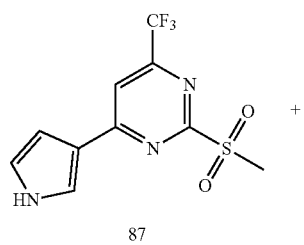

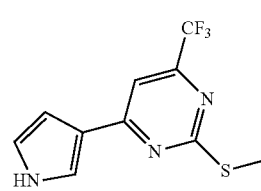

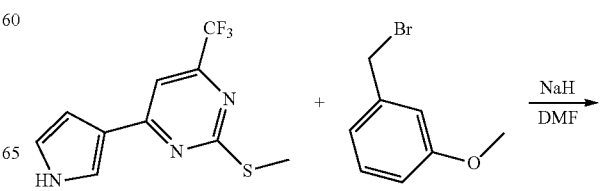

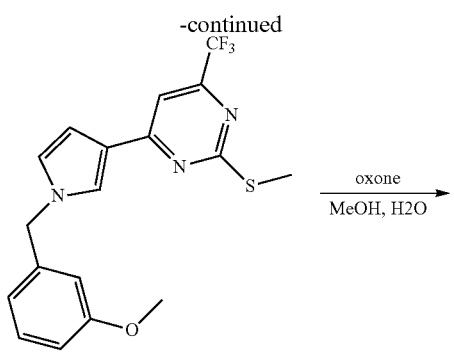

Step 1. Preparation of 4-(1-(3-methoxybenzyl)-1H-pyrrol-3-yl)-2-(methylthio)-6-(trifluoromethyl)pyrimidine To a solution of 2-(methylthio)-4-(1H-pyrrol-3-yl)-6-(trifluoromethyl)pyrimidine (30 mg, 0.11 mmol) in anhydrous DMF (2 mL) was added NaH (5 mg, 0.12 mmol) at 0° C. and stirred for 30 min. Then to the mixture was added 1-(bromomethyl)-3-methoxybenzene (24 mg, 0.12 mmol) and stirred at RT for 5 h. Then the reaction mixture was poured into water and extracted with EA (2×15 mL) and the organic layer was separated, dried over Na$_2$SO$_4$, filtered and concentrated. The crude product was purified by Pre-TLC (EtOAc/PE=1:7) to give the product (36 mg, 82%) as a white solid. Mass (m/z): 380.4 [M+H]$^+$.

Step 2. Preparation of 4-(1-(3-methoxybenzyl)-1H-pyrrol-3-yl)-2-(methylsulfonyl)-6-(trifluoromethyl)pyrimidine (89) and 4-(1-(3-methoxybenzyl)-1H-pyrrol-3-yl)-2-(methylsulfinyl)-6-(trifluoromethyl)pyrimidine (90)

To a solution of 4-(1-(3-methoxybenzyl)-1H-pyrrol-3-yl)-2-(methylthio)-6-(trifluoromethyl)pyrimidine (40 mg, 0.11 mmol) in MeOH (1.5 mL) was added oxone (203 mg, 0.33 mmol) in H$_2$O (1.5 mL). Then the mixture was stirred at RT for 3 h. The solvent was removed and extracted with DCM (20 mL). The organic layer was separated, dried over Na$_2$SO$_4$, filtered and concentrated. The crude product was purified by Pre-TLC (EtOAc/PE=3:2) to obtain 89 as a white solid (14 mg, 31%) and 90 as a white solid (11 mg, 24%). For 89, $^1$H NMR: (400 Mz, CDCl$_3$): δ 7.74 (s, 1H), 7.68 (s, 1H), 7.28 (t, J=8.0 Hz, 1H), 6.86 (dd, J=2.4, 8.4 Hz, 1H), 6.79-6.75 (m, 3H), 6.68 (s, 1H), 5.08 (s, 2H), 3.78 (s, 3H), 3.39 (s, 3H). Mass (m/z): 412.2 [M+H]$^+$. For 90, $^1$H NMR: (400 Mz, CDCl$_3$): δ 7.75 (s, 1H), 7.59 (s, 1H), 7.28 (t, J=8.0 Hz, 1H), 6.87 (dd, J=2.4, 8.4 Hz, 1H), 6.78-6.75 (m, 3H), 6.69 (s, 1H), 5.08 (s, 2H), 3.78 (s, 3H), 2.99 (s, 3H). Mass (m/z): 396.4 [M+H]$^+$.

4-(1-(4-methoxybenzyl)-1H-pyrrol-3-yl)-2-(methylsulfonyl)-6-(trifluoromethyl)pyrimidine (91) and 4-(1-(4-methoxybenzyl)-1H-pyrrol-3-yl)-2-(methylsulfinyl)-6-(trifluoromethyl)pyrimidine (92)

The titled compound 91 (5 mg, 11% yield) and 92 (5 mg, 11% yield) was prepared as two white solids from 87-01 (30 mg, 0.11 mmol) and 1-(bromomethyl)-4-methoxybenzene (24 mg, 0.12 mmol) according to the procedure for 89.

91 $^1$H NMR: (400 Mz, CDCl$_3$): δ 7.74-7.71 (m, 1H), 7.67 (s, 1H), 7.16-7.12 (m, 2H), 6.91-6.85 (m, 2H), 6.77-6.74 (m, 2H), 5.04 (s, 2H), 3.81 (s, 3H), 3.39 (s, 3H). Mass (m/z): 412.3 [M+H]$^+$.

92 $^1$H NMR: (400 Mz, CDCl$_3$): δ 7.74-7.72 (m, 1H), 7.57 (s, 1H), 7.16-7.13 (m, 2H), 6.91-6.88 (m, 2H), 6.76-6.74 (m, 2H), 5.04 (s, 2H), 3.80 (s, 3H), 2.98 (s, 3H). Mass (m/z): 396.4 [M+H]$^+$.

223

4-(1-(3-chlorobenzyl)-1H-pyrrol-3-yl)-2-(methyl-sulfonyl)-6-(trifluoromethyl)pyrimidine (93) and 4-(1-(3-chlorobenzyl)-1H-pyrrol-3-yl)-2-(methyl-sulfinyl)-6-(trifluoromethyl)pyrimidine (94)

224

4-(1-(4-chlorobenzyl)-1H-pyrrol-3-yl)-2-(methyl-sulfonyl)-6-(trifluoromethyl)pyrimidine (95) and 4-(1-(4-chlorobenzyl)-1H-pyrrol-3-yl)-2-(methyl-sulfinyl)-6-(trifluoromethyl)pyrimidine (96)

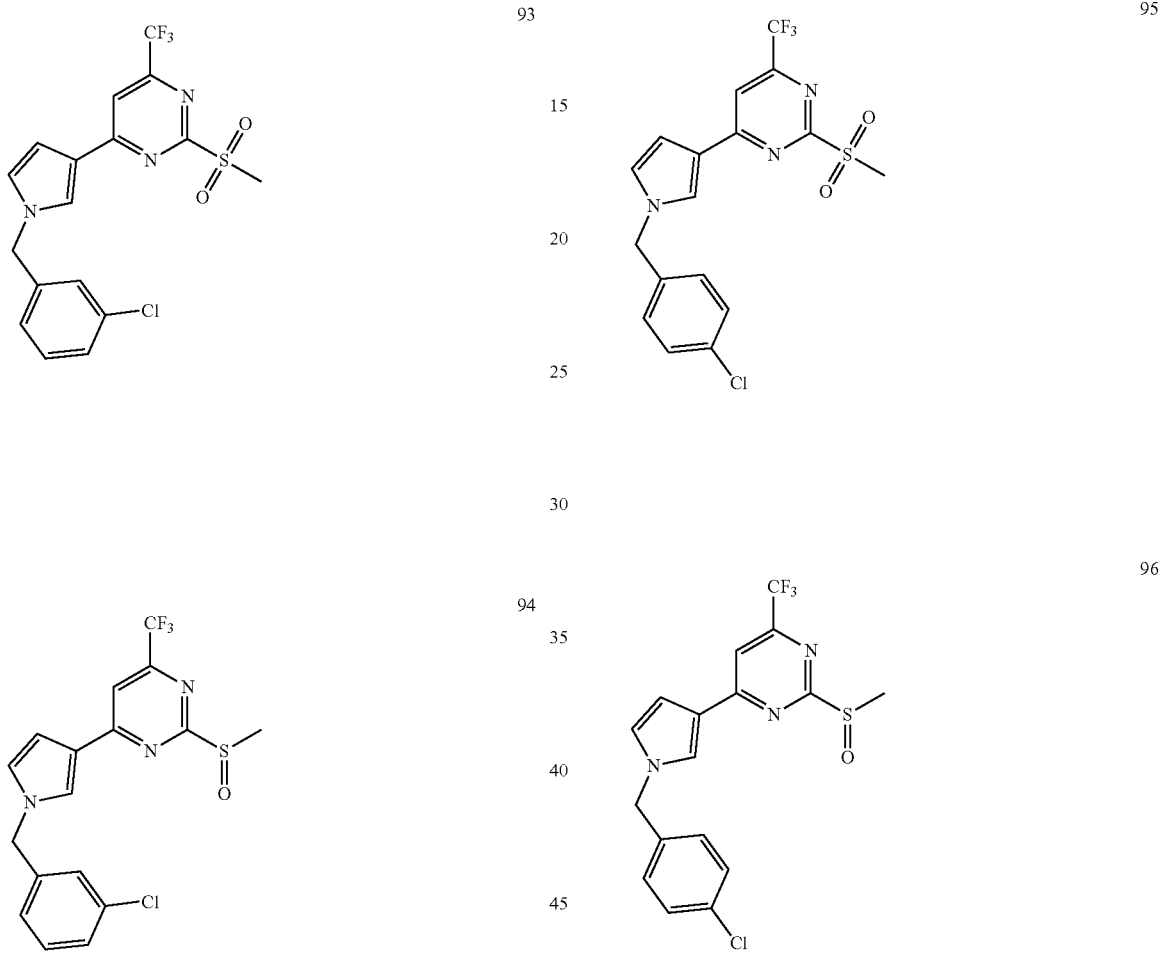

The titled compound 93 (5 mg, 11% yield) and 94 (5 mg, 11% yield) was prepared as two white solids from 87-01 (30 mg, 0.11 mmol) and 1-(bromomethyl)-3-chlorobenzene (24 mg, 0.12 mmol) according to the procedure for 89.

93 $^1$H NMR: (400 Mz, CDCl$_3$): δ 7.74-7.73 (m, 1H), 7.70 (s, 1H), 7.32-7.29 (m, 2H), 7.14 (s, 1H), 7.06-7.04 (m, 1H), 6.80-6.76 (m, 2H), 5.09 (s, 2H), 3.40 (s, 3H). Mass (m/z): 416.4 [M+H]$^+$.

94 $^1$H NMR: (400 Mz, CDCl$_3$): δ 7.77-7.73 (m, 1H), 7.60 (s, 1H), 7.31-7.29 (m, 2H), 7.14 (s, 1H), 7.06-7.04 (m, 1H), 6.80-6.74 (m, 2H), 5.09 (s, 2H), 2.99 (s, 3H). Mass (m/z): 340.6 [M+H]$^+$.

The titled compound 95 (5 mg, 11% yield) and 96 (5 mg, 11% yield) was prepared as two white solids from 87-01 (30 mg, 0.11 mmol) and 1-(bromomethyl)-4-chlorobenzene (24 mg, 0.12 mmol) according to the procedure for 89.

95 $^1$H NMR: (400 Mz, CDCl$_3$): δ 7.75-7.73 (m, 1H), 7.68 (s, 1H), 7.33 (d, J=8.4 Hz, 2H), 7.11 (d, J=8.4 Hz, 2H), 6.79-6.77 (m, 1H), 6.75-6.73 (m, 1H), 5.09 (s, 2H), 3.39 (s, 3H). Mass (m/z): 416.4 [M+H]$^+$.

96 $^1$H NMR: (400 Mz, CDCl$_3$): δ 7.75-7.72 (m, 1H), 7.59 (s, 1H), 7.33 (d, J=8.4 Hz, 2H), 7.10 (d, J=8.4 Hz, 2H), 6.79-6.77 (m, 1H), 6.75-6.73 (m, 1H), 5.08 (s, 2H), 2.99 (s, 3H). Mass (m/z): 400.6 [M+H]$^+$.

3-((3-(2-(methylsulfonyl)-6-(trifluoromethyl)pyrimidin-4-yl)-1H-pyrrol-1-yl)methyl)benzonitrile (97) and 3-((3-(2-(methylsulfinyl)-6-(trifluoromethyl) pyrimidin-4-yl)-1H-pyrrol-1-yl)methyl)benzonitrile (98)

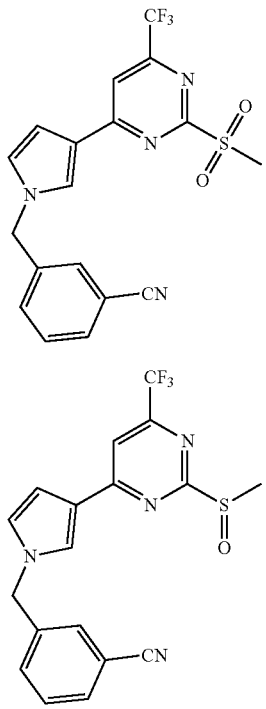

The titled compound 97 (5 mg, 11% yield) and 98 (5 mg, 11% yield) was prepared as two white solids from 87-01 (30 mg, 0.11 mmol) and 3-(bromomethyl)benzonitrile (24 mg, 0.12 mmol) according to the procedure for 89.

97 ¹H NMR: (400 Mz, CDCl₃): δ 7.77-7.75 (m, 1H), 7.72 (s, 1H), 7.64 (d, J=8.0 Hz, 1H), 7.50 (t, J=8.0 Hz, 1H), 7.42-7.38 (m, 2H), 6.83-6.81 (m, 1H), 6.78-6.76 (m, 1H), 5.17 (s, 2H), 3.40 (s, 3H). Mass (m/z): 407.3 [M+H]⁺.

98 ¹H NMR: (400 Mz, CDCl₃): δ 7.78-7.75 (m, 1H), 7.63-7.61 (m, 2H), 7.51-7.47 (m, 1H), 7.41-7.38 (m, 2H), 6.84-6.82 (m, 1H), 6.77-6.75 (m, 1H), 5.17 (s, 2H), 2.99 (s, 3H). Mass (m/z): 391.3 [M+H]⁺.

5-(2-(methylsulfonyl)-6-(trifluoromethyl)pyrimidin-4-yl)pyridin-2 (1H)-one (99)

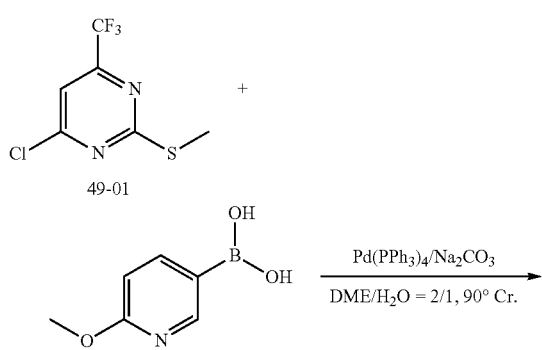

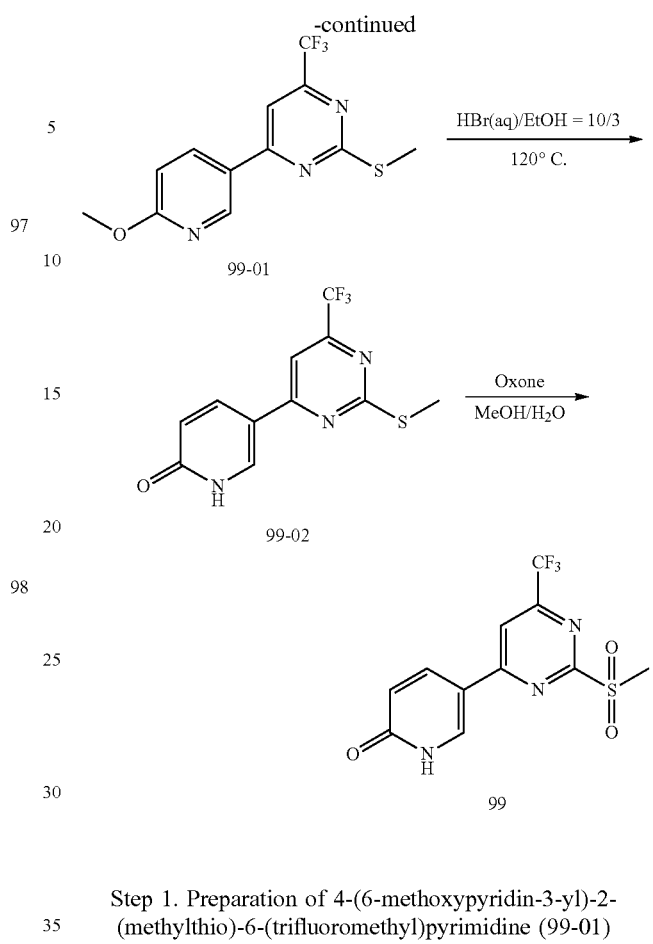

Step 1. Preparation of 4-(6-methoxypyridin-3-yl)-2-(methylthio)-6-(trifluoromethyl)pyrimidine (99-01)

To a solution of 4-chloro-2-(methylthio)-6-(trifluoromethyl)pyrimidine (49-01)(1 g, 4.4 mmol) and (6-methoxypyridin-3-yl)boronic acid (0.8 g, 5.3 mmol) in dioxane/H₂O (10 mL/5 mL) was added Pd(PPh₃)₄ (250 mg, 0.22 mmol) followed by Na₂CO₃ (930 mg, 8.7 mmol) under N₂ atmosphere. The reaction mixture was refluxed at 90° C. for 5 hrs. The reaction mixture was cooled to room temperature and filtered over celite. Solvents were removed from the filtrate in vacuo, and the residue was extracted by DCM and H₂O 3 times. The organic layer was combined, washed with brine, dried over Na₂SO₄ and further purified by silica gel column chromatography (PE/EA)=30/1 to give 917 mg of 4-(6-methoxypyridin-3-yl)-2-(methylthio)-6-(trifluoromethyl) pyrimidine as a colorless oil (70%). Mass (m/z): 302.05 [M+H]⁺.

Step 2. Preparation of 5-(2-(methylthio)-6-(trifluoromethyl)pyrimidin-4-yl)pyridin-2 (1H)-one (99-02)

To a solution of 4-(6-methoxypyridin-3-yl)-2-(methylthio)-6-(trifluoromethyl)pyrimidine (99-01)(917 mg, 3.05 mmol) in EtOH (10 mL) was added 3 mL HBr(aq) dropwise. The reaction mixture was refluxed at 120° C. for 3 hrs. The reaction mixture was cooled to room temperature, and alkalized to PH=6.0 with statured Na₂CO₃ solution. EtOH was then removed from the mixture by evaporation in vacuo, then the mixture was filtered. The solid part was dried to give 870 mg of 5-(2-(methylthio)-6-(trifluoromethyl)pyrimidin-4-yl)pyridin-2 (1H)-one as a white solid (98%). Mass (m/z): 288.03 [M+H]⁺.

Step 3. Preparation of 5-(2-(methylsulfonyl)-6-(trifluoromethyl)pyrimidin-4-yl)pyridin-2 (1H)-one (99)

An aqueous solution of Oxone (5 eq) was added dropwise to a solution of 5-(2-(methylthio)-6-(trifluoromethyl)pyrimidin-4-yl)pyridin-2 (1H)-one (99-02) (100 mg, 0.348 mmol) in MeOH. The reaction mixture was stirred at room temperature for 8 hrs. Solvents were evaporated from the reaction mixture, then the residue was extracted by EtOAc/H₂O 3 times. The organic layer was combined, washed with brine, dried over Na₂SO₄ and further purified by silica gel column chromatography (PE/EA=6/1) to give 70 mg of 5-(2-(methylsulfonyl)-6-(trifluoromethyl)pyrimidin-4-yl)pyridin-2 (1H)-one (99) in a yield of 63% as a white solid. ¹H NMR (400 MHz, CDCl3): δ 8.74 (s, 1H), 7.98 (d, J=7.2 Hz, 1H), 7.82 (s, 1H), 7.58 (d, J=7.2 Hz, 1H), 3.08 (s, 3H).

5-(2-(methylsulfonyl)-6-(trifluoromethyl)pyrimidin-4-yl)-1-(prop-2-yn-1-yl) pyridin-2 (1H)-one (100) and 5-(2-(methylsulfinyl)-6-(trifluoromethyl)pyrimidin-4-yl)-1-(prop-2-yn-1-yl) pyridin-2 (1H)-one (101)

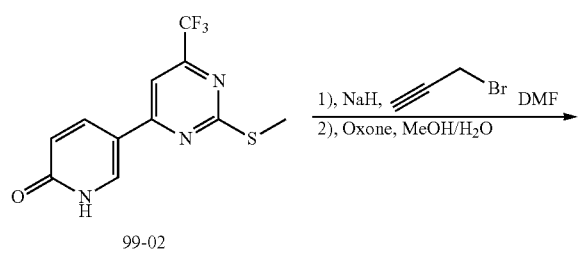

NaH (6 mg, 0.26 mmol) was added to a solution of 99-02 (67 mg, 0.23 mmol) in DMF in portions under N₂ atmosphere at 0° C. The reaction mixture was stirred at 0° C. for 30 min, followed by the addition of 3-bromoprop-1-yne (30 mg, 0.26 mmol) in portions. The whole reaction mixture was then stirred for 3 hrs at room temperature. The reaction mixture was extracted by EtOAc/H₂O (15 mL/15 mL) 3 times. The organic layer was combined, washed with brine, dried over Na₂SO₄ and further purified by silica gel column chromatography (PE/EA=1/1) to give 5-(2-(methylthio)-6-(trifluoromethyl)pyrimidin-4-yl)-1-(prop-2-yn-1-yl)pyridin-2 (1H)-one in a yield of 60% as a white solid (44 mg, 0.14 mmol).

An aqueous solution of Oxone (550 mg, 0.86 mmol) was added dropwise to a solution of 5-(2-(methylthio)-6-(trifluoromethyl)pyrimidin-4-yl)-1-(prop-2-yn-1-yl)pyridin-2 (1H)-one (40 mg, 0.12 mmol) in MeOH. The reaction mixture was stirred at room temperature for 8 hrs. Solvents were evaporated from the reaction mixture, then the residue was extracted by EtOAc/H₂O 3 times. The organic layer was combined, washed with brine, dried over Na₂SO₄ and further purified by silica gel column chromatography (PE/EA=6/1) to give 5-(2-(methylsulfonyl)-6-(trifluoromethyl)pyrimidin-4-yl)-1-(prop-2-yn-1-yl)pyridin-2 (1H)-one (100) in a yield of 65% (28 mg, 0.08 mmol) and 5-(2-(methylsulfinyl)-6-(trifluoromethyl)pyrimidin-4-yl)-1-(prop-2-yn-1-yl)pyridin-2 (1H)-one (101) in a yield of 12% (5 mg, 0.01 mmol) two white solids.

100 ¹H NMR (400 Hz, CDCl₃) δ 8.99 (d, J=2.8 Hz, 1H), 8.06 (dd, J=2.8, 8.6 Hz, 1H), 7.89 (s, 1H), 6.75 (d, J=9.6 Hz, 1H), 4.88 (d, J=2.8 Hz, 2H), 3.45 (s, 3H), 2.65 (t, J=2.8 Hz, 1H)

101 ¹H NMR (400 Hz, CDCl₃) δ 8.97 (d, J=2.4 Hz, 1H), 8.08 (dd, J=2.4, 8.6 Hz, 1H), 7.79 (s, 1H), 6.73 (d, J=9.6 Hz, 1H), 4.86 (t, J=1.2 Hz, 2H), 3.04 (s, 3H), 2.61 (t, J=2.8 Hz, 1H)

1-(2-azidoethyl)-5-(2-(methylsulfonyl)-6-(trifluoromethyl)pyrimidin-4-yl) pyridin-2 (1H)-one (102)

-continued

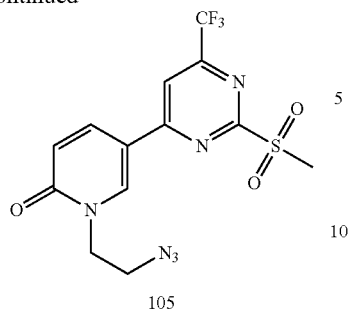
105

Step 1. Preparation of 1-(2-bromoethyl)-5-(2-(methylthio)-6-(trifluoromethyl)pyrimidin-4-yl)pyridin-2 (1H)-one (102-01)

NaH (17 mg, 0.70 mmol) was added to a solution of 99-02 (100 mg, 0.35 mmol) in DMF in portions under $N_2$ atmosphere at 0° C. The reaction mixture was stirred at 0° C. for 30 min, followed by the addition of 1,2-dibromoethane (327 mg, 1.74 mmol) in portions. The whole reaction mixture was then stirred for 3 hrs at room temperature. The reaction mixture was extracted by EtOAc/$H_2O$ (15 mL/15 mL) 3 times. The organic layer was combined, washed with brine, dried over $Na_2SO_4$ and further purified by silica gel column chromatography (PE/EA=1/1) to give –(2-bromoethyl)-5-(2-(methylthio)-6-(trifluoromethyl)pyrimidin-4-yl)pyridin-2 (1H)-one in a yield of 32% as alight yellow oil (45 mg, 0.11 mmol).

Step 2. Preparation of 1-(2-azidoethyl)-5-(2-(methylsulfonyl)-6-(trifluoromethyl)pyrimidin-4-yl) pyridin-2 (1H)-one (102)

The titled compound 102 (17 mg, 0.04 mmol) was prepared in a yield of 40% as a light yellow solid from 102-01 (40 mg, 0.1 mmol) and $NaN_3$ (66 mg, 1 mmol) according to the procedure for 59. $^1$H NMR (400 Hz, $CDCl_3$) δ 8.62 (d, J=2.4 Hz, 1H), 8.06 (dd. J=2.4, 9.6 Hz, 1H), 7.89 (s, 1H), 6.73 (d, J=9.6 Hz, 1H), 4.21 (t, J=5.6 Hz, 2H), 3.81 (t, J=5.6 Hz, 2H), 3.45 (s, 2H).

1-Benzyl-5-(2-(methylsulfonyl)-6-(trifluoromethyl) pyrimidin-4-yl)pyridin-2 (1H)-one (103)

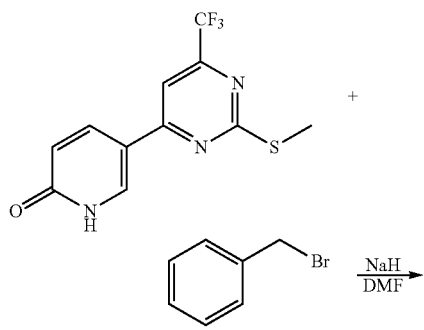

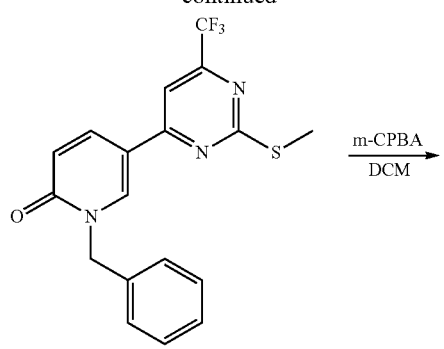

Step 1. Preparation of 1-Benzyl-5-(2-(methylthio)-6-(trifluoromethyl)pyrimidin-4-yl) pyridin-2 (1H)-one To a solution of 5-(2-(methylthio)-6-(trifluoromethyl)pyrimidin-4-yl) pyridine-2 (1H)-one (100 mg, 0.32 mmol) in anhydrous DMF (10 mL) was added NaH (8.4 mg, 0.35 mmol) at 0° C. and then stirred for 30 min. Then to the mixture was added benzyl bromide (66 mg, 0.38 mmol) and stirred at RT for 5 h. Then the reaction mixture was poured into water and extracted with EA (3×20 mL) and the organic layer was separated, dried over $Na_2SO_4$, filtered and concentrated. The crude product was purified by column chromatography (200-300 mesh silica gel, eluted with PE/EtOAc=10:1) to give the product (74 mg, 57%) as a white solid.

Mass (m/z): 378.4 [M+H]$^+$.

Step 2. Preparation of 1-Benzyl-5-(2-(methylsulfonyl)-6-(trifluoromethyl)pyrimidin-4-yl) pyridin-2 (1H)-one (103)

To a solution of 1-benzyl-5-(2-(methylthio)-6-(trifluoromethyl)pyrimidin-4-yl)pyridin-2 (1H)-one (10 mg, 0.03 mmol) in DCM (2 mL) was added m-CPBA (10 mg, 0.06 mmol) at RT. Then the mixture was stirred at RT for 3 h. The solvent was removed and extracted with DCM (3×15 ml). The organic layer was separated, dried over $Na_2SO_4$, filtered and concentrated. The crude product was purified by Pre-TLC (EtOAc/PE=1:2) to obtain 103 as a white solid (4.0 mg, 36%): $^1$H NMR (400 MHz, $CDCl_3$): δ 8.65 (d, J=2.8 Hz, 1H), 7.99 (dd, J=2.8, 9.6 Hz, 1H), 7.82 (s, 1H), 7.41-7.34 (m, 5H), 6.76 (d, J=9.6 Hz, 1H), 5.27 (s, 2H), 3.39 (s, 3H). Mass (m/z): 410.4 [M+H]$^+$.

1-(2-chlorobenzyl)-5-(2-(methylsulfonyl)-6-(trifluoromethyl)pyrimidin-4-yl)pyridin-2 (1H)-one (104)

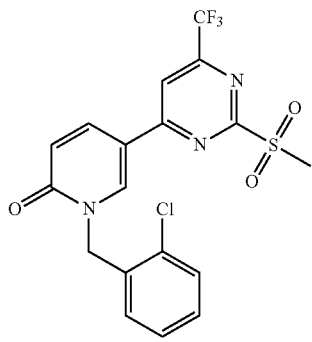 [SMILES: CS(=O)(=O)c1nc(-c2ccc(=O)n(Cc3ccccc3Cl)c2)cc(C(F)(F)F)n1]

The titled compound 104 (5 mg, 18%) was prepared as a white solid from 99-02 (20 mg, 0.07 mmol) and 1-(bromomethyl)-2-chlorobenzene (16 mg, 0.08 mmol) according to the procedure for 103.

$^1$H NMR: (400 Mz, CDCl$_3$): δ 8.67 (d, J=2.8 Hz, 1H), 8.00 (dd, J=2.8, 9.6 Hz, 1H), 7.86 (s, 1H), 7.33-7.30 (m, 3H), 7.25-7.22 (m, 1H), 6.76 (d, J=9.6 Hz, 1H), 5.24 (s, 2H), 3.42 (s, 3H).

Mass (m/z): 444.5 [M+H]$^+$.

1-(3-chlorobenzyl)-5-(2-(methylsulfonyl)-6-(trifluoromethyl)pyrimidin-4-yl)pyridin-2 (1H)-one (105)

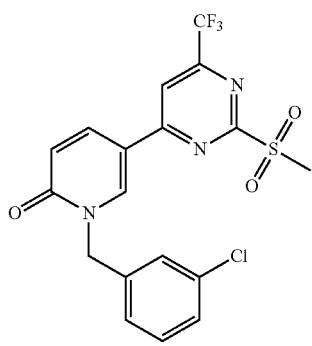 [SMILES: CS(=O)(=O)c1nc(-c2ccc(=O)n(Cc3cccc(Cl)c3)c2)cc(C(F)(F)F)n1]

The titled compound (5 mg, 18%) was prepared as a white solid from 99-02 (20 mg, 0.07 mmol) and 1-(bromomethyl)-3-chlorobenzene (16 mg, 0.08 mmol) according to the procedure for 103.

$^1$H NMR: (400 Mz, CDCl$_3$): δ 8.72 (d, J=2.8 Hz, 1H), 8.01 (dd, J=2.8, 9.6 Hz, 1H), 7.81 (s, 1H), 7.45-7.42 (m, 1H), 7.34-7.28 (m, 3H), 6.75 (d, J=9.6 Hz, 1H), 5.37 (s, 2H), 3.38 (s, 3H).

Mass (m/z): 444.4 [M+H]$^+$.

1-(4-chlorobenzyl)-5-(2-(methylsulfonyl)-6-(trifluoromethyl)pyrimidin-4-yl)pyridin-2 (1H)-one 106)

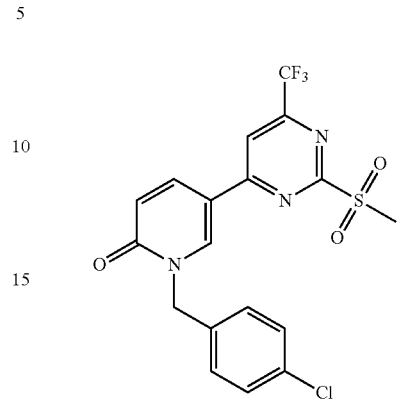

The titled compound 106 (6 mg, 21%) was prepared as a white solid from 99-02 (20 mg, 0.07 mmol) and 1-(bromomethyl)-4-chlorobenzene (16 mg, 0.08 mmol) according to the procedure for 103.

$^1$H NMR: (400 Mz, CDCl$_3$): δ 8.69 (d, J=2.4 Hz, 1H), 8.02 (dd, J=2.4, 9.6 Hz, 1H), 7.86 (s, 1H), 7.34-7.27 (m, 4H), 6.76 (d, J=9.6 Hz, 1H), 5.24 (s, 2H), 3.43 (s, 3H). Mass (m/z): 444.5 [M+H]$^+$.

1-(3-bromobenzyl)-5-(2-(methylsulfonyl)-6-(trifluoromethyl)pyrimidin-4-yl)pyridin-2 (1H)-one (107)

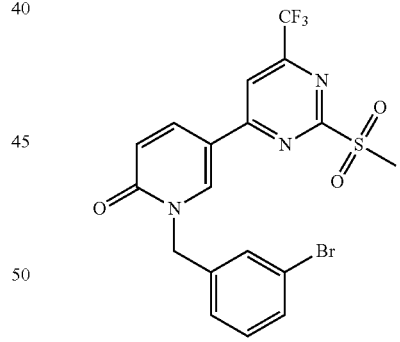

The titled compound (5 mg, 15%) was prepared as a white solid from 99-02 (20 mg, 0.07 mmol) and 1-(bromomethyl)-3-bromobenzene (20 mg, 0.08 mmol) according to the procedure for 103.

$^1$H-NMR (400 MHz, CDCl$_3$): δ 8.67 (d, J=2.8 Hz, 1H), 8.01 (dd, $^1$J=2.8 Hz, $^2$J=12.0 Hz, 1H), 7.84 (s, 1H), 7.48-7.46 (m, 2H), 7.29-7.18 (m, 2H), 6.77 (d, J=12.0 Hz, 1H), 5.24 (s, 2H), 3.42 (s, 3H).

Mass (m/z): 487.98 [M+H]$^+$.

233

1-(3-hydroxybenzyl)-5-(2-(methylsulfonyl)-6-(trifluoromethyl)pyrimidin-4-yl)pyridin-2 (1H)-one (108)

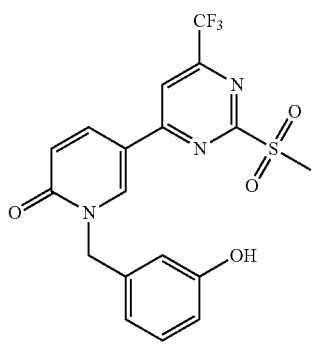

The titled compound 108 (5 mg, 18%) was prepared as a white solid from 99-02 (20 mg, 0.07 mmol) and (3-(bromomethyl)phenoxy)(tert-butyl)dimethylsilane (24 mg, 0.08 mmol) according to the procedure for 103.

$^1$H NMR (400 Hz, CDCl$_3$b) δ 8.66 (d, J=2.4 Hz, 1H), 7.97 (dd, J=2.4, 9.6 Hz, 1H), 7.83 (s, 1H), 7.24 (d, J=8.0 Hz, 1H), 6.92 (d, J=9.6 Hz, 1H). 6.84-6.86 (m, 1H), 6.80-6.83 (m, 1H). 6.74 (d, J=9.6 Hz. 1H), 5.20 (s, 2H), 3.41 (s, 3H).

1-(3-methoxybenzyl)-5-(2-(methylsulfonyl)-6-(trifluoromethyl)pyrimidin-4-yl)pyridin-2 (1H)-one (109)

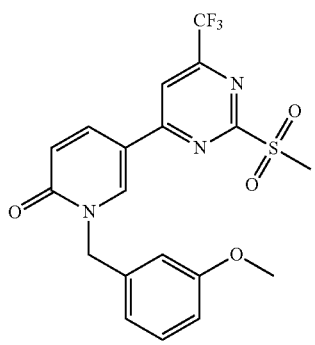 [SMILES: COc1cccc(Cn2cc(-c3cc(C(F)(F)F)nc(S(C)(=O)=O)n3)ccc2=O)c1]

The titled compound (4 mg, 14%) was prepared as a white solid from 99-02 (20 mg, 0.07 mmol) and 1-(bromomethyl)-3-methoxybenzene (16 mg, 0.08 mmol) according to the procedure for 103.

$^1$H NMR: (400 Mz, CDCl$_3$): δ 8.64 (d, J=2.8 Hz, 1H), 8.01 (dd, J=2.8, 9.6 Hz, 1H), 7.82 (s, 1H), 7.31-7.26 (m, 1H), 6.92-6.86 (m, 3H), 6.75 (d, J=9.6 Hz, 1H), 5.23 (s, 2H), 3.80 (s, 3H), 3.39 (s, 3H). Mass (m/z): 440.2 [M+H]$^+$.

234

1-(4-Methoxybenzyl)-5-(2-(methylsulfonyl)-6-(trifluoromethyl)pyrimidin-4-yl)pyridin-2 (1H)-one (110) and 1-(4-Methoxybenzyl)-5-(2-(methylsulfinyl)-6-(trifluoromethyl)pyrimidin-4-yl)pyridin-2 (1H)-one (111)

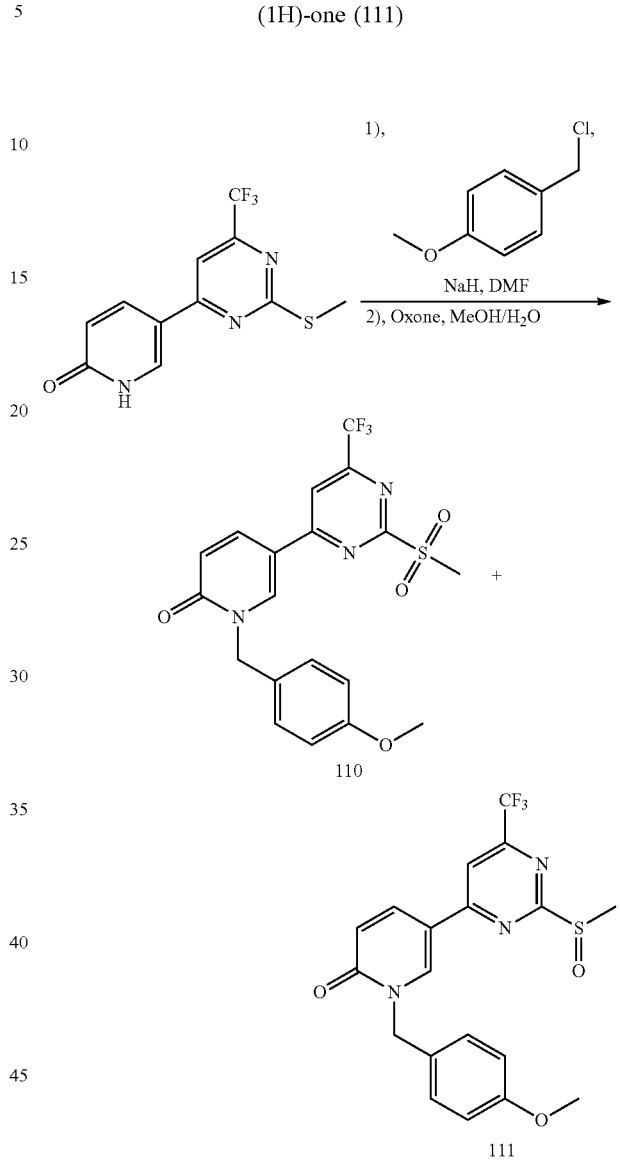

The titled compound 110 (5 mg, 0.011 mmol) and 111 (3 mg, 0.007 mmol) was prepared in a yield of 11% and 7% as two white solids from 99-02 (30 mg, 0.10 mmol) and 1-(chloromethyl)-4-methoxybenzene (22 mg, 0.11 mmol) according to the procedure for 100. For 110, $^1$H NMR: (400 Mz, CDCl$_3$): δ 8.63 (d, J=2.0 Hz, 1H), 7.97 (dd, J=2.0, 9.6 Hz, 1H), 7.81 (s, 1H), 7.32 (d, J=8.4 Hz, 2H), 6.90 (d, J=8.4 Hz, 2H), 6.73 (d, J=9.6 Hz, 1H), 5.19 (s, 2H), 3.79 (s, 3H), 3.39 (s, 3H). Mass (m/z): 440.2 [M+H]$^+$. For 111, $^1$H NMR: (400 Mz, CDCl$_3$): δ 8.67 (d, J=2.0 Hz, 1H), 7.99 (dd, J=2.0, 9.6 Hz, 1H), 7.70 (s, 1H), 7.32 (d, J=8.4 Hz, 2H), 6.89 (d, J=8.4 Hz, 2H), 6.72 (d, J=9.6 Hz, 1H), 5.22 (d, J=14.4 Hz, 1H), 5.18 (d, J=14.4 Hz, 1H), 3.79 (s, 3H), 3.00 (s, 3H). Mass (m/z): 424.3 [M+H]$^+$.

1-(3-ethoxybenzyl)-5-(2-(methylsulfonyl)-6-(trifluoromethyl)pyrimidin-4-yl)pyridin-2 (1H)-one (112)

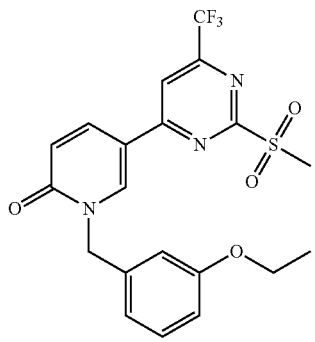 [SMILES: CCOc1cccc(Cn2cc(-c3cc(C(F)(F)F)nc(S(C)(=O)=O)n3)ccc2=O)c1]

The titled compound (2 mg) and TC009156 (1 mg) was prepared as two white solids from 99-02 (20 mg, 0.07 mmol) and 1-(bromomethyl)-3-ethoxybenzene (17 mg, 0.08 mmol) according to the procedure for 103.
$^1$H NMR (400 Hz, CDCl$_3$) δ 8.62 (d, J=2.4 Hz, 1H), 7.99 (dd, J=2.4, 9.6 Hz, 1H), 7.81 (s, 1H), 7.28 (dd, J=7.6, 8.8 Hz, 1H), 6.84-6.91 (m, 3H), 6.75 (d, J=9.6 Hz, 1H), 5.23 (s, 2H), 4.02 (q, J=6.8 Hz, 2H), 3.39 (s, 3H), 1.40 (t, J=6.8 Hz, 3H).

5-(2-(methylsulfonyl)-6-(trifluoromethyl)pyrimidin-4-yl)-1-(3-propoxybenzyl)pyridin-2 (1H)-one (113) and 5-(2-(methylsulfinyl)-6-(trifluoromethyl)pyrimidin-4-yl)-1-(3-propoxybenzyl)pyridin-2 (11H)-one (114)

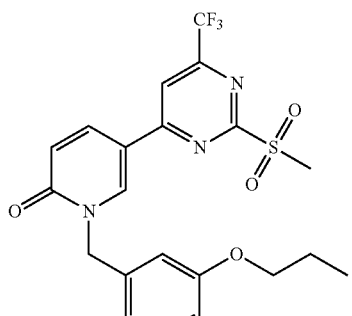

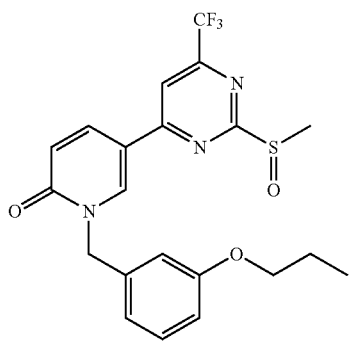

The titled compound 113 (2 mg) and 114 (2 mg) was prepared as two white solids from 99-02 (20 mg, 0.07 mmol) and 1-(bromomethyl)-3-propoxybenzene (18 mg, 0.08 mmol) according to the procedure for 103.

113 $^1$H NMR (400 Hz, CDCl$_3$) δ 8.62 (dd, J=2.4 Hz, 1H), 8.00 (dd, J=2.4, 9.6 Hz, 1H), 7.81 (s, 1H), 7.15-7.30 (m, 1H), 6.85-6.91 (m, 3H), 6.76 (d, J=9.6 Hz, 1H), 5.23 (s, 2H), 3.91 (t. J=6.4 Hzm 2H), 3.39 (s, 3H), 1.74-1.84 (m, 2H), 1.22 (t, J=7.6 Hz, 3H). LC-MS (ESI) m/z: calcd for [C$_{21}$H$_{21}$F$_3$N$_3$O$_4$S$^+$], 468.1, found 469.6.

114 LC-MS (ESI) m/z: calcd for [C$_{21}$H$_{21}$F$_3$N$_3$O$_3$S$^+$], 452.1, found 452.6.

5-(2-(methylsulfonyl)-6-(trifluoromethyl)pyrimidin-4-yl)-1-(3-(prop-2-yn-1-yloxy) benzyl) pyridin-2 (1H)-one (115)

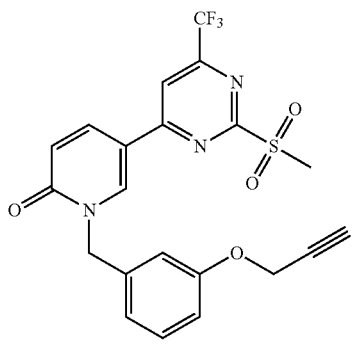 [SMILES: C#CCOc1cccc(Cn2cc(-c3cc(C(F)(F)F)nc(S(C)(=O)=O)n3)ccc2=O)c1]

The titled compound (30 mg, 0.02 mmol) was prepared in a yield of 24% as a white solid from 99-02 (30 mg, 0.1 mmol) and 1-(bromomethyl)-3-(prop-2-yn-1-yloxy)benzene (80 mg, 0.38 mmol) according to the procedure for 100. $^1$H NMR (400 Hz, CDCl$_3$) δ 8.66 (d, J=2.0 Hz, 1H), 8.03 (dd, J=2.0, 9.6 Hz, 1H), 7.90 (s, 1H), 7.27-7.23 (m, 1H), 6.93-6.88 (m, 3H), 6.70 (d, J=9.6 Hz, 1H), 5.19 (s, 2H), 4.63 (dd, J=1.2, 2.4 Hz, 2H), 3.36 (d, J=0.8 Hz, 3H), 2.52 (td, J=2.4, 1.2 Hz, 1H).

5-(2-(methylsulfinyl)-6-(trifluoromethyl)pyrimidin-4-yl)-1-(4-(trifluoromethoxy)benzyl)pyridin-2 (1H)-one (116) and 5-(2-(methylsulfonyl)-6-(trifluoromethyl)pyrimidin-4-yl)-1-(4-(trifluoromethoxy) benzyl)pyridin-2 (1H)-one (117)

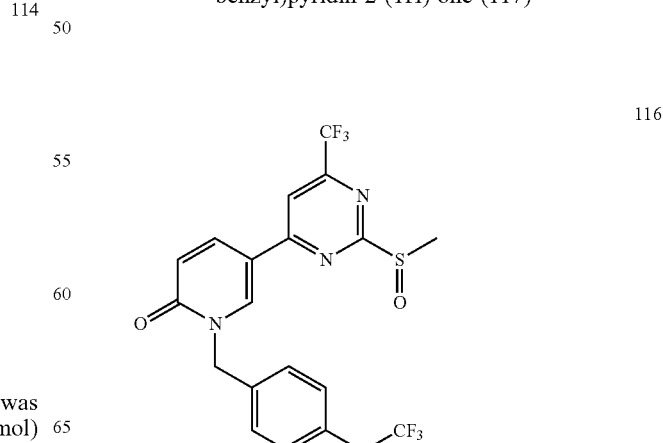

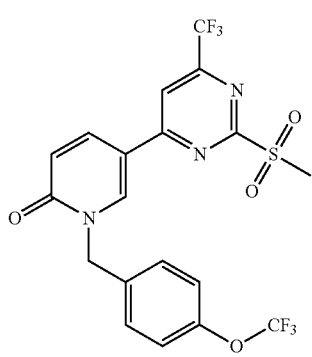

The titled compound 116 (3 mg, 90%) and 117 (2 mg, 6%) was prepared as two white solids from 99-02 (20 mg, 0.07 mmol) and 1-(bromomethyl)-4-(trifluoromethoxy)benzene (20 mg, 0.08 mmol) according to the procedure for 103.

116 $^1$H NMR: (400 Mz, CDCl$_3$): δ 8.73 (d, J=2.4 Hz, 1H), 8.00 (dd, J=2.4, 9.6 Hz, 1H), 7.73 (s, 1H), 7.38 (d, J=8.0 Hz, 2H), 7.18 (d, J=8.0 Hz, 2H), 6.72 (d, J=9.6 Hz, 1H), 5.26 (d, J=14.4 Hz, 1H), 5.22 (d, J=14.4 Hz, 1H), 2.99 (s, 3H). Mass (m/z): 478.4 [M+H]$^+$.

117 $^1$H NMR: (400 Mz, CDCl$_3$): δ 8.71 (d, J=2.8 Hz, 1H), 7.99 (dd, J=2.8, 9.6 Hz, 1H), 7.85 (s, 1H), 7.41 (dd, J=2.8, 8.0 Hz, 2H), 7.21 (d, J=8.0 Hz, 2H), 6.75 (d, J=9.6 Hz, 1H), 5.26 (s, 2H), 3.42 (s, 3H). Mass (m/z): 478.4 [M+H]$^+$.

3-((5-(2-(methylsulfonyl)-6-(trifluoromethyl)pyrimidin-4-yl)-2-oxopyridin-1 (2H)-yl)methyl)benzonitrile (118)

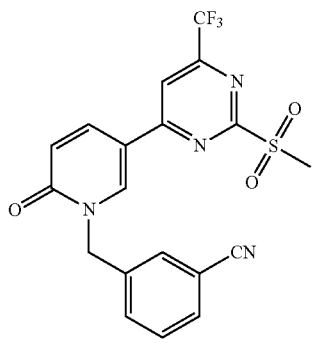 [SMILES: CS(=O)(=O)c1nc(-c2ccc(=O)n(Cc3cccc(C#N)c3)c2)cc(C(F)(F)F)n1]

The titled compound (4 mg, 13%) was prepared as a white solid from 99-02 (20 mg, 0.07 mmol) and 3-(bromomethyl)benzonitrile (16 mg, 0.08 mmol) according to the procedure for 103.

$^1$H NMR: (400 Mz, CDCl$_3$): δ 8.75 (d, J=2.4 Hz, 1H), 8.02 (dd, J=2.0, 9.6 Hz, 1H), 7.90 (s, 1H), 7.63-7.50 (m, 4H), 6.77 (d, J=9.6 Hz, 1H), 5.29 (s, 2H), 3.43 (s, 3H). Mass (m/z): 435.4 [M+H]$^+$.

4-((5-(2-(methylsulfonyl)-6-(trifluoromethyl)pyrimidin-4-yl)-2-oxopyridin-1 (2H)-yl)methyl)benzonitrile (119)

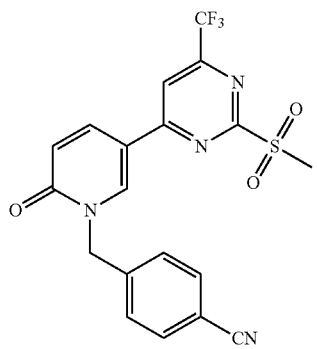 [SMILES: CS(=O)(=O)c1nc(-c2ccc(=O)n(Cc3ccc(C#N)cc3)c2)cc(C(F)(F)F)n1]

The titled compound (5 mg, 16%) was prepared as a white solid from 99-02 (20 mg, 0.07 mmol) and 4-(bromomethyl)benzonitrile (16 mg, 0.08 mmol) according to the procedure for 103.

$^1$H NMR: (400 Mz, CDCl$_3$): δ 8.75 (d, J=2.8 Hz, 1H), 8.01 (dd, 0.1=2.8, 9.6 Hz, 1H), 7.88 (s, 1H), 7.66 (d, J=8.4 Hz, 2H), 7.44 (d, J=8.4 Hz, 2H), 6.76 (d, J=9.6 Hz, 1H), 5.31 (s, 2H), 3.43 (s, 3H). Mass (m/z): 478.4 [M+H]~.

1-(3-ethynylbenzyl)-5-(2-(methylsulfonyl)-6-(trifluoromethyl)pyrimidin-4-yl) pyridin-2 (1H)-one (120) and 1-(3-ethynylbenzyl)-5-(2-(methylsulfinyl)-6-(trifluoromethyl)pyrimidin-4-yl)pyridin-2 (1H)-one (121)

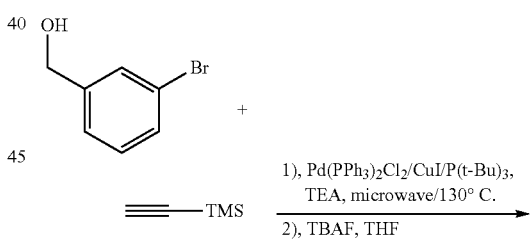

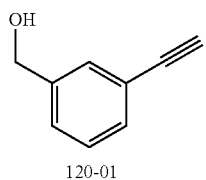

120-01

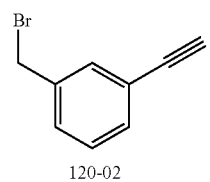

120-02

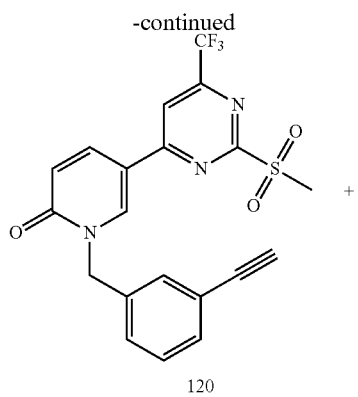

120

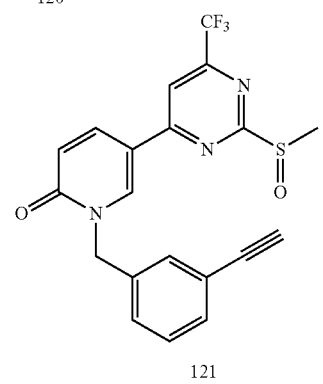

121

Step 1. Preparation of (3-ethynylphenyl)methanol (120-01)

To a solution of (3-bromophenyl)methanol (935 mg, 5 mmol) in dry TEA was added Pd(PPh$_3$)$_2$Cl$_2$ (175 mg, 0.25 mmol), CuI (48 mg, 0.25 mmol) and P(t-Bu)$_3$ (51 mg, 0.25 mmol) under N$_2$ atmosphere. The reaction mixture was stirred for 5 mins, followed by addition of ethynyltrimethylsilane(980 mg, 10 mmol) dropwise. The reaction mixture was then microwaved at 130° C. for 4 hrs. The reaction mixture was cooled to room temperature, filtered over celite. Solvents were removed from the filtrate in vacuo, then the residue was extracted by EtOAc/H$_2$O 3 times. The organic layer was combined, washed with brine, dried over Na$_2$SO$_4$ and further purified by silica gel column chromatography (PE/EA=4/1) to give 750 mg of (3-((trimethylsilyl)ethynyl)phenyl)methanol as a brown oil (73%).

To a solution of (3-((trimethylsilyl)ethynyl)phenyl) methanol (500 mg, 2.46 mmol) in THF was added TBAF (1 g, 4.92 mmol) in portions at 0° C. The reaction mixture was stirred at 0° C. to room temperature for 3 hrs. Solvents were removed from the mixture in vacuo, and the residue was extracted by EtOAc/H$_2$O 3 times. The organic layer was combined, washed with brine, dried over Na$_2$SO$_4$ and further purified by silica gel column chromatography (PE/EA=4/1) to give 184 mg of (3-ethynylphenyl)methanol (120-01) as a brown oil (57%).

Step 2. Preparation of 1-(bromomethyl)-3-ethynylbenzene (120-02)

To a solution of (3-ethynylphenyl)methanol (184 mg, 1.39 mmol) in DCM was added CBr$_4$ (557 mg, 1.74 mmol) in portions under N$_2$ atmosphere, followed by the addition of PPh$_3$ (455 mg, 1.74 mmol) in portions after stirring for 5-10 min. The reaction mixture was stirred at room temperature for 3 hrs. Solvents were removed from the reaction mixture in vacuo. The residue was dissolved in EtOAc and filtered. The filtrate was concentrated and further purified by silica gel column chromatography (PE/EA=30/1) to give 140 mg of 1-(bromomethyl)-3-ethynylbenzene as a colorless oil (52%). $^1$H NMR (400 Hz, CDCl$_3$) δ 7.51-7.53 (m, 1H), 7.36-7.44 (m, 2H), 7.28-7.32 (m, 1H), 4.45 (s, 2H), 3.10 (s, 1H).

Step 3. Preparation of 1-(3-ethynylbenzyl)-5-(2-(methylsulfonyl)-6-(trifluoromethyl) pyrimidin-4-yl) pyridin-2 (1H)-one (120) and 1-(3-ethynylbenzyl)-5-(2-(methylsulfinyl)-6-(trifluoromethyl)pyrimidin-4-yl)pyridin-2 (1H)-one (121)

The titled compound 120 (17 mg, 0.02 mmol) was prepared in a yield of 19% as a yellow solid from 99-02 (60 mg, 0.2 mmol) and 1-(bromomethyl)-3-ethynylbenzene (120-02) (38 mg, 0.19 mmol) according to the procedure for 100. $^1$H NMR (400 Hz, CDCl3) δ 8.01 (dd, J=2.8, 9.6 Hz, 1H), 7.87 (s, 1H), 7.71 (dd, J=3.2, 6 Hz, 1H), 7.52 (dd, J=3.6, 5.6 Hz, 1H), 7.56 (s, 1H), 7.34-7.32 (m, 2H), 6.75 (d, J=9.6 Hz, 1H), 5.34 (s, 2H), 3.40 (s, 3H), 3.08 (s, 1H). LC-MS (ESI) m/z: calcd for [C$_{20}$H$_{15}$F$_3$N$_3$O$_3$S$^+$], 434.0, found 434.0.

The titled compound 121 (18 mg, 0.02 mmol) was prepared in a yield of 19% as a yellow solid from 99-02 (60 mg, 0.2 mmol) and 1-(bromomethyl)-3-ethynylbenzene (120-02) (38 mg, 0.19 mmol) according to the procedure for 100. $^1$H NMR (400 Hz, CDCl$_3$) δ 8.03 (dd, J=2.4, 9.6 Hz, 1H), 7.76 (s, 1H), 7.71 (dd, J=3.2, 5.6 Hz, 1H), 7.52 (dd, J=3.2, 5.6 Hz, 1H), 7.44 (s, 1H), 7.36-7.30 (m, 2H), 6.75 (d, J=9.6 Hz, 1H), 5.24 (dd, J=14.4, 21.2 Hz, 2H), 3.08 (s, 1H), 3.01 (s, 3H). LC-MS (ESI) m/z: calcd for [C$_{20}$H$_{15}$F$_3$N$_3$O$_2$S$^+$], 418.1, found 418.1.

1-(4-ethynylbenzyl)-5-(2-(methylsulfonyl)-6-(trifluoromethyl)pyrimidin-4-yl)pyridin-2 (1H)-one (122)

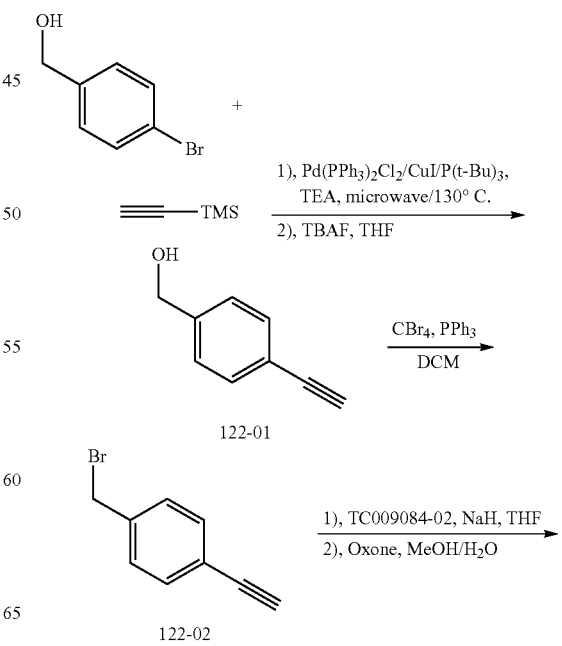

-continued

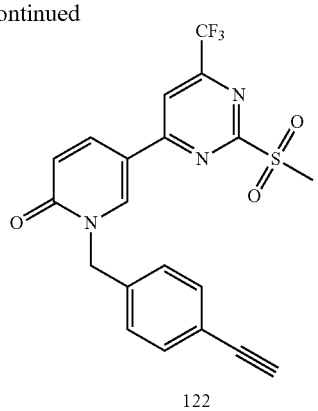

122

Step 1. Preparation of (4-ethynylphenyl)methanol (122-01)

To a solution of (4-bromophenyl)methanol (935 mg, 5 mmol) in dry TEA was added Pd(PPh$_3$)$_2$Cl$_2$ (175 mg, 0.25 mmol), CuI (48 mg, 0.25 mmol) and P(t-Bu)$_3$ (51 mg, 0.25 mmol) under N$_2$ atmosphere. The reaction mixture was stirred for 5 mins, followed by addition of ethynyltrimethylsilane(980 mg, 10 mmol) dropwise. The reaction mixture was then microwaved at 130° C. for 4 hrs. The reaction mixture was cooled to room temperature, filtered over celite. Solvents were removed from the filtrate in vacuo, then the residue was extracted by EtOAc/H$_2$O 3 times. The organic layer was combined, washed with brine, dried over Na$_2$SO$_4$ and further purified by silica gel column chromatography (PE/EA=4/1) to give 670 mg of (4-((trimethylsilyl)ethynyl)phenyl)methanol as a brown oil (66%).

To a solution of (4-((trimethylsilyl)ethynyl)phenyl)methanol (250 mg, 1.23 mmol) in THF was added TBAF (500 mg, 2.45 mmol) in portions at 0° C. The reaction mixture was stirred at 0° C. to room temperature for 3 hrs. Solvents were removed from the mixture in vacuo, and the residue was extracted by EtOAc/H$_2$O 3 times. The organic layer was combined, washed with brine, dried over Na$_2$SO$_4$ and further purified by silica gel column chromatography (PE/EA=4/1) to give 170 mg of (4-ethynylphenyl)methanol as a brown oil (100%). $^1$H NMR (400 Hz, CDCl3) S 7.45-7.49 (m, 2H), 7.21-7.26 (m, 2H), 4.69 (s, 1H), 4.65 (s, 2H).

Step 2. Preparation of 1-(bromomethyl)-4-ethynylbenzene (122-02)

To a solution of (4-ethynylphenyl)methanol (110 mg, 0.84 mmol) in dry DCM was added PBr$_3$ (450 mg, 1.67 mmol) dropwise at 0° C. The reaction mixture was stirred at 0° C. to room temperature for 3 hrs. The reaction was quenched by H$_2$O, then extracted by DCM/H$_2$O 3 times. The organic layer was combined, washed with brine, dried over Na$_2$SO$_4$ and further purified by silica gel column chromatography (PE/EA=10/1) to give 80 mg of 1-(bromomethyl)-4-ethynylbenzene as a colorless oil (50%). $^1$H NMR (400 Hz, CDCl$_3$) δ 7.45-7.48 (m, 2H), 7.33-7.36 (m, 2H), 4.47 (s, 2H), 3.13 (s, 1H).

Step 3. Preparation of 1-(4-ethynylbenzyl)-5-(2-(methylsulfonyl)-6-(trifluoromethyl) pyrimidin-4-yl)pyridin-2 (1H)-one (122)

The titled compound (120 mg, 0.26 mmol) was prepared in a yield of 64% as a yellow solid from 99-02 (130 mg, 0.45 mmol) and 1-(bromomethyl)-4-ethynylbenzene (122-02) (80 mg, 0.41 mmol) according to the procedure for 100. $^1$H NMR (400 Hz, CDCl3) δ 8.68 (d, J=2.4 Hz, 1H), 8.00 (dd, J=2.4, 9.6 Hz, 1H), 7.88 (s, 1H), 7.45 (d, J=8.0 Hz, 2H), 7.29 (d, J=8.0 Hz, 2H), 6.72 (d, J=9.6 Hz, 1H), 5.23 (s, 2H), 3.39 (s, 3H), 3.08 (s, 1H). LC-MS (ESI) m/z: calcd for [C$_{20}$H$_{15}$F$_3$N$_3$O$_3$S$^+$], 434.0, found 434.1.

1-(4-azidobenzyl)-5-(2-(methylsulfonyl)-6-(trifluoromethyl)pyrimidin-4-yl)pyridin-2 (1H)-one (123)

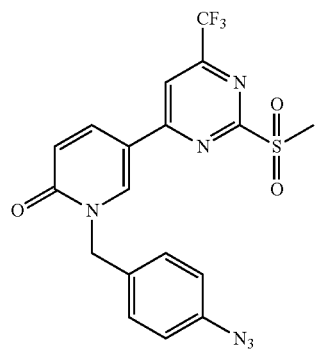 [SMILES: CS(=O)(=O)c1nc(-c2ccc(=O)n(Cc3ccc(N=[N+]=[N-])cc3)c2)cc(C(F)(F)F)n1]

The titled compound (13 mg, 0.029 mmol) was prepared in a yield of 29% as a yellow solid from 99-02 (46 mg, 0.10 mmol) and 1-azido-4-(bromomethyl)benzene (44 mg, 0.21 mmol) according to the procedure for 100. $^1$H NMR (400 Hz, CDCl3) δ 8.70 (d, J=2.8 Hz, 1H), 7.98 (dd, J=2.8, 9.6 Hz, 1H), 7.83 (s, 1H), 7.37 (d, J=8.4 Hz, 2H), 7.03 (d, J=8.4 Hz, 2H), 6.75 (d, J=9.6 Hz, 1H), 5.23 (s, 2H), 3.42 (s, 3H).

1-(4-chloro-2-fluorobenzyl)-5-(2-(methylsulfonyl)-6-(trifluoromethyl)pyridin-4-yl)pyridin-2 (1H)-one (124) and 1-(4-chloro-2-fluorobenzyl)-5-(2-(methylsulfinyl)-6-(trifluoromethyl)pyrimidin-4-yl)pyridin-2 (1H)-one (125)

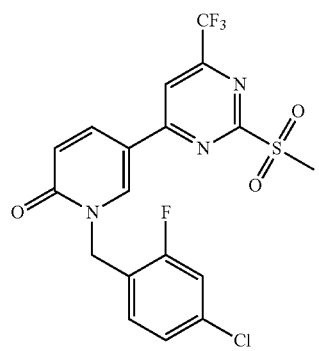

124

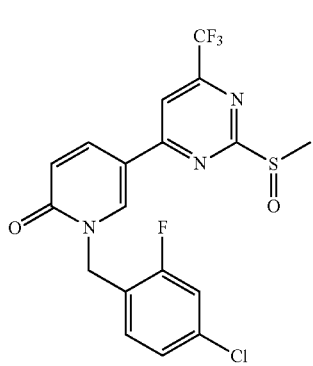

The titled compound 124 (3 mg, 9%) and 125 (2 mg, 6%) was prepared as two white solids from 99-02 (20 mg, 0.07 mmol) and 1-(bromomethyl)-4-chloro-2-fluorobenzene (18 mg, 0.08 mmol) according to the procedure for 103.

124 $^1$H NMR: (400 Mz, CDCl$_3$): δ 8.76 (d, J=2.8 Hz, 1H), 8.02 (dd, J=2.8, 9.6 Hz, 1H), 7.87 (s, 1H), 7.45 (t, J=8.0 Hz, 1H), 7.16-7.12 (m, 2H), 6.71 (d, J=9.6 Hz, 1H), 5.24 (s, 2H), 3.43 (s, 3H). Mass (m/z): 462.5 [M+H]$^+$.

125 $^1$H NMR: (400 Mz, CDCl$_3$): δ 8.79 (d, J=2.8 Hz, 1H), 8.04 (dd, J=2.4, 9.6 Hz, 1H), 7.75 (s, 1H), 7.45 (t, J=8.0 Hz, 1H), 7.15-7.12 (m, 2H), 6.70 (d, J=9.6 Hz, 1H), 5.27 (d, J=14.4 Hz, 1H), 5.22 (d, J=14.4 Hz, 1H), 3.03 (s, 3H). Mass (m/z): 446.3 [M+H]$^+$.

1-(2-chloro-4-methoxybenzyl)-5-(2-(methylsulfonyl)-6-(trifluoromethyl)pyrimidin-4-yl)pyridin-2(1H)-one (126)

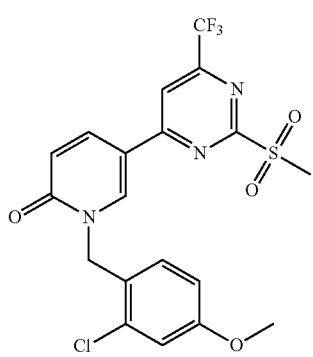 [SMILES: COc1ccc(Cn2cc(-c3cc(C(F)(F)F)nc(S(C)(=O)=O)n3)ccc2=O)c(Cl)c1]

The titled compound 126 (5 mg, 15%) was prepared as a white solid from 99-02 (20 mg, 0.07 mmol) and 1-(bromomethyl)-2-chloro-4-methoxybenzene (20 mg, 0.08 mmol) according to the procedure for 103.

$^1$H NMR: (400 Mz, CDCl$_3$): δ 8.73 (d, J=2.8 Hz, 1H), 8.00 (dd, J=2.8, 9.6 Hz, 1H), 7.81 (s, 1H), 7.39 (d, J=8.4 Hz, 1H), 6.98 (d, J=2.8 Hz, 1H), 6.83 (d, J=2.4, 8.4 Hz, 1H), 6.73 (d, J=9.6 Hz, 1H), 5.30 (s, 2H), 3.81 (s, 3H), 3.39 (s, 3H). Mass (m/z): 474.3 [M+H]$^+$.

1-(3,4-dimethoxybenzyl)-5-(2-(methylsulfonyl)-6-(trifluoromethyl)pyrimidin-4-yl)pyridin-2 (1H)-one (127) and 1-(3,4-dimethoxybenzyl)-5-(2-(methylsulfinyl)-6-(trifluoromethyl)pyrimidin-4-yl)pyridin-2 (1H)-one (128)

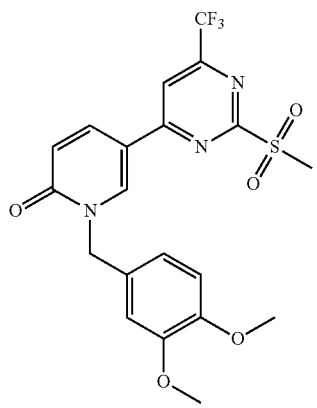

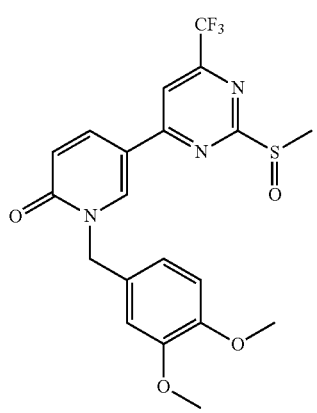

The titled compound 127 (6 mg, 15%) and 128 (4 mg, 10%) was prepared as two white solids from 99-02 (20 mg, 0.07 mmol) and 4-(bromomethyl)-1,2-dimethoxybenzene (19 mg, 0.08 mmol) according to the procedure for 103.

127 $^1$H NMR: (400 Mz, CDCl$_3$): δ 8.68 (d, J=2.4 Hz, 1H), 7.98 (dd, J=2.4, 9.6 Hz, 1H), 7.82 (s, 1H), 6.94 (s, 1H), 6.92 (d, J=8.0 Hz, 1H), 6.84 (d, J=8.0 Hz, 1H), 6.73 (d, J=9.6 Hz, 1H), 5.18 (s, 2H), 3.87 (s, 3H), 3.85 (s, 3H), 3.38 (s, 3H). Mass (m/z): 470.3 [M+H]$^+$.

128 $^1$H NMR: (400 Mz, DMSO-d6): δ 9.24 (d, J=2.8 Hz, 1H), 8.68 (s, 1H), 8.41 (dd, J=2.4, 9.6 Hz, 1H), 7.10 (d, J=2.8 Hz, 1H), 6.92 (d, J=8.4 Hz, 1H), 6.88 (dd, J=2.4, 8.4 Hz, 1H), 6.63 (d, J=9.6 Hz, 1H), 5.18 (s, 2H), 3.73 (s, 3H), 3.72 (s, 3H), 3.53 (s, 3H). Mass (m/z): 454.3 [M+H]$^+$.

1-(4-methoxy-3-(prop-2-yn-1-yloxy)benzyl)-5-(2-(methylsulfonyl)-6-(trifluoromethyl)pyrimidin-4-yl)pyridin-2 (1H)-one (129)

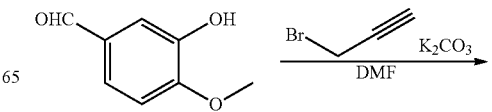

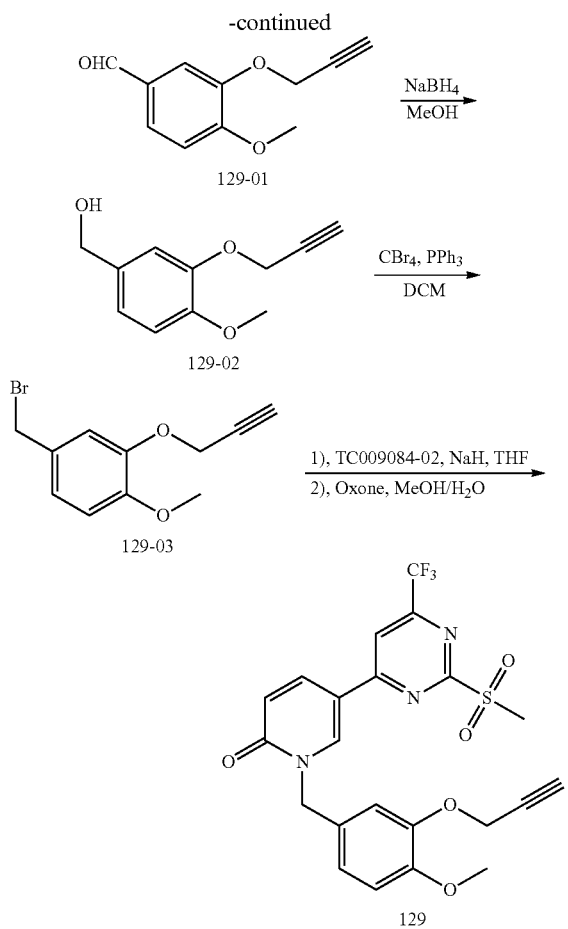

Step 1. Preparation of 4-methoxy-3-(prop-2-yn-1-yloxy)benzaldehyde (129-01)

K₂CO₃ (1.1 g, 8.0 mmol) was added to a solution of 3-hydroxy-4-methoxybenzaldehyde (1 g, 6.6 mmol) and 3-bromoprop-1-yne (0.95 g, 7.9 mmol) in DMF (10 mL). The reaction mixture was stirred at room temperature for 3 hrs. The reaction mixture was extracted by EtOAc and H₂O 3 times. The organic layer was combined, washed with brine, dried over Na₂SO₄, concentrated and further purified by silica gel column chromatography (PE/EA=4/1), to give 1.24 g of 4-methoxy-3-(prop-2-yn-1-yloxy)benzaldehyde as a yellow oil (100%). ¹H NMR (400 Hz, CDCl3) δ 7.50-7.53 (m, 2H), 7.00 (d, J=8.0 Hz, 1H), 4.81 (d, J=2.4 Hz, 2H), 3.95 (s, 3H), 2.53-2.55 (t, J=2.4 Hz, 1H).

Step 2. Preparation of (4-methoxy-3-(prop-2-yn-1-yloxy)phenyl)methanol (129-02)

To a solution of 4-methoxy-3-(prop-2-yn-1-yloxy)benzaldehyde (129-01)(1.24 g, 6.5 mmol) in anhydrous MeOH (15 mL) was added NaBH₄ (350 mg, 8.8 mmol) in portions at 0° C. under N₂ atmosphere. The reaction mixture was then stirred at 0° C. to room temperature for 3 hrs. The reaction was quenched by H₂O, then the solvents were removed from the mixture invacuo. The residue was extracted by EtOAc and H₂O 3 times. The organic layer was combined, washed with brine, dried over Na₂SO₄, concentrated and further purified by silica gel column chromatography (PE/EA=1/1) to give 1.07 g of (4-methoxy-3-(prop-2-yn-1-yloxy)phenyl)methanol as a white solid (75%). ¹H NMR (400 Hz, CDCl3) δ 7.07 (d, J=2.0 Hz, 1H), 6.97 (dd, J=2.0, 8.0 Hz, 1H), 4.78 (d, J=2.4 Hz, 2H), 4.63 (d, J=5.6 Hz, 2H), 3.87 (s, 3H), 2.51 (t, J=2.4 Hz, 1H).

Step 3. Preparation of 4-(bromomethyl)-1-methoxy-2-(prop-2-yn-1-yloxy)benzene (129-03)

To a solution of (4-methoxy-3-(prop-2-yn-1-yloxy)phenyl)methanol (129-02) (200 mg, 1.04 mmol) in DCM was added CBr₄ (432 mg, 1.30 mmol) in portions under N₂ atmosphere, followed by the addition of PPh₃ (341 mg, 1.30 mmol) in portions after stirring for 5-10 min. The reaction mixture was stirred at room temperature for 3 hrs. Solvents were removed from the reaction mixture in vacuo. The residue was dissolved in EtOAc and filtered. The filtrate was concentrated and further purified by silica gel column chromatography (PE/EA=10/1) to give 221 mg of 4-(bromomethyl)-1-methoxy-2-(prop-2-yn-1-yloxy)benzene (83%). ¹H NMR (400 Hz, CDCl3) δ 7.06-7.08 (m, 1H), 6.99-7.03 (m, 1H), 6.82-6.85 (m, 1H), 4.76-4.78 (m, 2H), 4.49 (s, 2H), 3.87 (s, 3H), 2.53 (t, J=2.4 Hz, 1H).

Step 4. Preparation of 1-(4-methoxy-3-(prop-2-yn-1-yloxy)benzyl)-5-(2-(methylsulfonyl)-6-(trifluoromethyl)pyrimidin-4-yl)pyridin-2 (1H)-one (129)

The titled compound 129 (24 mg, 0.04 mmol) was prepared in a yield of 13% as a white solid from 99-02 (74 mg, 0.29 mmol) and 4-(bromomethyl)-1-methoxy-2-(prop-2-yn-1-yloxy)benzene (129-03) (57 mg, 0.29 mmol) according to the procedure for 100. ¹H NMR (400 Hz, CDCl3) δ 8.67 (d, J=2.8 Hz, 1H), 7.96 (dd, J=2.8, 9.6 Hz, 1H), 7.82 (s, 1H), 7.10 (d, J=2.0 Hz, 1H), 7.01 (dd, J=2.0, 8.4 Hz, 1H), 6.88 (d, J=8.0 Hz, 1H), 6.74 (d, J=9.6 Hz, 1H), 5.20 (s, 2H), 4.76 (d, J=2.0 Hz, 2H), 3.88 (s, 3H), 43.46 (s, 3H), 2.55 (t, J=2.0 Hz, 1H). LC-MS (ESI) m/z: calcd for [C₂₂H₁₉F₃N₃O₅S⁺], 494.1, found 494.3.

1-(3-methoxy-4-(prop-2-yn-1-yloxy)benzyl)-5-(2-(methylsulfonyl)-6-(trifluoromethyl)pyrimidin-4-yl)pyridin-2 (1H)-one (130)

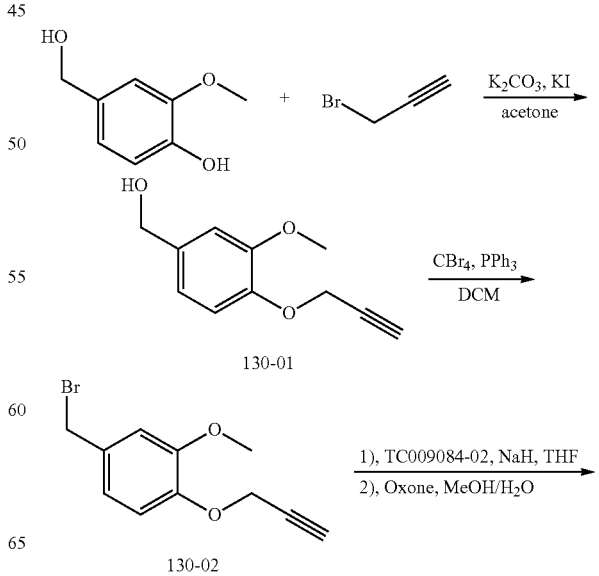

-continued

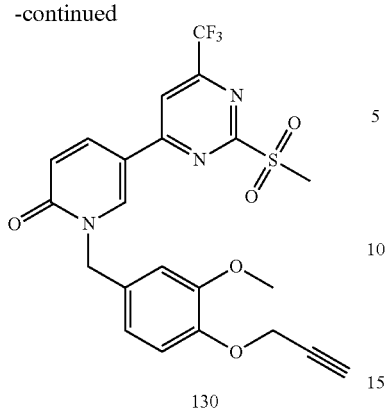

130

Step 1. Preparation of (3-methoxy-4-(prop-2-yn-1-yloxy)phenyl)methanol (130-01)

To a solution of 4-(hydroxymethyl)-2-methoxyphenol (770 mg, 4.6 mmol) in acetone was added $K_2CO_3$ (1.04 g, 5.5 mmol) and KI (910 mg, 5.5 mmol), followed by addition of 3-bromoprop-1-yne (650 mg, 5 mmol). The reaction mixture was refluxed at 75° C. for 8 hrs. The reaction mixture was cooled to room temperature, and solvents were removed in vacuo. The residue was extracted by EtOAc and $H_2O$ 3 times. The organic layer was combined, washed with brine, dried over $Na_2SO_4$, concentrated and further purified by silica gel column chromatography (PE/EA=4/1), to give 725 mg of (3-methoxy-4-(prop-2-yn-1-yloxy)phenyl)methanol as a yellow oil (182%).

Step 2. Preparation of 4-(bromomethyl)-2-methoxy-1-(prop-2-yn-1-yloxy)benzene (130-02)

To a solution of (3-methoxy-4-(prop-2-yn-1-yloxy)phenyl)methanol (130-01) (422 mg, 2.2 mmol) in DCM was added $CBr_4$ (910 mg, 2.7 mmol) in portions under $N_2$ atmosphere, followed by the addition of $PPh_3$ (720 mg, 2.70 mmol) in portions after stirring for 5-10 min. The reaction mixture was stirred at room temperature for 3 hrs. Solvents were removed from the reaction mixture in vacuo. The residue was dissolved in EtOAc and filtered. The filtrate was concentrated and further purified by silica gel column chromatography (PE/EA=10/1) to give 420 mg of 4-(bromomethyl)-2-methoxy-1-(prop-2-yn-1-yloxy)benzene (75%). $\delta^1H$ NMR (400 Hz, CDCl3) δ 6.94-6.99 (m, 3H), 4.76-4.78 (m, 2H), 4.50 (s, 2H), 3.89 (s, 3H), 2.51-2.52 (m, 1H).

Step 3. Preparation of 1-(3-methoxy-4-(prop-2-yn-1-yloxy)benzyl)-5-(2-(methylsulfonyl)-6-(trifluoromethyl)pyrimidin-4-yl)pyridin-2 (1H)-one (130)

The tided compound 130 (5 mg, 0.01 mmol) was prepared in a yield of 5% as a white solid from 99-02 (65 mg, 0.23 mmol) and 4-(bromomethyl)-2-methoxy-1-(prop-2-yn-1-yloxy)benzene (130-02) (54 mg, 0.23 mmol) according to the procedure for 100. $\delta^1H$ NMR (400 Hz, CDCl3) δ 8.69 (d, J=2.4 Hz, 1H), 7.98 (dd, J=2.4, 9.6 Hz, 1H), 7.83 (s, 1H), 7.02 (d, J=8.0 Hz, 1H), 6.97 (s, 1H), 6.92 (d, J=8.0 Hz, 1H), 6.75 (d, J=9.6 Hz, 1H), 5.20 (s, 2H), 4.76 (d, J=2.4 Hz, 2H), 3.87 (s, 3H), 3.40 (s, 3H), 2.51 (t, J=2.4 Hz, 1H). LC-MS (ESI) m/z: calcd for $[C_{22}H_{19}F_3N_3O_5S^+]$, 494.1, found 494.0.

1-([1,1'-biphenyl]-4-ylmethyl)-5-(2-(methylsulfonyl)-6-(trifluoromethyl)pyrimidin-4-yl)pyridin-2 (1H)-one (131)

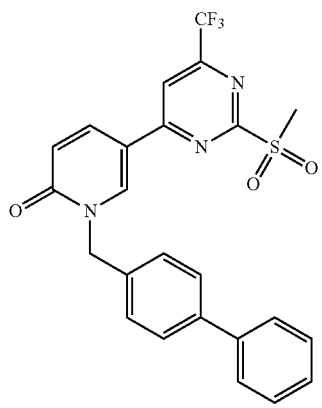 [SMILES: CS(=O)(=O)c1nc(-c2ccc(=O)n(Cc3ccc(-c4ccccc4)cc3)c2)cc(C(F)(F)F)n1]

The titled compound (7 mg, 0.015 mmol) was prepared in a yield of 42% as a white solid from 99-02 (10 mg, 0.04 mmol) and 4-(bromomethyl)-1,1'-biphenyl (12 mg, 0.05 mmol) according to the procedure for 100. $^1$H-NMR: (400 Mz, CDCl3): δ 8.72 (d, J=2.4 Hz, 1H), 8.01 (dd, $^1$J=2.4 Hz, $^2$J=10 Hz, 1H), 7.85 (s, 1H), 7.59-7.34 (m, 4H), 7.44-7.41 (m, 4H), 7.36-7.33 (m, 1H), 6.75 (d, J=10 Hz, 1H), 5.29 (s, 2H), 3.37 (s, 3H). Mass (m/z): 486.10[M+H]+.

1-(4-(1H-pyrazol-1-yl)benzyl)-5-(2-(methylsulfonyl)-6-(trifluoromethyl)pyrimidin-4-yl)pyridin-2 (1H)-one (132)

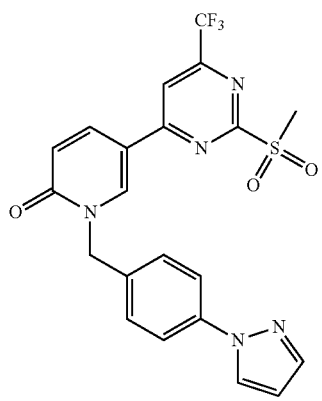 [SMILES: CS(=O)(=O)c1nc(-c2ccc(=O)n(Cc3ccc(-n4cccn4)cc3)c2)cc(C(F)(F)F)n1]

The titled compound (18 mg, 0.038 mmol) was prepared in a yield of 35% as a white solid from 99-02 (30 mg, 0.11 mmol) and 1-(4-(bromomethyl)phenyl)-1H-pyrazole (36 mg, 0.15 mmol) according to the procedure for 100. $^1$H-NMR (400 MHz, CDCl$_3$): δ 8.72 (d, J=2.0 Hz, 1H), 7.99 (m, 1H), 7.91 (d, J=2.0 Hz, 1H), 7.86 (s, 1H), 7.72-7.69 (m, 3H), 7.46 (d, J=9.2 Hz, 2H), 6.75 (d, J=9.2 Hz, 1H), 6.46 (m, 1H), 5.29 (s, 3H), 3.40 (s, 1H). Mass (m/z): 476.09 [M+H]+.

5-(2-(methylsulfonyl)-6-(trifluoromethyl)pyrimidin-4-yl)-1-(naphthalen-1-ylmethyl)pyridin-2 (1H)-one (133)

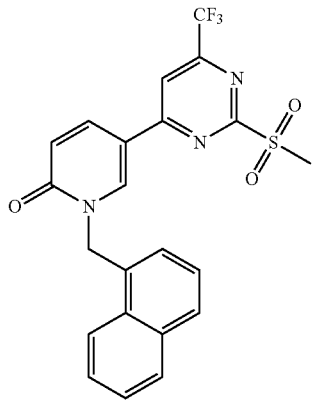 [SMILES: CS(=O)(=O)c1nc(-c2ccc(=O)n(Cc3cccc4ccccc34)c2)cc(C(F)(F)F)n1]

The titled compound (5 mg, 16%) was prepared as a white solid from 99-02 (20 mg, 0.07 mmol) and 1-(bromomethyl) naphthalene (18 mg, 0.08 mmol) according to the procedure for 103. $^1$H NMR: (400 Mz, CDCl$_3$): δ 8.43 (d, J=9.6 Hz, 1H), 8.02-7.91 (m, 4H), 7.68 (s, 1H), 7.58-7.42 (m, 4H), 6.83 (d, J=9.6 Hz, 1H), 5.72 (s, 2H), 3.18 (s, 3H). Mass (m/z): 460.3 [M+H]$^+$.

5-(2-(methylsulfonyl)-6-(trifluoromethyl)pyrimidin-4-yl)-1-(naphthalen-2-ylmethyl)pyridin-2 (1H)-one (134)

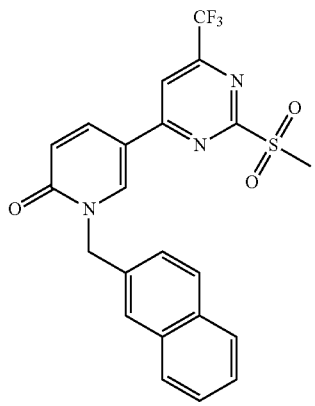 [SMILES: CS(=O)(=O)c1nc(-c2ccc(=O)n(Cc3ccc4ccccc4c3)c2)cc(C(F)(F)F)n1]

The titled compound (5 mg, 16%) was prepared as a white solid from 99-02 (20 mg, 0.07 mmol) and 2-(bromomethyl) naphthalene (18 mg, 0.08 mmol) according to the procedure for 103. $^1$H NMR: (400 Mz, CDCl$_3$): δ 8.68 (d, J=2.4 Hz, 1H), 8.00 (dd, J=2.4, 9.6 Hz, 1H), 7.87-7.81 (m, 4H), 7.52-7.45 (m, 4H), 6.78 (d, J=9.6 Hz, 1H), 5.43 (s, 2H), 3.29 (s, 3H). Mass (m/z): 460.3 [M+H]$^+$.

1-((2-methoxypyridin-4-yl)methyl)-5-(2-(methylsulfonyl)-6-(trifluoromethyl)pyrimidin-4-yl)pyridin-2 (1H)-one (135)

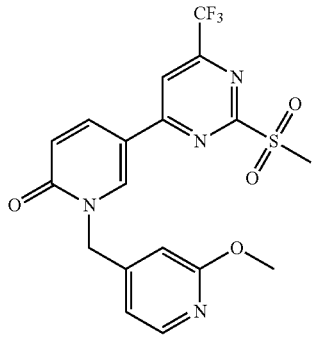 [SMILES: COc1cc(Cn2cc(-c3cc(C(F)(F)F)nc(S(C)(=O)=O)n3)ccc2=O)ccn1]

The titled compound (2 mg, 6%) was prepared as a white solid from 99-02 (20 mg, 0.07 mmol) and 4-(bromomethyl)-2-methoxypyridine (16 mg, 0.08 mmol) according to the procedure for 103. $^1$H NMR (400 Hz, CDCl$_3$) δ 8.69-8.70 (m, 1H), 8.16 (d, J=5.6 Hz, 1H), 8.04 (dd, J=2.4, 9.6 Hz, 1H). 7.88 (s. 1H), 6.82 (d, J=5.2 Hz, 1H), 6.79 (d, J=9.6 Hz, 1H). 5.24 (s. 2H), 3.95 (s, 3H), 3.43 (s, 3H).

1-(benzo[d][1,3]dioxol-5-ylmethyl)-5-(2-(methylsulfonyl)-6-(trifluoromethyl)pyrimidin-4-yl)pyridin-2 (1H)-one (136)

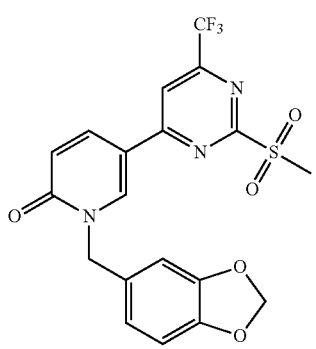 [SMILES: CS(=O)(=O)c1nc(-c2ccc(=O)n(Cc3ccc4c(c3)OCO4)c2)cc(C(F)(F)F)n1]

The titled compound (2 mg, 6%) was prepared as two white solid from 99-02 (20 mg, 0.07 mmol) and 5-(bromomethyl)benzo[d][1,3]dioxole (17 mg, 0.08 mmol) according to the procedure for 103.

$^1$H NMR (400 Hz, CDCl$_3$) δ 8.63 (d, J=2.4 Hz, 1H), 7.98 (dd, J=2.4, 9.6 Hz, 1H), 7.82 (s, 1H), 6.84-6.86 (m, 2H), 6.80 (d, J=8.4 Hz, 1H), 6.74 (d, J=9.6 Hz, 1H), 5.96 (s, 2H), 5.16 (s, 2H), 3.41 (s, 3H). LC-MS (ESI) m/z: calcd for [C$_{19}$H$_{15}$F$_3$N$_3$O$_5$S$^+$], 454.1, found 454.5.

1-((4-bromobenzo[d][1,3]dioxol-5-yl)methyl)-5-(2-(methylsulfonyl)-6-(trifluoromethyl)pyrimidin-4-yl)pyridin-2 (1H)-one (137) and 1-((4-bromobenzo[d][1,3]dioxol-5-yl)methyl)-5-(2-(methylsulfinyl)-6-(trifluoromethyl)pyrimidin-4-yl)pyridin-2 (1H)-one (138)

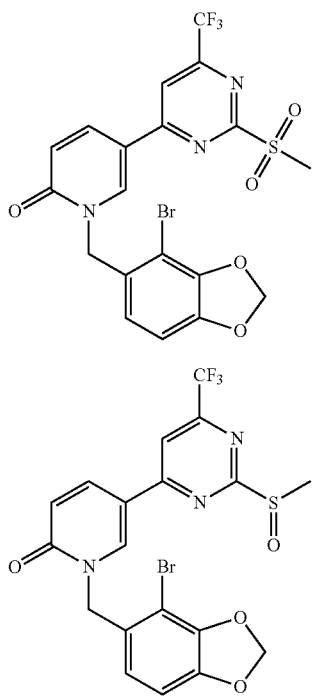

The titled compound 137 (5 mg, 13%) and 138 (4 mg, 100%) were prepared as two white solid from 99-02 (20 mg, 0.07 mmol) and 4-bromo-5-(bromomethyl)benzo[d][1,3]dioxole (24 mg, 0.08 mmol) according to the procedure for 103.

137 $^1$H NMR: (400 Mz, CDCl$_3$): δ 8.78 (d, J=2.8 Hz, 1H), 8.02 (dd, J=2.8, 9.6 Hz, 1H), 7.83 (s, 1H), 7.06 (s, 1H), 6.88 (s, 1H), 6.75 (d, J=9.6 Hz, 1H), 5.99 (s, 2H), 5.28 (s, 2H), 3.40 (s, 3H). Mass (m/z): 533.3 [M+H]$^+$.

138 $^1$H NMR: (400 Mz, CDCl$_3$): δ 8.80 (d, J=2.8 Hz, 1H), 8.05 (dd, J=2.8, 9.6 Hz, 1H), 7.73 (s, 1H), 7.06 (s, 1H), 6.85 (s, 1H), 6.74 (d, J=9.6 Hz, 1H), 5.98 (s, 2H), 5.29 (d, J=14.8 Hz, 1H), 5.25 (d, J=14.8 Hz, 1H), 3.01 (s, 3H). Mass (m/z): 517.3 [M+H]$^+$.

1-(3,4-dimethoxybenzyl)-5-(2-(methylsulfonyl)-6-(1H-pyrazol-1-yl)pyrimidin-4-yl)pyridin-2 (1H) one (139)

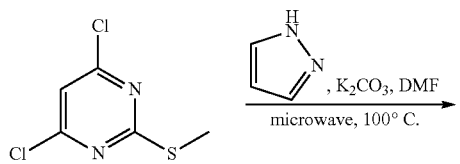

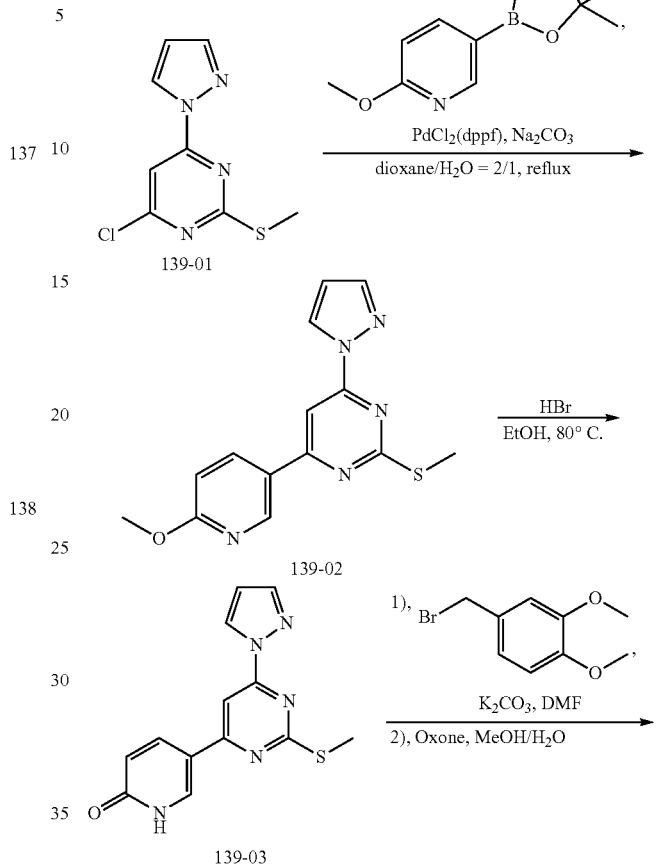

Step 1. Preparation of 4-chloro-2-(methylthio)-6-(1H-pyrazol-1-yl)pyrimidine (139-01)

The titled compound 139-01 was prepared in a yield of 40% (130 mg, 0.56 mmol) as a white solid from 4,6-dichloro-2-(methylthio)pyrimidine (300 mg, 1.55 mmol) and 1H-pyrazole (95 mg, 1.40 mmol) according to the procedure for 36.

Step 2. Preparation of 4-(6-methoxypyridin-3-yl)-2-(methylthio)-6-(1H-pyrazol-1-yl)pyrimidine (139-02)

The titled compound 139-02 was prepared in a yield of 86% (146 mg, 0.47 mmol) as a white solid from 139-01 (125 mg, 0.55 mmol) and 2-methoxy-5-(4,4,5,5-tetramethyl-1,3,2-dioxaborolan-2-yl)pyridine (140 mg, 0.61 mmol) according to the procedure for 99-01.

Step 3. Preparation of 5-(2-(methylthio)-6-(1H-pyrazol-1-yl)pyrimidin-4-yl)pyridin-2 (1H)-one (139-03)

The titled compound 139-03 was prepared in a yield of 54% (75 mg, 0.30 mmol) as a white solid from 139-02 (146 mg, 0.47 mmol) according to the procedure for 99-02.

Step 4. Preparation of 1-(3,4-dimethoxybenzyl)-5-(2-(methylsulfonyl)-6-(1H-pyrazol-1-yl)pyrimidin-4-yl)pyridin-2 (1H)-one (139)

The titled compound 139 was prepared in a yield of 14% (10 mg, 0.02 mmol) as a white solid from 139-03 (40 mg, 0.14 mmol) and 4-(bromomethyl)-1,2-dimethoxybenzene (32 mg, 0.14 mmol) according to the procedure for 99-01. $^1$H NMR (400 Hz, CDCl$_3$) δ 8.62 (d, J=2.4 Hz, 1H), 8.53 (d, J=2.4 Hz, 1H), 8.15 (s, 1H), 8.04 (dd, J=2.4, 9.6 Hz, 1H), 7.85 (d, J=0.8 Hz, 1H), 6.95-6.97 (m, 1H), 6.93 (d, J=2.4 Hz, 1H), 6.85-6.88 (m, 1H), 6.73 (d, J=9.6 Hz, 1H), 6.57 (dd, J=1.6, 2.4 Hz, 1H), 5.19 (s, 2H), 3.88 (s, 3H), 3.87 (s, 3H), 3.35 (s, 3H). LC-MS (ESI) m/z: calcd for [C$_{22}$H$_{22}$N$_5$O$_5$S$^+$], 468.1, found 468.5.

5-(2-(((1,1'-biphenyl]-4-ylmethyl)sulfonyl)-6-(trifluoromethyl)pyrimidin-4-yl)-1-(3,4-dimethoxybenzyl)pyridin-2 (1H)-one (140)

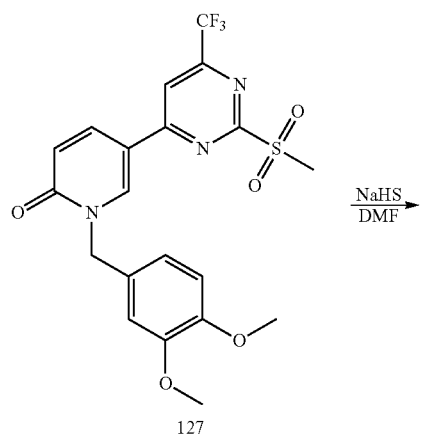

127

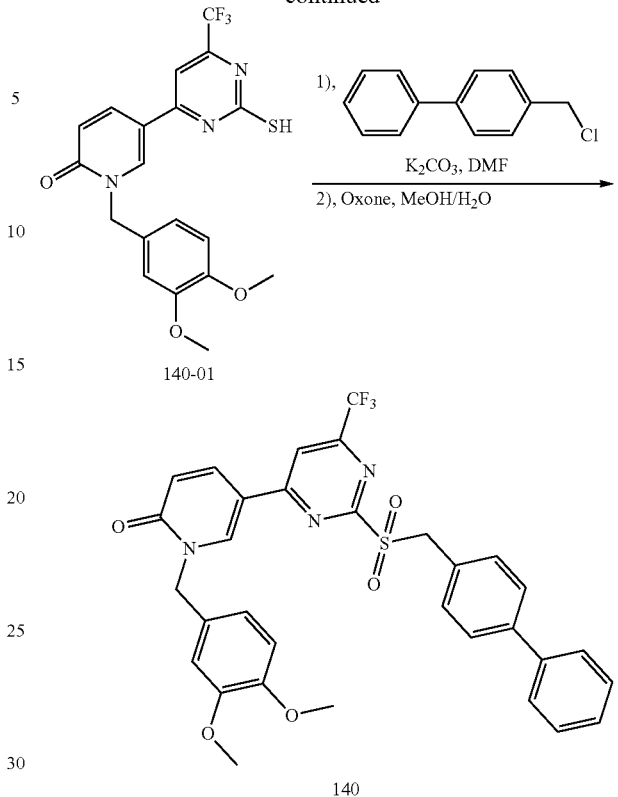

Preparation of 1-(3,4-dimethoxybenzyl)-5-(2-mercapto-6-(trifluoromethyl)pyrimidin-4-yl)pyridin-2 (1H)-one (140-01)

NaHS (28 mg, 0.38 mmol) was added to a solution of 1-(3,4-dimethoxybenzyl)-5-(2-(methylsulfonyl)-6-(trifluoromethyl)pyrimidin-4-yl)pyridin-2 (1H)-one (130) (60 mg, 0.13 mmol) in DMF (2 mL) under N$_2$ atmosphere. The reaction mixture was stirred at room temperature for 2 hrs. The reaction mixture was acidified to PH=5 by 1N HCl, then extracted by DCM/H$_2$O. The organic layer was combined, washed with brine, dried over Na$_2$SO$_4$ and further purified by silica gel column chromatography (PE/EA=1/1) to give 50 mg of 1-(3,4-dimethoxybenzyl)-5-(2-mercapto-6-(trifluoromethyl)pyrimidin-4-yl)pyridin-2 (1H)-one as a yellow solid (98%).

Preparation of 5-(2-(((1,1'-biphenyl]-4-ylmethyl)sulfonyl)-6-(trifluoromethyl)pyrimidin-4-yl)-1-(3,4-dimethoxybenzyl)pyridin-2 (1H)-one K$_2$CO$_3$ (10 mg, 0.07 mmol) was added to a solution of 1-(3,4-dimethoxybenzyl)-5-(2-mercapto-6-(trifluoromethyl)pyrimidin-4-yl)pyridin-2 (1H)-one (20 mg, 0.05 mmol) and 4-(chloromethyl)-1,1'-biphenyl (15 mg, 0.07 mmol) in DMF (2 mL). The reaction mixture was stirred at room temperature for 3 hrs. The reaction mixture was extracted by EtOAc and H$_2$O 3 times. The organic layer was combined, washed with brine, dried over Na$_2$SO$_4$, concentrated and further purified by silica gel column chromatography (PE/EA=4/1), to give 10 mg of 5-(2-(((1,1'-biphenyl]-4-ylmethyl)thio)-6-(trifluoromethyl)pyrimidin-4-yl)-1-(3,4-dimethoxybenzyl)pyridin-2 (1H)-one as a white solid (36%).

An aqueous solution of Oxone (50 mg, 0.08 mmol) was added dropwise to a solution of 5-(2-(([1,1'-biphenyl]-4-ylmethyl)thio)-6-(trifluoromethyl)pyrimidin-4-yl)-1-(3,4-dimethoxybenzyl)pyridin-2 (1H)-one (10 mg, 0.02 mmol) in MeOH (2 mL). The reaction mixture was stirred at room temperature for 8 hrs. Solvents were evaporated from the reaction mixture, then the residue was extracted by EtOAc/H₂O 3 times. The organic layer was combined, washed with brine, dried over Na₂SO₄ and further purified by silica gel column chromatography (PE/EA=10/1) to give 2 mg of 5-(2-(([1,1'-biphenyl]-4-ylmethyl)sulfonyl)-6-(trifluoromethyl)pyrimidin-4-yl)-1-(3,4-dimethoxybenzyl)pyridin-2 (1H)-one as a white solid (16%). LC-MS (ESI) m-z: calcd for $[C_{32}H_{27}F_3N_3O_5S_3^+]$, 622.2, found 622.4.

5-(2-(but-3-yn-1-ylsulfonyl)-6-(trifluoromethyl)pyrimidin-4-yl)-1-(3,4-dimethoxybenzyl)pyridin-2 (1H)-one (141)

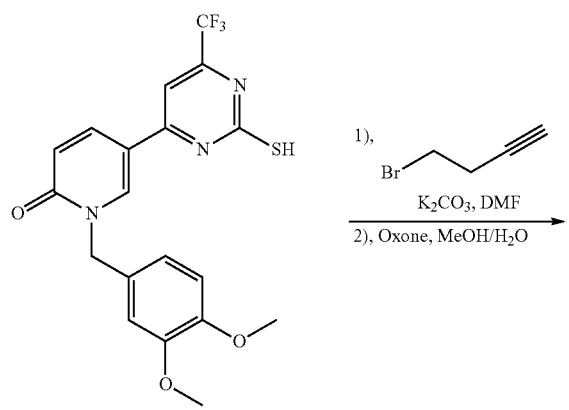

The titled compound was prepared in a yield of 15% (7 mg, 0.015 mmol) as a white solid from 140-01 (40 mg, 0.10 mmol) and 4-bromobut-1-yne (20 mg, 0.14 mmol) according to the procedure for 140. ¹H NMR (400 Hz, CDCl₃) δ 8.68 (d, J=2.4 Hz, 1H), 7.96 (dd, J=1.2, 9.6 Hz, 1H), 7.82 (s, 1H), 6.96~6.92 (m, 2H), 6.85 (d, J=8.0 Hz, 1H), 6.73 (d, J=9.6 Hz, 1H), 5.19 (s, 2H), 3.88 (s, 3H), 3.86 (s, 3H), 3.79 (t, J=7.2 Hz, 2H), 2.85 (dt, J=7.2, 2.8 Hz, 2H), 1.97 (t, J=2.8 Hz, 1H).

1-(3,4-dimethoxybenzyl)-5-(6-(trifluoromethyl)-2-(vinylsulfonyl)pyrimidin-4-yl)pyridin-2 (1H)-one (142)

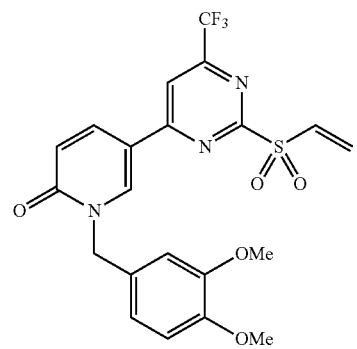 [SMILES: C=CS(=O)(=O)c1nc(-c2ccc(=O)n(Cc3ccc(OC)c(OC)c3)c2)cc(C(F)(F)F)n1]

The title compound was prepared in a yield of 69% (40 mg, 0.12 mmol) as a colorless oil from 140-01 (50 mg, 0.12 mmol) and 2-bromo-N,N-dimethylethanamine (0.18 mmol) according to the procedure for 140. 142: ¹HNMR (400 MHz, CDCl₃) δ 8.45 (d, J=2.8 Hz, 1H), 7.99 (dd, J=2.8, 9.6 Hz, 1H), 7.83 (s, 1H), 7.09 (dd, J=10.0, 16.4 Hz, 1H), 6.93-6.90 (m, 2H), 6.84 (d, J=8.4 Hz, 1H), 6.72 (d, J=9.6 Hz, 1H), 6.69 (d, J=17.2 Hz, 1H), 6.37 (d, J=10.0 Hz, 1H), 5.17 (s, 2H), 3.85 (s, 3H), 3.84 (s, 3H). Mass (m/z): 482.54 [M+H]⁺.

1-(3,4-dimethoxybenzyl)-5-(2-((2-methoxyethyl)sulfonyl)-6-trifluoromethyl)pyrimidin-4-yl)pyridin-2 (1H)-one (143)

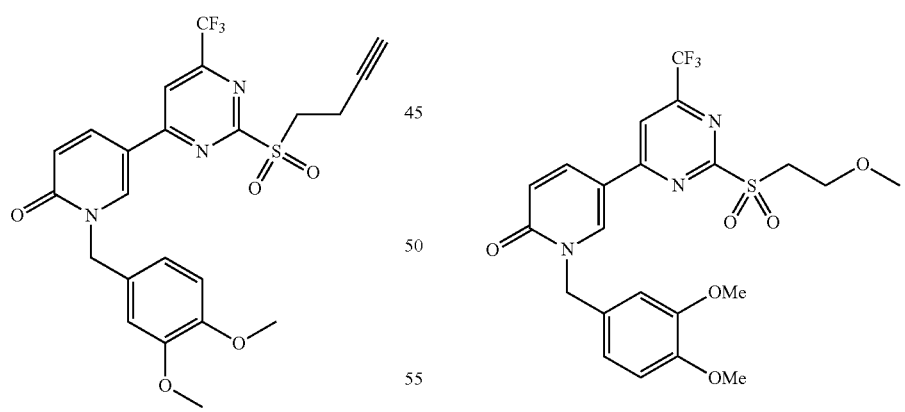

The titled compound was prepared in a yield of 68% (21 mg, 0.041 mmol) as a white solid from 140-01 (24 mg, 0.06 mmol) and 1-bromo-2-methoxyethane (12 mg, 0.09 mmol) according to the procedure for 140. ¹HNMR (400 MHz, CDCl₃) δ 8.68 (d, J=2.8 Hz, 1H), 8.01 (dd, J=2.8, 9.6 Hz, 1H), 7.81 (s, 1H), 6.95-6.92 (m, 2H), 6.85 (d, J=8.0 Hz, 1H), 6.75 (d, J=9.6 Hz, 1H), 5.19 (s, 2H), 3.59-3.85 (m, 8H), 3.80 (t, J=5.6 Hz, 2H), 3.16 (s, 3H). Mass (m/z): 514.43 [M+H]⁺.

257

1-(3,4-dimethoxybenzyl)-5-(2-((3-methoxypropyl)sulfonyl)-6-(trifluoromethyl)pyrimidin-4-yl)pyridin-2 (1H)-one (144)

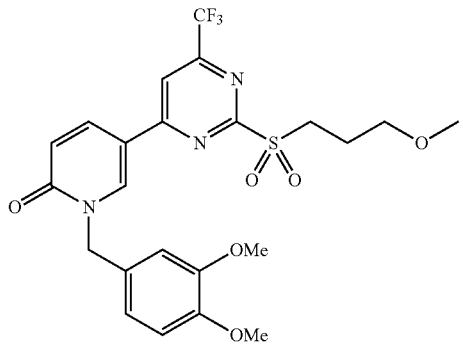 [SMILES: COCCCS(=O)(=O)c1nc(-c2ccc(=O)n(Cc3ccc(OC)c(OC)c3)c2)cc(C(F)(F)F)n1]

The titled compound was prepared in a yield of 80% (21 mg, 0.04 mmol) as a white solid from 140-01 (21 mg, 0.05 mmol) and 1-bromo-3-methoxypropane (11 mg, 0.075 mmol) according to the procedure for 140. ¹HNMR (400 MHz, CDCl₃) δ 8.70 (d, J=2.4 Hz, 1H), 7.99 (dd, J=2.4, 9.6 Hz, 1H), 7.81 (s, 1H), 6.96-6.91 (m, 2H), 6.85 (d, J=8.4 Hz, 1H), 6.74 (d, J=9.6 Hz, 1H), 5.19 (s, 1H), 3.87 (s, 3H), 3.86 (s, 3H), 3.69 (t, J=7.6 Hz, 2H), 3.52 (t, J=5.6 Hz, 2H), 3.30 (s, 3H), 2.21-2.14 (m, 2H). Mass (m/z): 528.49 [M+H]⁺.

1-(3,4-dimethoxybenzyl)-5-(2-((2-(2-methoxyethoxy)ethyl)thio)-6-(trifluoromethyl)pyrimidin-4-yl)pyridin-2 (1H)-one (145)

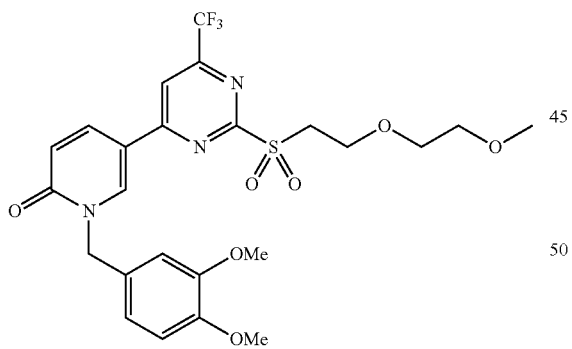

The titled compound was prepared in a yield of 71% (17 mg, 0.03 mmol) as a white solid from 140-01 (18 mg, 0.042 mmol) and 1-bromo-2-(2-methoxyethoxy)ethane (12 mg, 0.063 mmol) according to the procedure for 140. ¹HNMR (400 MHz, CDCl₃) δ 8.66 (d, J=2.8 Hz, 1H), 7.99 (dd, J=2.8, 9.6 Hz, 1H), 7.79 (s, 1H), 6.95-6.92 (m, 2H), 6.86 (d, J=8.0 Hz, 1H), 6.75 (d, J=9.6 Hz, 1H), 5.19 (s, 2H), 3.97 (t, J=6.0 Hz, 2H), 3.87-3.83 (m, 8H), 3.45-3.43 (m, 2H), 3.23-3.20 (m, 2H), 3.14 (s, 3H). Mass (m/z): 558.25 [M+H]⁺.

258

1-(3,4-dimethoxybenzyl)-5-(2-(heptylsulfonyl)-6-(trifluoromethyl)pyrimidin-4-yl)pyridin-2 (1H)-one (146)

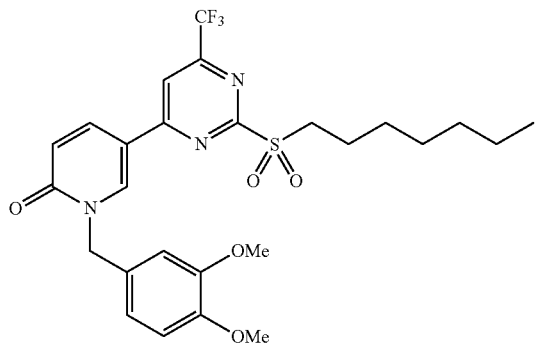 [SMILES: CCCCCCCS(=O)(=O)c1nc(-c2ccc(=O)n(Cc3ccc(OC)c(OC)c3)c2)cc(C(F)(F)F)n1]

The titled compound was prepared in a yield of 46% (13 mg, 0.023 mmol) as a white solid from 140-01 (21 mg, 0.05 mmol) and 1-bromo-3-methoxypropane (11 mg, 0.075 mmol) according to the procedure for 140. ¹HNMR (400 MHz, CDCl3) δ 8.69 (d, J=2.4 Hz, 1H), 7.98 (dd, J=2.8, 9.6 Hz, 1H), 7.79 (s, 1H), 6.94-6.90 (m, 2H), 6.84 (dm J=8.4 Hz, 1H), 6.75 (d, J=9.6 Hz, 1H), 5.19 (s, 2H), 3.86 (s, 3H), 3.85 (s, 3H), 3.56 (t, J=8.0 Hz, 2H), 1.90-1.84 (m, 2H), 1.34-1.24 (m, 6H), 0.86 (t, J=6.8 Hz, 3H). Mass (m/z): 554.27 [M+H]⁺

1-(3,4-dimethoxybenzyl)-5-(2-(pentylsulfonyl)-6-(trifluoromethyl)pyrimidin-4-yl)pyridin-2 (1H)-one (147)

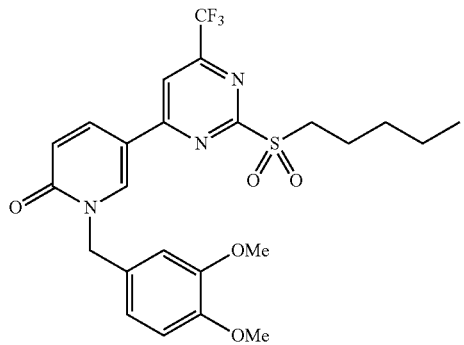 [SMILES: CCCCCS(=O)(=O)c1nc(-c2ccc(=O)n(Cc3ccc(OC)c(OC)c3)c2)cc(C(F)(F)F)n1]

The titled compound was prepared in a yield of 77% (21 mg, 0.04 mmol) as a white solid from 140-01 (22 mg, 0.052 mmol) and 1-bromopentane (12 mg, 0.078 mmol) according to the procedure for 140. Mass (m/z): 526.20 [M+H]⁺.

1-(3,4-dimethoxybenzyl)-5-(2-((2-(2-methoxyethoxy)ethyl)sulfonyl)-6-(trifluoromethyl)pyrimidin-4-yl)pyridin-2 (1H)-one (148)

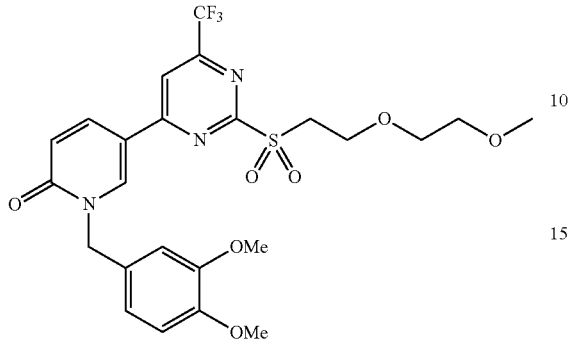

The titled compound was prepared in a yield of 74% (17 mg, 0.031 mmol) as a light yellow oil from 140-01 (18 mg, 0.042 mmol) and 1-bromo-2-(2-methoxyethoxy)ethane (12 mg, 0.063 mmol) according to the procedure for 140. $^1$HNMR (400 MHz, CDCl$_3$) δ 8.66 (d, J=2.8 Hz, 1H), 7.99 (dd, J=2.8, 9.6 Hz, 1H), 7.79 (s, 1H), 6.95-6.92 (m, 2H), 6.86 (d, J=8.0 Hz, 1H), 6.75 (d, J=9.6 Hz, 1H), 5.19 (s, 2H), 3.97 (t, J=6.0 Hz, 2H), 3.87-3.83 (m, 8H), 3.45-3.43 (m, 2H), 3.23-3.20 (m, 2H), 3.14 (s, 3H). Mass (m/z): 558.25 [M+H]$^+$.

1-(3,4-dimethoxybenzyl)-5-(2-((3-oxo-3-(pyrrolidin-1-yl)propyl)sulfonyl)-6-(trifluoromethyl)pyrimidin-4-yl)pyridin-2 (1H)-one (150)

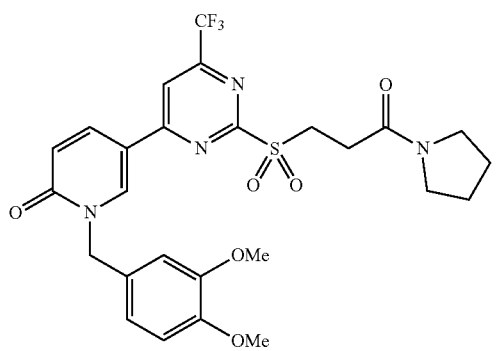

The titled compound was prepared in a yield of 49% (17 mg, 0.029 mmol) as a colorless syrup from 140-01 (25 mg, 0.059 mmol) and 3-bromo-1-(pyrrolidin-1-yl)propan-1-one (24 mg, 0.12 mmol) according to the procedure for 140. $^1$HNMR (400 MHz, CDCl$_3$) δ 8.77 (d, J=2.8 Hz, 1H), 7.99 (dd, J=2.8, 9.6 Hz, 1H), 7.83 (s, 1H), 6.98 (d, J=2.0 Hz, 1H), 6.96 (dd, J=2.0, 8.4 Hz, 1H), 6.84 (d, J=8.0 Hz, 1H), 6.72 (d, J=9.6 Hz, 1H), 5.20 (s, 2H), 3.96 (t, J=7.6 Hz, 2H), 3.86 (s, 3H), 3.84 (s, 3H), 3.40 (q, J=6.7 Hz, 4H), 2.92 (t, J=7.6 Hz, 2H), 1.99-1.92 (m, 2H), 1.87-1.80 (m, 2H). Mass (m/z): 581.25 [M+H]$^+$.

3-((4-(1-(3,4-dimethoxybenzyl)-6-oxo-1,6-dihydropyridin-3-yl)-6-(trifluoromethyl)pyrimidin-2-yl)sulfonyl)-N,N-dimethylpropanamide (149)

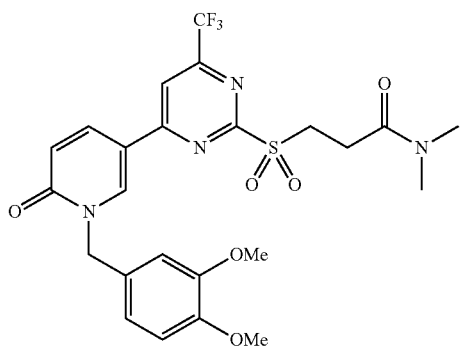 [SMILES: COc1ccc(Cn2cc(-c3cc(C(F)(F)F)nc(S(=O)(=O)CCC(=O)N(C)C)n3)ccc2=O)cc1OC]

The titled compound was prepared in a yield of 23% (6 mg, 0.011 mmol) as a white solid from 140-01 (20 mg, 0.047 mmol) and 3-bromo-N,N-dimethylpropanamide (13 mg, 0.071 mmol) according to the procedure for 140. $^1$HNMR (400 MHz, CDCl$_3$) δ 8.75 (d, J=2.4 Hz, 1H), 8.01 (dd, J=2.8, 9.6 Hz, 1H), 7.82 (s, 1H), 6.98-6.94 (m, 2H), 6.86 (d, J=8.0 Hz, 1H), 6.80 (d, J=9.6 Hz, 1H), 5.22 (s, 2H), 3.96 (t, J=7.2 Hz, 2H), 3.87 (s, 3H), 3.86 (s, 3H), 3.04-3.00 (m, 5H), 2.93 (s, 3H). Mass (m/z): 555.24 [M+H]$^+$.

4-((4-(1-(3,4-dimethoxybenzyl)-6-oxo-1,6-dihydropyridin-3-yl)-6-(trifluoromethyl)pyrimidin-2-yl)sulfonyl)-N,N-dimethylbutanamide (151)

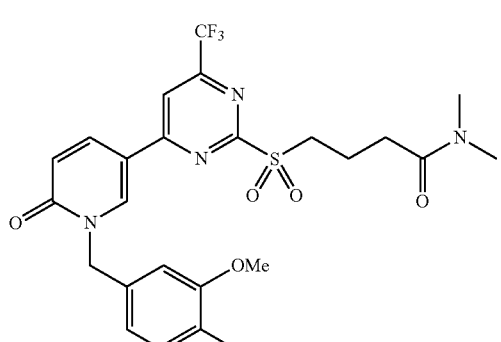

The titled compound was prepared in a yield of 15% (3 mg, 0.0053 mmol) as a white solid from 140-01 (15 mg, 0.035 mmol) and 4-bromo-N,N-dimethylbutanamide (21 mg, 0.11 mmol) according to the procedure for 140. $^1$HNMR (400 MHz, CDCl$_3$) δ 8.96 (d, J=2.4 Hz, 1H), 7.99 (dd, J=2.8, 9.6 Hz, 1H), 7.62 (s, 1H), 7.02 (d, J=2.0 Hz, 1H), 6.99 (dd, J=2.0, 8.0 Hz, 1H), 6.85 (d, J=8.0 Hz, 1H), 6.78 (d, J=9.6 Hz, 1H), 5.28 (s, 2H), 3.87 (s, 3H), 3.86 (s, 3H), 3.75 (t, J=7.2 Hz, 2H), 3.03 (s, 3H), 2.93 (s, 3H), 2.62 (t, J=6.8 Hz, 2H), 2.30-2.24 (m, 2H). Mass (m/z). 569.24 [M+H]$^+$.

1-(3,4-dimethoxybenzyl)-5-(2-((4-oxo-4-(pyrrolidin-1-yl)butyl)sulfonyl)-6-(trifluoromethyl)pyrimidin-4-yl)pyridin-2 (1H)-one (152)

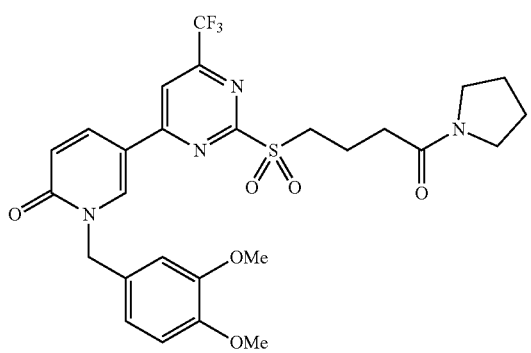 [SMILES: COc1ccc(Cn2cc(-c3cc(C(F)(F)F)nc(S(=O)(=O)CCCC(=O)N4CCCC4)n3)ccc2=O)cc1OC]

The titled compound was prepared in a yield of 28% (9 mg, 0.015 mmol) as a colorless oil from 140-01 (23 mg, 0.054 mmol) and 4-bromo-1-(pyrrolidin-1-yl)butan-1-one (36 mg, 0.16 mmol) according to the procedure for 140. ¹HNMR (400 MHz, CDCl₃) δ 9.07 (d, J=2.8 Hz, 1H), 7.96 (dd, J=2.8, 9.6 Hz, 1H), 7.82 (s, 1H), 7.04 (d, J=2.0 Hz, 1H), 7.01 (dd, J=2.0, 8.0 Hz, 1H), 6.84 (d, J=8.0 Hz, 1H), 6.72 (d, J=9.6 Hz, 1H), 5.29 (s, 2H), 3.86 (s, 3H), 3.85 (s, 3H), 3.81-3.77 (m, 2H), 3.40 (t, J=6.8 Hz, 4H), 2.54 (t, J=6.4 Hz, 2H), 2.29-2.22 (m, 2H), 1.96 (q, J=6.4 Hz, 2H), 1.87-1.82 (m, 2H). Mass (m/z): 595.24 [M+H]⁺.

1-(3,4-dimethoxybenzyl)-5-(2-((3-oxo-3-(piperidin-1-yl)propyl)sulfonyl)-6-(trifluoromethyl)pyrimidin-4-yl)pyridin-2 (1H)-one (153) and 1-(2-chloro-4,5-dimethoxybenzyl)-5-(2-((3-oxo-3-(piperidin-1-yl)propyl)sulfonyl)-6-(trifluoromethyl)pyrimidin-4-yl)pyridin-2 (1H)-one (154)

153

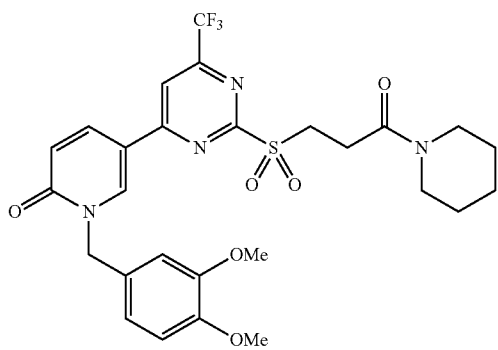

154

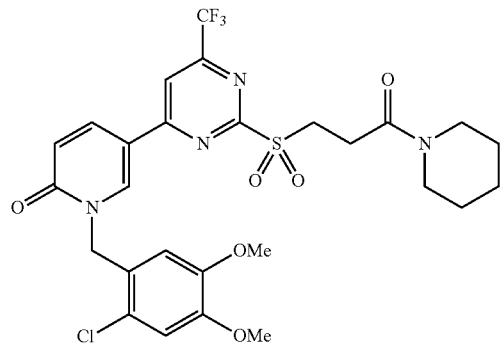

The titled compound 153 (8 mg, 20% yield) and 154 (3 mg, 7% yield) was prepared as two white solids from 140-01 (28 mg, 0.066 mmol) and 3-bromo-1-(piperidin-1-yl)propan-1-one (44 mg, 0.20 mmol) according to the procedure for 140. 153: ¹HNMR (400 MHz, CDCl₃) δ 8.75 (d, J=2.4 Hz, 1H), 8.02 (dd, J=2.4, 9.6 Hz, 1H), 7.82 (s, 1H), 6.98 (m, 1H), 6.97-6.95 (m, 1H), 6.86 (d, J=8.0 Hz, 1H), 6.82 (d, J=9.6 Hz, 1H), 5.23 (s, 2H), 3.97 (t, J=7.2 Hz, 2H), 3.88 (s, 3H), 3.87 (s, 3H), 3.51 (t, J=5.6 Hz, 2H), 3.44-3.41 (m, 2H), 3.03 (t, J=7.6 Hz, 2H), 1.66-1.53 (m, 6H). Mass (m/z): 595.28 [M+H]⁺: 154: ¹HNMR (400 MHz, CDCl₃) δ 8.87 (d, J=2.4 Hz, 1H), 8.07 (dd, J=2.4, 9.2 Hz, 1H), 7.82 (s, 1H), 7.11 (s, 1H), 6.91 (s, 1H), 6.80 (d, J=9.6 Hz, 1H), 5.33 (s, 2H), 3.95 (t, J=7.2 Hz, 2H), 3.87 (s, 3H), 3.86 (s, 3H), 3.52 (t, J=5.6 Hz, 2H), 3.42 (t, J=5.2 Hz, 2H), 3.03 (t, J=7.6 Hz, 2H), 1.68-1.63 (m, 2H), 1.62-1.59 (m, 2H), 1.56-1.51 (m, 2H). Mass (m/z): 629.24 [M+H]⁺.

1-(3,4-dimethoxybenzyl)-5-(2-((4-oxo-4-(piperidin-1-yl)butyl)sulfonyl)-6-(trifluoromethyl)pyrimidin-4-yl)pyridin-2 (1H)-one (155)

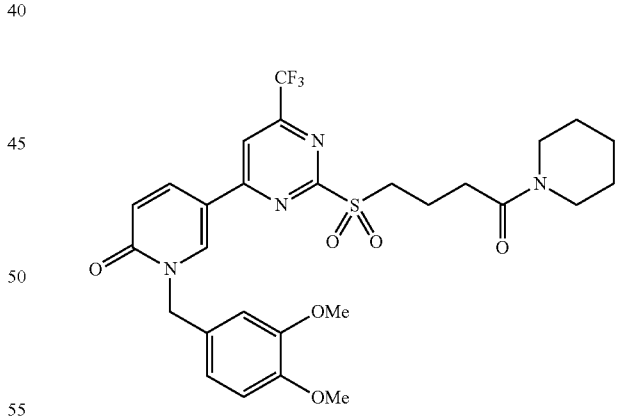

The titled compound was prepared in a yield of 75% (27 mg, 0.044 mmol) as a white solid from 140-01 (25 mg, 0.059 mmol) and 4-bromo-1-(piperidin-1-yl)butan-1-one (41 mg, 0.18 mmol) according to the procedure for 140. HNMR (400 MHz, CDCl₃) δ 8.99 (d, J=2.8 Hz, 1H), 7.98 (dd, J=2.8, 9.6 Hz, 1H), 7.83 (s, 1H), 7.01 (d, J=2.0 Hz, 1H), 6.97 (dd, J=2.0, 8.0 Hz, 1H), 6.83 (d, J=8.4 Hz, 1H), 6.72 (d, J=9.6 Hz, 1H), 5.25 (s, 2H), 3.85 (s, 3H), 3.84 (s, 3H), 3.77-3.73 (m, 2H), 3.48 (m, 2H), 3.37 (m, 2H), 2.58 (t, J=6.8 Hz, 2H), 2.28-2.21 (m, 2H), 1.65-1.59 (m, 2H), 1.54 (m, 2H), 1.47 (m, 2H). Mass (m/z): 609.27 [M+H]⁺.

1-(3,4-dimethoxybenzyl)-5-(2-((4-morpholino-4-oxobutyl)sulfonyl)-6-(trifluoromethyl)pyrimidin-4-yl)pyridin-2 (1H)-one (156) and 1-(2-chloro-4,5-dimethoxybenzyl)-5-(2-((4-morpholino-4-oxobutyl)sulfonyl)-6-(trifluoromethyl)pyrimidin-4-yl)pyridin-2 (1H)-one (157)

4-((4-(1-(3,4-dimethoxybenzyl)-6-oxo-1,6-dihydropyridin-3-yl)-6-(trifluoromethyl)pyrimidin-2-yl)sulfonyl)butanamide (158) and 4-((4-(1-(3,4-dimethoxybenzyl)-6-oxo-1,6-dihydropyridin-3-yl)-6-(trifluoromethyl)pyrimidin-2-yl)sulfinyl)butanamide 159

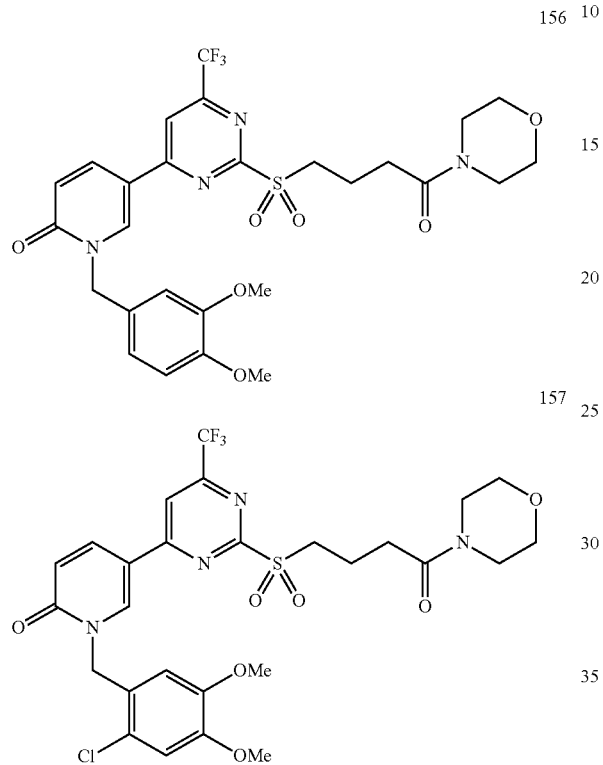

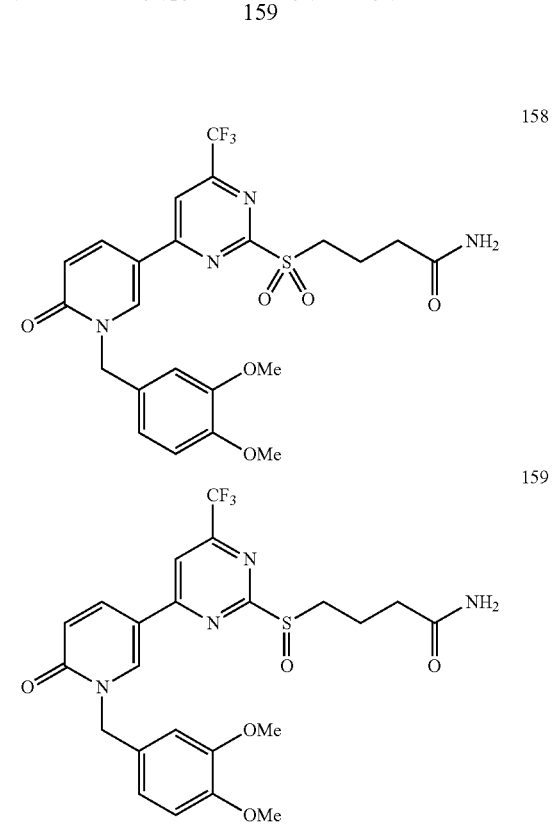

The titled compound 156 (3 mg, 100% yield) and 157 (11 mg, 34% yield) was prepared as two white solids from 140-01 (21 mg, 0.05 mmol) and 4-bromo-1-morpholinobutan-1-one (35 mg, 0.15 mmol) according to the procedure for 140. 156: $^1$HNMR (400 MHz, CDCl$_3$) δ 8.87 (d, J=2.4 Hz, 1H), 8.12 (dd, J=2.8, 9.6 Hz, 1H), 7.83 (s, 1H), 6.99 (d, J=2.0 Hz, 1H), 6.97 (dd, J=2.0, 8.0 Hz, 1H), 6.86 (d, J=8.0 Hz, 1H), 6.81 (d, J=9.6 Hz, 1H), 5.25 (s, 2H), 3.87 (s, 3H), 3.86 (s, 3H), 3.76-3.72 (m, 2H), 3.70-3.68 (m, 2H), 3.66-3.63 (m, 2H), 3.60-3.57 (m, 2H), 3.49-3.47 (m, 2H), 2.64 (t, J=6.8 Hz, 2H), 2.29 (q, J=6.8 Hz, 2H). Mass (m/z): 611.26 [M+H]$^+$;

157: $^1$HNMR (400 MHz, CDCl$_3$) δ 8.93 (d, J=2.4 Hz, 1H), 8.05 (dd, J=2.8, 10.0 Hz, 1H), 7.82 (s, 1H), 7.09 (s, 1H), 6.90 (s, 1H), 6.77 (d, J=10.0 Hz, 1H), 5.33 (s, 2H), 3.87 (s, 3H), 3.86 (s, 3H), 3.73 (t, J=7.2 Hz, 2H), 3.69-3.65 (m, 4H), 3.60-3.58 (m, 2H), 3.49-3.46 (m, 2H), 3.63 (t, J=6.8 Hz, 2H), 2.29 (q, J=6.8 Hz, 2H). Mass (m/z): 645.18 [M+H]$^+$.

The titled compound 158 (9 mg, 35% yield) and 159 (7 mg, 28% yield) was prepared as two white solids from 140-01 (20 mg, 0.047 mmol) and 4-bromobutanamide (24 mg, 0.14 mmol) according to the procedure for 140.

158: $^1$HNMR (400 MHz, CDCl$_3$) δ 8.79 (d, J=2.4 Hz, 1H), 7.97 (dd, J=2.8, 10.0 Hz, 1H), 7.82 (s, 1H), 6.98 (m, 1H), 6.96-6.94 (m, 1H), 6.86 (d, J=8.4 Hz, 1H), 6.74 (d, J=10.0 Hz, 1H), 5.63 (br, 1H), 5.54 (br, 1H), 5.23 (s, 2H), 3.87 (s, 3H), 3.86 (s, 3H), 3.70 (t, J=7.2 Hz, 2H), 2.50 (t, J=6.4 Hz, 2H), 2.29-2.21 (m, 2H); Mass (m/z): 541.27 [M+H]$^+$.

159: $^1$HNMR (400 MHz, CDCl$_3$) δ 8.69 (s, 1H), 7.70 (s, 1H), 6.97 (m, 1H), 6.95 (m, 1H), 6.86 (d, J=8.4 Hz, 1H), 6.74 (d, J=9.6 Hz, 1H), 5.73 (br, 1H), 5.55 (br, 1H), 5.20 (s, 2H), 5.87 (s, 3H), 5.86 (s, 3H), 3.33-3.20 (m, 2H), 2.46 (t, J=6.8 Hz, 2H), 2.11-2.07 (m, 2H); Mass (m/z): 525.24 [M+H]$^+$.

5-(6-(difluoromethyl)-2-(methylsulfonyl)pyrimidin-4-yl)-1-(3,4-dimethoxybenzyl)pyridin-2 (1H)-one (160)

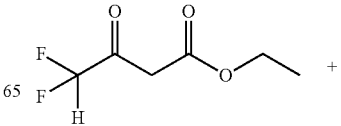

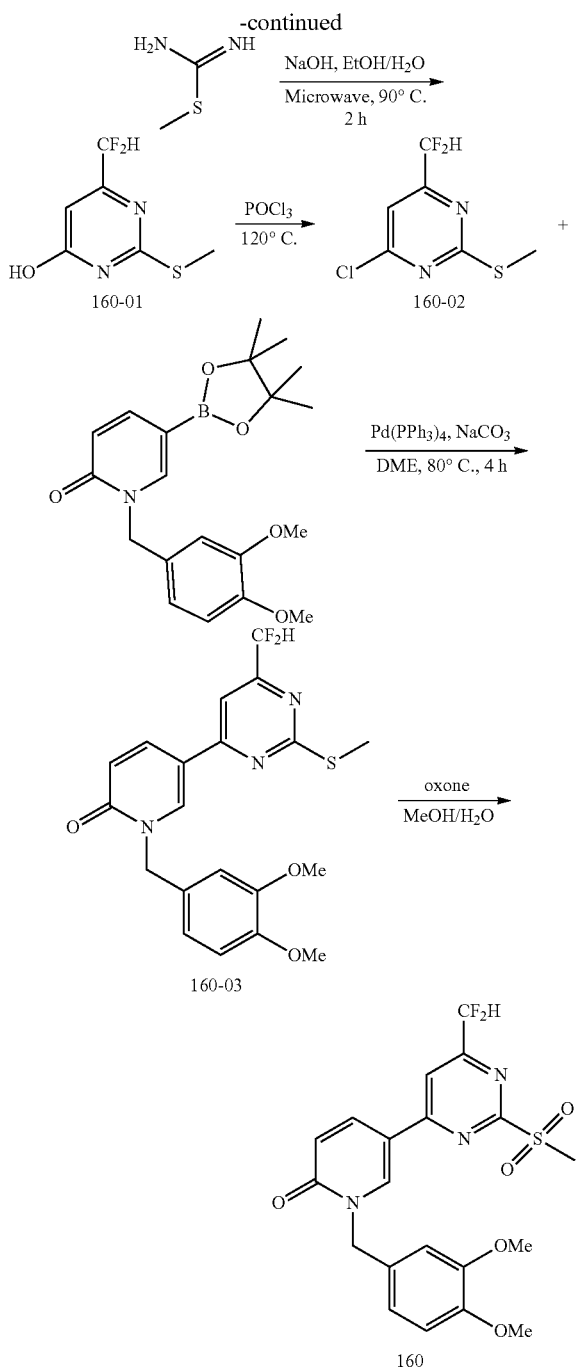

Step 3. The titled compound 160-03 was prepared in a yield of 66% (20 mg) as a white solid from 160-02 (27 mg, 0.13 mmol) according to the procedure for 99-01; Mass (m/z): 420.4 [M+H]$^+$.

Step 4. The titled compound 160 was prepared in a yield of 50% (10.7 mg) as a white solid from 160-03 (20 mg, 0.048 mmol) and Oxone (146 mg, 0.24 mmol) according to the procedure for 49. $^1$H NMR (400 Hz, CDCl$_3$) δ 8.61 (d, J=2.4 Hz, 1H), 7.99 (dd, J=2.4, 9.6 Hz, 1H), 7.81 (s, 1H), 6.94 (d, J=2.0 Hz, 1H), 6.92 (dd, J=2.0, 8.0 Hz, 1H), 6.85 (d, J=8.0 Hz, 1H), 6.74 (d, J=9.6 Hz, 1H), 6.62 (s, 0.6H), 6.48 (s, 0.4H), 5.29 (s, 2H), 3.86 (s, 6H), 3.35 (s, 3H); Mass (m/z): 452.5 [M+H]$^+$.

5-(6-(fluoromethyl)-2-(methylsulfonyl)pyrimidin-4-yl)-1-(3,4-dimethoxybenzyl)pyridin-2 (1H)-one (161)

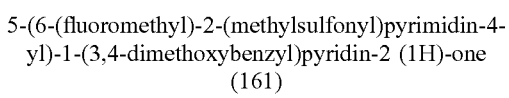

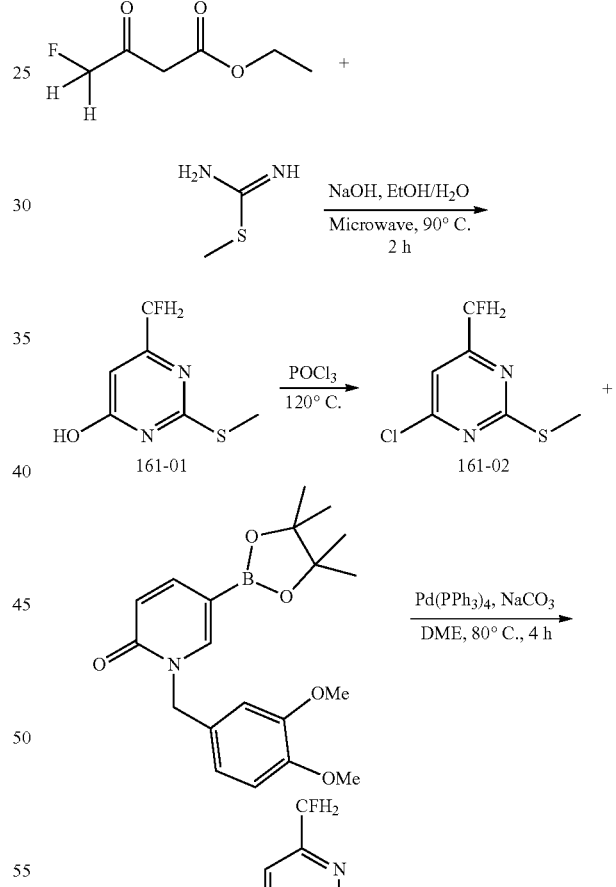

Step 1. The titled compound 160-01 was prepared in a yield of 80% (460 mg) as a white solid from ethyl 4,4-difluoro-3-oxobutanoate (495 mg, 3 mmol) and methyl carbamimidothioate (1.12 g, 6 mmol) according to the procedure for 43-01. $^1$H NMR (400 Hz, acetone-d$_6$) δ 6.83 (s, 0.66H), 6.69 (s, 1H), 6.56 (s, 0.58H), 6.34 (s, 1H), 2.52 (s, 3H); Mass (m/z): 193.5 [M+H]$^+$.

Step 2. The titled compound 160-02 was prepared in a yield of 90% (492 mg) as a white solid from 160-01 (500 mg, 2.6 mmol) and phosphorus oxychloride (4 ml) according to the procedure for 49-01. $^1$H NMR (400 Hz, CDCl$_3$) δ 7.25 (s, 1H), 6.59 (s, 0.24H), 6.44 (s, 0.46H), 6.29 (s, 0.24H), 2.58 (s, 3H); Mass (m/z): 211.2 [M+H]$^+$.

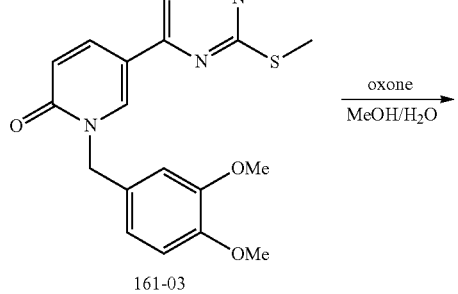

267

-continued

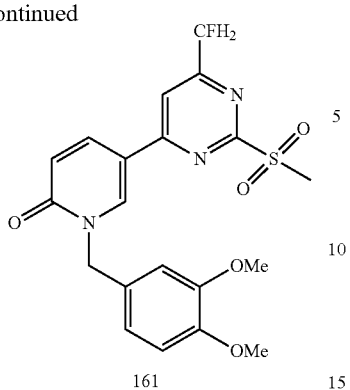

161

Step 1: The titled compound 161-01 was prepared in a yield of 86% (693 mg) as a white solid from ethyl 4-fluoro-3-oxobutanoate (677 mg, 4.6 mmol) and methyl carbamimidothioate (1.7 g, 9.3 mmol) according to the procedure for 43-01; Mass (m/z): 175.1 [M+H]⁺.

Step 2. The titled compound 161-02 was prepared in a yield of 76% (150 mg) as a white solid from 161-01 (180 mg, 1.03 mmol) and phosphorus oxychloride (2 ml) according to the procedure for 49-01. $^1$H NMR (400 Hz, CDCl$_3$) δ 7.16 (s. 1H), 5.42 (s. 1H), 5.30 (s, 1H), 2.56 (s, 3H).

Step 3. The titled compound 161-03 was prepared in a yield of 14% (12 mg) as a white solid from 161-02 (80 mg, 0.22 mmol) according to the procedure for 99-01. $^1$H NMR: (400 Mz, CDCl$_3$): δ 8.37 (d, J=2.4 Hz, 1H), 7.96 (dd, J=2.4, 9.6 Hz, 1H), 7.40 (s, 1H), 6.90 (d, J=2.0 Hz, 1H), 6.88 (dd, J=2.0, 8.0 Hz, 1H), 6.84 (d, J=8.0 Hz, 1H), 6.70 (d, J=9.6 Hz, 1H), 5.42 (s, 1H), 5.31 (s, 1H), 5.16 (s, 2H), 3.86 (s, 6H), 2.5 (s, 3H); Mass (m/z): 402.5 [M+H]⁺.

Step 4. The titled compound 161 was prepared in a yield of 36% (4.7 mg) as a white solid from 161-03 (12 mg, 0.031 mmol) and Oxone (48 mg, 0.078 mmol) according to the procedure for 49. $^1$H NMR: (400 Mz, CDCl3): δ 8.54 (d, J=2.4 Hz, 1H), 7.97 (dd, J=2.4, 9.6 Hz, 1H), 7.71 (s, 1H), 6.93 (d, J=2.0 Hz, 1H), 6.90 (dd, J=2.0, 8.0 Hz, 1H), 6.84 (d, J=8.0 Hz, 1H), 6.71 (d, J=9.6 Hz, 1H), 5.59 (s, 1H), 5.47 (s, 1H), 5.17 (s, 2H), 3.86 (s, 6H), 3.30 (s, 3H); Mass (m/z): 434.5 [M+H]⁺.

5-(5-chloro-2-(methylsulfonyl)-6-(trifluoromethyl)pyrimidin-4-yl)-1-(3,4-dimethoxybenzyl)pyridin-2(1H)-one (162)

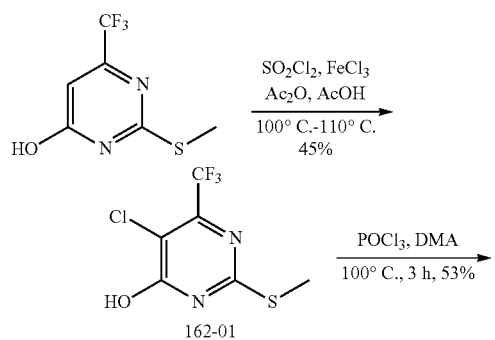

268

-continued

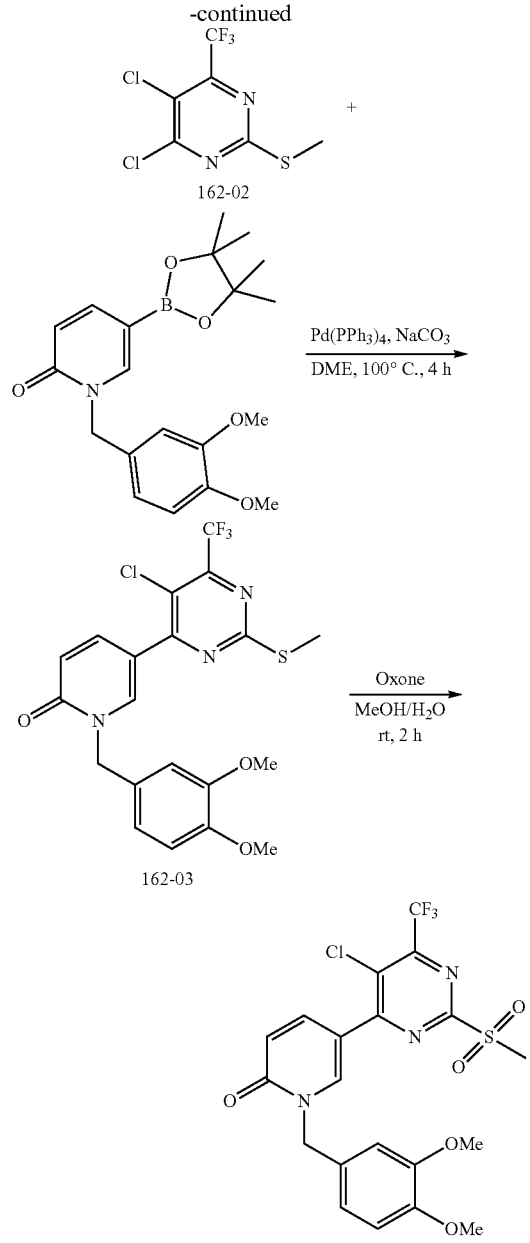

Step 1. Preparation of 5-chloro-2-(methylthio)-6-(trifluoromethyl)pyrimidin-4-ol (162-01): A solution of 2-(methylthio)-6-(trifluoromethyl)pyrimidin-4-ol (210 mg, 1 mmol) in AcOH (3 mL) was added Ac$_2$O (0.2 ml), FeCl$_3$ (40 mg) and SO$_2$Cl$_2$ (150 mg) Then refluxed at 110° C. for 6 h. The reaction mixture was cooled to room temperature, and solvent was removed in vacuo. The residue was extracted by DCM and icy H$_2$O 3 times. The organic layer was combined, washed with brine, dried over Na$_2$SO$_4$ and concentrated to give 110 mg of 5-chloro-2-(methylthio)-6-(trifluoromethyl)pyrimidin-4-ol (162-01) as a light yellow oid (45%). Mass (m/z): 245.5 [M+H]⁺.

Step 2. The titled compound 162-02 was prepared in a yield of 27% (12 mg) as a white solid from 162-01 (42 mg, 0.172 mmol) and phosphorus oxychloride (2 ml) according to the procedure for 49-01.

Step 3. The titled compound 162-03 was prepared in a yield of 42% (15 mg) as a white solid from 162-02 (20 mg, 0.076 mmol) according to the procedure for 99-01. Mass (m/z): 272.4 [M+H]⁺.

Step 4. The titled compound 162 was prepared in a yield of 40% (6.4 mg) as a white solid from 162-03 (15 mg, 0.032 mmol) and Oxone (100 mg, 0.016 mmol) according to the procedure for 67. $^1$H NMR: (400 Mz, CDCl$_3$): δ 8.41 (d, J=2.4 Hz, 1H), 8.10 (dd, J=2.4, 9.6 Hz, 1H), 6.93 (d, J=2.0 Hz, 1H), 6.90 (dd, J=2.0, 8.0 Hz, 1H), 6.86 (d, J=8.0 Hz, 1H), 6.70 (d, J=9.6 Hz, 1H), 5.16 (s, 2H)), 3.87 (s, 6H), 3.38 (s, 3H). Mass (m/z): 504.3 [M+H]⁺.

5-(6-acetyl-2-(methylsulfonyl)pyrimidin-4-yl)-1-(3,4-dimethoxybenzyl)pyridin-2 (1H)-one (163)

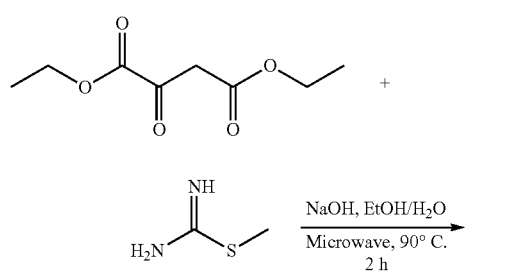

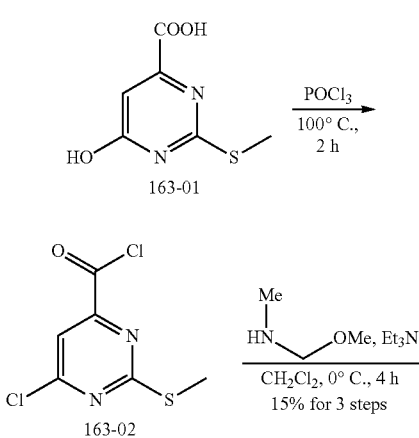

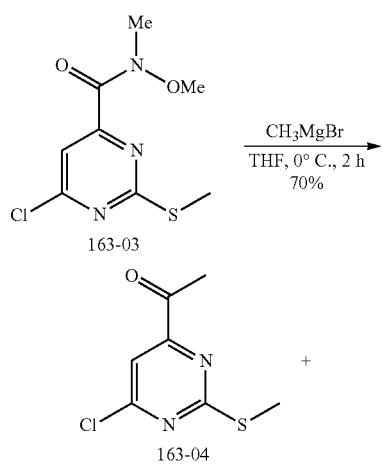

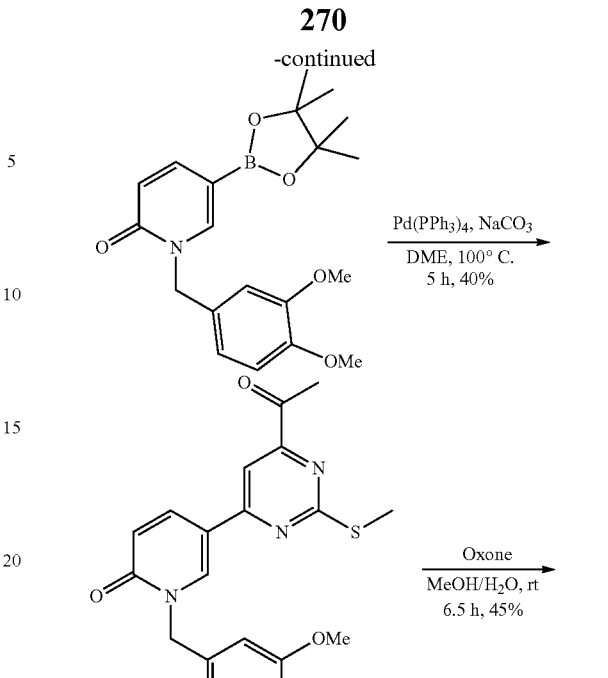

163-05

163

Step 1. The titled compound 163-01 was prepared according to the procedure for 43-01. Mass (m/z): 187.1 [M+H]⁺.

Step 2. The titled compound 163-02 was prepared from 163-01 (19.6 mg, 0.1 mmol) according to the procedure for for 49-01.

Step 3. To a mixture of 6-chloro-2-(methylthio)pyrimidine-4-carbonyl chloride (163-02) and N,O-dimethylhydroxylamine hydrochloride in CH$_2$C$_2$ at 0° C. was slowly added EtN$_3$. The reaction mixture was stirred at 0° C. for 4 h. The reaction mixture was quenched with NH$_4$Cl, The residue was extracted by CH$_2$Cl$_2$/H$_2$O 3 times. The organic layer was washed with brine, dried over Na$_2$SO$_4$ and further purified by silica gel column chromatography (PE/EA=5/1) to give 50 mg of 6-chloro-N-(methoxymethyl)-N-methyl-2-(methylthio)pyrimidine-4-carboxamide (163-03) as a light yellow oil (15% for three steps). $^1$H NMR: (400 Mz, CDCl$_3$): δ 7.14 (s, 1H), 3.74 (s, 3H), 3.34 (s, 3H), 2.59 (s, 3H). Mass (m/z): 248.0 [M+H]⁺.

Step 4. Methylmagnesium bromide was slowly added to a solution of 163-03 (42 mg) in dry THF under Ar at 0° C., the reaction mixture was stirred at 0° C. for 2 h. The reaction mixture was quenched with NH$_4$Cl, The residue was extracted by EtOAc/H$_2$O 3 times. The organic layer was washed with brine, dried over Na₂SO₄ and further purified by silica gel column chromatography (PE/EA=5/1) to give 24 mg of 1-(6-chloro-2-(methylthio)pyrimidin-4-yl)ethanone (163-04) as a light yellow oil (70%). ¹H NMR: (400 Mz, CDCl₃): δ 7.52 (s, 1H), 2.68 (s, 3H), 2.63 (s, 3H), 2.59 (s, 3H). Mass (m/z): 203.0 [M+H]⁺.

Step 5. The titled compound 163-05 was prepared in a yield of 40% (10 mg) as a white solid from 163-04 (19.6 mg, 0.1 mmol) according to the procedure for 99-01. Mass (m/z): 412.2 [M+H]⁺. Step 6. The titled compound 163 was prepared in a yield of 45% as a white solid from 200-05 (10 mg, 0.024 mmol) and Oxone (45 mg, 0.073 mmol) according to the procedure for 67.

¹H NMR: (400 Mz, CDCl3): δ 8.56 (d, J=2.8 Hz, 1H), 8.11 (s, 1H), 8.04 (dd, J=2.4, 9.6 Hz, 1H), 6.95 (d, J=2.0 Hz, 1H), 6.92 (dd, J=2.0, 8.0 Hz, 1H), 6.85 (d, J=8.0 Hz, 1H), 6.74 (d, J=9.6 Hz, 1H), 5.30 (s, 2H), 3.87 (s, 3H), 3.86 (s, 3H), 3.39 (s, 3H), 2.76 (s, 3H). Mass (m/z): 444.2 [M+H]⁺.

5-(6-(1,1-difluoroethyl)-2-(methylsulfonyl)pyrimidin-4-yl)-1-(3,4-dimethoxybenzyl)pyridin-2 (1H)-one (164)

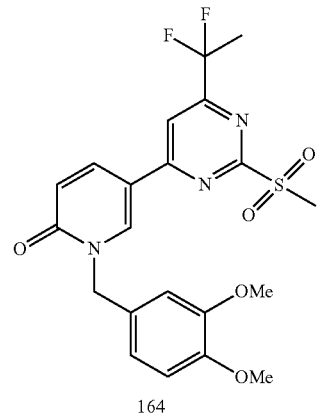

164

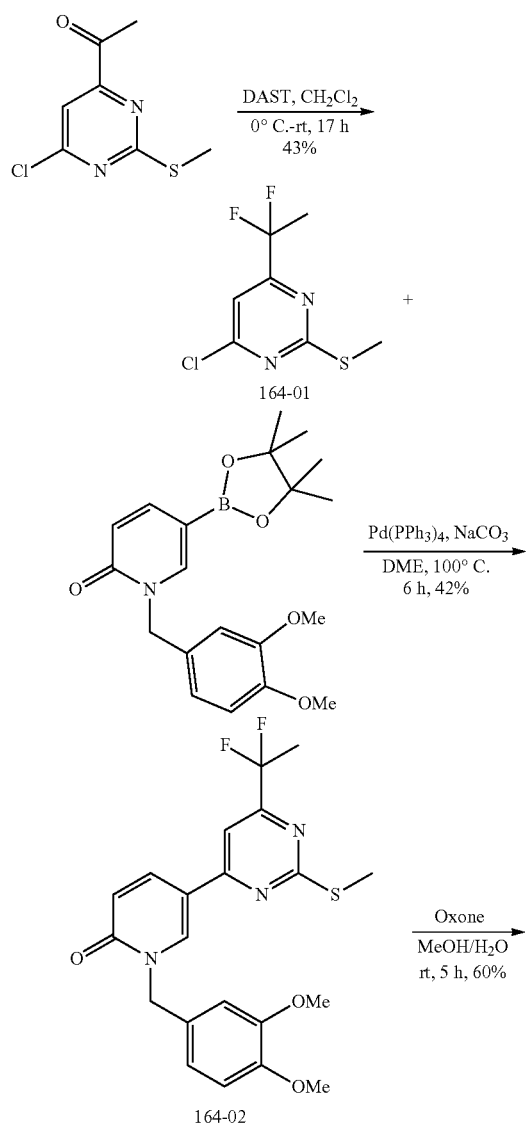

Step 1. A solution of 1-(6-chloro-2-(methylthio)pyrimidin-4-yl)ethanone (163-04) in CH₂Cl₂ was slowly added to cooled (0° C.) solution of DAST in CH₂Cl₂. The reaction mixture was warmed up to it and stirred at rt for 23 h. The reaction mixture was quenched with NaHCO₃ (sat. soln), The residue was extracted by CH₂Cl₂/H₂O 3 times. The organic layer was washed with brine, dried over Na₂SO₄ and further purified by silica gel column chromatography (PE/EA=5/1) to give 50 mg of 4-chloro-6-(1,1-difluoroethyl)-2-(methylthio)pyrimidine (164-01) as a light yellow oil (43%). ¹H NMR: (400 Mz, CDCl₃): δ 7.28 (s, 1H), 2.58 (s, 3H), 1.96 (m, 3H), Mass (m/z): 225.1 [M+H]⁺.

Step 2. The titled compound 164-02 was prepared in a yield of 42% (5 mg) as a white solid from 164-01 (6 mg, 0.027 mmol) according to the procedure for 99-01. Mass (m/z): 434.2 [M+H]⁺.

Step 3. The titled compound 164 was prepared in a yield of 60% as a white solid from 164-02 (5.4 mg, 0.013 mmol) and Oxone (23 mg, 0.037 mmol) according to the procedure for 67. H NMR: (400 Mz, CDCl3): δ 8.58 (s, 1H), 7.97 (d, 9.6 Hz, 1H), 7.73 (s, 1H), 6.93 (d, J=2.0 Hz, 1H), 6.92 (dd, J=2.0, 8.0 Hz, 1H), 6.83 (d, J=8.0 Hz, 1H), 6.72 (d, J=9.6 Hz, 1H), 5.18 (s, 2H), 3.87 (s, 3H), 3.86 (s, 3H), 3.35 (s, 3H), 2.18 (m, 3H). Mass (m/z): 466.2 [M+H]⁺.

5-(6-(difluoromethyl)-2-(methylsulfonyl)pyrimidin-4-yl)-1-(3,4-dimethoxybenzyl)-3-fluoropyridin-2 (1H)-one (165)

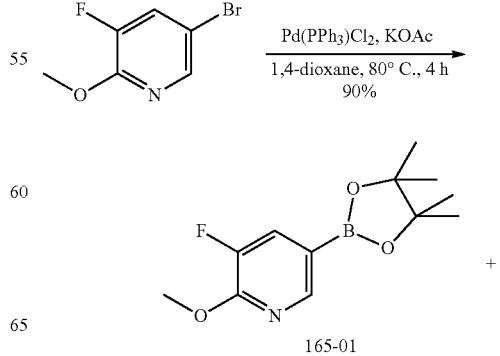

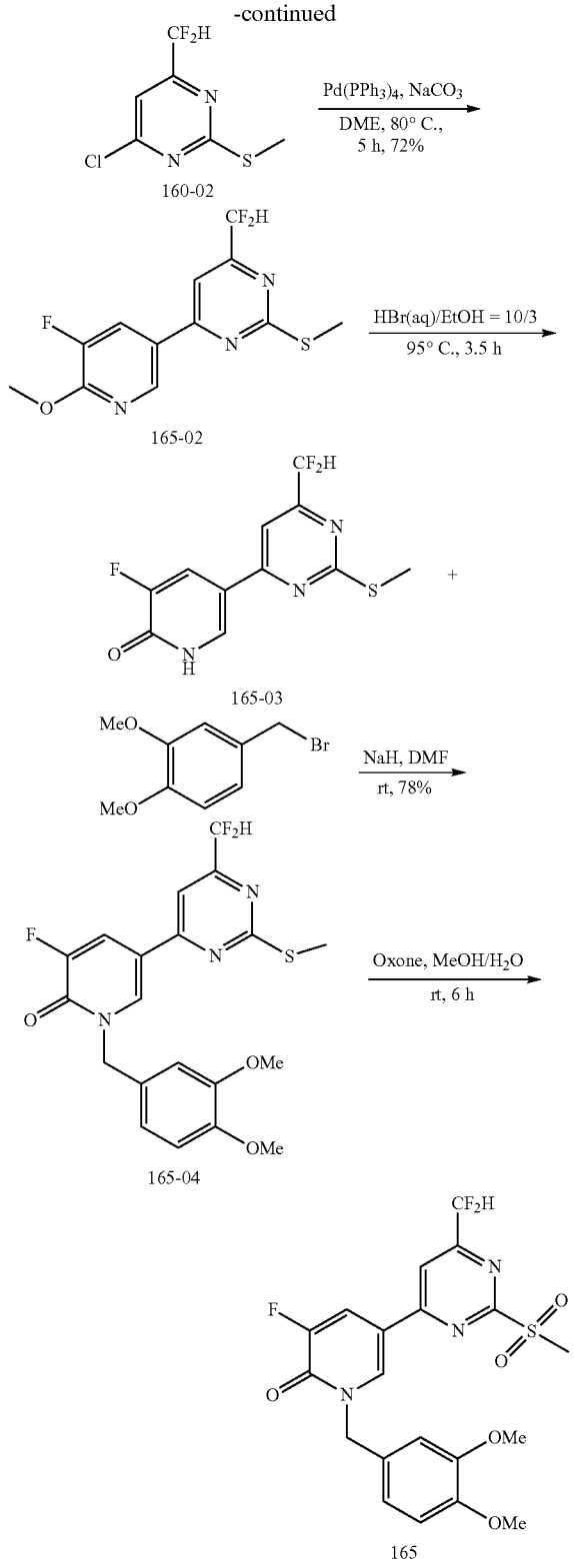

times. The organic layer was washed with brine, dried over Na₂SO₄ and further purified by silica gel column chromatography (PE/EA=9/1) to give 228 mg of 165-01 as a light yellow oil (90%). Mass (m/z): 254.2 [M+H]⁺.

Step 2. The titled compound 165-02 was prepared in a yield of 72% (130 mg) as a white solid from 160-02 (125 mg, 0.6 mmol) according to the procedure for 99-01. Mass (m/z): 302.1 [M+H]⁺.

Step 3. A solution of (165-02) in EtOH was slowly added HBr. The mixture solution was heated at 95° C. for 3.5 h. The reaction mixture was cooled to room temperature, and solvent was removed in vacuo. The residue was extracted by EtOAc 3 times. The organic layer was combined, washed with brine, dried over Na₂SO₄ and further purified by recrystallization by (PE/EA=1/9) to give 99 mg of 3-fluoro-2-methoxy-5-(4,4,5,5-tetramethyl-1,3,2-dioxaborolan-2-yl) pyridine (165-03) as a light yellow solid (80%). ¹H NMR: (400 Mz, DMSO-d6): δ 12.83 (s, 1H), 8.42 (s, 3H), 8.22 (dd, J=2.0, 12.0 Hz, 1H), 7.95 (s, 1H), 7.02 (s, 0.2H), 6.89 (s, 0.4H), 6.75 (s, 0.3H), 2.60 (s, 3H). Mass (m/z): 288.1 [M+H]⁺.

Step 4. To a mixture of 5-(6-(difluoromethyl)-2-(methylthio)pyrimidin-4-yl)-3-fluoropyridin-2 (1H)-one (50 mg, 0.17 mmol), 4-(bromomethyl)-1,2-dimethoxybenzene (60 mg, 0.26 mmol) in DMF (3 ml) was slowly added NaH (10 mg, 0.26 mmol) at 0° C. Then warm to RT for 6 h. The reaction mixture was then cooled and poured over ice. The residue was extracted by EtOAc 3 times. The organic layer was washed with brine, dried over Na₂SO₄ and further purified by silica gel column chromatography (PE/EA=2/1) to give 60 mg of 5-(6-(difluoromethyl)-2-(methylthio)pyrimidin-4-yl)-1-(3,4-dimethoxybenzyl)-3-fluoropyridin-2 (1H)-one (165-04) as a light yellow oil (78%). ¹H NMR: (400 Mz, CDCl3): δ 8.19 (s, 1H), 7.76 (dd, 2.0, 10.0 Hz, JH), 6.92-6.81 (m, 4H), 6.48 (s, 0.2H), 6.40 (s, 0.4H), 6.25 (s, 0.3H), 5.18 (s, 2H), 3.83 (s, 3H), 3.81 (s, 3H), 2.51 (s, 3H). Mass (m/z): 438.2 [M+H]⁺.

Step 4. The titled compound 165 was prepared in a yield of 66% as a white solid from 165-04 (59 mg, 0.14 mmol) and Oxone (250 mg, 0.41 mmol) according to the procedure for 67. H NMR: (400 Mz, CDCl3): δ 8.44 (s, 1H), 7.79-7.78 (m, 2H), 6.95-6.93 (m, 2H), 6.85 (d, J=8.0 Hz, 1H), 6.78 (s, 0.2H), 6.62 (s, 0.4H), 6.50 (s, 0.3H), 5.23 (s, 2H), 3.87 (s, 3H), 3.86 (s, 3H), 3.36 (s, 3H). Mass (m/z): 470.1 [M+H]⁺.

1-(3,4-dimethoxybenzyl)-5-(6-methyl-2-((2,2,2-trifluoroethyl)sulfonyl)pyrimidin-4-yl)pyridin-2 (1H)-one (166)

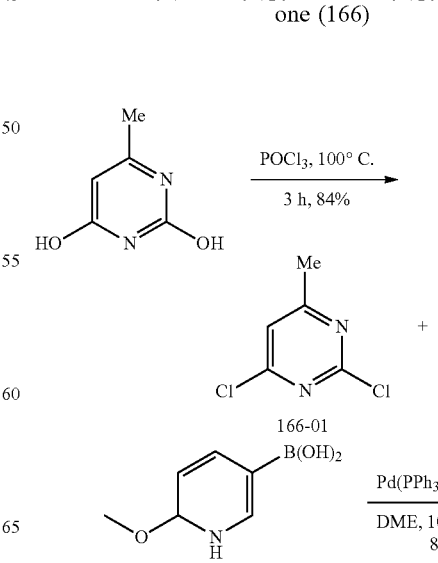

Step 1. A mixture of 5-bromo-3-fluoro-2-methoxypyridine (206 mg, 1.0 mmol), bis(pinacolato)diboron (508 mg, 2.0 mmol), Pd(PPh₃)Cl₂ (70.1 mg, 0.05 mmol), KOAc (294 mg, 3.0 mmol) and 1,4-dioxane (4 ml) was heated at 80° C. Under Ar for 4 h. The reaction mixture was then cooled and poured over ice. The residue was extracted by EtOAc 3

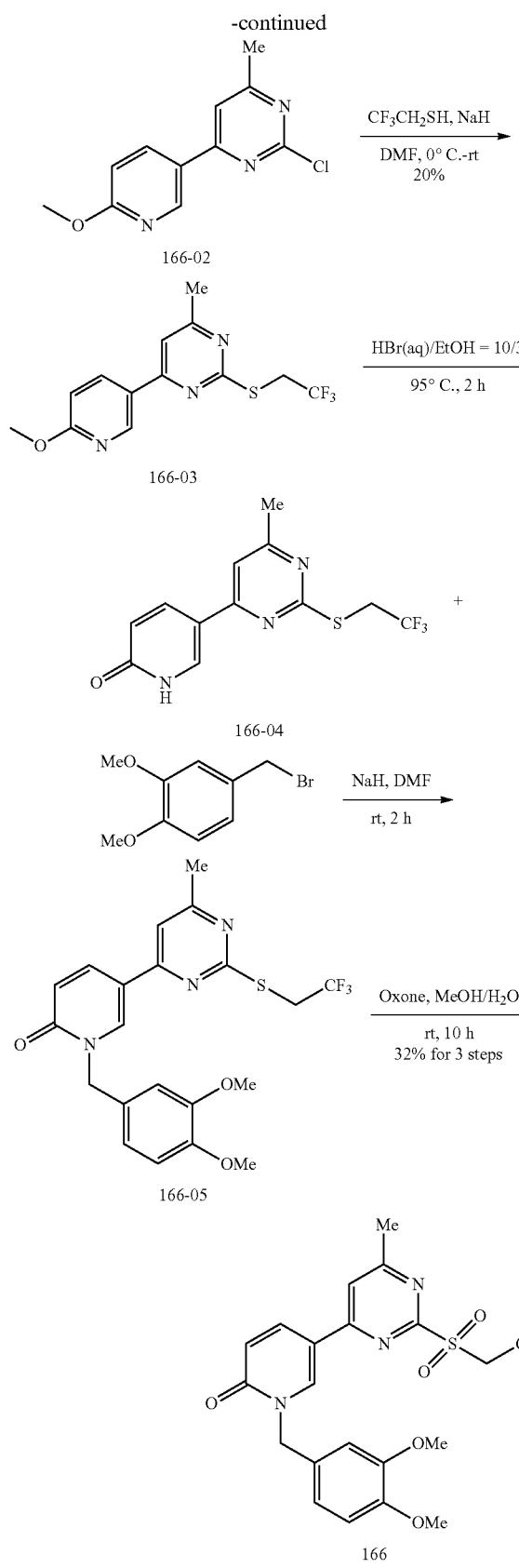

rimidine-2,4-diol (500 mg, 3.97 mmol) and phosphorus oxychloride (4 ml) according to the procedure for 49-01. Mass (m/z): 164.7 [M+H]$^+$.

Step 2. The titled compound 166-02 was prepared in a yield of 80% (188 mg) as a white solid from 166-01 (163 mg, 1.0 mmol) according to the procedure for 99-01. $^1$H NMR: (400 Mz, CDCl3): δ 9.27 (d, J=2.4 Hz, 1H), 8.66 (dd, J=2.4, 9.2 Hz, 1H), 7.09 (s, 1H), 6.88 (d, J=9.2 Hz, 1H), 4.03 (s, 6H), 2.56 (s, 3H). Mass (m/z): 236.1 [M+H]$^+$.

Step 3. To a mixture of 166-02 (146 mg, 0.61 mmol), CF$_3$CH$_2$SH (1.0 g,) in DMF (3 ml) was slowly added NaH (49 mg, 1.28 mmol) at 0° C. Then warm to RT for 18 h. The reaction mixture was then cooled and poured over ice. The residue was extracted by EtOAc 3 times. The organic layer was washed with brine, dried over Na$_2$SO$_4$ and further purified by silica gel column chromatography (PE/EA=5/1) to give 38 mg of 166-03 as a light yellow oil (20%). Mass (m/z): 316.2 [M+H]$^+$.

Step 4. The titled compound 166-04 was prepared as a white solid from 166-03 (3 mg, 0.013 mmol) according to the procedure for 165-03. Mass (m/z): 303.1 [M+H]$^+$.

Step 5. The titled compound 166-05 was prepared as a white solid from 166-04 (0.013 mmol) according to the procedure for 165-04. Mass (m/z): 452.2 [M+H]$^+$.

Step 6. The titled compound 166 was prepared in a yield of 32% (for 3 steps) as a white solid from 166-05 (0.013 mmol) and Oxone (20 mg, 0.032 mmol) according to the procedure for 67. H NMR: (400 Mz, CDCl$_3$): δ 8.60 (d, 9.6 Hz, 1H), 8.33 (dd, J=2.0, 8.0 Hz, 1H), 7.63 (s, 1H), 7.00-6.86 (m, 2H), 6.85 (d, J=8.4 Hz, 1H), 6.71 (d, J=9.2 Hz, 1H), 5.19 (s, 2H), 3.83 (s, 3H), 3.81 (s, 3H), 2.70 (s, 1H), 2.22-2.16 (m, 2H). Mass (m/z): 484.2 [M+H]$^+$.

5-(6-(difluoromethyl)-2-(methylsulfonyl)pyrimidin-4-yl)-1-(3-fluoro-4-methoxybenzyl)pyridin-2 (11H)-one (167) and 5-(6-(difluoromethyl)-2-(methylsulfinyl)pyrimidin-4-yl)-1-(3-fluoro-4-methoxybenzyl) pyridin-2 (1H)-one (168)

Step 1. The titled compound 166-01 was prepared in a yield of 84% (540 mg) as a white solid from 6-methylpy-

277

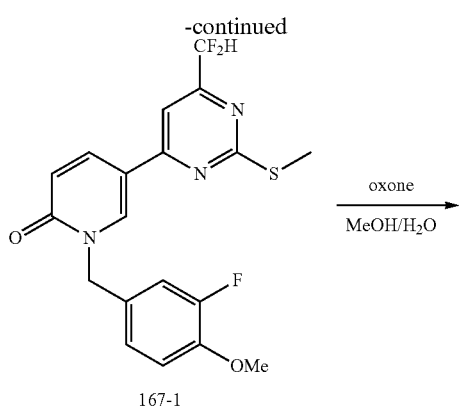

The titled compound 167 (12 mg, 25% yield) and 168 (6 mg, 13% yield) was prepared as two colorless oil from 5-(6-(difluoromethyl)-2-(methylthio)pyrimidin-4-yl)pyridin-2 (1H)-one (30 mg, 0.11 mmol) and 4-(bromomethyl)-2-fluoro-1-methoxybenzene (28 mg, 0.13 mmol) according to the procedure for 100. 167: $^1$HNMR (400 MHz, CDCl$_3$) δ 8.60 (d, J=2.8 Hz, 1H), 8.01 (dd, J=2.8, 9.6 Hz, 1H), 7.84 (s, 1H), 7.12 (t, J=2.0 Hz, 1H), 7.10 (m, 1H), 6.95 (t, J=8.4 Hz, 1H), 6.75 (d, J=9.6 Hz, 1H), 6.62 (t, J=54.4 Hz, 1H), 5.17 (s, 2H), 3.87 (s, 3H), 3.38 (s, 3H). Mass (m/z): 440.18[M+H]$^+$. 168: $^1$HNMR (400 MHz, CDCl$_3$) δ 8.60 (d, J=2.4 Hz, 1H), 8.03 (dd, J=2.8, 9.6 Hz, 1H), 7.73 (s, 1H), 7.12 (m, 1H), 7.10 (m, 1H), 6.94 (t, J=8.0 Hz, 1H), 6.75 (d, J=9.6 Hz, 1H), 6.64 (t, J=54.4 Hz, 1H) 5.18 (d, J=3.2 Hz, 2H), 3.87 (s, 3H), 2.99 (s, 3H). Mass (m/z): 424.18 [M+H]$^+$.

278

5-(6-(difluoromethyl)-2-(methylsulfonyl)pyrimidin-4-yl)-1-(4-methoxy-3-(trifluoromethyl)benzyl)pyridin-2 (1H)-one (169) and 5-(6-(difluoromethyl)-2-(methylsulfinyl)pyrimidin-4-yl)-1-(4-methoxy-3-(trifluoromethyl)benzyl)pyridin-2 (1H)-one (170)

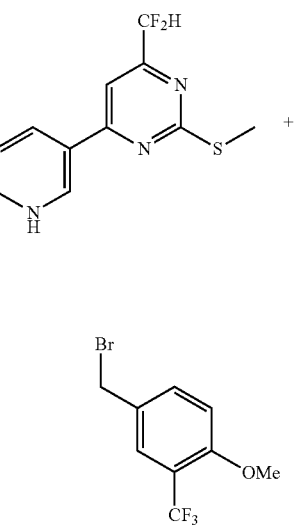

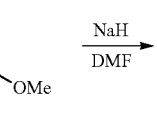

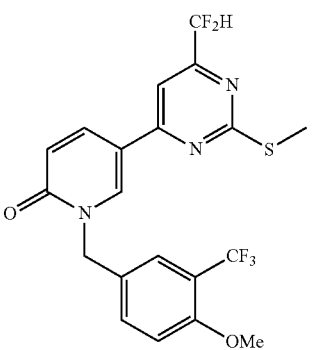

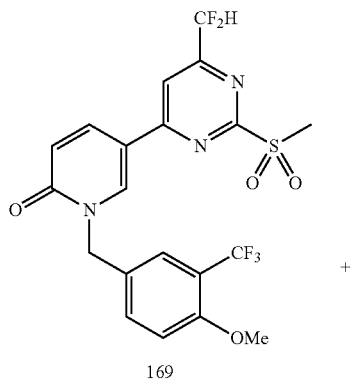

-continued

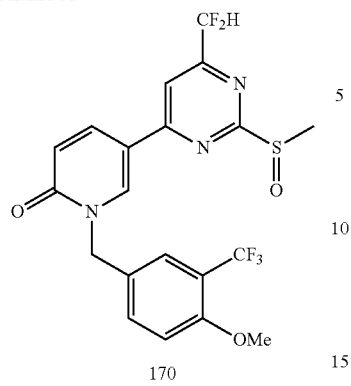

170

-continued

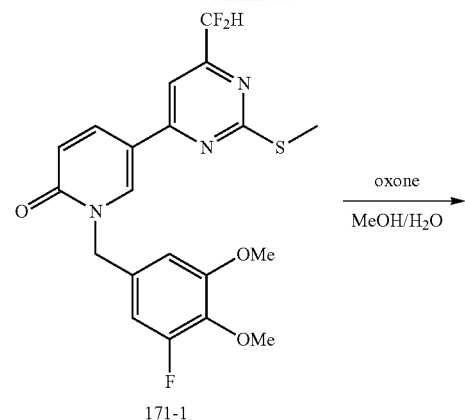

171-1

The titled compound 169 (13 mg, 25% yield) and 170 (10 mg, 19% yield) was prepared as two colorless oil from 5-(6-(difluoromethyl)-2-(methylthio)pyrimidin-4-yl)pyridin-2 (1H)-one (30 mg, 0.11 mmol) and 4-(bromomethyl)-1-methoxy-2-(trifluoromethyl)benzene (46 mg, 0.17 mmol) according to the procedure for 100. 169: $^1$HNMR (400 MHz, CDCl$_3$) J 8.63 (d, J=2.4 Hz, 1H), 8.02 (dd, J=2.8, 9.6 Hz, 1H), 7.86 (s, 1H), 7.58 (d, J=2.0 Hz, 1H), 7.56 (dd, J=2.4, 8.4 Hz, 1H), 7.01 (d, J=8.8 Hz, 1H), 6.74 (d, J=9.6 Hz, 1H), 6.62 (t, J=54.4 Hz, 1H), 5.21 (s, 2H), 3.89 (s, 3H), 3.37 (s, 3H). Mass (m/z): 490.21 [M+H]$^+$. 170: $^1$HNMR (400 MHz, CDCl$_3$) δ 8.67 (d, J=2.4 Hz, 1H), 8.03 (dd, J=2.8, 9.6 Hz, 1H), 7.75 (s, 1H), 7.58-7.54 (m, 2H), 7.00 (d, J=8.4 Hz, 1H), 6.75 (d, J=9.6 Hz, 1H), 6.63 (t, J=54.4 Hz, 1H), 5.22 (d, J=7.6 Hz, 2H), 3.89 (s, 3H), 2.99 (s, 3H). Mass (m/z): 474.18 [M+H]$^+$.

5-(6-(difluoromethyl)-2-(methylthio)pyrimidin-4-yl)-1-(3-fluoro-4,5-dimethoxybenzyl)pyridin-2 (1H)-one (171)

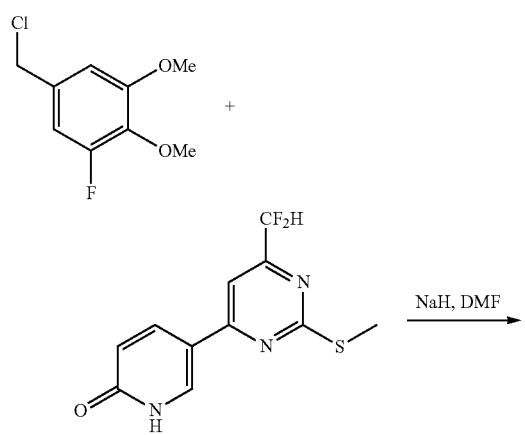

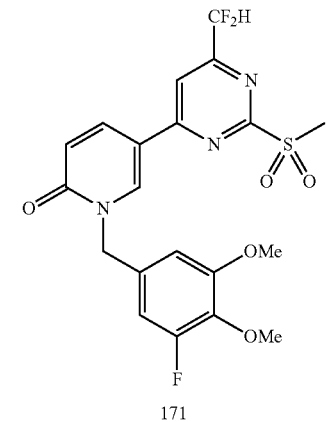

171

The titled compound 171 (12 mg, 25% yield) was prepared as white solid from 5-(6-(difluoromethyl)-2-(methylthio)pyrimidin-4-yl)pyridin-2 (1H)-one (30 mg, 0.11 mmol) and 5-(chloromethyl)-1-fluoro-2,3-dimethoxybenzene (30 mg, 0.15 mmol) according to the procedure for 100. $^1$HNMR (400 MHz, CDCl$_3$) δ 8.40 (d, J=2.4 Hz, 1H), 8.00 (dd, 2.8, 9.6 Hz, 1H), 7.34 (s, 1H), 6.73 (d, J=3.6 Hz, 1H), 6.70-6.67 (m, 1H), 6.46 (t, J=54.4 Hz, 1H), 5.14 (s, 2H), 3.90 (s, 3H), 3.86 (s, 3H), 2.57 (s, 3H). Mass (m/z): 438.26 [M+H]$^+$.

5-(6-(difluoromethyl)-2-((3-methoxybenzyl)sulfonyl)pyrimidin-4-yl)-1-(3,4-dimethoxybenzyl)pyridin-2 (1H)-one (172) and 5-(6-(difluoromethyl)-2-((3-methoxybenzyl)sulfinyl)pyrimidin-4-yl)-1-(3,4-dimethoxybenzyl)pyridin-2 (1H)-one (173)

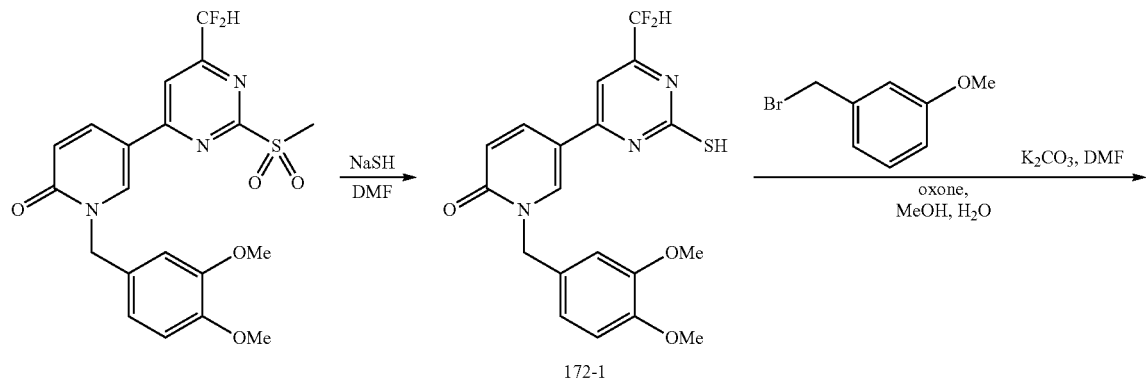

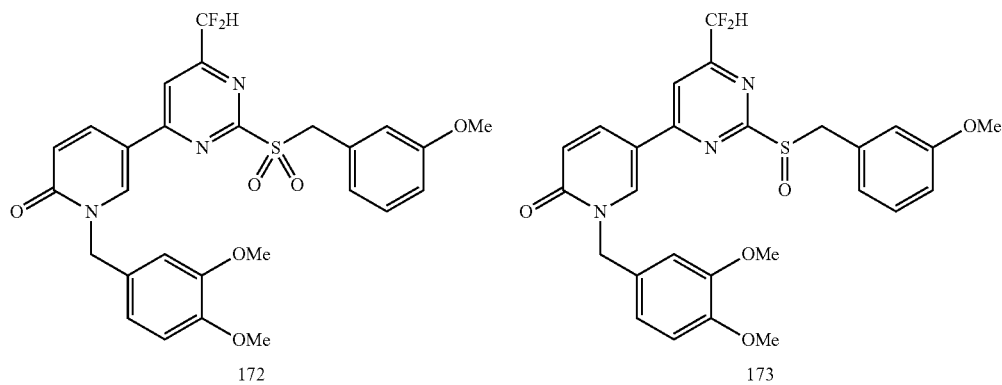

Step 1: The titled compound 172-1 was prepared as yellow oil from compound 160 (100 mg, 0.22 mmol) according to the procedure for 140-01, Mass (m/z): 406.21 [M+H]$^+$.

Step 2: The titled compound 172 (13 mg), and 173 (11 mg, 25% yield) were prepared as two white solids from 172-1 (24 mg, 0.059 mmol) and 1-(bromomethyl)-3-methoxybenzene (18 mg, 0.089 mmol) according to the procedure for 140. 172: $^1$HNMR (400 MHz, CDCl$_3$) δ 8.59 (d, J=2.4 Hz, 1H), 7.96 (dd, J=2.4, 9.6 Hz, 1H), 7.76 (s, 1H), 7.19 (t, J=8.4 Hz, 1H), 6.94 (t, J=2.0 Hz, 1H), 6.91-6.88 (m, 2H), 6.86-6.81 (m, 2H), 6.74 (d, J=9.6 Hz, 1H), 6.63 (t, J=54.4 Hz, 1H), 5.18 (s, 2H), 4.74 (s, 2H), 3.86 (s, 3H), 3.82 (s, 3H), 3.74 (s, 3H). Mass (m/z): 558.28 [M+H]$^+$. 173: $^1$HNMR (400 MHz, CDCl$_3$) δ 8.50 (d, J=2.4 Hz, 1H), 7.97 (dd, J=2.4, 9.6 Hz, 1H), 7.66 (s, 1H), 7.16 (t, J=8.0 Hz, 1H), 6.96 (m, 1H), 6.93 (dd, J=1.6, 8.4 Hz, 1H), 6.86 (d, J=8.0 Hz, 1H), 6.81 (dd, J=2.4, 8.4 Hz, 1H), 6.71 (m, 2H), 6.60 (t, J=54.4 Hz, 1H), 5.18 (s, 2H), 4.37 (d, J=12.8 Hz, 1H), 4.26 (d, J=12.8 Hz, 1H), 3.87 (s, 3H), 3.85 (s, 3H), 3.73 (s, 3H). Mass (m/z): 542.26 [M+H]$^+$.

5-(6-(difluoromethyl)-2-((3-methoxyphenyl)sulfonyl)pyrimidin-4-yl)-1-(3,4-dimethoxybenzyl)pyridin-2 (1H)-one (174) and 5-(6-(difluoromethyl)-2-((3-methoxyphenyl)sulfinyl)pyrimidin-4-yl)-1-(3,4-dimethoxybenzyl)pyridin-2 (1H)-one (175)

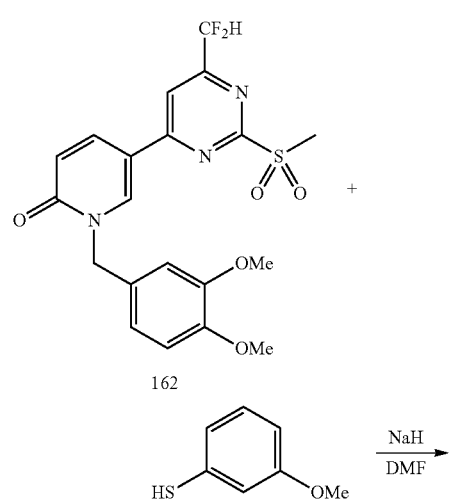

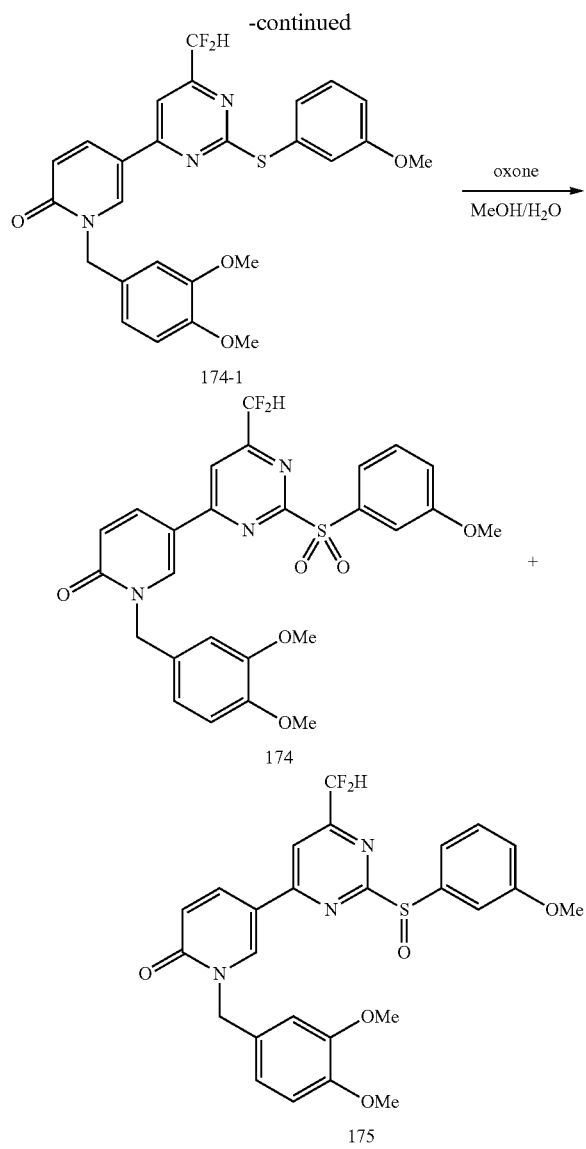

174-1

174

175

Step 1: At 0° C., to a stirred solution of 3-methoxybenzenethiol (14 mg, 0.099 mmol) in DMF (5 mL) was added NaH (5 mg, 0.13 mmol), which was stirred for 30 min, then compound 160 (30 mg, 0.066 mmol) was added to the above mixture and stirred for another 2 h, sat NH4Cl was added to quench the reaction, and extracted by EA for 3 times, concentrated the organic layer, and purified by flash chromatography with EA/PE (1/2), 30 mg colorless oil of 174-1 was obtained with a yield 89%. $^1$HNMR (400 MHz, CDCl$_3$) δ 8.17 (d, J=2.8 Hz, 1H), 7.79 (dd, J=2.8, 9.6 Hz, 1H), 7.36 (t, J=8.0 Hz, 1H), 7.31 (s, 1H), 7.23-7.21 (m, 2H), 7.03-7.00 (m, 1H), 6.93 (d, J=2.0 Hz, 1H), 6.82 (d, J=8.0 Hz, 1H), 6.78 (dd, J=2.0, 8.4 Hz, 1H), 6.63 (d, J=9.6 Hz, 1H), 6.40 (t, J=54.4 Hz, 1H), 5.02 (s, 2H), 3.86 (s, 3H), 3.84 (s, 3H), 3.80 (s, 3H). Mass (m/z): 512.22 [M+H]$^+$.

Step 2: The titled compound 174 (18 mg, 56% yield) and 175 (13 mg, 42% yield) was prepared as two white solids according to the procedure for 140. 174: $^1$HNMR (400 MHz, CDCl$_3$) δ 8.48 (d, J=2.8 Hz, 1H), 7.92 (dd, J=2.4, 9.6 Hz, 1H), 7.71 (s, 1H), 7.68-7.65 (m, 1H), 7.60 (dd, J=1.6, 2.4 Hz, 1H), 7.54-7.52 (m, 1H), 7.47 (t, J=8.0 Hz, 1H), 7.22-7.19 (m, 1H), 6.95 (d, J=2.0 Hz, 1H), 6.91 (dd, J=2.0, 8.0 Hz, 1H), 6.87 (d, J=8.0 Hz, 1H), 6.58 (t, J=54.4 Hz, 1H), 5.16 (s, 2H), 3.88 (s, 6H), 3.86 (s, 3H). Mass (m/z): 544.24 [M+H]$^+$. 175: $^1$HNMR (400 MHz, CDCl$_3$) δ 8.52 (d, J=2.4 Hz, 1H), 7.97 (dd, J=2.4, 9.6 Hz, 1H), 7.61 (s, 1H), 7.42 (m, 1H), 7.35-7.32 (m, 2H), 6.99-6.93 (m, 3H), 6.88 (d, J=8.8 Hz, 1H), 6.73 (d, J=9.6 Hz, 1H), 6.61 (t, J=54.4 Hz, 1H), 5.20 (d, J=6.8 Hz, 2H), 3.88 (s, 6H), 3.81 (s, 3H). Mass (m/z): 528.24 [M+H]$^+$.

4-((4-(difluoromethyl)-6-(1-(3,4-dimethoxybenzyl)-6-oxo-1,6-dihydropyridin-3-yl)pyrimidin-2-yl)sulfonyl)-N-methylbutanamide (176) and 4-((4-(difluoromethyl)-6-(1-(3,4-dimethoxybenzyl)-6-oxo-1,6-dihydropyridin-3-yl)pyrimidin-2-yl)sulfinyl)-N-methylbutanamide (177)

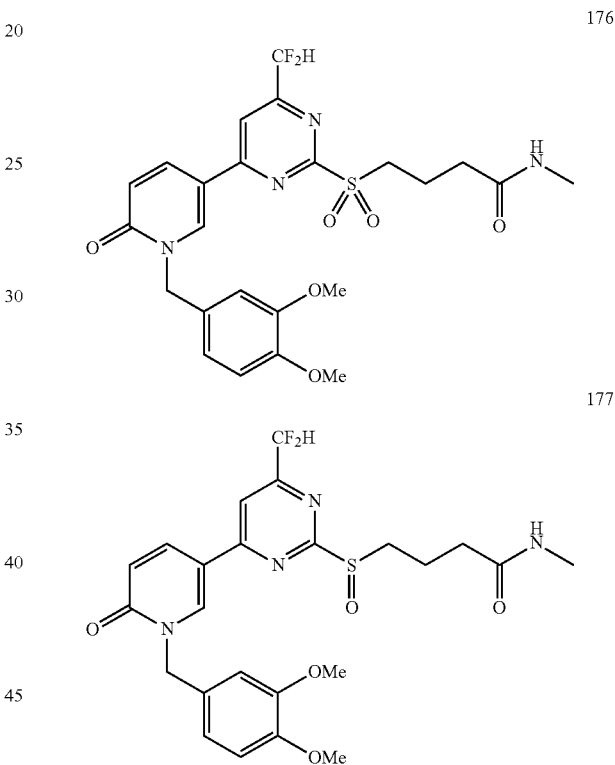

176

177

The titled compound 176 (6 mg, 14% yield) and 177 (3 mg, 7% yield) was prepared as two white solids from 172-1 (33 mg, 0.081 mmol) and 4-bromo-N-methylbutanamide (29 mg, 0.16 mmol) according to the procedure for 140. 176: $^1$HNMR (400 MHz, CDCl3) δ 8.85 (d, J=2.4 Hz, 1H), 7.98 (dd, J=2.4, 9.6 Hz, 1H), 7.81 (s, 1H), 7.02 (d, J=2.0 Hz, 1H), 7.00 (dd, J=2.0, 8.4 Hz, 1H), 6.87 (d, J=8.4 Hz, 1H), 6.75 (d, J=9.6 Hz, 1H), 6.65 (t, J=54.4 Hz, 1H), 5.59 (br, 1H), 5.28 (s, 2H), 3.88 (s, 3H), 3.87 (s, 3H), 3.68 (t, J=7.6 Hz, 2H), 2.80 (d, J=4.8 Hz, 3H), 2.44 (t, J=6.8 Hz, 2H), 2.29-2.22 (m, 2H). Mass (m/z): 537.38 [M+H]$^+$. 177: $^1$HNMR (400 MHz, CDCl$_3$) δ 8.64 (d, J=2.4 Hz, 1H), 8.01 (dd, J=2.8, 9.6 Hz, 1H), 7.70 (s, 1H), 6.99 (m, 1H), 6.96 (dd, J=2.0, 8.0 Hz, 1H), 6.86 (d, J=8.0 Hz, 1H), 6.76 (d, J=9.6 Hz, 1H), 6.64 (t, J=54.4 Hz, 1H), 5.78 (br, 1H), 5.22 (s, 2H), 3.87 (s, 3H), 3.86 (s, 3H), 3.29-3.21 (m, 2H), 2.79 (d, J=4.8 Hz, 3H), 2.41 (t, J=6.8 Hz, 2H), 2.12-2.05 (m, 2H). Mass (m/z): 521.35 [M+H]$^+$.

285

3-((4-(difluoromethyl)-6-(1-(3,4-dimethoxybenzyl)-6-oxo-1,6-dihydropyridin-3-yl)pyrimidin-2-yl)sulfonyl)-N-methylpropane-1-sulfonamide (178) and 3-((4-(difluoromethyl)-6-(1-(3,4-dimethoxybenzyl)-6-oxo-1,6-dihydropyridin-3-yl)pyrimidin-2-yl)sulfinyl)-N-methylpropane-1-sulfonamide (179)

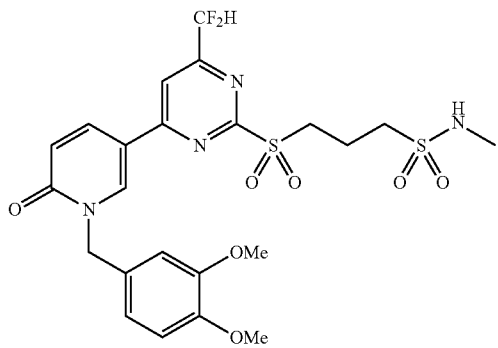
178

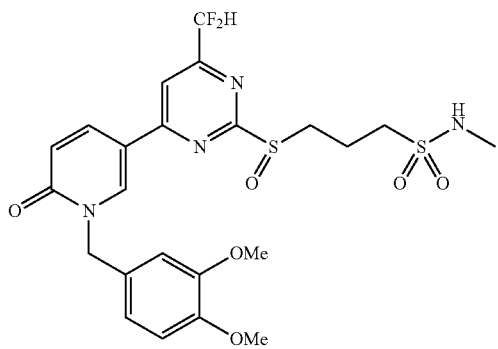
179

286

The titled compound 178 (7 mg, 16% yield) and 179 (4 mg, 100% yield) was prepared as two white solids from 172-1 (30 mg, 0.075 mmol) and 3-chloro-N-methylpropane-1-sulfonamide (27 mg, 0.16 mmol) according to the procedure for 140. 178: $^1$HNMR (400 MHz, CDCl$_3$) δ 8.69 (d, J=2.4 Hz, 1H), 7.98 (dd, J=2.8, 9.6 Hz, 1H), 7.83 (s, 1H), 6.98-6.96 (m, 2H), 6.87 (d, J=8.0 Hz, 1H), 6.76 (d, J=10.0 Hz, 1H), 6.65 (t, J=55.4 Hz, 1H), 5.22 (s, 2H), 3.88 (s, 3H), 3.87 (s, 3H), 3.82 (t, J=7.2 Hz, 2H), 3.26 (t, J=6.8 Hz, 2H), 2.83 (d, J=5.2 Hz, 3H), 2.47-2.40 (m, 2H). Mass (m/z): 573.40 [M+H]$^+$. 179: $^1$HNMR (400 MHz, CDCl$_3$) δ 8.63 (d, J=2.4 Hz, 1H), 8.00 (dd, J=2.4, 9.6 Hz, 1H), 7.72 (s, 1H), 6.98-6.95 (m, 2H), 6.87 (d, J=8.0 Hz, 1H), 6.77 (d, J=10.0 Hz, 1H), 6.65 (t, J=55.4 Hz, 1H), 5.21 (s, 2H), 4.39 (m, 1H), 3.88 (s, 3H), 3.87 (s, 3H), 3.48-3.43 (m, 1H), 3.40-3.33 (m, 1H), 3.20 (t, J=7.2 Hz, 2H), 2.80 (d, J=5.2 Hz, 3H), 2.50-2.43 (m, 1H), 2.25-2.16 (m, 1H). Mass (m/z): 557.40 [M+H]$^+$.

5-(2-((3-aminophenyl)sulfonyl)-6-(difluoromethyl)pyrimidin-4-yl)-1-(3,4-dimethoxybenzyl)pyridin-2(1H)-one (180) and 5-(2-((3-aminophenyl)sulfinyl)-6-(difluoromethyl)pyrimidin-4-yl)-1-(3,4-dimethoxybenzyl)pyridin-2(1H)-one (181)

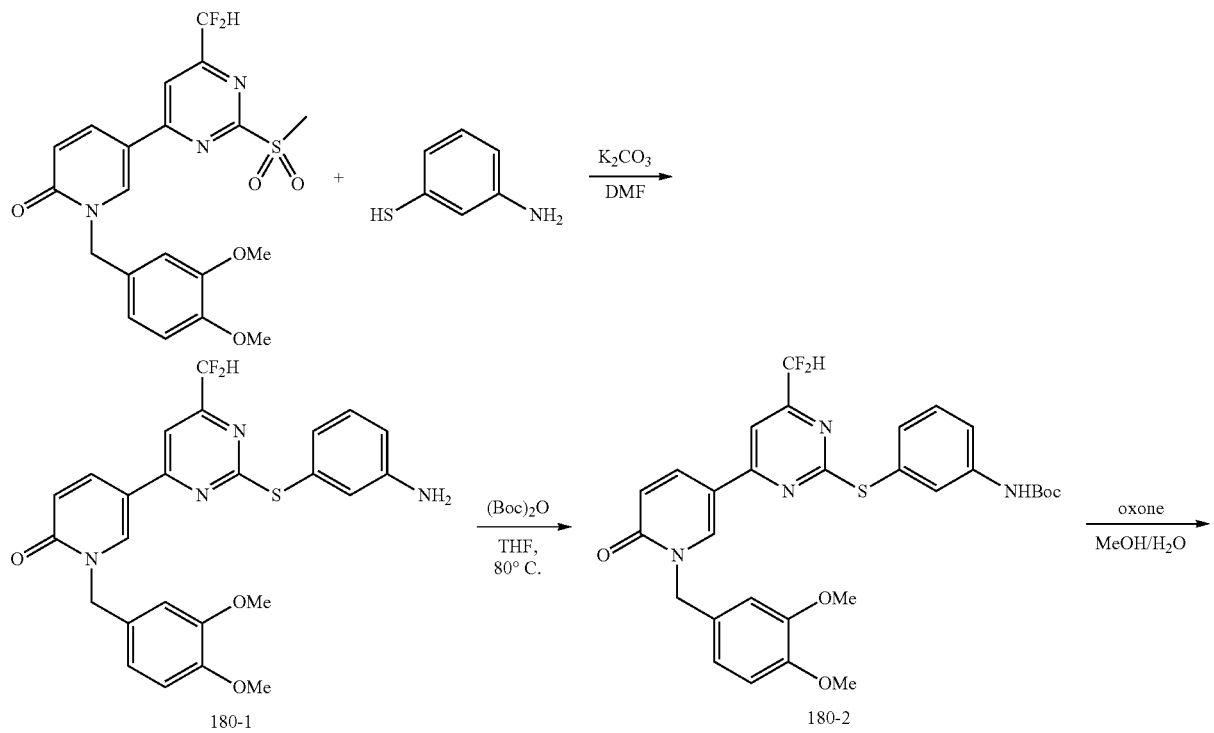

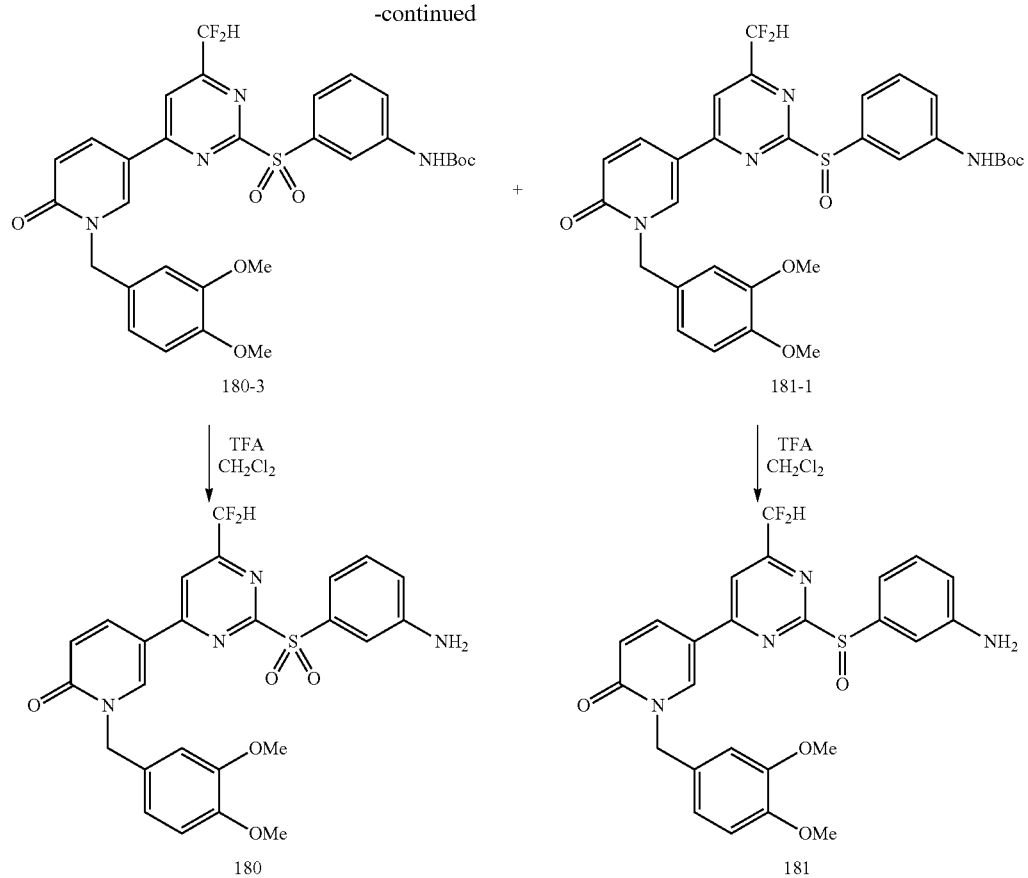

Step 1: The titled compound 180-1 (92 mg, 56% yield) was prepared as yellow syrup from 160 (100 mg, 0.22 mmol) and 3-aminobenzenethiol (41 mg, 0.33 mmol) according to the procedure for 174-1. ¹HNMR (400 MHz, CDCl₃) δ 8.20 (d, J=2.8 Hz, 1H), 7.80 (dd, J=2.4, 9.6 Hz, 1H), 7.31 (m, 1H), 7.24 (d, J=8.0 Hz, 1H), 7.04-6.99 (m, 2H), 6.93 (s, 1H), 6.68-6.79 (m, 2H), 6.63 (d, J=9.6 Hz, 1H), 6.41 (t, J=55.4 Hz, 1H), 5.05 (s, 2H), 3.86 (s, 3H), 3.85 (s, 3H). Mass (m/z). 497.49 [M+H]⁺.

Step 2: a solution of amine 180-1 (90 mg, 0.17 mmol) in dry THF (5 mL) was blanked with Ar, then a solution of (Boc)2O (54 mg, 0.25 mmol) in dry THF (2 mL) was added, when the addition was complete, the mixture was stirred at 60° C. overnight, concentrated the reaction mixture and purified by flash chromatography (EA/PE=2/1), 56 mg of 180-2 was obtained, yield: 55%. ¹HNMR (400 MHz, CDCl₃) δ 8.17 (d, J=2.4 Hz, 1H), 7.80 (dd, J=2.4, 9.6 Hz, 1H), 7.37-7.28 (m, 3H), 6.91 (d, J=1.6 Hz, 1H), 6.81-6.74 (m, 2H), 6.66-6.62 (m, 2H), 6.41 (t, J=55.4 Hz, 1H), 5.04 (s, 2H), 3.86 (s, 3H), 3.84 (s, 3H), 1.50 (s, 9H). Mass (m/z): 597.46 [M+H]⁺.

Step 3: The titled compound 180-3 and 181-1 was prepared as both colorless oil according to the procedure for 67.180-3: Mass (m/z): 629.47 [M+H]⁺, 181-1: Mass (m/z): 613.45 [M+H]⁺.

Step 4: compound 183-3 (31 mg, 0.049 mmol) was dissolved in CH₂Cl₂ (5 mL), then TFA (1 mL) was added, the whole system was stirred for 30 min, concentrated and purified by Prep-HPLC, 9.0 mg white solid of 180 was obtained, yield: 35%. ¹HNMR (400 MHz, CDCl₃) δ 8.52 (d, J=2.4 Hz, 1H), 7.95 (dd, J=2.4, 9.6 Hz, 1H), 7.73 (s, 1H), 7.41 (d, J=7.8 Hz, 1H), 7.33-7.29 (m, 2H), 6.95-6.88 (m, 3H), 6.78 (d, J=9.6 Hz, 1H), 6.59 (t, J=55.4 Hz, 1H), 5.18 (s, 2H), 3.88 (s, 6H). Mass (m/z): 529.45 [M+H]⁺.

Step 5: the tile compound 181 (4 mg, 0.0078 mmol, 24% yield) was prepared from 181-1 (17 mg, 0.032 mmol) according to the procedure for 180. ¹HNMR (400 MHz, CDCl₃) δ 8.55 (s, 1H), 7.98 (d, J=9.6 Hz, 1H), 7.62 (s, 1H), 7.33-7.23 (m, 4H), 6.97-6.87 (m, 3H), 6.78 (d, J=9.2 Hz, 1H), 6.61 (t, J=54.4 Hz, 1H), 5.21 (d, J=8.0 Hz, 2H), 3.87 (s, 6H). Mass (m/z): 513.41 [M+H]⁺.

N-(3-((4-(difluoromethyl)-6-(1-(3,4-dimethoxybenzyl)-6-oxo-1,6-dihydropyridin-3-yl)pyrimidin-2-yl)sulfonyl)phenyl)acetamide (182)

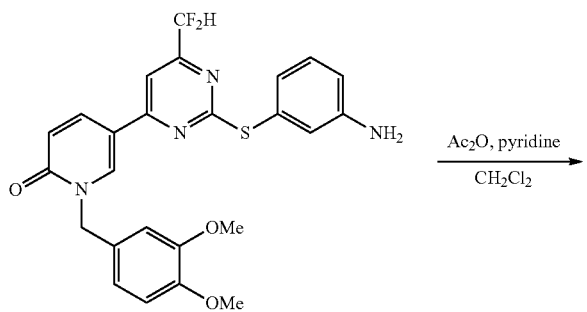

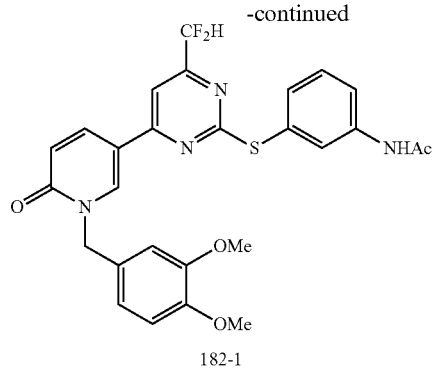

182-1

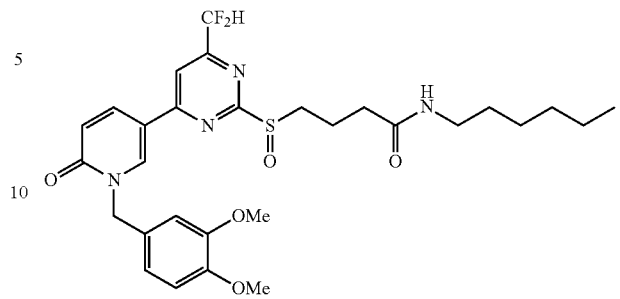

184

The titled compound 183 (3 mg, 3% yield) and 184 (1 mg, 1% yield) was prepared as two white solids from 172-1 (42 mg, 0.17 mmol) and 4-bromo-N-hexylbutanamide (45 mg, 0.11 mmol) according to the procedure for 140. 183: $^1$HNMR (400 MHz, CDCl$_3$) δ 8.88 (d, J=2.4 Hz, 1H), 7.98 (dd, J=2.8, 9.6 Hz, 1H), 7.81 (s, 1H), 7.02 (d, J=2.0 Hz, 1H), 7.00 (dd, J=2.0, 8.0 Hz, 1H), 6.86 (d, J=8.0 Hz, 1H), 6.74 (d, J=9.6 Hz, 1H), 6.64 (t, J=54.4 Hz, 1H), 5.56 (t, J=4.4 Hz, 1H), 5.27 (s, 2H), 3.87 (s, 3H), 3.86 (s, 3H), 3.68 (t, J=7.2 Hz, 2H), 3.24-3.19 (m, 2H), 3.43 (t, J=6.8 Hz, 2H), 2.28-2.21 (m, 2H), 1.50-1.43 (m, 2H), 1.29-1.22 (m, 6H), 0.86 (t, J=6.8 Hz, 3H). Mass (m/z): 607.40 [M+H]$^+$. 184: $^1$HNMR (400 MHz, CDCl$_3$) δ 8.64 (d, J=2.0 Hz, 1H), 8.00 (dd, J=2.4, 9.6 Hz, 1H), 7.70 (s, 1H), 6.98 (m, 1H), 6.96-6.94 (m, 1H), 6.86 (d, J=8.4 Hz, 1H), 6.75 (d, J=9.6 Hz, 1H), 6.64 (t, J=54.4 Hz, 1H), 5.70 (br, 1H), 5.21 (s, 2H), 3.88 (s, 3H), 3.87 (s, 3H), 3.23-3.19 (m, 2H), 2.40 (t, J=6.8 Hz, 2H), 2.28-2.19 (m, 2H), 1.48-1.43 (m, 2H), 1.31-1.26 (m, 6H), 0.86 (t, J=6.8 Hz, 3H). Mass (m/z): 591.40 [M+H]$^+$.

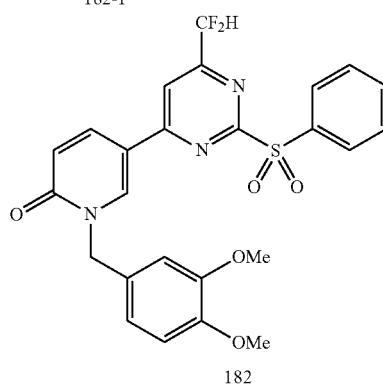

182

Step 1: to a stirred solution of 180-1 (20 mg, 0.037 mmol) in CH$_2$C$_2$ (5 mL) was added Ac2O (19 mg, 0.19 mmol) and pyridine (29 mg, 0.37 mmol) successively, which was stirred for 5 h, concentrated and purified by flash chromatography (EA/PE=2/1) 17 mg of white solid was obtained, yield: 85%. Mass (m/z): 539.47 [M+H]$^+$.

Step 2: The titled compound 182-1 (6 mg, 33% yield) was prepared as colorless oil according to the procedure for 67. $^1$HNMR (400 MHz, CDCl$_3$) δ 8.61 (s, 1H), 8.15 (m, 1H), 8.02-7.90 (m, 2H), 7.83-7.81 (m, 1H), 7.75-7.68 (m, 2H), 7.53 (d, J=8.4 Hz, 1H), 7.01-6.93 (m, 2H), 6.79-6.74 (m, 1H), 6.47 (t, J=54.4 Hz, 1H), 5.25 (s, 2H), 3.92 (s, 3H), 3.87 (s, 3H), 2.21 (s, 3H). Mass (m/z): 571.41 [M+H]$^+$.

4-((4-(difluoromethyl)-6-(1-(3,4-dimethoxybenzyl)-6-oxo-1,6-dihydropyridin-3-yl)pyrimidin-2-yl)sulfonyl)-N-hexylbutanamide (183) and 4-((4-(difluoromethyl)-6-(1-(3,4-dimethoxybenzyl)-6-oxo-1,6-dihydropyridin-3-yl)pyrimidin-2-yl)sulfinyl)-N-hexylbutanamide (184)

N-(3-((4-(difluoromethyl)-6-(1-(3,4-dimethoxybenzyl)-6-oxo-1,6-dihydropyridin-3-yl)pyrimidin-2-yl)sulfonyl)propyl)acetamide (185)

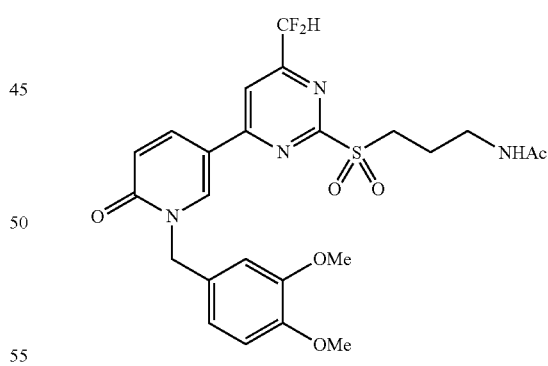

The titled compound 185 (10 mg, 27% yield) was prepared as white solid from 172-1 (28 mg, 0.069 mmol) and N-(3-bromopropyl)acetamide (23 mg, 0.13 mmol) according to the procedure for 140. $^1$HNMR (400 MHz, CDCl$_3$) δ 8.65 (d, J=2.8 Hz, 1H), 8.00 (dd, J=2.8, 9.6 Hz, 1H), 7.81 (s, 1H), 6.98 (d, J=2.0 Hz, 1H), 6.96 (dd, J=2.0, 8.4 Hz, 1H), 6.86 (d, J=8.0 Hz, 1H), 6.75 (d, J=10.0 Hz, 1H), 6.64 (t, J=54.4 Hz, 1H), 5.94 (br, 1H), 5.22 (s, 2H), 3.87 (s, 3H), 3.86 (s, 3H), 3.60 (t, J=7.2 Hz, 2H), 3.46 (q, J=6.8 Hz, 2H), 2.17-2.10 (m, 2H), 1.97 (s, 3H). Mass (m/z): 537.21 [M+H]$^+$.

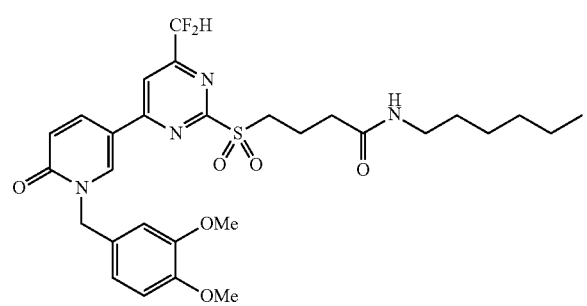

183

291

5,5'-(2,2'-(propane-1,3-diyldisulfonyl)bis(6-(difluoromethyl)pyrimidine-4,2-diyl))bis(1-(3,4-dimethoxybenzyl)pyridin-2 (1H)-one) (186)

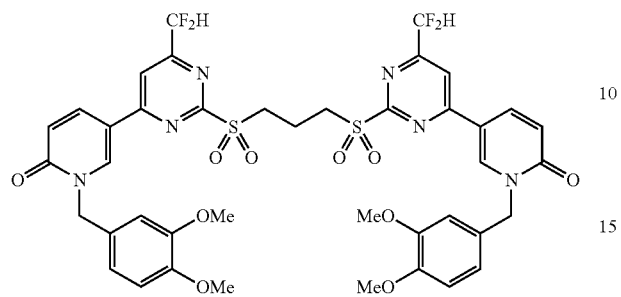

The titled compound 186 (26 mg, 59% yield) was prepared as white solid from 172-1 (69 mg, 0.17 mmol) and 1,3-dibromopropane (10 mg, 0.048 mmol) according to the procedure for 140.

$^1$HNMR (400 MHz, CDCl$_3$) δ 8.66 (d, J=2.8 Hz, 1H), 7.96 (dd, J=2.4, 9.6 Hz, 1H), 7.81 (s, 1H), 6.97 (d, J=2.0 Hz, 1H), 6.95 (dd, J=2.0, 8.4 Hz, 1H), 6.84 (d, J=8.4 Hz, 1H), 6.73 (d, J=10.0 Hz, 1H), 6.60 (t, J=54.4 Hz, 1H), 5.19 (s, 2H), 3.88 (t, J=7.2 Hz, 1H), 3.85 (s, 3H), 3.84 (s, 3H), 2.61 (qu, J=7.2 Hz, 1H), 1.25 (t, J=6.8 Hz, 1H), Mass (m/z): 915.21[M+H]

Synthesis of Compounds 187-200

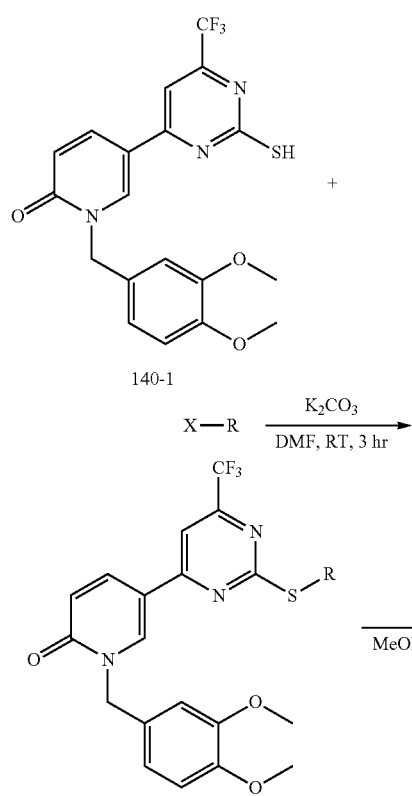

292

-continued

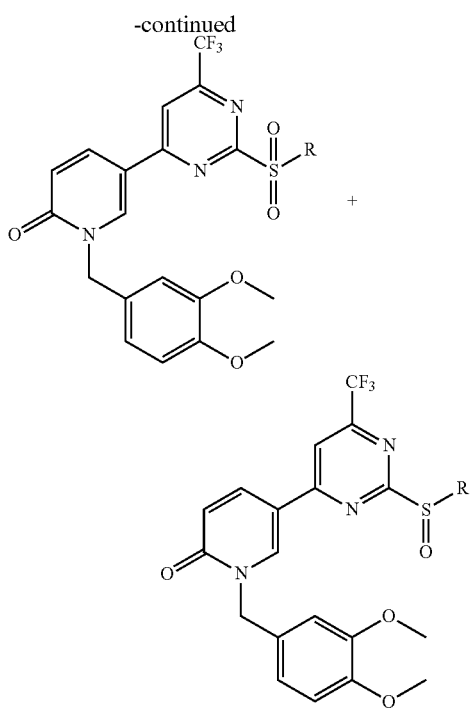

X = Cl, Br, I

1-(3,4-dimethoxybenzyl)-5-(6-fluoro-2-(methylsulfonyl)pyrimidin-4-yl)pyridin-2 (1H)-one (201)

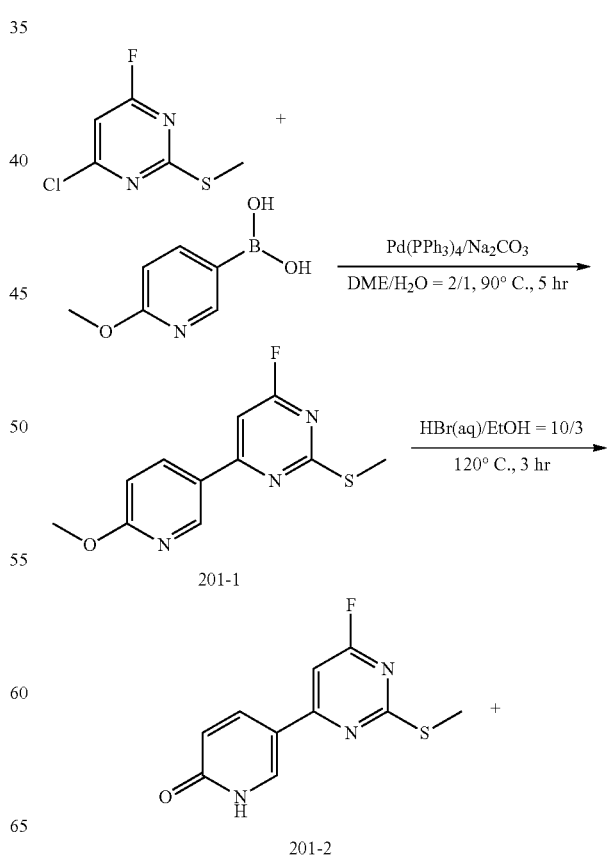

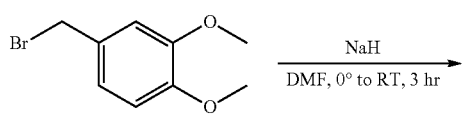
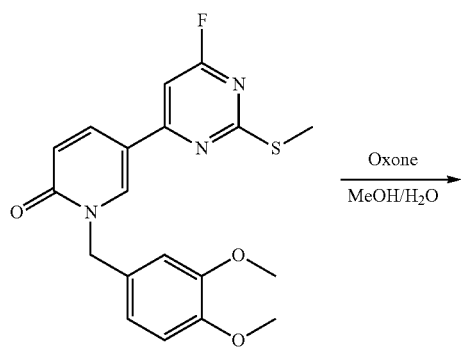
5-(6-(difluoromethyl)-2-(methylsulfinyl)pyrimidin-4-yl)-1-(3,4-dimethoxybenzyl)pyridin-2 (1H)-one (202)
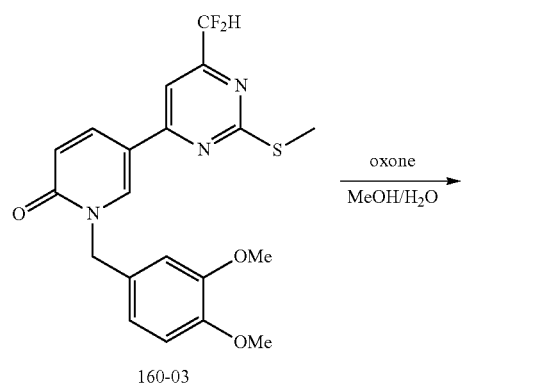
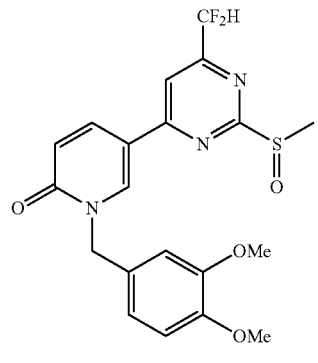
1-(3,4-dimethoxybenzyl)-5-(6-(fluoromethyl)-2-(methylsulfinyl) pyrimidin-4-yl)pyridin-2 (1H)-one (203)
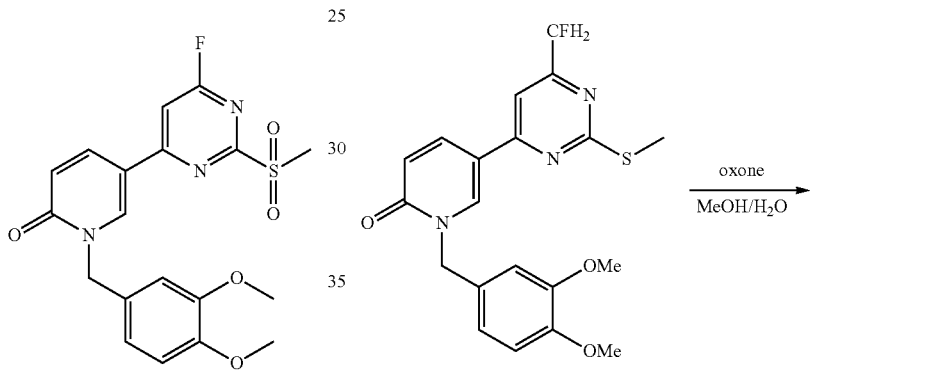
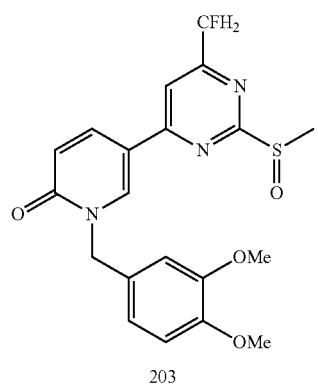
Synthesis of Compounds 204-217
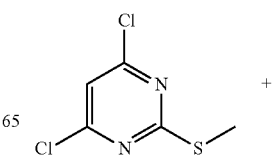

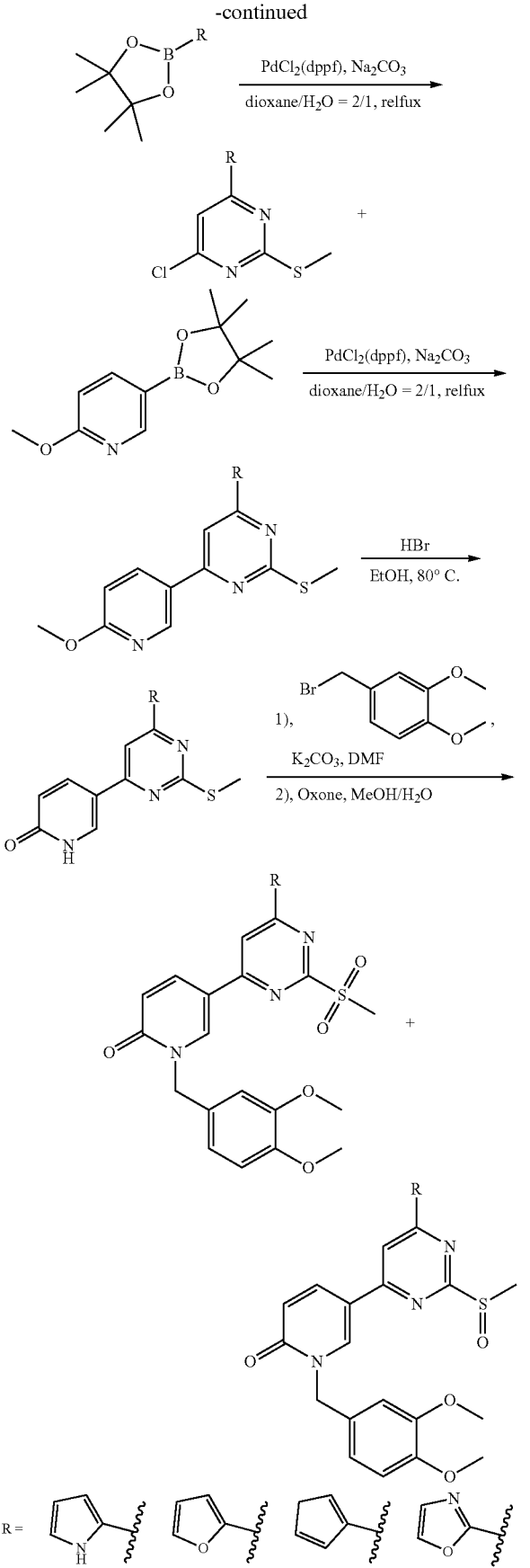
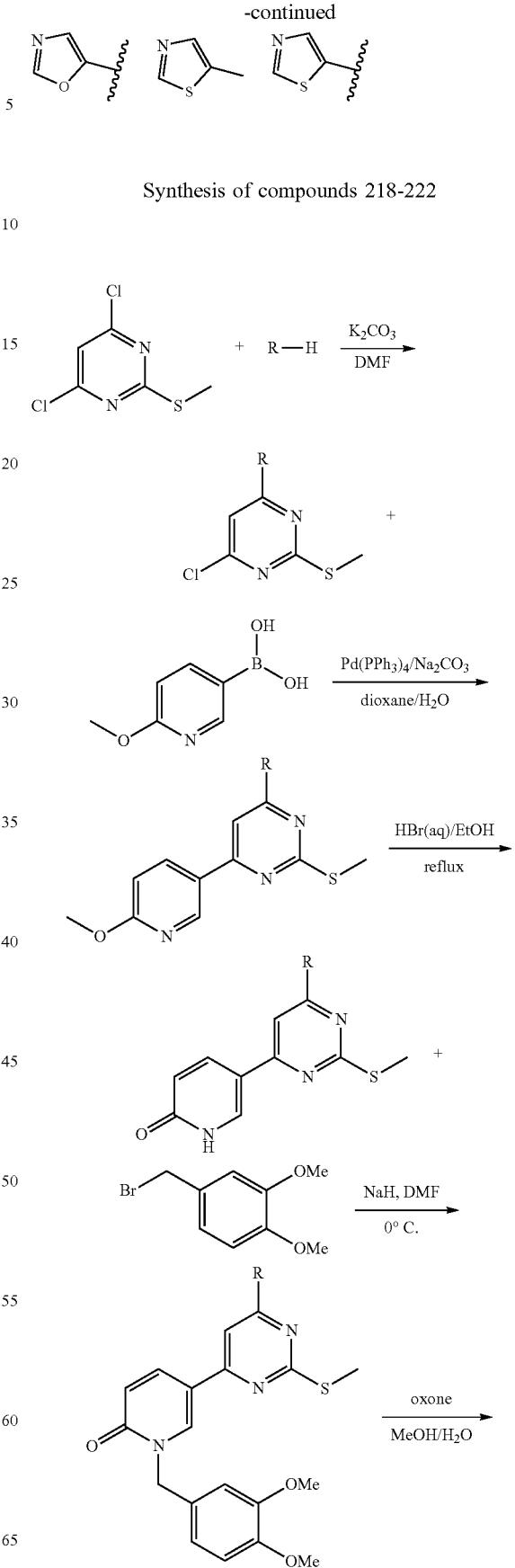
Synthesis of compounds 218-222

-continued
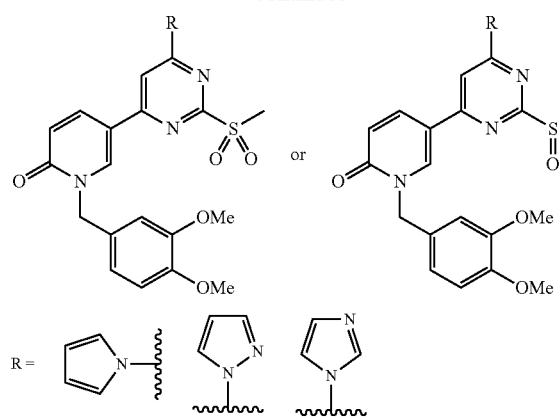
Synthesis of compounds 223-268
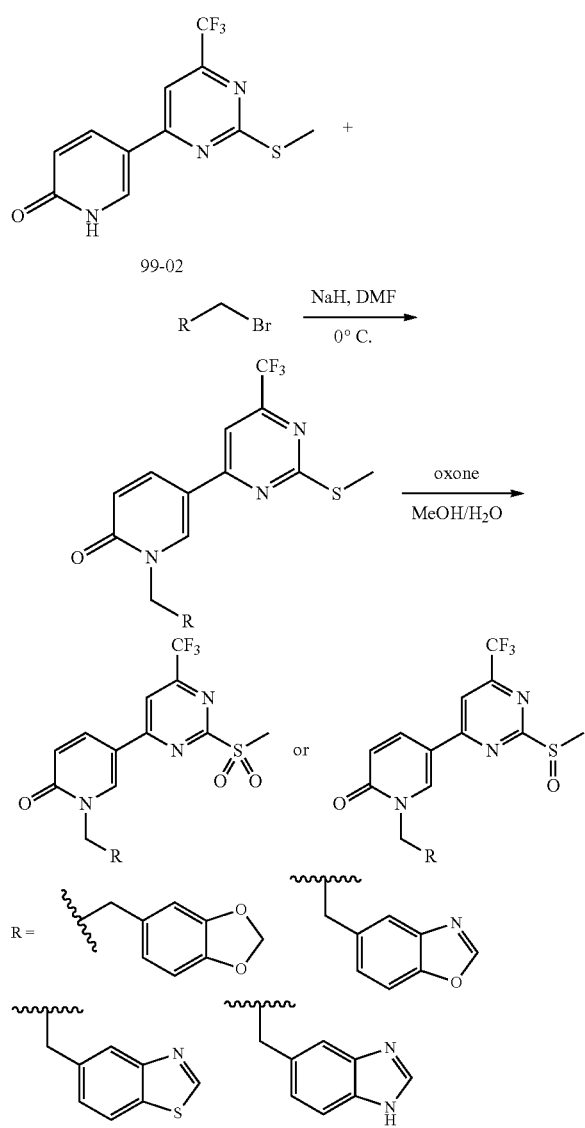

299
1-(3,4-dimethoxybenzyl)-5-(2-(methylsulfonyl)-6-propionylpyrimidin-4-yl)pyridin-2 (1H)-one (269)
300
5-(6-(1,1-difluoropropyl)-2-(methylsulfonyl)pyrimidin-4-yl)-1-(3,4-dimethoxybenzyl)pyridin-2 (1H)-one (270)
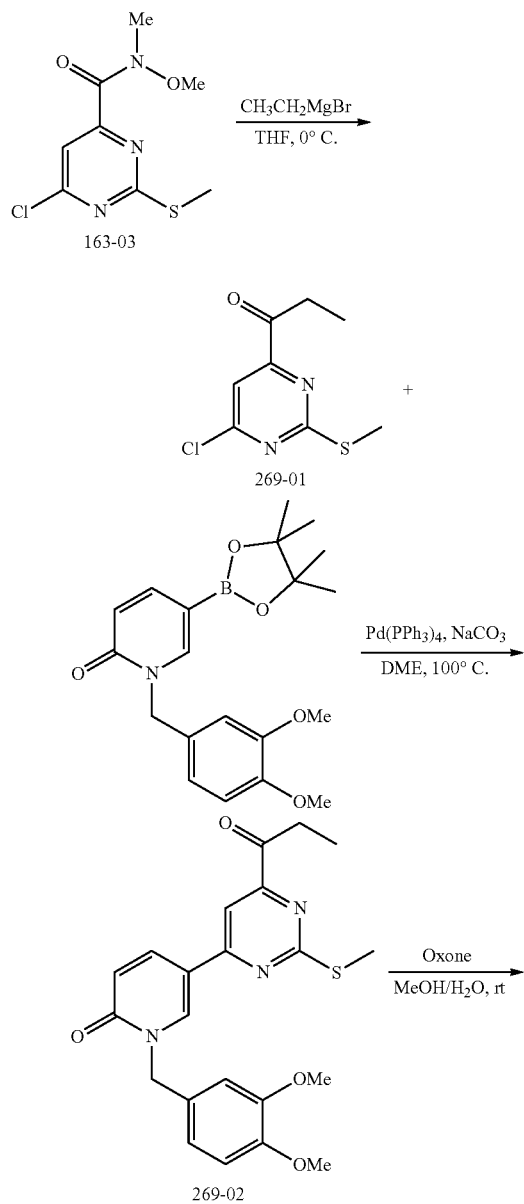
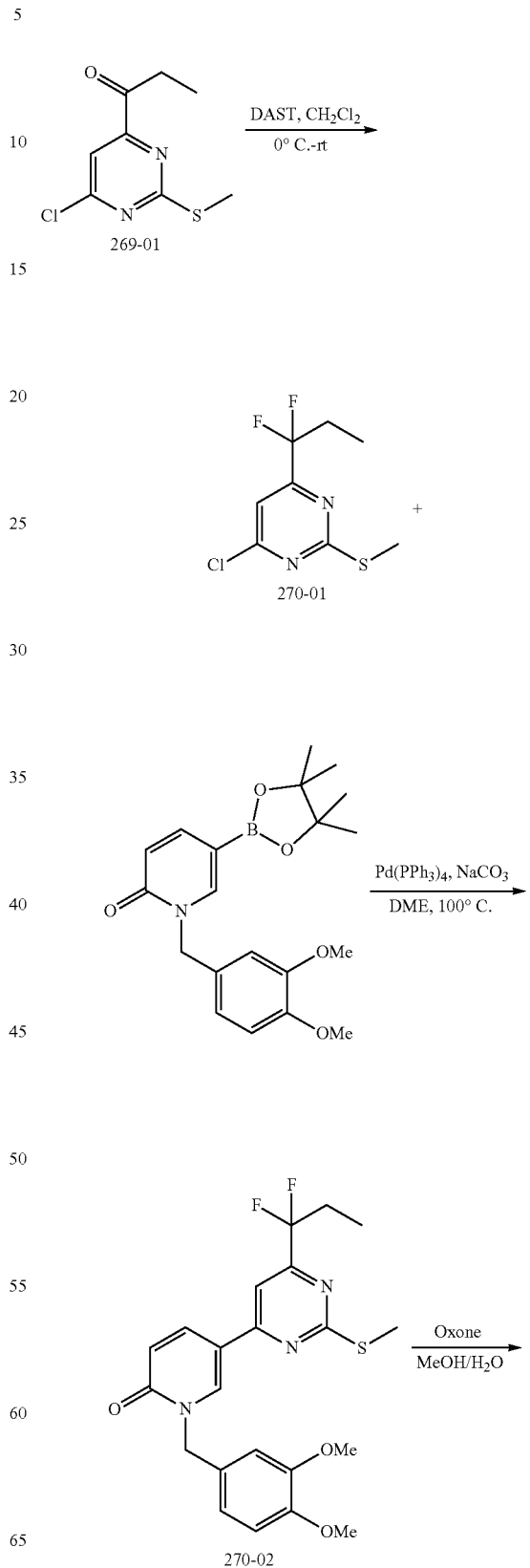

-continued
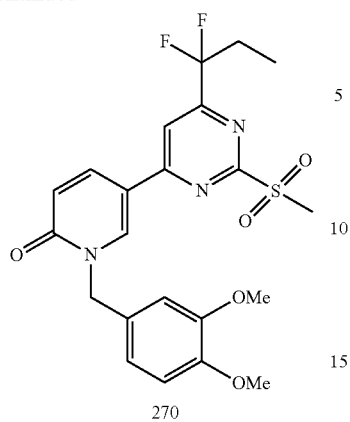
270
5-(6-benzoyl-2-(methylsulfonyl)pyrimidin-4-yl)-1-(3,4-dimethoxybenzyl)pyridin-2(1H)-one (271)
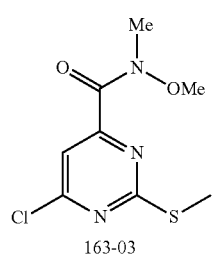
163-03
PhMgBr
THF, 0° C.
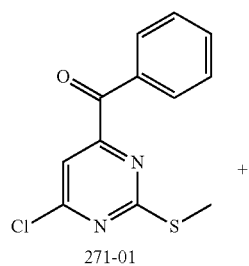
271-01
+
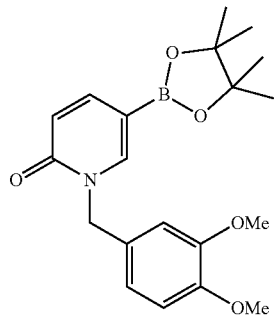
Pd(PPh₃)₄, NaCO₃
DME, 100° C.
-continued
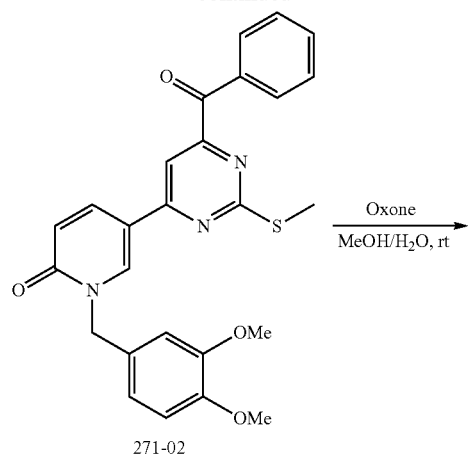
271-02
Oxone
MeOH/H₂O, rt
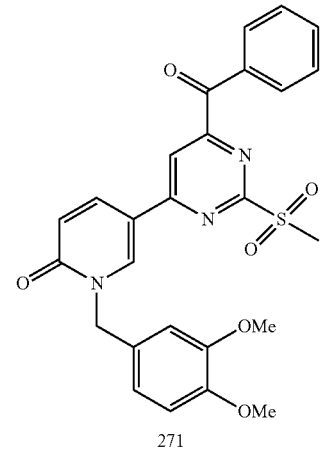
271
5-(2-((3-(benzyloxy)propyl)sulfonyl)-6-(difluoromethyl)pyrimidin-4-yl)-1-(3,4-dimethoxybenzyl)pyridin-2(1H)-one (9272) and 5-(6-(difluoromethyl)-2-((3-hydroxypropyl)sulfonyl)pyrimidin-4-yl)-1-(3,4-dimethoxybenzyl)pyridin-2(1H)-one (9273)
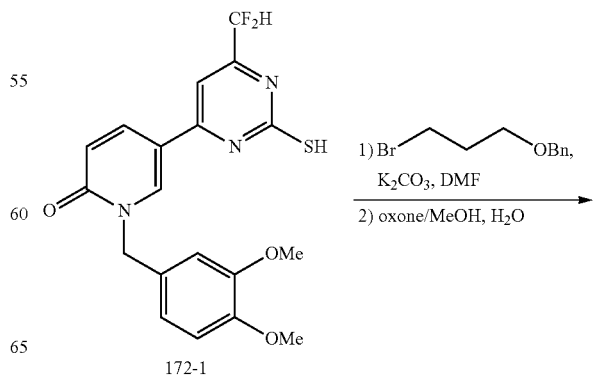
172-1
1) Br~~~OBn,
K₂CO₃, DMF
2) oxone/MeOH, H₂O

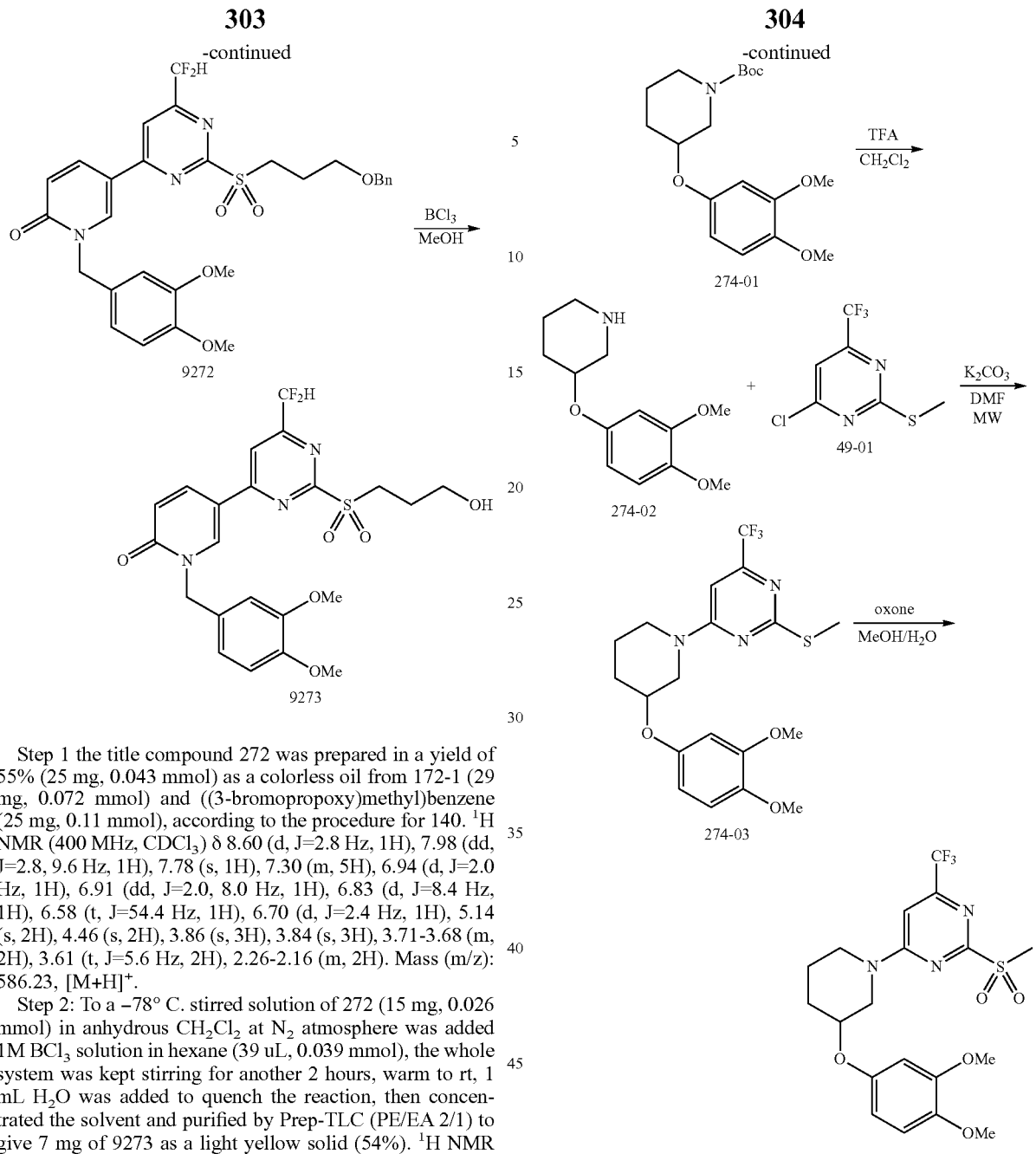

Step 1 the title compound 272 was prepared in a yield of 55% (25 mg, 0.043 mmol) as a colorless oil from 172-1 (29 mg, 0.072 mmol) and ((3-bromopropoxy)methyl)benzene (25 mg, 0.11 mmol), according to the procedure for 140. $^1$H NMR (400 MHz, CDCl$_3$) δ 8.60 (d, J=2.8 Hz, 1H), 7.98 (dd, J=2.8, 9.6 Hz, 1H), 7.78 (s, 1H), 7.30 (m, 5H), 6.94 (d, J=2.0 Hz, 1H), 6.91 (dd, J=2.0, 8.0 Hz, 1H), 6.83 (d, J=8.4 Hz, 1H), 6.58 (t, J=54.4 Hz, 1H), 6.70 (d, J=2.4 Hz, 1H), 5.14 (s, 2H), 4.46 (s, 2H), 3.86 (s, 3H), 3.84 (s, 3H), 3.71-3.68 (m, 2H), 3.61 (t, J=5.6 Hz, 2H), 2.26-2.16 (m, 2H). Mass (m/z): 586.23, [M+H]$^+$.

Step 2: To a −78° C. stirred solution of 272 (15 mg, 0.026 mmol) in anhydrous CH$_2$Cl$_2$ at N$_2$ atmosphere was added 1M BCl$_3$ solution in hexane (39 uL, 0.039 mmol), the whole system was kept stirring for another 2 hours, warm to rt, 1 mL H$_2$O was added to quench the reaction, then concentrated the solvent and purified by Prep-TLC (PE/EA 2/1) to give 7 mg of 9273 as a light yellow solid (54%). $^1$H NMR (400 MHz, CDCl$_3$) δ 8.65 (d, J=2.8 Hz, 1H), 8.00 (dd, J=2.4, 9.6 Hz, 1H), 7.81 (s, 1H), 6.96-6.93 (m, 2H), 6.87-6.82 (m, 1H), 6.77 (d, J=9.6 Hz, 1H), 6.50 (t, J=54.4 Hz, 1H), 5.19 (s, 2H), 4.53 (t, J=6.4 Hz, 1H), 3.88-3.80 (m, 8H), 3.72-3.68 (m, 2H), 2.18-2.12 (m, 2H). Mass (m/z): 496.26, [M+H]$^+$.

4-(3-(3,4-dimethoxyphenoxy)piperidin-1-yl)-2-(methylsulfonyl)-6-(trifluoromethyl)pyrimidine (274)

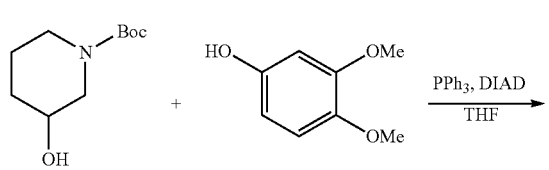

Step 1: To PPh$_3$ (0.98 g, 3.75 mmol) in 5 mL of dry THF at 0° C. was added DIAD (0.74 mL, 3.75 mmol) dropwise. The solution was allowed to stir for 10 min, then a solution containing tert-butyl 3-hydroxypiperidine-1-carboxylate (0.5 g, 2.5 mmol) in THF (2 mL) was added and stirred at 0° C. for another 10 min, 3,4-dimethoxyphenol (0.39 g, 2.5 mmol) was added, the solution was warmed to r.t overnight, concentrated the solvent, and purified by flash column chromatography (PE/EA 5/1), 0.19 g colorless oil of 274-01 was obtained, yield: 23%, Mass (m/z): 338.48, [M+H]$^+$.

Step 2: To a solution of 274-01 (0.39 g, 1.16 mmol) in CH$_2$Cl$_2$ (10 mL) was added TFA (3 mL), which was stirred at r.t for 2 hrs, concentrated the solvent and resolved in ethyl acetate (5 mL) aqueous NaHCO$_3$ was added to neutralize the acid, separate the organic layer and the water layer was extracted with ethyl acetate for three times, combined the organic phase, dried, concentrated and purified by flash column chromatography (CH$_2$Cl$_2$/MeOH 10/1). 0.27 g yellow oil of 274-02 was obtained, yield: 100%. Mass (m/z): 238.20, [M+H]$^+$.

Step 3: 274-02 (38 mg, 0.16 mmol), 49-01 (30 mg, 0.13 mmol) and K$_2$CO$_3$ (28 mg, 0.2 mmol) was mixed together in dry DMF (2 mL) in a microwave tube, the reaction was microwaved at 90° C. for 2 hrs. cooled to r.t. water was added, and the organic layer was extracted with ethyl acetate for three times, the organic layer was combined, dried and further purified by flash column chromatography (EA/PE 1/8) to give 54 mg of 274-03 as a colorless oil, yield: 96%. Mass (m/z): 430.15, [M+H]$^+$.

Step 4: the title compound 274 was prepared in a yield of 59% as a white solid from 274-03 (27 mg, 0.063 mmol) and Oxone (0.19 g, 0.31 mmol) according to the procedure for 71. $^1$H NMR (400 MHz, DMSO-d$_6$) δ 7.57 (s, 1H), 6.83 (d, J=8.4 Hz, 1H), 6.53-6.52 (m, 1H), 6.47-6.41 (m, 1H), 4.62 (m, 1H), 4.54-4.42 (m, 1H), 4.28-4.21 (m, 1H), 4.07-4.00 (m, 1H), 3.91-3.85 (m, 1H), 3.68 (s, 6H), 3.13 (s, 3H), 2.02-1.98 (m, 2H), 1.88-1.82 (m, 2H). Mass (m/z): 462.20 [M+H]$^+$.

6-(1-(3,4-dimethoxybenzyl)-6-oxo-1,6-dihydropyridin-3-yl)-3-methyl-2-(methylsulfonyl)pyrimidin-4(3H)-one (275)

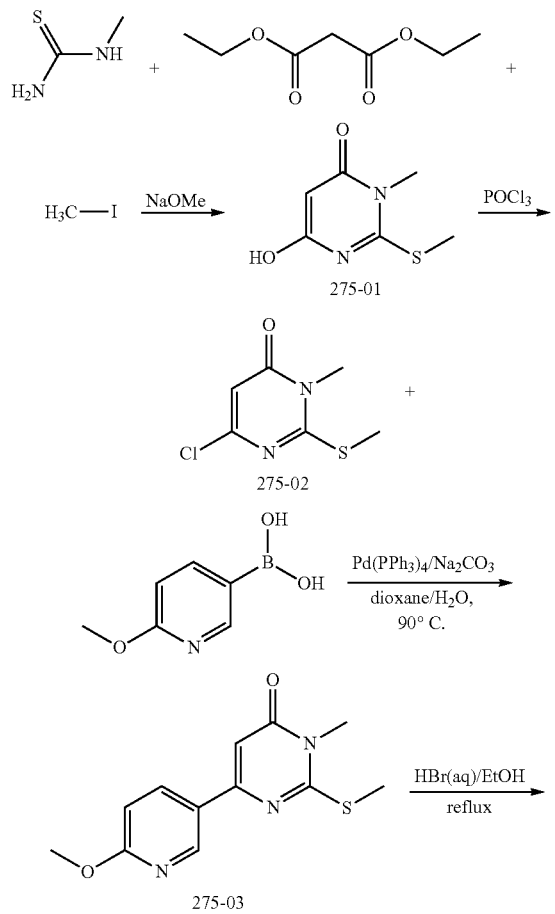

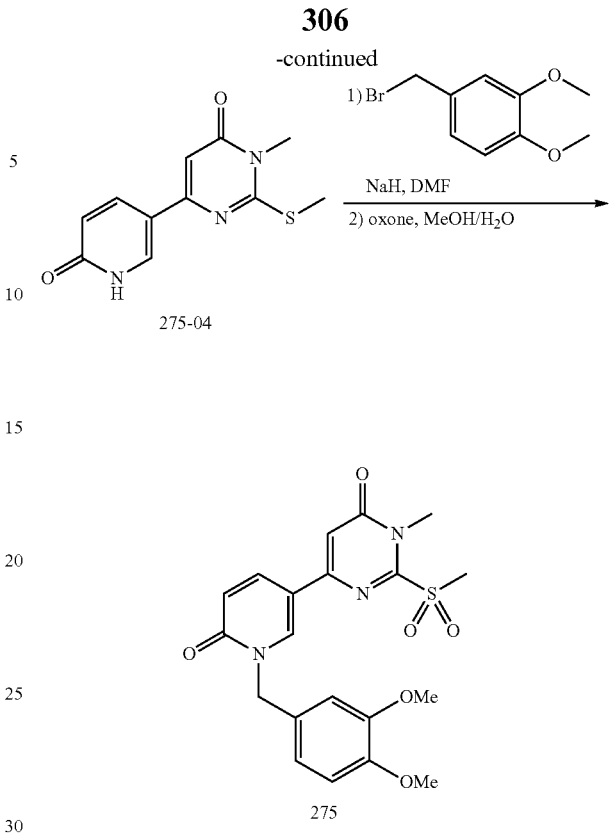

Step 1: A mixture of 2.25 g (0.025 mol) of N-methylthiourea, 2.7 g (0.05 mol) of sodium methylate, 10 mL of MeOH and 4.0 g (0.025 mol) of malonic acid diethyl ester was boiled for 3 hours under reflux, 3.55 g (0.025 mol) of was then added dropwise at about 50° C. and the mixture was stirred for a further 0.5 hrs at 50° C. The salt which crystallized out was filtered off and was then dissolved in 20 mL of water. The solution was neutralized by adding glacial acetic acid, the precipitate was then filtered off, and 3 g (0.017 mol) of 275-01 was obtained as a white solid, yield: 69.8%. Mass (m/z): 172.03, [M+H]$^+$.

Step 2: The titled compound 275-02 was prepared in a yield of 67.7% (0.9 g, 4.72 mmol) as a white solid from 275-01 (1.2 g, 6.97 mmol) and phosphorus oxychloride (10 ml) according to the procedure for 49-01. Mass (m/z): 190.65, [M+H]$^+$.

Step 3: The titled compound 275-03 was prepared in a yield of 85.4% (1.06 g, 4.03 mmol) as a white solid from 275-02 (0.9 g, 4.72 mmol) according to the procedure for 99-01. Mass (m/z): 264.30, [M+H]$^+$.

Step 4: The titled compound 275-04 was prepared without purification (1.06 g) as a white solid from 275-03 (1.06 g, 4.03 mmol) according to the procedure for 99-02. Mass (m/z): 250.23, [M+H]$^+$.

Step 5: The titled compound 275 was prepared in a yield of 6.6% (15 mg, 0.035 mmol) as a light yellow oil from 275-04 (0.13 g, 0.53 mmol) and 4-(bromomethyl)-1,2-dimethoxybenzene (0.15 g, 0.64 mmol) according to the procedure for 99-01. $^1$H NMR (400 MHz, CDCl$_3$) δ 7.93 (d, J=2.8 Hz, 1H), 7.70 (dd, J=2.4, 6.8 Hz, 1H), 6.87 (m, 3H), 6.71 (d, J=9.6 Hz, 1H), 6.61 (s, 1H), 5.10 (s, 2H), 3.89 (s, 3H), 3.86 (s, 3H), 3.79 (s, 3H), 3.22 (s, 3H). Mass (m/z): 432.35, [M+H]$^+$.

307

1-(3,4-dimethoxybenzyl)-5-(2-((4-hydroxybutyl)sulfonyl)-6-(trifluoromethyl)pyrimidin-4-yl)pyridin-2(1H)-one (276)

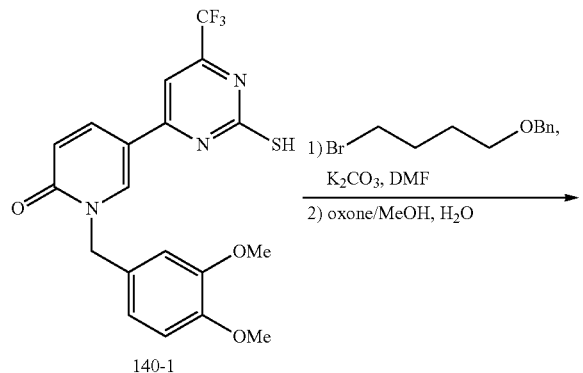

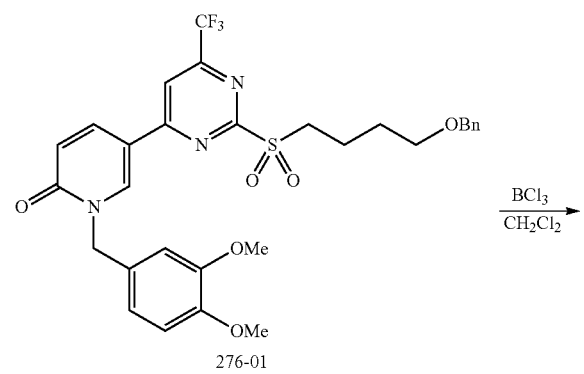

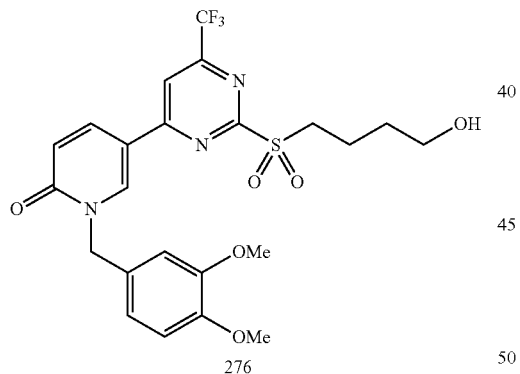

Step 1: The title compound 276-01 was prepared in a yield of 33.3% (25 mg, 0.04 mmol) as a colorless oil from 140-1 (50 mg, 0.12 mmol) and ((4-bromobutoxy)methyl)benzene (44 mg, 0.18 mmol), according to the procedure for 140. Mass (m/z): 618.47, [M+H]⁺.

Step 2. The titled compound 276 was prepared in a yield of 47.5% (10 mg, 0.019 mmol) as a white solid from 276-01 (0.013 mmol) according to the procedure for 273. ¹H NMR (400 MHz, CDCl₃) δ 8.72 (d, J=2.4 Hz, 1H), 7.99 (dd, J=2.4, 9.6 Hz, 1H), 7.81 (s, 1H), 6.96-6.92 (m, 2H), 6.86 (d, J=8.0 Hz, 1H), 6.77 (d, J=9.6 Hz, 1H), 5.21 (s, 2H), 3.88 (s, 3H), 3.87 (s, 3H), 3.71 (t, J=6.0 Hz, 2H), 3.66-3.62 (m, 2H), 2.06-1.99 (m, 2H), 1.80-1.73 (m, 2H). Mass (m/z): 528.59, [M+H]⁺.

308

5-(2-((3-(benzyloxy)-3-phenylpropyl)sulfinyl)-6-(difluoromethyl)pyrimidin-4-yl)-1-(3,4-dimethoxybenzyl)pyridin-2(1H)-one (277) and 5-(2-((3-(benzyloxy)-3-phenylpropyl)sulfonyl)-6-(difluoromethyl)pyrimidin-4-yl)-1-(3,4-dimethoxybenzyl)pyridin-2(1H)-one (278)

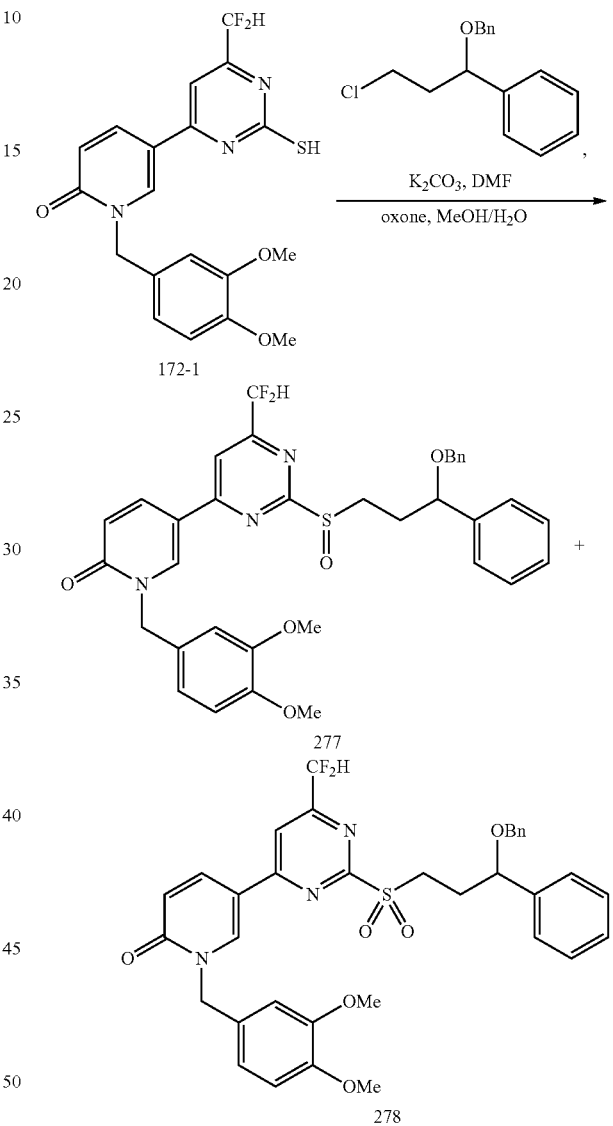

The title compound 277 (8 mg, 0.012 mmol) and 278 (10 mg, 0.015 mmol) was prepared as a colorless oil from 172-1 (55 mg, 0.12 mmol) and (1-(benzyloxy)-3-chloropropyl)benzene (47 mg, 0.18 mmol), according to the procedure for 140. 277: ¹HNMR (400 MHz, CDCl₃) δ 8.53 (s, 1H), 7.97 (m, 1H), 7.71 (m, 1H), 7.65 (s, 1H), 7.53 (m, 1H), 7.37-7.28 (m, 8H), 7.23 (m, 1H), 6.94 (m, 1H), 6.90-6.87 (m, 1H), 6.83-6.80 (dd, J=1.6, 8.4 Hz, 1H), 6.73-6.70 (m, 1H), 4.55 (q, J=4.4 Hz, 1H), 4.48-4.40 (m, 1H), 4.32-4.15 (m, 2H), 3.86 (d, J=2.4 Hz, 3H), 3.85 (s, 3H), 3.40-3.32 (m, 1H), 3.26-3.08 (m, 1H). Mass (m/z): 646.45[M+H]⁺; 278: ¹H NMR (400 MHz, CDCl3) δ 8.58 (d, J=2.8 Hz, 1H), 7.97 (dd, J=2.4, 9.6 Hz, 1H), 7.76 (s, 1H), 7.39-7.29 (m, 7H), 7.28 (m, 3H), 6.94 (d, J=2.0 Hz, 1H), 6.90 (dd, J=1.6, 8.0 Hz, 1H), 6.83 (d, J=8.4 Hz, 1H), 6.71 (d, J=9.6 Hz, 1H), 6.54 (t, J=54.4 Hz, 1H), 5.14 (d, J=2.0 Hz, 2H), 4.56 (dd, J=4.8, 8.0 Hz, 1H), 4.48 (d, J=11.6 Hz, 1H), 4.27 (d, J=12.0 Hz, 1H), 3.86 (s, 3H), 3.84 (s, 3H), 3.82-3.74 (m, 1H), 3.66-3.57 (m, 1H), 2.38-2.23 (m, 2H). Mass (m/z): 662.53, [M+H]$^+$.

5-(2-((3-chloro-3-phenylpropyl)sulfonyl)-6-(difluoromethyl)pyrimidin-4-yl)-1-(3,4-dimethoxybenzyl)pyridin-2 (1H)-one (279)

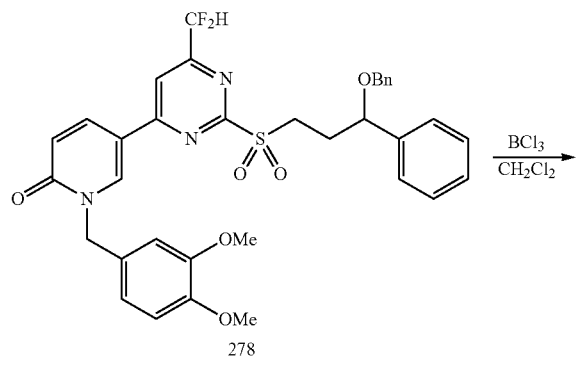

278

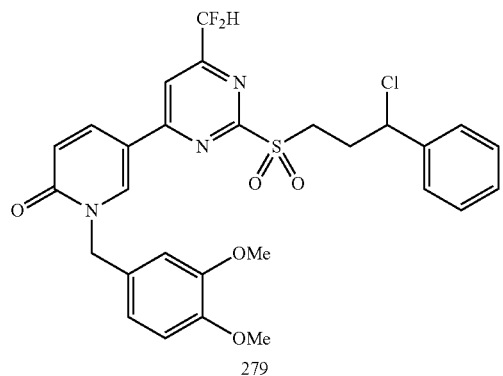

279

The titled compound 279 was prepared in a yield of 100% (14 mg, 0.024 mmol) as a white solid from 278 (16 mg, 0.024 mmol) according to the procedure for 273. $^1$H NMR (400 MHz, CDCl$_3$) δ 8.63 (d, J=2.0 Hz, 1H), 7.98 (dd, J=1.6, 9.6 Hz, 1H), 7.81 (s, 1H), 7.38-7.37 (m, H), 6.95 (m, 1H), 6.93 (2.0, 8.0 Hz, 1H), 6.85 (d, J=8.0 Hz, 1H), 6.76 (d, J=9.2 Hz, 1H), 6.60 (t, J=54.4 Hz, 1H), 5.19 (s, 2H), 5.11 (dd, J=5.6, 8.0 Hz, 1H), 3.87 (s, 3H), 3.86 (s, 3H), 3.82-3.75 (m, 1H), 3.71-3.63 (m, 1H), 2.71-2.57 (m, 2H). Mass (m/z): 590.42, [M+H]$^+$.

5-(2-((3-(benzyloxy)-3-phenylpropyl)sulfinyl)-6-(trifluoromethyl)pyrimidin-4-yl)-1-(3,4-dimethoxybenzyl)pyridin-2 (1H)-one (280) and 5-(2-((3-(benzyloxy)-3-phenylpropyl)sulfonyl)-6-(trifluoromethyl)pyrimidin-4-yl)-1-(3,4-dimethoxybenzyl)pyridin-2 (1H)-one (281)

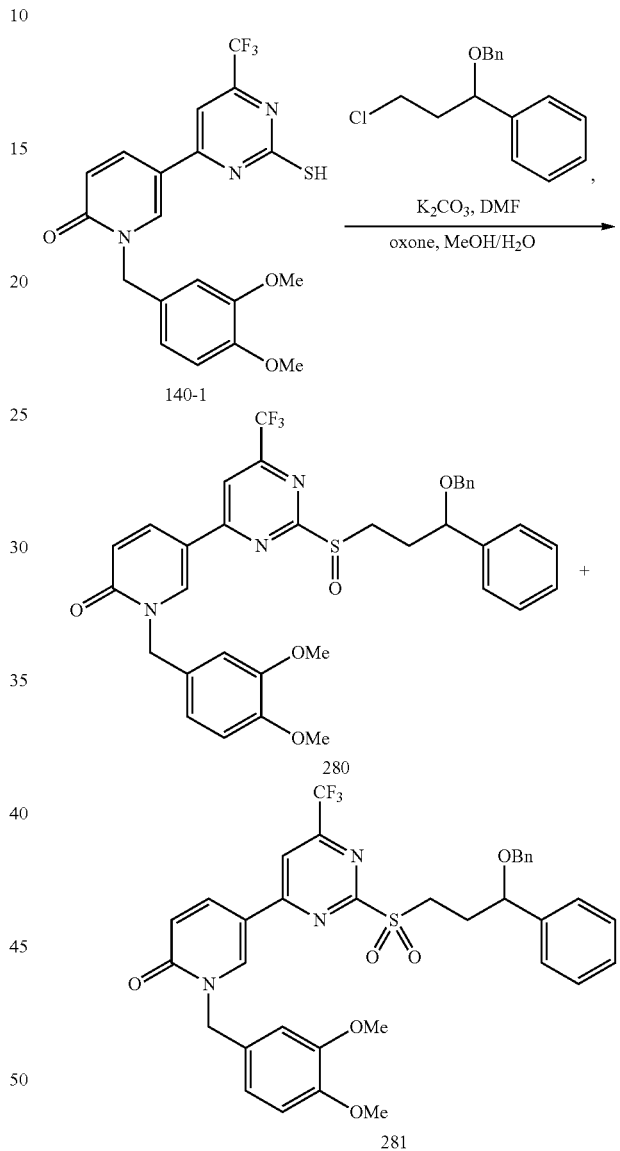

The title compound 280 (4.8 mg, 0.0072 mmol) and 281 (15 mg, 0.022 mmol) was prepared as white solid from 140-1 (55 mg, 0.12 mmol) and (1-(benzyloxy)-3-chloropropyl)benzene (44 mg, 0.17 mmol), according to the procedure for 140. 280: $^1$H NMR (400 MHz, CDCl$_3$) δ 8.70 (t, J=2.4 Hz, 1H), 7.99 (td, J=2.4, 9.6 Hz, 1H), 7.67 (d, J=2.4 Hz, 1H), 7.39-7.22 (m, 10H), 6.97 (t, J=2.4 Hz, 1H), 6.93-6.90 (m, 1H), 6.83 (dd, J=1.2 8.4 Hz, 1H), 6.77 (dd, J=0.8, 9.6 Hz, 1H), 5.25-5.11 (m, 2H), 4.58 (q, J=4.0 Hz, 0.7H), 4.49-4.42 (m, 1.57H), 4.29 (d, J=12.0 Hz, 0.60H), 4.21 (d, J=12.0 Hz, 0.55H), 3.87 (d, J=2.4 Hz, 3H), 3.85 (s, 3H), 3.46-3.38 (m, 1H), 3.33-3.26 (m, 0.70H), 3.23-3.16 (m, 0.70H), 2.48-2.31 (m, 1H), 2.14-2.00 (m, 1H). Mass (m/z): 664.28, [M+H]$^+$.

281: $^1$H NMR (400 MHz, CDCl$_3$) δ 8.87 (d, J=2.0 Hz, 1H), 8.01 (dd, J=2.0, 9.6 Hz, 1H), 7.80 (s, 1H), 7.40-7.26 (m, 10H), 6.95 (s, 1H), 6.92 (d, J=8.4 Hz, 1H), 6.84-6.79 (m, 2H), 5.19 (s, 2H), 4.57 (m, 1H), 4.49 (d, J=11.6 Hz, 1H), 4.27 (d, J=11.6 Hz, 1H), 3.87-3.79 (m, 7H), 3.69-3.62 (m, 1H), 2.41-2.25 (m, 2H); Mass (m/z): 680.28, [M+H]$^+$.

5-(2-((3-(benzyloxy)-3-phenylpropyl)sulfonyl)-6-(fluoromethyl)pyrimidin-4-yl)-1-(3,4-dimethoxybenzyl)pyridin-2 (1H)-one (282)

7.38-7.26 (m, 9H), 6.93 (s, 1H), 6.89 (d, J=8.0 Hz, 1H), 6.83 (d, J=8.0 Hz, 1H), 6.70 (d, J=9.6 Hz, 1H), 5.54 (s, 1H), 5.42 (s, 1H), 5.17-5.09 (m, 2H), 4.56-4.45 (m, 2H), 4.29-4.25 (m, 1H), 3.86 (s, 3H), 3.85 (s, 3H), 3.79-3.72 (m, 1H), 3.61-3.54 (m, 1H), 2.34-2.21 (m, 2H). Mass (m/z). 644.45, [M+H]$^+$.

5-(6-(difluoromethyl)-2-(3-(2-fluorobenzyloxy)-3-phenylpropylsulfinyl)pyrimidin-4-yl)-1-(3-fluoro-4-methoxybenzyl)pyridin-2 (1H)-one (283) and 5-(6-(difluoromethyl)-2-(3-(2-fluorobenzyloxy)-3-phenylpropylsulfonyl)pyrimidin-4-yl)-1-(3-fluoro-4-methoxybenzyl)pyridin-2 (1H)-one (284)

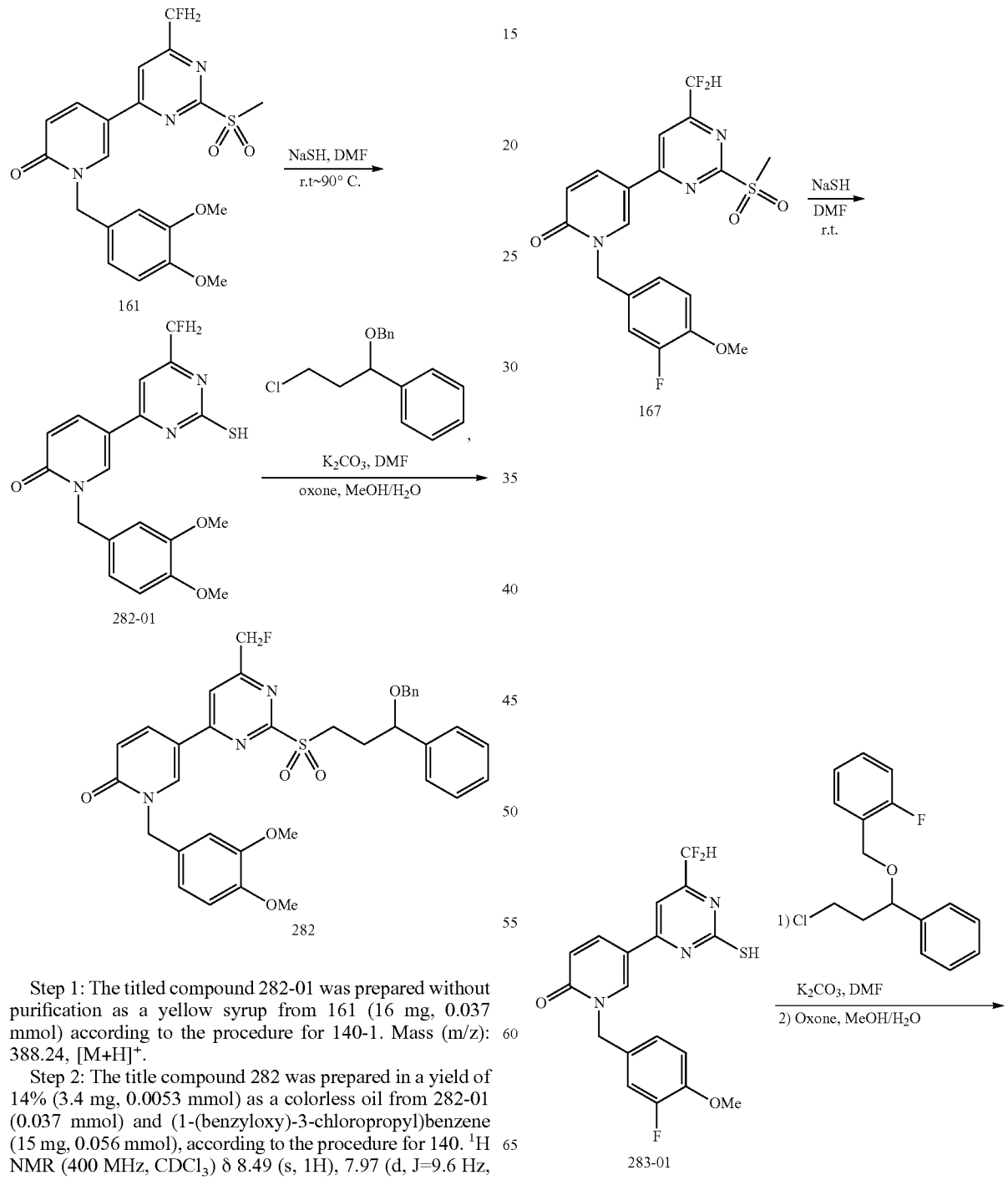

Step 1: The titled compound 282-01 was prepared without purification as a yellow syrup from 161 (16 mg, 0.037 mmol) according to the procedure for 140-1. Mass (m/z): 388.24, [M+H]$^+$.

Step 2: The title compound 282 was prepared in a yield of 14% (3.4 mg, 0.0053 mmol) as a colorless oil from 282-01 (0.037 mmol) and (1-(benzyloxy)-3-chloropropyl)benzene (15 mg, 0.056 mmol), according to the procedure for 140. $^1$H NMR (400 MHz, CDCl$_3$) δ 8.49 (s, 1H), 7.97 (d, J=9.6 Hz, 1H), 7.72-7.71 (m, 1H), 7.66 (s, 1H), 7.54-7.54 (m, 1H),

313

-continued

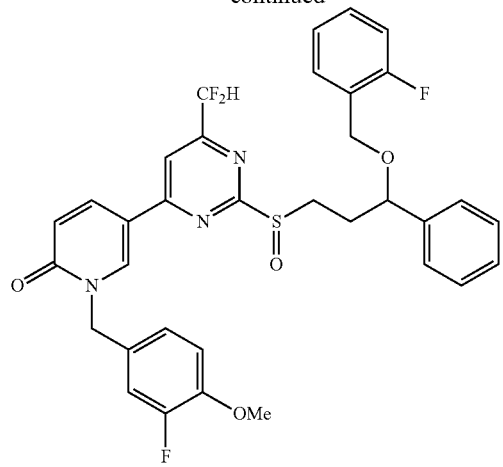

283

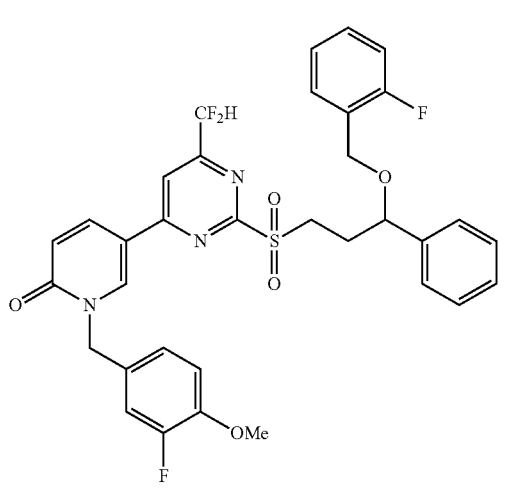

284

Step 1. The compound 283-01 was prepared in a yield of 99% as 285 mg yellow solid from compound 167 (292 mg, 0.67 mmol) according to the procedure for 140-01. Mass (m/z): 394.41[M+H]⁺.

Step 4. The titled compound 283 (25.5 mg, 16.7%) and 284 (5.1 mg, 3.3%) were prepared as both yellow solid from 283-01 (100 mg, 025 mmol) and 1-((3-chloro-1-phenyl-propoxy)methyl)-2-fluorobenzene (106 mg, 0.38 mmol) according to the procedure for 140. 283: ¹HNMR (400 MHz, CDCl₃) δ 8.60 (s, 1H), 7.99 (d, J=9.6 Hz, 1H), 7.70 (s, 1H), 7.32-7.29 (m, 6H), 7.10-7.06 (m, 3H), 7.00-6.88 (m, 2H), 6.72 (d, J=9.6 Hz, 1H), 6.58 (t, J=54.5 Hz, 1H), 5.13 (m, 2H), 4.57 (m, 1H), 4.50-4.26 (m, 3H), 3.84 (s, 3H), 3.42-3.11 (m, 2H), 2.43-2.30 (m, 1H), 2.09-2.00 (m, 1H). Mass (m/z): 652.20 [M+H]⁺. 284: ¹HNMR (400 MHz, CDCl₃) δ 8.57 (s, 1H), 7.99 (d, J=9.6 Hz, 1H), 7.81 (s, 1H), 7.38-7.32 (m, 7H), 7.10 (m, 3H), 7.00 (t, J=9.6 Hz, 1H), 6.91 (t, J=9.6 Hz, 1H), 6.75 (d, J=9.6 Hz, 1H), 6.55 (t, J=54.4 Hz, 1H), 5.13 (s, 2H), 4.56 (m, 1H), 4.49 (d, J=12.0 Hz, 1H), 4.37 (d, J=12.0 Hz, 1H), 3.85 (s, 3H), 3.84-3.76 (m, 1H), 3.65-3.57 (m, 1H), 2.34-2.26 (m, 2H). Mass (m/z): 668.21[M+H]⁺

314

5-(2-(3-(2,4-difluorobenzyloxy)-3-phenylpropylsulfinyl)-6-(difluoromethyl)pyrimidin-4-yl)-1-(3-fluoro-4-methoxybenzyl)pyridin-2 (1H)-one (285) and 5-(2-(3-(2,4-difluorobenzyloxy)-3-phenylpropylsulfonyl)-6-(difluoromethyl)pyrimidin-4-yl)-1-(3-fluoro-4-methoxybenzyl)pyridin-2 (1H)-one (286)

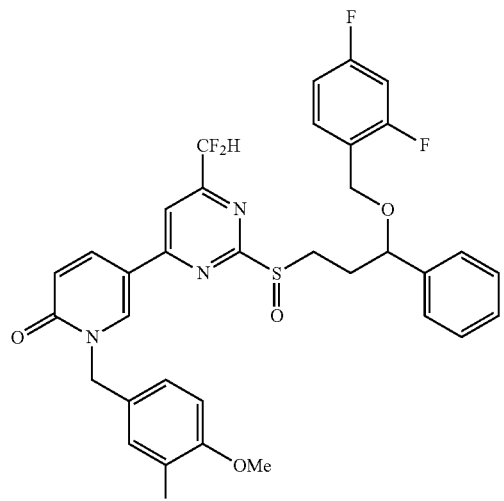

285

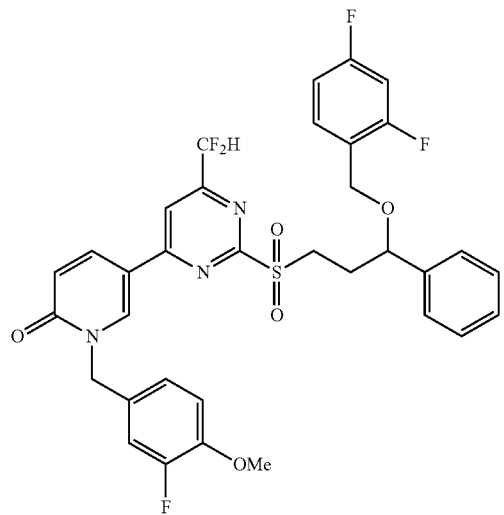

286

The titled compound 285 (14.3 mg, 10.3%), and 286 (15.0 mg, 8.1%) were prepared as both yellow solid from 283-01 (100 mg, 0.25 mmol) and 1-((3-chloro-1-phenylpropoxy) methyl)-2,4-difluorobenzene (112 mg, 0.38 mmol) according to the procedure for 140. 285: ¹HNMR (400 MHz, CDCl₃) δ 8.62 (s, 1H), 7.98 (d, J=9.2 Hz, 1H), 7.70 (s, 1H), 7.33-7.28 (m, 6H), 7.12 (d, J=9.6 Hz, 2H), 6.91 (t, J=8.4 Hz, 1H), 6.83-6.72 (m, 3H), 6.59 (t, J=54.4 Hz, 1H), 5.15 (s, 2H), 4.56 (m, 1H), 4.44-4.21 (m, 3H), 3.85 (s, 3H), 3.40-3.11 (m, 2H), 2.46-2.24 (m, 1H). Mass (m/z): 670.19[M+H]⁺. 286: ¹HNMR (400 MHz, CDCl₃) δ 8.57 (s, 1H), 8.00 (d, J=9.2 Hz, 1H), 7.81 (s, 1H), 7.39-7.29 (m, 6H), 7.10 (d, J=10.4 Hz, 2H), 6.93 (t, J=8 Hz, 1H), 6.84 (t, J=8 Hz, 1H), 6.79 (m, 2H), 6.56 (t, J=54.4 Hz, 1H), 5.15 (s, 2H), 4.57 (m, 1H), 4.44 (d, J=11.6 Hz, 1H), 4.34 (d, J=12.0 Hz, 1H), 3.86

(s, 3H), 3.80-3.72 (m, 1H), 3.64-3.56 (m, 1H), 2.34-2.26 (m. 2H). Mass (m/z): 686.16[M+H]⁺.

5-(6-(difluoromethyl)-2-((3-hydroxy-3-phenylpropyl)sulfonyl)pyrimidin-4-yl)-1-(3-fluoro-4-methoxybenzyl)pyridin-2 (1H)-one (287)

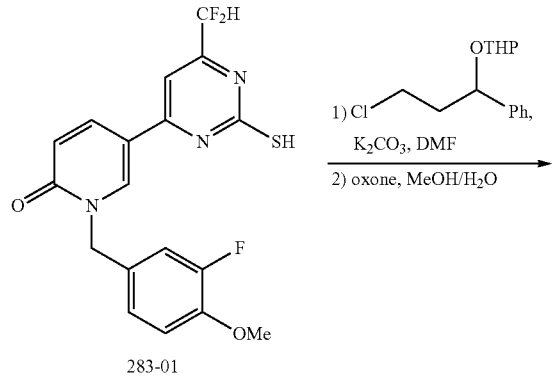

283-01

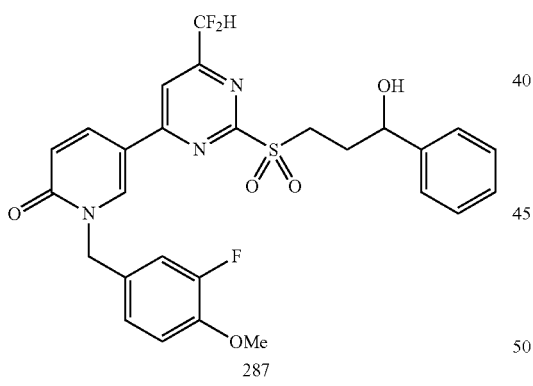

287

The title compound 287 (13 mg, 0.023 mmol) was prepared as a white solid from 283-01 (59 mg, 0.15 mmol) and 2-(3-chloro-1-phenylpropoxy)tetrahydro-2H-pyran (58 mg, 0.23 mmol), according to the procedure for 140. ¹H NMR (400 MHz, CDCl₃) δ 8.65 (d, J=2.4 Hz, 1H), 8.01 (dd, J=2.4, 9.6 Hz, 1H), 7.83 (s, 1H), 7.38-7.29 (m, 5H), 7.13-7.10 (m, 2H), 6.94 (t, J=8.4 Hz, 1H), 6.79 (d, J=9.6 Hz, 1H), 6.61 (t, J=54.4 Hz, 1H), 5.18 (s, 2H), 4.96 (dd, J=5.2, 7.6 Hz, 1H), 3.87 (s, 3H), 3.82-3.66 (m, 2H), 2.37-2.25 (m, 2H). Mass (m/z): 560.13, [M+H]⁺.

N-((3s,5s,7s)-adamantan-1-yl)-4-((4-(difluoromethyl)-6-(1-(3,4-dimethoxybenzyl)-6-oxo-1,6-dihydropyridin-3-yl)pyrimidin-2-yl)sulfonyl)butanamide (288)

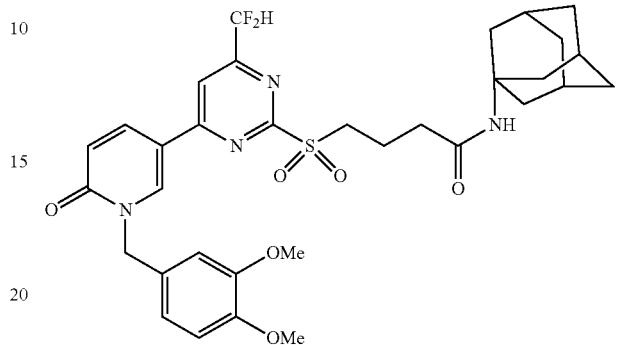

288

The titled compound 288 (3.2 mg, 5.6% yield) was prepared as white solid from 172-1 (58 mg, 0.14 mmol) and N-((3s,5s,7s)-adamantan-1-yl)-4-bromobutanamide (78 mg, 0.26 mmol) according to the procedure for 140. ¹HNMR (400 MHz, CDCl₃) δ 8.83 (d, J=2.8 Hz, 1H), 7.98 (dd, J=2.4, 9.6 Hz, 1H), 7.81 (s, 1H), 7.01-6.96 (m, 2H), 6.86 (d, J=8.4 Hz, 1H), 6.74 (d, J=4.8 Hz, 1H), 6.65 (t, J=54.4 Hz, 1H), 5.35 (m, 1H), 5.27 (s, 3H), 3.87 (s, 3H), 3.86 (s, 3H), 3.65 (t, J=7.2 Hz, 2H), 2.35 (t, J=6.4 Hz, 2H), 2.23 (m, 3H), 2.03 (m, 5H), 1.96 (m, 6H) 1.63 (m, 3H). Mass (m/z): 657.51[M+H]⁺;

N-((3s,5s,7s)-adamantan-1-yl)-4-((4-(1-(3,4-dimethoxybenzyl)-6-oxo-1,2,3,6-tetrahydropyridin-3-yl)-6-(trifluoromethyl)pyrimidin-2-yl)sulfonyl)butanamide (289)

EC50=0.42 nM

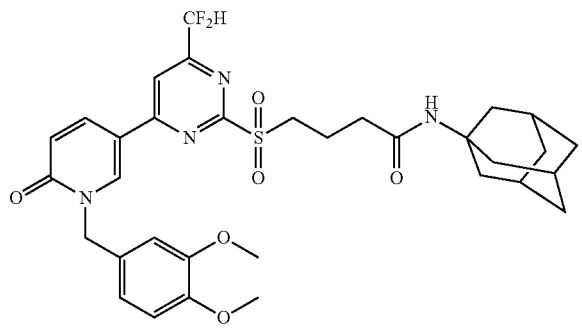

289

The titled compound (9 mg, 16% yield) was prepared as a white solid from 140-01 (40 mg, 0.094 mmol) and N-((1S,3s)-adamantan-1-yl)-4-bromobutanamide (30 mg, 0.1 mmol) according to the procedure for 140. ¹H NMR (400 MHz, CDCl₃) δ 8.85 (d, 1H, J=2.4 Hz), 7.96 (dd, 1H, J=2.4, 9.6 Hz), 7.81 (s, 1H), 6.99 (d, 1H, J=2.0 Hz), 6.70 (dd, 1H, J=2.0, 4.0 Hz), 6.84 (d, 1H, J=8.0 Hz), 6.72 (d, 1H, J=9.6 Hz), 5.26 (s, 2H), 3.87 (s, 3H), 3.86 (s, 3H), 3.67 (t, 2H, J=7.2 Hz), 2.36 (t, 2H, J=6.8 Hz), 2.26-2.22 (m, 2H), 2.04-2.01 (m, 3H), 1.96-1.95 (m, 6H), 1.27-1.24 (m, 6H). $^{13}$C NMR (100 MHz, CDCl$_3$): δ 169.89, 166.32, 165.48, 162.06, 157.76, 157.41, 149.46, 141.88, 135.81, 130.02, 127.87, 121.46, 121.22, 113.16, 112.08, 111.99, 111.36, 56.15, 56.08, 53.15, 52.32, 50.99, 41.79, 36.39, 35.15, 29.51, 27.35, 25.67, 22.83, 18.83. HRMS (ESI): calculated for [C$_{33}$H$_{38}$F$_3$N$_4$O$_6$S$^+$], 675.2459, found 675.2479.

2-(3-(benzyloxy)-3-phenylpropylsulfinyl)-4-(thiophen-2-yl)-6-(trifluoromethyl)pyrimidine (290) and 2-(3-(benzyloxy)-3-phenylpropylsulfonyl)-4-(thiophen-2-yl)-6-(trifluoromethyl)pyrimidine (291)

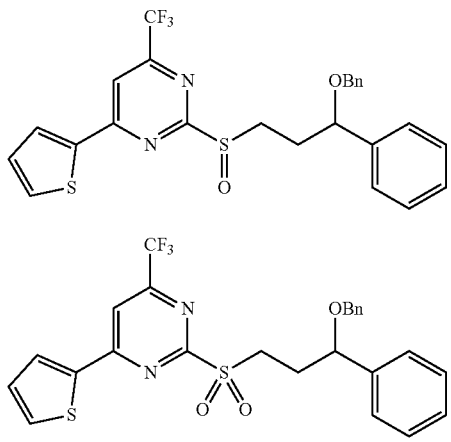

The titled compounds 290 (13.5 mg, 17.2% yield) and 291 (21.2 mg, 26.2% yield) was prepared as both white solid from 1-02 (30 mg, 0.12 mmol) and (1-(benzyloxy)-3-chloropropyl)benzene (47 mg, 0.18 mmol) according to the procedure for 140. 290: $^1$HNMR (400 MHz, CDCl$_3$) δ 7.98 (d, J=4.4 Hz, 1H), 7.79 (d, J=1.6 Hz, 1H), 7.71-7.69 (m, 1H), 7.35-7.28 (m, 8H), 7.24-7.22 (m, 3H), 4.57 (q, J=4.0 Hz, 1H), 4.49-4.42 (m, 1H), 4.30 (d, J=12.0 Hz, 1H), 4.22 (d, J=12 Hz, 1H), 3.46-3.38 (m, 1H), 3.32-3.15 (m, 1H), 2.48-2.32 (m, 1H). Mass (m/z): 503.27[M+H]$^+$. 291: $^1$HNMR (400 MHz, CDCl$_3$) δ 7.99 (d, J=3.6 Hz, 1H), 7.89 (s, 1H), 7.73 (d, J=5.2 Hz, 1H), 7.38-7.28 (m, 10H), 7.23 (t, J=4.4 Hz, 1H), 4.58 (q, J=4.0 Hz, 1H), 4.51 (d, J=12.0 Hz, 1H), 4.30 (d, J=12.0 Hz, 1H), 3.89-3.81 (m, 1H), 3.72-3.6 (m, 1H), 2.44-2.31 (m, 2H). Mass (m/z): 519.28[M+H]$^+$.

2-((3-chloro-3-phenylpropyl)sulfonyl)-4-(thiophen-2-yl)-6-(trifluoromethyl)pyrimidine (292)

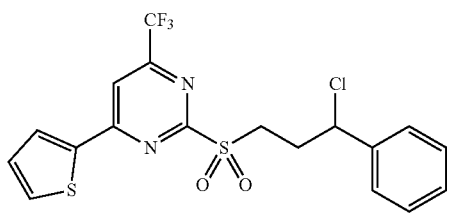

The titled compound 292 was prepared in a yield of 71.2% (13 mg, 0.029 mmol) as a light yellow oil from 291 (18.8 mg, 0.036 mmol) according to the procedure for 273. $^1$HNMR (400 MHz, CDCl$_3$) δ 8.03 (dd, J=1.2, 4.0 Hz, JH), 7.94 (s, 1H), 7.77 (dd, J=1.2, 4.8 Hz, 1H), 7.42-7.33 (m, 5H), 7.31-7.27 (m, 1H), 5.12 (m, 1H), 3.88-3.80 (m, 1H), 3.77-3.69 (m, 1H), 2.76-2.67 (m, 2H). Mass (m/z): 447.17, [M+H]$^+$.

5-(2-((3-(benzyloxy)-3-phenylpropyl)sulfonyl)quinazolin-4-yl)-1-(3,4-dimethoxybenzyl)pyridin-2(1H)-one (293)

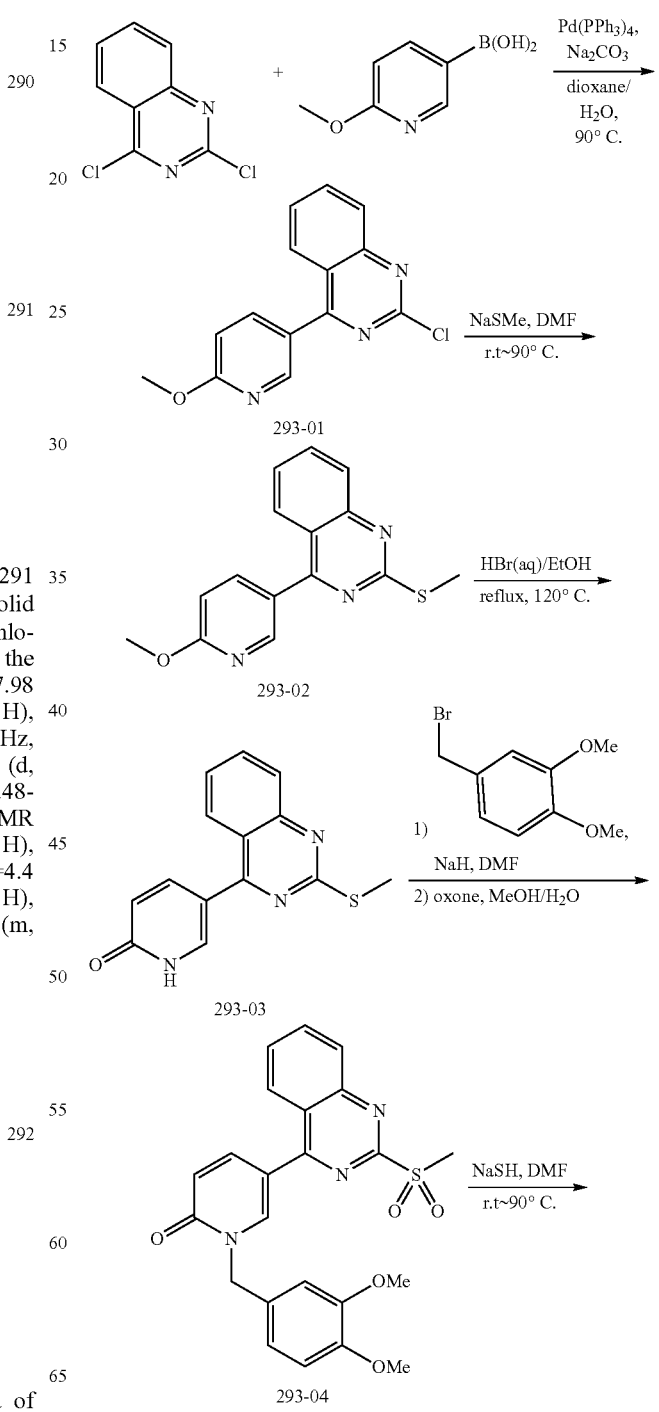

319
-continued

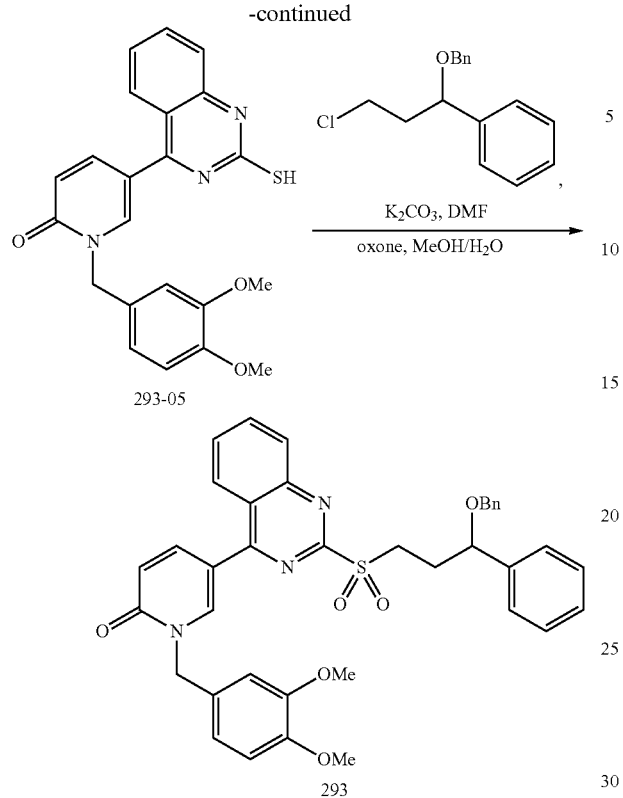

Step 1: The titled compound 293-01 was prepared in a yield of 63.7% (0.87 g, 3.2 mmol) as a white solid from 2,4-dichloroquinazoline (1.0 g, 5.02 mmol) and (6-methoxypyridin-3-yl)boronic acid (0.52 g, 3.35 mmol) according to the procedure for 99-01. Mass (m/z): 272.17, [M+H]$^+$.

Step 2: The titled compound 293-02 was prepared as described above for the synthesis of 140-1, NaSMe was used instead, 0.6 g of yellow solid was obtained, which was used directly in the next step without further purification. Mass (m/z): 284.13, [M+H]$^+$.

Step 3: The titled compound 293-03 was prepared without purification (0.5 g) as a yellow solid from 293-02 (0.6 g) according to the procedure for 99-02. Mass (m/z): 270.20, [M+H]$^+$.

Step 4: The titled compound 293-04 was prepared in a yield of 2.4% (16 mg, 0.035 mmol) as a colorless oil from 293-03 (0.4 g, 1.48 mmol) and 4-(bromomethyl)-1,2-dimethoxybenzene (0.34 g, 1.48 mmol) according to the procedure for 99-01. Mass (m/z): 452.21, [M+H]$^+$.

Step 5: The titled compound 293-05 was prepared without purification as a yellow syrup from 293-04 (16 mg, 0.035 mmol) according to the procedure for 140-1. Mass (m/z): 406.18, [M+H]$^+$.

Step 6: The title compound 293 was prepared in a yield of 8.57% (2.0 mg, 0.003 mmol) as a colorless oil from 293-05 (0.035 mmol) and (1-(benzyloxy)-3-chloropropyl)benzene (14 mg, 0.053 mmol), according to the procedure for 140. $^1$H NMR (400 MHz, CDCl$_3$) δ 8.21 (m, 1H), 8.07 (m, 3H), 7.87 (m, 1H), 7.75-7.71 (m, 1H), 7.36-7.26 (m, 11H), 6.98 (s, 1H), 6.94-6.92 (m, 1H), 6.84-6.82 (m, 1H), 6.77-6.75 (m, 1H), 5.18 (s, 2H), 4.58 (t, J=5.6 Hz, 1H), 4.48 (d, J=1 Hz, 1H), 4.29 (d, J=11.2 Hz, 1H), 3.88 (s, 3H), 3.86 (s, 3H), 3.75-3.67 (m, 2H), 2.40-2.32 (m, 2H). Mass (m/z): 662.32, [M+H]$^+$.

320

5-(2-(3-(benzyloxy)-3-phenylpropylsulfinyl)-6-methylpyrimidin-4-yl)-1-(3,4-dimethoxybenzyl)pyridin-2 (1H)-one (294) and 5-(2-(3-(benzyloxy)-3-phenylpropylsulfonyl)-6-methylpyrimidin-4-yl)-1-(3,4-dimethoxybenzyl)pyridin-2 (1H)-one (295)

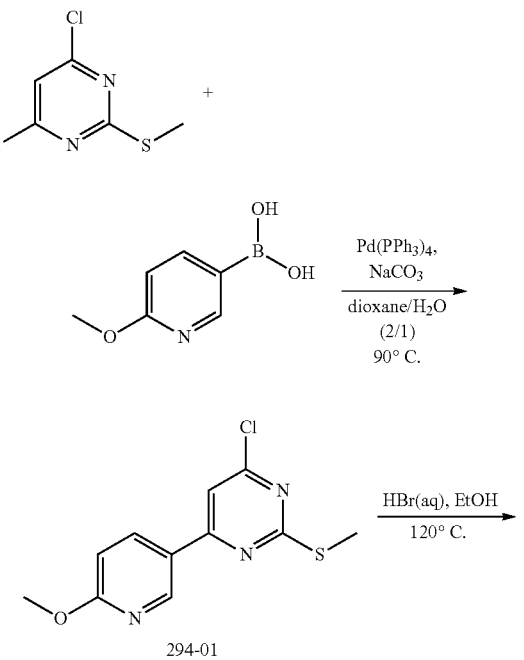

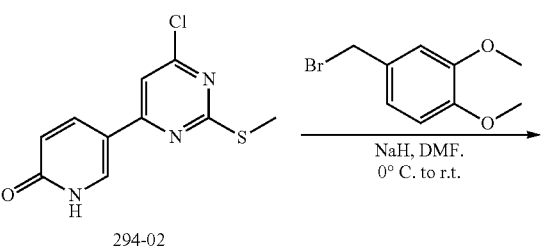

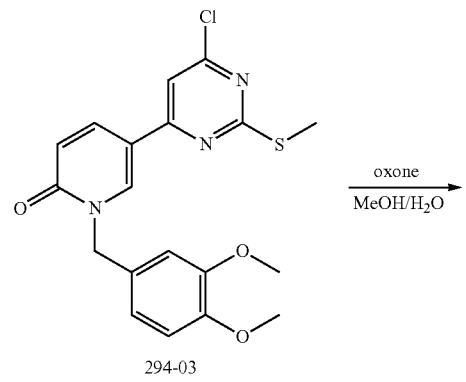

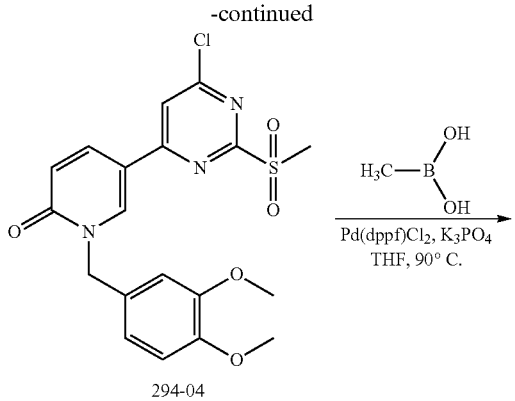

294-04

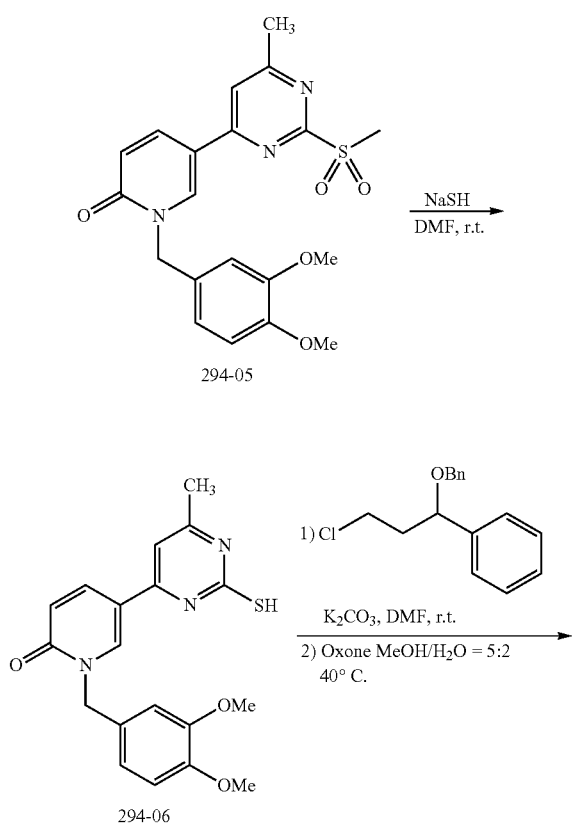

294-05

294-06

294

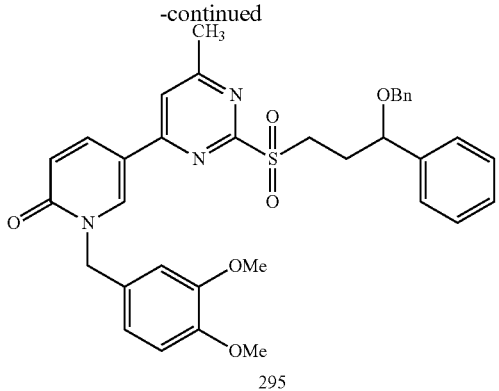

295

Step 1: A mixture of 4,6-dichloro-2-(methylthio)pyrimidine (6.7 g, 0.034 mol), 6-methoxypyridin-3-ylboronic acid (3.5 g, 0.023 mol), $Na_2CO_3$ (10.8 g, 0.10 mol) and $Pd(PPh_3)_4$ (1.0 g, 0.86 mmol) in 1,4-dioxane (50 mL) and $H_2O$ (25 mL) was heated to 90° C. The reaction mixture was stirred for 3 h under $N_2$. Evaporation to remove the 1,4-dioxane, the mixture was diluted by $H_2O$. The aqueous layer was extracted by EtOAc for 3 times. The organic layer was combined, washed by brine, dried over $Na_2SO_4$ and further purified by silica gel column chromatography (PE: EA=300:1 to 100:1) to give 5.3 g of 294-01 as white solid (86.9/6). Mass (m/z); 269.16[M+H]$^+$.

Step 2. The compound 294-02 was prepared in a yield of 92.0% (4.62 g) as light yellow solid from 294-01 (5.3 g, 19.8 mmol) according to the procedure for 99-02. Mass (m/z): 254.16[M+H]$^+$.

Step 3. The compound 294-03 was prepared in a yield of 53.6% (3.87 g) as white solid from 294-02 (4.52 g, 17.9 mmol) according to the procedure for 85-01. Mass (m/z): 404.20[M+H]$^+$.

Step 4. The compound 294-04 was prepared in a yield of 82.8% (3.46 g) as yellow solid from 294-3 (3.87 g, 9.6 mmol) and Oxone (11.8 g, 19.2 mmol) according to the procedure for 85. Mass (m/z): 436.59[M+H]$^+$.

Step 5. $Pd(dppf)Cl_2$ (214 mg, 0.29 mmol) was added to the solution of 294-04 (1.3 g, 2.98 mmol), methylboronic acid (180 mg, 3.01 mmol) and $K_3PO_4$ (1.58 g 7.44 mmol) in THF (15 mL) under $N_2$. The mixture was heated to 90° C. and stirred overnight. The reaction mixture was diluted by $H_2O$, extracted by EtOAc for 3 times. The organic layer was combined, washed by brine, dried over $Na_2SO_4$. Evaporation to remove the solvent, further purified by pre-TLC (DCM:MeOH=20:1) to give 77.8 mg of 294-05 as light yellow oil (5.9%). Mass (m/z): 416.12, [M+H]$^+$.

Step 6. The compound 294-06 was prepared as yellow oil from compound 294-05 (78 mg, 0.19 mmol) according to the procedure for 140-01. Mass (m/z): 370.11 [M+H]$^+$.

Step 7. The titled compound 294 (5.2 mg, 18.2%), and 295 (3.2 mg, 10.9%) were prepared as White solid and colorless oil from 294-06 (0.19 mmol) and (1-(benzyloxy)-3-chloropropyl)benzene (74 mg, 0.28 mmol) according to the procedure for 140. 294: $^1$HNMR (400 MHz, CDCl$_3$) δ 8.44 (s, 1H), 7.91 (d, J=9.6 Hz, 1H), 7.72-7.51 (m, 1H), 7.36-7.29 (m, 8H), 7.23 (m, 2H), 6.94 (s, 1H), 6.89-6.86 (m, 1H), 6.81 (d, J=8 Hz, 1H), 6.69 (dd, J=3.2, 9.6 Hz, 1H), 5.12 (m, 2H), 4.56 (q, J=4 Hz, 1H), 4.47-4.40 (m, 1H), 4.32-4.17 (m. 2H), 3.85 (s, 3H), 3.84 (s, 3H), 3.35-3.09 (m, 2H), 2.60 (s, 3H), 2.41-2.31 (m, 1H). Mass (m/z); 610.46 [M+H]$^+$; 295: $^1$HNMR (400 MHz, CDCl$_3$) δ 8.44 (d, J=2.8 Hz, 1H), 7.90 (dd, J=2.4, 9.6 Hz, 1H), 7.38-7.27 (m, 10H), 6.93 (d, J=2.0 Hz. 1H), 6.88 (dd, J=2.0. 8.0 Hz, 1H), 6.82 (d, J=8.4 Hz, 1H), 6.68 (dd, J=9.6 Hz, 1H), 5.12 (m, 2H), 4.56 (m, 1H), 4.48 (d, J=11.6 Hz, 1H), 4.29 (d, J=11.6 Hz, 1H), 3.86 (s, 3H), 3.84 (s, 3H), 3.82-3.72 (m, 1H), 3.62-3.55 (m, 1H), 2.61 (s, 3H), 2.35-2.20 (m, 3H). Mass (m/z): 626.48 [M+H]+.

1-(3,4-dimethoxybenzyl)-5-(6-(2-fluorophenyl)-2-(methylsulfonyl)pyrimidin-4-yl)pyridin-2 (1H)-one (296)

5-(2-((3-(benzyloxy)-3-phenylpropyl)sulfinyl)-6-(2-fluorophenyl)pyrimidin-4-yl)-1-(3,4-dimethoxybenzyl)pyridin-2 (1H)-one (297) and 5-(2-((3-(benzyloxy)-3-phenylpropyl)sulfonyl)-6-(2-fluorophenyl)pyrimidin-4-yl)-1-(3,4-dimethoxybenzyl)pyridin-2 (1H)-one (298)

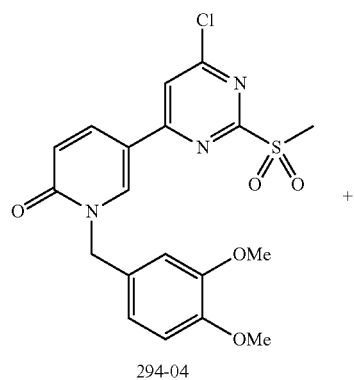

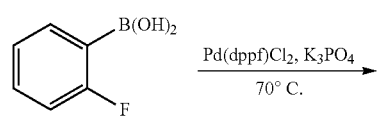

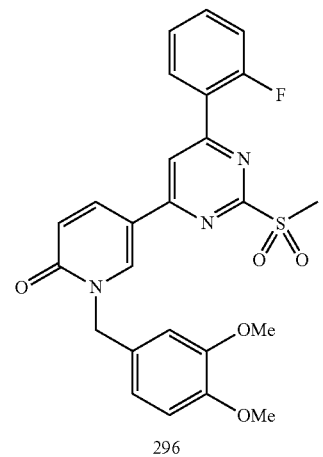

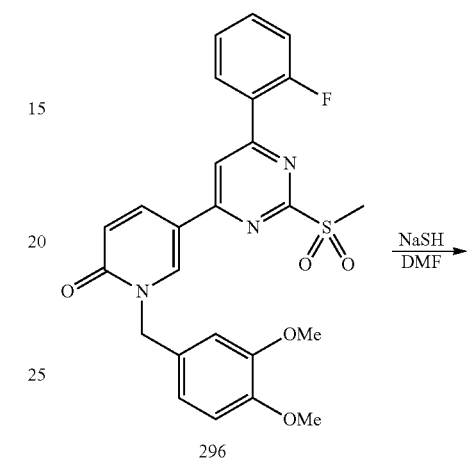

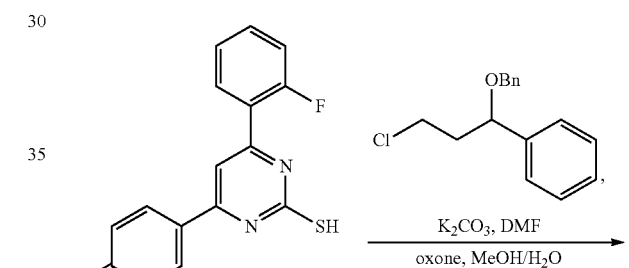

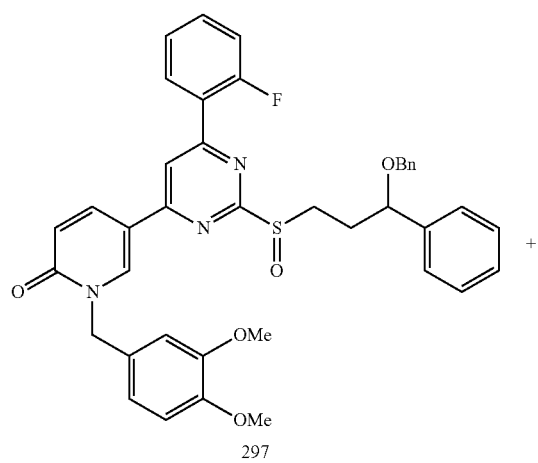

The titled compound 296 (0.13 g, 76%) were prepared as brown solid from 294-04 (0.15 g, 0.35 mmol) and (2-fluorophenyl)boronic acid (59 mg, 0.42 mmol) according to the procedure for 294-05. $^1$H NMR (400 Hz, CDCl$_3$) δ 8.58 (s, 1H), 8.26 (t, J=6.8 Hz, 1H), 8.09-8.01 (m, 2H), 7.58-7.53 (m, 1H), 7.35 (t, J=7.2 Hz, 1H), 7.24 (m, 1H), 7.00-6.94 (m, 2H), 6.87-6.85 (m, 1H), 6.75-6.74 (m, 1H), 5.21 (s, 2H), 3.89 (s, 3H), 3.87 (s, 3H), 3.40 (s, 3H). Mass (m/z): 496.30, [M+H]+.

-continued

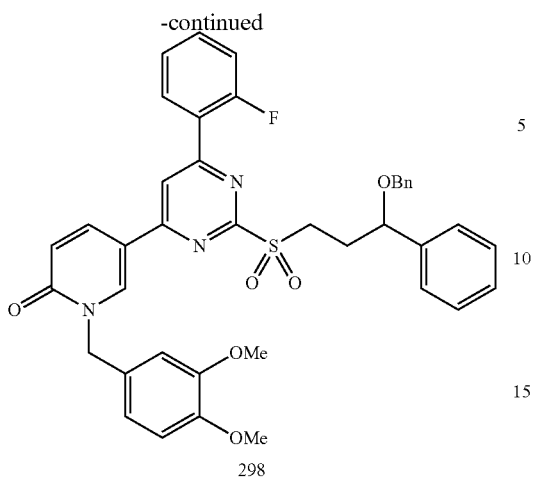

298

Step 1: The titled compound 297-01 was prepared without purification as a yellow solid from 304 (70 mg, 0.14 mmol) according to the procedure for 140-01. Mass (m/z): 450.18, [M+H]$^+$.

Step 2: The title compound 297 (13 mg, 0.019 mmol) and 298 (15 mg, 0.021 mmol) was prepared as a colorless oil from 297-01 (48 mg, 0.11 mmol) and (1-(benzyloxy)-3-chloropropyl)benzene (44 mg, 0.17 mmol), according to the procedure for 140. 297: $^1$H NMR (400 MHz, CDCl3) δ 8.60 (m, 1H), 8.20 (m, 1H), 8.01-7.95 (m, 2H), 7.53 (m, 1H), 7.31-7.20 (m, 12H), 6.87-6.92 (m, 2H), 6.83-6.74 (m, 2H), 5.19 (s, 2H), 4.59-4.57 (m, 0.6H), 4.49-4.41 (m, 1.49H), 4.32 (d, J=11.6 Hz, 0.57H), 4.21 (d, J=11.6 Hz, 0.54H), 3.87, 3.85 (s*2, 6H), 3.43-3.20 (m, 2H), 2.43-2.37 (m, 2H). Mass (m/z): 690.29, [M+H]$^+$. 298: $^1$H NMR (400 MHz, CDCl$_3$) δ 8.54 (s, 1H), 8.20 (t, J=7.6 Hz, 1H), 8.06 (s, 1H), 7.99 (d, J=9.6 Hz, 1H), 7.56-7.51 (m, 1H), 7.35-7.23 (m, 12H), 6.96 (s, 1H), 6.92 (d, J=8.4 Hz, 1H), 6.84-6.82 (m, 1H), 6.73 (d, J=9.6 Hz, 1H), 5.16 (s, 2H), 4.59-4.56 (m, 1H), 4.50 (d, J=11.6 Hz, 1H), 4.30 (d, J=11.6 Hz, 1H), 3.91-3.85 (m, 7H), 3.69-3.62 (m, 1H), 2.40-2.32 (m, 2H). Mass (m/z): 706.27, [M+H]$^+$.

5-(2-((3-(benzyloxy)-3-phenylpropyl)sulfinyl)-6-(thiophen-2-yl)pyrimidin-4-yl)-1-(3,4-dimethoxybenzyl)pyridin-2(1H)-one (299) and 5-(2-((3-(benzyloxy)-3-phenylpropyl)sulfonyl)-6-(thiophen-2-yl)pyrimidin-4-yl)-1-(3,4-dimethoxybenzyl)pyridin-2(1H)-one (300)

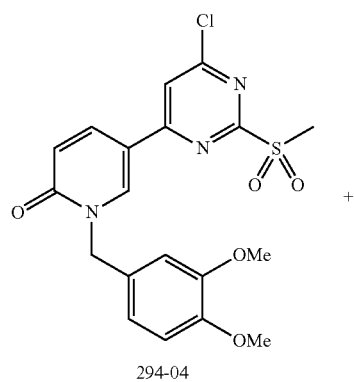

294-04

+

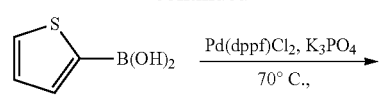

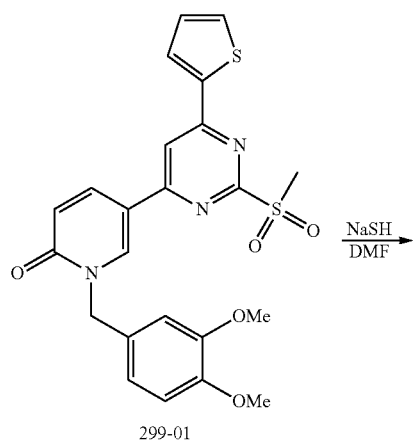

299-01

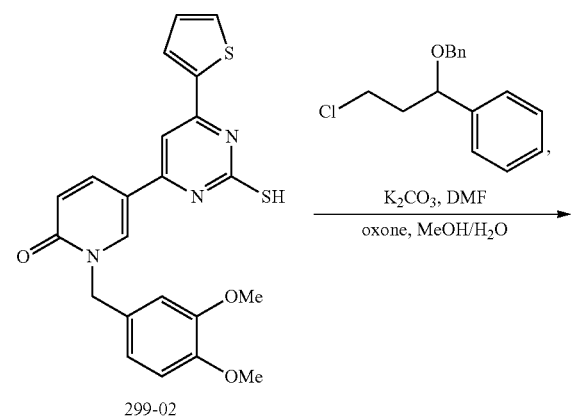

299-02

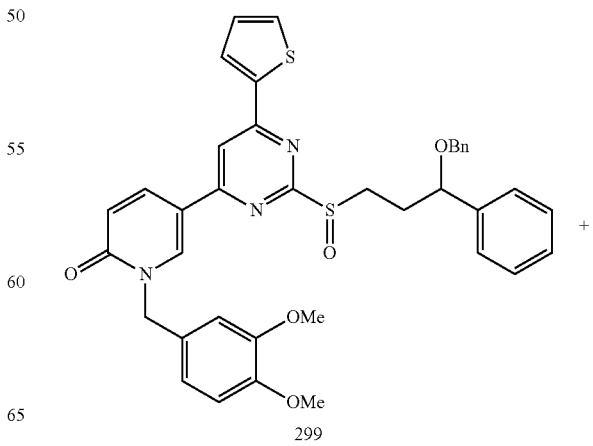

299

+

-continued

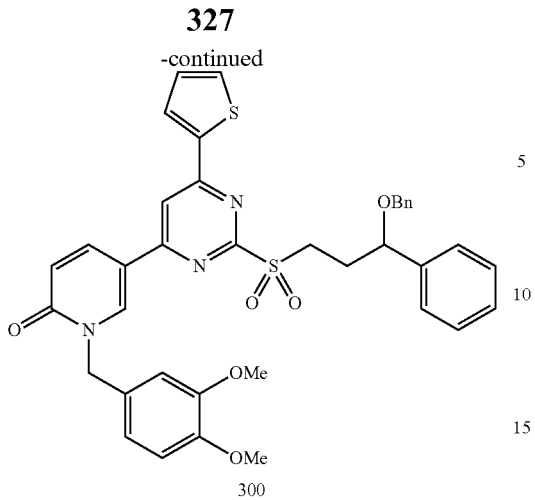

300

Step 1: The title compound 299-01 (0.15 g, 0.31 mmol) was prepared in a yield of 91% as a brown solid from 294-04 (0.15 g, 0.34 mmol) and thiophen-2-ylboronic acid (52 mg, 0.41 mmol), according to the procedure for 294-05. Mass (m/z): 484.10, [M+H]$^+$.

Step 2: The titled compound 299-02 was prepared without purification as a yellow solid from 299-01 (0.15 g, 0.31 mmol) according to the procedure for 140-1. Mass (m/z): 438.07, [M+H]$^+$.

Step 3: The title compound 299 (6 mg, 0.0089 mmol) and 300 (10 mg, 0.014 mol) was prepared as colorless oil from 299-02 (0.31 mmol) and (1-(benzyloxy)-3-chloropropyl)benzene (96 mg, 0.37 mmol), according to the procedure for 140. 299: $^1$H NMR (400 MHz, CDCl$_3$) δ 8.64 (s, 1H), 8.00 (d, J=8.4 Hz, 1H), 7.89 (m, 1H), 7.62 (t, J=4.8 Hz, 2H), 7.34-7.19 (m, 11H), 6.97 (m, 1H), 6.92 (dd, J=7.6 Hz, 1H), 6.82 (m, 1H), 6.76 (d, J=8.4 Hz, 1H), 5.24-5.11 (m, 2H), 4.58-4.56 (m, 0.58H), 4.50-4.41 (m, 1.62H), 4.32 (d, J=11.6 Hz, 0.60H), 4.21 (d, J=11.6 Hz, 0.62H), 3.87 (s, 3H), 3.85 (s, 3H), 3.47-3.40 (m, 1H), 3.35-3.29 (m, 0.54H), 3.25-3.19 (m, 0.53H), 2.46-2.34 (n, 1H), 2.15-2.10 (m, 1H). Mass (m/z): 678.17, [M+H]$^+$. 300: $^1$H NMR (400 MHz, CDCl$_3$) δ 8.58 (s, 1H), 7.95 (d, J=7.6 Hz, 1H), 7.87 (d, J=2.8 Hz, 1H), 7.65 (s, 1H), 7.60 (d, J=5.2 Hz, 1H), 7.39-7.26 (m, 10H), 7.17 (t, J=4.0 Hz, 1H), 6.97 (s, 1H), 6.92 (d, J=8.4 Hz, 1H), 6.83 (d, J=8.0 Hz, 1H), 6.73 (d, J=8.8 Hz, 1H), 5.17 (s, 2H), 4.60-4.57 (m, 1H), 4.51 (d, J=11.6 Hz, 1H), 4.31 (d, J=12.0 Hz, 1H), 3.92-3.79 (m, 7H), 3.70-3.63 (m, 1H), 2.42-2.30 (m, 2H). Mass (m/z): 694.20, [M+H]$^+$.

3-fluoro-1-(3-fluoro-4-methoxybenzyl)-5-(2-(3-(2-fluorobenzyloxy)-3-phenylpropylsulfinyl)thieno[2,3-d]pyrimidin-4-yl)pyridin-2 (1H)-one (301) and 3-fluoro-1-(3-fluoro-4-methoxybenzyl)-5-(2-(3-(2-fluorobenzyloxy)-3-phenylpropylsulfonyl)thieno[2,3-d]pyrimidin-4-yl)pyridin-2 (1H)-one (302)

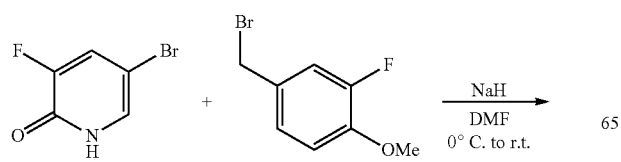

-continued

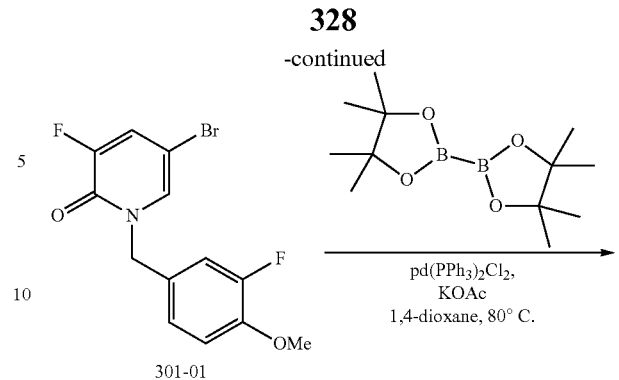

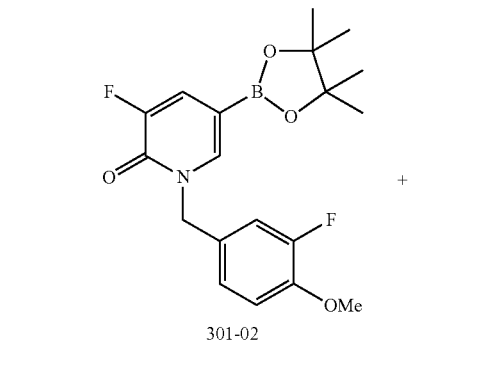

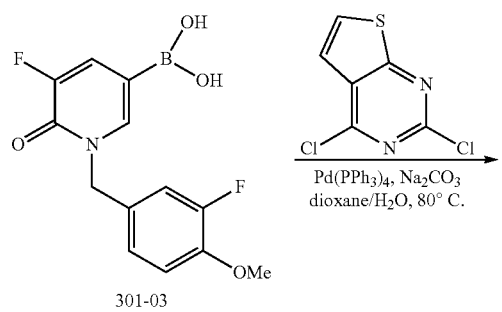

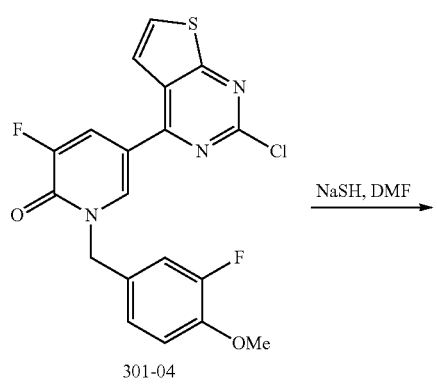

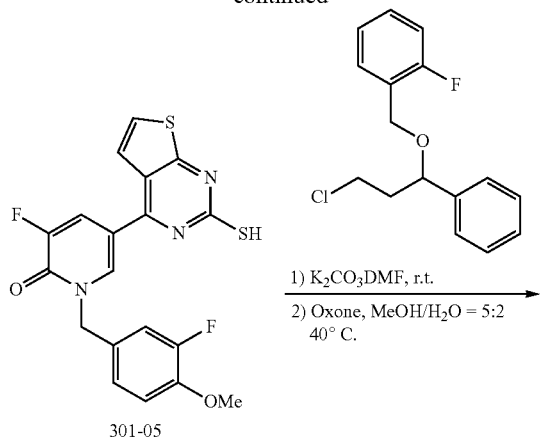

301-05

1) K₂CO₃DMF, r.t.
2) Oxone, MeOH/H₂O = 5:2
40° C.

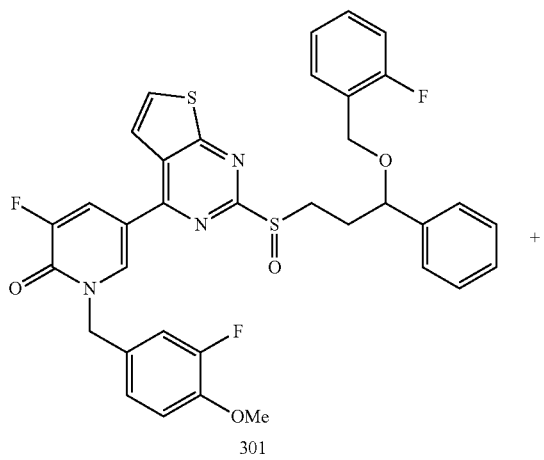

301

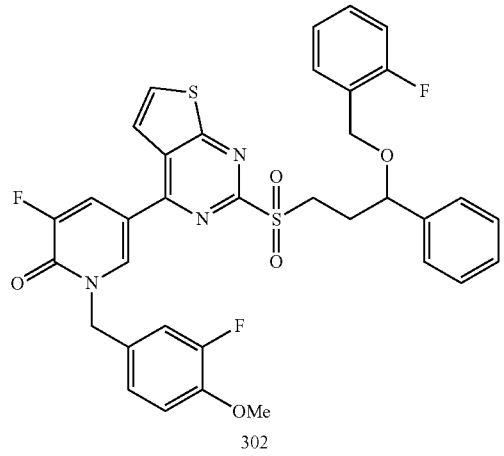

302

Step 1. The compound 301-01 was prepared in a yield of 70.6% as white solid (3.73 g) from 5-bromo-3-fluoropyridin-2 (1H)-one (3.0 g, 16.0 mmol) and 4-(bromomethyl)-2-fluoro-1-methoxybenzene (3.8 g, 17.0 mmol) according to the procedure for 165-04. Mass (m/z): 329.98, [M+H]⁺.

Step 2. Pd(PPh₃)₂Cl₂ (442 mg, 0.60 mmol) was added to the mixture of 301-01 (2.0 g, 6.05 mmol), 4,4,4',4',5,5,5',5'-octamethyl-2,2'-bi(1,3,2-dioxaborolane) (3.1 g, 12.1 mmol) and KOAc (1.78 g, 18.2 mmol) in 1,4-dioxane (40 mL) under N₂. Then the mixture was heated to 80° C., stirred for 3 h. Evaporation to remove the solvent, the residue was washed by EtOAc to give the mixture of 301-02 and 301-03 as brown powder in a yield of 98%. The product was used without further purification. 301-2: Mass (m/z): 379.17, [M+H]⁺, 301-03: Mass (m/z): 296.01 [M+H]⁺.

Step 3. The compound 301-04 was prepared in a yield of 69.8% as yellow solid (77.5 mg) from the mixture (100 mg) of 301-02 and 301-03 and 2,4-dichlorothieno[2,3-d]pyrimidine (100 mg, 0.3 mmol) according to the procedure for 99-01. Mass (m/z): 419.99, [M+H]⁺.

Step 4. The compound 301-05 was prepared as yellow oil from compound 301-04 (77.5 mg, 0.18 mmol) according to the procedure for 140-01. Mass (m/z): 418.01 [M+H]⁺.

Step 5. The titled compound 301 (8.5 mg, 6.3%), and 302 (5.5 mg, 5.5%) were prepared as both white solid from 301-5 and 1-((3-chloro-1-phenylpropoxy)methyl)-2-fluorobenzene (75 mg, 0.27 mmol) according to the procedure for 140. 301: ¹HNMR (400 MHz, CDCl₃) δ 8.04 (s, 1H), 7.75 (m, 2H), 7.42 (d, J=6 Hz, 1H), 7.34-7.28 (m, 7H), 7.16 (d, J=10.4 Hz, 2H), 7.10-6.92 (m, 3H), 5.27-5.16 (m, 2H), 4.59-4.36 (m, 2H), 4.32-4.20 (m, 1H), 3.87 (s, 3H), 3.41-3.18 (m, 1H), 2.46-2.31 (m, 1H), 2.13-1.95 (m, 1H). Mass (m/z): 676.13[M+H]⁺. 302: ¹HNMR (400 MHz, CDCl₃) δ 8.05 (s, 1H), 7.87 (d, J=6.0 Hz, 1H), 7.80 (dd, J=2.4, 10.0 Hz, 1H), 7.48 (d, J=6.0 Hz, 1H), 7.37-7.27 (m, 7H), 7.16-7.08 (m, 3H), 7.02-6.92 (m, 2H), 5.21 (m, 2H), 4.57 (m, 1H), 4.49 (d, J=12.0 Hz, 1H), 4.36 (d, J=12.0 Hz, 1H), 3.87 (s, 3H), 3.85-3.77 (m, 1H), 3.69-3.61 (m, 1H), 2.35-2.27 (m, 2H). Mass (m/z): 692.14, [M+H]⁺.

3-fluoro-1-(3-fluoro-4-methoxybenzyl)-5-(6-methyl-2-((3-oxobutyl)sulfonyl)pyrimidin-4-yl)pyridin-2 (1H)-one (303)

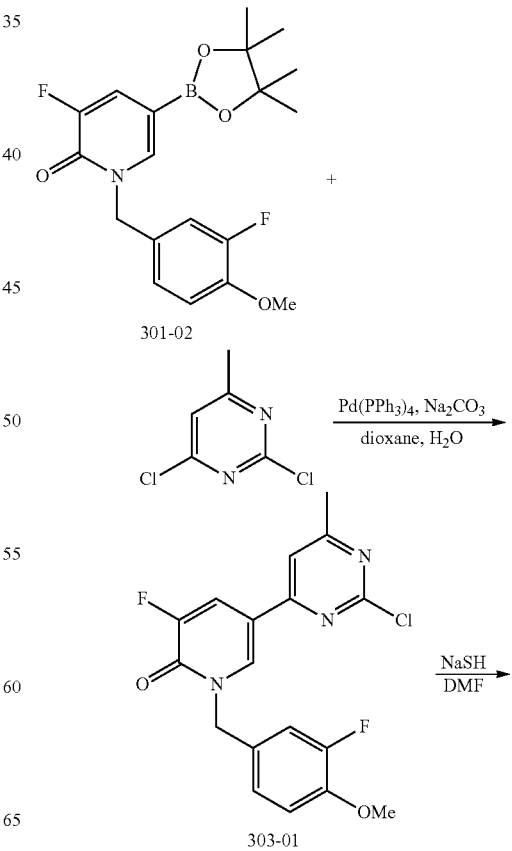

301-02

303-01

331
-continued

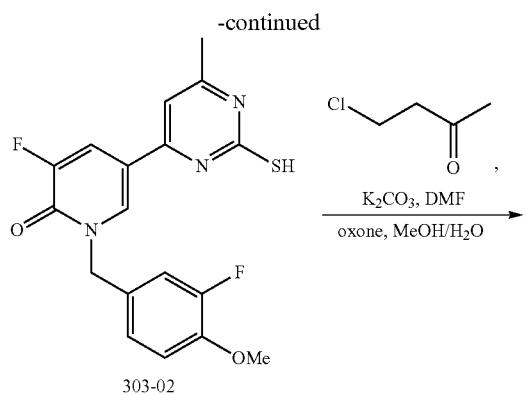

Step 1: The titled compound 303-01 was prepared in a yield of 92.5% (0.74 g, 1.96 mmol) as a light yellow solid from 2,4-dichloro-6-methylpyrimidine (0.52 g, 3.19 mmol) and 301-02 (0.8 g, 2.12 mmol) according to the procedure for 99-01. Mass (m/z): 378.11, [M+H]$^+$.

Step 2: The titled compound 303-02 was prepared without purification as a yellow solid (0.58 g) from 303-01 (0.74 g, 1.96 mmol) according to the procedure for 140-1. Mass (m/z): 376.09, [M+H]$^+$.

Step 3: The title compound 303 (4 mg, 0.0084 mmol) was prepared in a yield of 14% as a white solid from 303-02 (24 mg, 0.06 mmol) and 4-chlorobutan-2-one (7.8 mg, 0.07 mmol), according to the procedure for 140. H NMR (400 MHz, CDCl$_3$) δ 8.37 (dd, J=1.2, 2.0 Hz, 1H), 7.72 (dd, J=2.4, 10.0 Hz, 1H), 7.40 (s, 1H), 7.17 (d, J=9.6 Hz, 2H), 6.94 (t, J=8.4 Hz, 1H), 5.21 (s, 2H), 3.87 (s, 3H), 3.85-3.83 (m, 2H), 3.10 (t, J=7.6 Hz, 2H), 2.66 (s, 3H). Mass (m/z): 478.07, [M+H]$^+$.

332

3-fluoro-1-(3-fluoro-4-methoxybenzyl)-5-(2-((3-((2-fluorobenzyl)oxy)butyl)sulfinyl)-6-methylpyrimidin-4-yl)pyridin-2 (1H)-one (304) and 3-fluoro-1-(3-fluoro-4-methoxybenzyl)-5-(2-((3-((2-fluorobenzyl)oxy)butyl)sulfonyl)-6-methylpyrimidin-4-yl)pyridin-2 (1H)-one (305)

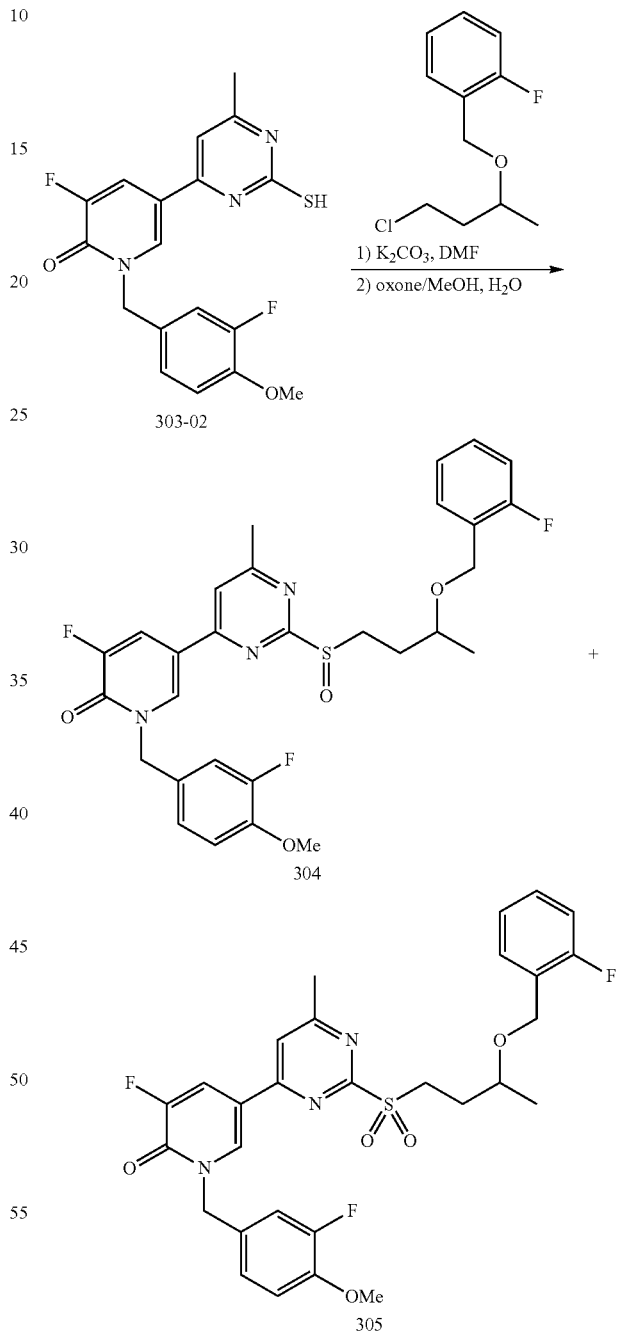

The title compound 304 (30 mg, 0.052 mmol) and 305 (66 mg, 0.11 mmol) was prepared as both white solid from 303-02 (70 mg, 0.19 mmol) and 1-(((4-chlorobutan-2-yl)oxy)methyl)-2-fluorobenzene (53 mg, 0.25 mmol), according to the procedure for 140. 304: $^1$H NMR (400 MHz, CDCl$_3$) δ 8.30 (s, 1H), 7.75-7.71 (m, 1H), 7.38-7.32 (m, 1H), 7.27 (s, 1H) 7.24-7.18 (m, 1H), 7.12-7.09 (m, 2H), 7.07-7.01 (m, 1H), 6.99-6.88 (m, 2H), 5.17 (m, 2H), 4.63 (d, J=12.0 Hz, 0.5H), 4.56-4.49 (m, 1H), 4.37 (d, J=12.0 Hz, 0.5H), 3.86 (s, 3H), 3.78-3.74 (m, 0.56H), 3.67-3.61 (m, 0.59H), 3.41-3.33 (m, 0.58H), 3.30-3.18 (m, 1H), 3.15-3.07 (m, 0.60H), 2.64 (s, 3H), 2.25-2.17 (m, 0.72H), 2.15-2.05 (m, 0.71H), 1.98-1.89 (m, 0.62H), Mass (m/z): 572.18, [M+H]⁺. 305: ¹H NMR (400 Hz, CDCl₃) δ 8.32 (m, 1H), 7.76 (dd, J=2.4, 10.0 Hz, 1H), 7.42 (s, 1H), 7.38 (td, J=1.6, 7.6 Hz, 11H), 7.29-7.23 (m, 1H), 7.13-7.08 (m, 3H), 7.03-6.98 (m, 1H), 6.92 (t, J=8.4 Hz, 1H), 5.19 (d, J=14.4 Hz, 1H), 5.11 (d, J=14.4 Hz, 1H), 4.63 (d, J=11.6 Hz, 1H), 4.49 (d, J=11.6 Hz, 11H), 3.85 (s, 3H), 3.83-3.78 (m, 1H), 3.77-3.72 (m, 1H), 3.58-3.50 (m, 1H), 2.63 (s, 3H), 2.19-2.10 (m, 1H), 2.08-1.98 (m, 1H). Mass (m/z): 588.17, [M+H]⁺.

1'-(3,4-dimethoxybenzyl)-2-((3-((2-fluorobenzyl)oxy)-3-phenylpropyl)sulfonyl)-6-methyl-[4,5'-bipyrimidin]-2'(1'H)-one (306) and 1'-(benzo[d][1,3]dioxol-5-ylmethyl)-2-((3-((2-fluorobenzyl)oxy)-3-phenylpropyl)sulfonyl)-6-methyl-[4,5'-bipyrimidin]-2'(1'H)-one (307)

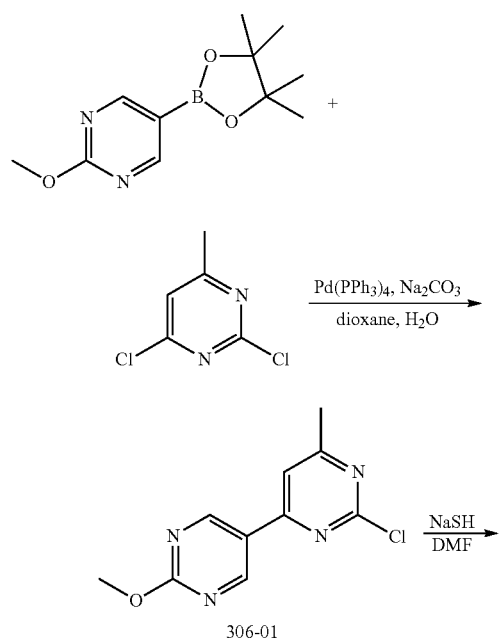

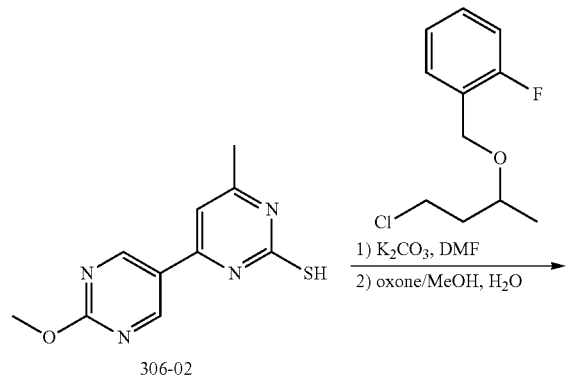

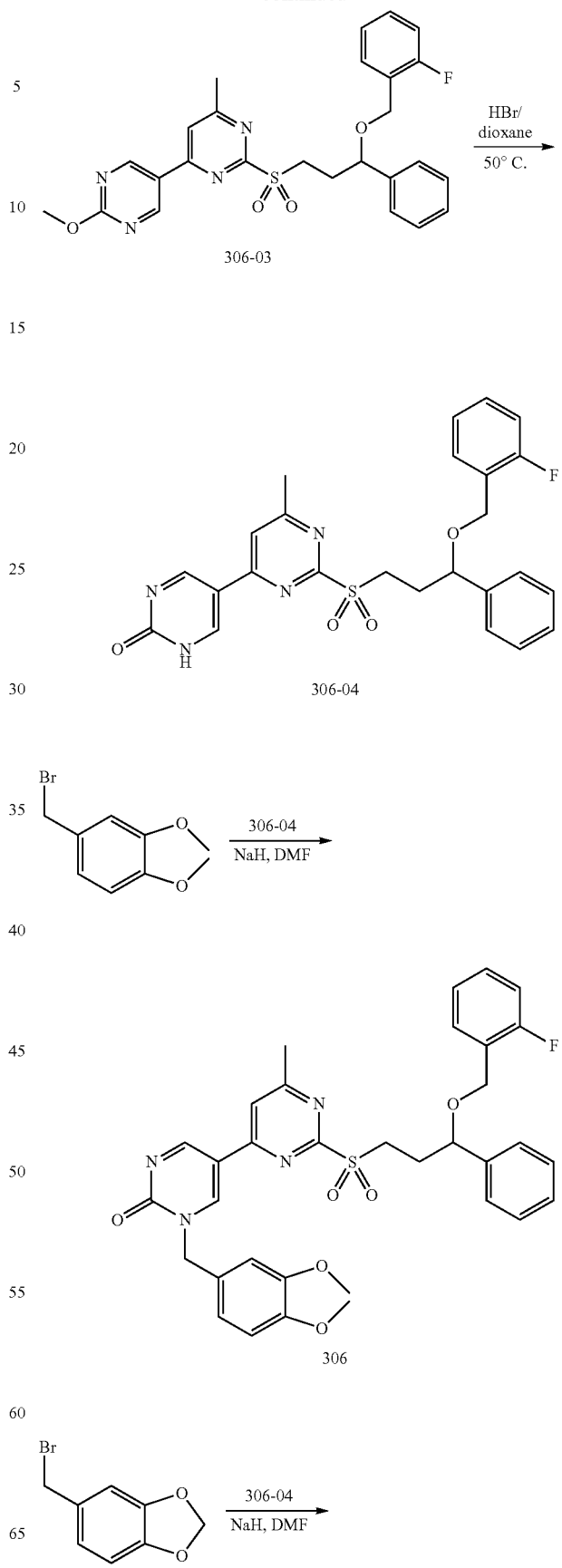

335
-continued

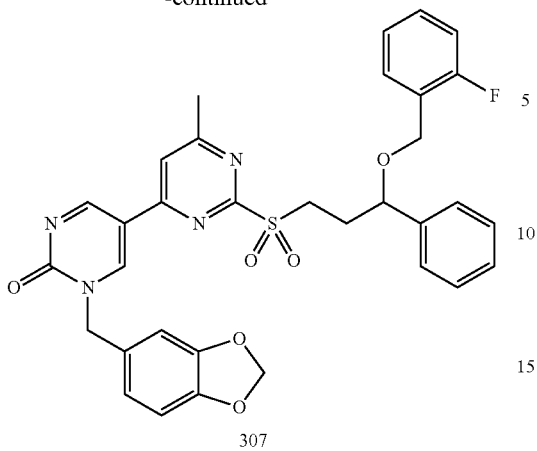

307

Step 1. The titled compound 306-01 was prepared in a yield of 100% (1.66 g, 7.0 mmol) as a white solid from 2,4-dichloro-6-methylpyrimidine (1.5 g, 9.24 mmol) according to the procedure for 99-01. Mass (m/z): 237.11, 239.12, [M+H]+.

Step 2: The titled compound 306-02 was prepared without purification as a yellow solid (0.2 g) from 306-01 (0.25 g, 1.06 mmol) according to the procedure for 140-01. Mass (m/z): 235.23, [M+H]+.

Step 3: The title compound 306-03 (21 mg, 0.047 mmol) was prepared in a yield of 8.5% as a white solid from 306-02 (0.13 g, 0.55 mmol) and 1-(((4-chlorobutan-2-yl)oxy)methyl)-2-fluorobenzene (0.18 g, 0.83 mmol), according to the procedure for 140. Mass (m/z): 509.31, [M+H]+.

Step 4: The titled compound 306-04 was prepared without purification (21 mg) as a yellow syrup from 306-03 (21 mg, 0.047 mmol) according to the procedure for 99-02. Mass (m/z): 495.29, [M+H]+.

Step 5: The titled compound 306 (2 mg, 0.003 mmol) was prepared in a yield of (21%) as a white solid from 306-04 (7 mg, 0.014 mmol) according to the procedure for 85-01. 1H NMR (400 MHz, CDCl3) δ 8.92 (s, 1H), 7.61 (m, 1H), 7.39-7.30 (m, 7H), 7.28-7.24 (m, 1H), 7.12 (dt, J=0.8, 7.2 Hz, 1H), 7.03-6.99 (m, 2H), 6.97 (d, J=8.0 Hz, 1H), 6.85 (d, J=8.0 Hz, 1H), 5.15 (s, 2H), 4.57 (q, J=4.4 Hz, 1H), 4.49 (d, J=11.6 Hz, 1H), 4.36 (d, J=12.0 Hz, 1H), 3.88 (s, 3H), 3.86 (s, 3H), 3.79-3.73 (m, 1H), 3.63-3.55 (m, 1H), 2.65 (s, 3H), 2.25-2.21 (m, 2H). Mass (m/z): 645.29, [M+H]+.

Step 6: The titled compound 307 (2.5 mg, 0.004 mmol) was prepared in a yield of (14.3%) as a white solid from 306-04 (14 mg, 0.028 mmol) according to the procedure for 85-01. Mass (m/z): 629.31, [M+H]+.

336

1-(cyclohexylmethyl)-5-(2-(3-(2,4-difluorobenzyloxy)-3-phenylpropylsulfinyl)-6-methylpyrimidin-4-yl)-3-fluoropyridin-2 (1H)-one (308) and 1-(cyclohexylmethyl)-5-(2-(3-(2,4-difluorobenzyloxy)-3-phenylpropylsulfonyl)-6-methylpyrimidin-4-yl)-3-fluoropyridin-2 (1H)-one (309)

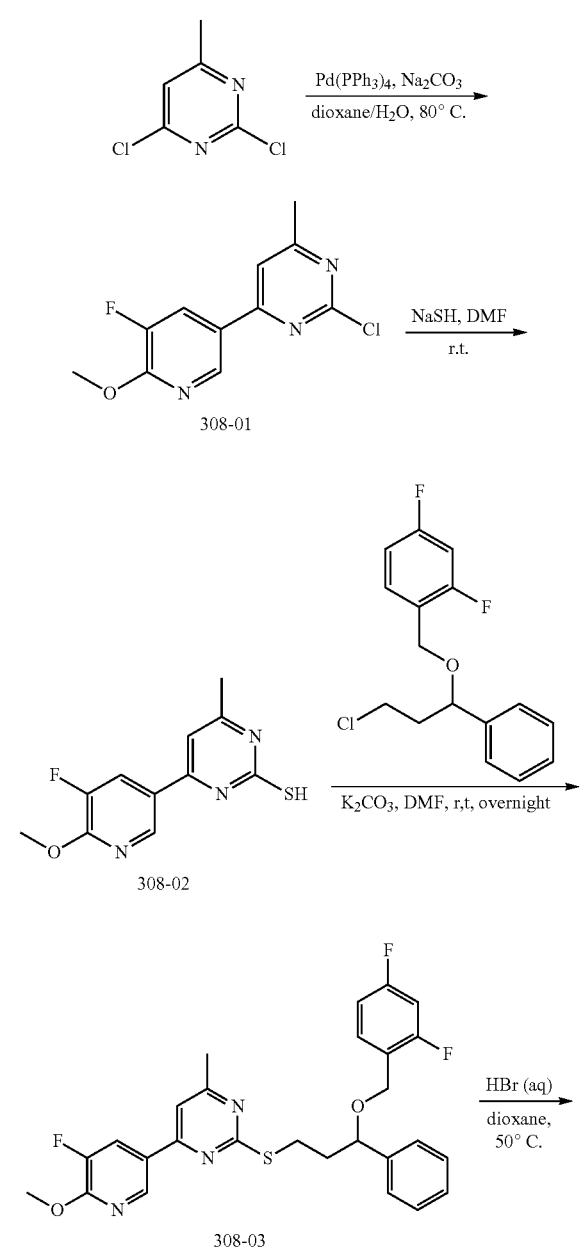

337

-continued

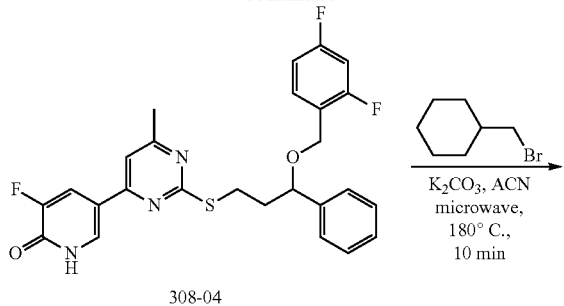
308-04

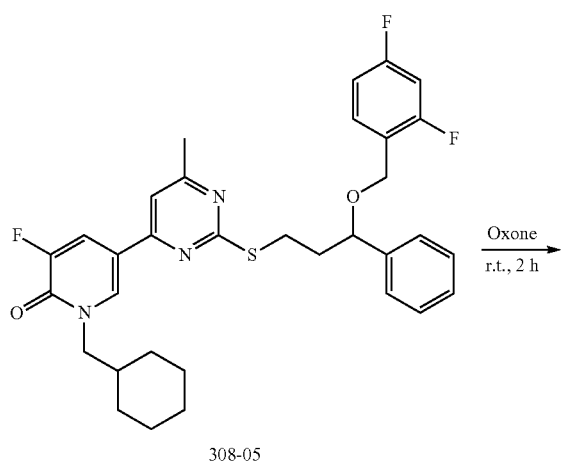
308-05

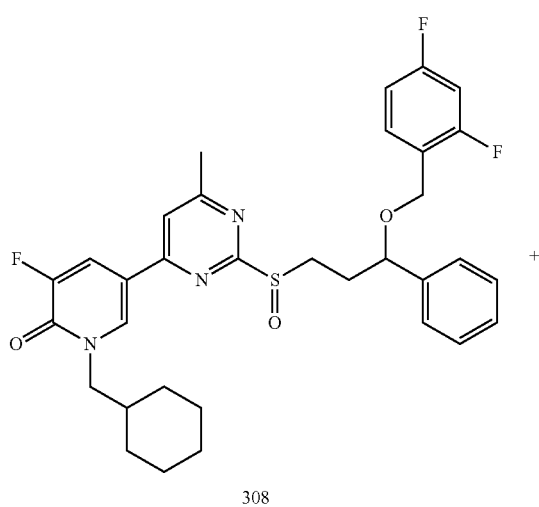
308

338

-continued

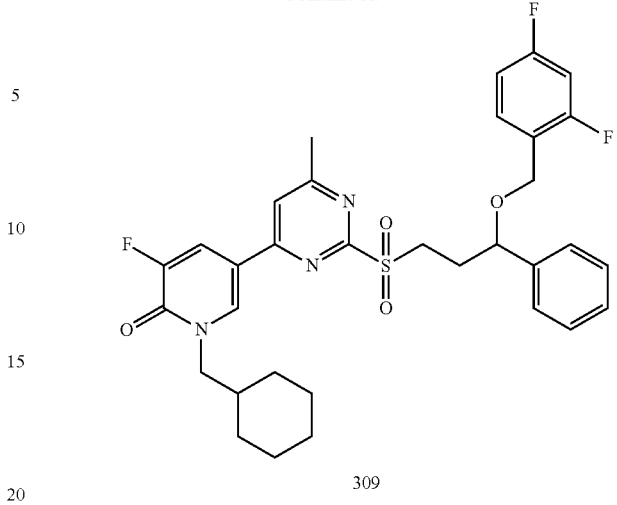
309

Step 1. The compound 308-01 was prepared in a yield of 81.0% as white solid (2.46 g) from 165-01 and 2,4-dichloro-6-methylpyrimidine (2.93 g, 18.0 mmol) according to the procedure for 99-01. Mass (m/z): 254.00, [M+H]$^+$.

Step 2. The compound 308-02 was prepared in a yield of 86.9% as yellow solid (2.12 g) from compound 308-01 (2.46 g, 9.7 mmol) according to the procedure for 140-01. Mass (m/z): 418.04 [M+H]$^+$.

Step 3. $K_2CO_3$ (397 mg, g 2.88 mmol) was added to the solution of 308-02 (390 mg, 1.44 mmol) and 1-((3-chloro-1-phenylpropoxy)methyl)-2,4-difluorobenzene (469 mg, 1.58 mmol) in DMF (15 mL) under $N_2$. Then the reaction mixture was stirred at room temperature overnight. The reaction was quenched by water, extracted by EtOAc for 3 times. The organic layer was combined, washed by brine, dried over $Na_2SO_4$. Evaporation to remove the solvent to give 308-03 as light yellow oil (850 mg). The cruel product was used without further purification. Mass (m/z): 513.32 [M+H]$^+$.

Step 4. The HBr (aq, 5 mL) was added to the solution of 308-03 (500 mg, 0.98 mmol) in 1,4-dioxane (10 mL). Then the reaction mixture was stirred at 50° C. for 1.5 h. The reaction mixture was cooled to room temperature, diluted by water. Filtration to give 437 mg 308-04 as a orange solid (89.7%). Mass (m/z): 498.18 [M+H]$^+$.

Step 5. The mixture of 308-04 (67 mg, 0.13 mmol), (bromomethyl)cyclohexane (166 mg, 0.94 mmol) and $K_2CO_3$ (83 mg, 0.94 mmol) in ACN (5 mL) was reacted under microwave at 180° C. for 11 min. The reaction mixture was diluted by water, extracted by EtOAc for 3 times. The organic layer was combined, washed by brine, dried over $Na_2SO_4$ and further purified by silica gel column chromatography (PE:EA=5.1) to give 39 mg 308-05 as colorless oil (48.8%). Mass (m/z): 594.26 [M+H]$^+$.

Step 6. The titled compounds 308 (12.5 mg, 29.8%) and 309 (5.6 mg, 14.8%) were prepared as both white solid from 308-05 (39 mg, 0.066 mmol) according to the procedure for 80 and 81. 308: $^1$HNMR (400 MHz, CDCl$_3$) δ 8.16 (s, 1H), 7.72-7.69 (m, 2H), 7.54-7.51 (m, 1H), 7.36-7.26 (m, 5H), 6.86-6.71 (m, 2H), 4.56-4.53 (m, 1H), 4.45-4.35 (m, 2H), 4.32-4.20 (m, 2H), 3.93 (d, J=7.2 Hz, 2H), 3.35-3.05 (m, 2H), 2.62 (s, 3H), 2.47-2.21 (m, 2H), 2.08-2.00 (m, 1H), 1.92-1.87 (m, 1H), 1.75-1.63 (m, 6H), 1.44-1.40 (m, 2H). Mass (m/z): 610.28[M+H]$^+$. 309: $^1$HNMR (400 MHz, CDCl$_3$) δ 8.16 (s, 1H), 7.71 (dd, J=2.4, 10 Hz, 1H), 7.39-7.32 (m, 7H), 6.88-6.83 (m, 1H), 6.81-6.76 (m, 1H), 4.58-4.55 (m, 1H), 4.46 (d, J=11.6 Hz, 1H), 4.35 (d, J=11.6 Hz, 1H), 3.93 (d, J=7.6 Hz, 2H), 3.80-3.72 (m, 1H), 3.62-3.55 (m, 1H), 2.64 (s, 3H), 2.40-2.25 (m, 2H), 1.94-1.86 (m, 1H), 1.75-1.64 (m, 6H), 1.27-1.17 (m, 4H). Mass (m/z): 626.20[M+H]⁺.

5-(2-((3-((2,4-difluorobenzyl)oxy)-3-phenylpropyl) sulfinyl)-6-methylpyrimidin-4-yl)-1-(3-ethoxybenzyl)-3-fluoropyridin-2 (1H)-one (310) and 5-(2-((3-((2,4-difluorobenzyl)oxy)-3-phenylpropyl)sulfonyl)-6-methylpyrimidin-4-yl)-1-(3-ethoxybenzyl)-3-fluoropyridin-2 (1H)-one (311)

The titled compounds 310 (9.3 mg, 21.5%) and 311 (13.6 mg, 26.4%) were prepared as colorless oil and white solid from 308-04 (100 mg, 0.21 mmol) and 1-(bromomethyl)-3-ethoxybenzene (50.0 mg, 0.23 mmol) according to the procedure for 80 and 81. 310: ¹HNMR (400 MHz, CDCl₃) δ 8.21 (s, 1H), 7.74-7.69 (m, 2H), 7.54-7.51 (m, 1H), 7.36-7.28 (m, 6H), 7.25 (m, 1H), 6.94-6.80 (m, 4H), 5.23 (s, 2H), 4.55 (m, 1H), 4.45-4.42 (m, 4H), 4.03-3.97 (m, 2H), 3.33-3.30 (m, 2H), 2.61 (s, 3H), 1.38 (t, J=7.2 Hz, 3H). Mass (m/z): 648.20[M+H]⁺; 311: ¹HNMR (400 MHz, CDCl₃) δ 8.21 (s, 1H), 7.74-7.69 (m, 1H), 7.53 (m, 1H), 7.38-7.28 (m, 7H), 6.89-6.83 (m, 5H), 5.22 (s, 2H), 4.56 (m, 1H), 4.42 (d, J=11.6 Hz, 1H), 4.34-4.28 (m, 2H), 4.02 (q, J=7.2 Hz, 2H), 3.77-3.69 (m, 1H), 3.60-3.52 (m, 1H), 2.62 (s, 1H), 1.38 (t, J=6.8 Hz, 3H). Mass (m/z): 664.16[M+H]⁺.

5-(2-(3-(2,4-difluorobenzyloxy)-3-phenylpropylsulfonyl)-6-methylpyrimidin-4-yl)-3-fluoro-1-(piperidin-4-ylmethyl)pyridin-2 (1H)-one (312)

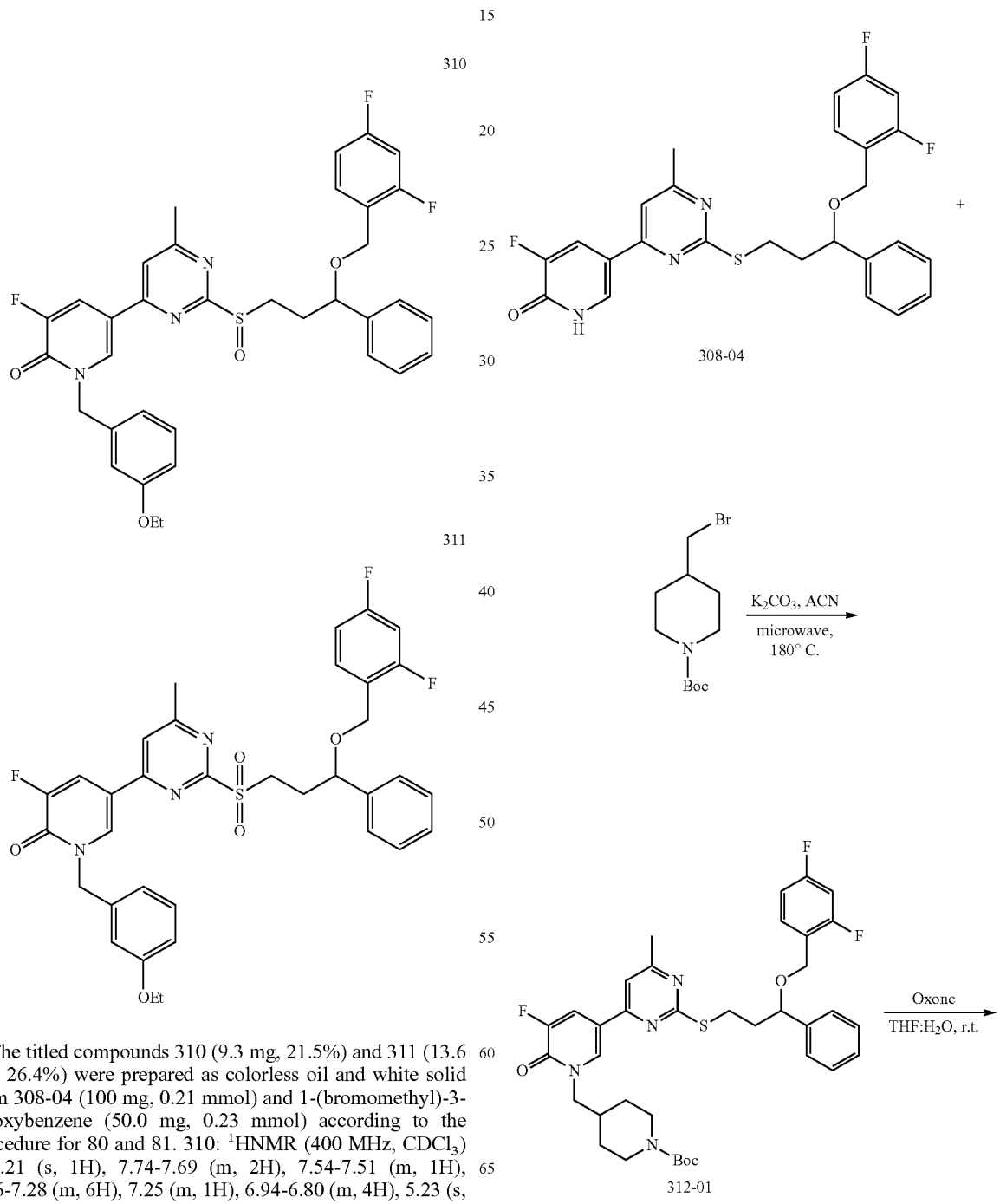

341

-continued

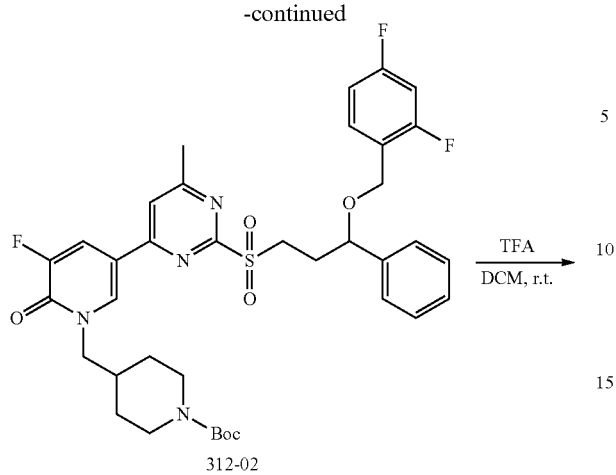

312-02

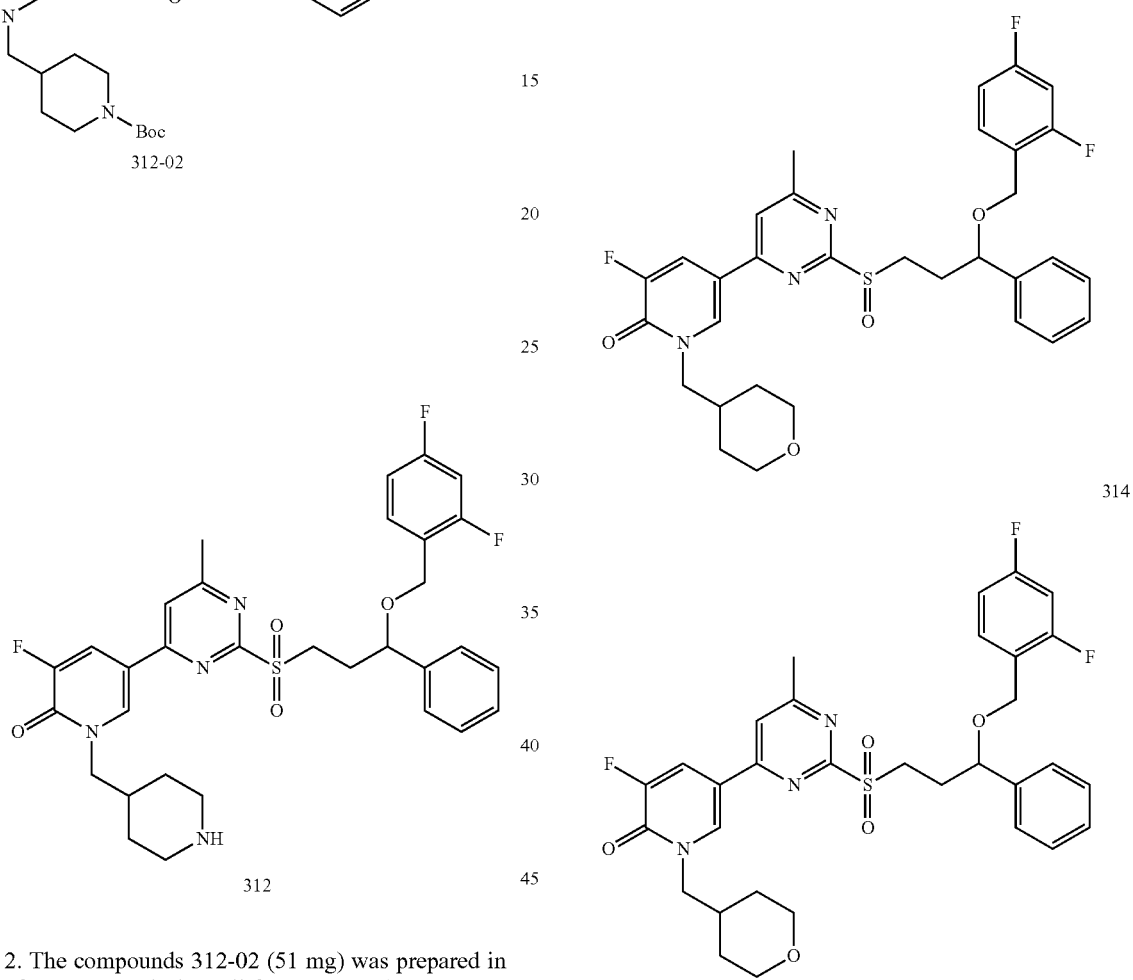

312

Step 2. The compounds 312-02 (51 mg) was prepared in a yield of 97.5% as colorless oil from 312-01 (50 mg, 0.07 mmol) according to the procedure for 81. Mass (m/z): 727.27, [M+H]+.

Step 3. TFA (0.5 mL) was added to the solution of 312-02 (51 mg, 0.07 mmol) in DCM. The reaction mixture was stirred at room temperature for 2 h. NaHCO$_3$(aq) was added to the mixture to neutralized the left TFA. The aqueous phase was extracted by DCM for 3 times. The organic layer was combined, washed by brine, dried over Na$_2$SO$_4$, further purified by silica gel column chromatography (DCM: MeOH=10:1) to give 312 as 19 mg white solid. $^1$HNMR (400 MHz, DMSO-d$_6$) δ 8.69 (s, 1H), 8.12 (s, 2H), 7.73-7.65 (m, 1H), 7.50-7.44 (m, 1H), 7.39-7.32 (m, 4H), 7.22-7.17 (m, 1H), 7.07-7.03 (m, 1H), 4.62-4.59 (m, 1H), 4.34 (d, J=5.2 Hz, 2H), 4.03 (d, J=7.2 Hz, 2H), 3.78-3.71 (m, 1H), 3.66-3.58 (m, 1H), 3.33 (s, 3H), 3.28 (d, J=13.6 Hz, 1H), 2.85-2.78 (m, 1H), 2.57 (s, 2H), 2.19-1.98 (m, 4H), 1.73-1.55 (m, 2H), 1.47-1.34 (n, 2H). Mass (m/z): 627.21[M+H]+

342

5-(2-(3-(2,4-difluorobenzyloxy)-3-phenylpropylsulfinyl)-6-methylpyrimidin-4-yl)-3-fluoro-1-((tetrahydro-2H-pyran-4-yl)methyl)pyridin-2 (1H)-one (313) and 5-(2-(3-(2,4-difluorobenzyloxy)-3-phenylpropylsulfonyl)-6-methylpyrimidin-4-yl)-3-fluoro-1-((tetrahydro-2H-pyran-4-yl)methyl)pyridin-2 (1H)-one (314)

The titled compounds 313 (11.7 mg, 16.3%) and 314 (8.5 mg, 11.2%) were prepared as light yellow solid and white solid from 308-04 (50 mg, 0.10 mmol) and 4-(bromomethyl) tetrahydro-2H-pyran (179 mg, 1.0 mmol) according to the procedure for 80 and 81. 313: $^1$HNMR (400 MHz, CDCl$_3$) δ 8.185 (s, 1H), 7.73 (dd, J=2.4, 10 Hz, 1H), 7.40-7.32 (m, 7H), 6.87-6.75 (m, 2H), 4.58 (m, 1H), 4.46 (d, J=11.6 Hz, 1H), 4.35 (d, J=11.6, 1H), 3.99 (d, J=7.2 Hz, 3H), 3.79-3.72 (m, 1H), 3.62-3.54 (m, 1H), 3.38-3.31 (t, J=11.6 Hz, 2H), 2.64 (s, 3H), 2.36-2.16 (m, 4H), 1.56 (d, J=11.2 Hz, 2H), 1.47-1.41 (m, 2H). Mass (m/z): 612.46 [M+H]+. 314: $^1$HNMR (400 MHz, CDCl$_3$) δ 8.20 (s, 1H), 7.73-7.69 (m, 1H), 7.36-7.27 (m, 7H), 6.86-6.71 (m, 2H), 4.56 (m, 1H), 4.46-4.25 (m, 3H), 3.99 (d, J=6.8 Hz, 3H), 3.34 (m, 3H), 2.62 (m, 3H), 2.46-1.98 (m, 4H), 1.55-1.40 (m, 4H). Mass (m/z): 628.43[M+H]+.

343

1-(3,4-dichlorobenzyl)-5-(2-(3-(2,4-difluorobenzy-loxy)-3-phenylpropylsulfinyl)-6-methylpyrimidin-4-yl)-3-fluoropyridin-2 (1H)-one (315) and 1-(3,4-dichlorobenzyl)-5-(2-(3-(2,4-difluorobenzyloxy)-3-phenylpropylsulfonyl)-6-methylpyrimidin-4-yl)-3-fluoropyridin-2 (1H)-one (316)

344

1-(benzo[d][1,3]dioxol-5-ylmethyl)-5-(2-((3-((2,4-difluorobenzyl)oxy)-3-phenylpropyl)sulfonyl)-6-methylpyrimidin-4-yl)-3-fluoropyridin-2 (1H)-one (317)

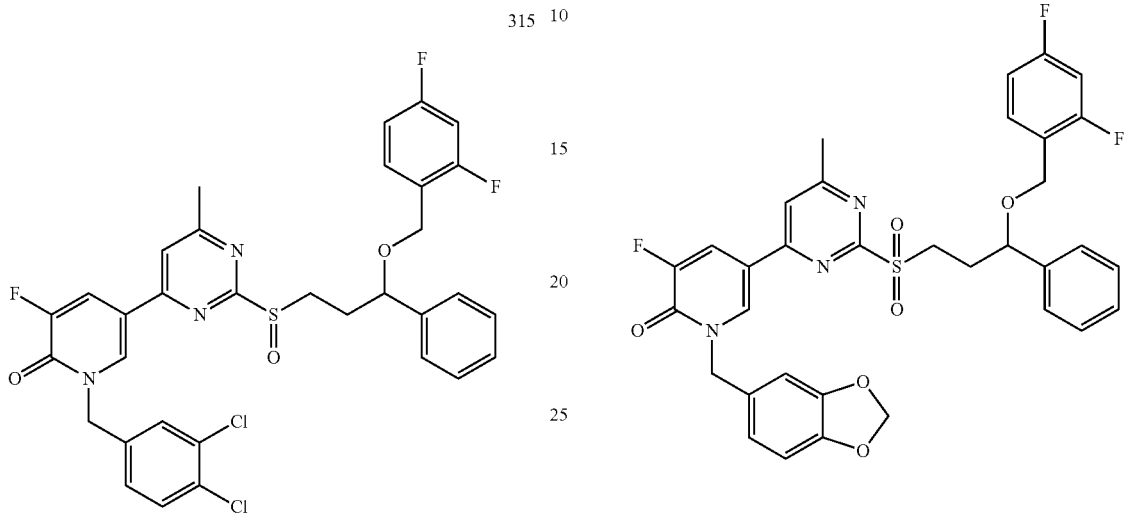

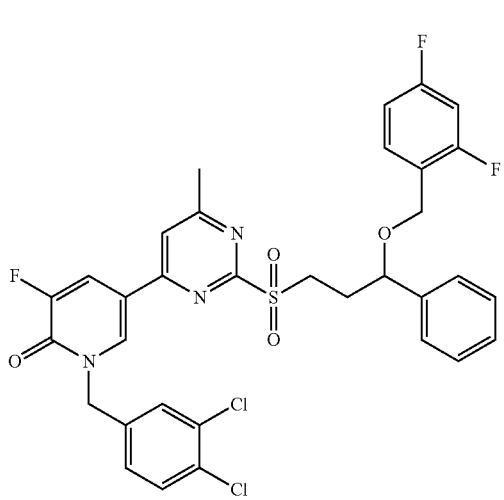

The titled compounds 315 (11.4 mg, 26.5%) and 316 (17.5 mg, 30.4%) were prepared as light yellow solid and white solid from 308-04 (102 mg, 0.21 mmol) and 4-(bromomethyl)-1,2-dichlorobenzene (55.4 mg, 0.23 mmol) according to the procedure for 81 and 82. 315: ¹HNMR (400 MHz, CDCl₃) δ 8.32 (s, 1H), 7.74-7.69 (m, 1H), 7.45 (s, 1H), 7.43 (dd, J=2.0, 8.4 Hz. 1H), 7.35-7.29 (m, 7H), 7.23-7.20 (m, 1H), 6.86-6.70 (m, 2H), 5.21 (s, 2H), 4.56-4.21 (m, 4H), 3.35-3.05 (m, 2H), 2.62 (s, 3H), 2.5-2.31 (m, 2H). Mass (m/z): 656.33[M+H]; 316: ¹HNMR (400 MHz, CDCl₃) δ 8.29 (s, 1H), 7.74 (dd, J=2.0, 9.6 Hz, 1H), 7.45-7.30 (m, 9H), 7.21 (dd, J=2.0, 8.0 Hz, 1H), 6.87-6.82 (m, 1H), 6.80-6.74 (m, 1H), 5.20 (s, 2H), 4.57 (dd, J=4.8, 8.4 Hz. 1H), 4.45 (d, J=11.6 Hz, 1H), 4.34 (d, J=11.6 Hz, 1H), 3.79-3.72 (m, 1H), 3.61-3.53 (m, 1H), 2.64 (s, 3H), 2.39-2.23 (m, 2H). Mass (m/z): 672.30[M+H]⁺

The titled compounds 317 (15.3 mg) were prepared in a yield of 12.8% as white solid from 308-04 (90 mg, 0.18 mmol) and 5-(bromomethyl)benzo[d][1,3]dioxole (43 mg, 0.20 mmol) according to the procedure for 85. ¹HNMR (400 MHz, CDCl₃) δ 8.23 (s, 1H), 7.72 (dd, 2.0, 9.6 Hz, 1H), 7.39-7.28 (m, 7H), 6.85 (m, 3H), 6.79-6.74 (m, 2H), 5.94 (s, 2H), 6.15 (s, 2H), 4.56 (m, 1H), 4.45 (d, J=12.0 Hz, 1H), 4.34 (d, J=12.0 Hz, 1H), 3.77-3.68 (m, 1H), 3.60-3.53 (m. 1H), 2.62 (s, 3H), 2.38-2.20 (m, 2H). Mass (m/z): 664.38 [M+H]⁺.

1-(benzo[d][1,3]dioxol-5-ylmethyl)-3-fluoro-5-(2-(3-(2-fluorobenzyloxy)-3-phenylpropylsulfonyl)-6-methylpyrimidin-4-yl)pyridin-2 (1H)-one (318)

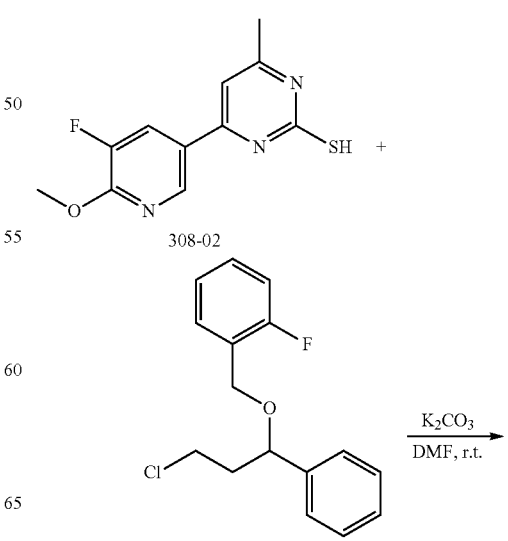

345

-continued

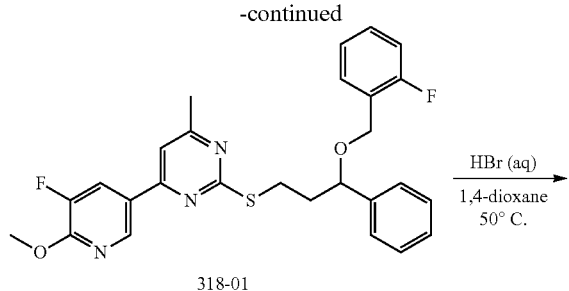

318-01

HBr (aq)
1,4-dioxane
50° C.

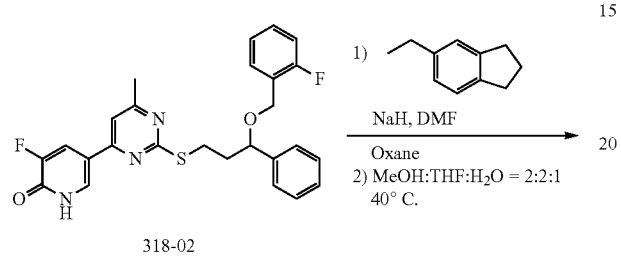

318-02

1) <image showing ethyl-indane>

NaH, DMF
Oxane
2) MeOH:THF:H₂O = 2:2:1
40° C.

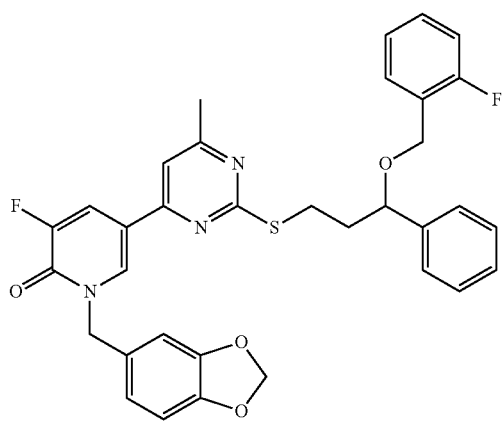

318

Step 1. The compound 318-01 (2.26 g) was prepared as light yellow oil from 308-02 (1 g, 3.98 mmol) and 1-((3-chloro-1-phenylpropoxy)methyl)-2-fluorobenzene (1.22 g, 4.38 mmol) according to the procedure for 308-03. Mass (m/z): 494.16[M+H]⁺.

Step 2. The compound 318-02 (1.77 g) was prepared in a yield of 92.6% as light yellow oil from 318-01 (2.20 g, 4.46 mmol) according to the procedure for 308-04. Mass (m/z): 480.29 [M+H]⁺.

Step 3. The titled compound 318 (98.3 mg) was prepared in a yield of 36.9% as white solid from 318-02 (200 mg, 0.42 mmol) and 5-(bromomethyl)benzo[d][1,3]dioxole (100 mg, 0.46 mmol) according to the procedure for 85. 318: $^1$H NMR (400 MHz, CDCl₃) δ 8.24 (s, 1H), 7.72 (dd, J=2.4, 10 Hz, 1H), 7.39-7.27 (m, 8H), 7.12 (t, J=7.6 Hz, 1H), 7.03 (t, J=9.6 Hz, 1H), 6.85 (d, J=9.2 Hz, 2H), 6.78 (d, J=8.0 Hz, 1H), 5.95 (s, 2H), 5.14 (s, 2H), 4.58 (dd, J=4.8, 8.4 Hz, 1H), 4.50 (d, J=12.0 Hz, 1H), 4.37 (d, J=12.0 Hz, 1H), 3.81-3.74 (m, 1H), 3.62-3.54 (m, 1H), 2.63 (s. 3H), 2.34-2.26 (m, 2H). Mass (m/z): 664.38[M+H]⁺

346

1-(benzo[c][1,2,5]thiadiazol-5-ylmethyl)-3-fluoro-5-(2-(3-(2-fluorobenzyloxy)-3-phenylpropylsulfonyl)-6-methylpyrimidin-4-yl)pyridin-2 (1H)-one (319)

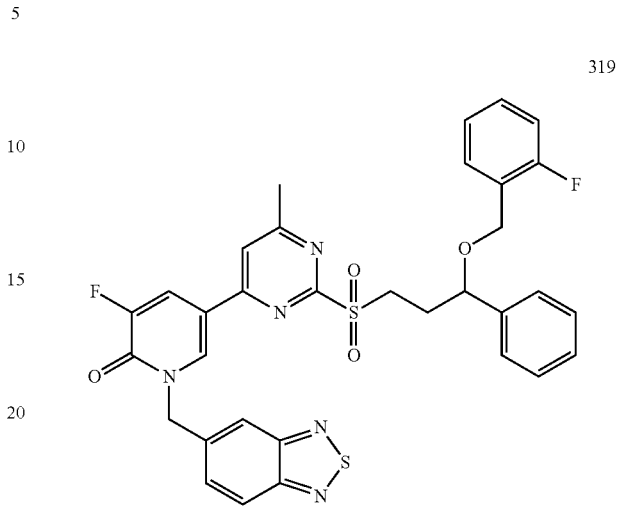

319

The titled compound 319 (30.1 mg) was prepared in a yield of 25.1% as light yellow solid from 318-02 (100 mg, 0.21 mmol) and 5-(bromomethyl)benzo[c][1,2,5]thiadiazole (58 mg, 0.23 mmol) according to the procedure for 85. $^1$HNMR (400 MHz, CDCl₃) δ 8.37 (s, 1H), 8.02 (d, J=8.8 Hz, 1H), 7.87 (s. 1H), 7.78 (dd, J=2.4, 9.6 Hz, 1H), 7.60 (dd, J=2.0, 8.8 Hz, 1H), 7.38 (s, 1H), 7.36-7.30 (m, 7H), 7.10 (t, J=7.4 Hz, 1H), 7.00 (t, J=10.0 Hz, 1H), 5.43 (s, 2H), 4.56 (dd, J=8.0, 4.4 Hz, 1H), 4.49 (d, J=12.0 Hz, 1H), 4.36 (d, J=12.0 Hz, 1H), 3.82-3.75 (m, 1H), 3.61-3.53 (m, 1H), 2.63 (s, 3H), 2.33-2.19 (m, 2H). Mass (m/z): 660.42[M+H]⁺.

1-(benzo[d][1,3]dioxol-4-ylmethyl)-3-fluoro-5-(2-(3-(2-fluorobenzyloxy)-3-phenylpropylsulfonyl)-6-methylpyrimidin-4-yl)pyridin-2 (1H)-one (320)

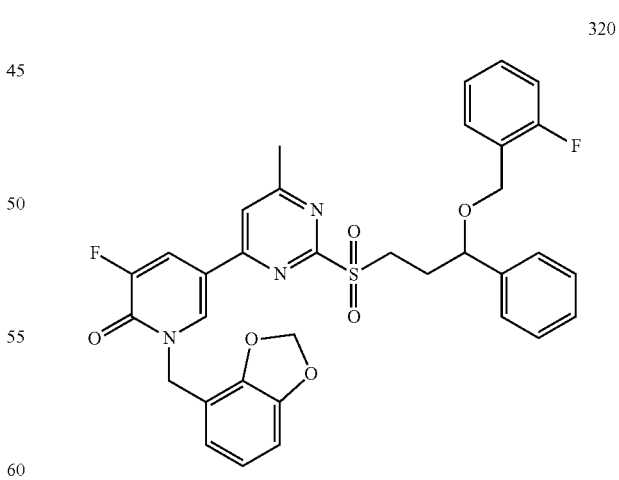

320

The titled compound 320 (71.7 mg) was prepared in a yield of 53.3% as light yellow solid from 318-02 (100 mg, 0.21 mmol) and 4-(bromomethyl)benzo[d][1,3]dioxole (49.8 mg, 0.23 mmol) according to the procedure for 85. $^1$HNMR (400 MHz, CDCl₃) δ 8.53 (s, 1H), 7.67 (dd, J=2.4, 10.0 Hz, 1H), 7.39-7.31 (m, 8H), 7.10 (t, J=7.2 Hz, 1H), 6.99

(t, J=9.6 Hz, 1H), 6.93-6.91 (m, 1H), 6.83-6.78 (m, 2H), 5.22 (s, 2H), 4.58 (dd, J=4.8, 8.0 Hz, 1H), 4.49 (d, J=11.6 Hz, 1H), 4.37 (d, J=11.6 Hz, 1H), 3.79-3.72 (m, 1H), 3.62-3.55 (M, 1H), 2.63 (s, 3H), 2.36-2.24 (m, 2H). Mass (m/z): 646.24 [M+H]$^+$ 3-fluoro-5-(2-(3-(2-fluorobenzyloxy)-3-phenylpropylsulfonyl)-6-methylpyrimidin-4-yl)-1-((2-methoxypyridin-4-yl)methyl)pyridin-2 (1H)-one (321)

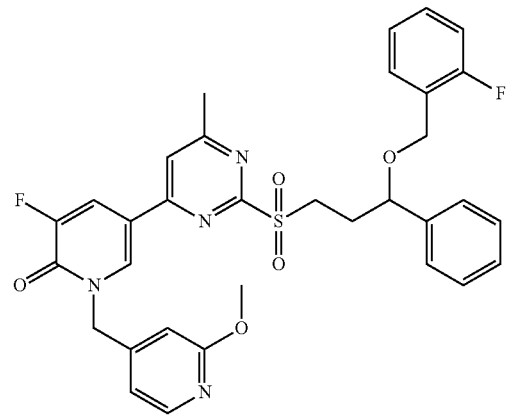

321

The titled compound 321 (55.5 mg) was prepared in a yield of 46.0% as white solid from 318-02 (105 mg, 0.22 mmol) and 4-(bromomethyl)-2-methoxypyridine (40 mg, 0.20 mmol) according to the procedure for 85. $^1$HNMR (400 MHz, CDCl$_3$) δ 8.29 (s, 1H), 8.15 (d, J=5.6 Hz, 1H), 7.78 (dd, J=2.0, 9.6 Hz, 1H), 7.41 (s, 1H), 7.39-7.27 (m, 7H), 7.10 (t, J=7.6 Hz, 1H), 7.00 (t, J=9.6 Hz, 1H), 6.80 (d, J=4.8 Hz, 1H), 6.59 (s, 1H), 5.21 (s, 2H), 4.56 (m, 1H), 4.49 (d, J=11.6 Hz, 1H), 4.37 (d, J=12.0 Hz, 1H), 3.92 (s, 3H), 3.83-3.75 (m, 1H), 3.61-3.53 (m, 1H), 2.63 (s, 3H), 2.34-2.26 (m, 2H). Mass (m/z): 633.36[M+H]$^+$ 1-((1H-benzo[d]imidazol-6-yl)methyl)-3-fluoro-5-(2-(3-(2-fluorobenzyloxy)-3-phenylpropylsulfonyl)-6-methylpyrimidin-4-yl)pyridin-2 (1H)-one (322)

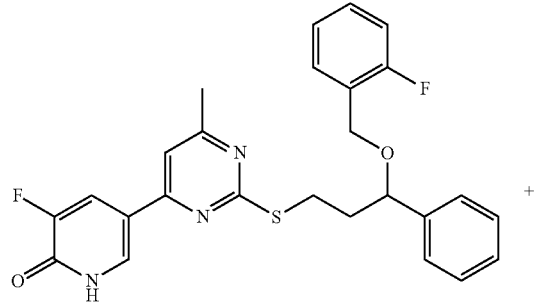

318-02

-continued

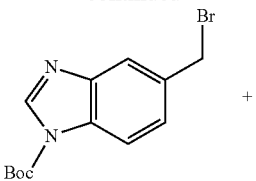

+

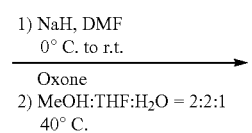

1) NaH, DMF
0° C. to r.t.

Oxone
2) MeOH:THF:H$_2$O = 2:2:1
40° C.

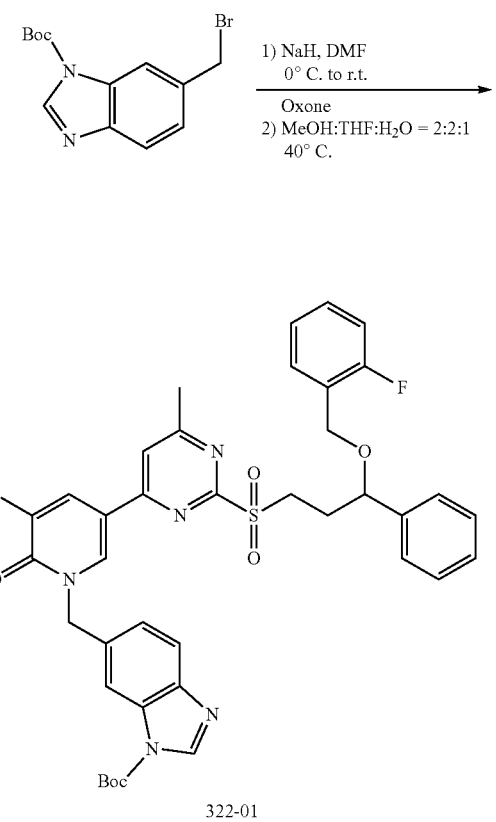

322-01

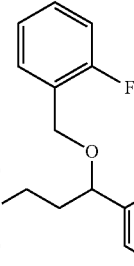

+

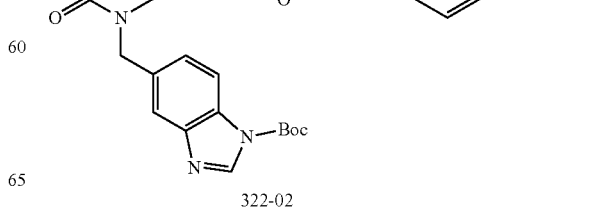

TFA
DCM, r.t.

322-02

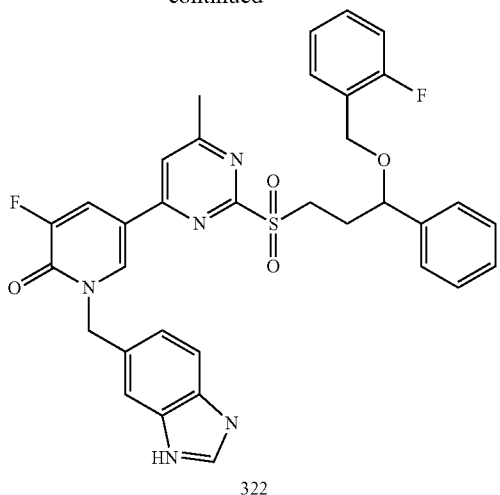

322

Step 1. The compounds 322-01 and 322-02 was prepared from 318-02 (253 mg, 0.53 mmol) and the mixture of tert-butyl 5-(bromomethyl)-1H-benzo[d]imidazole-1-carboxylate and tert-butyl 6-(bromomethyl)-1H-benzo[d]imidazole-1-carboxylate (181 mg, 0.58 mmol) according to the procedure for 85. Mass (m/z): 742.24[M+H]$^+$.

Step 2. The titled compound 322 (9 mg) was prepared in a yield of 2.4% as light yellow solid from the mixture of 322-01 and 322-02 according to the procedure for 312. 322: $^1$HNMR (400 MHz, DMSO-d$_6$) δ 8.91 (s. 1H), 8.42 (br, 1H), 8.13 (s, 2H), 7.73-7.63 (m, 2H), 7.40-7.28 (m, 8H), 7.15-7.11 (m, 2H), 5.39 (s, 2H), 4.60 (m, 1H), 4.34 (dd, 12.0, 16.4 Hz, 2H), 4.03 (dd, J=6.8, 14.0 Hz, 3H), 3.77-3.59 (m, 2H), 2.57 (s, 3H). Mass (m/z): 642.33[M+H]$^+$.

5-((3-fluoro-5-(2-(3-(2-fluorobenzyloxy)-3-phenyl-propylsulfonyl)-6-methylpyrimidin-4-yl-2-oxopyridin-1 (2H)-yl)methyl)benzo[c][1,2,5]oxadiazole 1-oxide (323)

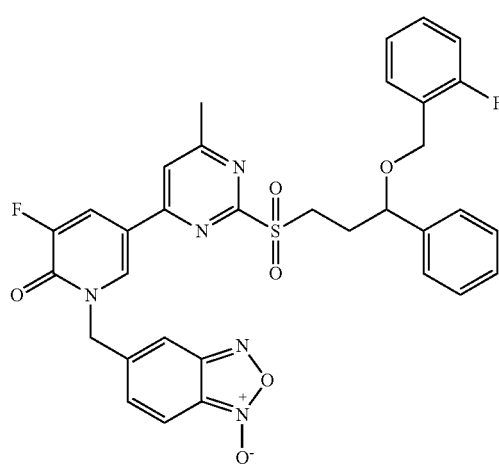

323

The titled compound 323 (14.7 mg) was prepared in a yield of 11.7% (2 steps) as white solid from 318-02 (50 mg, 0.11 mmol) and 5-(bromomethyl)benzo[c][1,2,5]oxadiazole according to the procedure for 85. $^1$HNMR (400 MHz, CDCl$_3$) δ 8.37 (s, 1H), 7.77 (dd, J=2.0, 9.6 Hz, 1H), 7.40-7.28 (m, 9H), 7.10 (t, J=6.4 Hz, 1H), 7.00 (t, J=9.6 Hz, 1H), 5.24 (s, 2H), 4.55 (m, 1H), 4.50 (d, J=12.0 Hz, 1H), 4.37 (d, J=12.0 Hz, 1H), 3.82-3.75 (m, 1H), 3.61-3.54 (m, 1H), 2.64 (s, 3H), 2.35-2.23 (m, 2H). Mass (m/z): 660.09 [M+H]$^+$.

1-(3,4-dimethoxybenzyl)-3-fluoro-5-(6-methyl-2-(methylsulfonyl)pyrimidin-4-yl)pyridin-2 (1H)-one (324)

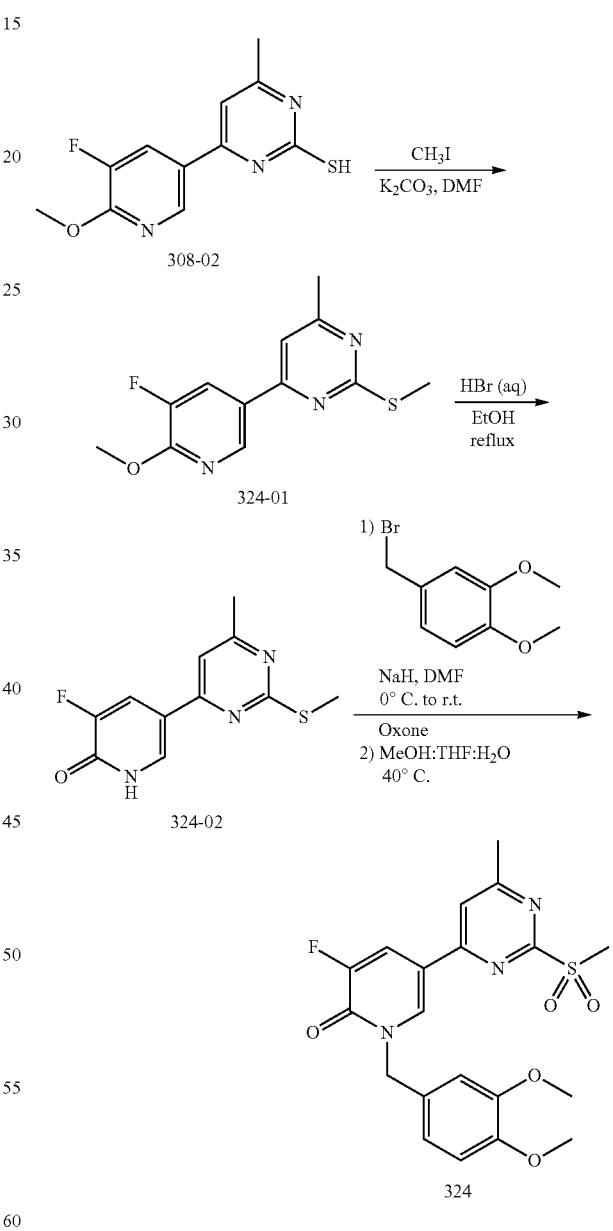

Step 1. CH$_3$I (85 mg. 0.6 mmol) was added to the mixture of 308-02 (100 mg, 0.4 mmol), K$_2$CO$_3$ (83 mg, 0.6 mmol) and DMF (10 mL) under 0° C., then the reaction mixture was warmed to room temperature, stirred overnight. The reaction mixture was quenched by water, extracted by EtOAc for 3 times, dried over Na$_2$SO$_4$. Evaporation to remove the solvent to give 324-01 (221 mg) as yellow solid. The cruel product was used without further purification. Mass (m/z): 267.16[M+H]+.

Step 2. HBr (aq, 3 mL) was added to the solution of 324-01 in EtOH under 0° C. Then the reaction mixture was refluxed for 2 h. Evaporation to remove the solvent, the residue was diluted by water, filtrated to give cruel product 324-02 as yellow solid. The cruel product was used without further purification. Mass (m/z): 253.12[M+H]+.

Step 3. The compounds 324 (65.4 mg) was prepared in a yield of 75.8% (2 steps) as white solid from 324-02 (50 mg, 0.2 mmol) and t 4-(bromomethyl)-1,2-dimethoxybenzene (16 mg, 0.4 mmol) according to the procedure for 85. ¹HNMR (400 MHz, CDCl₃) δ 8.31 (s, 1H), 7.71 (dd, J=2.4, 9.6 Hz, 1H), 7.36 (s, 1H), 6.95 (d, J=10.0 Hz, 2H), 6.862 (d, J=8.0 Hz, 1H), 5.22 (s, 2H), 3.88 (s, 3H), 3.87 (s, 3H), 3.33 (s, 3H), 2.66 (s, 3H). Mass (m/z): 434.11 [M+H]+

3-fluoro-5-(2-(3-(2-fluorobenzyloxy)-3-phenylpropylsulfonyl)-6-methylpyrimidin-4-yl)pyridin-2 (1H)-one (325)

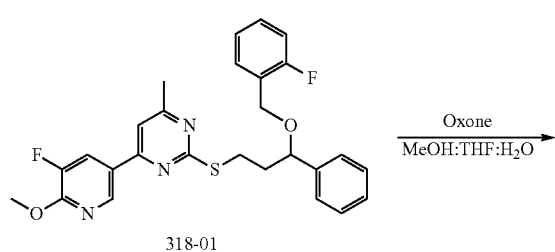

318-01

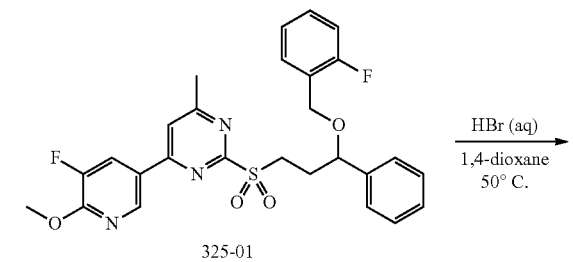

325-01

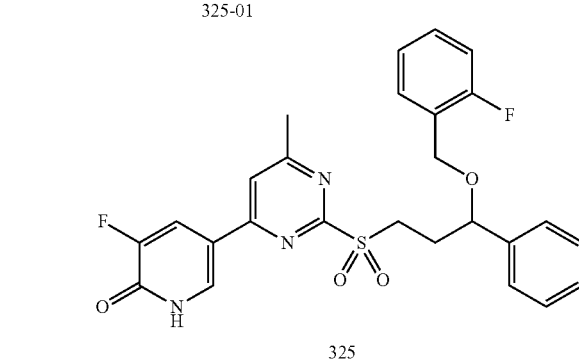

325

Step 1. The compounds 325-01 (331 mg) was prepared in a yield of 22.6% as colorless oil from 318-01 (1.5 g, 3.04 mmol) according to the procedure for 81. Mass (m/z): 326.24[M+H]+.

Step 2. The titled compound 325 (232.3 mg) was prepared in a yield of 72.3% as white solid from 325-01 (315 mg, 0.97 mmol) according to the procedure for 99-02. ¹HNMR (400 MHz, CDCl₃) δ 8.28 (d, J=2.0 Hz, 1H), 7.99 (dd, J=2.4, 10.4 Hz, 1H), 7.47 (s, 1H), 7.40-7.30 (m, 7H), 7.12 (t, J=7.6 Hz, 1H), 7.02 (t, J=9.6 Hz, 1H), 4.58 (m, 1H), 4.52 (d, J=11.6 Hz, 1H), 4.3 (d, J=11.6 Hz, 1H), 3.85-3.77 (m, 1H), 3.65-3.58 (m, 1H), 2.66 (s, 3H), 2.35-2.27 (m, 2H). Mass (m/z): 512.25 [M+H]+.

1-(benzo[d]thiazol-5-ylmethyl)-3-fluoro-5-(2-(3-(2-fluorobenzyloxy)-3-phenylpropylsulfonyl)-6-methylpyrimidin-4-yl)pyridin-2 (1H)-one (326)

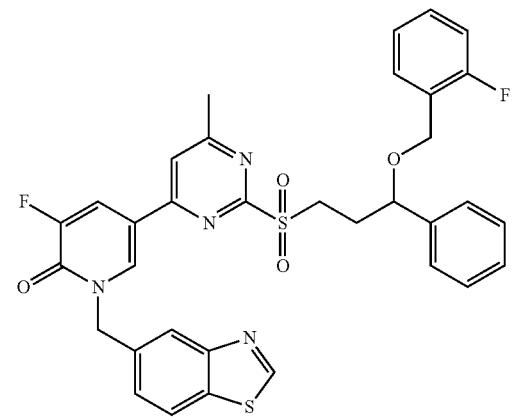

326

The titled compound 326 was prepared in a yield of 21.2% as light yellow solid (21.2 g) from 325 (30 mg, 0.058 mmol) and 5-(bromomethyl)benzo[d]thiazole (28.5 mg, 0.12 mmol) according to the procedure for 85-01. ¹HNMR (400 MHz, CDCl₃) δ 9.02 (s, 1H), 8.36 (s, 1H), 8.13 (d, J=8.4 Hz, 1H), 7.99 (s, 1H), 7.73 (m, 1H), 7.53 (m, 2H), 7.37-7.28 (m, 7H), 7.10 (t, J=7.6 Hz, 1H), 7.00 (t, J=9.6 Hz, 1H), 5.39 (m, 3H), 4.55 (m, 1H), 4.50 (d, J=11.6 Hz, 1H), 4.37 (d, J=12.0 Hz, 1H), 4.21 (t, J=5.6 Hz, 1H), 3.81-3.74 (m, 1H), 3.61-3.53 (m. 1H), 2.63 (s, 3H). Mass (m/z): 659.31 [M+H]+.

3-fluoro-5-(2-(3-(2-fluorobenzyloxy)-3-phenylpropylsulfonyl)-6-methylpyrimidin-4-yl)-1-((1-methyl-1H-indazol-5-yl)methyl)pyridin-2 (1H)-one (327) and 5-((3-fluoro-5-(2-(3-(2-fluorobenzyloxy)-3-phenylpropylsulfonyl)-6-methylpyrimidin-4-yl)pyridin-2-yloxy)methyl)-1-methyl-1H-indazole (328)

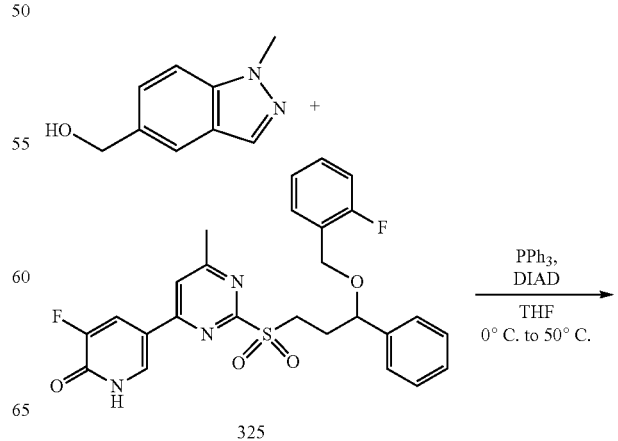

325

353

-continued

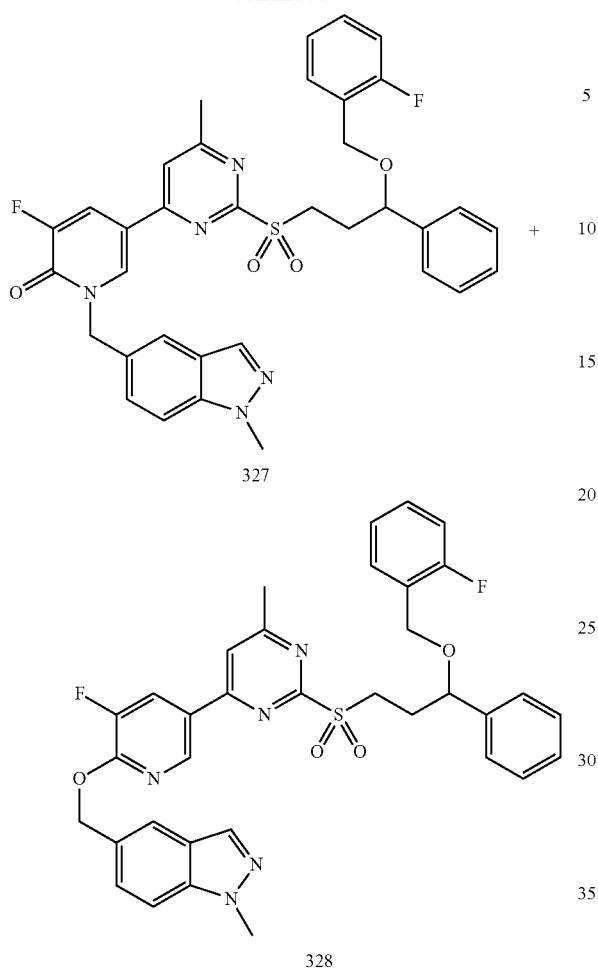

327

328

DIAD (24 mg, 0.12 mmol) was added to the solution of 325 (30 mg, 0.06 mmol), (1-methyl-1H-indazol-5-yl)methanol (10 mg, 0.06 mmol) and PPh$_3$ (30 mg, 012 mmol) in THF at 0° C. under N$_2$. Then the reaction mixture was heated to 50° C. and stirred for 2 h. Evaporation to remove the solvent, the residue was diluted by water, extracted by EtOAc for 3 times. The organic layer was combined, washed by brine, dried over Na$_2$SO$_4$, further purified by pre-TLC (PE:EA=1:1) to give the titled compounds 327 (15 mg, 38.1%) as light yellow solid and 328 (7 mg, 19.1%) as white solid. 327: $^1$HNMR (400 MHz, CDCl$_3$) δ 8.31 (dd, J=0.8, 2.0 Hz, 1H), 7.96 (s, 1H), 7.74-7.69 (m, 2H), 7.54-7.51 (m, 1H), 7.44 (dd, J=1.2, 8.8 Hz, 1H), 7.38-7.30 (m, 8H), 7.09 (td, J=0.8, 7.6 Hz, 1H), 7.00 (m, 1H), 5.34 (m, 2H), 4.55 (m, 1H), 4.49 (d, J=12.0 Hz, 1H), 4.36 (d, J=12.0 Hz, 1H), 4.05 (s, 3H), 3.78-3.72 (m, 1H), 3.60-3.52 (m. 1H), 2.59 (s, 3H), 2.36-2.20 (m, 2H). Mass (m/z): 656.41[M+H]$^+$. 328: $^1$HNMR (400 MHz, CDCl$_3$) δ 8.68 (d, J=2.0, 1H), 8.13 (dd, J=2.0, 10.4 Hz, 1H), 7.99 (m, 1H), 7.88 (m, 1H), 7.73-7.69 (m, 1H), 7.63 (s, 1H), 7.57-7.51 (m, 2H), 7.49-7.30 (m, 6H), 7.12 (td, J=1.2, 7.6 Hz, 1H), 7.01 (m, 1H), 5.66 (s, 2H), 4.59 (m, 1H), 4.52 (d, J=12.0 Hz, 1H), 4.39 (d, J=12.0 Hz, 1H), 4.09 (s, 3H), 3.85-3.77 (m, 1H), 3.66-3.59 (m, 1H), 2.68 (s, 3H), 2.40-2.26 (m, 2H). Mass (m/z): 656.51[M+H]$^+$.

354

1-(benzo[d]oxazol-5-ylmethyl)-3-fluoro-5-(2-((3-((2-fluorobenzyl)oxy)-3-phenylpropyl)sulfonyl)-6-methylpyrimidin-4-yl)pyridin-2 (1H)-one (329)

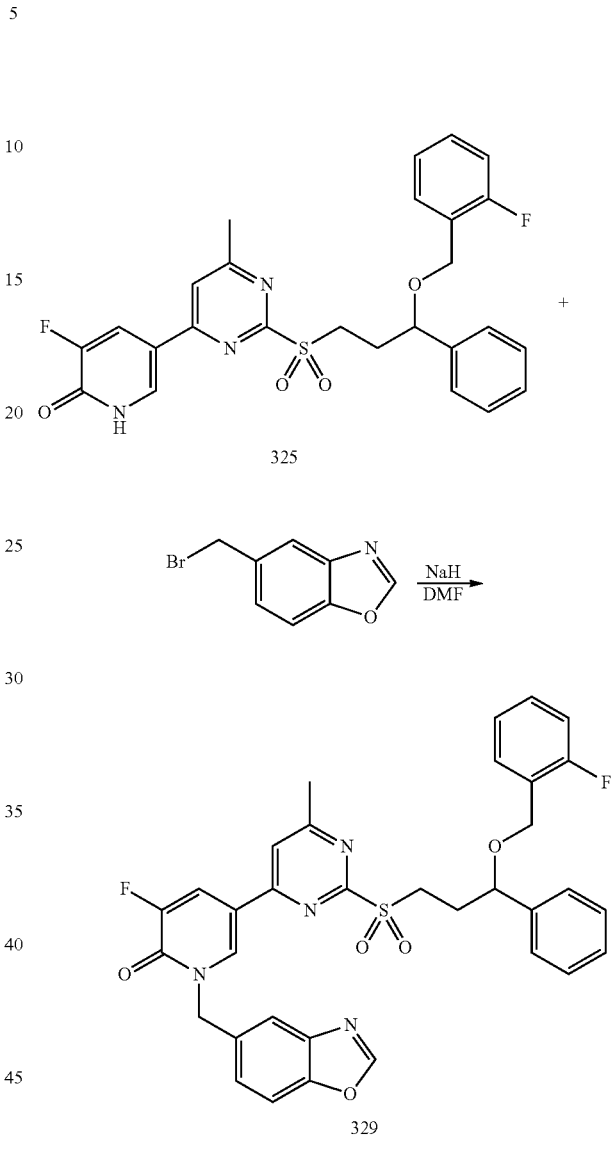

325

329

The titled compound 329 was prepared in a yield of 65.2% as light yellow solid (9 mg, 0.015 mmol) from 325 (12 mg, 0.023 mmol) and 5-(bromomethyl)benzo[d]oxazole (7.3 mg, 0.035 mmol) according to the procedure for 85-01. $^1$H NMR (400 MHz, CDCl$_3$) δ 8.31 (q, J=1.2 Hz, 1H), 8.11 (s, 1H), 7.77 (d, J=1.6 Hz, 1H), 7.75 (dd, J=2.4, 9.6 Hz, 1H), 7.59 (d, J=8.8 Hz, 1H), 7.45 (dd, J=1.6, 8.4 Hz, 1H), 7.36-7.30 (m, 7H), 7.27-7.23 (m, 1H), 7.12 (dt, J=1.2, 7.2 Hz, 1H), 7.00-6.97 (m, 1H), 5.37 (s, 2H), 4.57 (dd, J=4.8, 8.4 Hz, 1H), 4.50 (d, J=12.0 Hz, 1H), 4.37 (d, J=12.0 Hz, 1H), 3.82-3.74 (m, 1H), 3.61-3.54 (m, 1H), 2.62 (s, 1H), 2.36-2.23 (m, 2H). Mass (m/z). 643.33, [M+H]$^+$.

3-fluoro-5-(2-(3-(2-fluorobenzyloxy)-3-phenylpropylsulfonyl)-6-methylpyrimidin-4-yl)-1-((1-methyl-1H-benzo[d][1,2,3]triazol-5-yl)methyl)pyridin-2 (1H)-one (330)

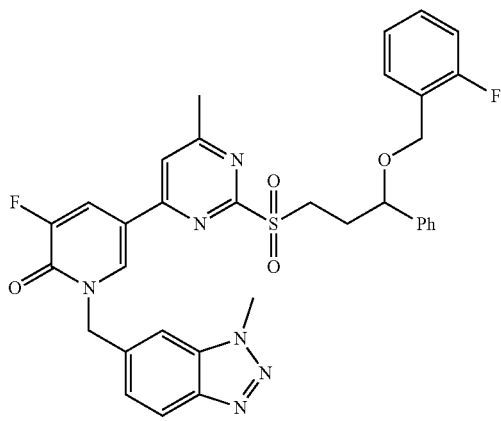

330

The titled compound 330 was prepared in a yield of 52.9% as light yellow solid (17 mg) from 325 (25 mg, 0.049 mmol) and 5-(bromomethyl)-1-methyl-1H-benzo[d][1,2,3]triazole (22 mg, 0.098 mmol) according to the procedure for 85-01. $^1$HNMR (400 MHz, CDCl$_3$) δ 8.33 (s, 1H), 8.06 (s, 1H), 7.78 (dd, J=1.6, 9.6 Hz, 1H), 7.60 (dd, J=8.4, 24.8 Hz, 2H), 7.42 (s, 1H), 7.38-7.28 (m, 6H), 7.09 (td, J=1.2, 7.6 Hz, 1H), 7.02 (m, 1H), 5.42 (s, 2H), 4.57 (m, 1H), 4.49 (d, J=11.6 Hz, 1H), 4.36 (d, J=11.6 Hz, 1H), 4.30 (s, 3H), 3.80-3.72 (m, 1H), 3.60-3.53 (m, 1H), 2.61 (s, 3H), 2.35-2.23 (m, 3H). Mass (m/z): 657.47[M+H]$^+$.

1-((2,3-dihydrobenzo[b][1,4]dioxin-6-yl)methyl)-3-fluoro-5-(2-(3-(2-fluorobenzyloxy)-3-phenylpropylsulfonyl)-6-methylpyrimidin-4-yl)pyridin-2 (1H)-one (331)

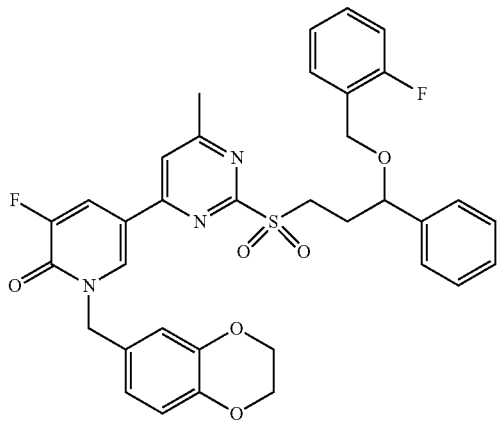

331

The titled compound 331 was prepared in a yield of 83.3% as white solid (17 mg) from 325 (40 mg, 0.08 mmol) and 6-(bromomethyl)-2,3-dihydrobenzo[b][1,4]dioxine (36 mg, 0.16 mmol) according to the procedure for 85-01. $^1$HNMR (400 MHz, CDCl$_3$) δ 8.20 (m, 1H), 7.72 (dd, J=2.4, 9.6 Hz, 1H), 7.39-7.27 (m, 8H), 7.10 (td, J=1.2, 7.2 Hz, 1H), 7.00 (m, 1H), 6.86 (m, 3H), 5.12 (s, 2H), 4.58 (m, 1H), 4.50 (d, J=12.0 Hz, 1H), 4.37 (d, J=12.0 Hz, 1H), 4.22 (s, 4H), 3.80-3.73 (m, 1H), 3.61-3.54 (m, 1H), 2.63 (m, 3H), 2.34-2.24 (m, 2H). Mass (m/z): 660.51 [M+H]$^+$

3-fluoro-5-(2-((3-((2-fluorobenzyl)oxy)-3-phenylpropyl)sulfonyl)-6-methylpyrimidin-4-yl)-1-(4-methoxy-3-(prop-2-yn-1-yloxy)benzyl)pyridin-2 (1H)-one (332)

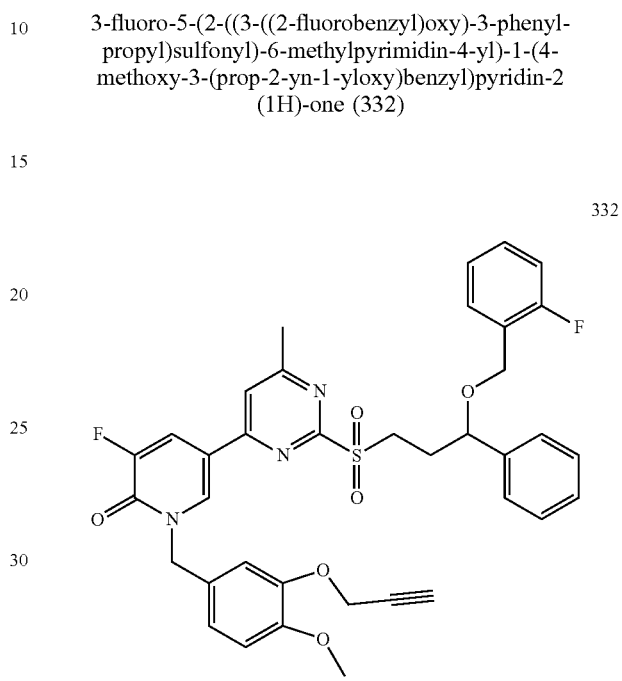

332

The titled compound 332 (16 mg, 21% yield) was prepared as a white solid from 325 (50 mg, 0.11 mmol) and 4-(bromomethyl)-1-methoxy-2-(prop-2-yn-1-yloxy)benzene (32 mg, 0.13 mmol) according to the procedure for 85-01. $^1$H NMR (400 MHz, CDCl$_3$) δ 8.27 (m, 1H), 7.70 (dd, J=2.4, 10 Hz, 1H), 7.39-7.23 (m, 8H), 7.13-7.07 (m, 2H), 7.03-6.90 (m, 2H), 6.85 (d, J=8.3 Hz, 1H), 5.19 (s, 2H), 4.74 (d, J=2.4 Hz, 2H), 4.58-4.54 (d, J=11.8 Hz, 1H), 4.49 (d, J=11.8 Hz, 1H), 4.35 (d, J=11.8 Hz, 1H), 3.84 (s, 3H), 3.80-3.73 (m, 1H), 3.62-3.54 (m, 11H), 2.61 (s, 3H), 2.53 (t, J=2.4 Hz, 1H), 2.39-2.21 (m, 3H). Mass (m/z): 686.23, [M+H]$^+$.

1-(benzo[d][1,3]dioxol-5-ylmethyl)-3-fluoro-5-(6-methyl-2-((3-phenyl-3-(pyridin-3-yloxy)propyl)sulfonyl)pyrimidin-4-yl)pyridin-2 (1H)-one (333)

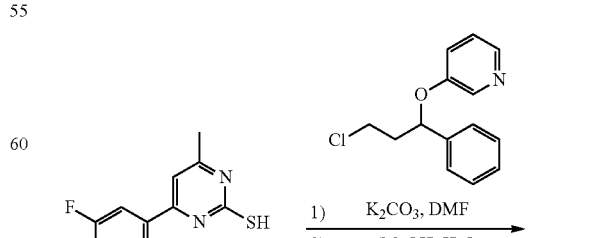

308-02

358

1-(benzo[d][1,3]dioxol-5-ylmethyl)-3-fluoro-5-(6-(fluoromethyl)-2-(methylsulfonyl)pyrimidin-4-yl)pyridin-2(1H)-one (334)

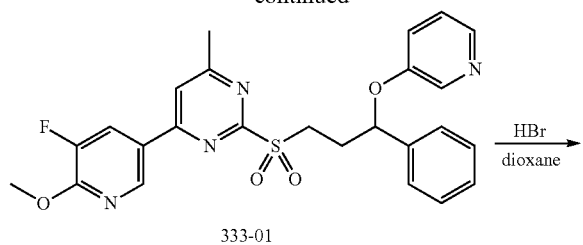

333-01

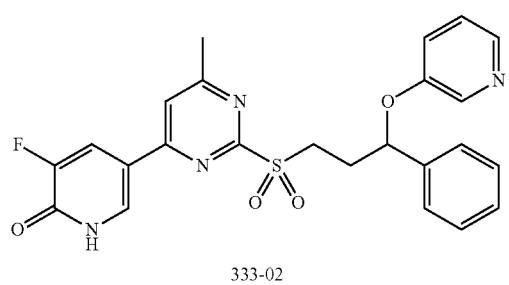

333-02

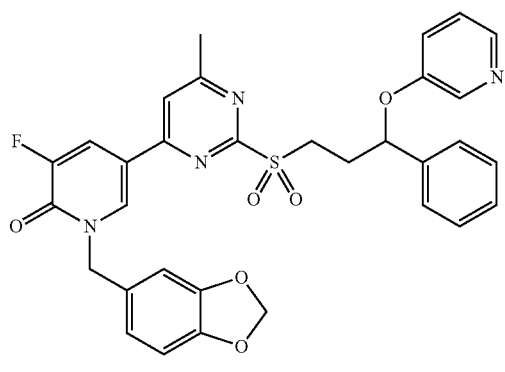

333

Step 1: The title compound 333-01 (0.06 g, 0.12 mmol) was prepared in a yield of 17% as a white solid from 308-02 (0.18 g, 0.72 mmol) and 3-(3-chloro-1-phenylpropoxy)pyridine (0.23 g, 0.93 mmol), according to the procedure for 140. Mass (m/z): 495.29, [M+H]$^+$.

Step 2: The titled compound 333-02 was prepared without purification (24 mg) as a white solid from 333-01 (60 mg, 0.012 mmol) according to the procedure for 99-02. Mass (m/z): 481.19, [M+H]$^+$.

Step 3 The titled compound 333 (12 mg, 0.02 mmol, 40% yield) was prepared as a white solid from 333-02 (24 mg, 0.05 mmol) and 5-(bromomethyl)benzo[d][1,3]dioxole (16 mg, 0.075 mmol) according to the procedure for 85-01. $^1$H NMR (400 MHz, CDCl3) δ 8.24 (q, J=1.2 Hz, 1H), 8.21 (m, 1H), 8.14 (m, 1H), 7.71 (dd, J=2.4, 9.6 Hz, 1H), 7.37-7.27 (m, 6H), 7.09-7.08 (m, 2H), 6.86 (dd, J=1.6, 6.8 Hz, 2H), 6.79 (dd, J=1.6, 6.8 Hz, 1H), 5.95 (s, 2H), 5.40 (dd, J=5.2, 7.6 Hz, 1H), 5.17 (d, J=2.0 Hz, 2H), 3.85-3.69 (m, 2H), 2.62 (s, 3H), 2.57-2.51 (m, 2H). Mass (m/z): 615.27, [M+H]$^+$.

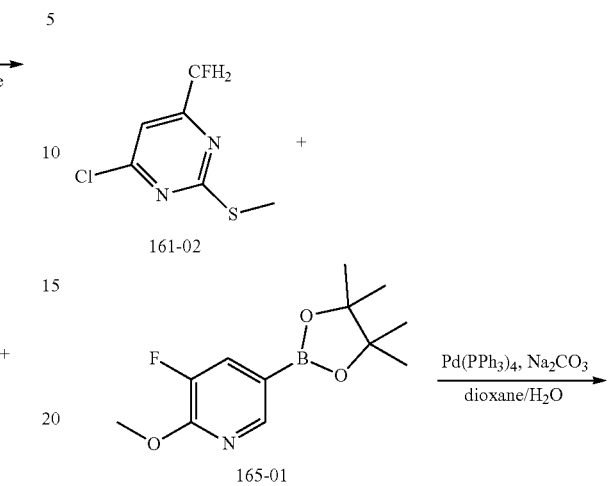

161-02

165-01

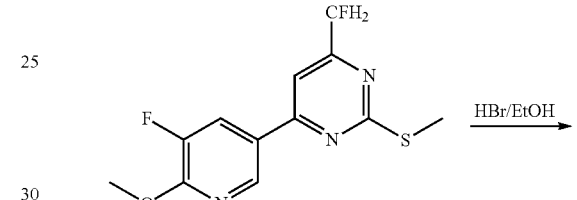

334-01

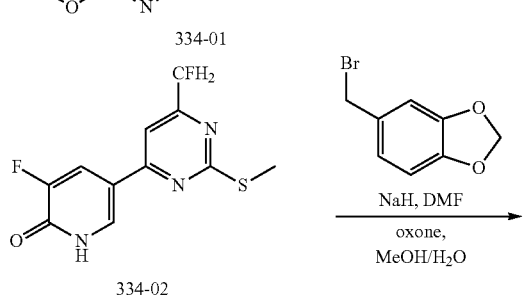

334-02

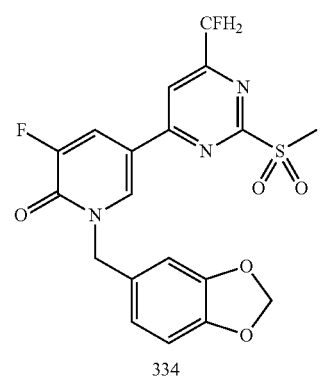

334

Step 1: The titled compound 334-01 was prepared in a yield of 26.7% (2.86 g, 2.13 mmol) as a white solid from 161-02 (1.54 g, 8.0 mmol) according to the procedure for 99-01. Mass (m/z): 284.23, [M+H]$^+$.

Step 2: The titled compound 334-02 was prepared without purification (2.50 g) as a yellow solid from 334-01 (2.86 g, 2.13 mmol) according to the procedure for 99-02. Mass (m/z): 270.19, [M+H]$^+$.

Step 3. The titled compound 334 was prepared in a yield of 79.7% (0.7 g, 1.61 mmol) as a colorless oil from 334-02

(0.5 g, 2.01 mmol) and 5-(bromomethyl)benzo[d][1,3]dioxole (0.48 g, 2.21 mmol) according to the procedure for 99-01. $^1$H NMR (400 MHz, CDCl$_3$) δ 8.35 (q, J=1.2 Hz, 1H), 7.81 (dd, J=2.4, 9.6 Hz, 1H), 7.70 (m, 1H), 6.88-6.86 (m, 2H), 6.80 (d, J=8.4 Hz, 1H), 5.95 (s, 2H), 5.61 (s, 1H), 5.49 (s, 1H), 5.19 (s, 2H), 3.34 (s, 3H). Mass (m/z): 436.26, [M+H]$^+$.

1-(benzo[d][1,3]dioxol-5-ylmethyl)-3-fluoro-5-(2-((3-((2-fluorobenzyl)oxy)-3-phenylpropyl)sulfonyl)-6-(fluoromethyl)pyrimidin-4-yl)pyridin-2 (1H)-one (335)

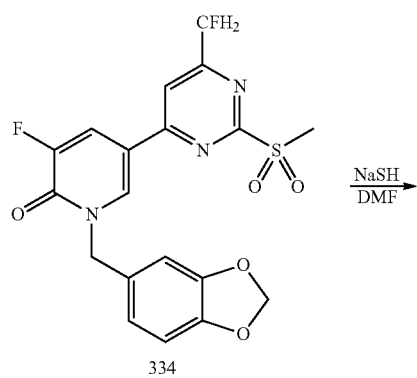

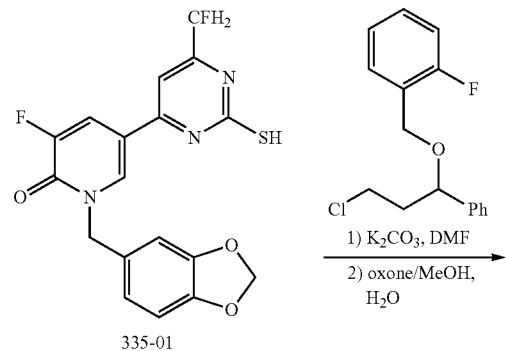

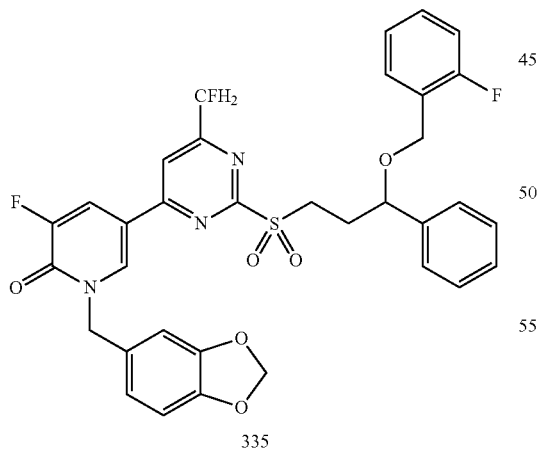

Step 1: The titled compound 335-01 was prepared without purification as a yellow solid (0.6 g) from 334 (0.6 g, 1.38 mmol) according to the procedure for 140-1. Mass (m/z): 390.30, [M+H]$^+$.

Step 2: The title compound 335 (28 mg, 0.042 mmol) was prepared in a yield of 18.3% as a white solid from 335-01 (89 mg, 0.23 mmol) and 1-((3-chloro-1-phenylpropoxy)methyl)-2-fluorobenzene (83 mg, 0.3 mmol), according to the procedure for 140. $^1$H NMR (400 MHz, CDCl$_3$) δ 8.30 (dd, J=0.8, 2.4 Hz, 1H), 7.80 (dd, J=2.4, 9.6 Hz, 1H), 7.66 (d, J=0.8 Hz, 1H), 7.39-7.25 (m, 7H), 7.12 (dt, J=0.8, 7.2 Hz, 1H), 7.03-6.99 (m, 1H), 6.86 (m, 1H), 6.84 (d, J=1 Hz, 1H), 6.78-6.76 (m, 1H), 5.95 (s, 2H), 5.56 (s, 1H), 5.44 (s, 1H), 5.19 (m, 2H), 4.57 (dd, J=4.8, 8.0 Hz, 1H), 4.50 (d, J=12.0 Hz, 1H), 4.36 (d, J=11.6 Hz, 1H), 3.81-3.73 (m, 1H), 3.61-3.53 (m, 1H), 2.36-2.21 (m, 2H). Mass (m/z): 664.40, [M+H]$^+$.

5-(2-((3-((2-fluorobenzyl)oxy)-3-phenylpropyl)sulfonyl)-6-methylpyrimidin-4-yl)-1-((1-methyl-1H-benzo[d]imidazol-5-yl)methyl)pyridin-2 (1H)-one and 5-(2-((3-((2-fluorobenzyl)oxy)-3-phenylpropyl)sulfonyl)-6-methylpyrimidin-4-yl)-1-((1-methyl-1H-benzo[d]imidazol-6-yl)methyl)pyridin-2 (1H)-one (336)

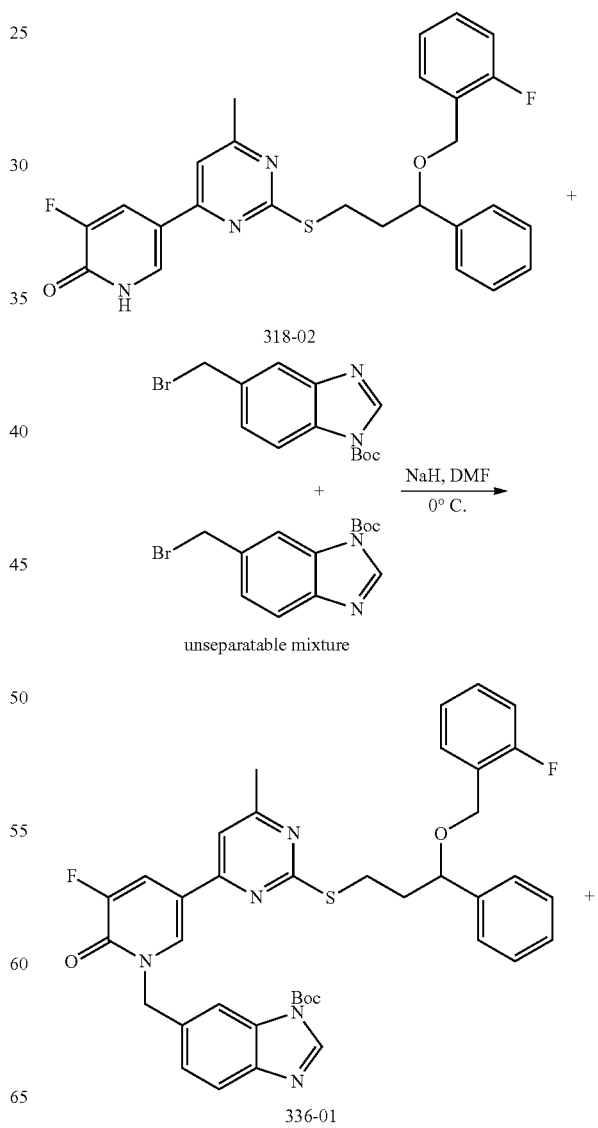

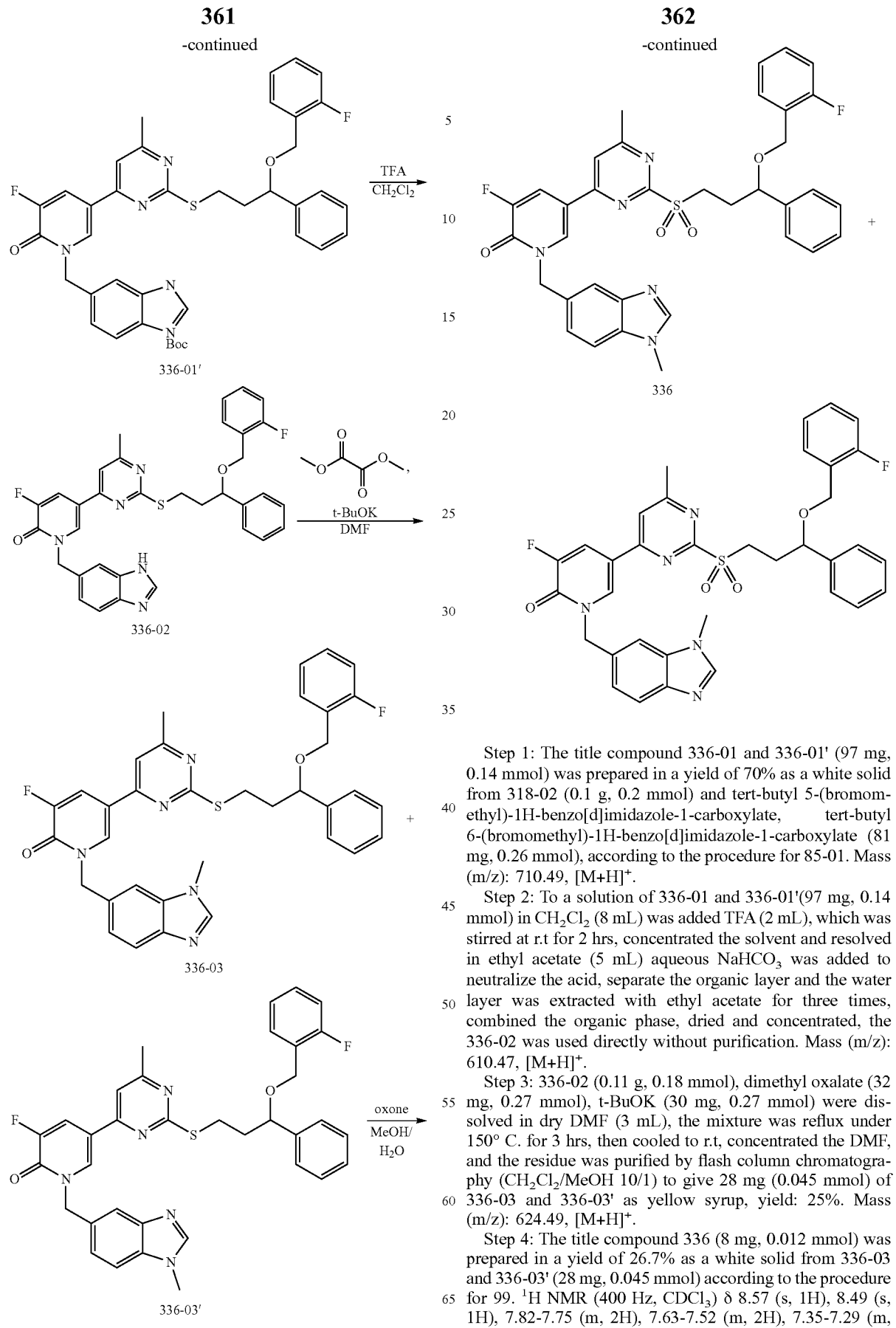

Step 1: The title compound 336-01 and 336-01' (97 mg, 0.14 mmol) was prepared in a yield of 70% as a white solid from 318-02 (0.1 g, 0.2 mmol) and tert-butyl 5-(bromomethyl)-1H-benzo[d]imidazole-1-carboxylate, tert-butyl 6-(bromomethyl)-1H-benzo[d]imidazole-1-carboxylate (81 mg, 0.26 mmol), according to the procedure for 85-01. Mass (m/z): 710.49, [M+H]$^+$.

Step 2: To a solution of 336-01 and 336-01'(97 mg, 0.14 mmol) in CH$_2$Cl$_2$ (8 mL) was added TFA (2 mL), which was stirred at r.t for 2 hrs, concentrated the solvent and resolved in ethyl acetate (5 mL) aqueous NaHCO$_3$ was added to neutralize the acid, separate the organic layer and the water layer was extracted with ethyl acetate for three times, combined the organic phase, dried and concentrated, the 336-02 was used directly without purification. Mass (m/z): 610.47, [M+H]$^+$.

Step 3: 336-02 (0.11 g, 0.18 mmol), dimethyl oxalate (32 mg, 0.27 mmol), t-BuOK (30 mg, 0.27 mmol) were dissolved in dry DMF (3 mL), the mixture was reflux under 150° C. for 3 hrs, then cooled to r.t, concentrated the DMF, and the residue was purified by flash column chromatography (CH$_2$Cl$_2$/MeOH 10/1) to give 28 mg (0.045 mmol) of 336-03 and 336-03' as yellow syrup, yield: 25%. Mass (m/z): 624.49, [M+H]$^+$.

Step 4: The title compound 336 (8 mg, 0.012 mmol) was prepared in a yield of 26.7% as a white solid from 336-03 and 336-03' (28 mg, 0.045 mmol) according to the procedure for 99. $^1$H NMR (400 Hz, CDCl$_3$) δ 8.57 (s, 1H), 8.49 (s, 1H), 7.82-7.75 (m, 2H), 7.63-7.52 (m, 2H), 7.35-7.29 (m, 7H), 7.25-7.21 (m, 1H), 7.09 (t, J=6.4 Hz, 1H), 7.00-6.96

(m, 1H), 5.38 (s, 2H), 4.56-4.53 (m, 1H), 4.48 (d, J=11.6 Hz, 1H), 4.36 (d, J=12.0 Hz, 1H), 4.02 (s, 3H), 3.80-3.72 (m, 1H), 3.61-3.54 (m, 1H), 2.56 (s, 3H), 2.32-2.24 (m, 2H). Mass (m/z): 656.53, [M+H]⁺.

5-(2-((3-(1H-benzo[d]imidazol-1-yl)propyl)sulfo-nyl)-6-methylpyrimidin-4-yl)-3-fluoro-1-((1-methyl-1H-benzo[d][1,2,3]triazol-6-yl)methyl)pyridin-2(1H)-one (337)

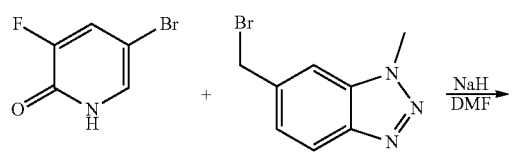

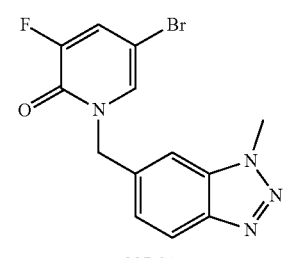

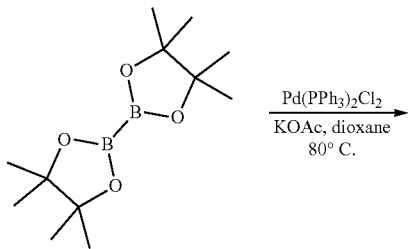

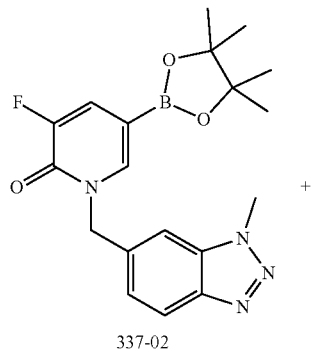

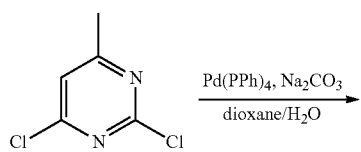

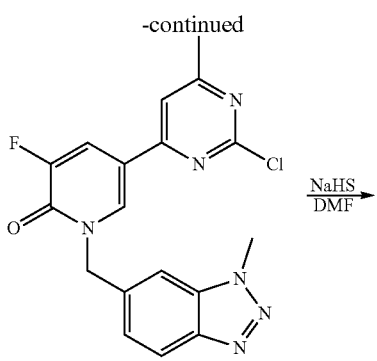

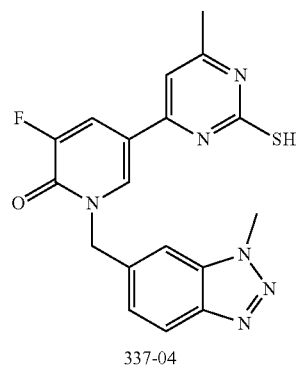

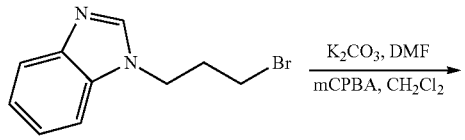

Step 1: The title compound 337-01 (0.7 g, 2.08 mmol) was prepared in a yield of 63.6% as a white solid from 5-bromo-3-fluoropyridin-2(1H)-one (0.76 g, 3.96 mmol) and 6-(bro-momethyl)-1-methyl-1H-benzo[d][1,2,3]triazole (0.75 g, 3.3 mmol), according to the procedure for 85-01. Mass (m/z): 337.25, 339.23, [M+H]⁺.

Step 2: The title compound 337-02 (0.5 g, 1.30 mmol) was prepared in a yield of 62.5% as a white solid from 337-01 (0.7 g, 2.08 mmol) according to the procedure for 165-01. Mass (m/z): 385.43, [M+H]⁺.

Step 3: The titled compound 337-03 was prepared in a yield of 100% (0.5 g, 1.30 mmol) as a white solid from 337-02 (0.5 g, 1.30 mmol) and 2,4-dichloro-6-methylpy-rimidine (0.32 g, 1.97 mmol) according to the procedure for 99-01. Mass (m/z): 385.34, [M+H]⁺.

Step 4. The titled compound 337-04 was prepared without purification as a yellow solid (0.43 g) from 337-03 (0.5 g, 1.30 mmol) according to the procedure for 140-1. Mass (m/z): 383.36, [M+H]⁺.

Step 5: The title compound 337 (10 mg, 0.017 mmol) was prepared in a yield of 18.3% as a white solid from 337-04 (50 mg, 0.13 mmol) and 1-(3-bromopropyl)-1H-benzo[d]imidazole (40 mg, 0.17 mmol), according to the procedure for 140. ¹H NMR (400 Hz, CDCl3) δ 8.61 (s, 1H), 8.27 (m, 1H), 7.95-7.93 (m, 1H), 7.76-7.74 (m, 1H), 7.68 (m, 1H), 7.63-7.53 (m, 3H), 7.39 (s, 1H), 7.25-7.24 (m, 2H), 5.55 (s, 2H), 4.88-4.86 (m, 2H), 4.29 (s, 3H), 3.71 (t, J=5.6 Hz, 2H), 2.70-2.67 (m, 2H), 2.61 (s, 3H). Mass (m/z): 573.68, [M+H]⁺.

5-(2-((3-(1H-benzo[d]imidazol-1-yl)propyl)sulfonyl)-6-methylpyrimidin-4-yl)-1-(benzo[d][1,3]dioxol-5-ylmethyl)-3-fluoropyridin-2 (1H)-one (338)

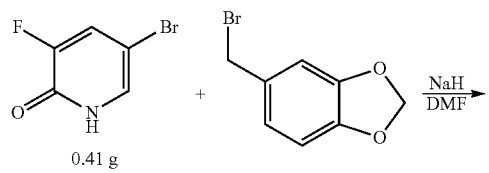

0.41 g

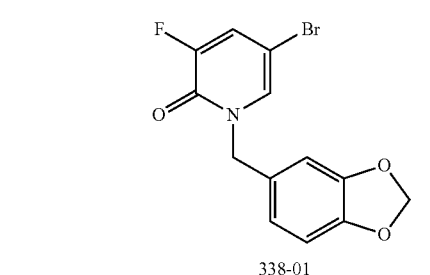

338-01

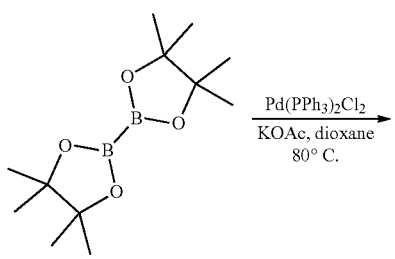

338-02

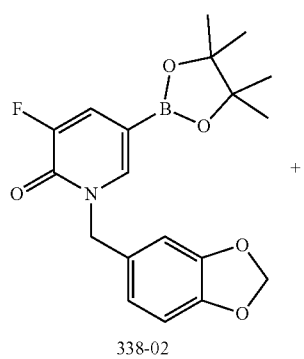

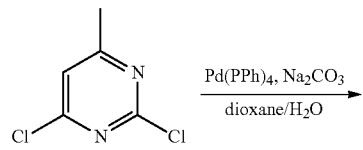

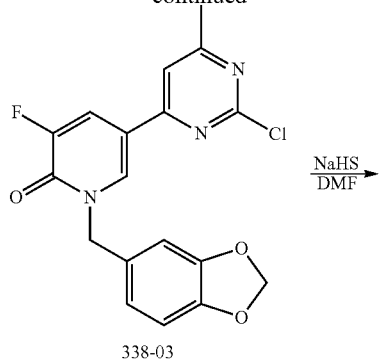

338-03

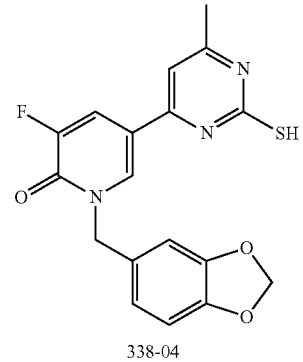

338-04

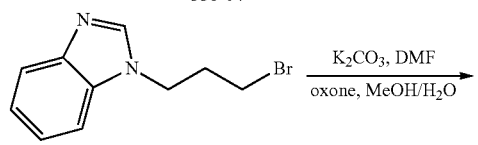

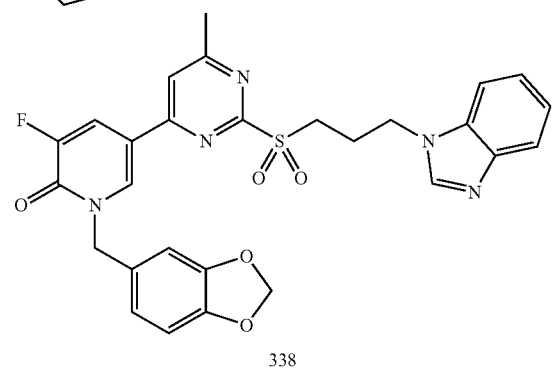

338

Step 1: The title compound 338-01 (0.48 g, 1.47 mmol) was prepared in a yield of 83.7% as a white solid from 5-bromo-3-fluoropyridin-2 (1H)-one (0.41 g, 2.12 mmol) and 5-(bromomethyl)benzo[d][1,3]dioxole (0.38 g, 1.77 mmol), according to the procedure for 85-01. Mass (m/z): 326.15, 328.15, [M+H]⁺.

Step 2: The title compound 338-02 (0.5 g, 1.34 mmol) was prepared in a yield of 91.2%/as a white solid from 338-01 (0.488 g, 1.47 mmol) according to the procedure for 165-01. Mass (m/z): 374.38, [M+H]⁺.

Step 3. The titled compound 338-03 was prepared in a yield of 53.7% (0.27 g, 0.72 mmol) as a white solid from 338-02 (0.5 g, 1.34 mmol) according to the procedure for 99-01. Mass (m/z): 374.28, [M+H]⁺.

Step 4: The titled compound 338-04 was prepared without purification as a yellow solid (0.3 g) from 338-03 (0.27 g, 0.72 mmol) according to the procedure for 140-1. Mass (m/z): 372.37, [M+H]⁺.

Step 5: The title compound 338 (25 mg) was prepared in a yield of 34.2% as a white solid from 338-04 (50 mg, 0.13 mmol) and 1-(3-bromopropyl)-1H-benzo[d]imidazole (41.6 mg, 0.17 mmol), according to the procedure for 140. ¹HNMR (400 MHz, DMSO-d$_6$) δ 8.78 (m, 1H), 8.34 (s, 1H), 8.12 (dd, J=2.4, 11.2 Hz, 1H), 8.07 (s, 1H), 7.65-7.63 (m, 1H), 7.57-7.55 (m, 1H), 7.19-7.17 (m, 2H), 7.02 (d, J=1.2 Hz, 1H), 6.91 (dd, J=1.6, 8.0 Hz, 1H), 6.88 (d, J=8.0 Hz, 1H), 5.97 (s, 2H), 5.19 (s, 2H), 4.43 (t, J=6.8 Hz, 2H), 3.72 (m, 2H), 2.52 (s, 3H), 2.27-2.17 (m, 2H). Mass (m/z): 562.59, [M+H]⁺.
Synthesis of Compounds 339-361
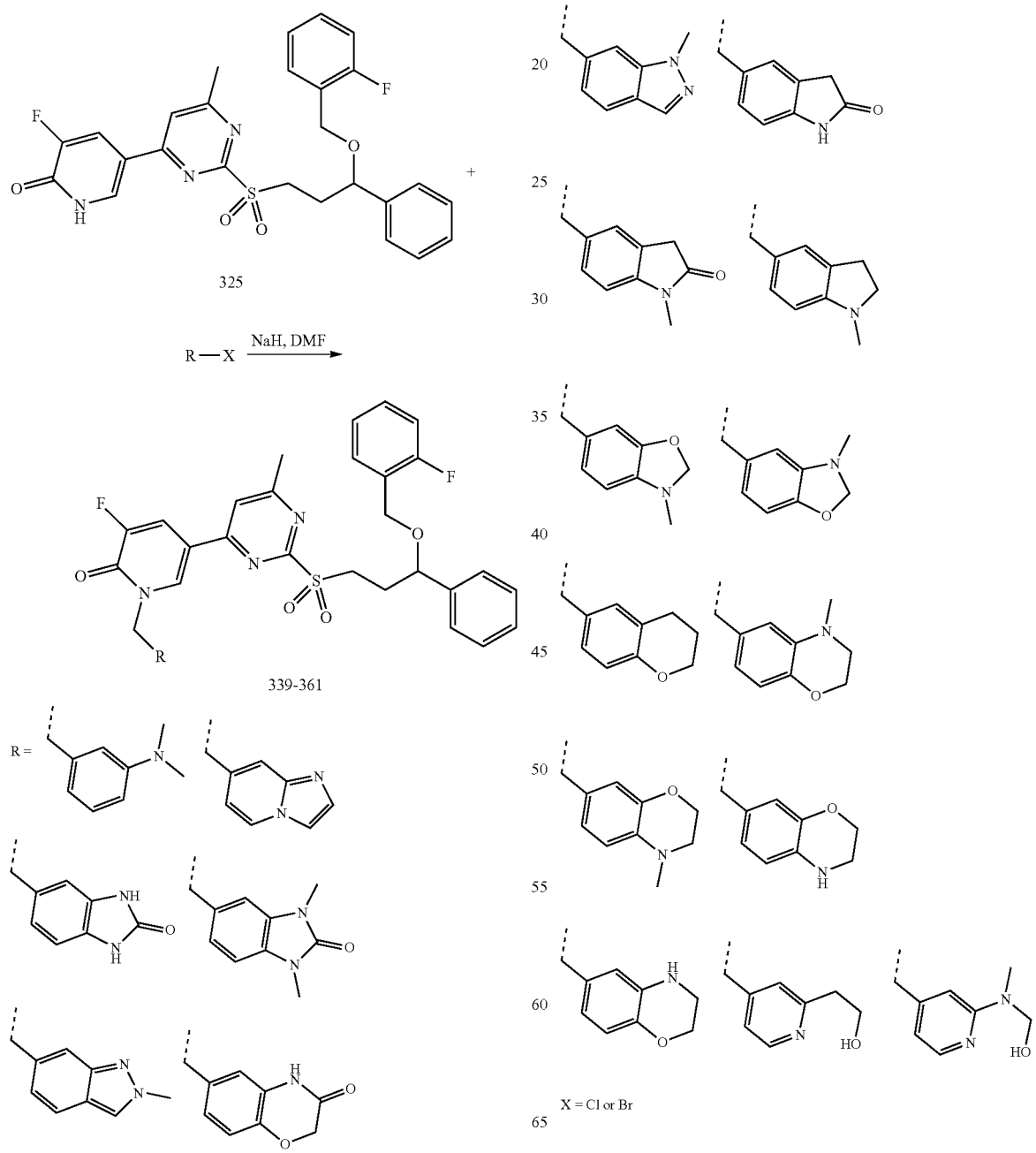

369
Synthesis of Compounds 36, 364, 366
370
Synthesis of Compounds 363, 365, 367
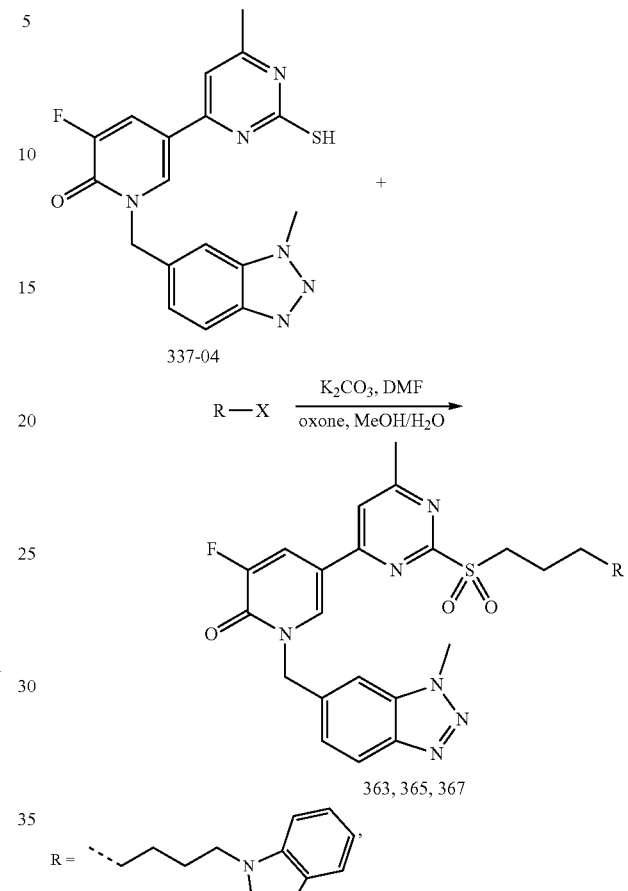
337-04
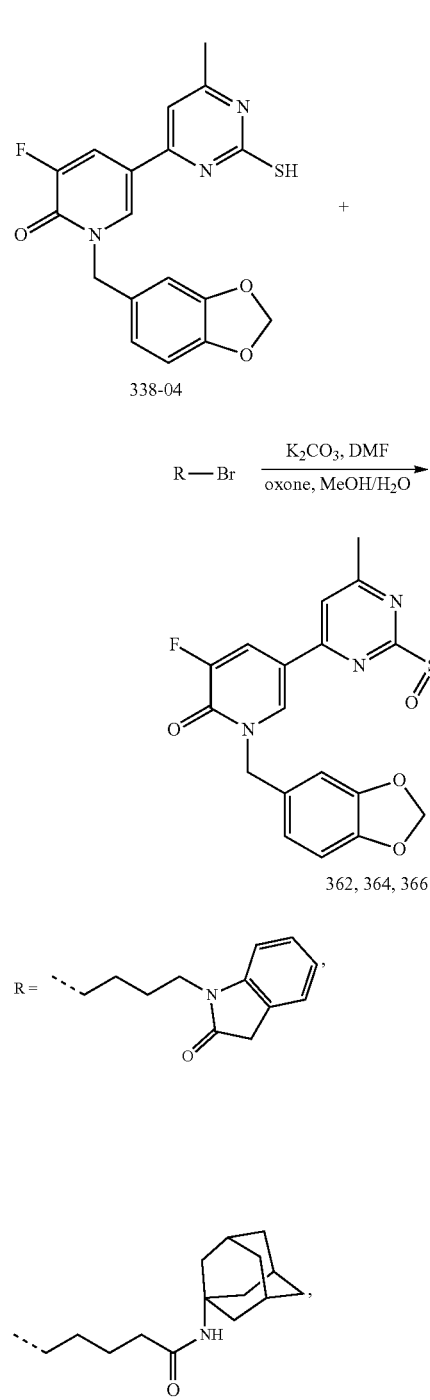
338-04
362, 364, 366
Synthesis of Compounds 368, 369
363, 365, 367
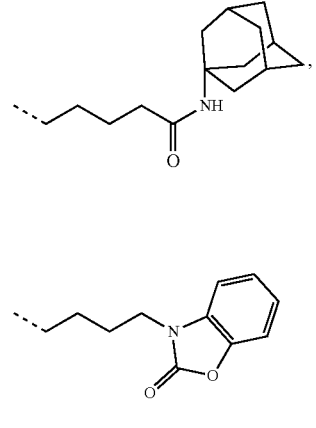
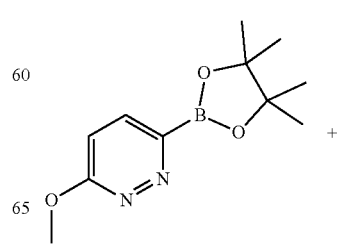

371
-continued
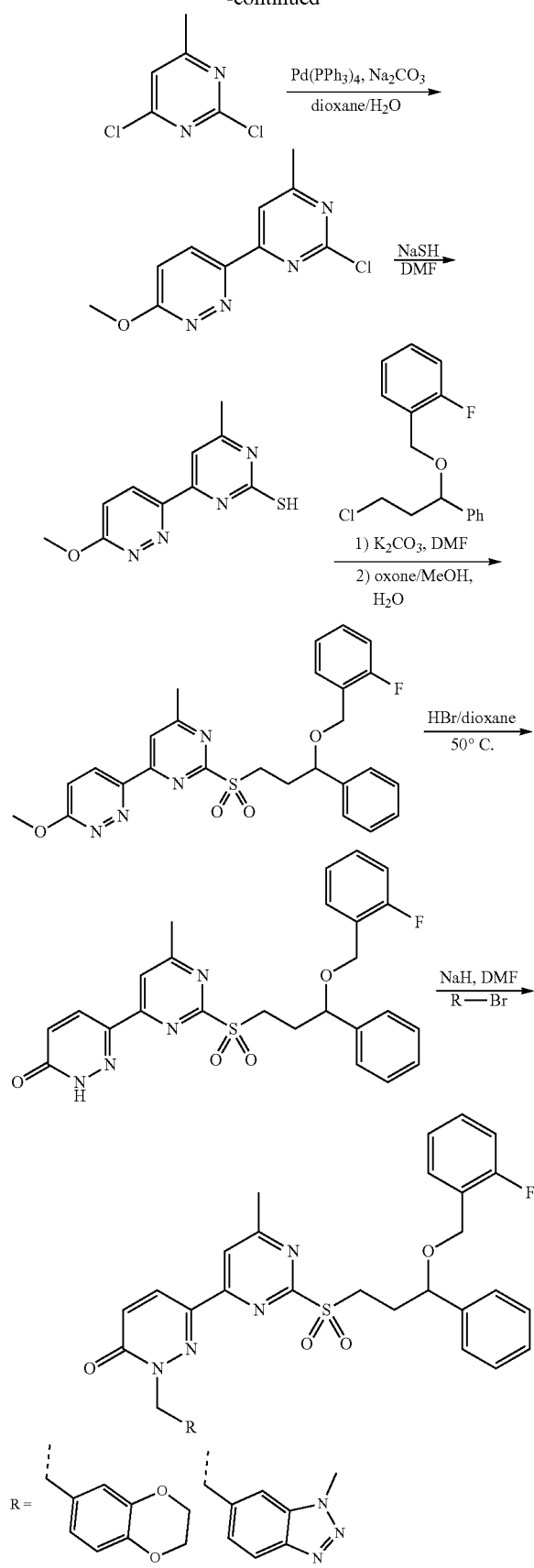
372
Synthesis of Compounds 370-375
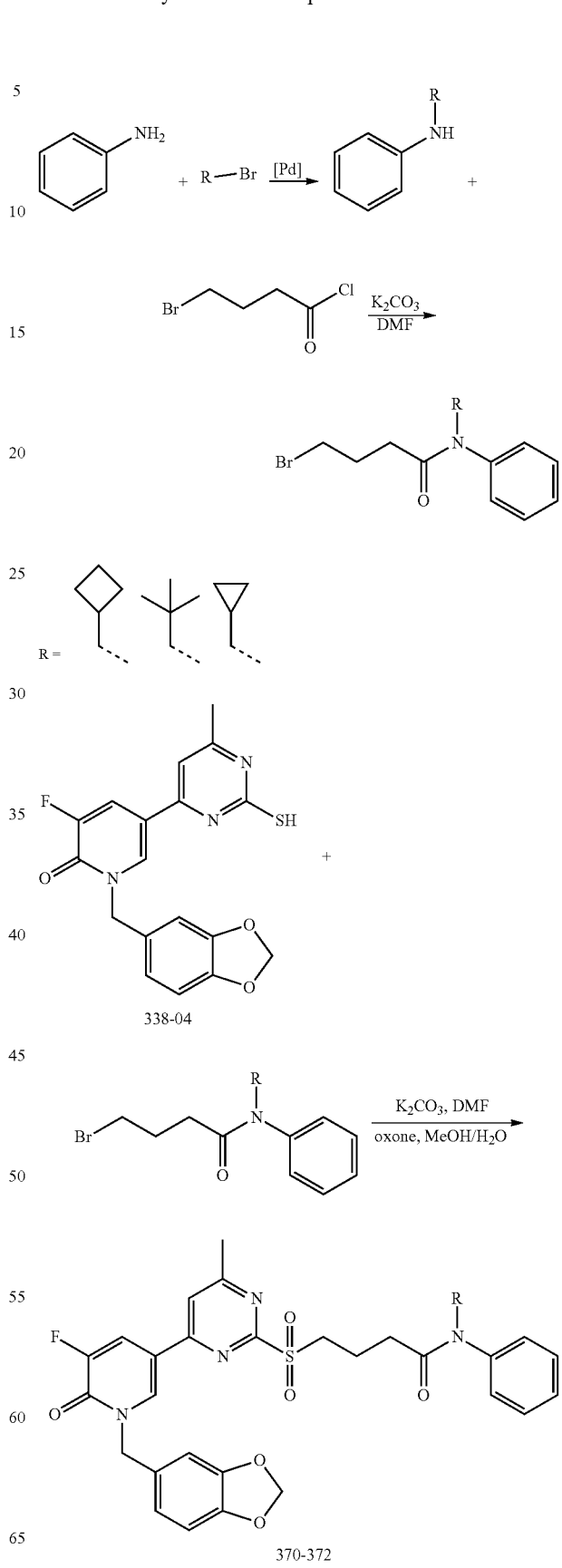
338-04
370-372

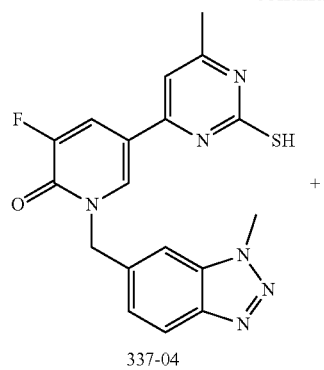
337-04
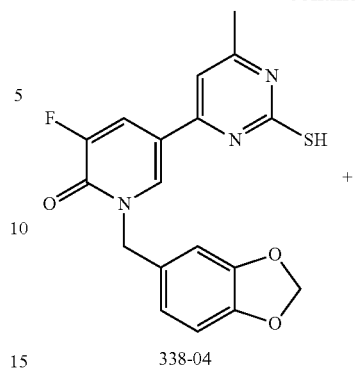
338-04
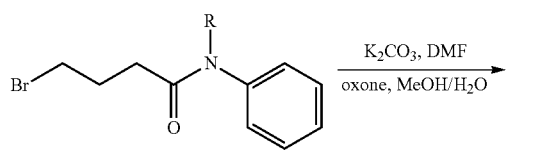
K₂CO₃, DMF
oxone, MeOH/H₂O
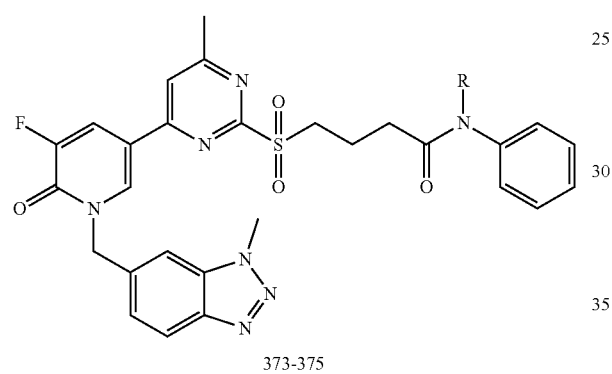
373-375
Synthesis of Compounds 376-381
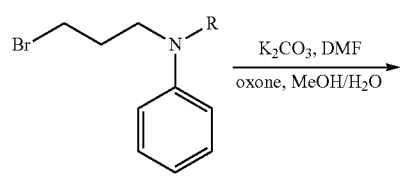
K₂CO₃, DMF
oxone, MeOH/H₂O
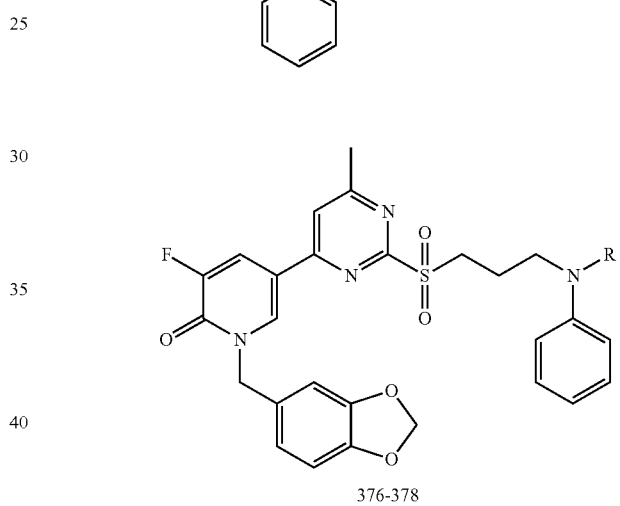
376-378
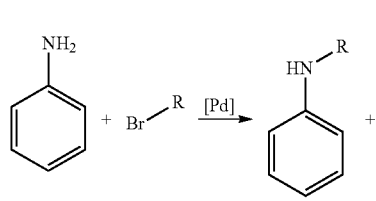
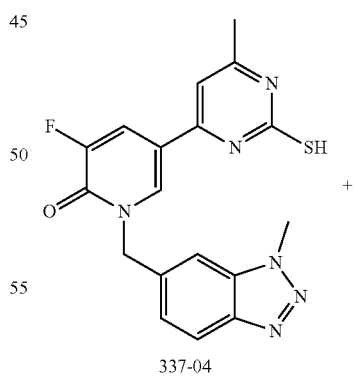
337-04
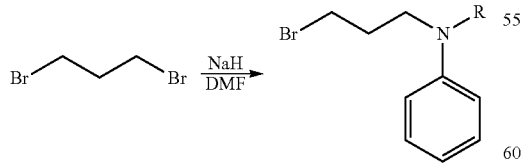
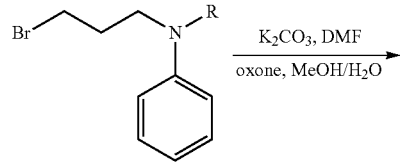
K₂CO₃, DMF
oxone, MeOH/H₂O
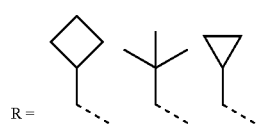

-continued
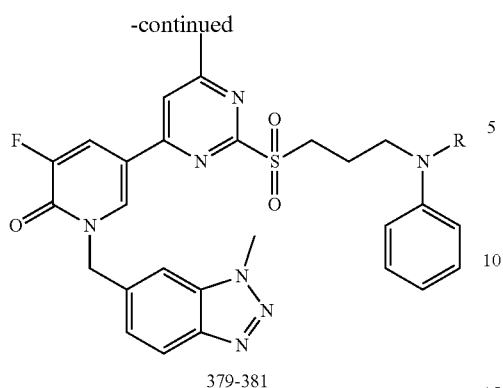
379-381
Synthesis of Compounds 382
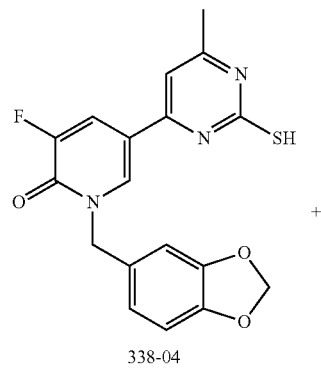
338-04
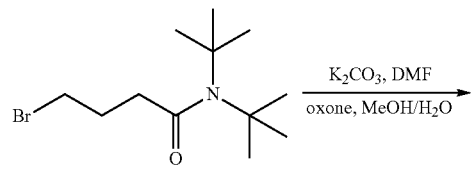
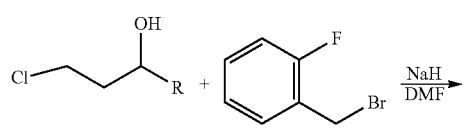
382
Synthesis of Compounds 383-400
-continued
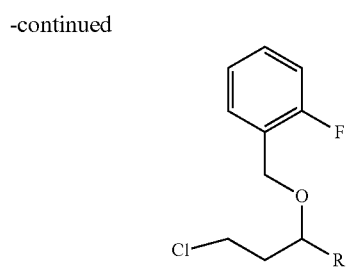
R = 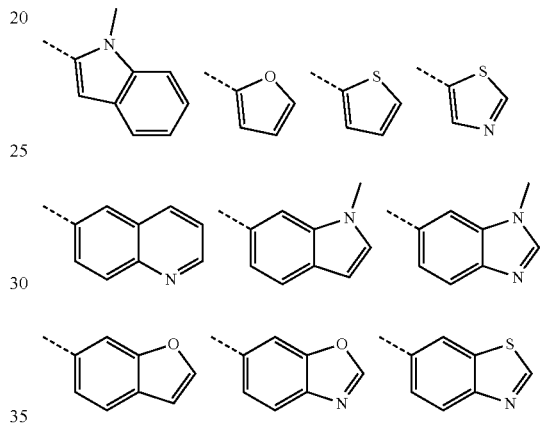
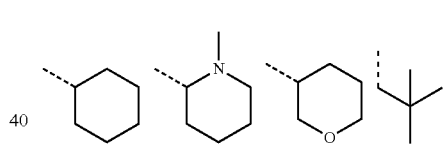
338-04
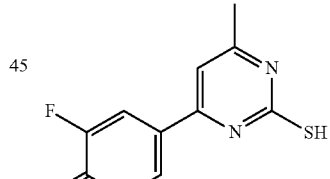
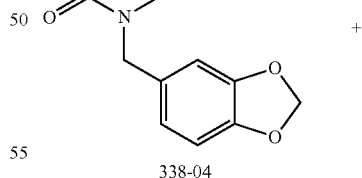
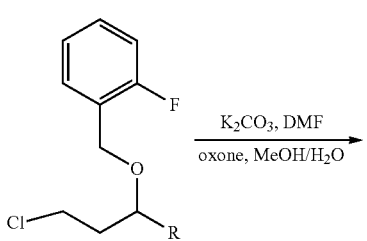

-continued

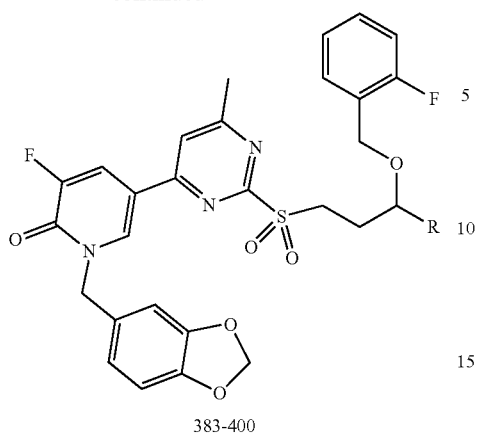

383-400

Synthesis of Compounds 401-421

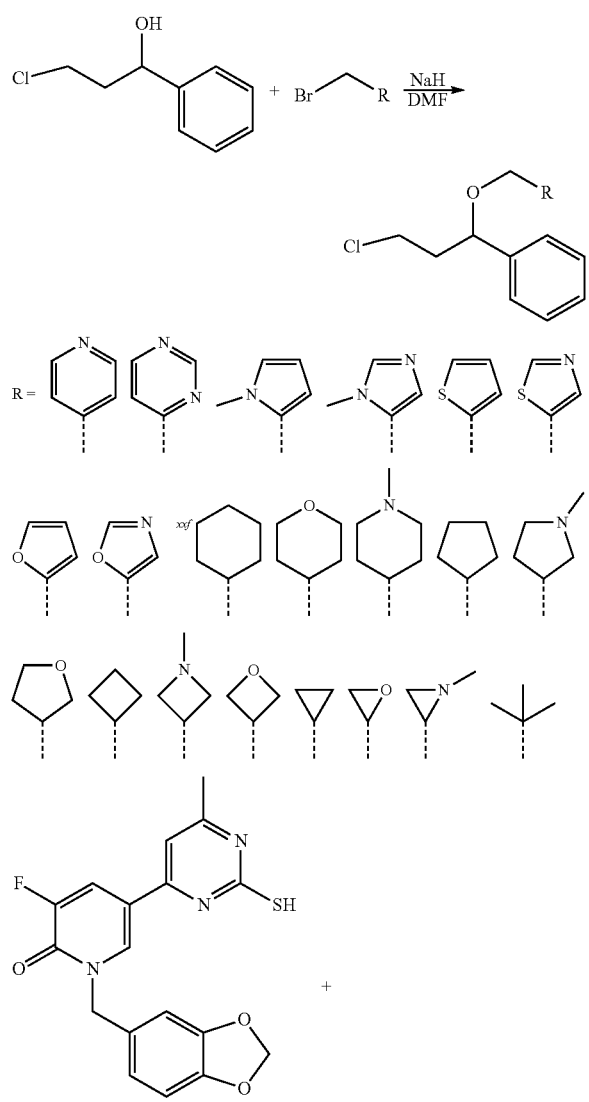

-continued

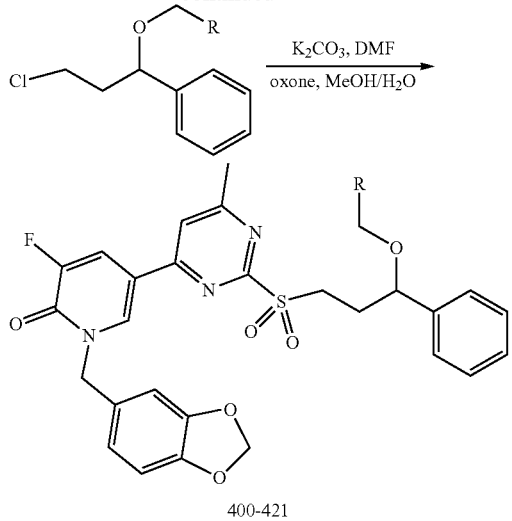

400-421

Apoptosis Inhibition Assay

U2OS_Bim cells (a U2OS stable cell line transfected with a Bim transgene) were cultured in DMEM culture medium (Gibico). On day one, U2OS_Bim cells were plated in 96-well plates at a density of 3000 cells per well. On day two, cells were pretreated with compounds for one hour. Then cells were treated with 0.1 μg/mL doxycycline (DOX) to trigger apoptosis. 24 hours after DOX treatment, cell viability was determined by measuring the ATP levels using the Cell Titer-Glo kit (G7570, Promega), according to the manufacturer's instructions. Luminescence was recorded with a PerkinElmer EnSpire Multimode Plate Reader. Survived cells were normalized to those cells treated with DMSO. zVAD (20 μM) was used as a positive control. Activity data for compounds 1-886 are represented as means f standard deviation of duplicates; activity data for compounds 187-274 are estimated based on preliminary results.

Biological Activity Data, EC 50

| Compound | EC50 |
|---|---|
| hit | 1-10 uM |
| 1 | 1-10 uM |
| 2 | 1-10 uM |
| 3 | 1-10 uM |
| 4 | 1-10 uM |
| 5 | 1-10 uM |
| 6 | <100 uM |
| 7 | 1-10 uM |
| 8 | <100 uM |
| 9 | 1-10 uM |
| 10 | 1-10 uM |
| 11 | 1-10 uM |
| 12 | 1-10 uM |
| 13 | 1-10 uM |
| 14 | 1-10 uM |
| 15 | 1-10 uM |
| 16 | 1-10 uM |
| 17 | <100 uM |
| 18 | 1-20 uM |
| 19 | 1-10 uM |
| 20 | 1-10 uM |
| 21 | <100 uM |
| 22 | 1-20 uM |
| 23 | 1-10 uM |
| 24 | 1-10 uM |
| 25 | 1-10 uM |
| 26 | 1-10 uM |

-continued

| Compound | EC50 |
|---|---|
| 27 | 1-10 uM |
| 28 | <100 uM |
| 29 | 1-10 uM |
| 30 | 1-10 uM |
| 31 | 1-10 uM |
| 32 | 1-10 uM |
| 33 | <100 uM |
| 34 | <100 uM |
| 35 | 1-10 uM |
| 36 | 1-10 uM |
| 37 | 1-10 uM |
| 38 | <100 uM |
| 39 | <100 uM |
| 40 | <100 uM |
| 41 | <100 uM |
| 42 | <100 uM |
| 43 | 1-20 uM |
| 44 | 1-10 uM |
| 45 | 1-10 uM |
| 46 | 1-20 uM |
| 47 | 1-10 uM |
| 48 | <100 uM |
| 49 | <100 uM |
| 50 | <100 uM |
| 51 | 1-10 uM |
| 52 | <100 uM |
| 53 | <100 uM |
| 54 | 1-20 uM |
| 55 | 1-20 uM |
| 56 | 1-20 uM |
| 57 | <100 uM |
| 58 | <100 uM |
| 59 | 1-10 uM |
| 60 | <100 uM |
| 61 | <100 uM |
| 62 | <100 uM |
| 63 | <100 uM |
| 64 | <100 uM |
| 65 | <100 uM |
| 66 | 1-10 uM |
| 67 | <100 uM |
| 68 | 1-20 uM |
| 69 | 1-10 uM |
| 70 | 1-10 uM |
| 71 | <100 uM |
| 72 | 1-10 uM |
| 73 | 1-10 uM |
| 74 | <100 uM |
| 75 | 1-20 uM |
| 76 | 1-20 uM |
| 77 | < 100 uM |
| 78 | <100 uM |
| 79 | <100 uM |
| 80 | <100 uM |
| 81 | <100 uM |
| 82 | <100 uM |
| 83 | 1-10 uM |
| 84 | 1-10 uM |
| 85 | 1-10 uM |
| 86 | <100 uM |
| 87 | <100 uM |
| 88 | <100 uM |
| 89 | <100 uM |
| 90 | <100 uM |
| 91 | <100 uM |
| 92 | <100 uM |
| 93 | <100 uM |
| 94 | <100 uM |
| 95 | <100 uM |
| 96 | <100 uM |
| 97 | <100 uM |
| 98 | <100 uM |
| 99 | <100 uM |
| 100 | 1-1000 nM |
| 101 | 1-10 uM |
| 102 | 1-10 uM |
| 103 | 1-10 uM |

-continued

| Compound | EC50 |
|---|---|
| 104 | 1-1000 nM |
| 105 | 1-1000 nM |
| 106 | 1-1000 nM |
| 107 | 1-1000 nM |
| 108 | 1-10 uM |
| 109 | 1-1000 nM |
| 110 | 1-1000 nM |
| 111 | 1-1000 nM |
| 112 | 1-1000 nM |
| 113 | 1-1000 nM |
| 114 | 1-10 uM |
| 115 | 1-1000 nM |
| 116 | 1-10 uM |
| 117 | 1-20 uM |
| 118 | 1-20 uM |
| 119 | 1-10 uM |
| 120 | 1-1000 nM |
| 121 | 1-1000 nM |
| 122 | 1-1000 nM |
| 123 | <100 uM |
| 124 | 1-1000 nM |
| 125 | 1-10 uM |
| 126 | 1-1000 nM |
| 127 | 1-1000 nM |
| 128 | 1-1000 nM |
| 129 | 1-1000 nM |
| 130 | 1-1000 nM |
| 131 | 1-1000 nM |
| 132 | 1-1000 nM |
| 133 | 1-10 uM |
| 134 | 1-10 uM |
| 135 | 1-1000 nM |
| 136 | 1-1000 nM |
| 137 | 1-1000 nM |
| 138 | 1-1000 nM |
| 139 | 1-10 uM |
| 140 | 1-1000 nM |
| 141 | 1-1000 nM |
| 142 | 1-10 uM |
| 143 | 1-1000 nM |
| 144 | 1-1000 nM |
| 145 | 1-1000 nM |
| 146 | 1-1000 nM |
| 147 | 1-1000 nM |
| 148 | 1-1000 nM |
| 149 | 1-1000 nM |
| 150 | 1-1000 nM |
| 151 | 1-1000 nM |
| 152 | 1-1000 nM |
| 153 | 1-1000 nM |
| 154 | 1-1000 nM |
| 155 | 1-1000 nM |
| 156 | 1-1000 nM |
| 157 | 1-1000 nM |
| 158 | <100 uM |
| 159 | <100 uM |
| 160 | 1-1000 nM |
| 161 | 1-1000 nM |
| 162 | 1-1000 nM |
| 163 | 1-1000 nM |
| 164 | 1-1000 nM |
| 165 | 1-1000 nM |
| 166 | 1-10 uM |
| 167 | 1-1000 nM |
| 168 | 1-1000 nM |
| 169 | 1-1000 nM |
| 170 | 1-1000 nM |
| 171 | 1-1000 nM |
| 172 | 1-1000 nM |
| 173 | 1-10 uM |
| 174 | 1-1000 nM |
| 175 | 1-1000 nM |
| 176 | 1-10 uM |
| 177 | <100 uM |
| 178 | 1-1000 nM |
| 179 | <100 uM |
| 180 | 1-1000 nM |

| Compound | EC50 |
|---|---|
| 181 | 1-1000 nM |
| 182 | 1-1000 nM |
| 183 | 1-1000 nM |
| 184 | 1-1000 nM |
| 185 | 1-10 uM |
| 186 | 1-1000 nM |
| 187 | <10 uM |
| 188 | <10 uM |
| 189 | <10 uM |
| 190 | <10 uM |
| 191 | <10 uM |
| 192 | <10 uM |
| 193 | <10 uM |
| 194 | <10 uM |
| 195 | <10 uM |
| 196 | <10 uM |
| 197 | <10 uM |
| 198 | <10 uM |
| 199 | <10 uM |
| 200 | <10 uM |
| 201 | <10 uM |
| 202 | <10 uM |
| 203 | <10 uM |
| 204 | <10 uM |
| 205 | <10 uM |
| 206 | <10 uM |
| 207 | <10 uM |
| 208 | <10 uM |
| 209 | <10 uM |
| 210 | <10 uM |
| 211 | <10 uM |
| 212 | <10 uM |
| 213 | <10 uM |
| 214 | <10 uM |
| 215 | <10 uM |
| 216 | <10 uM |
| 217 | <10 uM |
| 218 | <10 uM |
| 219 | <10 uM |
| 220 | <10 uM |
| 221 | <10 uM |
| 222 | <10 uM |
| 223 | <10 uM |
| 224 | <10 uM |
| 225 | <10 uM |
| 226 | <10 uM |
| 227 | <10 uM |
| 228 | <10 uM |
| 229 | <10 uM |
| 230 | <10 uM |
| 231 | <10 uM |
| 232 | <10 uM |
| 233 | <10 uM |
| 234 | <10 uM |
| 235 | <10 uM |
| 236 | <10 uM |
| 237 | <10 uM |
| 238 | <10 uM |
| 239 | <10 uM |
| 240 | <10 uM |
| 241 | <10 uM |
| 242 | <10 uM |
| 243 | <10 uM |
| 244 | <10 uM |
| 245 | <10 uM |
| 246 | <10 uM |
| 247 | <10 uM |
| 248 | <10 uM |
| 249 | <10 uM |
| 250 | <10 uM |
| 251 | <10 uM |
| 252 | <10 uM |
| 253 | <10 uM |
| 254 | <10 uM |
| 255 | <10 uM |
| 256 | <10 uM |
| 257 | <10 uM |
| 258 | <10 uM |
| 259 | <10 uM |
| 260 | <10 uM |
| 261 | <10 uM |
| 262 | <10 uM |
| 263 | <10 uM |
| 264 | <10 uM |
| 265 | <10 uM |
| 266 | <10 uM |
| 267 | <10 uM |
| 268 | <10 uM |
| 269 | <10 uM |
| 270 | <10 uM |
| 271 | <10 uM |

Biological Activity Data, EC 50

| Compound | EC50 |
|---|---|
| 272 | 1-1000 nM |
| 273 | 1-10 uM |
| 274 | <100 uM |
| 275 | <100 uM |
| 276 | 1-1000 nM |
| 277 | 1-1000 nM |
| 278 | 1-1000 nM |
| 279 | 1-1000 nM |
| 280 | 1-1000 nM |
| 281 | 1-1000 nM |
| 282 | 1-1000 nM |
| 283 | 1-1000 nM |
| 284 | 1-1000 nM |
| 285 | 1-1000 nM |
| 286 | 1-1000 nM |
| 287 | 1-1000 nM |
| 288 | 1-1000 nM |
| 289 | 1-1000 nM |
| 290 | 1-10 uM |
| 291 | 1-10 uM |
| 292 | 1-10 uM |
| 293 | 1-1000 nM |
| 294 | 1-1000 nM |
| 295 | 1-1000 nM |
| 296 | 1-10 uM |
| 297 | <100 uM |
| 298 | <100 uM |
| 299 | <100 uM |
| 300 | 1-1000 nM |
| 301 | 1-10 uM |
| 302 | 1-1000 nM |
| 303 | <100 uM |
| 304 | <100 uM |
| 305 | 1-1000 nM |
| 307 | 1-1000 nM |
| 308 | <100 uM |
| 309 | 1-10 uM |
| 310 | 1-10 uM |
| 311 | 1-1000 nM |
| 312 | <100 uM |
| 313 | 1-10 uM |
| 314 | 1-1000 nM |
| 315 | <100 uM |
| 316 | 1-10 uM |
| 317 | 1-1000 nM |
| 318 | 1-1000 nM |
| 319 | 1-1000 nM |
| 320 | 1-1000 nM |
| 321 | 1-1000 nM |
| 322 | 1-1000 nM |
| 323 | 1-1000 nM |
| 324 | 1-10 uM |
| 325 | 1-10 uM |
| 326 | 1-1000 nM |
| 327 | 1-1000 nM |
| 328 | <100 uM |

| Compound | EC50 |
|---|---|
| 329 | 1-1000 nM |
| 330 | 1-1000 nM |
| 331 | 1-1000 nM |
| 332 | 1-1000 nM |
| 333 | 1-1000 nM |
| 334 | 1-10 uM |
| 335 | 1-1000 nM |
| 336 | 1-1000 nM |
| 337 | 1-1000 nM* |
| 338 | 1-1000 nM* |
| 339 | 1-1000 nM* |
| 340 | 1-1000 nM* |
| 341 | 1-1000 nM* |
| 342 | 1-1000 nM* |
| 343 | 1-1000 nM* |
| 344 | 1-1000 nM* |
| 345 | 1-1000 nM* |
| 346 | 1-1000 nM* |
| 347 | 1-1000 nM* |
| 348 | 1-1000 nM* |
| 349 | 1-1000 nM* |
| 350 | 1-1000 nM* |
| 351 | 1-1000 nM* |
| 352 | 1-1000 nM* |
| 353 | 1-1000 nM* |
| 354 | 1-1000 nM* |
| 355 | 1-1000 nM* |
| 356 | 1-1000 nM* |
| 357 | 1-1000 nM* |
| 358 | 1-1000 nM* |
| 359 | 1-1000 nM* |
| 360 | 1-1000 nM* |
| 361 | 1-1000 nM* |
| 362 | 1-1000 nM* |
| 363 | 1-1000 nM* |
| 364 | 1-1000 nM* |
| 365 | 1-1000 nM* |
| 366 | 1-1000 nM* |
| 367 | 1-1000 nM* |
| 368 | 1-1000 nM* |
| 369 | 1-1000 nM* |
| 370 | 1-1000 nM* |
| 371 | 1-1000 nM* |
| 372 | 1-1000 nM* |
| 373 | 1-1000 nM* |
| 374 | 1-1000 nM* |
| 375 | 1-1000 nM* |
| 376 | 1-1000 nM* |
| 377 | 1-1000 nM* |
| 378 | 1-1000 nM* |
| 379 | 1-1000 nM* |
| 380 | 1-1000 nM* |
| 381 | 1-1000 nM* |
| 382 | 1-1000 nM* |
| 383 | 1-1000 nM* |
| 384 | 1-1000 nM* |
| 385 | 1-1000 nM* |
| 386 | 1-1000 nM* |
| 387 | 1-1000 nM* |
| 388 | 1-1000 nM* |
| 389 | 1-1000 nM* |
| 390 | 1-1000 nM* |
| 391 | 1-1000 nM* |
| 392 | 1-1000 nM* |
| 393 | 1-1000 nM* |
| 394 | 1-1000 nM* |
| 395 | 1-1000 nM* |
| 396 | 1-1000 nM* |
| 397 | 1-1000 nM* |
| 398 | 1-1000 nM* |
| 399 | 1-1000 nM* |
| 400 | 1-1000 nM* |
| 401 | 1-1000 nM* |
| 402 | 1-1000 nM* |
| 403 | 1-1000 nM* |
| 404 | 1-1000 nM* |
| 405 | 1-1000 nM* |
| 406 | 1-1000 nM* |
| 407 | 1-1000 nM* |
| 408 | 1-1000 nM* |
| 409 | 1-1000 nM* |
| 410 | 1-1000 nM* |
| 411 | 1-1000 nM* |
| 412 | 1-1000 nM* |
| 413 | 1-1000 nM* |
| 414 | 1-1000 nM* |
| 415 | 1-1000 nM* |
| 416 | 1-1000 nM* |
| 417 | 1-1000 nM* |
| 418 | 1-1000 nM* |
| 419 | 1-1000 nM* |
| 420 | 1-1000 nM* |
| 421 | 1-1000 nM* |

*Est.

The invention claimed is:

1. A sulfonyl or sulfinyl, pyrimidinyl compound of formula I:

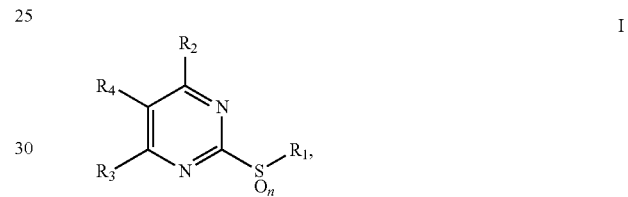

or a stereoisomer, hydrate, salt or acetate of said compound, wherein:

n is 1 or 2;

R1 is substituted or unsubstituted C1-C18 hydrocarbyl, or substituted or unsubstituted C1-C18 heterohydrocarbyl;

R2 is substituted or unsubstituted heteroatom, or substituted or unsubstituted C1-C18 hydrocarbyl, or substituted or unsubstituted C1-C18 heterohydrocarbyl;

R3 is substituted 5-pyridin-2 (1H)-one; and

R4 is H or halide, wherein the heterohydrocarbyl comprises 1-5 heteroatoms that are N, S, O or P, including 1-5 nitrogen atoms, which heteroatoms may be substituted, wherein substituents are selected from: —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR'", —NR" CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, wherein R', R" and R'" each independently refer to hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4) alkyl groups, wherein when R' and R" are attached to the same nitrogen atom, they can be combined with the nitrogen atom to form a 5-, 6- or 7-membered ring, wherein R3 is N-substituted with substituted or unsubstituted benzyl, wherein substituents for the benzyl are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO2R', —NR'—C(O)NR"R''', —NR'—SO$_2$NR"R''', —NH—C(NH2)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, in a number ranging from zero to the total number of open valences on the aromatic ring system; and where R', R" and R''' are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl, and -A-(CH$_2$)r-B—, wherein A and B are attached to adjacent atoms of the benzyl ring and wherein A and B are independently —CH$_2$—, —O—, —NH—, —S—, —S(O)—, —S(O)$_2$—, —S(O)$_2$NR'— or a single bond, and r is an integer of from 1 to 3, wherein a single bond of the new ring so formed may be replaced with a double bond, or two of the substituents on adjacent atoms of the benzyl ring may be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—, and the substituent R' in —NR'— and —S(O)$_2$NR'— is hydrogen or unsubstituted (C1-C6)alkyl.

2. The compound of claim 1 wherein:
R1 is substituted or unsubstituted C1-C18 alkyl or substituted or unsubstituted C1-C18 heteroalkyl.

3. The compound of claim 1 wherein:
R1 is substituted or unsubstituted C1-C4 alkyl.

4. The compound of claim 1 wherein:
R1 is Me.

5. The compound of claim 1 wherein:
R2 is CH$_3$, F, CH$_2$F, CHF$_2$, or CF$_3$.

6. The compound of claim 1 wherein:
R3 is N-substituted with 3,4-disubstituted benzyl.

7. The compound of claim 1 wherein:
R3 is 3-substituted with F.

8. The compound of claim 1 wherein:
R4 is H.

9. The compound claim 1 wherein:
R1 is substituted or unsubstituted C1-C18 alkyl or substituted or unsubstituted C1-C18 heteroalkyl;
R2 is CH$_3$, F, CH$_2$F, CHF$_2$, or CF$_3$; and
R4 is H.

10. The compound of claim 1 wherein:
R1 is substituted or unsubstituted C1-C4 alkyl;
R2 is CH$_3$, F, CH$_2$F, CHF$_2$, or CF$_3$, and
R4 is H.

11. The compound of claim 1 wherein:
R1 is Me;
R2 is CH$_3$, F, CH$_2$F, CHF$_2$, or CF$_3$, and
R4 is H.

12. The compound of claim 1 wherein the compound has structure selected from Table 4a or 4b.

13. The compound of claim 1 having a structure of Table 4a or 4b.

14. A pharmaceutical composition comprising a compound of claim 1 and a pharmaceutically-acceptable excipient, in unit dosage form selected from a pill, tablet, capsule, or lozenge.

\* \* \* \* \*